US008524900B2

(12) United States Patent
Albrecht et al.

(10) Patent No.: US 8,524,900 B2
(45) Date of Patent: Sep. 3, 2013

(54) FUSED HETEROCYCLIC DERIVATIVES AND METHODS OF USE

(75) Inventors: Brian K. Albrecht, Cambridge, MA (US); David Bauer, Sudbury, MA (US); Christiane M. Bode, Somerville, MA (US); Shon Booker, Thousand Oaks, CA (US); Alessandro Boezio, Somerville, MA (US); Deborah Choquette, Medford, MA (US); Derin D'Amico, Newbury Park, CA (US); Jean-Christophe Harmange, Andover, MA (US); Satoko Hirai, Cambridge, MA (US); Richard T. Lewis, Farmingham, MA (US); Longbin Liu, Thousand Oaks, CA (US); Julia Lohman, Cambridge, MA (US); Mark H. Norman, Thousand Oaks, CA (US); Michele Potashman, Cambridge, MA (US); Aaron C. Siegmund, Ventura, CA (US); Stephanie K. Springer, Cambridge, MA (US); Markian Stec, Moorpark, CA (US); Ning Xi, Thousand Oaks, CA (US); Kevin Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/309,488

(22) Filed: Dec. 1, 2011

(65) Prior Publication Data

US 2012/0148531 A1    Jun. 14, 2012

Related U.S. Application Data

(60) Division of application No. 12/009,123, filed on Jan. 15, 2008, which is a continuation-in-part of application No. 11/879,034, filed on Jul. 13, 2007.

(60) Provisional application No. 60/830,882, filed on Jul. 14, 2006.

(51) Int. Cl.
| C07D 487/04 | (2006.01) |
| C07D 403/12 | (2006.01) |
| C07D 403/14 | (2006.01) |
| C07D 401/12 | (2006.01) |
| C07D 401/14 | (2006.01) |
| C07D 413/14 | (2006.01) |
| A61K 31/5025 | (2006.01) |
| A61K 31/4353 | (2006.01) |
| A61K 31/4523 | (2006.01) |
| A61P 35/00 | (2006.01) |

(52) U.S. Cl.
USPC ........................................... 544/236; 514/248

(58) Field of Classification Search
USPC .................................... 544/236; 514/248
See application file for complete search history.

(56) References Cited

U.S. PATENT DOCUMENTS

| 3,489,755 | A | 1/1970 | Lombardino et al. |
| 4,260,255 | A | 4/1981 | Wachs et al. |
| 4,886,805 | A | 12/1989 | Bru-Magniez et al. |
| 5,459,132 | A | 10/1995 | Bru-Magniez et al. |
| 6,043,369 | A | 3/2000 | Schefczik |
| 6,403,588 | B1 | 6/2002 | Hayakawa et al. |
| 6,653,320 | B2 | 11/2003 | Hayakawa et al. |
| 7,173,033 | B2 * | 2/2007 | Igarashi et al. ............... 514/248 |
| 2002/0151549 | A1 | 10/2002 | Hayakawa et al. |
| 2005/0261297 | A1 * | 11/2005 | Igarashi et al. ............... 514/248 |
| 2007/0093490 | A1 | 4/2007 | Prien et al. |
| 2007/0265272 | A1 | 11/2007 | Cheng et al. |

FOREIGN PATENT DOCUMENTS

| EP | 0156734 A | 10/1985 |
| EP | 0163240 | 12/1985 |
| EP | 0254623 | 1/1988 |
| EP | 1481977 A | 12/2004 |
| EP | 1640010 A1 | 3/2006 |
| EP | 1719756 A1 | 8/2006 |
| JP | 2004-277337 A | 10/2004 |
| TW | 200801007 | 1/2008 |
| WO | WO 02/12236 | 2/2002 |
| WO | WO 03/074525 | 9/2003 |
| WO | WO 2005/010005 | 2/2005 |
| WO | WO 2005/077953 | 8/2005 |
| WO | WO 2006/015123 | 2/2006 |
| WO | WO 2006/018727 | 2/2006 |
| WO | WO 2006/052913 | 5/2006 |
| WO | WO 2006/058752 | 6/2006 |
| WO | WO 2006/124354 | 11/2006 |
| WO | WO 2006/124692 | 11/2006 |
| WO | WO 2006/135667 | 12/2006 |
| WO | WO 2007/007919 | 1/2007 |

(Continued)

OTHER PUBLICATIONS

Office action dated Aug. 8, 2012 in corresponding Taiwanese Patent Application No. 96125670.

Abdel-Rahman et al., "Synthesis of some new thioeters of 1,2,4-triazine-3-hydrazones and assays for their anticancer and anti-human immune virus activities", *Framaco, Societa Chimica Italiana*, Pavia It. vol. 48, No. 3, 397-406 (1993).

Adelstein et al., "Antiarrhythmic agents, synthesis and biological activity of some tetrazole and oxadiazole analogs of 4-dialkylamino. 2.2-diarylbutyramides," *Journal of Medicinal Chemistry*, vol. 16, No. 4, 309-312, 1973.

Albright et al., "Syntesis and anxiolytic activity of 6-(substituted-henyl)-1,2,4-triazolo[4,3-b]pyridazines", *Journal of Medicinal Chemistry*, vol. 24, No. 5, 592-600 (1981).

(Continued)

*Primary Examiner* — Venkataraman Balasubramanian
(74) *Attorney, Agent, or Firm* — Olga Mekhovich

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

8 Claims, No Drawings

(56) References Cited

FOREIGN PATENT DOCUMENTS

| WO | WO 2007/013673 | 2/2007 |
|---|---|---|
| WO | WO 2007/025540 | 3/2007 |
| WO | WO 2007/064797 | 6/2007 |
| WO | WO 2007/075567 | 7/2007 |
| WO | WO 2007/106236 | 9/2007 |
| WO | WO 2007/110437 | 10/2007 |
| WO | WO 2007/113226 | 10/2007 |
| WO | WO 2007/138472 | 12/2007 |
| WO | WO 2008/008539 A | 1/2008 |
| WO | WO 2008/051805 A | 5/2008 |
| WO | WO 2008/155378 A | 12/2008 |

OTHER PUBLICATIONS

Berthold et al., "Hochtemperaturammonolyse von Urantrichlorid und Urantetrachlorid", *Angewandte Chemie*, vol. 77, No. 9, 428 (1965).
Brady et al., "Intramolecular [2+2] ketene cycloadditions. Synthesis of isoflavones and 3-aroylbenzofurans", *Journal of Organic Chemistry*, vol. 53, No. 7, 1353-1356 (1988).
BRN 5619657 (date unavailable).
Caddick et al., "Observations on the intramolecular Heck reactions of aromatic chlorides using palladium/imidazolium salts", *Tetrahedron Letters*, vol. 43, No. 51, 9347-9350 (2002).
*Cecil Textbook of Medicine*, edited by Bennet, J.C. and Plum F., 20$^{th}$ ed, V 1, 1004-1010, 1996.
Cohen et al., Current Opinion in Chem Biology, 3,459-465, 1999.
Database Beilstein, Beilstein Institute for Organic Chemistry, Frankfurt-Main, DE; 1966, XP002508050, Compound with Registry No. 1793-33-5.
Database Beilstein, Beilstein Institute for Organic Chemistry, Frankfurt-Mai, DE; 1966, XP002508051, Compound with Registry No. 10551-98-0.
Database Caplus [Online] Chemical Abstracts Service, Columbus, Ohio, US: 1990, XP002508046, Database accession No. 2006:594185 Compound with RN No. 929905-67-9.
Database Caplus [Online] Chemical Abstracts Service, Columbus, Ohio, US: 1997, XP002508047, Database accession No. 1997:84644 Compound with RN No. 186449-67-2.
Database Caplus [Online] Chemical Abstracts Service, Columbus, Ohio, US: 1996, XP002508048, Database accession No. 1996:576042Compound with RN No. 182261-66-1.
Database Caplus [Online] Chemical Abstracts Service, Columbus, Ohio, US: 1990, XP002508049, Database accession No. 1990:216834 Compound with RN No. 127157-68-0.
Dermer et al., *Bio/Technology*, 1994, 12:320.
Fabbro et al., *Pharmacology & Therapeutics* 93, 79-98, 2002.
Freshney et al., *Culture of Animal Cells, A Manual of basic technique*, Alan R. Liss, Inc., 1983, New York, p. 4.
Golub, et al., *Science*, 286, 531-537, 1999.
Labouta et al., "Synthesis of some substituted triazolo no 4,3-B 3 /4 not 1,2,4, 3 /4 triazines as potential anticancer agents", Monatshefte fur Chenmie, Springer Verlag. Wien, AT. vol. 119, No. 5, 591-596 (1988).
Lombardino et al., "Preparation and new reactions of imidazo not 1,2-alpha ¾ pyridines", *Journal of Organic Chemistry*, vol. 30, No. 7, 2403-2407, (1965).
Mass, R.D., *Int. J. Radiation Oncology Bio. Phys*. vol. 58(3): 932-940, 2004/.
McClure et al., "Structure-activity relationships of triazolopyridien oxazole p38 inhibitors: Identification of candidates for clinical development," *Bioorganic & Medicinal Chemistry Letters*, 16: 4339-4344, 2006.
Noble, et al., "Protein kinase inhibitors: insights into drug design from structure," *Science*, 303:1800-1805, 2004.
Potts et al., "1,2,4-Triazoles, XII. Derivatives of the sigma-Triazolo[4,3-alpha]pyridine Ring System", *Journal of Organic Chemistry*, vol. 31, No. 1, 251-260 (1966).
Powell, et al., *British Journal of Dermatology*, 141: 802-810, 1999.
Reimlinger et al., "3-Benzoylamino-1,2,4-triazoles from N-Dichloromethylene-benzamide and Amidrazones", *Synthesis*, 433 (1970).
Vippagunta, et al., "Crystalline solids," *Adanced Drug Delivery Reviews*, 48:3-26 (2001).
West, et al., "Solid state chemistry and its applications," *Wiley*, New York, 358 & 365 (1988).

\* cited by examiner

FUSED HETEROCYCLIC DERIVATIVES AND METHODS OF USE

This application is a divisional patent application of and claims benefit to U.S. patent application Ser. No. 12/009,123 filed Jan. 15, 2008, which is a continuation-in-part of and claims benefit to U.S. patent application Ser. No. 11/879,034 filed Jul. 13, 2007, which in turn claims benefit of Provisional Application No. 60/830,882 filed Jul. 14, 2006, the specifications of which are incorporated herein by reference in their entireties.

REFERENCE TO THE SEQUENCE LISTING

The present application is being filed along with a Sequence Listing in electronic format. The Sequence Listing is provided as a file entitled A 1151 US DIV.txt, created Feb. 17, 2012 which is 1.12 KB in size. The information in the electronic format of the Sequence Listing is incorporated herein by reference in its entirety.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins, which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327:239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis.

HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun, 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met proto-oncogene have been postulated to play a role in microglial reactions to CNS injuries (Oncogene, 8:219-222 (1993)).

Metastatic SCC cells overexpress c-Met and have enhanced tumoregenesis and metastasis in vivo [G. Gong et al., Oncogene, 23:6199-6208 (2004)]. C-Met is required for tumor cell survival [N. Shinomiya et al., Cancer Research, 64:7962-7970 (2004)]. For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Sugen application WO 05/010005 describes certain Triazolotriazine compounds that are c-met inhibitors. Diamon Shamrock Corp. application WO 83/00864 discloses certain Triazolotriazine compounds that are useful as anti-inflammatory agents. Yamanouchi applications EP 1481955 and US 2005/0261297 disclose certain nitrogen-containing heterocyclic compounds that are therapeutic agents having a bone formation-stimulating effect.

Compounds of the current invention are inhibitors of c-Met.

DESCRIPTION OF THE INVENTION

A class of compounds useful in treating cancer and angiogenesis is defined by Formulae I, II, III, IV, V, VI and VII

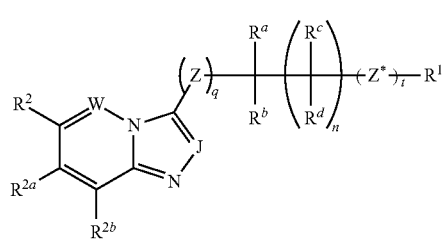
I

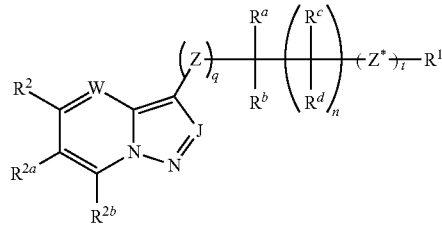
II

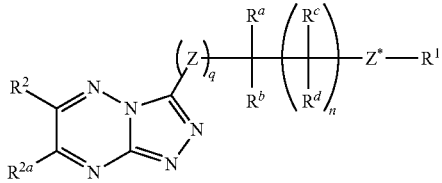
III

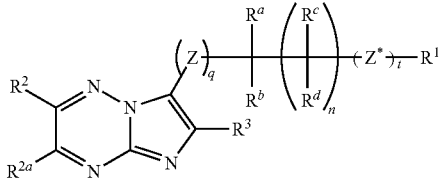
IV

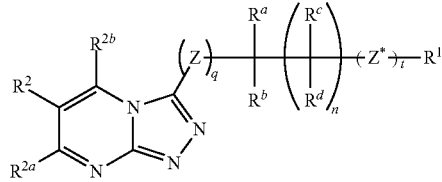
V

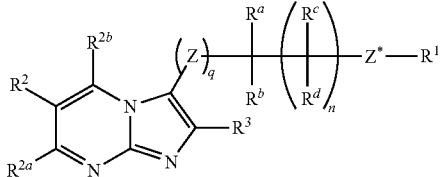
VI

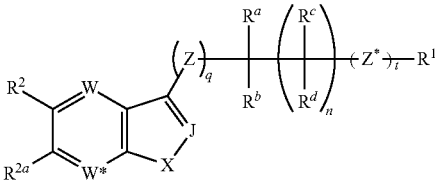
VII enantiomers, diastereomers, salts and solvates thereof wherein
J is N or $CR^3$;
W is N or $CR^{2b}$;
W* is N or $CR^{2b}$;
X is O or S;
Z and Z* are independently —O—, —S(O)$_v$—, or —NR$^5$—;
$R^a$, $R^b$, $R^c$ and $R^d$ are each independently H, halo, alkyl, alkenyl, alkynyl, haloalkyl, cycloalkyl, cycloalkenyl, heterocyclo, aryl, heteroaryl, —NO$_2$, —CN, —NR$^5$R$^{5a}$, —OR$^4$, —C(=O)R$^4$, —C(=O)OR$^4$; —C(=O)NR$^5$R$^{5a}$, —N(R$^5$)C(=O)NR$^5$R$^{5a}$, —OC(=O)NR$^5$R$^{5a}$, —S(O)$_v$R$^4$, —S(O)$_2$NR$^5$R$^{5a}$, —N(R$^5$)SO$_2$R$^4$ any of which may be optionally independently substituted with one or more R$^{10}$ groups as allowed by valance;
or $R^a$ and $R^b$ together with the carbon atom to which they are bonded may combine to form a 3-10 membered cycloalkyl, a 3-10 membered cycloalkenyl ring, or a heterocyclo ring, any of which may be optionally substituted with one or more $R^{10}$ groups as allowed by valance;

or $R^c$ and $R^d$ together with the carbon atom to which they are bonded may combine to form a 3-10 membered cycloalkyl, a 3-10 membered cycloalkenyl ring, or a heterocyclo ring, any of which may be optionally substituted with one or more $R^{10}$ groups as allowed by valance;

or $R^a$ and/or $R^b$ may combine with any $R^c$ or $R^d$ to form a partially or fully saturated 3-8 membered cycloalkyl ring or heterocyclo ring, either of which may be optionally substituted with one or more $R^{10}$ groups as allowed by valance;

or $R^a$ and $R^b$ may combine to form a carbonyl group;

or $R^c$ and $R^d$ attached to the same carbon atom may combine to form a carbonyl group;

$R^1$ is aryl, heteroaryl or heterocyclo any of which may be optionally independently substituted with one or more $R^{10}$ groups as allowed by valance;

$R^2$ is
(i) H, halo, cyano, nitro, or
(ii) alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —$OR^4$, —$S(O)_vR^4$, —$NR^5R^{5a}$, —$C(=O)R^4$, —$C(=S)R^4$, —$C(=O)OR^4$, —$C(=S)OR^4$, —$C(=O)NR^5R^{5a}$, —$C(=S)NR^5R^{5a}$, —$N(R^5)C(=O)NR^5R^{5a}$, —$N(R^5)C(=S)NR^5R^{5a}$, —$N(R^5)C(=O)R^4$, —$N(R^5)C(=S)R^4$, —$OC(=O)NR^5R^{5a}$, —$OC(=S)NR^5R^{5a}$, —$SO_2NR^5R^{5a}$, —$N(R^5)SO_2R^4$, —$N(R^5)SO_2NR^5R^{5a}$, —$N(R^5)C(=O)OR^4$, —$N(R^5)C(=S)OR^4$, —$N(R^5)SO_2R^4$, any of which may be optionally independently substituted with one or more $R^{10}$ as allowed by valance, provided that in compounds of formula I when W and J are both N, $R^2$ is other than
(a) —$NR^5R^{5a}$ where $R^5$ and $R^{5a}$ are independently H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl; and
(b) phenyl substituted with a group

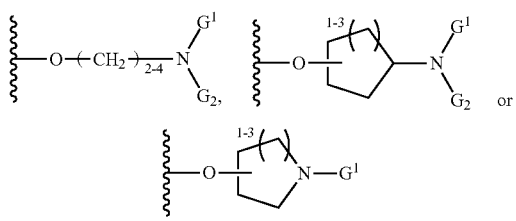

where $G^1$ and $G^2$ are independently alkyl, cycloalkyl, or $G^1$ and $G^2$ together with the nitrogen atom to which they are attached combine to form a 5- to 8-membered heterocyclo ring;

$R^{2a}$, $R^{2b}$ and $R^3$ are independently selected at each occurrence from H, halo, cyano, nitro, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, —$OR^4$, —$S(O)_vR^4$, —$NR^5R^{5a}$, —$C(=O)R^4$, —$C(=S)R^4$, —$C(=O)OR^4$, —$C(=S)OR^4$, —$C(=O)NR^5R^{5a}$, —$C(=S)NR^5R^{5a}$, —$N(R^5)C(=O)NR^5R^{5a}$, —$N(R^5)C(=S)NR^5R^{5a}$, —$N(R^5)C(=O)R^4$, —$N(R^5)C(=S)R^4$, —$OC(=O)NR^5R^{5a}$, —$OC(=S)NR^5R^{5a}$, —$SO_2NR^5R^{5a}$, —$N(R^5)SO_2R^4$, —$N(R^5)SO_2NR^5R^{5a}$, —$N(R^5)C(=O)OR^4$, —$N(R^5)C(=S)OR^4$, —$N(R^5)$ $SO_2R^4$, any of which may be optionally independently substituted with one or more $R^{10}$ groups as allowed by valance;

$R^4$ is independently selected at each occurrence from H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl, any of which may be optionally independently substituted as allowed by valance with one or more $R^{10}$ groups;

$R^5$ and $R^{5a}$ are independently selected at each occurrence from H, alkyl, haloalkyl, cycloalkyl, alkenyl, alkynyl, aryl, heteroaryl, heterocyclo, arylalkyl, heteroarylalkyl, heterocycloalkyl, and cycloalkylalkyl, any of which may be optionally substituted as allowed by valance with one or more $R^{10}$; or $R^5$ and $R^{5a}$ may combine to form a heterocyclo ring optionally substituted with one or more $R^{10}$;

$R^{10}$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^4$, -(alkylene)$_m$-$S(O)_vR^4$, -(alkylene)$_m$-$NR^5R^{5a}$, -(alkylene)$_m$-$C(=O)R^4$, -(alkylene)$_m$-$C(=S)R^4$, -(alkylene)$_m$-$C(=O)OR^4$, -(alkylene)$_m$-$OC(=O)R^4$, -(alkylene)$_m$-$C(=S)OR^4$, -(alkylene)$_m$-$C(=O)NR^5R^{5a}$, -(alkylene)$_m$-$C(=S)NR^5R^{5a}$, -(alkylene)$_m$-$N(R^5)C(=O)NR^5R^{5a}$, -(alkylene)$_m$-$N(R^5)C(=S)NR^5R^{5a}$, -(alkylene)$_m$-$N(R^5)C(=O)R^4$, -(alkylene)$_m$-$N(R^5)C(=S)R^4$, -(alkylene)$_m$-$OC(=O)NR^5R^{5a}$, -(alkylene)$_m$-$OC(=S)NR^5R^{5a}$, -(alkylene)$_m$-$SO_2NR^5R^{5a}$, -(alkylene)$_m$-$N(R^5)SO_2R^4$, -(alkylene)$_m$-$N(R^5)SO_2NR^5R^{5a}$, -(alkylene)$_m$-$N(R^5)C(=O)OR^4$, -(alkylene)$_m$-$N(R^5)C(=S)OR^4$, or -(alkylene)$_m$ -$N(R^5)SO_2R^4$;

wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-$OR^4$, -(alkylene)$_m$-$S(O)_vR^4$, -(alkylene)$_m$-$NR^5R^{5a}$, -(alkylene)$_m$-$C(=O)R^4$, -(alkylene)$_m$-$C(=S)R^4$, -(alkylene)$_m$-$C(=O)OR^4$, -(alkylene)$_m$-$OC(=O)R^4$, -(alkylene)$_m$-$C(=S)OR^4$, -(alkylene)$_m$-$C(=O)NR^5R^{5a}$, (alkylene)$_m$-$C(=S)NR^5R^{5a}$, -(alkylene)$_m$-$N(R^5)C(=O)NR^5R^{5a}$, -(alkylene)$_m$-$N(R^5)C(=S)NR^5R^{5a}$, -(alkylene)$_m$-$N(R^5)C(=O)R^4$, -(alkylene)$_m$-$N(R^5)C(=S)R^4$, -(alkylene)$_m$-$OC(=O)NR^5R^{5a}$, -(alkylene)$_m$-$OC(=S)NR^5R^{5a}$, -(alkylene)$_m$-$SO_2NR^5R^{5a}$, -(alkylene)$_m$-$N(R^5)SO_2R^4$, -(alkylene)$_m$-$N(R^5)SO_2NR^5R^{5a}$, -(alkylene)$_m$-$N(R^5)C(=O)OR^4$, -(alkylene)$_m$-$N(R^5)C(=S)OR^4$, or -(alkylene)$_m$ -$N(R^5)SO_2R^4$;

and further wherein any two $R^{10}$ groups attached to the same atom or attached to adjacent atoms may combine to form an optionally substituted 3- to 8 membered ring system;

m is 0 or 1;
n is 0, 1 or 2;
q and t are each independently 0 or 1;
v is 0, 1 or 2.

Preferred compounds include compounds wherein $R^1$ is phenyl, naphthyl, benzodioxolyl, benzooxazolyl, benzoisoxazolyl, pyridinyl, pyrimidinyl, pyrazinyl, pyrimidinyl, pyrazidinyl, isoquinolinyl, quinolinyl, quinazolinyl, quinazolinonyl, quinoxalinyl, naphthyridinyl, benzotriazinyl, triazolopyridinyl, triazolopyrimidinyl, triazolopyridazinyl, imidazopyridinyl, imidazopyrimidinyl, imidazopyridazinyl, pyrrolopyridinyl, pyrrolopyrimidinyl, pyrrolopyridazinyl, pyrazolopyridinyl, pyrazolopyrimidinyl, pyrazolopyridazinyl, cinnolinyl, thienopyridinyl, thienopyrimidinyl, thienopyridazinyl, furopyridinyl, furopyrimidinyl, furopyrazidinyl, benzofuranyl, benzoimidazolyl, indolyl, benzoisoxazolyl, benzothiazolyl, or benzoisothiazolyl any of which may be optionally independently substituted with one or more R[10] groups as allowed by valance.
Preferred R[1] groups include
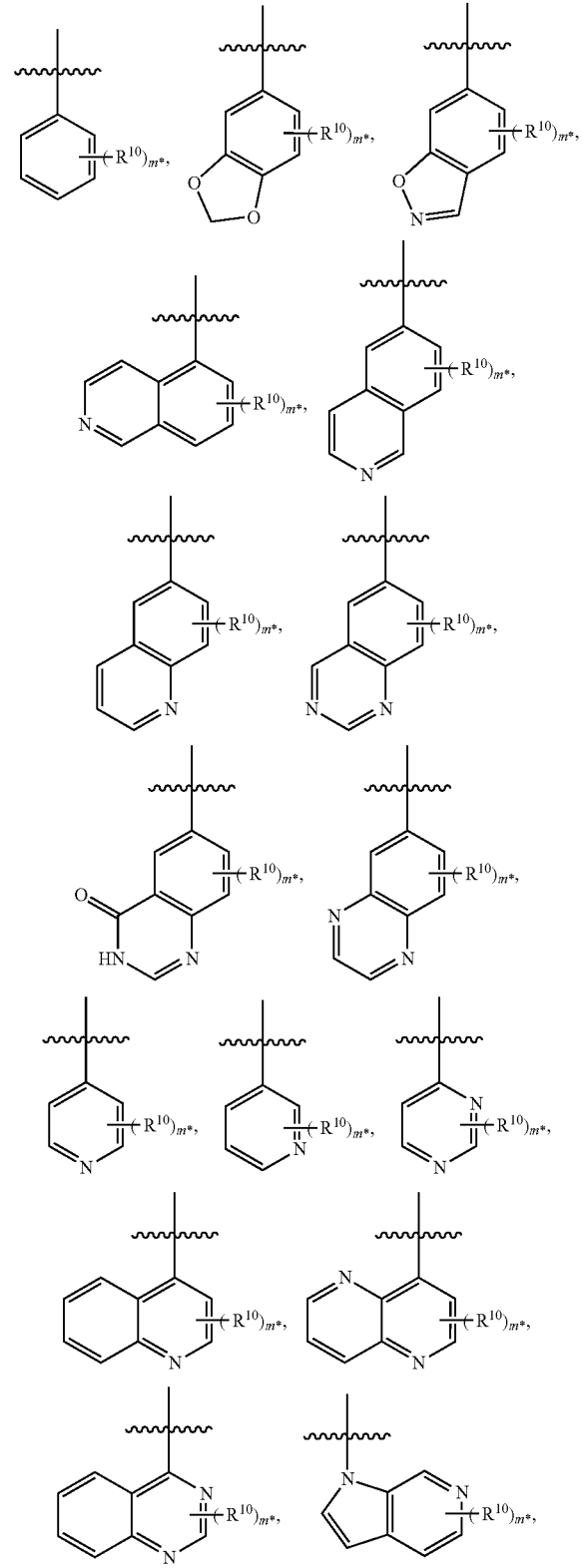
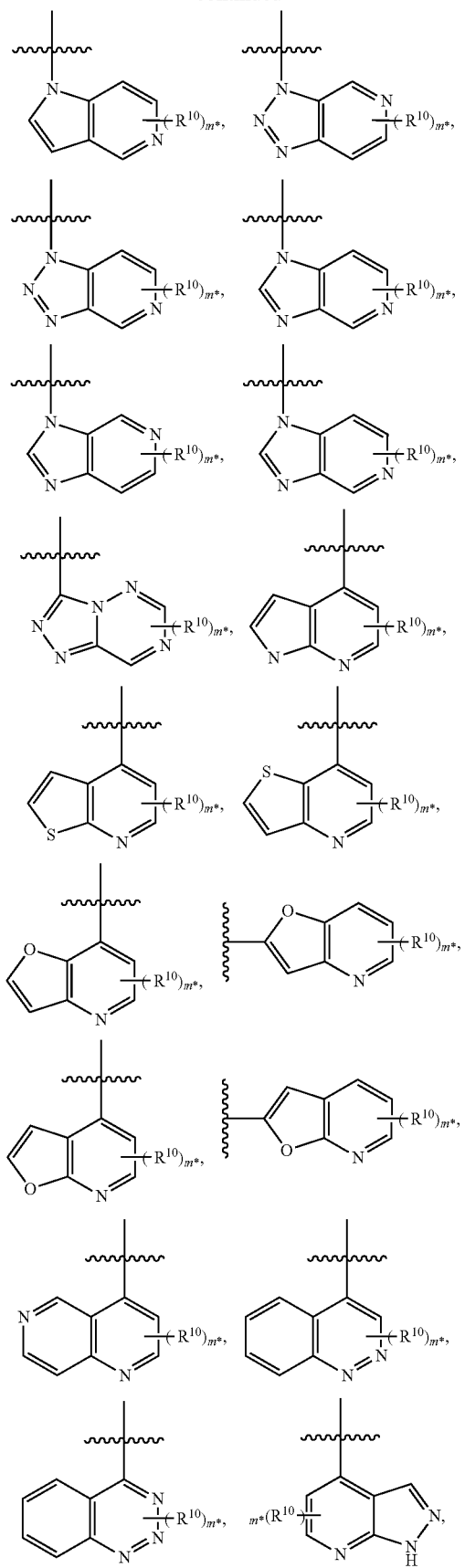

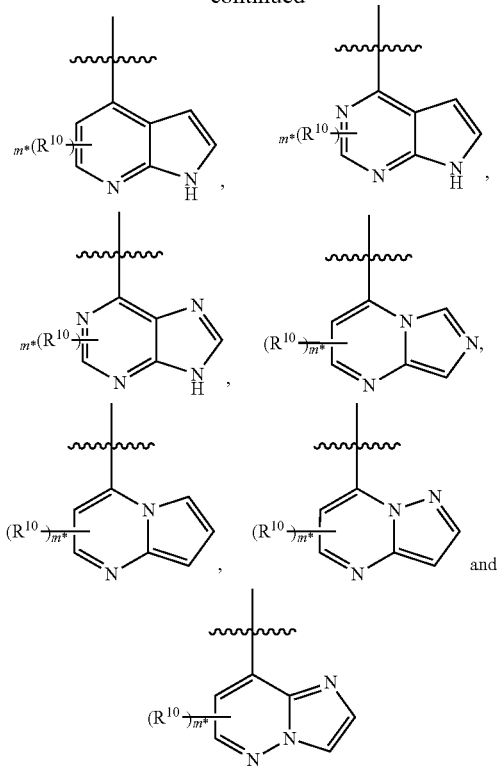

where m* is 0, 1, 2, 3, 4, 5 or 6, as allowed by valence.
Especially preferred R¹ groups include

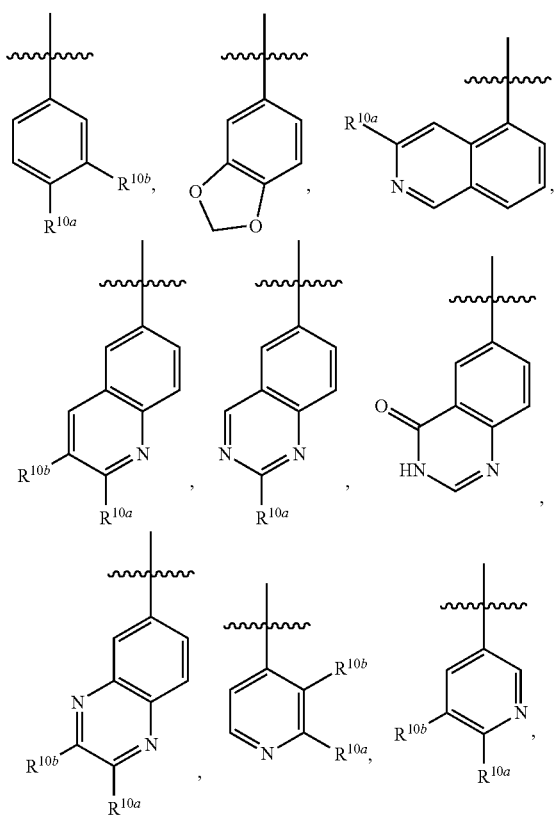

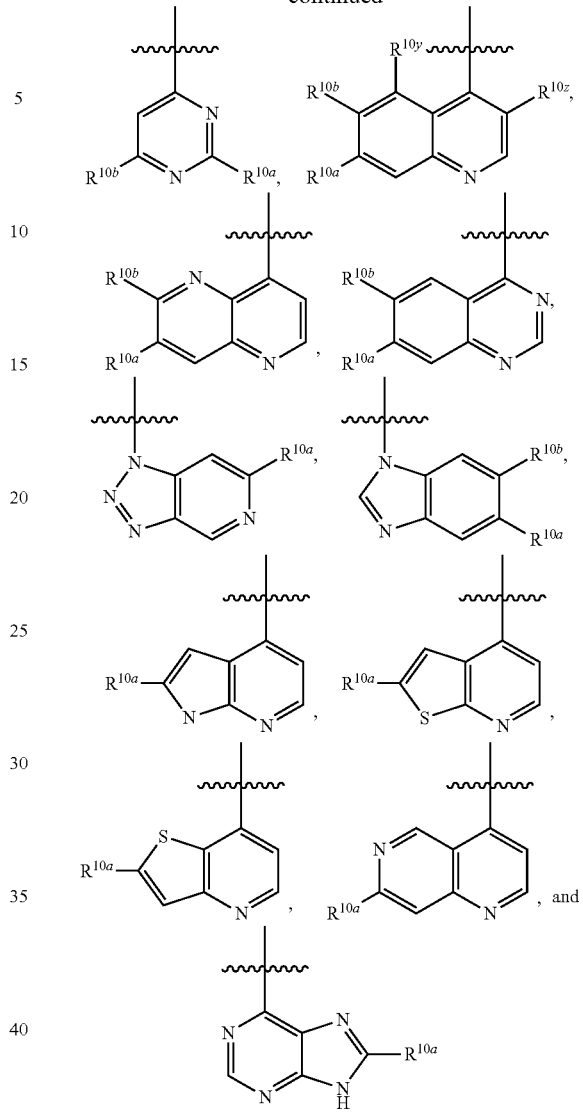

where $R^{10a}$, $R^{10b}$, $R^{10y}$ and $R^{10z}$ are independently absent, halo, cyano, nitro, alkyl, alkenyl, alkynyl, haloalkyl, -(alkylene)$_m$-OR⁴, -(alkylene)$_m$-NR⁵R$^{5a}$, -(alkylene)$_m$-C(=O)R⁴, -(alkylene)$_m$-C(=O)OR⁴, -(alkylene)$_m$-OC(=O)R⁴, -(alkylene)$_m$-C(=O)NR⁵R$^{5a}$, -(alkylene)$_m$-N(R⁵)C(=O)NR⁵R$^{5a}$, -(alkylene)$_m$-N(R⁵)C(=O)R⁴, -(alkylene)$_m$-OC(=O)NR⁵R$^{5a}$, or -(alkylene)$_m$-N(R⁵)C(=O)OR⁴;

or where $R^{10a}$ and $R^{10b}$ combine to form an optionally substituted 3- to 8-membered ring system.

Most preferred R¹ groups include moieties that are either unsubstituted or independently substituted as allowed by valance with one or more halo, cyano, nitro, alkyl, alkenyl, alkynyl, haloalkyl, -(alkylene)$_m$-OR⁴, -(alkylene)$_m$-NR⁵R$^{5a}$, -(alkylene)$_m$-C(=O)R⁴, -(alkylene)$_m$-C(=O)OR⁴, -(alkylene)$_m$-OC(=O)R⁴, -(alkylene)$_m$-C(=O)NR⁵R$^{5a}$, -(alkylene)$_m$-N(R⁵)C(=O)NR⁵R$^{5a}$, -(alkylene)$_m$-N(R⁵)C(=O)R⁴, -(alkylene)$_m$-OC(=O)NR⁵R$^{5a}$, or -(alkylene)$_m$-N(R⁵)C(=O)OR⁴.

Preferred compounds of the present invention further include compounds wherein R² is H, halo, cyano, alkynyl, —C(=O)NR⁵R$^{5a}$, —N(R⁵)C(=O)R⁴, —N(R⁵)C(=O)OR⁴, phenyl, naphthyl, pyrrolyl, imidazolyl, pyrazolyl, triazolyl, tetrazolyl, furanyl, thienyl, oxazolyl, isoxazolyl, thiazolyl, isothiazolyl, pyridinyl, tetrahydropyridinyl, pyridinonyl, pyrazinyl, pyrimidinyl, pyridazinyl, indolyl, isoindolyl, indolinyl, indolinonyl, isoidolinyl, isoindolinonyl, dihydrobenzofuranyl, dihydroisobenzofuranyl, benzofuranyl, isobenzofuranyl, quinolinyl, isoquinolinyl, quinazolinyl, quinazolinonyl, tetrahydroquinolinyl, tetrahydroisoquinolinyl, dihydroquinolinonyl, dihydroisoquinolinonyl, quinoxalinyl, tetrahydroquinoxalinyl, benzomorpholinyl, dihydrobenzodioxinyl, imidazopyridinyl, naphthyridinyl, benzotriazinyl, triazolopyridinyl, triazolopyrimidinyl, triazolopyridazinyl, imidazopyridinyl, imidazopyrimidinyl, imidazopyridazinyl, pyrrolopyridinyl, pyrrolopyrimidinyl, pyrrolopyridazinyl, pyrazolopyridinyl, pyrazolopyrimidinyl, pyrazolopyridazinyl, cinnolinyl, thienopyrrolyl, tetrahydrothienopyrrolyl, dihydrothienopyrrolonyl, thienopyridinyl, thienopyrimidinyl, thienopyridazinyl, furopyridinyl, furopyrimidinyl, furopyrazidinyl, benzofuranyl, benzoimidazolyl, benzoisoxazolyl, benzothiazolyl, or benzoisothiazolyl any of which may be optionally independently substituted with one or more $R^{10}$ groups as allowed by valance.

Preferred $R^2$ groups include (a) halo, alkynyl, —C(=O)NR$^5$R$^{5a}$, —N(R$^5$)C(=O)R$^4$ or —N(R$^5$)C(=O)OR$^4$ any of which may be optionally independently substituted with one or more $R^{10}$ groups as allowed by valance; and (b) an aryl, heteroaryl or heterocyclo ring system selected from

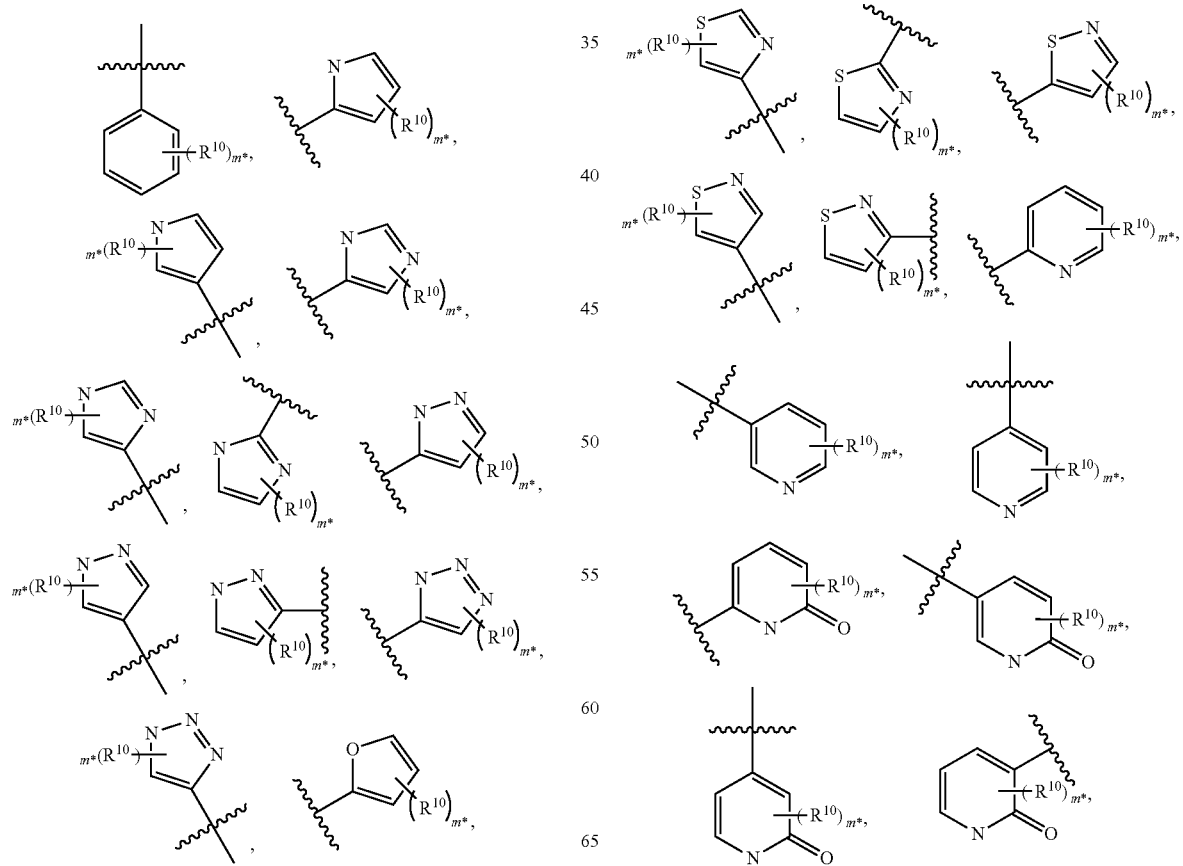

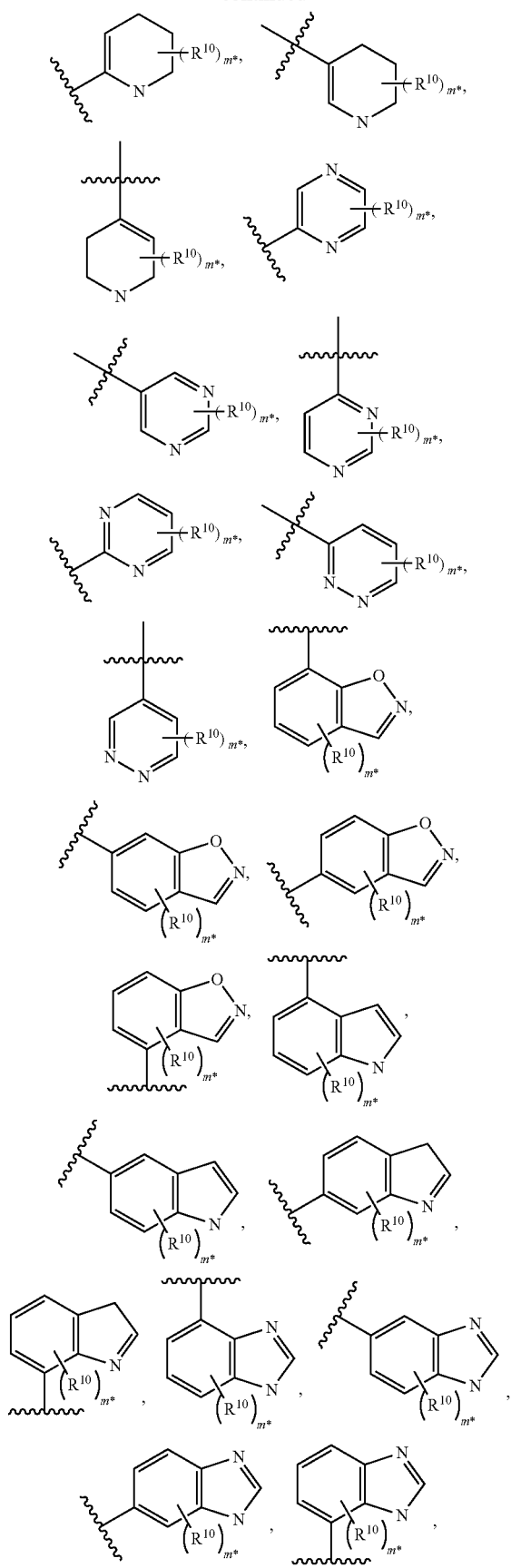
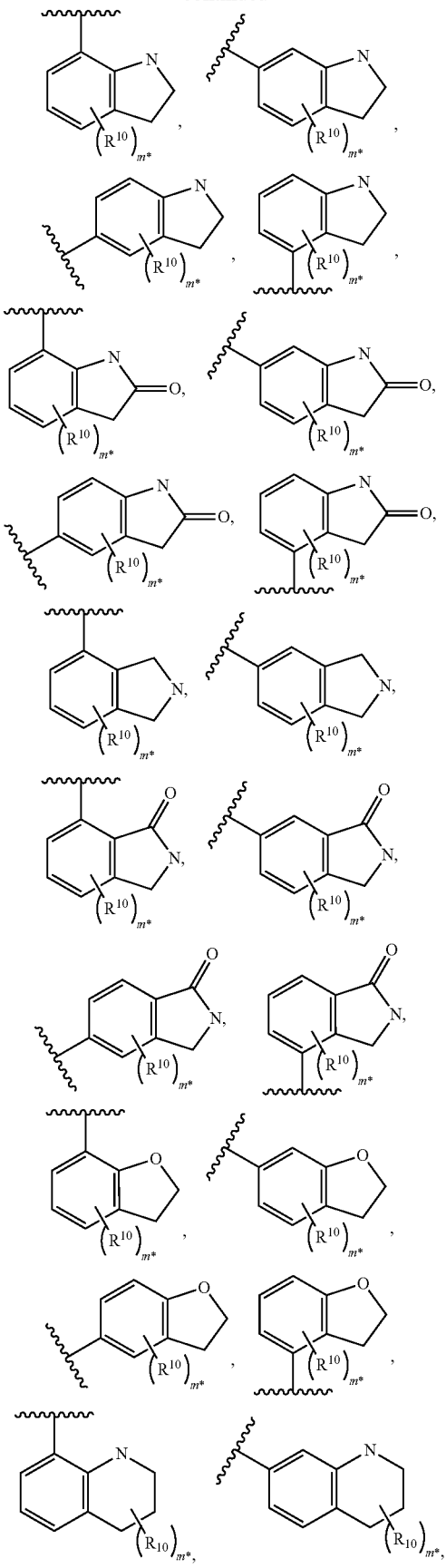

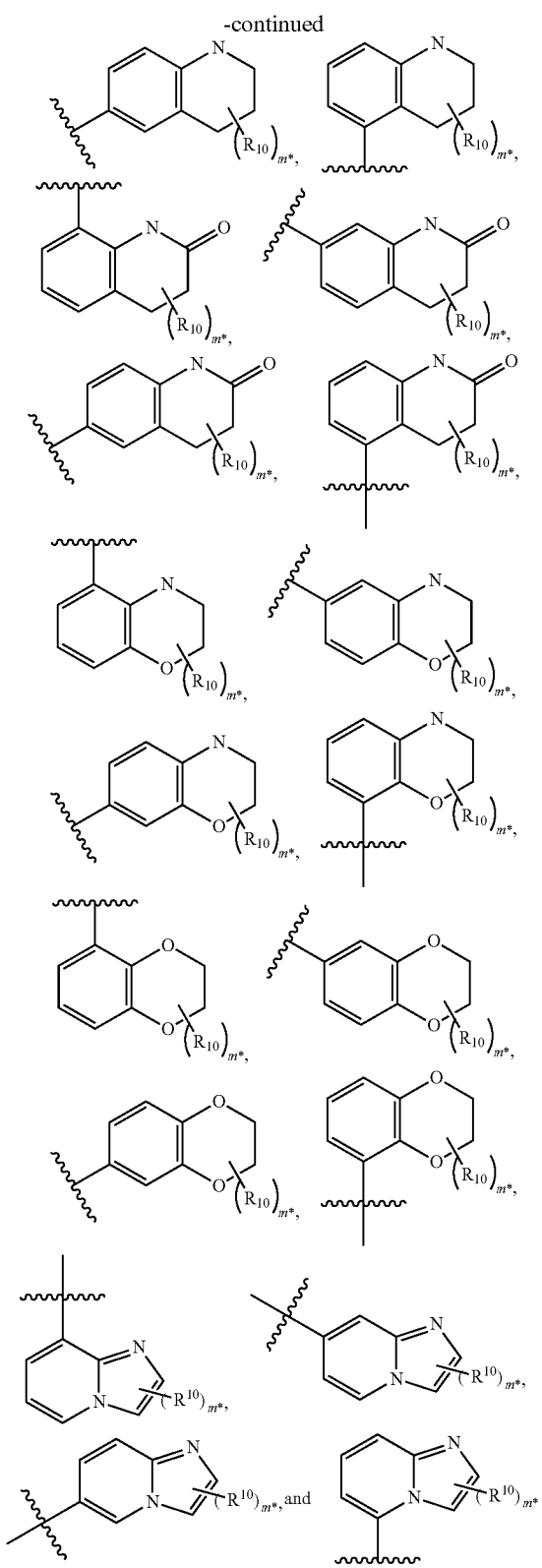

where m* is 0, 1, 2, 3, 4, 5 or 6, as allowed by valence.

Preferred compounds of the present invention include compounds having either or both of preferred $R^1$ groups and preferred $R^2$ groups either alone or in any combination thereof.

Preferred compounds of the present invention include compounds wherein $R^a$, $R^b$, $R^c$ and $R^d$ groups are independently hydrogen, alkyl (especially methyl), and halogen (especially fluorine).

Preferred compounds within the scope of formula I and II include compounds of the following formualae IA, IB, IC, ID and IIA

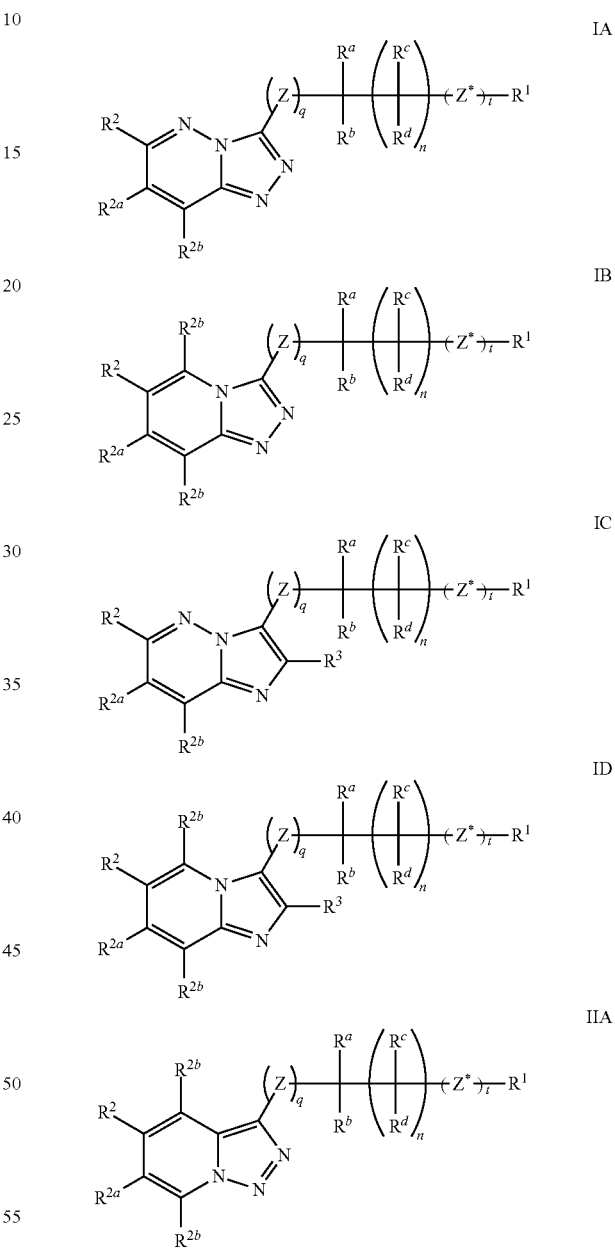

enantiomers, diastereomers, salts and solvates thereof, wherein variables $R^a$, $R^b$, $R^c$, $R^d$, $R^1$, $R^2$, $R^{2a}$, $R^{2b}$, $R^3$, Z, Z*, n, q and t are as previously defined above. Preferred compounds of formulae IA, IB, IC, ID and IIA include compounds having any of the preferred $R^1$ groups and $R^2$ groups, either alone or in any combination thereof.

Preferred compounds within the scope of formula I and II also include compounds having the following formula IE, IF, IIB and IIC

IE

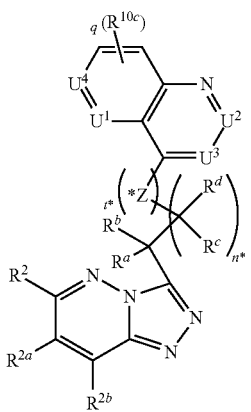

IF

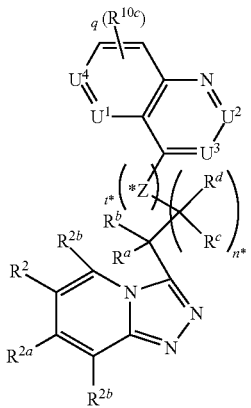

IIB

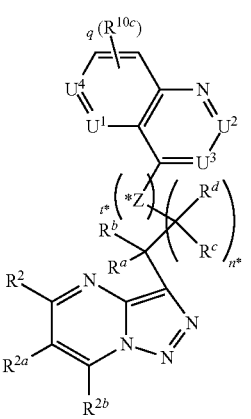

IIC

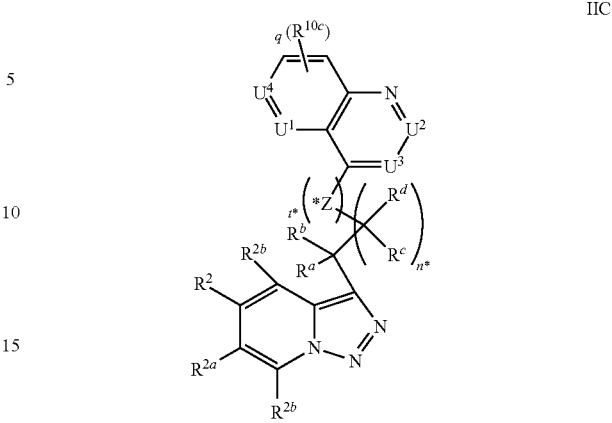

enantiomers, diastereomers, salts and solvates thereof
wherein variables $R^a$, $R^b$, $R^c$, $R^d$, $R^2$, $R^{2a}$, $R^{2b}$, and $Z^*$, are as previously defined above, provided that in compounds of formula IE $R^2$ is not phenyl substituted with a group $$\begin{array}{l}\xi\!-\!\!O\!-\!(CH_2)_{2-4}\!-\!N\diagup^{G^1}_{G^2}, \quad \xi\!-\!\!O\!-\!\!\left(\!\right)_{1-3}\!\!-\!N\diagup^{G^1}_{G^2} \text{ or}\end{array}$$

$$\xi\!-\!\!O\!-\!\!\left(\!\right)_{1-3}\!\!N\!-\!G^1$$

where $G^1$ and $G^2$ are independently alkyl, cycloalkyl, or $G^1$ and $G^2$ together with the nitrogen atom to which they are attached combine to form a 5- to 8-membered heterocyclo ring; and further wherein q is 0, 1, 2 or 3;

n* is 0, 1 or 2;

t* is 0 or 1

$U^1$, $U^2$, $U^3$ and $U^4$ are each independently C, or N; and $R^{10c}$ at each occurence is independently selected from the groups listed in the definition of $R^{10}$ previously described above.

Preferred compounds of formulae IE, IF, IIB and IIC include compounds having any of the preferred $R^2$ groups described above.

Preferred compounds within the scope of formulae IE and IF include compounds of the following formula IEi, IEii, IEiii, IEiv, IFi, IFii, IFiii and IFiv

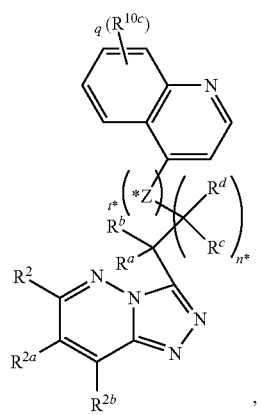
IEi
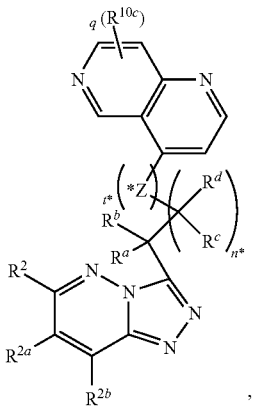
IEii
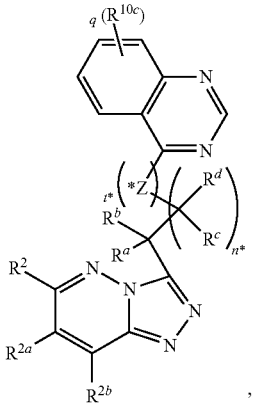
IEiii
IEiv
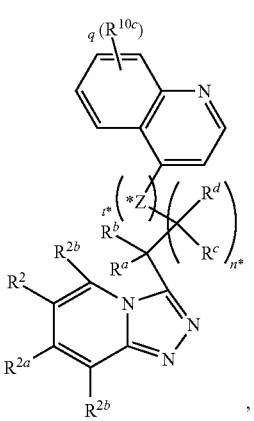
IFi
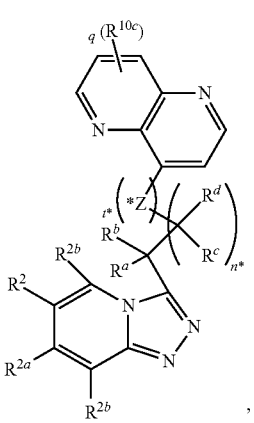
IFii
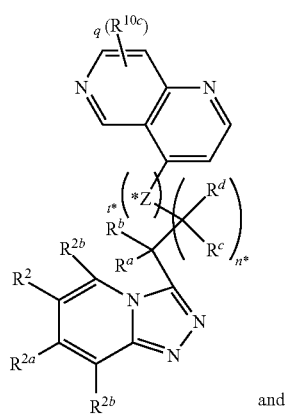
IFiii
and -continued

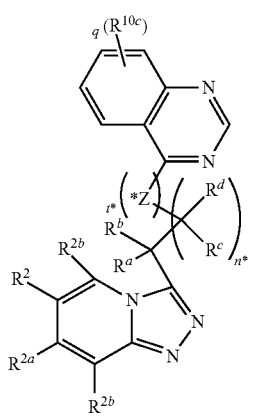

enantiomers, diastereomers, salts and solvates thereof.

Preferred compounds within the scope of formula I further include compounds of the following formula IEA and IFA

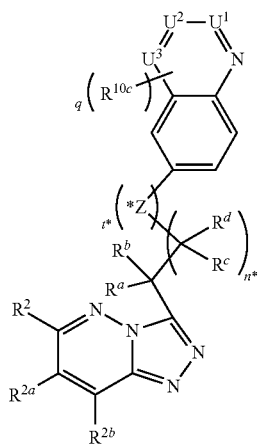

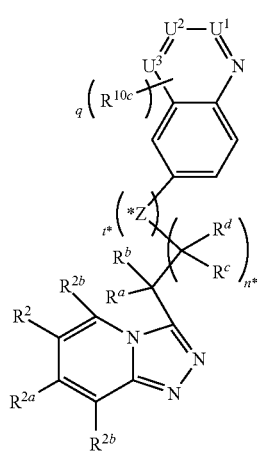

enantiomers, diastereomers, salts and solvates thereof wherein variables $R^a$, $R^b$, $R^c$, $R^d$, $R^2$, $R^{2a}$, $R^{2b}$, $R^{10c}$, $U^1$, $U^2$, $U^3$, $Z^*$, $n^*$, $q$, and $t^*$ are as previously defined above provided that in compounds of formula IEA $R^2$ is not phenyl substituted with a group

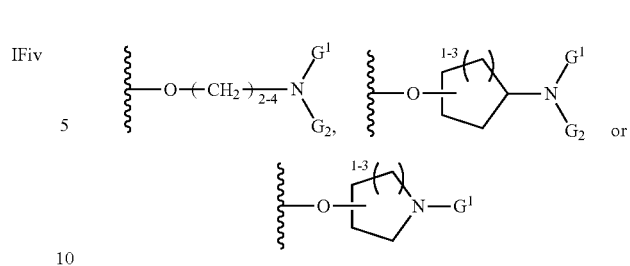

where $G^1$ and $G^2$ are independently alkyl, cycloalkyl, or $G^1$ and $G^2$ together with the nitrogen atom to which they are attached combine to form a 5- to 8-membered heterocyclo ring. Preferred compounds of formulae IEA and IFA include compounds having any of the preferred $R^2$ groups described above.

Preferred compounds of formulae IEA and IFA include compounds of formulae IEAi, IEAii, IEAiii, IFAi, IFAii and IFAiii

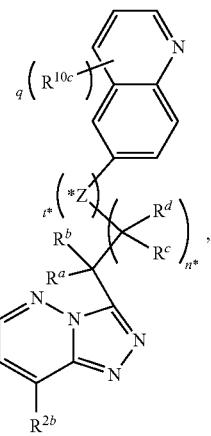

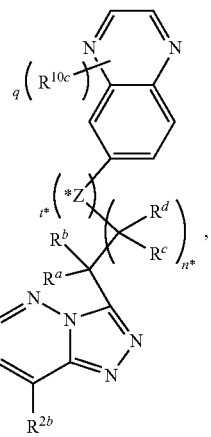

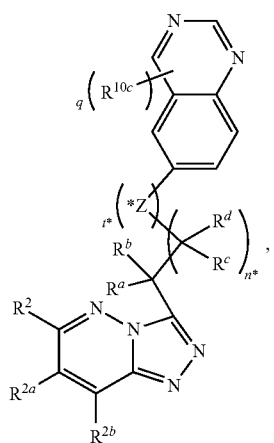

IEAiii

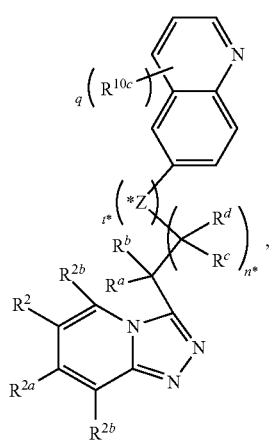

IFAi

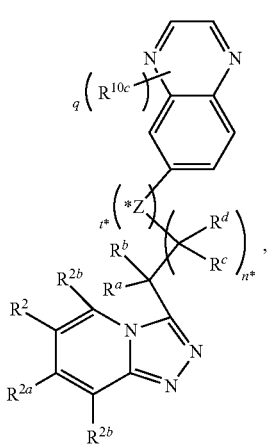

IFAii


IFAiii enantiomers, diastereomers, salts and solvates thereof.

Preferred compounds within the scope of formula I further include compounds of the following formula IG or IH

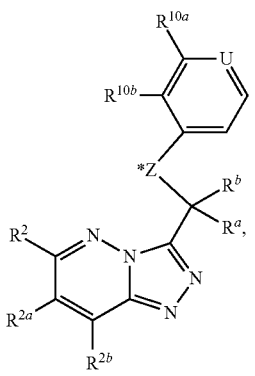

IG

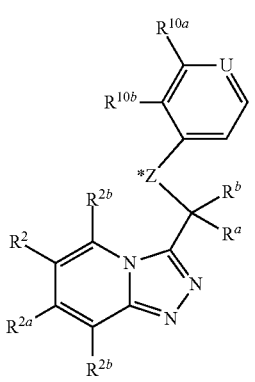

IH

Wherein U is $CR^{10c}$ or N, and variables $R^a$, $R^b$, $R^2$, $R^{2a}$, $R^{2b}$, $R^{10a}$, $R^{10b}$, $R^{10c}$, and $Z^*$, are as previously defined above, provided that in compounds of formula IG $R^2$ is not phenyl substituted with a group

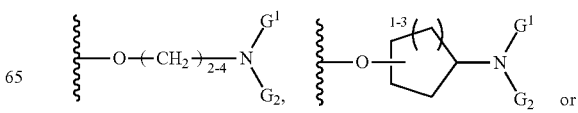

or

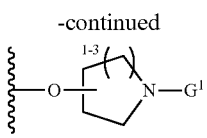

where $G^1$ and $G^2$ are independently alkyl, cycloalkyl, or $G^1$ and $G^2$ together with the nitrogen atom to which they are attached combine to form a 5- to 8-membered heterocyclo ring. Preferred compounds of formulae IG and IH include compounds having any of the preferred $R^2$ groups described above.

Preferred compounds of the present invention include the compounds exemplified herein.

The invention also relates to pharmaceutical compositions containing the above compounds, together with a pharmaceutically acceptable vehicle or carrier.

The invention also relates to a method of treating cancer in a subject using the above compounds.

The invention also relates to a method of reducing tumor size in a subject using the above compounds.

The invention also relates to a method of reducing metastasis in a tumor in a subject, using the above compounds.

The invention also relates to a method of treating HGF-mediated disorders in a subject using the above compounds.

Indications

Compounds of the present invention would be useful for, but not limited to, the prevention or treatment of angiogenesis related diseases. The compounds of the invention have c-Met inhibitory activity. The compounds of the invention are useful in therapy as antineoplasia agents or to minimize deleterious effects of HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemagi-nomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, lck, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

Definitions

"Angiogenesis" is defined as any alteration of an existing vascular bed or the formation of new vasculature, which benefits tissue perfasion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. Phenyl substituted with —O—CH$_2$—O— forms the aryl benzodioxolyl substituent.

The term "heterocyclyl" (or "heterocyclo") embraces saturated, and partially saturated and heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term(s) "Formulas I, II, III, IV, V, VI and VII" either alone or in combination includes any sub formulas.

The compounds of the invention are endowed with c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of c-Met.

The present invention comprises a pharmaceutical composition comprising a therapeutically effective amount of a compound of the current invention in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of the current invention.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of the current invention may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl) amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide.

6-fluoro-N-(4-(1-methylethyl)phenyl)-2-((4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-((4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;

N-(4-(pentafluoroethyl)-3-(((2S)-2-pyrrolidinylmethyl)oxy) phenyl)-2-((4-pyridinylmethyl)amino)-3-pyridinecarboxamide;

N-(3-((3-azetidinylmethyl)oxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-(3-pyridinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide;

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;

N-(4,4-dimethyl-1-oxo-1,2,3,4-tetrahydro-isoquinolin-7-yl)-2-(1H-indazol-6-ylamino)-nicotinamide;

N-[4-(tert-butyl)-3-(3-piperidylpropyl)phenyl][2-(1H-indazol-6-ylamino)(3-pyridyl)]carboxamide;

N[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747, 498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTINT™ (trastuzumab), which may be used to treat breast cancer and other forms of cancer, and RITUXANT™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA);

ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I, II, III, IV, V, VI and VII.

Also included in the family of compounds of the current are the pharmaceutically acceptable salts and solvates thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the current invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of the current invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the current invention. When a basic group and an acid group are present in the same molecule, a compound of the current invention may also form internal salts.

General Synthetic Procedures

The compounds of the invention can be synthesized according to the following procedures.

The following abbreviations are used throughout the specification:

HOAc—acetic acid
MeCN, $CH_3CN$—acetonitrile
$NH_3$—ammonia
$NH_4Cl$—ammonium chloride
Ar—argon
HBTA—O-benzotriazol-1-yl-N,N,N',N'-tetramethyluronium hexafluorophosphate
HATU O—(7-azabenzotriazol-1-yl)-N,N,N',N'-tetramethyluronium hexafluorophosphate
PyBop—benzotriazol-1-yl-oxy-tripyrrolidino-phosphonium hexafluorophosphate
$Pd_2(dba)_3$—bis(dibenzylideneacetone) palladium
BINAP—2,2'-bis(diphenylphosphino)-1,1'-binaphthyl
TEAC—bis(tetra-ethylammonium)carbonate
$BBr_3$—boron tribromide
BSA—bovine serum albumin
$Br_2$—bromine
BOC—butyloxycarbonyl
$Cs_2CO_3$—cesium carbonate
$CHCl_3$—chloroform
$CDCl_3$—chloroform deuterated
Cu—copper
CuI—copper(I) iodide
$Et_2O$—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
$H_2$—hydrogen
$H_2O_2$—hydrogen peroxide
Fe—iron
LiHMDS—lithium bis(trimethylsilyl)-amide
LDA—Lithium diisopropylamide
MCPBA—meta-chloroperbenzoic acid
$MgSO_4$—magnesium sulfate
MeOH, $CH_3OH$—methanol
MeI—methyl iodide
$CH_2Cl_2$, DCM—methylene chloride
NMP—N—methylpyrrolidinone
ML, ml—milliliter
$N_2$—nitrogen
Pd/C—palladium on carbon
$Pd(OAc)_2$—palladium acetate
$Pd(OH)_2$—palladium hydroxide
$Pd(PPh_3)_4$—palladium tetrakis triphenylphosphine
$Pd(dppf)Cl_2$—1,1-bis(diphenylphosphino)ferrocene palladium chloride
PBS—phosphate buffered saline
$POCl_3$—phosphorous oxychloride
$K_2CO_3$—potassium carbonate
KOH—potassium hydroxide
RT—room temperature NaHCO₃—sodium bicarbonate
NaBH₄—sodium borohydride
NaBH₃CN—sodium cyanoborohydride
NaOtBu—sodium tert-butoxide
NaOH—sodium hydroxide
NaClO₂—sodium chlorite
NaCl—sodium chloride
NaHPO₄—sodium biphospate
NaH—sodium hydride
NaI—sodium iodide
Na₂SO₄—sodium sulfate
TBTU—O-benzotriazol-1-yl-N,N,N',N'-tetramethyluronium tetrafluoroborate
THF—tetrahydrofuran
Et₃N, TEA—triethylamine
TFA—trifluoroacetic acid
P(t-bu)₃—tri(tert-butyl)phosphine
H₂O—water General Method A

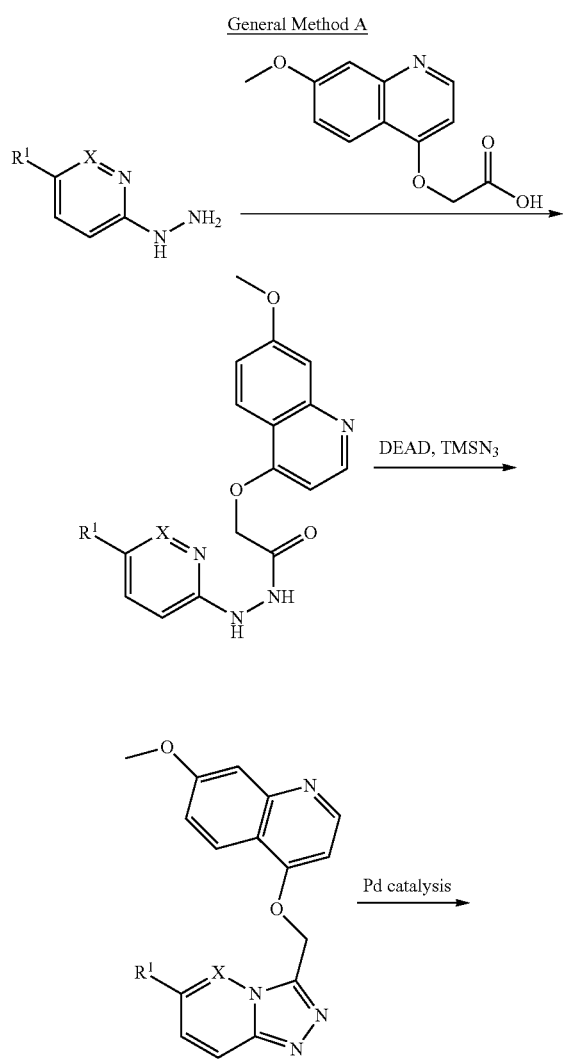

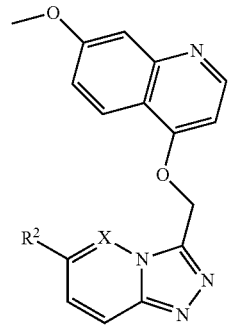

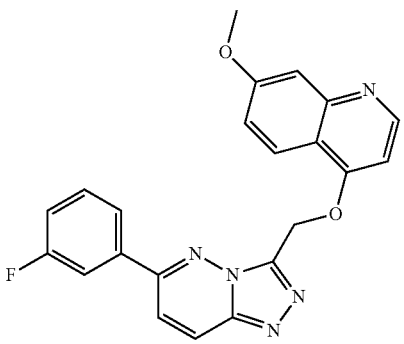 [SMILES: COc1ccc2c(OCc3nnc4ccc(-c5cccc(F)c5)nn34)ccnc2c1]

EXAMPLE 1

4-((6-(3-fluorophenyl)-[1,2,4]triazolo[4,3-b]pyridazin-3-yl)methoxy)-7-methoxyquinoline Step 1.

2-(7-methoxyquinolin-4-yloxy)acetic acid

A 250-mL, 3-neck, rb flask equipped with a magnetic stirbar, a reflux condenser and a powder funnel was charged with potassium hydroxide (6.0 g, 90 mmol) then 2-hydroxyacetic acid (5.0 g, 65 mmol) with stirring. The solid reactants gradually reacted and liquified as significant heat was generated. Upon dissolution of all the reagents, flask containing the hot syrupy liquid was immersed in a 170° C. oil bath, then a solution of 4-chloro-7-methoxyquinoline (5.0 g, 26 mmol) in anhydrous DMSO (20 mL, 4 vol wrt quinoline) was added dropwise over 20-30 min via addition funnel. The resulting brown solution was maintained in the oil bath with stirring. After 2.5 h, the flask was removed from the oil bath, then quenched by the addition of water (100 mL, 5 vol wrt DMSO). The resulting brown solution was immersed in an ice bath, and the mixture was neutralized by the dropwise addition of 6 N HCl (15 mL, 1 equiv to KOH), which resulted in the formation of a thick yellow ppt and brought the mixture to pH 3. The mixture was filtered and washed with water and ACN. The solid products were dried under vacuum to yield 2-(7-methoxyquinolin-4-yloxy)acetic acid (2.16 g, 36% yield) as a yellow solid. (ESI, pos. ion) m/z: 234.1 (M+H).

Step 2.

N'-(6-chloropyridazin-3-yl)-2-(7-methoxyquinolin-4-yloxy)acetohydrazide

A mixture of 1-(6-chloropyridazin-3-yl)hydrazine (0.372 g, 2.57 mmol), 1-hydroxy-7-aza-benzotriazole (0.350 g, 2.57 mmol), EDC (0.641 g, 3.34 mmol), 2-(7-methoxyquinolin-4-yloxy)acetic acid (0.600 g, 2.57 mmol) and diisopropylethylamine (1.34 ml, 7.72 mmol) in DMF (20 mL) was allowed to stir at 50° C. for 2 h. Concentrated. Reconstitued in MeCN (30 mL). Concentrated with cooling. Product crashed out of solution and was isolated by filtration. Used without further purification. (ESI, pos. ion) m/z: 234.1 (M+H).
Step 3.

4-((6-chloro-[1,2,4]-triazolo[4,3-b]pyridazin-3-yl)methoxy)-7-methoxyquinoline

N'-(6-chloropyridazin-3-yl)-2-(7-methoxyquinolin-4-yloxy)acetohydrazide (2.53 g, 7.0 mmol) was suspended in tetrahydrofuran (50 mL) then added triphenylphosphine (2.8 g, 11 mmol) and trimethylsilyl azide (1.4 ml, 11 mmol). To this suspension, was added diethylazodicarboxylate (2.0 ml, 13 mmol) in rapid drops with a syringe. The mixture became clear and hot to the touch. The reaction mixture was heated at 50° C. for 30 minutes. The reaction mixture was concentrated in vacuo. The remaining oil was triturated with diethyl ether. A gel-like solid formed which was collected on a glass frit, washing with diethyl ether. The solid was then triturated with ethyl acetate, and finally acetonitrile. An amorphous solid formed which was collected on a glass frit, washing with acetonitrile. The solid was further dried under high vacuum. In addition, the ethyl acetate filtrate was concentrated in vacuo. The remaining oil was then triturated with acetonitrile. An amorphous solid formed and was collected on a glass frit, washing with acetonitrile. The solid was further dried under high vacuum affording 4-((6-chloro-[1,2,4]triazolo[4,3-b]pyridazin-3-yl)methoxy)-7-methoxyquinoline as a tan solid. MS (ESI, pos. ion) m/z: 342.1 (M+1).
Step 4.

4-((6-(3-fluorophenyl)-[1,2,4]triazolo[4,3-b]pyridazin-3-yl)methoxy)-7-methoxyquinoline 3-fluorophenylboronic acid (0.092 g, 0.66 mmol) was added to a suspension of 4-((6-chloro-[1,2,4]triazolo[4,3-b]pyridazin-3-yl)methoxy)-7-methoxyquinoline (0.150 g, 0.44 mmol) in 2.5 mL dimethylformamide, followed by the addition of potassium carbonate (0.18 g, 1.3 mmol) in 0.6 mL water. $PdCl_2(dppf)-CH_2Cl_2$ adduct (0.018 g, 0.022 mmol) was added and the flask was purged with argon, sealed and heated at 80° C. for four hours. Purification by MPLC (eluted with 5 then 10% MeOH in $CH_2Cl_2$) afforded the product as an off-white solid (78 mg, 44%). (ESI, pos. ion) m/z: 402.1 (M+H).

General Method B.

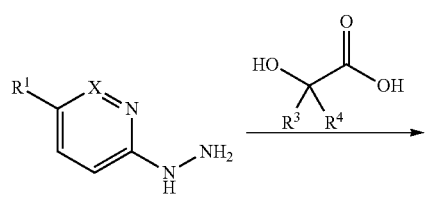

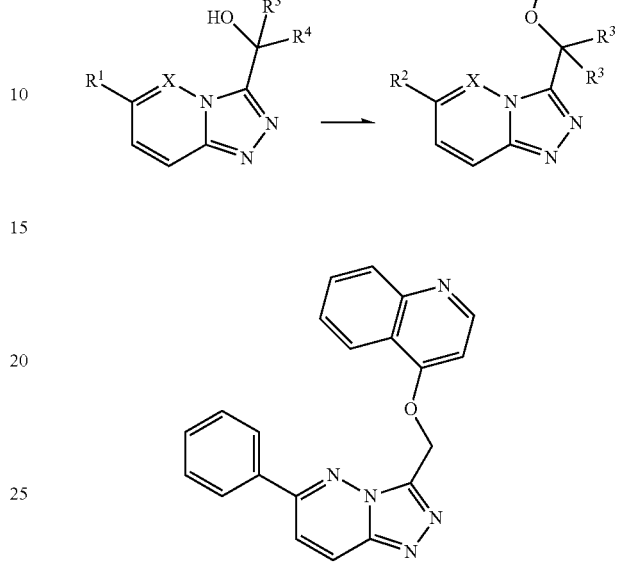

EXAMPLE 2

4-((6-phenyl-[1,2,4]triazolo[4,3-b]pyridazin-3-yl)methoxy)quinoline

Step 1.

(6-phenyl-[1,2,4]triazolo[4,3-b]pyridazin-3-yl)methanol

A mixture of 1-(6-phenylpyridazin-3-yl)hydrazine (2.00 g, 10.7 mmol), glycolic acid (0.825 g, 10.8 mmol), p-TsOH.H₂O (2.55 g, 13.4 mmol) in PhMe (50 mL) was refluxed for 14 h. PhMe was removed in vacuo. The resulting solids were diluted with water (30 mL). The mixture was brought to pH~10 with 2N NaOH. The solids were isolated solid by filtration, washed with water and dried under vacuum to give an off white solid which was used without further purification. (ESI, pos. ion) m/z: 227.0 (M+H).
Step 2.

4-((6-phenyl-[1,2,4]triazolo[4,3-b]pyridazin-3-yl)methoxy)quinoline

Cesium carbonate (335 mg, 1027 μmol) was added to a mixture of 4-chloroquinoline (465 mg, 2054 μmol) and above alcohol (112 mg, 685 μmol) in DMSO (1.8 mL) at RT. The reaction mixture was stirred at 120° C. under microwave irradiation for 2 h. The reaction mixture was diluted with EtOAc and washed with water. The water layer was extracted with EtOAC. The organic layer was dried over $MgSO_4$, filtered and concentrated in vacuo. Purification by MPLC ($CH_2Cl_2$/MeOH+1% $NH_4OH$: 100/0 to 95/5) afforded the title compound. (ESI, pos. ion) m/z: 354.1 (M+H).

In addition to the above reaction, potassium hydride in DME can also be utilized in a similar manner.

General Method C.

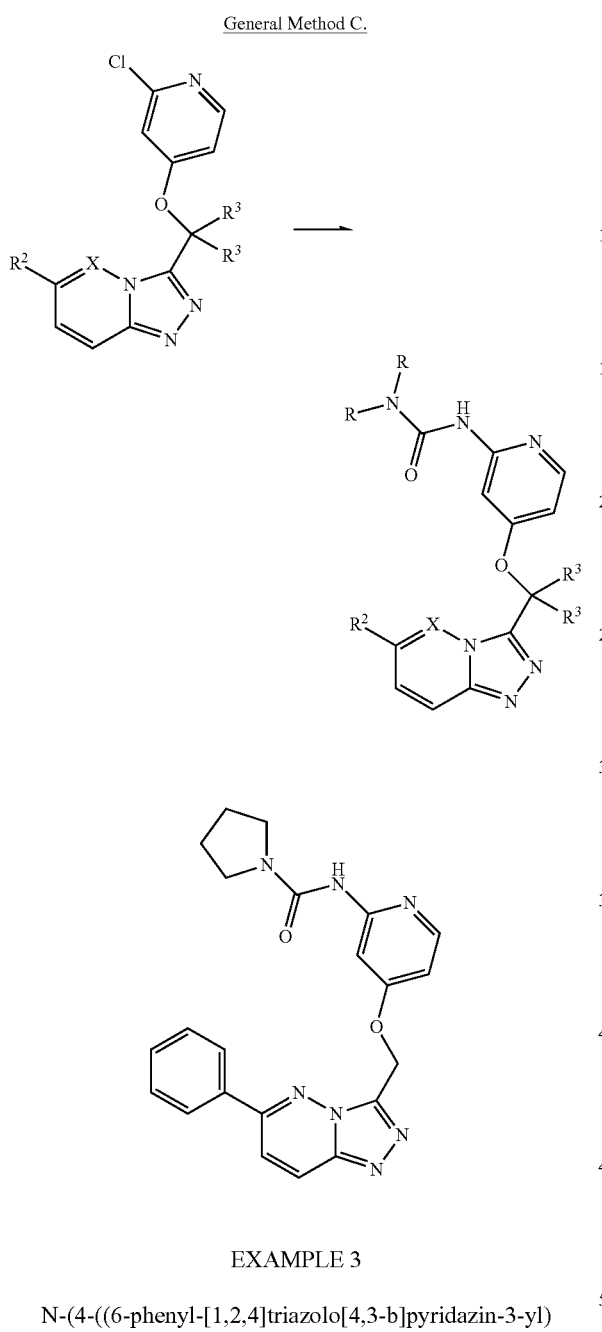

EXAMPLE 3

N-(4-((6-phenyl-[1,2,4]triazolo[4,3-b]pyridazin-3-yl)methoxy)pyridin-2-yl)pyrrolidine-1-carboxamide Step 1.

4-((6-phenyl-[1,2,4]triazolo[4,3-b]pyridazin-3-yl)methoxy)pyridin-2-amine

To an argon purged flask was added cesium carbonate (0.24 g, 0.73 mmol), 3-((2-chloropyridin-4-yloxy)methyl)-5-phenyl-3aH-pyrazolo[4,3-b]pyridine (0.0820 g, 0.24 mmol), tris(dibenzylideneacetone)dipalladium (o) (0.0056 g, 0.0061 mmol), rac-2,2'-bis(diphenylphosphino)-1,1'-binaphthyl (0.0091 g, 0.015 mmol). The mixture was taken up in dioxane (8 mL) followed by the addition of benzophenone imine (0.049 ml, 0.29 mmol). The mixture was heated to reflux for 6 h. The mixture was cooled to room temperature and filtered through a plug of silica gel which was washed with a large amount of 10% MeOH in CH$_2$Cl$_2$. The resulting mixture was concentrated. The mixture was reconstituted in THF (5 mL) and 1M HCl (5 mL) and allowed to stir for 3 h then concentrated under reduced pressure. The resulting residue was triturated with ether (3×20 mL) and suspended in 9% sodium carbonate. The solid was isolated by filtration and utilized without further purification. (ESI, pos. ion) m/z: 319.1 (M+H).

Step 2.

N-(4-((6-phenyl-[1,2,4]triazolo[4,3-b]pyridazin-3-yl)methoxy)pyridin-2-yl)pyrrolidine-1-carboxamide To the resulting solid in THF (5 mL) was added TRIETHYLAMINE (0.17 ml, 1.2 mmol) followed by phenyl chloroformate (0.15 ml, 1.2 mmol). The mixture was allowed to stir for 2 h. Added pyrrolidine (0.14 ml, 1.7 mmol) and stirred for an additional 2 h. The reaction mixture was concentrated, reconstituted in DMSO and purified via HPLC. (ESI, pos. ion) m/z: 416.2 (M+H).

General Method D.

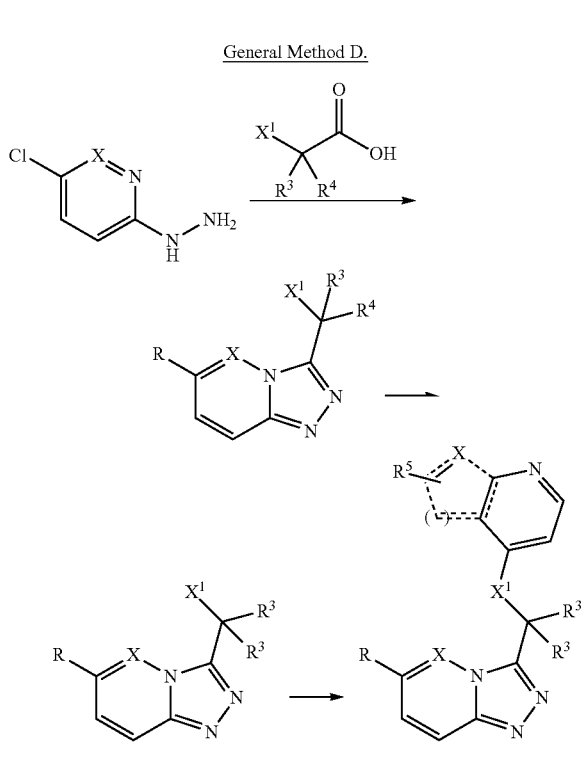

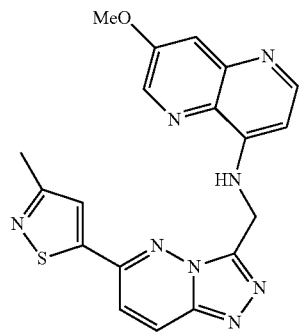 [SMILES: COc1cnc2c(NCc3nnc4ccc(-c5cc(C)ns5)nn34)ccnc2c1]

EXAMPLE 4

7-methoxy-N-((6-(3-methylisothiazol-5-yl)-[1,2,4]triazolo[4,3-b]pyridazin-3-yl)methyl)-1,5-naphthyridin-4-amine

1) Preparation of 3-methyl-5-trimethylstannyl)isothiazole

Butyllithium (1.6M in hexanes, 18.9 ml, 30.3 mmol) was added to a stirred solution of 3-methylisothiazole (2.73 g, 27.5 mmol) in THF (80 mL) at −78° C. The reaction mixture was stirred at −78° C. for 30 min and chlorotrimethylstannane (1M in THF, 27.5 ml, 27.5 mmol) was added dropwise. After 1 h at −78° C. for 1 h, the reaction mixture was quenched with a saturated aqueous solution of NaHCO$_3$. The water layer was extracted with Et$_2$O. The organic extracts were combined, dried over MgSO$_4$, filtered and concentrated in vacuo. The material (6.97 g) was taken forward without further purification MS m/z=264.1. Calc'd for C7H13NSSn: 261.94

2) Preparation of tert-butyl (6-(3-methylisothiazol-5-yl)-[1,2,4]triazolo[4,3-b]pyridazin-3-yl)methylcarbamate

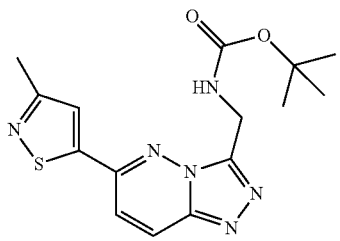 [SMILES: Cc1cc(-c2ccc3nnc(CNC(=O)OC(C)(C)C)n3n2)sn1]

A pressure vessel was purged with Ar and charged with tert-butyl (6-chloro-[1,2,4]triazolo[4,3-b]pyridazin-3-yl)methylcarbamate (5.00 g, 17.6 mmol), tris(dibenzylideneacetone)dipalladium (0) (0.807 g, 0.881 mmol), 2-dicyclohexylphosphinobiphenyl (0.618 g, 1.76 mmol). DMF (50 mL) was added, immediately followed by 3-methyl-5-(trimethylstannyl)isothiazole (6.46 g, 24.7 mmol). The reaction mixture was stirred at 100° C. for 1 h. Two more portions of tris(dibenzylideneacetone)dipalladium(0) (0.807 g, 0.881 mmol) and 2-dicyclohexylphosphinobiphenyl (0.618 g, 1.76 mmol) were added every hour for the first two hours of stirring. Reaction was then stirred was at 100° C. overnight, cooled to room temperature and concentrated in vacuo. Purification by MPLC (EtOAC/MeOH: 100/0 to 90/10) afforded the title compound (1.80 g, 30% yield). MS m/z=347.1 [M+H]$^+$. Calc'd for C15H18N6O2S: 346.41

3) Preparation of (6-(3-methylisothiazol-5-yl)-[1,2,4]-triazolo[4,3-b]pyridazin-3-yl)methanamine

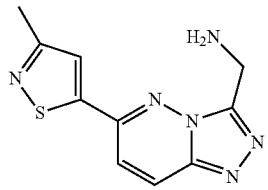 [SMILES: Cc1cc(-c2ccc3nnc(CN)n3n2)sn1]

Trifluoroacetic acid (2889 µl, 37505 µmol) was added to a stirred suspension of tert-butyl (6-(3-methylisothiazol-5-yl)-[1,2,4]triazolo[4,3-b]pyridazin-3-yl)methylcarbamate (464 mg, 1339 µmol) in DCM (10 mL) at RT. The reaction mixture was stirred at RT for 45 min. and then concentrated in vacuo. 2M NH$_3$ in MeOH was added. Purification by MPLC (DCM/MeOH+1% NH$_4$OH) afforded the title compound (226 mg, 69% yield). MS m/z=247.1 [M+H]$^+$. Calc'd for C10H10N6S: 246.30.

4) 7-methoxy-N-((6-(3-methylisothiazol-5-yl)-[1,2,4]-triazolo[4,3-b]pyridazin-3-yl)methyl)-1,5-naphthyridin-4-amine

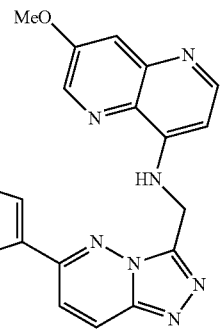

(6-(3-methylisothiazol-5-yl)-[1,2,4]triazolo[4,3-b]pyridazin-3-yl)methanamine (548 mg, 2225 µmol) and 8-chloro-3-methoxy-1,5-naphthyridine (576 mg, 2959 µmol) were charged in a microwave vial. 2-butanol (7 mL) was added and the reaction mixture was stirred at 120° C. under micro-waves irradiation for 8 h. 2M NH$_3$ in MeOH was added. Purification by MPLC (DCM/MeOH+1% NH$_4$OH: 100/0 to 90/10) afforded the title compound (720 mg, 80% yield). MS m/z=405.1 [M+H]$^+$. Calc'd for C19H16N8OS: 404.46

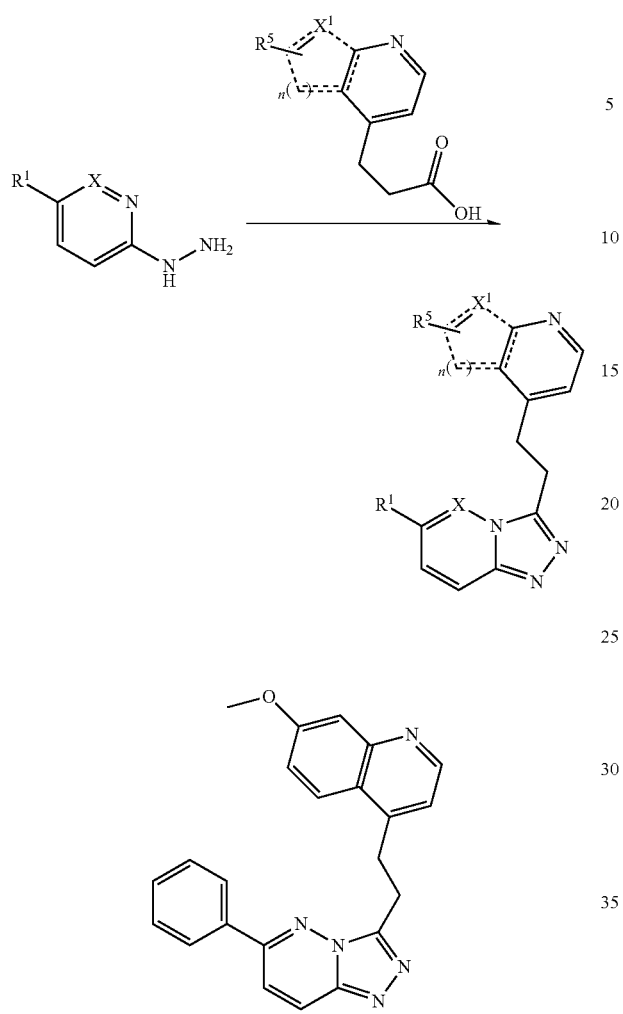

Step 2.

7-methoxy-4-(2-(6-phenyl-[1,2,4]triazolo[4,3-b]
pyridazin-3-yl)ethyl)quinoline

Ethyl 3-(7-methoxyquinolin-4-yl)propanoate (156 mg, 0.60 mmol) was combined with 1-(6-phenylpyridazin-3-yl) hydrazine (115 mg, 0.62 mmol) and pTsOH.H$_2$O(140 mg, 0.72 mmol). The mixture was microwaved at 150° C. for 60 minutes. The residue was taken up in DMSO and purified by HPLC and neutralized to yield the desired product as an off-white solid. (ESI, pos. ion) m/z: 382.1 (M+H).

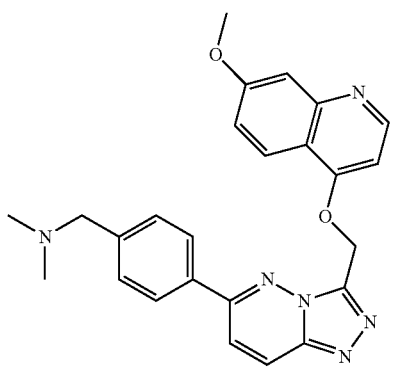 [SMILES: COc1ccc2c(OCc3nnc4ccc(-c5ccc(CN(C)C)cc5)nn34)ccnc2c1]

EXAMPLE 6

(4-(3-((7-methoxyquinolin-4-yloxy)methyl)-[1,2,4]
triazolo[4,3-b]pyridazin-6-yl)phenyl)-N,N-dimethyl-
methanamine A mixture of 4-(3-((7-methoxyquinolin-4-yloxy)methyl)-[1,2,4]triazolo[4,3-b]pyridazin-6-yl)benzaldehyde (prepared according to General Method A) (0.150 g, 0.36 mmol) and dimethylamine, 2.0 m solution in thf (0.36 ml, 0.73 mmol) in THF (5 mL) was allowed to stir for 20 min. Added sodium triacetoxyborohydride (0.15 g, 0.73 mmol) and stirred for 4 h. Concentrated. Suspended in DMSO, filtered through a 0.45 uM acrodisc. Purified on RPHPLC. Took fractions that contained product and made basic with 9% sodium carbonate. Removed volatiles in vacuo. Product crashed out and was isolated by filtration. MS m/z=441.2 [M+1]$^+$. Calc'd for C$_{25}$H$_{24}$N$_6$O$_2$: 440.2.

EXAMPLE 5

7-methoxy-4-(2-(6-phenyl-[1,2,4]triazolo[4,3-b]
pyridazin-3-yl)ethyl)quinoline

Step 1.

Ethyl 3-(7-methoxyquinolin-4-yl)propanoate 4-chloro-7-methoxyquinoline (0.35 g, 2 mmol), tri-t-butylphosphonium tetrafluoroborate (0.05 g, 0.2 mmol), and tris(dibenzylideneacetone)dipalladium (0) (0.08 g, 0.09 mmol) were combined. The reaction vessel was purged and flushed with nitrogen three times, followed by addition of 3-ethoxy-3-oxopropylzinc bromide in THF (10 mL, 5 mmol, 0.5 M). The reaction mixture was microwaved at 150° C. for 60 minutes. Upon completion, ammonium hydroxide (10 mL) was added. After 30 minutes the mixture was filtered and the filtrate was partitioned between water and ethyl acetate. Extracted with ethyl acetate (3×20 mL). The organic layers were combined, washed with brine, dried over magnesium sulfate, and concentrated. Purified by MPLC with a gradient of 20 to 50% EtOAc in CH$_2$Cl$_2$. (ESI, pos. ion) m/z: 354.1 (M+H).

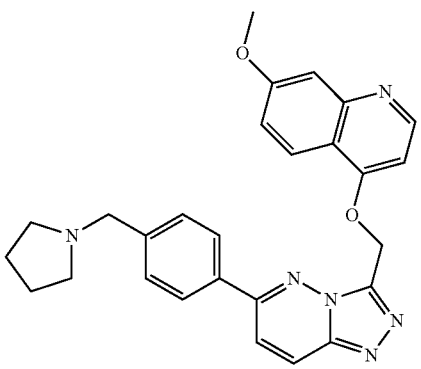 [SMILES: COc1ccc2c(OCc3nnc4ccc(-c5ccc(CN6CCCC6)cc5)nn34)ccnc2c1]

EXAMPLE 7

7-methoxy-4-((6-(4-(pyrrolidin-1-ylmethyl)phenyl)-[1,2,4]triazolo[4,3-b]pyridazin-3-yl)methoxy)quinoline Prepared in a similar manner as (4-(3-((7-methoxyquinolin-4-yloxy)methyl)-[1,2,4]triazolo[4,3-b]pyridazin-6-yl)phenyl)-N,N-dimethylmethanamine.

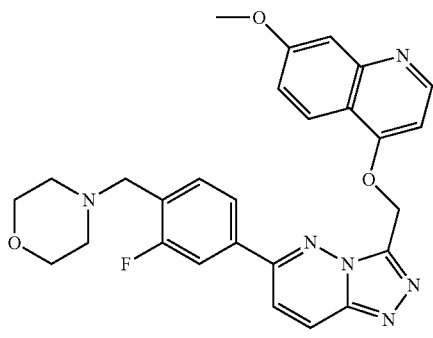 [SMILES: COc1ccc2c(OCc3nnc4ccc(-c5ccc(CN6CCOCC6)c(F)c5)nn34)ccnc2c1]

EXAMPLE 8

4-((6-(3-fluoro-4-(morpholinomethyl)phenyl)-[1,2,4]triazolo[4,3-b]pyridazin-3-yl)methoxy)-7-methoxyquinoline Prepared in a similar manner as above (4-(3-((7-methoxyquinolin-4-yloxy)methyl)-[1,2,4]triazolo[4,3-b]pyridazin-6-yl)phenyl)-N,N-dimethylmethanamine

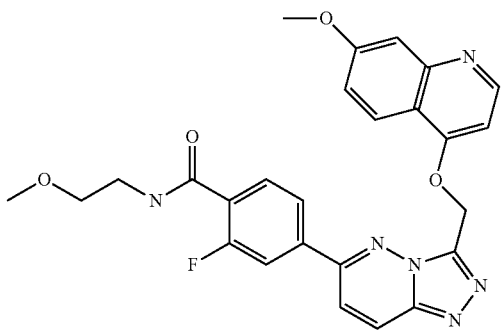 [SMILES: COCCNC(=O)c1ccc(-c2ccc3nnc(COc4ccnc5cc(OC)ccc45)n3n2)cc1F]

EXAMPLE 9

2-fluoro-N-(2-methoxyethyl)-4-(3-((7-methoxyquinolin-4-yloxy)methyl)-[1,2,4]triazolo[4,3-b]pyridazin-6-yl)benzamide A mixture of methyl 2-fluoro-4-(3-((7-methoxyquinolin-4-yloxy)methyl)-[1,2,4]triazolo[4,3-b]pyridazin-6-yl)benzoate (0.488 g, 1.06 mmol) (prepared according to General Method A) and lithium hydroxide hydrate (0.223 g, 5.31 mmol) in THF (20 mL), water (5 mL) and MeOH (5 mL) was heated to 40° C. for 3 h. Brought to near neutral pH with 1M HCl. Concentrated. Azeotroped with MeCN (20 mL) and PhMe (20 mL). Used without further purification. A mixture of 2-methoxyethylamine (0.033 ml, 0.38 mmol), HATU (0.24 g, 0.62 mmol), Hunig'sBase (0.24 ml, 1.4 mmol), 2-fluoro-4-(3-((7-methoxyquinolin-4-yloxy)methyl)-[1,2,4]triazolo[4,3-b]pyridazin-6-yl)benzoic acid (0.153 g, 0.34 mmol) in DMF was allowed to stir at room temperature for 1 h. Concentrated. Purified on RPHPLC. Took fractions containing product and made basic with 9% sodium carbonate. The volatiles were removed in vacuo and the product was isolated by filtration. Dried under vacuum. MS m/z=503.2 [M+1]$^+$. Calc'd for $C_{26}H_{23}FN_6O_4$: 502.5.

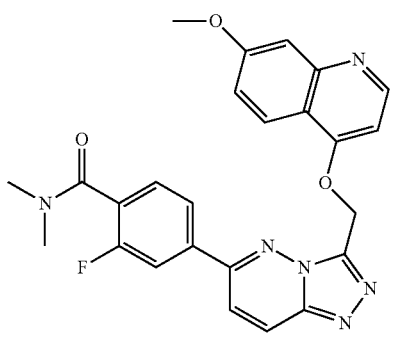 [SMILES: COc1ccc2c(OCc3nnc4ccc(-c5ccc(C(=O)N(C)C)c(F)c5)nn34)ccnc2c1]

EXAMPLE 10

2-fluoro-4-(3-((7-methoxyquinolin-4-yloxy)methyl)-[1,2,4]triazolo[4,3-b]pyridazin-6-yl)-N,N-dimethylbenzamide Prepared in a similar manner as 2-fluoro-N-(2-methoxyethyl)-4-(3-((7-methoxyquinolin-4-yloxy)methyl)-[1,2,4]triazolo[4,3-b]pyridazin-6-yl)benzamide.

EXAMPLE 11

2-fluoro-4-(3-((7-methoxyquinolin-4-yloxy)methyl)-[1,2,4]-triazolo[4,3-b]pyridazin-6-yl)benzamide Prepared in a similar manner as 2-fluoro-N-(2-methoxyethyl)-4-(3-((7-methoxyquinolin-4-yloxy)methyl)-[1,2,4]triazolo[4,3-b]pyridazin-6-yl)benzamide.

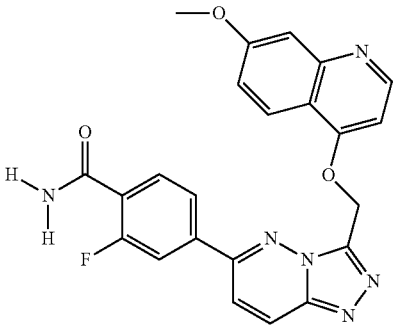 [SMILES: COc1ccc2c(OCc3nnc4ccc(-c5ccc(C(N)=O)c(F)c5)nn34)ccnc2c1]

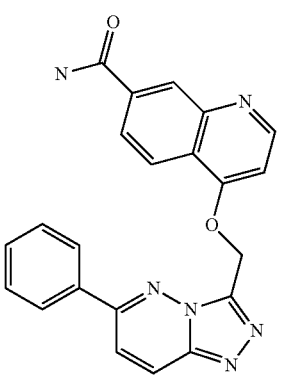 [SMILES: NC(=O)c1ccc2c(OCc3nnc4ccc(-c5ccccc5)nn34)ccnc2c1]

EXAMPLE 12

4-((6-phenyl-[1,2,4]triazolo[4,3-b]pyridazin-3-yl)methoxy)quinoline-7-carboxamide A mixture of 4-((6-phenyl-[1,2,4]triazolo[4,3-b]pyridazin-3-yl)methoxy)quinoline-7-carbonitrile (0.300 g, 0.793 mmol) and SULFURIC ACID (3.00 ml, 56.3 mmol) was heated at 90° C. for 30 min. Quenched onto ice and sodium bicarbonate. Isolated solid by filtration and purified on RPHPLC. Fractions containing product were treated with 9% sodium carbonate. Removed volatiles. Product crashed out and was isolated by filtraton. MS m/z=397.1 [M+1]$^+$. Calc'd for $C_{22}H_{16}N_6O_2$: 396.4.

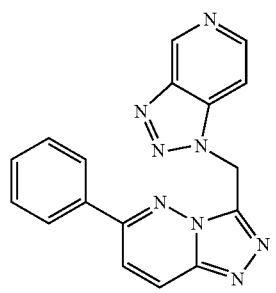 [SMILES: c1ccc(-c2ccc3nnc(Cn4nnc5cnccc54)n3n2)cc1]

EXAMPLE 13

1-((6-phenyl-[1,2,4]-triazolo[4,3-b]pyridazin-3-yl)methyl)-1H-[1,2,3]-triazolo[4,5-c]pyridine Step 1.

To a solution of ethyl 2-(3-nitropyridin-4-ylamino)acetate (1.41 g, 6.26 mmol) (prepared according to J. Med. Chem. (1991), 34, 2993.) in THF (10 mL), MeOH (10 mL) and water (5 mL) at 0° C. was added lithium hydroxide, monohydrate (0.522 ml, 18.8 mmol). Stirred at 0° C. for 30 min. Acidified to pH~4 with conc. HCl. Concentrated. Azeotroped with MeCN (40 mL) followed by PhMe (30 mL). Took up in DMF (30 mL). Added 1-(6-phenylpyridazin-3-yl)hydrazine (1.17 g, 6.26 mmol), diisopropylethylamine (3.27 ml, 18.8 mmol) followed by HATU (3.57 g, 9.39 mmol). Stirred for 30 min. Concentrated. Partitioned between DCM (30 mL) and water (30 mL). Filtered and isolated solid material. Washed with water (10 mL) and DCM (10 mL). Dried under vacuum. MS m/z=366.1 [M+1]$^+$. Calc'd for $C_{17}H_{15}N_7O_3$: 365.4.

Step 2.

To a mixture of 2-(3-nitropyridin-4-ylamino)-N'-(6-phenylpyridazin-3-yl)acetohydrazide (0.663 g, 1.81 mmol), triphenylphosphine (0.952 g, 3.63 mmol) and trimethylsilyl azide (0.482 ml, 3.63 mmol) in THF (10 mL) at room temperature was added diisopropyl azodicarboxylate (0.715 ml, 3.63 mmol). Heated to ~70° C. for 30 min. Reaction is complete. Concentrated. Purified on silica gel. 0 to 7% MeOH in $CH_2Cl_2$ with 1% $NH_4OH$. MS m/z=348.1 [M+1]$^+$. Calc'd for $C_{17}H_{13}N_7O_2$: 347.3.

Step 3.

To a mixture of 3-nitro-N-((6-phenyl-[1,2,4]triazolo[4,3-b]pyridazin-3-yl)methyl)pyridin-4-amine (0.373 g, 1.07 mmol) in THF (10 mL), MeOH (5 mL), EtOH (10 mL) was added Raney Nickel (wet, washed, ~1 g wet). Stirred for 20 min. Reaction is complete. Filtered through a 0.45 μm acrodisc. Concentrated. Used without further purification. MS m/z=318.1 [M+1]$^+$. Calc'd for $C_{17}H_{15}N_7$: 317.4.

Step 3.

To a solution of N4-((6-phenyl-[1,2,4]triazolo[4,3-b]pyridazin-3-yl)methyl)pyridine-3,4-diamine (0.0640 g, 0.202 mmol) in HOAc (5 mL) was added sodium nitrite (0.0153 g, 0.222 mmol) in water (2 mL). Stirred for 1 h. Concentrated. Took up in DMSO and purified on RPHPLC. Took fractions containing product and made basic with 9% sodium carbonate and removed volatiles in vacuo. Product crashed out and was isolated by filtration. MS m/z=329.2[M+1]$^+$. Calc'd for $C_{17}H_{12}N_8$: 328.3.

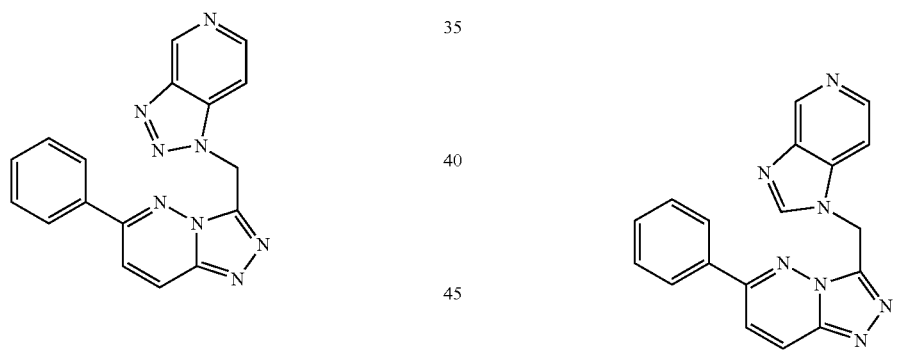

EXAMPLE 14

3-((1H-imidazo[4,5-c]pyridin-1-yl)methyl)-6-phenyl-[1,2,4]triazolo[4,3-b]pyridazine A mixture of N4-((6-phenyl-[1,2,4]triazolo[4,3-b]pyridazin-3-yl)methyl)pyridine-3,4-diamine (0.0650 g, 0.20 mmol), triethyl orthoformate (5.0 ml, 30 mmol), and p-TsOH (0.0039 g, 0.020 mmol) was heated at 60° C. After 2 h reaction is complete. Reaction was concentrated. Took up in DMSO and purified on RPHPLC. Fractions containing product were treated with 9% sodium carbonate and volatiles removed. Collected product by filtration. MS m/z=328.1 [M+1]$^+$. Calc'd for $C_{18}H_{13}N_7$: 327.3.

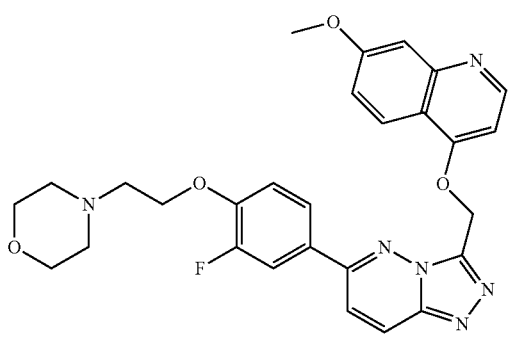 [SMILES: COc1ccc2c(OCc3nnc4ccc(-c5ccc(OCCN6CCOCC6)c(F)c5)nn34)ccnc2c1]

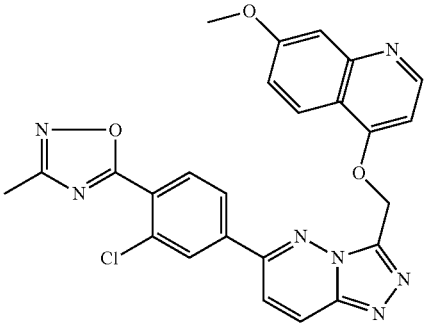

EXAMPLE 15

4-((6-(3-fluoro-4-(2-morpholinoethoxy)phenyl)-[1,2,4]triazolo[4,3-b]pyridazin-3-yl]methoxy)-7-methoxyquinoline To a mixture of 4-(2-hydroxyethyl)morpholine (0.0964 ml, 0.788 mmol), triphenylphosphine (0.238 g, 0.909 mmol), 2-fluoro-4-(3-((7-methoxyquinolin-4-yloxy)methyl)-[1,2,4]triazolo[4,3-b]pyridazin-6-yl)phenol (0.253 g, 0.606 mmol) (prepared according to General Method A) in THF (10 mL) was added DEAD (0.144 ml, 0.909 mmol). Stirred at room temperature for 1 h. Concentrated. Purified on RPHPLC. Fractions containing product were treated with 9% sodium carbonate. Removed volatiles in vacuo. Product crashed out and was isolated by filtration. MS m/z=531.2 [M+1]$^+$. Calc'd for $C_{28}H_{27}FN_6O_4$: 530.5.

EXAMPLE 17

4-((6-(3-chloro-4-(3-methyl-1,2,4-oxadiazol-5-yl)phenyl)-[1,2,4]triazolo[4,3-b]pyridazin-3-yl]methoxy)-7-methoxyquinoline HATU (0.370 g, 0.974 mmol) and 2-chloro-4-(3-((7-methoxyquinolin-4-yloxy)methyl)-[1,2,4]triazolo[4,3-b]pyridazin-6-yl)benzoic acid (0.300 g, 0.650 mmol) were taken up in DMF (5 mL). Added Hunig's Base (0.339 ml, 1.95 mmol). Stirred for 10 min. Added (Z)—N'-hydroxyacetamidine (0.289 g, 3.90 mmol). Stirred for an additional 30 min. Removed DMF in vacuo. Suspended in water. Isolated product by filtration. The resulting solid was allowed to try under vacuum. Split into 3 portions and separately took up in dioxane (4 mL) in a microwave tube and heated for 12 min at 150° C. Combined all 3 reactions. Concentrated. Purified on RPHPLC. Took fractions containing product and made basic with 9% sodium carbonate. Removed volatiles in vacuo. Product crashed out and was isolated by filtration. MS m/z=500.0 [M+1]$^+$. Calc'd for $C_{25}H_{18}ClN_7O_3$: 499.1.

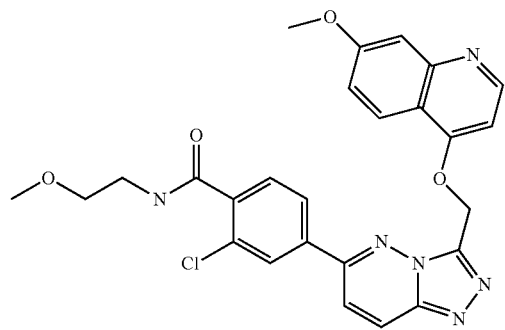 [SMILES: COCCNC(=O)c1ccc(-c2ccc3nnc(COc4ccnc5cc(OC)ccc45)n3n2)cc1Cl]

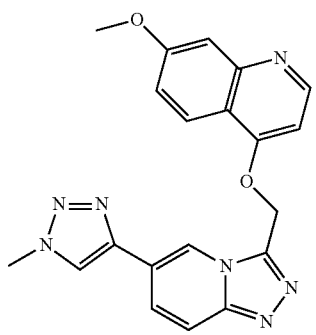 [SMILES: COc1ccc2c(OCc3nnc4ccc(-c5cn(C)nn5)cn34)ccnc2c1]

EXAMPLE 16

2-chloro-N-(2-methoxyethyl)-4-(3-((7-methoxyquinolin-4-yloxy)methyl)-1,2,4]triazolo[4,3-b]pyridazin-6-ylbenzamide Prepared in a similar manner as 2-fluoro-N-(2-methoxyethyl)-4-(3-((7-methoxyquinolin-4-yloxy)methyl)-[1,2,4]triazolo[4,3-b]pyridazin-6-yl)benzamide. MS m/z=519.1 [M+1]$^+$. Calc'd for $C_{26}H_{23}ClN_6O_4$: 518.9.

EXAMPLE 18

7-methoxy-4-((6-(1-methyl-1H-1,2,3-triazol-4-yl)-[1,2,4]-triazolo[4,3-a]pyridin-3-yl)methoxy)quinoline Step 1.

Tri-t-butylphosphonium tetrafluoroborate (0.0377 g, 0.130 mmol), tris(dibenzylideneacetone)dipalladium (0.0594 g, 0.0649 mmol), trimethylsilylacetylene (1.82 ml, 13.0 mmol), 4-((6-bromo-[1,2,4]triazolo[4,3-a]pyridin-3-yl)methoxy)-7-methoxyquinoline (0.500 g, 1.30 mmol) were taken up in dioxane (10 mL) and triethylamine (3 mL). Added CuI.

Sealed in a tube and heated at 80° C. for 3 h. Concentrated. Took up in MeOH and added solid potassium carbonate (large excess). Allowed to stir for 30 min. Filtered through a plug of Celite and concentrated. Took up in 10% MeOH in DCM and filtered through a plug of silica gel to afford 4-((6-ethynyl-[1, 2,4]triazolo[4,3-a]pyridin-3-yl)methoxy)-7-methoxyquinoline. MS m/z=331.0 [M+1]⁺. Calc'd for $C_{19}H_{14}N_4O_2$: 330.3.

Step 2. To a mixture of 4-((6-ethynyl-[1,2,4]triazolo[4,3-a]pyridin-3-yl)methoxy)-7-methoxyquinoline (0.200 g, 0.605 mmol), trimethylsilylmethyl azide (0.156 g, 1.21 mmol), sodium ascorbate (0.240 g, 1.21 mmol) in THF (4 mL) and water (1 mL) was added 1 drop of a copper sulfate (0.00966 g, 0.0605 mmol) solution. Stirred for 1 h. Concentrated. Suspended in water and extracted with $CH_2Cl_2$ (3×5 mL). Dried over sodium sulfate and concentrated. Took up crude mixture in DMF (4 mL). Added cesium fluoride (0.368 g, 2.42 mmol) and heated to 60° for 1 h. Concentrated. Purified on RPHPLC. Fractions containing product were treated with 9% sodium carbonate and volatiles were removed in vacuo. Product crashed out of solution and was isolated by filtration. MS m/z=388.1 [M+1]⁺. Calc'd for $C_{20}H_{17}N_7O_2$: 387.4.

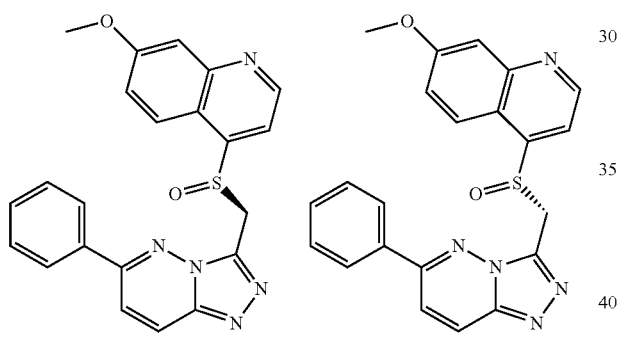

EXAMPLE 19

(R/S)-7-methoxy-4-((6-phenyl-[1,2,4]-triazolo[4,3-b]pyridazin-3-yl)methylsulfinyl)quinoline In a 50 mL round bottom flask under $N_2$ were dissolved 7-methoxy-4-((6-phenyl-[1,2,4]triazolo[4,3-b]pyridazin-3-yl)methylthio)quinoline (prepared according to General Method B) (220 mg, 551 µmol) in 5.5 mL of DCM then cooled down at −78° C. and treated with solid m-CPBA (77%) (124 mg, 716 µmol) then warmed slowly to rt over 3 h. The reaction mixture was diluted with DCM then neutralized with $NaHCO_3$ (sat.). The aqueous phase was extracted 3× with DCM then the organic layer was dried over $Na_2SO_4$, filtered and concentrated under reduced pressure. The crude mixture was purified by MPLC (ISCO) with DCM/DCM: MeOH:NH₄OH (90:10:1) 100:0 to 90:10 to afforded 7-methoxy-4-((6-phenyl-[1,2,4]triazolo[4,3-b]pyridazin-3-yl)methylsulfinyl)quinoline (109 mg, 47.6% yield) as a white solid. MS m/z=415.1 [M+1]⁺. Calc'd for $C_{22}H_{17}N_5O_2S$: 416.0.

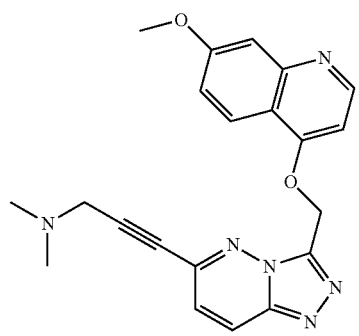 [SMILES: COc1ccc2c(OCc3nnc4ccc(C#CCN(C)C)nn34)ccnc2c1]

EXAMPLE 20

3-(3-((7-methoxyquinolin-4-yloxy)methyl)-[1,2,4] triazolo[4,3-b]pyridazin-6-yl)-N,N-dimethylprop-2-yn-1-amine In a 10 mL sealed tube under $N_2$ were dissolved dichlorobis(triphenylphosphine)palladium (41 mg, 59 µmol), N,N-dimethylprop-2-yn-1-amine (97 mg, 1170 µmol), 4-((6-chloro-[1,2,4]triazolo[4,3-b]pyridazin-3-yl)methoxy)-7-methoxyquinoline (prepared according to General Method A) (200 mg, 585 µmol), TRIETHYLAMINE (1631 µl, 11704 µmol) and COPPER(I) IODIDE (11 mg, 59 µmol) in 3 mL of MeCN then stirred and heated at 80° C. for 10 h. The crude reaction mixture was directly purified by MPLC (ISCO) with DCM/DCM:MeOH:NH₄OH (90:10:1) 95:5 to afforded 3-(3-((7-methoxyquinolin-4-yloxy)methyl)-[1,2,4]triazolo[4,3-b]pyridazin-6-yl)-N,N-dimethylprop-2-yn-1-amine (26 mg, 11% yield) as a yellow solid. MS m/z=388.2 [M+1]⁺. Calc'd for $C_{21}H_{20}N_6O_2$: 389.2.

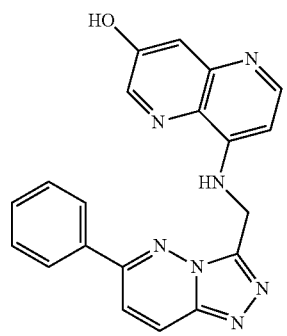 [SMILES: Oc1cnc2c(NCc3nnc4ccc(-c5ccccc5)nn34)ccnc2c1]

EXAMPLE 21

8-((6-phenyl-[1,2,4]triazolo[4,3-b]pyridazin-3-yl)methylamino)-1,5-naphthyridin-3-ol.

In a 25 mL sealed tube was dissolved 7-methoxy-N-((6-phenyl-[1,2,4]triazolo[4,3-b]pyridazin-3-yl)methyl)-1,5-naphthyridin-4-amine (prepared according to General Method D) (300 mg, 782 µmol) in 5 mL of concentrated HBr then stirred and heated at 100° C. for 48 h. The reaction mixture was diluted with DCM and $H_2O$ then neutralized with NaOH (1N) to neutral pH. The aqueous phase was extracted 3× with DCM then the organic layer was dried over $Na_2SO_4$, filtered and concentrated under reduced pressure.

The crude mixture was purified by MPLC (ISCO) with DCM: MeOH:NH₄OH (90:10:1) and then triturated with hot EtOH to afforded 8-((6-phenyl-[1,2,4]triazolo[4,3-b]pyridazin-3-yl)methylamino)-1,5-naphthyridin-3-ol (230 mg, 79.6% yield) as a tan solid. MS m/z=369.1 [M+1]⁺. Calc'd for C₂₀H₁₅N₇O: 370.0.

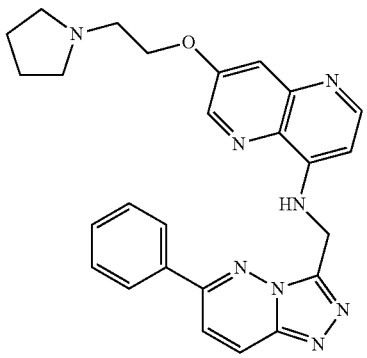 [SMILES: c1ccc(-c2ccc3nnc(CNc4ccnc5cc(OCCN6CCCC6)cnc45)n3n2)cc1]

EXAMPLE 22

N-((6-phenyl-[1,2,4]triazolo[14,3-b]pyridazin-3-yl)methyl)-7-(2-(pyrrolidin-1-yl)ethoxy)-1,5-naphthyridin-4-amine In a 10 mL sealed tube under N₂ were dissolved CESIUM CARBONATE (221 mg, 677 μmol), 8-((6-phenyl-[1,2,4]triazolo[4,3-b]pyridazin-3-yl)methylamino)-1,5-naphthyridin-3-ol (50 mg, 135 μmol), 1-(2-chloroethyl)pyrrolidine hydrochloride (46 mg, 271 μmol) and SODIUM IODIDE (41 mg, 271 μmol) in 1 mL of DMSO then stirred and heated at 75° C. for 3 h. The reaction mixture was diluted with H₂O and the aqueous phase was extracted 3× with DCM then the organic layer was dried over Na₂SO₄, filtered and concentrated under reduced pressure. The crude mixture was purified by MPLC (ISCO) with DCM/DCM:MeOH:NH₄OH (90:10:1)100:0 to 90:10 to afforded N-((6-phenyl-[1,2,4]triazolo[4,3-b]pyridazin-3-yl)methyl)-7-(2-(pyrrolidin-1-yl)ethoxy)-1,5-naphthyridin-4-amine (7 mg, 11% yield) as a yellow solid. MS m/z=466.2 [M+1]⁺. Calc'd for C₂₆H₂₆N₈O: 467.0.

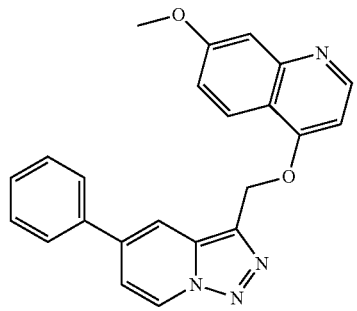 [SMILES: COc1ccc2c(OCc3nnn4ccc(-c5ccccc5)cc34)ccnc2c1]

EXAMPLE 23

7-Methoxy-4-((5-phenyl-1,2,3]triazolo[1,5-a]pyridin-3-yl)methoxy)quinoline a) 5-Phenyl-[1,2,3]triazolo[1,5-a]pyridine-3-carboxylate. To a solution of methyl 2-(4-phenylpyridin-2-yl)acetate (see Lohse, O.; Thevenin, P.; Waldvogel, E. *Synlett* 1999, 1, 45-48) (0.504 g, 2.22 mmol) in 12 mL CH₃CN was added DBU (0.501 ml, 3.33 mmol) and the mixture cooled in an ice bath. To the solution, 4-acetamidobenzenesulfonyl azide (0.533 g, 2.22 mmol) was added and the mixture allowed to warm to rt. The mixture was stirred at rt for 5 h then evaporated. The residue was diluted with CH₂Cl₂, washed with water, brine, dried over Na₂SO₄, and filtered. The title compound was obtained after purification via flash chromatography.

b) (5-Phenyl-[1,2,3]triazolo[1,5-a]pyridin-3-yl)methanol. To a cooled (ice bath) suspension of lithium tetrahydroaluminate (0.0929 g, 2.45 mmol) in 2 mL THF (anhy) was added slowly a solution of methyl 5-phenyl-[1,2,3]triazolo[1,5-a]pyridine-3-carboxylate (0.310 g, 1.22 mmol) in 20 mL THF (internal temp remained <20 C). The mixture was allowed to stir in the ice bath 10 minutes. The mixture was diluted with EtOAc, washed with water, sat. NaHCO₃, the organic layer dried over Na₂SO₄, and filtered. The aqueous layer still had uv activity so a solution of Rochelle's salt and EA were added and the mixture stirred 30 min. The organic layer was washed with sat NaHCO₃, dried over Na₂SO₄, filtered, combined with main portion and evaporated. The title compound was isolated as a yellow solid.

c) 7-Methoxy-4-((5-phenyl-[1,2,3]triazolo[1,5-a]pyridin-3-yl)methoxy)quinoline. A sealable tube was charged with Pd₂dba₃ (0.219 g, 0.239 mmol), di-tert-butyl(1-(naphthalen-1-yl)naphthalen-2-yl)phosphine (0.190 g, 0.477 mmol), (5-phenyl-[1,2,3]triazolo[1,5-a]pyridin-3-yl)methanol (0.215 g, 0.955 mmol), 4-chloro-7-methoxyquinoline (0.222 g, 1.15 mmol), Cs₂CO₃ (0.622 g, 1.91 mmol) and dioxane (3 mL). The tube was blanketed with N₂, sealed and heated at 100 C for 45 min. The mixture was allowed to cool to rt and evaporated. The residue was purified via flash chromatography using a 1% NH₄OH in MeOH in CH₂Cl₂ gradient. The title compound was collected as a tan solid. M/Z=405.1 [M+Na], calc 382.415 for C₂₃H₁₈N₄O₂.

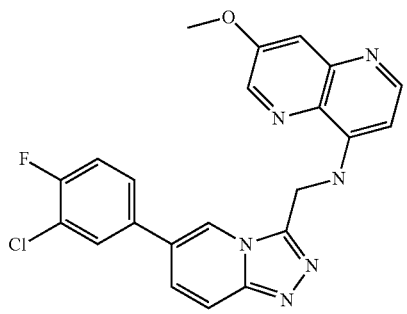 [SMILES: COc1cnc2c(NCc3nnc4ccc(-c5ccc(F)c(Cl)c5)cn34)ccnc2c1]

EXAMPLE 24

N-((6-(3-Chloro-4-fluorophenyl)-[1,2,4]triazolo[4,3-a]pyridin-3-yl)methyl)-7-methoxy-1,5-naphthyridin-4-amine a) N'-(5-bromopyridin-2-yl)-2-(tert-butoxycarbonylamino)acetohydrazide. A suspension of 1-(5-bromopyridin-2-yl)hydrazine (4.00 g, 21 mmol), 2-(tert-butoxycarbonyl)acetic acid (3.7 g, 21 mmol), and HATU (12 g, 32 mmol) in 50 mL CH₃CN was cooled to −78 (solid precipitates to prevent stirring). The flask was removed from bath gradually allow to warm. When stirring resumed, triethylamine (8.9 ml, 64 mmol) was added and the mixture stirred for 1 h, then evaporated. The residue was dissolved with CH₂Cl₂, washed with water, brine, and the organic layer dried over Na$_2$SO$_4$, filtered and evaporated. The mixture was purified via flash chromatography using a EtOAc in hexanes gradient. The title compound was collected as a yellow oil.

b) tert-Butyl (6-bromo-[1,2,4]triazolo[4,3-a]pyridin-3-yl)methylcarbamate. To a solution of N'-(5-bromopyridin-2-yl)-2-(tert-butoxycarbonylamino)acetohydrazide (2.2 g, 6.4 mmol) in THF (30 mL) was added triphenylphosphine (2.5 g, 9.6 mmol) and TMS azide (1.3 ml, 9.6 mmol). DEAD (1.8 ml, 11 mmol) was added dropwise rapidly and the mixture heated at 55 C 1 h. The solvent was evaporated and the residue dissolved in CH$_2$Cl$_2$, washed with water, brine, dried over Na$_2$SO$_4$, and filtered. The mixture was purified via flash chromatography using a EtOAc in CH$_2$Cl$_2$ gradient. The title compound obtained as a tan solid (664 mg, 32%).

c) N-((6-Bromo-[1,2,4]triazolo[4,3-a]pyridin-3-yl)methyl)-7-methoxy-1,5-naphthyridin-4-amine. To a suspension of tert-butyl (6-bromo-[1,2,4]triazolo[4,3-a]pyridin-3-yl) methylcarbamate (0.900 g, 2.75 mmol) in CH$_2$Cl$_2$ (10 mL) was added TFA (0.848 ml, 11.0 mmol) and the mixture stirred at rt. After 30 minutes additional TFA (0.848 ml, 11.0 mmol) was added, and the mixture stirred at rt 2 h more then concentrated. The residue was taken up into 2-butanol (5 mL) and combined with 8-chloro-3-methoxy-1,5-naphthyridine (0.535 g, 2.75 mmol) in a 5 mL microwave vessel. The vessel was sealed and the mixture heated in the microwave for 10 min at 120 C with a 60 sec prestir. The mixture was concentrated, diluted with DCM and stirred with 2N NaOH (pH 14) for 30 minutes. The solid was filtered to afford the title compound as a beige solid.

d) N-((6-(3-Chloro-4-fluorophenyl)-[1,2,4]triazolo[4,3-a]pyridin-3-yl)methyl)-7-methoxy-1,5-naphthyridin-4-amine
A sealable tube was charged with PdCl$_2$(dppf)-CH$_2$Cl$_2$ Adduct (0.064 g, 0.078 mmol), N-((6-bromo-[1,2,4]triazolo[4,3-a]pyridin-3-yl)methyl)-7-methoxy-1,5-naphthyridin-4-amine (0.120 g, 0.31 mmol), 3-chloro-4-fluorophenylboronic acid (0.057 g, 0.33 mmol), sat NaHCO$_3$ (0.75 ml, >0.69 mmol) and dioxane (2 mL). The vessel was sealed and the mixture heated at 80 for 2.5 h. The mixture was allowed to cool to rt and diluted with water, causing a tan solid to precipitate. CH$_2$Cl$_2$ (1 mL) was added and the solid filtered. The title compound was obtained after purification via flash chromatography (using a MeOH in CH$_2$Cl$_2$ gradient) as a tan solid. M/Z=435.1 [M+H], calc 434.8604 for C$_{22}$H$_{16}$ClFN$_6$O.

The following compounds were prepared using the same method as described for N-((6-(3-chloro-4-fluorophenyl)-[1,2,4]triazolo[4,3-a]pyridin-3-yl)methyl)-7-methoxy-1,5-naphthyridin-4-amine:

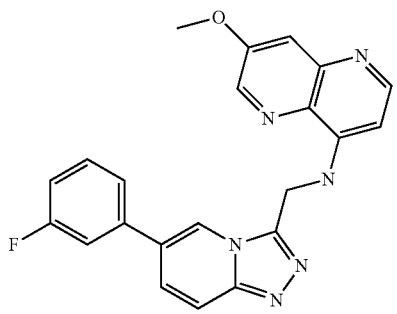 [SMILES: COc1cnc2c(NCc3nnc4ccc(-c5cccc(F)c5)cn34)ccnc2c1]

EXAMPLE 25

N-((6-(3-Fluorophenyl)-[1,2,4]-triazolo[4,3-a]pyridin-3-yl)methyl)-7-methoxy-1,5-naphthyridin-4-amine M/Z=401.2 [M+H], calc 401.4153 for C$_{22}$H$_{17}$FN$_6$O.

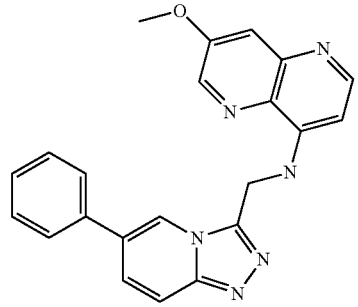 [SMILES: COc1cnc2c(NCc3nnc4ccc(-c5ccccc5)cn34)ccnc2c1]

EXAMPLE 26

7-Methoxy-N-((6-phenyl-[1,2,4]-triazolo[4,3-a]pyridin-3-yl)methyl)-1,5-naphthyridin-4-amine M/Z=383.2 [M+H], calc 382.4252 for C$_{22}$H$_{18}$N$_6$O.

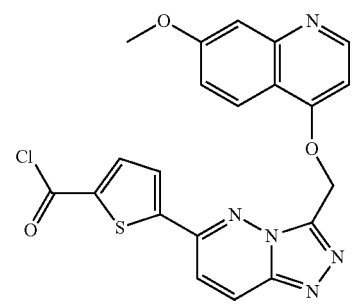 [SMILES: COc1ccc2c(OCc3nnc4ccc(-c5ccc(C(=O)Cl)s5)nn34)ccnc2c1]

5-(3-((7-methoxyquinolin-4-yloxy)methyl)-[1,2,4]triazolo[4,3-b]pyridazin-6-yl)thiophene-2-carbonyl chloride To a suspension of 5-(3-((7-methoxyquinolin-4-yloxy)methyl)-[1,2,4]triazolo[4,3-b]pyridazin-6-yl)thiophene-2-carboxylic acid (prepared according to general method A) (0.500 g, 1.15 mmol) in dichloromethane at 0° C. was added thionyl chloride (1.26 ml, 17.3 mmol) dropwise. Three drops DMF were added and the solution was stirred at room temp for three hours. The solution was concentrated to a brown residue and taken forward without further purification.

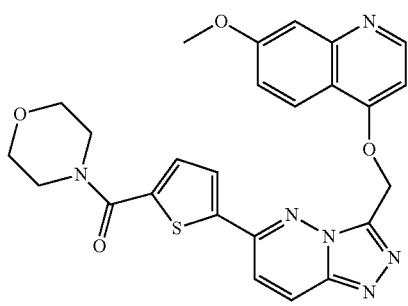

EXAMPLE 27

(5-(3-((7-methoxyquinolin-4-yloxy)methyl)-[1,2,4]triazolo[4,3-b]pyridazin-6-yl)thiophen-2-yl)(morpholino)methanone To a solution of 5-(3-((7-methoxyquinolin-4-yloxy)methyl)-[1,2,4]triazolo[4,3-b]pyridazin-6-yl)thiophene-2-carbonyl chloride (0.260 g, 0.58 mmol) in dichloromethane (5 mL) was added N-ethyl-N-isopropylpropan-2-amine (0.15 ml, 0.86 mmol) and morpholine (0.15 ml, 1.7 mmol). The solution was stirred at room temperature for two hours then was concentrated in vacuo. The brown residue was purified via MPLC chromatography (eluted with 0-5% methanol in dichloromethane) to yield the product as a tan solid. MS m/z=503.0 [M+1]$^+$. Calc'd for $C_{25}H_{22}N_6O_4S$: 502.1.

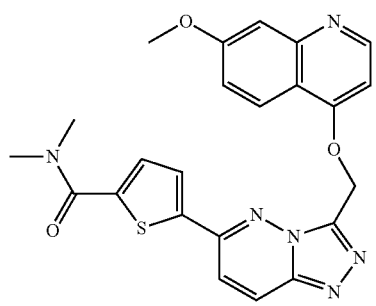

EXAMPLE 29

5-(3-((7-methoxyquinolin-4-yloxy)methyl)-[1,2,4]triazolo[4,3-b]pyridazin-6-yl)-N,N-dimethylthiophene-2-carboxamide To a solution of 5-(3-((7-methoxyquinolin-4-yloxy)methyl)-[1,2,4]triazolo[4,3-b]pyridazin-6-yl)thiophene-2-carbonyl chloride (0.260 g, 0.58 mmol) in dichloromethane was added N-ethyl-N-isopropylpropan-2-amine (0.20 ml, 1.2 mmol) and dimethylamine (1.4 ml, 2.9 mmol). The solution was stirred at room temperature for one hour then was concentrated in vacuo. The residue was triturated with water and filtered; the resulting precipitate was triturated with acetonitrile and filtered to yield the product as an off-white solid. MS m/z=461.0 [M+1]$^+$. Calc'd for $C_{23}H_{20}N_6O_3S$: 460.1.

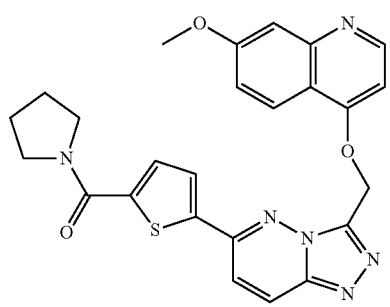 [SMILES: COc1ccc2c(OCc3nnc4ccc(-c5ccc(C(=O)N6CCCC6)s5)nn34)ccnc2c1]

EXAMPLE 28

(5-(3-((7-methoxyquinolin-4-yloxy)methyl)-[1,2,4]triazolo[4,3-b]pyridazin-6-yl)thiophen-2-yl)(pyrrolidin-1-yl)methanone Prepared by a method similar to (5-(3-((7-methoxyquinolin-4-yloxy)methyl)-[1,2,4]triazolo[4,3-b]pyridazin-6-yl)thiophen-2-yl)(morpholino)methanone. MS m/z=487.1 [M+1]$^+$. Calc'd for $C_{25}H_{22}N_6O_3S$: 486.2

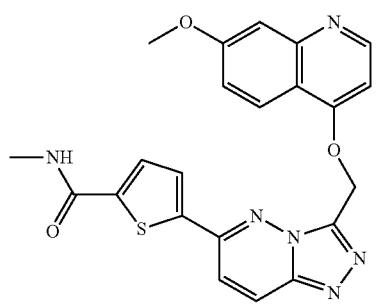 [SMILES: CNC(=O)c1ccc(-c2ccc3nnc(COc4ccnc5cc(OC)ccc45)n3n2)s1]

EXAMPLE 30

5-(3-((7-methoxyquinolin-4-yloxy)methyl)-[4,2,4]triazolo[4,3-b]pyridazin-6-yl)-N-methylthiophene-2-carboxamide Prepared by a method similar to (5-(3-((7-methoxyquinolin-4-yloxy)methyl)-[1,2,4]triazolo[4,3-b]pyridazin-6-yl)thiophen-2-yl)(morpholino)methanone. MS m/z=447.0 [M+1]$^+$. Calc'd for $C_{22}H_{18}N_6O_3S$: 446.1

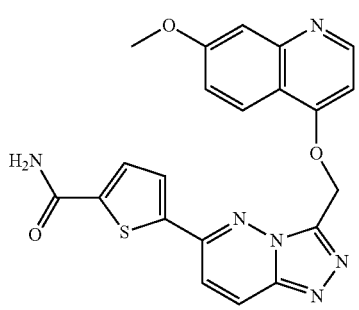 [SMILES: COc1ccc2c(OCc3nnc4ccc(-c5ccc(C(N)=O)s5)nn34)ccnc2c1]

EXAMPLE 31

5-(3-((7-methoxyquinolin-4-yloxy)methyl)-[1,2,4]triazolo[4,3-b]pyridazin-6-yl)thiophene-2-carboxamide Prepared by a method similar to (5-(3-((7-methoxyquinolin-4-yloxy)methyl)-[1,2,4]triazolo[4,3-b]pyridazin-6-yl)thiophen-2-yl)(morpholino)methanone. MS m/z=433.0 [M+1]$^+$. Calc'd for $C_{21}H_{16}N_6O_3S$: 432.1.

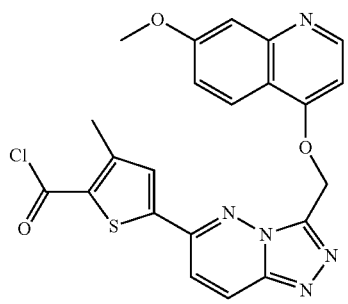 [SMILES: COc1ccc2c(OCc3nnc4ccc(-c5cc(C)c(C(=O)Cl)s5)nn34)ccnc2c1]

5-(3-((7-methoxyquinolin-4-yloxy)methyl)-[1,2,4]triazolo[4,3-b]pyridazin-6-yl)-3-methylthiophene-2-carbonyl chloride To a suspension of 5-(3-((7-methoxyquinolin-4-yloxy)methyl)-[1,2,4]triazolo[4,3-b]pyridazin-6-yl)-3-methylthiophene-2-carboxylic acid (prepared by General Method A) (0.150 g, 0.335 mmol) in dichloromethane (2 mL) was added thionyl chloride (0.734 ml, 10.1 mmol and DMF (1 drop). The solution was stirred at room temp for three hours then concentrated and taken forward without further purification.

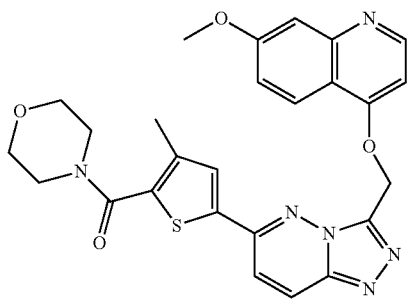 [SMILES: COc1ccc2c(OCc3nnc4ccc(-c5cc(C)c(C(=O)N6CCOCC6)s5)nn34)ccnc2c1]

EXAMPLE 32

(5-(3-((7-methoxyquinolin-4-yloxy)methyl)-[1,2,4]triazolo[4,3-b]pyridazin-6-yl)-3-methylthiophen-2-yl)(morpholino)methanone To a solution of 5-(3-((7-methoxyquinolin-4-yloxy)methyl)-[1,2,4]triazolo[4,3-b]pyridazin-6-yl)-3-methylthiophene-2-carbonyl chloride (0.100 g, 0.21 mmol) in dichloromethane (2 mL) at 0° C. was added morpholine (0.19 g, 2.1 mmol). The solution was stirred at room temperature twenty minutes, then was concentrated and purified by MPLC chromatography (eluted with 3% methanol in dichloromethane) to yield a yellow solid. Trituration in acetonitrile and filtration afforded the product as a white solid. MS m/z=517.2 [M+1]$^+$. Calc'd for $C_{26}H_{24}N_6O_4S$: 516.2.

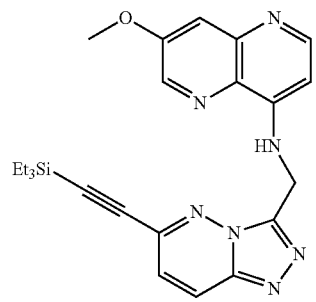

7-methoxy-N-((6-(2-(triethylsilyl)ethynyl)-[1,2,4]triazolo[4,3-b]pyridazin-3-yl)methyl)-1,5-naphthyridin-4-amine To an argon flushed pressure vial (15 mL) was added copper (I)iodide (0.0070 g, 0.037 mmol), PdCl$_2$(dppf)-CH$_2$Cl$_2$Adduct (0.012 g, 0.015 mmol), N-((6-chloro-[1,2,4]triazolo[4,3-b]pyridazin-3-yl)methyl)-7-methoxy-1,5-naphthyridin-4-amine (0.050 g, 0.15 mmol), and triethyl (ethynyl)silane (0.13 ml, 0.73 mmol) in acetonitrile (2 mL) followed by triethylamine (0.61 ml, 4.4 mmol). The vial was sealed and stirred at room temperature overnight The solution was concentrated and purified by MPLC (eluted with 0-10% (90:10:1 DCM:MeOH:NH$_4$OH)) to yield the product as a light yellow solid. MS m/z=446.1 [M+1]$^+$. Calc'd for $C_{23}H_{27}N_7OSi$: 445.2.

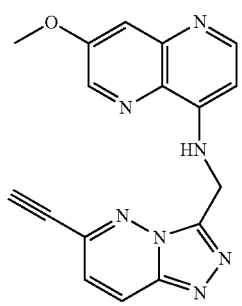 [SMILES: C#Cc1ccc2nnc(CNc3ccnc4cc(OC)cnc34)n2n1]

EXAMPLE 33

N-((6-ethynyl-[1,2,4]triazolo[4,3-b]pyridazin-3-yl)methyl)-7-methoxy-1,5-naphthyridin-4-amine To a solution of 7-methoxy-N-((6-(2-(triethylsilyl)ethynyl)-[1,2,4]triazolo[4,3-b]pyridazin-3-yl)methyl)-1,5-naphthyridin-4-amine (0.360 g, 0.808 mmol) in acetic acid (8 mL) was added TBAF (1.21 ml, 1.21 mmol). The mixture was stirred at room temperature overnight, additional TBAF (1.21 ml, 1.21 mmol) was added and the mixture was heated to 50° C. for five hours. The mixture was concentrated and purified via MPLC (eluted with 0-10% (1:10:90 NH$_4$OH:MeOH:DCM) in dichloromethane) to yield the product as an off-white solid. MS m/z=332.0 [M+1]$^+$. Calc'd for C$_{17}$H$_{13}$N$_7$O: 331.1.

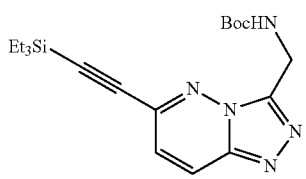

tert-butyl(6-(2-(triethylsilyl)ethynyl)-[1,2,4]triazolo[4,3-b]pyridazin-3-yl)methylcarbamate A 1 L-round-bottomed flask flushed with argon was charged with tert-butyl (6-chloro-[1,2,4]triazolo[4,3-b]pyridazin-3-yl)methylcarbamate (12.00 g, 42.3 mmol), Pd(dppf)Cl$_2$—CH$_2$Cl$_2$ adduct (3.45 g, 4.23 mmol), copper iodide (2.01 g, 10.6 mmol) at room temperature. Acetonitrile (400 mL) was added followed by triethyl(ethynyl)silane (37.9 ml, 211 mmol). Upon stirring the reaction mixture turned dark red. Triethylamine (177 ml, 1269 mmol) was added via cannula over five minutes. The first drops resulted in a change of color to light yellow/orange. At the end of the addition, the reaction mixture was dark red again. After stirring at 50° C. for one hour, the mixture was cooled to room temperature and concentrated in vacuo. Purification by MPLC (ISCO, EtOAc/MeOH: 100/0 to 90/10) afforded the desired product. The material was taken forward without further purification. MS m/z=388.3 [M+1]$^+$. Calc'd for C$_{19}$H$_{29}$NSO$_2$Si: 387.2.

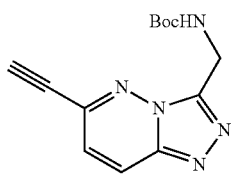 [SMILES: C#Cc1ccc2nnc(CNC(=O)OC(C)(C)C)n2n1]

tert-butyl(6-ethynyl-[1,2,4]triazolo[4,3-b]pyridazin-3-yl)methylcarbamate

Potassium fluoride (2M in water, 27.6 ml, 55.3 mmol) was added to a stirred suspension of tert-butyl6-(2-(triethylsilyl)ethynyl)-[1,2,4]triazolo[4,3-b]pyridazin-3-yl)methylcarbamate (3.57 g, 9.21 mmol) in acetonitrile (56 mL) at room temperature. The reaction mixture turned dark immediately, and was stirred at room temp for twenty minutes until complete. The mixture was concentrated in vacuo, triturated with water and filtered to yield the product as a brown solid (2.46 g). MS m/z=274.1 [M+1]$^+$. Calc'd for C$_{13}$H$_{15}$N$_5$O$_2$: 273.1.

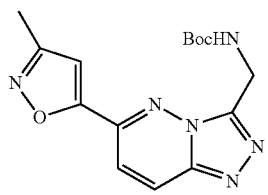 [SMILES: Cc1cc(-c2ccc3nnc(CNC(=O)OC(C)(C)C)n3n2)on1]

tert-butyl(6-(3-methylisoxazol-5-yl)-[1,2,4]-triazolo[4,3-b]pyridazin-3-yl)methylcarbamate To a solution of nitroethane (1.02 ml, 14.3 mmol) in benzene (50 mL) was added phenyl isocyanate (3.12 ml, 28.5 mmol). The mixture was stirred at 50° C. for twenty minutes followed by the addition of tert-butyl (6-ethynyl-[1,2,4]triazolo[4,3-b]pyridazin-3-yl)methylcarbamate (3.00 g, 11.0 mmol) and triethylamine (0.0765 ml, 0.549 mmol). The mixture was stirred at 50° C. for six hours then at room temperature overnight. The mixture was cooled to room temperature, filtered and the resulting brown precipitate was washed with additional benzene. The filtrate was concentrated to yield the product as a black solid. MS m/z=331.1 [M+1]$^+$. Calc'd for C$_{15}$H$_{18}$N$_6$O$_3$: 330.1.

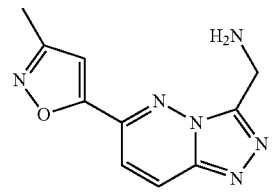 [SMILES: Cc1cc(-c2ccc3nnc(CN)n3n2)on1]

(6-(3-methylisoxazol-5-yl)-[1,2,4]-triazolo[4,3-b]pyridazin-3-yl)methanamine

To a solution of tert-butyl (6-(3-methylisoxazol-5-yl)-[1,2,4]triazolo[4,3-b]pyridazin-3-yl)methylcarbamate (3.63 g, 11.0 mmol) in dichloromethane (50 mL) was added trifluoroacetic acid (16.9 ml, 220 mmol) and the mixture was stirred at room temperature for one hour. The mixture was concentrated, taken up in a solution of ammonia in methanol (2.0 M) and purified by MPLC chromatography (eluted with 0-10% (1:10:90 NH$_4$OH:MeOH:DCM) in DCM) to yield the product as a brown solid. MS m/z=230.8 [M+1]$^+$. Calc'd for C$_{10}$H$_{10}$N$_6$O: 230.1.

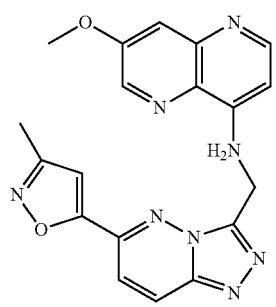 [SMILES: COc1cnc2c(NCc3nnc4ccc(-c5cc(C)no5)nn34)ccnc2c1]

EXAMPLE 34

7-methoxy-N-((6-(3-methylisoxazol-5-yl)-[1,2,4]-triazolo[4,3-b]pyridazin-3-yl)methyl)-1,5-naphthyridin-4-amine To a microwave vial (10-20 mL) was added (6-(3-methylisoxazol-5-yl)-[1,2,4]triazolo[4,3-b]pyridazin-3-yl)methanamine (1.00 g, 4.34 mmol) and 8-chloro-3-methoxy-1,5-naphthyridine (1.10 g, 5.65 mmol) in 2-butanol (12 mL). The suspension was stirred at 120° C. under microwave irradiation for four hours. The mixture was concentrated and taken up in ammonia in methanol (2.0 M) then purified by MPLC chromatography (eluted with 0-10% methanol in dichloromethane) to yield the product as a tan solid. MS m/z=389.0 [M+1]$^+$. Calc'd for $C_{19}H_{16}N_8O_2$: 388.1

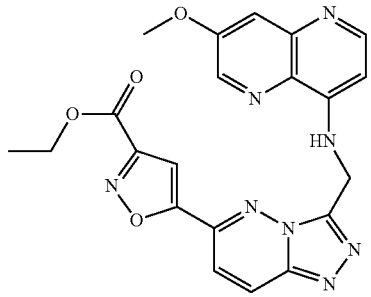 [SMILES: CCOC(=O)c1cc(-c2ccc3nnc(CNc4ccnc5cc(OC)cnc45)n3n2)on1]

EXAMPLE 35

Ethyl-5-(3-((7-methoxy-1,5-naphthyridin-4-ylamino)methyl)-[1,2,4]-triazolo[4,3-b]pyridazin-6-yl)isoxazole-3-carboxylate Prepared by a method similar to 7-methoxy-N-((6-(3-methylisoxazol-5-yl)-[1,2,4]triazolo[4,3-b]pyridazin-3-yl)methyl)-1,5-naphthyridin-4-amine. MS m/z=446.6 [M+1]$^+$. Calc'd for $C_{21}H_{18}N_8O_4$: 446.2.

EXAMPLE 36

5-(3-((7-methoxy-1,5-naphthyridin-4-ylamino)methyl)-[1,2,4]triazolo[4,3-b]pyridazin-6-yl]isoxazole-3-carboxylic acid To a solution of ethyl 5-(3-((7-methoxy-1,5-naphthyridin-4-ylamino)methyl)-[1,2,4]triazolo[4,3-b]pyridazin-6-yl)isoxazole-3-carboxylate (0.045 g, 0.10 mmol) in methanol (1 mL) and water (0.5 mL) was added sodium hydroxide (6M, 0.050 ml, 0.30 mmol). The mixture was stirred at 50° C. for two hours, then was concentrated and diluted with water (2 mL). 2M HCL was added dropwise until precipitation was observed, the tan solid was collected by filtration. The solid was taken up in isopropanol and heated to 100° C. The resulting suspension was cooled to room temperature and filtered to yield the product as a tan solid. MS m/z=418.6 [M+1]$^+$. Calc'd for $C_{19}H_{14}N_8O_4$: 418.1.

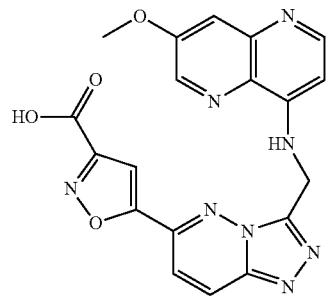 [SMILES: COc1cnc2c(NCc3nnc4ccc(-c5cc(C(=O)O)no5)nn34)ccnc2c1]

tert-butyl-(6-(3-((tetrahydro-2H-pyran-2-yloxy)methyl)isoxazol-5-yl)-[1,2,4]triazolo[4,3-b]pyridazin-3-yl)methylcarbamate Prepared by a method similar to tert-butyl-(6-(3-methylisoxazol-5-yl)-[1,2,4]triazolo[4,3-b]pyridazin-3-yl)methylcarbamate. MS m/z=430.7 [M+1]$^+$. Calc'd for $C_{20}H_{26}N_6O_5$: 430.2.

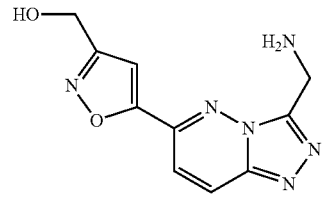 [SMILES: NCc1nnc2ccc(-c3cc(CO)no3)nn12]

(5-(3-(aminomethyl)-[1,2,4]triazolo[4,3-b]pyridazin-6-yl)isoxazol-3-yl)methanol

To a solution of tert-butyl (6-(3-((tetrahydro-2H-pyran-2-yloxy)methyl)isoxazol-5-yl)-[1,2,4]triazolo[4,3-b]pyridazin-3-yl)methylcarbamate (4.73 g, 11.0 mmol) in dichloromethane (50 mL) was added trifluoroacetic acid (16.9 ml, 220 mmol). The mixture was stirred at room temperature for one hour, then was concentrated, taken up in 2.0 M ammonia in methanol and purified by MPLC chromatography (eluted with 0-10% (1:10:90 NH$_4$OH:MeOH:DCM) in DCM) to yield the product as a tan solid. MS m/z=246.9 [M+1]$^+$. Calc'd for $C_{10}H_{10}N_6O_2$: 246.1.

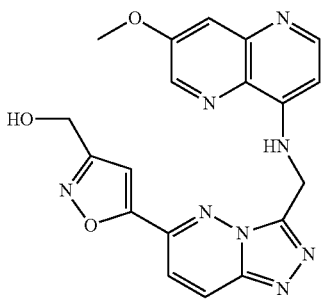 [SMILES: COc1cnc2c(NCc3nnc4ccc(-c5cc(CO)no5)nn34)ccnc2c1]

EXAMPLE 37

(5-(3-((7-methoxy-1,5-naphthyridin-4-ylamino)methyl)-[1,2,4]triazolo[4,3-b]pyridazin-6-yl)isoxazol-3-yl)methanol Prepared by a method similar to 7-methoxy-N-((6-(3-methylisoxazol-5-yl)-[1,2,4]triazolo[4,3-b]pyridazin-3-yl)methyl)-1,5-naphthyridin-4-amine MS m/z=404.6 [M+1]$^+$. Calc'd for $C_{19}H_{16}N_8O_3$: 404.1.

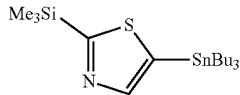

5-(tributylstannyl)-2-(trimethylsilyl)thiazole

To a stirred solution of butyllithium (0.763 ml, 1.91 mmol) in diethyl ether (10 mL) at −78° C. was added dropwise over 30 minutes a solution of 2-(trimethylsilyl)thiazole (0.300 ml, 1.91 mmol) in ether (5 mL). The solution was stirred at −78° C. for one hour, followed by the addition of chlorotrimethylstannane (1.59 ml, 1.59 mmol) in THF over 15 minutes. After an additional hour at −78° C., the solution was washed with saturated bicarbonate and extracted with diethyl ether. Organic extracts were dried over magnesium sulfate and filtered then concentrated in vacuo to yield the product as a colorless oil.

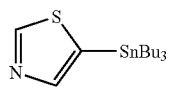

5-(tributylstannyl)thiazole

To a solution of 2-(trimethylsilyl)-5-(trimethylstannyl)thiazole (0.509 g, 1.6 mmol) in 5 mL THF was added 2 N HCl (1.0 mL). The solution was stirred at room temperature for one hour. The solution was diluted with diethyl ether and washed with sodium bicarbonate. Organic extracts were dried over magnesium sulfate and filtered then concentrated to yield the product as a colorless oil.

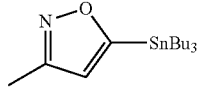

3-methyl-5-(tributylstannyl)isoxazole

To a solution of nitroethane (0.0952 ml, 1.33 mmol) in benzene (2 mL) was added phenyl isocyanate (0.291 ml, 2.66 mmol). The solution was stirred at 50° C. for ten minutes followed by the addition of triethylamine (0.00925 ml, 0.0666 mmol) and tributyl(ethynyl)stannane (0.365 ml, 1.27 mmol). The mixture was left to stir at 50° C. overnight. The solution was diluted with water and filtered though a celite plug, the resulting filtrate was extracted with toluene. Organic extracts were dried over magnesium sulfate and filtered then concentrated to yield the product as a yellow oil.

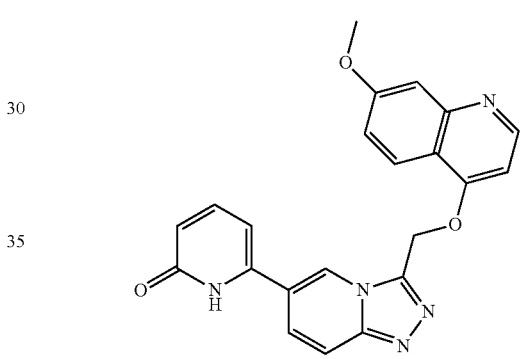

EXAMPLE 38

In a pressure vessel, 3N HCl (1.2 ml, 3.5 mmol) was added to 4-)(6-(6-fluoropyridin-2-yl)-[1,2,4]triazolo[4,3-a]pyridin-3-yl)methoxy)-7-methoxyquinoline (0.071 g, 0.18 mmol) in dioxane (0.60 mL). The reaction mixture was then heated at 100° C. for 3.5 h. Concentrated HCl (0.300 mL, 9.9 mmol) was added and the reaction was heated at 100° C. for 2 h. The reaction mixture was concentrated in vacuo, and then dried on high vacuum.

Triethylamine (0.74 ml, 5.3 mmol) was added to the compound, and it was allowed to stir for one hour until the free base crashed out of solution.

The compound was dissolved partially in DCM/MeOH, however, fully dissolved after addition of hot DMSO. The compound was purified via flash chromatograph, eluting with 0-10% MeOH/NH$_4$OH in DCM. The compound was sonicated in DCM and filtered to remove the triethylamine-hydrochloride salt, and yielded 6-(3-((7-methoxyquinolin-4-yloxy)methyl)-[1,2,4]triazolo[4,3-a]pyridin-6-yl)pyridin-2 (1H)-one.

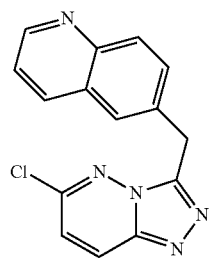 [SMILES: Clc1ccc2nnc(Cc3ccc4ncccc4c3)n2n1]

EXAMPLE 39

6-((6-Chloro-[1,2,4]triazolo[4,3-b]pyridazin-3-yl)methyl)quinoline

A mixture of 1-(6-chloropyridazin-3-yl)hydrazine (1.67 g, 12 mmol), 2-(quinolin-6-yl)acetic acid (1.65 g, 8.8 mmol), and HCl (2000 µl, 24 mmol) was heated in an oil bath at 110° C. for 20 min before it was heated in a microwave (Personal Chemistry) at 180° C.& 15 min. The mixture was quenched with a solution of NaOH (1.2 g, 5 mL) slowly until the suspension is neutral in pH. The mixture was filtered and washed with $H_2O$ (2×5 mL). A brown solid was obtained (2.2 g). The solid was treated with aqueous $Na_2CO_3$ (3 g, 20 mL, pH ~11) and heated at 50° C. for 30 min. The blue mixture was cooled to room temperature, and filtered. The black solid was washed with $H_2O$ and lyophilized to give the product.

LCMS: calc'd for $C_{15}H_{10}ClN_5$: 295.1. found 296.1 (M+1).

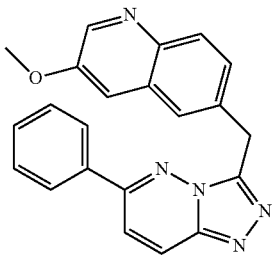 [SMILES: COc1cnc2ccc(Cc3nnc4ccc(-c5ccccc5)nn34)cc2c1]

EXAMPLE 40

3-Methoxy-6-((6-phenyl-[1,2,4]triazolo[4,3-b]pyridazin-3-yl)methyl)quinoline

A mixture of tert-butyl 2-(3-methoxyquinolin-6-yl)acetate (148 mg) and 1-(6-phenylpyridazin-3-yl)hydrazine (126 mg) in HCl (conc., 0.3 mL) was heated at 100° C. for 5 min and was subject to microwave heating (180° C., 15 min) The yellow sludge was quenched with NaOH (5N, 1 mL). The pink mixture was filtered and washed with NaOH (1 N, 1 mL), $H_2O$ (2 mL). The solid was suspended in DMF (2 mL)-DCM (2 mL). MeI (0.2 mL) was added followed by the addition of NaOH (2N, 1 mL). After 2 h, the mixture was partitioned between DCM (10 mL) and aqueous $Na_2SO_3$ (5 mL). The organic was dried over $MgSO_4$, concentrated, and purified in silica (1-15% MeOH in DCM) to give the product as a yellow powder.

LCMS: calc'd for $C_{22}H_{17}N_5O$: 367.1. found 368.2 (M+1).

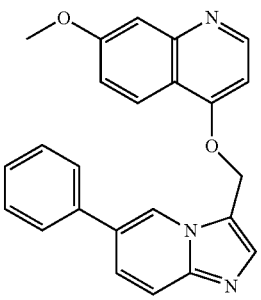 [SMILES: COc1ccc2c(OCc3cnc4ccc(-c5ccccc5)cn34)ccnc2c1]

EXAMPLE 41

4-(3-((7-methoxyquinolin-4-yloxy)methyl)-[1,2,4]triazolo[4,3-b]pyridazin-6-yl)-2-methylbut-3-yn-2-ol 1) 6-bromoH-imidazo[1,2-a]pyridine-3-carbaldehyde

A 250 mL RB flask was charged with DMF (21.3 ml, 274 mmol) and cooled to 0° C.; phosphorus oxychloride (2.46 ml, 26.4 mmol) was added dropwise. This was stirred for 1 hour, then 6-bromoH-imidazo[1,2-a]pyridine (2.00 g, 10.2 mmol) was added in one portion. This was stirred at 100° C. for 5 hours and at room temperature for 16 hours. The flask was cooled to 0° C. and slowly neutralized with 6N aq. NaOH and sat. aq. $NaHCO_3$, resulting in the formation of a precipitate which was collected by filtration to give 6-bromoH-imidazo[1,2-a]pyridine-3-carbaldehyde as a yellow-orange solid.

2) (6-bromoH-imidazo[1,2-a]pyridin-3-yl)methanol

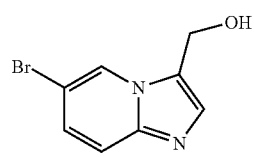 [SMILES: OCc1cnc2ccc(Br)cn12]

A 50 mL RB flask was charged with sodium borohydride (0.074 g, 2.0 mmol) and water (0.84 ml, 47 mmol), then cooled to 0° C. A solution of 6-bromoH-imidazo[1,2-a]pyridine-3-carbaldehyde (0.8792 g, 3.9 mmol), methanol (6.3 ml, 156 mmol), and DCM was added slowly. This was allowed to warm to room temperature. The mixture was concentrated, then the yellow residue was triturated with water and filtered to give (6-bromoH-imidazo[1,2-a]pyridin-3-yl)methanol as a yellow solid.

3) 4-((6-bromoH-imidazo[1,2-a]pyridin-3-yl)methoxy)-7-methoxyquinoline

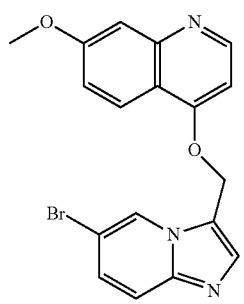 [SMILES: COc1ccc2c(OCc3cnc4ccc(Br)cn34)ccnc2c1]

A 10-20 mL microwave vial was charged with (6-bromoH-imidazo[1,2-a]pyridin-3-yl)methanol (0.756 g, 3.3 mmol), 4-chloro-7-methoxyquinoline (0.81 g, 4.2 mmol), cesium carbonate (2.2 g, 6.7 mmol), and DMSO (8.00 ml, 113 mmol), sealed, and placed in a Personal Chemistry microwave at 100° C. for 2 hours. The reaction mixture was added dropwise to a flask containing water, resulting in the formation of a precipitate which was collected by filtration. The solid was dissolved in a combination of MeOH/DCM and filtered. The filtrate was concentrated and triturated with EtOAc/DCM. The solid was dissolved in a small amount of hot MeOH and DCM and purified by chromatography using a 40 g ISCO column, eluting with a gradient of 1-7% MeOH (with 10% NH4OH)/DCM over 40 minutes.

4) 4-(3-((7-methoxyquinolin-4-yloxy)methyl)-[1,2,4]triazolo[4,3-b]pyridazin-6-yl)-2-methylbut-3-yn-2-ol A 16 mm test tube was charged with 4-((6-bromoH-imidazo[1,2-a]pyridin-3-yl)methoxy)-7-methoxyquinoline (0.0607 g, 0.16 mmol), phenylboronic acid (0.039 g, 0.32 mmol), SPhos (0.0065 g, 0.016 mmol), Potassium phosphate (0.10 g, 0.47 mmol), Pd2(dba)3 (0.0036 g, 0.0039 mmol), and 1-butanol (0.014 ml, 0.16 mmol), then stirred at 100° C. for 16 hours. The reaction mixture was diluted with chloroform (15 mL) and washed with water (15 mL), sat. aq. NaHCO3 (15 mL), and brine (15 mL); the organic layer was dried with MgSO4, filtered, and concentrated. This was purified using the prep HPLC machine using a gradient of 10% MeCN/water to 95% MeCN/water over 20 min. The fractions were combined and the product free based by diluting with 10% MeOH/HCCl3 (30 mL) and washing with sat. aq. NaHCO3 (30 mL). The organic layer was dried with MgSO4, filtered, and concentrated, then the resulting yellow solid was submitted to the Analytical Chemistry group for purification. This was returned as the formic acid salt in water, which was concentrated, free based with sat. NaHCO3 (5 mL), diluted with water (15 mL), and extracted with 10% MeOH/HCCl3 (3×25 mL). The combined organics were dried with MgSO4, filtered, and concentrated to yield 7-methoxy-4-((6-phenylH-imidazo[1,2-a]pyridin-3-yl)methoxy)quinoline. MS (ESI pos. ion) m/z: 382 (MH+). Calc'd exact mass for $C_{24}H_{19}N_3O_2$: 381.

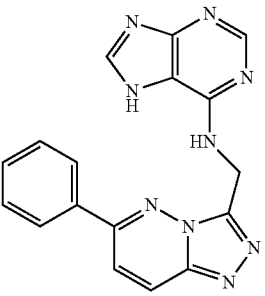 [SMILES: c1ccc(-c2ccc3nnc(CNc4ncnc5nc[nH]c45)n3n2)cc1]

EXAMPLE 42

N-((6-phenyl-[1,2,4]triazolo[4,3-b]pyridazin-3-yl)methyl)-7H-purin-6-amine

A 15 mL tube was charged with (6-phenyl-[1,2,4]triazolo[4,3-b]pyridazin-3-yl)methanamine (0.100 g, 0.444 mmol), 6-chloropurine (0.103 g, 0.666 mmol), and sec-butanol (3.00 ml, 32.4 mmol), sealed, then heated in a 100° C. oil bath for 5 hours. The reaction mixture was concentrated and the yellow residue was purified by MPLC using a 40 g RediSep column, eluting with a gradient of 3-8% MeOH/DCM over 80 minutes. N-((6-phenyl-[1,2,4]triazolo[4,3-b]pyridazin-3-yl)methyl)-7H-purin-6-amine (0.0500 g, 32.8% yield) was isolated as the hydrochloride salt.

MS (ESI pos. ion) m/z: 344 (MH+). Calc'd exact mass for $C_{23}H_{18}FN_5O_2$: 343.

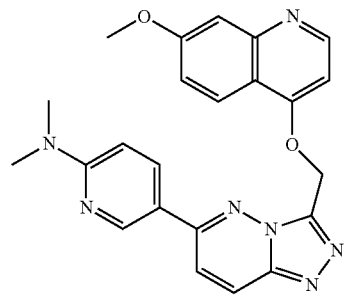 [SMILES: COc1ccc2c(OCc3nnc4ccc(-c5ccc(N(C)C)nc5)nn34)ccnc2c1]

EXAMPLE 43

5-(3-((7-methoxyquinolin-4-yloxy)methyl)-[1,2,4]triazolo[4,3-b]pyridazin-6-yl)-N,N-dimethylpyridin-2-amine A 48 mL tube was charged with 6-(dimethylamino)pyridin-3-ylboronic acid (0.109 g, 0.658 mmol), 4-((6-chloro-[1,2,4]triazolo[4,3-b]pyridazin-3-yl)methoxy)-7-methoxyquinoline (0.150 g, 0.439 mmol), and DMF (3.00 ml, 38.6 mmol), and stirred for 10 minutes. A solution of potassium carbonate (0.182 g, 1.32 mmol) and water (0.696 ml, 38.6 mmol) was added, followed by PdCl2(dppf)-CH2Cl2Adduct (0.0358 g, 0.0439 mmol). The tube was flushed with argon, sealed, and heated in a 80° C. oil bath for 5 hours. The mixture was concentrated, and the residue was triturated with water to give a brown solid which was purified by MPLC using a 40 g column, eluting with 1-5% MeOH/DCM over 40 minutes to give 5-(3-((7-methoxyquinolin-4-yloxy)methyl)-[1,2,4,]triazolo[4,3-b]pyridazin-6-yl)-N,N-dimethylpyridin-2-amine as a dark green solid.

MS (ESI pos. ion) m/z: 428 (MH+). Calc'd exact mass for C$_{23}$H$_{18}$FN$_5$O$_2$: 427.

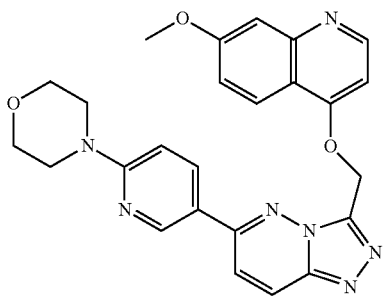 [SMILES: COc1ccc2c(OCc3nnc4ccc(-c5ccc(N6CCOCC6)nc5)nn34)ccnc2c1]

EXAMPLE 44

7-methoxy-4-((6-(6-morpholinopyridin-3-yl)-[1,2,4]triazolo[4,3-b]pyridazin-3-yl)methoxy)quinoline Prepared in a similar manner as 5-(3-((7-methoxyquinolin-4-yloxy)methyl)-[1,2,4,]triazolo[4,3-b]pyridazin-6-yl)-N,N-dimethylpyridin-2-amine
MS (ESI pos. ion) m/z: 470 (MH+). Calc'd exact mass for C$_{23}$H$_{18}$FN$_5$O$_2$: 469.

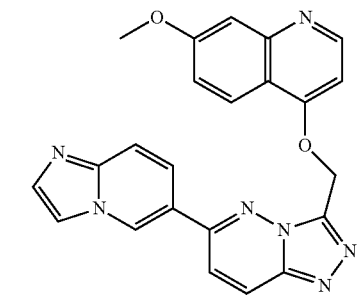 [SMILES: COc1ccc2c(OCc3nnc4ccc(-c5ccc6nccn6c5)nn34)ccnc2c1]

EXAMPLE 45

4-((6-(H-imidazo[1,2-a]pyridin-6-yl)-[1,2,4]triazolo[4,3-b]pyridazin-3-yl)methoxy)-7-methoxyquinoline Prepared in a similar manner as 5-(3-((7-methoxyquinolin-4-yloxy)methyl)-[1,2,4]triazolo[4,3-b]pyridazin-6-yl)-N,N-dimethylpyridin-2-amine MS (ESI pos. ion) m/z: 424 (MH+). Calc'd exact mass for C$_{23}$H$_{17}$N$_7$O$_2$: 423.

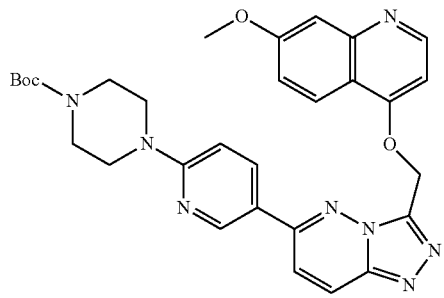 [SMILES: COc1ccc2c(OCc3nnc4ccc(-c5ccc(N6CCN(C(=O)OC(C)(C)C)CC6)nc5)nn34)ccnc2c1]

EXAMPLE 46 tert-butyl 4-(5-(3-((7-methoxyquinolin-4-yloxy)methyl)-[1,2,4]triazolo[4,3-b]pyridazin-6-yl)pyridin-2-yl)piperazine-1-carboxylate Prepared in a similar manner as 5-(3-((7-methoxyquinolin-4-yloxy)methyl)-[1,2,4]triazolo[4,3-b]pyridazin-6-yl)-N,N-dimethylpyridin-2-amine MS (ESI pos. ion) m/z: 569 (MH+). Calc'd exact mass for C$_{30}$H$_{32}$N$_8$O$_4$: 568.

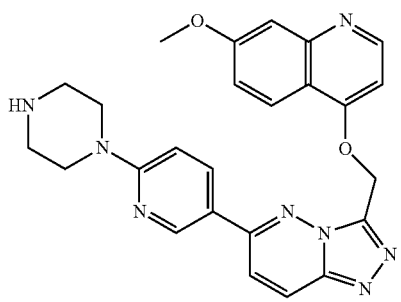 [SMILES: COc1ccc2c(OCc3nnc4ccc(-c5ccc(N6CCNCC6)nc5)nn34)ccnc2c1]

EXAMPLE 47

7-methoxy-4-((6-(6-(piperazin-1-yl)pyridin-3-yl)-[1,2,4]-triazolo[4,3-b]pyridazin-3-yl)methoxy)quinoline A 50 mL recovery flask was charged with tert-butyl 4-(5-(3-((7-methoxyquinolin-4-yloxy)methyl)-[1,2,4]triazolo[4,3-b]pyridazin-6-yl)pyridin-2-yl)piperazine-1-carboxylate (0.250 g, 0.44 mmol), TFA (0.75 ml, 9.6 mmol), and DCM (1.50 ml, 23 mmol), then stirred at room temperature for 1.5 hours. The reaction mixture was concentrated, then quenched with sat. aq. NaHCO$_3$. The mixture was diluted with DCM (60 mL), resulting in an emulsion. The emulsion was filtered to give a brown solid. The solid was triturated with a combination of DCM/MeOH/MeCN and filtered to give 7-methoxy-4-((6-(6-(piperazin-1-yl)pyridin-3-yl)-[1,2,4]triazolo[4,3-b]pyridazin-3-yl)methoxy)quinoline.
MS (ESI pos. ion) m/z: 469 (MH+). Calc'd exact mass for C$_{25}$H$_{24}$N$_8$O$_2$: 468.

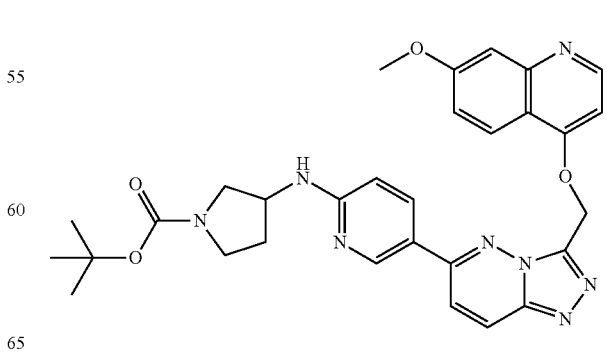

EXAMPLE 48 tert-butyl 3-(5-(3-((7-methoxyquinolin-4-yloxy)methyl)-[1,2,4]-triazolo[4,3-b]pyridazin-6-yl)pyridin-2-ylamino)pyrrolidine-1-carboxylate 1) 4-((6-(6-fluoropyridin-3-yl)-[1,2,4]triazolo[4,3-b]pyridazin-3-yl)methoxy)-7-methoxyquinoline

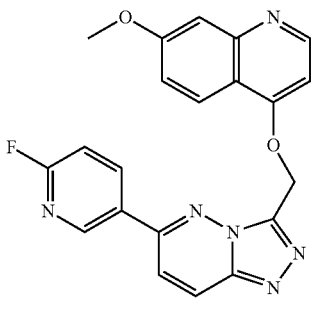 [SMILES: COc1ccc2c(OCc3nnc4ccc(-c5ccc(F)nc5)nn34)ccnc2c1]

Prepared in a similar manner as 5-(3-((7-methoxyquinolin-4-yloxy)methyl)-[1,2,4]triazolo[4,3-b]pyridazin-6-yl)-N,N-dimethylpyridin-2-amine 2) tert-butyl 3-(5-(3-((7-methoxyquinolin-4-yloxy)methyl)-[1,2,4]triazolo[4,3-b]pyridazin-6-yl)pyridin-2-ylamino)pyrrolidine-1-carboxylate A 0.5-2 mL microwave vial was charged with 4-((6-(6-fluoropyridin-3-yl)-[1,2,4]triazolo[4,3-b]pyridazin-3-yl)methoxy)-7-methoxyquinoline (0.100 g, 0.249 mmol), tert-butyl 3-aminopyrrolidine-1-carboxylate (0.116 g, 0.622 mmol), and DMSO (4.00 ml, 56.4 mmol), sealed and placed in a Personal Chemistry microwave for 1 hour at 100° C. and then 30 minutes at 120° C. Water was added slowly to the reaction mixture until a precipitate formed. The solid was collected and purified by MPLC using a 40 g RediSep column, eluting with a gradient of 3-6% MeOH/DCM over 40 minutes. The solid was triturated with MeCN and filtered; the mother liquor was concentrated to give tert-butyl 3-(5-(3-((7-methoxyquinolin-4-yloxy)methyl)-[1,2,4]triazolo[4,3-b]pyridazin-6-yl)pyridin-2-ylamino)pyrrolidine-1-carboxylate.

MS (ESI pos. ion) m/z: 569 (MH+). Calc'd exact mass for $C_{30}H_{32}N_8O_4$: 568.

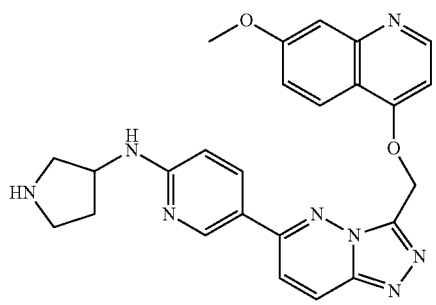 [SMILES: COc1ccc2c(OCc3nnc4ccc(-c5ccc(NC6CCNC6)nc5)nn34)ccnc2c1]

EXAMPLE 49

5-(3-((7-methoxyquinolin-4-yloxy)methyl)[1,2,4]triazolo[4,3-b]pyridazin-6-yl)-N-(pyrrolidin-3-yl)pyridin-2-amine Prepared in a similar manner as 7-methoxy-4-((6-(6-(piperazin-1-yl)pyridin-3-yl)-[1,2,4]triazolo[4,3-b]pyridazin-3-yl)methoxy)quinoline.

MS (ESI pos. ion) m/z: 469 (MH+). Calc'd exact mass for $C_{25}H_{24}N_8O_2$: 468.

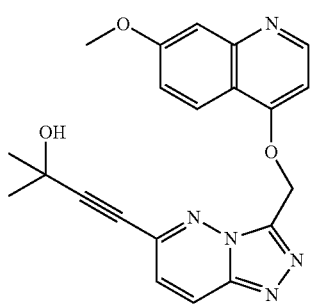 [SMILES: COc1ccc2c(OCc3nnc4ccc(C#CC(C)(C)O)nn34)ccnc2c1]

EXAMPLE 50

4-(3-((7-methoxyquinolin-4-yloxy)methyl)-[1,2,4]triazolo[4,3-b]pyridazin-6-yl)-2-methylbut-3-yn-2-ol A 25×200 mm test tube was charged with 4-((6-chloro-[1,2,4]triazolo[4,3-b]pyridazin-3-yl)methoxy)-7-methoxyquinoline (0.150 g, 0.439 mmol), 2-methylbut-3-yn-2-ol (0.213 ml, 2.19 mmol), copper (I) iodide (0.0209 g, 0.110 mmol), triethylamine (1.83 ml, 13.2 mmol), and acetonitrile (5.00 ml, 96.2 mmol), flushed with argon, sealed, and placed in a 90° C. oil bath for 30 minutes. PdCl2(dppf)-CH$_2$Cl$_2$Adduct (0.0358 g, 0.0439 mmol) was added in one portion, the tube flushed with argon, sealed, then heated in a 90° C. oil bath for 4 hours. The reaction mixture was filtered thru a pad of silica gel (eluting with EtOAc/DCM/MeOH), then concentrated to yield a dark brown oil. This was purified by MPLC, using a 40 g RediSep column, eluting with 1-7% MeOH/DCM over 40 minutes. The appropriate fractions were collected to give 4-(3-((7-methoxyquinolin-4-yloxy)methyl)-[1,2,4]triazolo[4,3-b]pyridazin-6-yl)-2-methylbut-3-yn-2-ol (0.0877 g, 51.3% yield).

MS (ESI pos. ion) m/z: 390 (MH+). Calc'd exact mass for $C_{21}H_{19}N_5O_3$: 389.

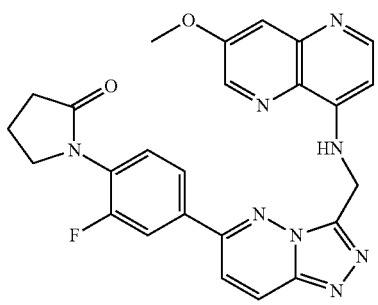 [SMILES: COc1cnc2c(NCc3nnc4ccc(-c5ccc(N6CCCC6=O)c(F)c5)nn34)ccnc2c1]

EXAMPLE 51

1-(2-fluoro-4-(3-((7-methoxy-1,5-naphthyridin-4-ylamino)methyl)-[1,2,4]triazolo[4,3-b]pyridazin-6-yl)phenyl)pyrrolidin-2-one 1) 1-(4-chloro-2-fluorophenyl)pyrrolidin-2-one

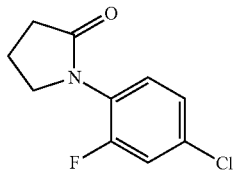 [SMILES: O=C1CCCN1c1ccc(Cl)cc1F]

A 100 mL sealed tube was charged with 4-chloro-2-fluoro-1-iodobenzene (0.498 ml, 3.90 mmol), pyrrolidin-2-one (0.598 ml, 7.80 mmol), (1R,2R)-cyclohexane-1,2-diamine (0.0703 ml, 0.585 mmol), potassium phosphate (1.66 g, 7.80 mmol), copper (I) iodide (0.0223 g, 0.117 mmol), and 1,4-dioxane (4.00 ml, 46.8 mmol), then flushed with argon, sealed, and placed in a 110° C. oil bath for 17 hours. The reaction mixture was filtered through a pad of silica gel, eluting with EtOAc and DCM, then the filtrate was concentrated to yield a brown oil This was purified by column chromatography using a 40 g ISCO column, eluting with a gradient of 3-5% MeOH/DCM over 30 minutes to give 1-(4-chloro-2-fluorophenyl)pyrrolidin-2-one (0.903 g, 108% yield) as a yellow solid.

2) 1-(2-fluoro-4-(4,4,5,5-tetramethyl-1,3,2-dioxaborolan-2-yl)phenyl)pyrrolidin-2one

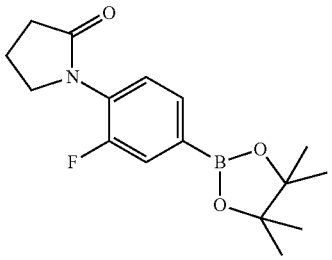 [SMILES: CC1(C)OB(c2ccc(N3CCCC3=O)c(F)c2)OC1(C)C]

A 48 mL sealed tube was charged with 1-(4-chloro-2-fluorophenyl)pyrrolidin-2-one (0.444 g, 2.08 mmol), pinacol diborane (1.06 g, 4.16 mmol), X-Phos (0.0991 g, 0.208 mmol), Pd2dba3 (0.0571 g, 0.0623 mmol), potassium acetate (0.408 g, 4.16 mmol), and 1,4-dioxane (4.62 ml, 54.0 mmol), flushed with argon, sealed, then placed in a 90° C. oil bath for 5 hours. The reaction mixture was diluted with EtOAc (100 mL) and washed with water (100 mL), sat. NaHCO$_3$ (100 mL), and brine (100 mL), dried with MgSO$_4$, filtered, and concentrated. This was purified by MPLC using a 40 g RediSep column, eluting with 1-5% MeOH/DCM over 40 minutes. The fractions were concentrated to give 1-(2-fluoro-4-(4,4,5,5-tetramethyl-1,3,2-dioxaborolan-2-yl)phenyl)pyrrolidin-2-one, ~85% pure, as an orange oil that solidified upon standing.

3) tert-butyl (6-(3-fluoro-4-(2-oxopyrrolidin-1-yl)phenyl)-[1,2,4]triazolo[4,3-b]pyridazin-3-yl)methylcarbamate

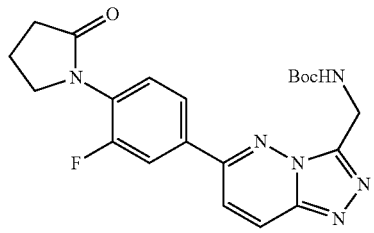 [SMILES: CC(C)(C)OC(=O)NCc1nnc2ccc(-c3ccc(N4CCCC4=O)c(F)c3)nn12]

A 48 mL sealed tube was charged with tert-butyl (6-chloro-[1,2,4]triazolo[4,3-b]pyridazin-3-yl)methylcarbamate (0.150 g, 0.529 mmol), 1-(2-fluoro-4-(4,4,5,5-tetramethyl-1,3,2-dioxaborolan-2-yl)phenyl)pyrrolidin-2-one (0.242 g, 0.793 mmol), PdCl2(dppf)-CH$_2$Cl$_2$Adduct (0.0432 g, 0.0529 mmol), cesium carbonate (0.689 g, 2.11 mmol), 1,4-dioxane (3.62 ml, 42.3 mmol), and water (0.905 ml, 50.2 mmol), flushed with argon, sealed, then placed in a 80° C. oil bath for 5 hours. The contents were transferred to a flask and concentrated. The solid was triturated with water to give a red residue, which was purified by MPLC using a 40 g RediSep column, eluting with 2-6% MeOH/DCM over 40 minutes. tert-butyl (6-(3-fluoro-4-(2-oxopyrrolidin-1-yl)phenyl)-[1,2,4]triazolo[4,3-b]pyridazin-3-yl)methylcarbamate (0.117 g, 51.9% yield) was isolated as a tan solid.

4) 1-(4-(3-(aminomethyl)-[1,2,4]triazolo[4,3-b]pyridazin-6-yl)-2-fluorophenyl)pyrrolidin-2-one

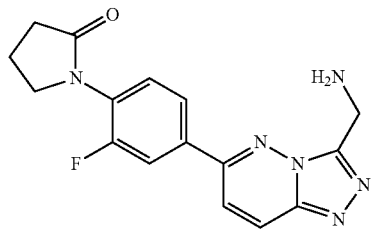 [SMILES: NCc1nnc2ccc(-c3ccc(N4CCCC4=O)c(F)c3)nn12]

A 50 mL recovery flask was charged with tert-butyl (6-(3-fluoro-4-(2-oxopyrrolidin-1-yl)phenyl)-[1,2,4]triazolo[4,3-b]pyridazin-3-yl)methylcarbamate (0.117 g, 0.274 mmol), TFA (0.0211 ml, 0.274 mmol), and DCM (0.0177 ml, 0.274 mmol), then stirred open to air at room temperature for 2 hours. The mixture was concentrated, then taken up in MeOH. K$_2$CO$_3$ was added, and this was stirred for 1 hour. The mixture was concentrated, then the residue was taken up in MeOH/CHCl$_3$ then filtered. The filtrate was evaporated, taken up in water, then passed through a reverse phase C$_{18}$ column, eluting with MeOH/DCM, then concentrated.

5) 1-(2-fluoro-4-(3-((7-methoxy-1,5-naphthyridin-4-ylamino)methyl)-[1,2,4,]triazolo[4,3-b]pyridazin-6-yl)phenyl)pyrrolidin-2-one A 0.5-2 mL microwave vial was charged with 1-(4-(3-(aminomethyl)-[1,2,4]triazolo[4,3-b]pyridazin-6-yl)-2-fluorophenyl)pyrrolidin-2-one (0.0792 g, 0.243 mmol), 8-chloro-3-methoxy-1,5-naphthyridine (0.0590 g, 0.303 mmol), and butan-2-ol (1.00 ml, 0.243 mmol), sealed, then placed in a Personal Chemistry Microwave for 4 hours at 120° C. The mixture was concentrated, then triturated with MeOH to give 1-(2-fluoro-4-(3-((7-methoxy-1,5-naphthyridin-4-ylamino)methyl)-[1,2,4]triazolo[4,3-b]pyridazin-6-yl)phenyl)pyrrolidin-2-one as the hydrochloric salt.

MS (ESI pos. ion) m/z: 485 (MH+). Calc'd exact mass for $C_{25}H_{21}FN_{88}O_2$: 484.

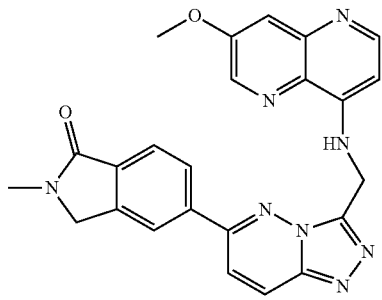 [SMILES: COc1cnc2c(NCc3nnc4ccc(-c5ccc6c(c5)CN(C)C6=O)nn34)ccnc2c1]

EXAMPLE 52

5-(3-((7-methoxy-1,5-naphthyridin-4-ylamino)methyl)-[1,2,4]triazolo[4,3-b]pyridazin-6-yl)-2-methylisoindolin-1-one 1) 4-bromo-2-(hydroxymethyl)-N-methylbenzamide

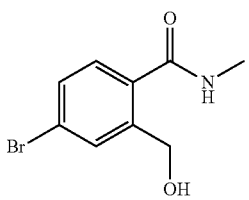

A 500 mL RB flask was charged with aluminum(III) chloride (4.1 g, 31 mmol) and 10 mL of 1,2-dichloroethane (90 ml, 1142 mmol), then cooled to 0° C. A separate 250 mL flask was charged with 90 mL of 1,2-dichloroethane (90 ml, 1142 mmol) and cooled to 0° C.; methylamine (gas) (1.8 g, 59 mmol) was bubbled through the solution for 10 minutes. The dichloroethane solution was slowly poured into the aluminum chloride solution, resulting in the formation of a thick white slush. This was warmed to room temperature. 5-bromoisobenzofuran-1(3H)-one (5.00 g, 23 mmol) was added in one portion and the reaction mixture was stirred for 2.5 hours and quenched with water. The mixture was filtered to remove the solid impurities, then the filtrate was washed with 0.5N aqueous HCl (100 mL) and brine (200 mL). The organic layer was dried with MgSO₄, filtered, and concentrated to give a white solid. This was triturated with EtOAc and filtered to give 4-bromo-2-(hydroxymethyl)-N-methylbenzamide (3.34 g, 58% yield) as a white solid.

2) 5-bromo-2-methylisoindolin-1-one

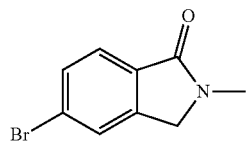

A 150 mL sealed tube was charged with 4-bromo-2-(hydroxymethyl)-N-methylbenzamide (3.34 g, 13.7 mmol) and 1,3-dimethylimidazolidin-2-one (40.4 ml, 369 mmol). The solution was cooled to 0° C. and Isopropylmagnesium chloride (15.3 ml, 30.5 mmol) was added slowly. The tube was capped and the reaction mixture was stirred at room temperature for 30 minutes. This was recooled to 0° C. and N,N,N,N-tetramethylphosphorodiamidoyl chloride (2.64 ml, 17.8 mmol) was added in one portion; this mixture was stirred at room temperature for 4 hours. The tube was placed in a 150° C. oil bath for 1 hour. The mixture was then diluted with EtOAc (100 mL), then washed with 1M aqueous HCl. The aqueous layer was extracted with ethyl acetate (3×100 mL) and then the combined organics were washed with water (100 mL) and brine (100 mL), dried with MgSO₄, filtered, then concentrated to give a yellow oil. This was purified by column chromatography, eluting with 1-4% MeOH/DCM to give 5-bromo-2-methylisoindolin-1-one (1.774 g, 57.3% yield) as a yellow solid.

3) 2-methyl-5-(4,4,5,5-tetramethyl-1,3,2-dioxaborolan-2-yl)isoindolin-1-one

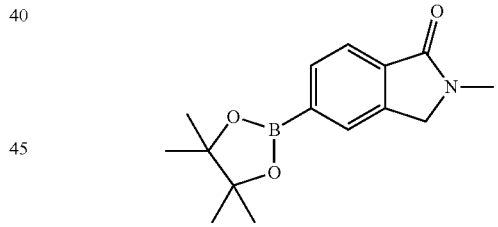

Prepared in a similar manner as 1-(2-fluoro-4-(4,4,5,5-tetramethyl-1,3,2-dioxaborolan-2-yl)phenyl)pyrrolidin-2-one.

4) tert-butyl (6-(2-methyl-1-oxoisoindolin-5-yl)-[1,2,4]triazolo[4,3-b]pyridazin-3-yl)methylcarbamate

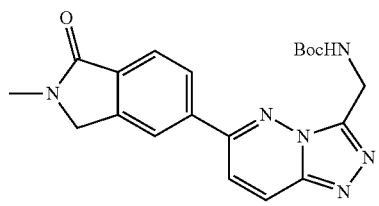 [SMILES: CN1Cc2cc(-c3ccc4nnc(CNC(=O)OC(C)(C)C)n4n3)ccc2C1=O]

Prepared in a similar manner as tert-butyl (6-(3-fluoro-4-(2-oxopyrrolidin-1-yl)phenyl)-[1,2,4]triazolo[4,3-b]pyridazin-3-yl)methylcarbamate.

5) 5-(3-(aminomethyl)-[1,2,4]triazolo[4,3-b]pyridazin-6-yl)-2-methylisoindolin-1-one

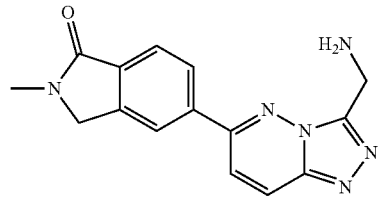 [SMILES: CN1Cc2cc(-c3ccc4nnc(CN)n4n3)ccc2C1=O]

Prepared in a similar manner as 1-(4-(3-(aminomethyl)-[1,2,4]triazolo[4,3-b]pyridazin-6-yl)-2-fluorophenyl)pyrrolidin-2-one.

6) 5-(3-((7-methoxy-1,5-naphthyridin-4-ylamino)methyl)-[1,2,4]triazolo[4,3-b]pyridazin-6-yl)-2-methylisoindolin-1-one Prepared in a similar manner as 1-(2-fluoro-4-(3-((7-methoxy-1,5-naphthyridin-4-ylamino)methyl)-[1,2,4]triazolo[4,3-b]pyridazin-6-yl)phenyl)pyrrolidin-2-one.
MS (ESI pos. ion) m/z: 453 (MH+). Calc'd exact mass for $C_{24}H_{20}N_8O_2$: 452.

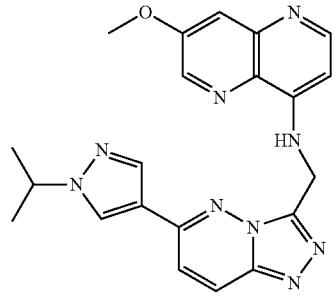 [SMILES: COc1cnc2c(NCc3nnc4ccc(-c5cnn(C(C)C)c5)nn34)ccnc2c1]

EXAMPLE 53

N-((6-(1-isopropyl-1H-pyrazol-4-yl)-[1,2,4]triazolo[4,3-b]pyridazin-3-yl)methyl)-7-methoxy-1,5-naphthyridin-4-amine 1) tert-butyl (6-(1-isopropyl-1H-pyrazol-4-yl)-[1,2,4]triazolo[4,3-b]pyridazin-3-yl)methylcarbamate

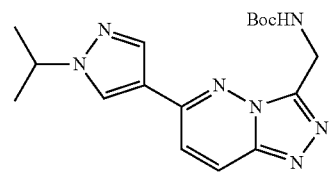 [SMILES: CC(C)n1cc(-c2ccc3nnc(CNC(=O)OC(C)(C)C)n3n2)cn1]

Prepared in a similar manner as tert-butyl (6-(3-fluoro-4-(2-oxopyrrolidin-1-yl)phenyl)-[1,2,4]triazolo[4,3-b]pyridazin-3-yl)methylcarbamate.

2) (6-(1-isopropyl-1H-pyrazol-4-yl)-[1,2,4]triazolo[4,3-b]pyridazin-3-yl)methanamine hydrochloride

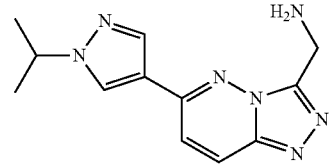 [SMILES: CC(C)n1cc(-c2ccc3nnc(CN)n3n2)cn1]

Prepared in a similar manner as 1-(4-(3-(aminomethyl)-[1,2,4]triazolo[4,3-b]pyridazin-6-yl)-2-fluorophenyl)pyrrolidin-2-one.

3) N-((6-(1-isopropyl-1H-pyrazol-4-yl)-[1,2,4]triazolo[4,3-b]pyridazin-3-yl)methyl)-7-methoxy-1,5-naphthyridin-4-amine Prepared in a similar manner as 1-(2-fluoro-4-(3-((7-methoxy-1,5-naphthyridin-4-ylamino)methyl)-[1,2,4]triazolo[4,3-b]pyridazin-6-yl)phenyl)pyrrolidin-2-one. MS (ESI pos. ion) m/z: 416 (MH+). Calc'd exact mass for $C_{21}H_{21}N_9O_2$: 415.

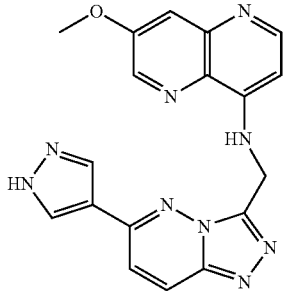 [SMILES: COc1cnc2c(NCc3nnc4ccc(-c5cn[nH]c5)nn34)ccnc2c1]

EXAMPLE 54

N-((6-(1H-pyrazol-4-yl)-[1,2,4]triazolo[4,3-b]pyridazin-3-yl)methyl)-7-methoxy-1,5-naphthyridin-4-amine A 48 mL sealed tube was charged with N-((6-chloro-[1,2,4]triazolo[4,3-b]pyridazin-3-yl)methyl)-7-methoxy-1,5-naphthyridin-4-amine (0.150 g, 0.439 mmol), 1H-pyrazol-4-ylboronic acid (0.0737 g, 0.658 mmol), and DMF (3.00 ml, 38.6 mmol). A solution of potassium carbonate (0.182 g, 1.32 mmol) and water (0.696 ml, 38.6 mmol) was added, followed by PdCl2(dppf)-CH2Cl2Adduct (0.0358 g, 0.0439 mmol). The tube was flushed with argon, sealed, then placed in a 90° C. oil bath for 5 hours. The mixture was concentrated and the black solid was triturated with water to remove $K_2CO_3$, then purified by column chromatography using a 40 g RediSep column, eluting with 30-70% (90:10:1 DCM:MeOH:NH4OH solution) in DCM over 40 minutes. Pure fractions were collected to give N-((6-(1H-pyrazol-4-yl)-[1,2,4]triazolo[4,3-b]pyridazin-3-yl)methyl)-7-methoxy-1,5-naphthyridin-4-amine as a white solid.

MS (ESI pos. ion) m/z: 374 (MH+). Calc'd exact mass for $C_{18}H_{15}N_9O$: 373.

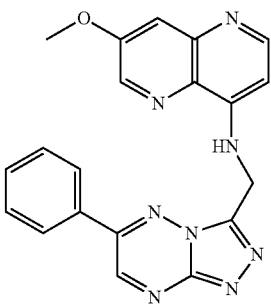 [SMILES: COc1cnc2c(NCc3nnc4ncc(-c5ccccc5)nn34)ccnc2c1]

EXAMPLE 55

7-methoxy-N-((6-phenyl-[1,2,4]-triazolo-[4,3-b][1,2,4]triazin-3-yl)methyl)-1,5-naphthyridin-4-amine 1) 3-(azidomethyl)-6-phenyl-[1,2,4]triazolo[4,3-b][1,2,4]triazine

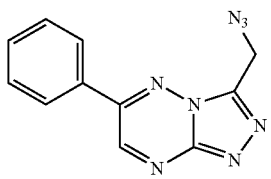 [SMILES: [N-]=[N+]=NCc1nnc2ncc(-c3ccccc3)nn12]

A 16 mm test tube was charged with (6-phenyl-[1,2,4]triazolo[4,3-b][1,2,4]triazin-3-yl)methanol (0.500 g, 2.20 mmol), Reactant 2 (0.951 ml, 4.40 mmol), DBU (0.663 ml, 4.40 mmol), and toluene (8.16 ml, 77.0 mmol), flushed with argon, sealed, then stirred at room temperature for 3 hours. The dark maroon mixture was concentrated and the resulting dark purple/black oil was purified by column chromatography using a gradient of 3-5% MeOH/DCM over 20 minutes. 3-(azidomethyl)-6-phenyl-[1,2,4]triazolo[4,3-b][1,2,4]triazine was isolated as a brown solid.

2) (6-phenyl-[1,2,4]triazolo[4,3-b][1,2,4]triazin-3-yl)methanamine

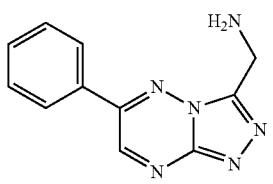 [SMILES: NCc1nnc2ncc(-c3ccccc3)nn12]

A 50 mL RB flask was charged with 3-(azidomethyl)-6-phenyl-[1,2,4]triazolo[4,3-b][1,2,4]triazine (0.3492 g, 1.38 mmol) and THF (14.0 ml, 171 mmol), resulting in a dark brown solution. Triphenylphosphine (0.545 g, 2.08 mmol) and water (0.0998 ml, 5.54 mmol) were added, and the flask was placed in a 65° C. oil bath for 2 hours. The reaction mixture was concentrated to give a thick brown oil, which was purified by column chromatography using an 80 g ISCO column, eluting with a gradient of 5% MeOH (containing NH₄OH)/DCM to 10% MeOH (containing NH₄OH)/DCM over 40 minutes. (6-phenyl-[1,2,4]triazolo[4,3-b][1,2,4]triazin-3-yl)methanamine was isolated as a yellow solid.

3) 7-methoxy-N-((6-phenyl-[1,2,4]triazolo[4,3-b][1,2,4]triazin-3-yl)methyl)-1,5-naphthyridin-4-amine Prepared in a similar manner as 1-(2-fluoro-4-(3-((7-methoxy-1,5-naphthyridin-4-ylamino)methyl)-[1,2,4]triazolo[4,3-b]pyridazin-6-yl)phenyl)pyrrolidin-2-one.

MS (ESI pos. ion) m/z: 385 (MH+). Calc'd exact mass for $C_{20}H_{16}N_8O$: 384.

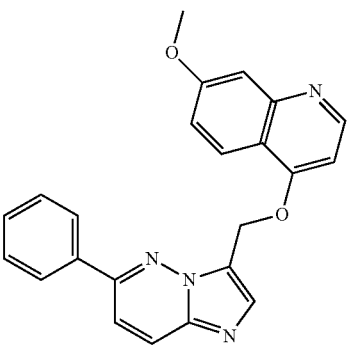 [SMILES: COc1ccc2c(OCc3cnc4ccc(-c5ccccc5)nn34)ccnc2c1]

EXAMPLE 56

(6-Phenylimidazo[1,2-b]pyridazin-3-yl)methanol

To a mixture of (6-chloroimidazo[1,2-b]pyridazin-3-yl)methanol (see Galtier, C. et al, *Antiviral Chemistry & Chemotherapy*, 2003, 14, 177-182) (0.200 g, 1.09 mmol), phenylboronic acid (0.133 g, 1.09 mmol), PdCl₂(dppf)-CH₂Cl₂ (0.0445 g, 0.0545 mmol) in dioxane was added sat NaHCO₃ (1.20 ml, >2.40 mmol). The mixture was blanketed with N₂, the vessel sealed and heated at 80 C for 1 h. The mixture was allowed to cool to rt and diluted with EtOAc. The organic phase was washed with water, then sat. NaHCO₃, dried over Na₂SO₄, filtered and evaporated. The mixture was purified via flash chromatography using a gradient of 0% to 10% MeOH in EtOAc. The title compound was collected as a white solid.

The following compounds were prepared according to the method described for (6-phenylimidazo[1,2-b]pyridazin-3-yl)methanol:
(6-(3-Fluorophenyl)imidazo[1,2-b]pyridazin-3-yl)methanol
(6-(3,4-Difluorophenyl)imidazo[1,2-b]pyridazin-3-yl)methanol
(6-(3,4,5-Trifluorophenyl)imidazo[1,2-b]pyridazin-3-yl)methanol 7-Methoxy-4-((6-phenylimidazo[1,2-b]pyridazin-3-yl)methoxy)quinoline In a microwave vessel, (6-phenylimidazo[1,2-b]pyridazin-3-yl)methanol (0.075 g, 0.33 mmol), 4-chloro-7-methoxyquinoline (0.19 g, 1.00 mmol), Cs₂CO₃ (0.22 g, 0.67 mmol) and 0.7 mL DMSO were combined and the vessel sealed. The mixture was pre-stirred for 2 min, followed by microwave heating for 2 h at 120 C, then 1 h at 130 C. The mixture was allowed to cool to rt, diluted with water to precipitate a cream solid. The solid was collected and rinsed with water. The solid was purified via flash chromatography using a 0% to 5% MeOH in EtOAc gradient to afford the title compound as a yellow solid. M/Z=383.2 [M+H], calc 382.4212 for $C_{23}H_{18}N_4O_2$.

The following compounds were prepared using the method described for 7-methoxy-4-((6-phenylimidazo[1,2-b]pyridazin-3-yl)methoxy)quinoline:

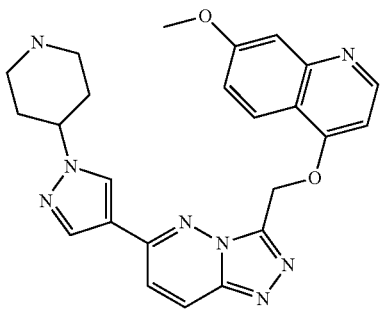

EXAMPLE 59

7-Methoxy-4-((6-(1-(piperidin-4-yl)-1H-pyrazol-4-yl)-[1,2,4]triazolo[4,3-b]pyridazin-3-yl)methoxy)quinoline In a 50 mL sealable flask was charged with $PdCl_2$(dppf)-$CH_2Cl_2$ adduct (0.011 g, 0.013 mmol), 4-((6-chloro-[1,2,4]triazolo[4,3-b]pyridazin-3-yl)methoxy)-7-methoxyquinoline (0.150 g, 0.44 mmol), tert-butyl 4-(4-(4,4,5,5-tetramethyl-1,3,2-dioxaborolan-2-yl)-1H-pyrazol-1-yl)piperidine-1-carboxylate (0.18 g, 0.48 mmol), sat $NaHCO_3$ (0.75 ml, >0.97 mmol) and 4 mL dioxane. The vessel was sealed and the mixture heated at 80 C for 22 h. The mixture was allowed to cool to rt and diluted with EtOAc, the organic layer washed with water, sat. NaHCO3, dried over $Na_2SO_4$, filtered and evaporated. The residue was dissolved in 5 mL $CH_2Cl_2$ and TFA (1.20 ml, 16 mmol) was added. The mixture was stirred at rt for 10 min and evaporated. The residue was taken up into $CH_2Cl_2$ and stirred with minimal 2N NaOH for 1 h (ph basic). The mixture was evaporated and purified by prep hplc. The title compound was obtained as an off-white solid. M/Z=457.3 [M+H], calc 456.5076 for $C_{24}H_{24}N_8O_2$.

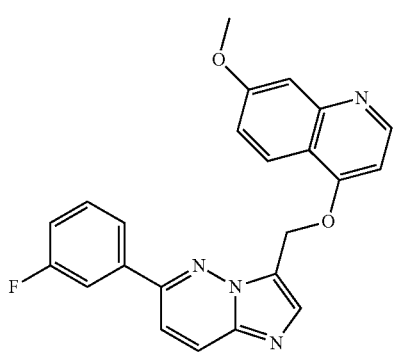 [SMILES: COc1ccc2c(OCc3cnc4ccc(-c5cccc(F)c5)nn34)ccnc2c1]

EXAMPLE 57

4-((6-(3-Fluorophenyl)imidazol-[1,2-b]pyridazin-3-yl)methoxy)-7-methoxyquinoline M/Z=401.2 [M+H], calc 400.4113 for $C_{23}H_{17}FN_4O_2$.

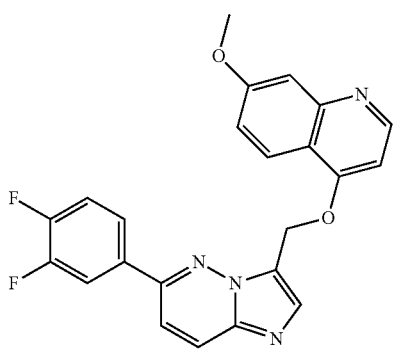 [SMILES: COc1ccc2c(OCc3cnc4ccc(-c5ccc(F)c(F)c5)nn34)ccnc2c1]

EXAMPLE 58

4-((6-(3,4-Difluorophenyl)imidazo[1,2-b]pyridazin-3-yl)methoxy)-7-methoxyquinoline M/Z=419.2 [M+H], calc 418.4014 for $C_{23}H_{16}F_2N_4O_2$.

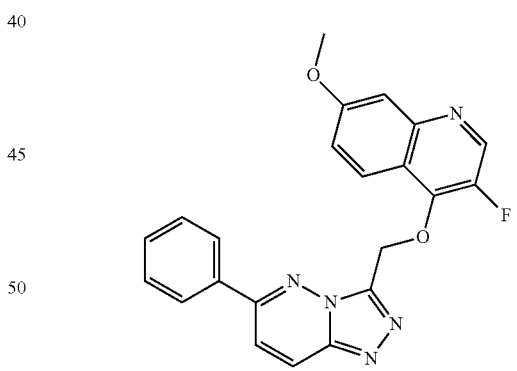

EXAMPLE 60

3-Fluoro-7-methoxy-4-((6-phenyl-[1,2,4]triazolo[4,3-b]pyridazin-3-yl)methoxy)quinoline A sealable tube was charged with $Pd_2dba_3$ (0.20 g, 0.22 mmol), racemic-2-(di-t-butylphosphino)-1,1'-binaphthyl (0.18 g, 0.44 mmol), (6-phenyl-[1,2,4]triazolo[4,3-b]pyridazin-3-yl)methanol (0.100 g, 0.44 mmol), 4-chloro-3-fluoro-7-methoxyquinoline (0.14 g, 0.66 mmol), cesium carbonate (0.29 g, 0.88 mmol), and toluene and sealed. The mixture was heated at 100 C for 12 h. The mixture was allowed to cool to rt and the solid filtered, and rinsed with toluene. The solid was stirred with a mixture of EA, MeOH, CH$_2$Cl$_2$ and filtered. The filtrate was purified via flash chromatography using a MeOH in CH$_2$Cl$_2$ gradient. The resulting solid was triturated with CH$_2$Cl$_2$/Hexanes then purified by prep hplc. The title compound was collected as a white solid. M/Z=402.1 [M+H], calc 401.3994 for C$_{22}$H$_{16}$FN$_5$O$_2$.

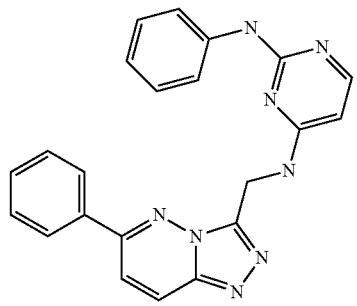 [SMILES: c1ccc(Nc2nccc(NCc3nnc4ccc(-c5ccccc5)nn34)n2)cc1]

EXAMPLE 61

N-2-Phenyl-N-4-((6-phenyl-[1,2,4]triazolo[4,3-b]pyridazin-3-yl)methyl)pyrimidine-2,4-diamine hydrochloride 2-Chloro-N-((6-phenyl-[1,2,4]triazolo[4,3-b]pyridazin-3-yl)methyl)pyrimidin-4-amine (0.036 g, 0.11 mmol) was combined with 500 mL aniline and heated at 70 C for 2 h, at which point 300 mL aniline more was added and stirred an additional 30 minutes. The mixture was allowed to cool to rt. Ether (5 mL) was added and the mixture stirred. The title compound was collected as a white solid. M/Z=395.2 [M+H], calc 394.4402 for C$_{22}$H$_{18}$N$_8$.

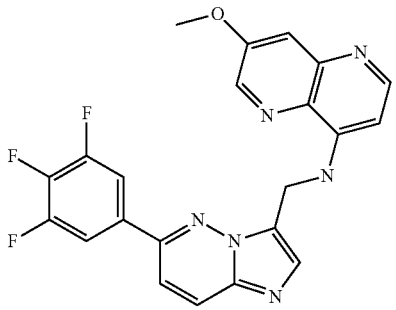 [SMILES: COc1cnc2c(NCc3cnc4ccc(-c5cc(F)c(F)c(F)c5)nn34)ccnc2c1]

EXAMPLE 62

7-Methoxy-N-((6-(3,4,5-trifluorophenyl)imidazo[1,2-b]pyridazin-3-yl)methyl)-1,5-naphthyridin-4-amine a) (6-(3,4,5-Trifluorophenyl)imidazo[1,2-b]pyridazin-3-yl)methanamine. To a suspension of (6-(3,4,5-trifluorophenyl)imidazo[1,2-b]pyridazin-3-yl)methanol (0.442 g, 1.6 mmol) in CH$_2$Cl$_2$ (5 mL) was added Mesyl-Cl (0.37 ml, 4.7 mmol) and triethylamine (0.66 ml, 4.7 mmol)-slight exotherm, place flask in water bath- and the mixture stirred at rt 1 h. The mixture was concentrated in vacuo (without heating the flask) and the residue dissolved in DMF (2 mL) and azidosodium (0.23 g, 3.5 mmol) was added in one portion. After 45 minutes, additional azidosodium (0.40 g, 6.0 mmol) was added and the mixture stirred 1 h longer. The mixture was diluted with EtOAc, washed with water, brine, (back extract aq layer) and dry organic layer over Na$_2$SO$_4$, filter and evaporate. The azide intermediate was dissolved in THF (4 mL) and trimethylphosphine 1M in THF (2.4 ml, 2.4 mmol) was added. The reaction mixture was stir at rt until the bubbling stops, plus an additional 2 minutes, then water (1 mL) was added. The mixture was diluted with EtOAc, washed with NaHCO$_3$ solution, sat. NaHCO3, (back extract aq layer), then dry organic layer over Na$_2$SO$_4$, filter and evaporate. The residue was purified via flash chromatography using a 1% NH$_4$OH in MeOH in CH$_2$Cl$_2$ gradient to afford the title compound as a tan solid.

b) 7-Methoxy-N-((6-(3,4,5-trifluorophenyl)imidazo[1,2-b]pyridazin-3-yl)methyl)-1,5-naphthyridin-4-amine. The title compound was prepared according to Method D, with the addition of 1 equivalent TFA. M/Z=437.1 [M+H], calc 436.3955 for C$_{22}$H$_{15}$F$_3$N$_6$O.

2-Methyl-5-(4,4,5,5-tetramethyl-1,3,2-dioxaborolan-2-yl)isoindolin-1-one

In a sealable tube was combined Pd$_2$dba$_3$ (0.0270 g, 0.0295 mmol), 2-(dicyclohexylphosphino)-2',4',6'-tri-1-propyl-1,1'-biphenyl (0.0563 g, 0.118 mmol), 4,4,5,5-tetramethyl-2-(4,4,5,5-tetramethyl-1,3,2-dioxaborolan-2-yl)-1,3,2-dioxaborolane (0.450 g, 1.77 mmol), 5-bromo-2-methylisoindolin-1-one (see Tsuritani, T., et al Synlett 2006, 5 801-803) (0.267 g, 1.18 mmol), potassium acetate (0.232 g, 2.36 mmol) and 2 mL dioxane. The mixture was blanketed with N$_2$, sealed and heated at 80 C for 22 h. The mixture was allowed to cool to rt then diluted with EtOAc, and the organic layer washed with water, sat. NaHCO$_3$, then dried over Na$_2$SO$_4$, filtered and evaporated. The residue was purified via flash chromatography using a EtOAc in CH$_2$Cl$_2$ gradient. The title compound was collected as a tan solid.

tert-Butyl 4-(4-(4,4,5,5-tetramethyl-1,3,2-dioxaborolan-2-O-1H-pyrazol-1-yl)piperidine-1-carboxylate The title compound was prepared according procedures known in the art.

1-Ethyl-4-(4,4,5,5-tetramethyl-1,3,2-dioxaborolan-2-yl)-1H-pyrazole

A 150 mL sealable tube was charged with Pd$_2$dba$_3$ (0.216 g, 0.235 mmol), 2-(dicyclohexylphosphino)-2',4',6'-tri-1-propyl-1,1'-biphenyl (0.224 g, 0.471 mmol), 4,4,5,5-tetramethyl-2-(4,4,5,5-tetramethyl-1,3,2-dioxaborolan-2-yl)-1,3,2-dioxaborolane (7.47 g, 29.4 mmol), 4-bromo-1-ethyl-1H-pyrazole (see Ivachtchenko, A. V., et al J. Het. Chem. 2004, 41, 931-939) (4.12 g, 23.5 mmol), potassium acetate (4.62 g, 47.1 mmol) and dioxane (10 mL). The mixture was blanketed with N$_2$, the vessel sealed and heated at 85 C for 22 h. Allow the mixture to cool to rt and dilute with EtOAc, wash with water, sat. NaHCO$_3$, then dry organic layer over Na$_2$SO$_4$, filter and evaporate. The mixture was purified via flash chromatography using an EtOAc in CH$_2$Cl$_2$ gradient. Use I$_2$ stain to develop tlc (compound not uv active at 254). The title compound was collected as a mixture with pinacol diborane.

1-(2-Methoxyethyl)-4-(4,4,5,5-tetramethyl-1,3,2-dioxaborolan-2-yl)-1H-pyrazole

The title compound was prepared in the same manner as 1-ethyl-4-(4,4,5,5-tetramethyl-1,3,2-dioxaborolan-2-yl)-

1H-pyrazole, using 1-(2-methoxyethyl)-4-bromo-1H-pyrazole (see Ivachtchenko, A. V., et al *J. Het. Chem.* 2004, 41, 931-939).

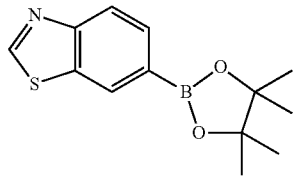 [SMILES: CC1(C)OB(c2ccc3ncsc3c2)OC1(C)C]

6-(4,4,5,5-tetramethyl-1,3,2-dioxaborolan-2-yl)benzo[d]thiazole

Prepared from 6-bromobenzo[d]thiazole according to the above procedures.

1-Cyclobutyl-4-(4,4,5,5-tetramethyl-1,3,2-dioxaborolan-2-O-1H-pyrazole a) 4-Bromo-1-cyclobutyl-1H-pyrazole. To a cooled (0 C) stirred solution of 4-bromo-1H-pyrazole (5.360 g, 36.47 mmol) in DMF (50 mL) was added sodium hydride (1.925 g, 80.23 mmol) slowly. The mixture was allowed to stir in the ice bath 30 min and bromocyclobutane (3.433 ml, 36.47 mmol) was added. The vessel was sealed and the reaction mixture heated at 95 C for 23 h. The mixture was allowed to cool to rt and diluted with 200 mL EtOAc, washed with 500 mL water, then 2×100 mL water, sat NaHCO₃, then the organic layer dried over Na₂SO₄, filtered and evaporated. The mixture was purified via flash chromatography using a CH₂Cl₂ in hexanes gradient. (I2 stain for visualization).

The title compound was collected as a colorless liquid.

b) 1-Cyclobutyl-4-(4,4,5,5-tetramethyl-1,3,2-dioxaborolan-2-yl)-1H-pyrazole. The title compound was prepared in the same manner as described for 1-ethyl-4-(4,4,5,5-tetramethyl-1,3,2-dioxaborolan-2-yl)-1H-pyrazole.

1-Isopropyl-4-(4,4,5,5-tetramethyl-1,3,2-dioxaborolan-2-yl)-1H-pyrazole a) 4-bromo-1-isopropyl-1H-pyrazole. A sealable vessel was charged with potassium carbonate (3.76 g, 27.2 mmol), 4-bromo-1H-pyrazole (4.00 g, 27.2 mmol), and 10 mL DMF. To this mixture, 2-iodopropane (3.27 ml, 32.7 mmol) was added and the vessel sealed. The mixture was heated at 80 C for 16 h and allowed to cool to rt. The mixture was diluted with EtOAc, extracted with water, water, sat NaHCO3, and the organic layer dried over Na₂SO₄, filtered and evaporated. The mixture was purified via flash chromatography using a EtOAc in CH2Cl2 gradient. The desired compound (as determined by TLC, I2 stain) was collected as a colorless liquid.

b) 1-isopropyl-4-(4,4,5,5-tetramethyl-1,3,2-dioxaborolan-2-yl)-1H-pyrazole. The title compound was prepared in the same manner as described for 1-ethyl-4-(4,4,5,5-tetramethyl-1,3,2-dioxaborolan-2-yl)-1H-pyrazole.

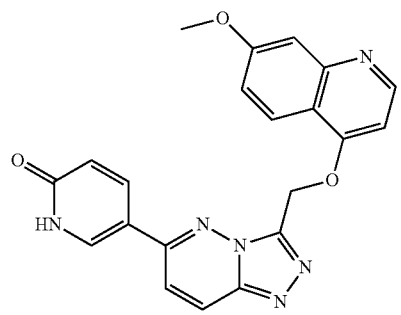 [SMILES: COc1ccc2c(OCc3nnc4ccc(-c5ccc(=O)[nH]c5)nn34)ccnc2c1]

EXAMPLE 63

Intermediate 4-((6-(6-fluoropyridin-3-yl)-[1,2,4]triazolo[4,3-b]pyridazin-3-yl)methoxy)-7-methoxyquinoline was prepared as described in general Method A.

5-(3-((7-Methoxyquinolin-4-yloxy)methyl)-[1,2,4]-triazolo[4,3-b]pyridazin-6-yl)pyridin-2(1H)-one 4-((6-(6-Fluoropyridin-3-yl)-[1,2,4]triazolo[4,3-b]pyridazin-3-yl)methoxy)-7-methoxyquinoline (0.121 g, 0.30 mmol) was suspended in dioxane (1 mL) then added 3M aqueous hydrochloric acid (2.0 ml, 6.0 mmol). The reaction mixture was then heated at 100° C. for 1 hour. The mixture was concentrated under vacuum and the remaining solid was dissolved in methanol (4 mL) then added triethylamine (0.42 ml, 3.0 mmol). The mixture was stirred at room temperature for 1 hour then concentrated under vacuum. The sample was purified by flash chromatography eluting with 15% 7N NH₃ in methanol/dichloromethane to afford 5-(3-((7-methoxyquinolin-4-yloxy)methyl)-[1,2,4]triazolo[4,3-b]pyridazin-6-yl)pyridin-2(1H)-one as a pale orange solid.

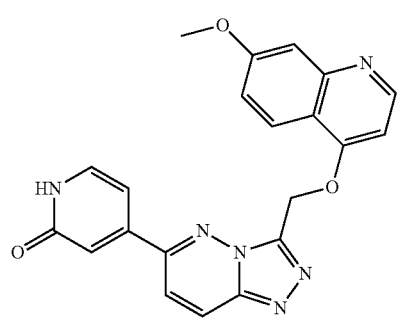 [SMILES: COc1ccc2c(OCc3nnc4ccc(-c5cc[nH]c(=O)c5)nn34)ccnc2c1]

EXAMPLE 64

4-(3-((7-Methoxyquinolin-4-yloxy)methyl)-[1,2,4]triazolo[4,3-b]pyridazin-6-yl)pyridin-2(1H)-one was prepared as previously described for 5-(3-((7-methoxyquinolin-4-yloxy)methyl)-[1,2,4]triazolo[4,3-b]pyridazin-6-yl)pyridin-2(1H)-one.

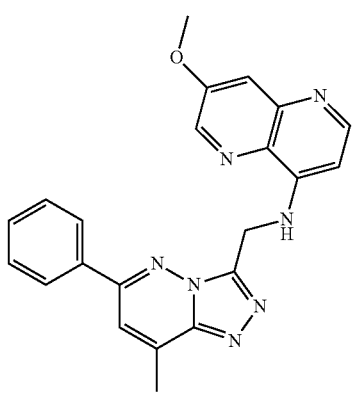 [SMILES: COc1cnc2c(NCc3nnc4c(C)cc(-c5ccccc5)nn34)ccnc2c1]

EXAMPLE 65

Synthesis of the Hydrazine Intermediate

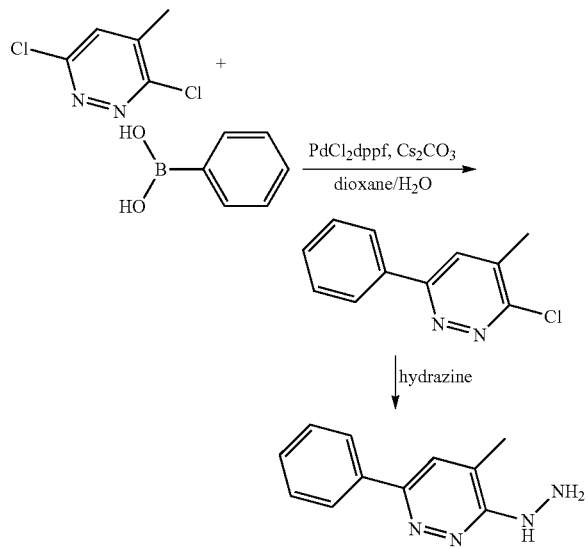

Step 1.

3,6-Dichloro-4-methylpyridazine (1.00 g, 6.1 mmol) was mostly dissolved in dioxane (22.5 mL) then added phenylboronic acid (0.82 g, 6.7 mmol), PdCl$_2$(dppf)-CH$_2$Cl$_2$Adduct (0.25 g, 0.31 mmol) and a solution of cesium carbonate (6.0 g, 18 mmol) in water (7.5 mL). The reaction mixture was heated at 80° C. for 6 hours. The reaction mixture was concentrated under vacuum and the remaining solid was triturated with water. The solid was collected on a glass frit, washing well with water. The sample was purified by flash chromatography eluting with 1:4 ethyl acetate/hexane to afford 3-chloro-4-methyl-6-phenylpyridazine as an off-white solid.

MS (ESI pos. ion) m/z: 205.2 (MH$^+$).

Step 2.

3-Chloro-4-methyl-6-phenylpyridazine (0.510 g, 2.49 mmol) was dissolved in hydrazine (1.56 ml, 49.8 mmol) then the reaction mixture was heated at 100° C. for 1.5 hours. The precipitate that had formed in the mixture was collected and washed with $^i$PrOH. The solid was dried under high vacuum to afford 1-(4-methyl-6-phenylpyridazin-3-yl)hydrazine as a pale yellow solid.

MS (ESI pos. ion) m/z: 201.1 (MH$^+$).

The remaining synthesis of 7-methoxy-N-((8-methyl-6-phenyl-[1,2,4]triazolo[4,3-b]pyridazin-3-yl)methyl)-1,5-naphthyridin-4-amine was conducted as described in general Method B.

Synthesis of the 1-Methyl-5-(4,4,5,5-tetramethyl-1,3,2-dioxaborolan-2-yl)pyridin-2(1H)-one Intermediate

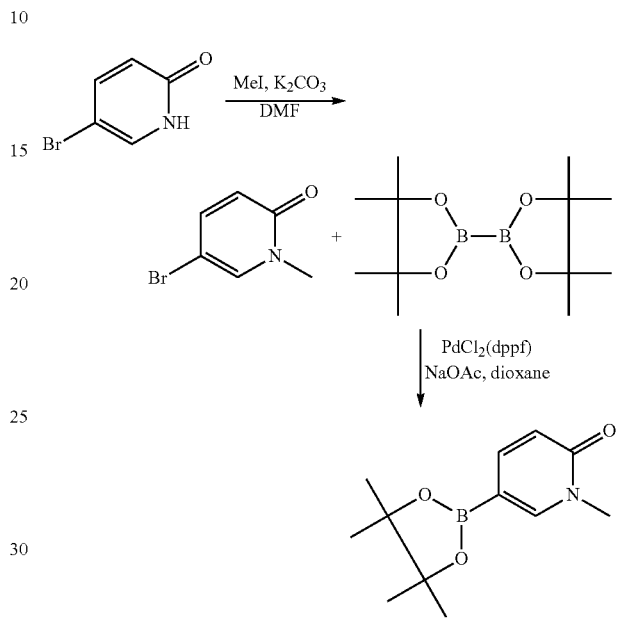

Step 1.

5-Bromopyridin-2(1H)-one (0.250 g, 1.44 mmol) was dissolved in DMF (3 mL) then added iodomethane (0.0943 ml, 1.51 mmol) and potassium carbonate (0.218 g, 1.58 mmol). The reaction was stirred at room temperature overnight. The reaction mixture was concentrated under vacuum. The remaining residue was dissolved in ethyl acetate then washed with water and brine. The aqueous layer was back-extracted with ethyl acetate (3×). The organic layers were combined and dried over sodium sulfate then concentrated under vacuum to afford 5-bromo-1-methylpyridin-2(1H)-one as an orange waxy solid.

MS (ESI pos. ion) m/z: 188.0 and 190.0 (MH$^+$).

Step 2.

5-Bromo-1-methylpyridin-2(1H)-one (0.100 g, 0.532 mmol) was suspended in dioxane (2 mL) then added 4,4,5,5-tetramethyl-2-(4,4,5,5-tetramethyl-1,3,2-dioxaborolan-2-yl)-1,3,2-dioxaborolane (0.203 g, 0.798 mmol), PdCl2(dppf)-CH$_2$Cl$_2$Adduct (0.0217 g, 0.0266 mmol) and sodium acetate (0.109 g, 1.33 mmol). The reaction mixture was heated at 120° C. for 5.5 hours then at 130° C. for 3 hours. The reaction mixture was filtered through a pad of Celite, washing with MeOH. The filtrate was concentrated under vacuum. The remaining black residue was then dissolved in dichloromethane and filtered through another pad of Celite, washing well with dichloromethane. The filtrate was concentrated under vacuum and the remaining black residue was further dried under high vacuum to afford 1-methyl-5-(4,4,5,5-tetramethyl-1,3,2-dioxaborolan-2-yl)pyridin-2(1H)-one as a black solid.

MS (ESI pos. ion) m/z: 236.1 (MH$^+$).

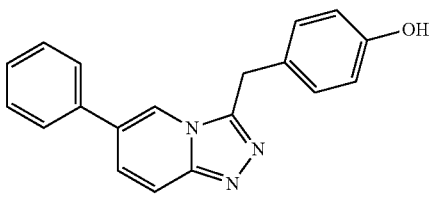 [SMILES: Oc1ccc(Cc2nnc3ccc(-c4ccccc4)cn23)cc1]

EXAMPLE 66

Intermediate 3-(4-methoxybenzyl)-6-phenyl-[1,2,4]triazolo[4,3-a]pyridine was prepared as described in general Method A.

4-((6-phenyl-[1,2,4]-triazolo[4,3-a]pyridin-3-yl)methyl)phenol 3-(4-Methoxybenzyl)-6-phenyl-[1,2,4]triazolo[4,3-a]pyridine (0.057 g, 0.18 mmol) was dissolved in dichloromethane (2.5 mL) then cooled to 0° C. A 1M solution of boron tribromide (0.72 ml, 0.72 mmol) in dichloromethane was added slowly. The reaction mixture was stirred at 0° C. for 2 hours. A precipitate was present in the reaction mixture. The reaction was quenched with ice chips and stirred overnight at room temperature. A solid remained in the mixture. The reaction mixture was diluted with dichloromethane/methanol to give a clear mixture then washed with saturated aqueous sodium bicarbonate and brine. The organic layer was dried over sodium sulfate and concentrated under vacuum. The sample was purified by preparative TLC eluting with 7% methanol in dichloromethane which afforded 4-((6-phenyl-[1,2,4]triazolo[4,3-a]pyridin-3-yl)methyl)phenol as an off-white solid

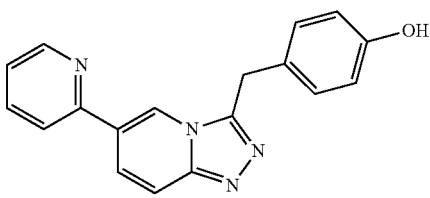 [SMILES: Oc1ccc(Cc2nnc3ccc(-c4ccccn4)cn23)cc1]

EXAMPLE 67

4-((6-(Pyridin-2-yl)-[1,2,4]triazolo[4,3-a]pyridin-3-yl)methyl)phenol was prepared as previously described for 4-((6-phenyl-[1,2,4]triazolo[4,3-a]pyridin-3-yl)methyl)phenol.

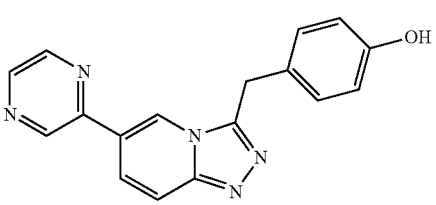 [SMILES: Oc1ccc(Cc2nnc3ccc(-c4cnccn4)cn23)cc1]

EXAMPLE 68

4-((6-(Pyrazin-2-yl)-[1,2,4]triazolo[4,3-a]pyridin-3-yl)methyl)phenol was prepared as previously described for 4-((6-phenyl-[1,2,4]triazolo[4,3-a]pyridin-3-yl)methyl)phenol.

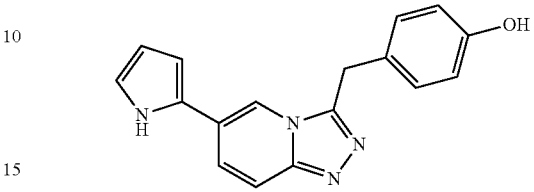

EXAMPLE 69

4-((6-(1H-Pyrrol-2-yl)-[1,2,4]triazolo[4,3-a]pyridin-3-yl)methyl)phenol was prepared as previously described for 4-((6-phenyl-[1,2,4]triazolo[4,3-a]pyridin-3-yl)methyl)phenol.

6-bromoquinoxaline

To a solution of 4-bromobenzene-1,2-diamine (4.0 g, 21 mmol) in 60 mL of EtOH was added 40% glyoxal aldehyde (4.1 ml, 32 mmol) solution in water. The resulting mixture was refluxed for 10 hours. The mixture was concentrated in vacuo and the residue was diluted in 100 mL of EtOAc. The organic solution was washed with 40 mL of satd. NaHCO$_3$ and 40 mL of brine, dried over Na$_2$SO$_4$ and concentrated in vacuo. The residue was purified by a silca gel column chromatography (5% EtOAc/hex to EtOAC) to give light yellow solid 6-bromoquinoxaline. MS (ESI, pos. ion) m/z: 208.9 (M+1).

tert-butyl 2-(quinoxalin-6-yl)acetate

To a solution of 6-bromoquinoxaline (1.40 g, 7 mmol), tris(dibenzylideneacetone)dipalladium (o) (0.6 g, 0.7 mmol) and Q-phos (1.0 g) in 25 mL of THF was added Reactant 2 (27 ml, 27 mmol) three time in 3 hours. The reaction was heated at 50 oC for 16 hours and was quenched with 50 mL of satd. NH4Cl. The mixture was diluted with 60 mL of EtOAc. The organic phase was separated, washed with brine, dried over Na2SO4 and concentrated in vacuo to give red oil. The residue was purified by a silica gel column chromatography (5% EtOAc/hex to EtOAC) twice to give red solid tert-butyl 2-(quinoxalin-6-yl)acetate. MS (ESI, pos. ion) m/z: 245.1 (M+1).

6-((6-phenyl-[1,2,4]triazolo[4,3-b]pyridazin-3-yl)methyl)quinoxaline

A mixture of tert-butyl 2-(quinoxalin-6-yl)acetate (0.15 g, 0.6 mmol), 1-(6-phenylpyridazin-3-yl)hydrazine (0.1 g, 0.7 mmol) and p-toluenesulfonic acid monohydrate (0.1 g, 0.6 mmol) in 3 mL of dioxane was heated with microwave at 150° C. for 1 hour in a microwave tube. The mixture was diluted with 70 mL of EtOAc and 40 mL of satd. NaHCO$_3$ solution. The organic phase was separated and was washed with 40 mL of brine, dried over Na$_2$SO$_4$ and concentrated in vacuo. The residue was purified by a silica gel column chromatography (EtOAc to 15% MeOH/EtOAc) to give light yellow solid as desired product 6-((6-phenyl-[1,2,4]triazolo[4,3-b]pyridazin-3-yl)methyl)quinoxaline.

6-bromoquinazolin-4(3H)-one

A solution of 5-bromoisatoic anhydride (5.0 g, 21 mmol) and formamidinium acetate (2.2 g, 21 mmol) in 60 mL of i-PrOH was heated at reflux for 10 hours. The reaction mixture was cooled to rt and the white solid was collected by filtration. The white solid was washed with small amount of i-PrOH and dried in air to give desired product 6-bromoquinazolin-4(3H)-one. MS (ESI, pos. ion) m/z: 224.9 (M+1).

tert-butyl 2-(4-oxo-3,4-dihydroquinazolin-6-yl)acetate

To a solution of 6-bromoquinazolin-4(3H)-one (1.00 g, 4 mmol), tris(dibenzylideneacetone)dipalladium (o) (0.4 g, 0.4 mmol) and Q-phos (0.8 g) in 25 mL of THF was added Reactant 2 (27 ml, 13 mmol) three time in 5 hours. The reaction was heated at 50° C. for 16 hours and was quenched with 50 mL of satd. NH$_4$Cl. The mixture was diluted with 60 mL of EtOAc. The organic phase was separated, washed with brine, dried over Na2SO4 and concentrated in vacuo to give red oil. The residue was purified by a silica gel column chromatography (5% EtOAc/hex to EtOAC) twice to give orange solid tert-butyl 2-(4-oxo-3,4-dihydroquinazolin-6-yl)acetate. MS (ESI, pos. ion) m/z: 261.1 (M+1).

2-(4-oxo-3,4-dihydroquinazolin-6-yl)acetic acid

A solution of tert-butyl 2-(4-oxo-3,4-dihydroquinazolin-6-yl)acetate (0.25 g, 0.96 mmol) in 10 mL of satd.HCl in EtOAc was stirred at rt for 4 hours. The mixture was concentrated in vacuo at rt, and the residue was used in the next reaction without further purification. MS (ESI, pos. ion) m/z: 205.1 (M+1).

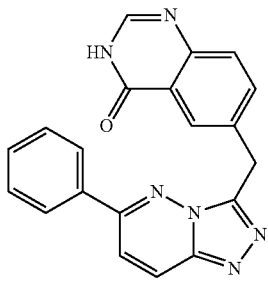 [SMILES: O=c1[nH]cnc2ccc(Cc3nnc4ccc(-c5ccccc5)nn34)cc12]

EXAMPLE 70

6-((6-phenyl-[1,2,4]-triazolo[4,3-b]pyridazin-3-yl) methyl)quinazolin-4(3H)-one A mixture of 2-(4-oxo-3,4-dihydroquinazolin-6-yl)acetic acid (0.10 g, 0.5 mmol), 1-(6-phenylpyridazin-3-yl)hydrazine (0.1 g, 0.6 mmol) and p-toluenesulfonic acid monohydrate (0.09 g, 0.5 mmol) in 3 mL of dioxane was heated with microwave at 150° C. for 1 hour in a microwave tube. The mixture was diluted with 70 mL of EtOAc and 40 mL of satd. NaHCO3 solution. The organic phase was separated and was washed with 40 mL of brine, dried over Na2SO4 and concentrated in vacuo. The residue was purified by a silica gel column chromatography (EtOAc to 15% MeOH/EtOAc) to give light yellow solid as desired product 6-((6-phenyl-[1,2,4]triazolo[4,3-b]pyridazin-3-yl)methyl)quinazolin-4(3H)-one. MS (ESI, pos. ion) m/z: 355.1 (M+1).

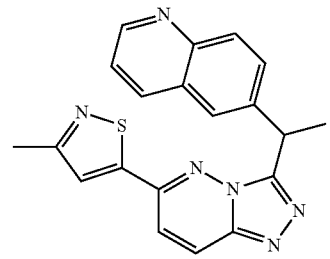 [SMILES: Cc1cc(-c2ccc3nnc(C(C)c4ccc5ncccc5c4)n3n2)sn1]

EXAMPLE 71

6-(1-(6-(3-methylisothiazol-5-yl)-[1,2,4]-triazolo[4, 3-b]pyridazin-3-yl)ethyl)quinoline To a solution of 5-bromo-3-methylisothiazole (1.00 g, 5.6 mmol) in 10 mL of THF at −45° C. (CH$_3$CN/dry ice) was added isopropylmagnesium chloride LiCl complex (7.9 ml, 7.9 mmol) (LiCl complex, 1M in THF). The mixture was stirred at −45° C. for 20 minutes and was added zinc chloride, 0.5m in thf (17 ml, 8.4 mmol) slowly via a syringe. The mixture was then warmed up to rt and continued to stir for additional 30 minutes. 6-(1-(6-chloro-[1,2,4]triazolo[4,3-b]pyridazin-3-yl)ethyl)quinoline (0.5787 g, 1.9 mmol), tris (dibenzylideneacetone)dipalladium (o) (0.51 g, 0.56 mmol) and Q-Phos (0.65 g) in 15 mL of N,N-dimethyl acetamide was added to the reaction mixture. The reaction was warmed up to 50° C. for 6 h and was quenched with 50 mL of satd. NH$_4$Cl aq. solution. The mixture was extracted with 150 mL of EtOAc and the organic phase was washed with 60 mL of brine. The aqueous phases were extracted with 100 mL EtOAc again. The combined organic phases were dried over Na$_2$SO$_4$ and concentrated in vacuo. The residue was purified by a silica gel column chromatography (EtOAc to 15% MeOH in EtOAc) to give red solid as desired product 6-(1-(6-(3-methylisothiazol-5-yl)-[1,2,4]triazolo[4,3-b]pyridazin-3-yl)ethyl)quinoline. MS (ESI, pos. ion) m/z: 373.2 (M+1).

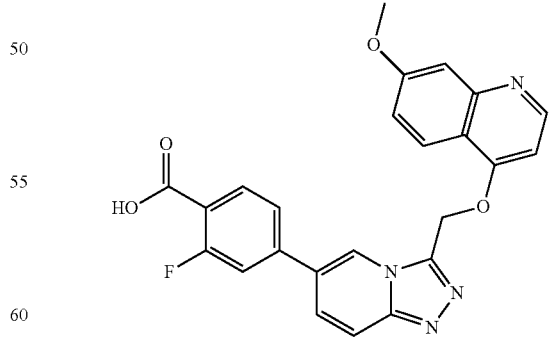

Methyl 2-fluoro-4-(3-((7-methoxyquinolin-4-yloxy)methyl)-[1,2,4]triazolo[4,3-a]pyridin-6-yl)benzoate (0.368 g, 0.803 mmol) was diluted with dioxane (17 mL) and to the solution was added lithium hydroxide (0.0384 g, 1.61 mmol) in water (8 mL). The reaction mixture was heated at 40° C. for 4.5 hours. The reaction mixture was concentrated in vacuo to remove most of the dioxane and water (not concentrated to dryness).

To the crude mixture, water (8 mL) was added. Dropwise, 1N HCl was added to pH=7. The neutral solution was then filtered through a frit and the crude solid product was washed with MeCN and a small amount of MeOH. The final acid product was concentrated, and carried on to the acid chloride.

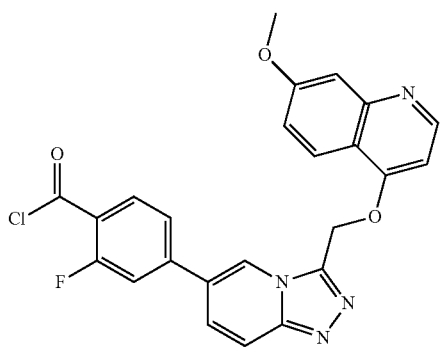 [SMILES: COc1ccc2c(OCc3nnc4ccc(-c5ccc(C(=O)Cl)c(F)c5)cn34)ccnc2c1]

To a suspension of 2-fluoro-4-(3-((7-methoxyquinolin-4-yloxy)methyl)-[1,2,4]triazolo[4,3-a]pyridin-6-yl)benzoic acid (0.150 g, 0.338 mmol) in DCM (1.5 mL) at 0° C. was added dropwise thionyl chloride (0.370 ml, 5.06 mmol). DMF (1 drop) was added and the solution was allowed to stir at room temperature for 5 h. The reaction mixture was concentrated in vacuo to a light brown solid. The material was taken on crude for synthesis of the following amide.

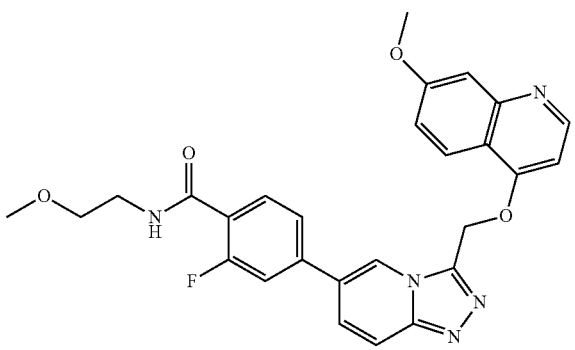 [SMILES: COCCNC(=O)c1ccc(-c2ccc3nnc(COc4ccnc5cc(OC)ccc45)n3c2)cc1F]

EXAMPLE 72

2-fluoro-N-(2-methoxyethyl)-4-(3-((7-methoxyquinolin-4-yloxy)methyl)-[1,2,4,]triazolo[4,3-a]pyridin-6-yl)benzamide To a solution of N-ethyl-N-isopropylpropan-2-amine (0.077 ml, 0.44 mmol) and 2-fluoro-4-(3 #7-methoxyquinolin-4-yloxy)methyl)-[1,2,4]triazolo[4,3-a]pyridin-6-yl)benzoyl chloride-HCl (0.088 g, 0.18 mmol) in DCM (1.25 mL) was added 2-methoxyethanamine (0.023 ml, 0.26 mmol) dropwise. The solution was stirred at room temperature for 5 h. The crude material was concentrated and then triturated with sodium bicarbonate and washed with water. The resultant solid was dissolved in DCM/MeOH and concentrated.

The crude material was dissolved in DCM/MeOH and was purified via flash chromatography, eluting with 0-10% MeOH/NH₄OH in DCM to yield 2-fluoro-N-(2-methoxyethyl)-4-(3-((7-methoxyquinolin-4-yloxy)methyl)-[1,2,4]triazolo[4,3-a]pyridin-6-yl)benzamide.

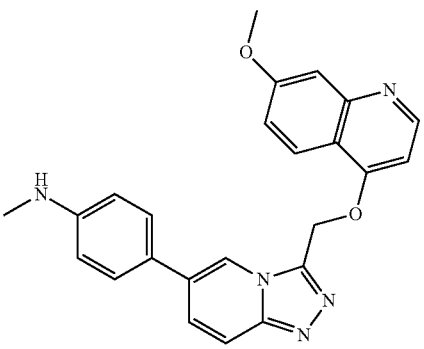 [SMILES: CNc1ccc(-c2ccc3nnc(COc4ccnc5cc(OC)ccc45)n3c2)cc1]

EXAMPLE 73 tert-butyl 4-(3-((7-methoxyquinolin-4-yloxy)methyl)-[1,2,4]triazolo[4,3-a]pyridin-6-yl)phenyl(methyl)carbamate (0.067 g, 0.13 mmol) was dissolved in MeOH (1.7 mL) and to the solution was added concentrated HCl (0.50 ml, 6.0 mmol). The reaction mixture was stirred at room temperature overnight. Upon completion, the crude mixture was concentrated in vacuo.

The solid that remained after concentration was dissolved in MeOH and to the solution was added triethylamine (0.23 ml, 1.6 mmol). The reaction was allowed to stir for 1 h. The crude mixture was concentrated in vacuo.

The compound was purified using via flash chromatography, eluting with 5-8% MeOH/NH₄OH in DCM to yield 4-(3-((7-methoxyquinolin-4-yloxy)methyl)-[1,2,4]triazolo[4,3-a]pyridin-6-yl)-N-methylbenzenamine as a yellow solid.

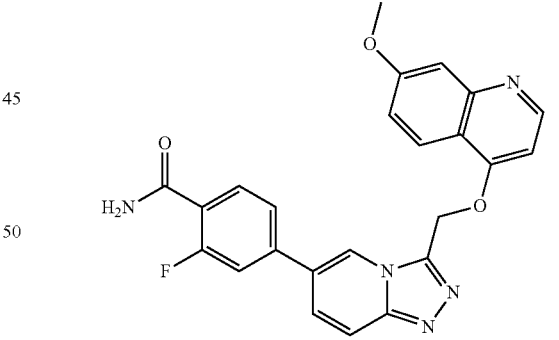

EXAMPLE 74

A solution of 2-fluoro-4-(3-((7-methoxyquinolin-4-yloxy)methyl)-[1,2,4]triazolo[4,3-a]pyridin-6-yl)benzoic acid (0.192 g, 0.43 mmol), HATU (0.26 g, 0.69 mmol), and Hunig's Base (0.30 ml, 1.7 mmol) in DMF (10.75 mL) was allowed to stir for 30 minutes. Ammonia (0.0093 ml, 0.43 mmol) was then bubbled through the mixture for another 30 minutes.

The solution was concentrated in vacuo and purified using via flash chromatography, eluting with 5-10% MeOH/

NH$_4$OH in DCM. There remained an unidentified peak in the NMR, so the solid was triturated in MeCN, filtered, and quickly washed with DCM to wash through the impurities. Concentration in vacuo yielded 2-fluoro-4-(3-((7-methoxyquinolin-4-yloxy)methyl)-[1,2,4]triazolo[4,3-a]pyridin-6-yl)benzamide as an off-white solid.

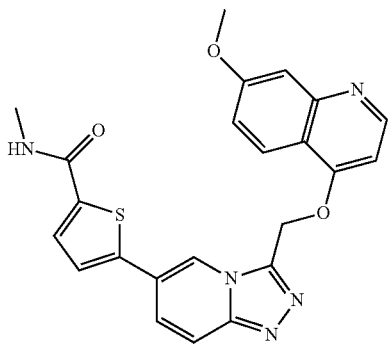 [SMILES: CNC(=O)c1ccc(-c2ccc3nnc(COc4ccnc5cc(OC)ccc45)n3c2)s1]

EXAMPLE 75

To a solution of 5-(3-((7-methoxyquinolin-4-yloxy)methyl)-[1,2,4]triazolo[4,3-a]pyridin-6-yl)thiophene-2-carbonyl chloride (0.150 g, 0.33 mmol) and Hunig's Base (0.17 ml, 1.00 mmol) in DCM (2.5 mL) was added methanamine (0.17 ml, 0.33 mmol) in THF dropwise. The solution was stirred at room temperature for 3 hours, at which point an additional 1.5 equivalents of amine were added. The solution was concentrated in vacuo and purified via flash chromatography eluting with 3-8% MeOH:NH$_4$OH in DCM. There remained an impurity, so the product was triturated with MeCN, filtered and washed with DCM to yield 5-(3-((7-methoxyquinolin-4-yloxy)methyl)-[1,2,4]triazolo[4,3-a]pyridin-6-yl)-N-methylthiophene-2-carboxamide (0.0276 g, 19% yield) as an amorphous tan solid.

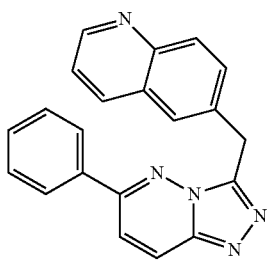 [SMILES: c1ccc(-c2ccc3nnc(Cc4ccc5ncccc5c4)n3n2)cc1]

EXAMPLE 76

6-((6-Phenyl-[1,2,4]triazolo[4,3-b]pyridazin-3-yl)methyl)quinoline

To a 50 ml round-bottomed flask was added 2-(quinolin-6-yl)acetic acid (0.60 g, 3.2 mmol), CH$_2$Cl$_2$ (20 ml) and oxalyl chloride (4.0 ml, 8.0 mmol, 2 M in CH$_2$Cl$_2$) and DMF (0.2 mL of a solution of 1 drop DMF in 1 mL CH$_2$Cl$_2$). After 3 d, an additional 2.5 eq. of oxalyl chloride was added. After 4 h, toluene (1 mL) was added and the mixture was concentrated. Toluene (3 mL) was added and again concentrated. The residue was taken up in CH$_2$Cl$_2$ (20 mL) and 1-(6-phenylpyridazin-3-yl)hydrazine (0.60 g, 3.2 mmol) was added.

The mixture was stirred for 17 h and then concentrated. The mixture was then taken up in phosphorous oxychloride (20 ml, 220 mmol) and heated at 100° C. for 15 h. Toluene (5 mL) was added and the solution was concentrated. Another 5 mL toluene was added to the residue and once again it was concentrated. The brown solid residue was taken up in sat. NaHCO$_3$ and extracted with EtOAc (4×150 mL) and 25% iPrOH/CHCl$_3$ (3×150 mL). The combined extracts were washed with brine, dried (Na$_2$SO$_4$) and concentrated onto silica. Purification by silica gel chromatography (0 to 5% MeOH (2M in NH$_3$)/CH$_2$Cl$_2$) afforded the title compound as a tan solid. MS (ESI, pos. ion) m/z: 338 (M+1).

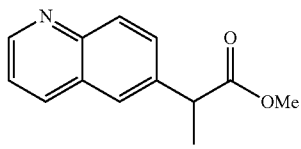 [SMILES: COC(=O)C(C)c1ccc2ncccc2c1]

Methyl 2-(quinolin-6-yl)propanoate

To a 250 ml round-bottomed flask was added lithium bis(trimethylsilyl)amide (2.0 g, 12 mmol) and tetrahydrofuran (75 ml). The mixture was cooled to −78° C. and methyl 2-(quinolin-6-yl)acetate (2.0 g, 9.9 mmol) was added as a solution in 1 ml THF. This was stirred at −78° C. for 30 min and then methyl iodide (0.75 ml, 12 mmol) was added. This was stirred for 30 min at −78° C. and then allowed to warm to rt. The mixture was quenched with sat NH$_4$Cl (40 mL) and diluted with water (200 mL). The mixture was concentrated in vacuo to remove the THF and then was extracted with EtOAc (2×100 ml). The combined extracts were washed with brine (50 ml), dried (Na$_2$SO$_4$) and concentrated onto silica. Purification by silica gel chromatography (20 to 60% EtOAc/hexane) afforded the title compound as a brown oil (1.8 g, 85%). MS (ESI, pos. ion) m/z: 216 (M+1).

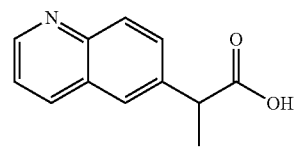

2-(Quinolin-6-yl)propanoic acid

To a 15 ml round-bottomed flask was added methyl 2-(quinolin-6-yl)propanoate (1.0 g, 4.7 mmol), methanol (5.0 ml, 12 mmol) and aq. sodium hydroxide (5 M, 2.3 ml, 12 mmol). The mixture was stirred at 25° C. for 24 h. The mixture was neutralized with aq. HCl (5 M, 2.3 mL, 12 mmol). After sitting overnight a white precipitate had formed. The mixture was filtered and the filtercake was washed with water and then dried in vacuo to afford the title compound as a white solid (0.72 g, 77%). MS (ESI, pos. ion) m/z: 202 (M+1).

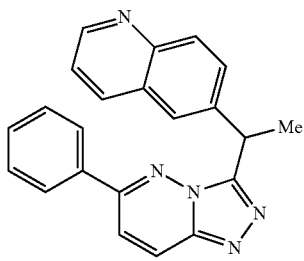 [SMILES: CC(c1ccc2ncccc2c1)c1nnc2ccc(-c3ccccc3)nn12]

EXAMPLE 77

6-(1-(6-Phenyl-[1,2,4]triazolo[4,3-b]pyridazin-3-yl)ethyl)quinoline

To a 2-5 ml Personal Chemistry microwave vial was added 2-(quinolin-6-yl)propanoic acid (0.25 g, 1.2 mmol), 1-(6-phenylpyridazin-3-yl)hydrazine (0.42 g, 2.2 mmol) and conc. HCl (2 mL). The mixture was heated in the microwave at 160° C. for 8 h. After cooling to rt, the mixture was poured into sat. NaHCO$_3$ (100 mL) and then extracted with EtOAc (4×75 mL). The combined extracts were washed with brine, dried (Na$_2$SO$_4$) and concentrated onto silica. Purification by silica gel chromatography (1.0 to 4.5% MeOH (2 M in NH$_3$)/CH$_2$Cl$_2$) afforded the title compound as an off-white solid (0.23 g, 53% yield). MS (ESI, pos. ion) m/z: 352 (M+1).

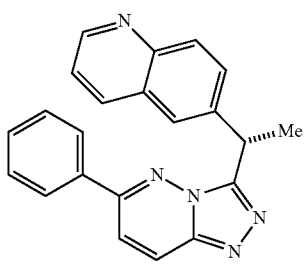 [SMILES: C[C@@H](c1ccc2ncccc2c1)c1nnc2ccc(-c3ccccc3)nn12]

EXAMPLE 78

(S)-6-(1-(6-phenyl-[1,2,4]triazolo[4,3-b]pyridazin-3-yl)ethyl)quinoline

Isolated from chiral separation of 6-(1-(6-phenyl-[1,2,4]triazolo[4,3-b]pyridazin-3-yl)ethyl)quinoline. Column: Chiralpak AS-H (250×21 mm) Mobile Phase: A: Liquid CO$_2$. B: Methanol (0.1% DEA). Isocratic: 75:25 (A:B). Flow rate: 70.0 mL/min. Outlet Pressure: 100 bar. Retention time: 4.38 min. Enantiomeric purity: >99% ee. MS (ESI, pos. ion) m/z: 352 (M+1).

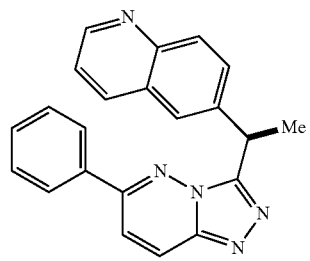 [SMILES: C[C@H](c1ccc2ncccc2c1)c1nnc2ccc(-c3ccccc3)nn12]

EXAMPLE 79

(R)-6-(1-(6-phenyl-[1,2,4]-triazolo[4,3-b]pyridazin-3-yl)ethyl)quinoline (AMG 2121451)

Isolated from chiral separation of 6-(1-(6-phenyl-[1,2,4]triazolo[4,3-b]pyridazin-3-yl)ethyl)quinoline. Column: Chiralpak AS-H (250×21 mm). Mobile Phase: A: Liquid CO$_2$. B: Methanol (0.1% DEA). Isocratic: 75:25 (A:B). Flow rate: 70.0 mL/min. Outlet Pressure: 100 bar. Retention time: 4.90 min. Enantiomeric purity: 96.8% ee. MS (ESI, pos. ion) m/z: 352 (M+1).

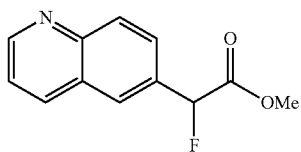 [SMILES: COC(=O)C(F)c1ccc2ncccc2c1]

Methyl 2-fluoro-2-(quinolin-6-yl)acetate

To a 250 ml round-bottomed flask was added lithium bis(trimethylsilyl)amide (2.0 g, 12 mmol) and tetrahydrofuran (75 ml). The mixture was cooled to −78° C. and methyl 2-(quinolin-6-yl)acetate (2.0 g, 9.9 mmol) was added as a solution in 1 ml THF. After stirring at −78° C. for 30 min, n-fluorobenzenesulfonimide (3.8 g, 12 mmol) was added as a 1 M solution in THF. This was stirred for 30 min at −78° C. and then allowed to warm to rt. The mixture was quenched with sat NH$_4$Cl (50 mL) and diluted with water (200 mL). The mixture was concentrated in vacuo to remove the THF and then was extracted with EtOAc (2×100 ml). The combined extracts were washed with brine (100 ml), dried (Na$_2$SO$_4$) and concentrated onto silica. Purification by silica gel chromatography (20 to 60% EtOAc/hexane) afforded the title compound as a tan solid. MS (ESI, pos. ion) m/z: 220 (M+1).

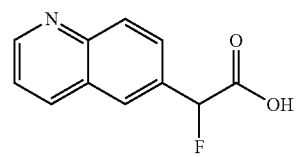 [SMILES: O=C(O)C(F)c1ccc2ncccc2c1]

2-Fluoro-2-(quinolin-6-yl)acetic acid

To a solution containing methyl 2-fluoro-2-(quinolin-6-yl)acetate (0.49 g, 2.2 mmol) in methanol (3.0 ml) was added sodium hydroxide (5 M, 1.0 ml, 5.0 mmol). The mixture was stirred at rt for 48 h and then neutralized with 5 N HCl (1.0 mL). The solution was allowed to sit overnight during which time a precipitate formed. The solution was filtered and the filtercake washed with cold water then dried under vacuum to afford the title compound as a tan solid. MS (ESI, pos. ion) m/z: 206 (M+1).

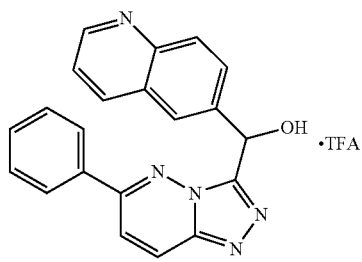 [SMILES: OC(c1ccc2ncccc2c1)c1nnc2ccc(-c3ccccc3)nn12]

EXAMPLE 80

(6-Phenyl-[1,2,4]triazolo[4,3-b]pyridazin-3-yl)(quinolin-6-yl)methanol TFA salt

To a 2-5 ml Personal Chemistry microwave vial was added 2-fluoro-2-(quinolin-6-yl)acetic acid (0.20 g, 0.98 mmol), 1-(6-phenylpyridazin-3-yl)hydrazine (0.27 g, 1.5 mmol) and conc. hydrochloric acid (2.0 ml, 66 mmol). The mixture was heated at 160° C. for 6 h in the microwave. After cooling to rt, the mixture was poured into sat. NaHCO$_3$ (100 mL) and extracted with 25% iPrOH/CHCl$_3$ (4×50 mL). The combined extracts were dried (Na$_2$SO$_4$) and concentrated onto silica. Purification by silica gel chromatography (2.0 to 6.5% MeOH (2 M in NH$_3$)/CH$_2$Cl$_2$) followed by further purification by Prep-HPLC (Phenomenex Synergi 4u MAX-RP 80A 150× 21.20 mm, 10 to 65% CH$_3$CN(0.1% TFA)/H$_2$O(0.1% TFA) over 15 min then 65% CH$_3$CN for 5 minutes at 20 ml/min) with the fractions containing product concentrated to afford the title compound as a tan solid (0.10 g, 22% yield). MS (ESI, pos. ion) m/z: 354 (M+1).

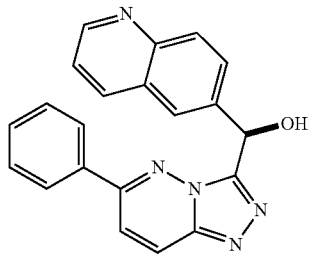 [SMILES: O[C@H](c1ccc2ncccc2c1)c1nnc2ccc(-c3ccccc3)nn12]

EXAMPLE 81

(R)-(6-Phenyl-[1,2,4]triazolo[4,3-b]pyridazin-3-yl)(quinolin-6-yl)methanol

Isolated from chiral separation of racemic (6-phenyl-[1,2,4]triazolo[4,3-b]pyridazin-3-yl)(quinolin-6-yl)methanol TFA salt (AMG 2120533). Column: Chirotechnology AS-H column, 4.6 mm×15 cm. Mobile phase: 70/30 Carbon dioxide/0.2% diethylamine in ethanol. Flow rate: 4.0 mL/min. Temperature: 40° C. Back pressure: 100 bar. Retention time: 1.65 min. Enantiomeric purity: >99% ee. MS (ESI, pos. ion) m/z: 354 (M+1).

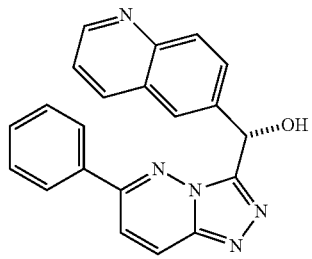 [SMILES: O[C@@H](c1ccc2ncccc2c1)c1nnc2ccc(-c3ccccc3)nn12]

EXAMPLE 82

(S)-(6-Phenyl-[1,2,4]triazolo[4,3-b]pyridazin-3-yl)(quinolin-6-yl)methanol

Isolated from chiral separation of racemic (6-phenyl-[1,2,4]triazolo[4,3-b]pyridazin-3-yl)(quinolin-6-yl)methanol TFA salt (AMG 2120533). Column: Chirotechnology AS-H column, 4.6 mm×15 cm. Mobile phase: 70/30 Carbon dioxide/0.2% diethylamine in ethanol. Flow rate: 4.0 mL/min. Temperature: 40° C. Back pressure: 100 bar. Retention time: 2.22 min. Enantiomeric purity: >99% ee. MS (ESI, pos. ion) m/z: 354 (M+1).

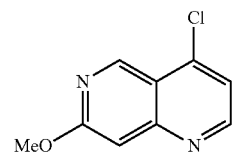

Step 1: 4-amino-3-bromo-2-chloropyridine.

4-amino-2-chloropyridine (50 g, 388 mmol) was dissolved in glacial acetic acid (500 mL). To this solution was added N-bromosuccinamide (75 g, 426 mmol,) portionwise at room temperature (water bath cooling was provided to control the exothermicity). The reaction mixture was stirred at RT for 1 h at which point the reaction was found complete (as monitored by TLC). Solvent was removed under reduced pressure followed by azeotropic distillation with ethanol. The crude product was purified by column chromatography on silica gel (230-400 mesh) eluting with ethyl acetate hexane mixture.

Step 2: 4-amino-3-bromo-2-methoxypyridine.

Methanol (350 mL) was charged in a two-neck round bottom flask equipped with a guard tube and septum and cooled to 0° C. Sodium metal (23 g) was added to it slowly in pieces. After all sodium metal had dissolved, 4-amino-3-bromo-2-chloro pyridine (23 g, 178 mmol) was added and the solution was heated at 180° C. in a pressure vessel for 5-6 h. The reaction mixture was then cooled to 0° C. and adjusted to pH 8 by addition of conc. HCl. Solvent was removed under reduced pressure and the residue was suspended in ethyl acetate. Undissolved impurities were removed by filtration and the filtrate was concentrated under reduced pressure to obtain pure product.

Step 3: 5-[(3-Bromo-2-methoxy-pyridin-4-ylamino)-methylene]-2,2-dimethyl-[1,3]dioxane-4,6-dione.

A two necked round bottomed flask equipped with a reflux condenser was charged with Meldrum's acid (15.6 g, 108 mmol) and trimethyl orthoformate (143 mL). The reaction mixture was heated 100° C. for 2 h. 4-amino-3-bromo-2-methoxypyridine (22 g, 108 mmol) was added and heating was continued for an additional 4 h at 100° C. The reaction mixture was allowed to cool to RT, diluted with hexane and filtered to obtain the product as a yellow solid.

Step 4: 8-Bromo-7-methoxy-1H-[1,6]naphthyridin-4-one.

A two neck round bottomed flask equipped with an air condenser was charged with 5-[(3-Bromo-2-methoxy-pyridin-4-ylamino)-methylene]-2,2-dimethyl-[1,3]dioxane-4,6-dione (23 g, 64 mmol) and diphenyl ether (230 mL). The reaction mixture was heated at 250° C. for 30 min under nitrogen atmosphere after which it was cooled to RT, diluted with hexane and filtered to obtain a dark solid. The crude product was refluxed in hexane for 30 min and filtered to obtained 8-Bromo-7-methoxy-1H-[1,6]naphthyridin-4-one as a brown solid.

Step 5: 7-Methoxy-1H-[1,6]naphthyridin-4-one.

8-Bromo-7-methoxy-1H-[1,6]naphthyridin-4-one (12 g, 33.5 mmol) was dissolved in anhydrous methanol (240 mL) and 10% Dry Pd/C (2.4 g) was added carefully in portions. This was followed by portionwise addition of ammonium formate (24 g) which caused an exotherm. The reaction mixture was heated to reflux for 1 h. The reaction mixture was cooled to room temperature, filtered through Celite, and washed with hot methanol. The filtrate was concentrated and the residue purified by column chromatography on silica gel (230-400 mesh) eluting with ethyl acetate-methanol.

Step 6: 4-Chloro-7-methoxy-[1,6]naphthyridine.

A two neck round bottomed flask equipped with $CaCl_2$ guard tube was charged with 7-Methoxy-1H-[1,6]naphthyridin-4-one (28 g, 159 mmol) and $POCl_3$ (280 mL). The reaction mixture was stirred at RT for 3 h. The reaction mixture was poured into ice water and the pH was carefully adjusted to 8 with solid sodium carbonate (highly exothermic reaction). The product was extracted with EtOAc. The combined organic layer was washed with water, dried over $Na_2SO_4$ and concentrated. The crude product was purified by column chromatography on silica gel (230-400 mesh) eluting with ethyl acetate hexane mixture.

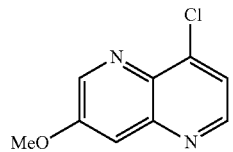 [SMILES: COc1cnc2c(Cl)ccnc2c1]

Step 1: 3-Bromo-5-methoxypyridine.

Sodium (12 g) was dissolved in methanol (150 mL) while cooling, and excess MeOH was removed under reduced pressure to obtain NaOMe, which was azeotroped with toluene (2×100 mL). A solution of 3,5-dibromopyridine (100 g) in DMSO (500 mL) was added to sodium methoxide and the mixture was stirred at 90° C. for 2 h. After cooling to RT, aqueous NaOH solution (3 M, 300 mL) was added and the mixture was extracted with $Et_2O$. The ethereal layer was washed with brine and dried over $Na_2SO_4$. After concentration the crude product obtained was purified by flash column chromatography (Hexane:EtOAc 85:15) to afford pure product 3-bromo-5-methoxy pyridine.

Step 2: 3-amino-5-methoxypyridine.

3-Bromo-5-methoxypyridine (15 g) was added to a pressure vessel, and $CuSO_4$ (3.9 g) and 25% aq ammonia (150 mL) were added. The reaction mixture was stirred for 4 h at 135° C., then cooled to RT, basified with aqueous NaOH solution, and extracted with $CH_2Cl_2$. After evaporation of volatiles, 3-amino-5-methoxypyridine was obtained as yellow solid.

Step 3: 5-[(5-Methoxy-pyridin-3-ylamino)-methylene]-2,2-dimethyl-[1,3]dioxane-4,6-dione.

A two-necked round bottomed flask equipped with a reflux condenser was charged with Meldrum's acid (14.4 g, 100 mmol) and trimethylorthoformate (100 mL). The reaction mixture was heated at 100-105° C. for 2 h. 5-amino-3-methoxy pyridine (12.5 g, 100 mmol) was added to the reaction mixture and heating was continued for an additional 4 h at the same temperature. The reaction mixture was allowed to cool to RT, diluted with hexane and filtered to obtain the product as light yellow solid.

Step 4: -Methoxy-1H-[1,5]naphthyridin-4-one.

A two-necked round bottomed flask equipped with an air condenser was charged with 5-[(5-Methoxy-pyridin-3-ylamino)-methylene]-2,2-dimethyl-[1,3]dioxane-4,6-dione (18 g) and diphenyl ether (180 mL). The reaction mixture was heated at 240-250° C. for 5 min under $N_2$ atmosphere after which it was cooled to RT, diluted with hexane and filtered to obtain a dark solid. The crude product was refluxed in hexane for 30 min and filtered to obtain product as a brown solid.

Step 5: 8-chloro-3-methoxy-1,5-naphthyridine.

A two-necked round bottomed flask equipped with an air condenser (protected with $CaCl_2$ guard tube) was charged with 7-Methoxy-1H-[1,5]naphthyridin-4-one (13 g) and $POCl_3$ (65 mL). The reaction mixture was allowed to reflux at 120° C. for 12 h. The $POCl_3$ was removed in vacuo and azeotroped twice with toluene. EtOAc (75 mL) was added and the reaction mixture was stirred at 50-60° C. for 15-20 min. EtOAc removed separated by decantation. The organic layers were combined and concentrated. The obtained crude was dissolved in EtOAc (50 ml) and a washed with satd. aqueous sodium bicarbonate. The organic layer was dried over $Na_2SO_4$ and concentrated. The resulting solids were suspended in hexane, stirred for 15 min, filtered and dried under vacuum.

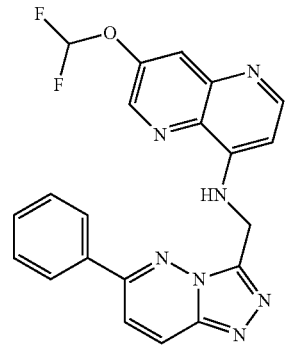 [SMILES: FC(F)Oc1cnc2c(NCc3nnc4ccc(-c5ccccc5)nn34)ccnc2c1]

EXAMPLE 83

7-(difluoromethoxy)-N-((6-phenyl-[1,2,4]triazolo[4,3-b]pyridazin-3-yl)methyl)-1,5-naphthyridin-4-amine DMF (0.5 mL) and water (0.1 mL) were added to a pressure vessel containing 8-((6-phenyl-[1,2,4]triazolo[4,3-b]pyridazin-3-yl)methylamino)-1,5-naphthyridin-3-ol (50 mg, 135 µmol), sodium 2-chloro-2,2-difluoroacetate (47 mg, 311 µmol), cesium carbonate (62 mg, 190 µmol). The reaction mixture was stirred at 100° C. for 18 h, cooled to RT and concentrated in vacuo. Purification by MPLC (DCM/MeOH+

1% NH₄OH: 100/0 to 90/10) afforded the title compound (10 mg, 17% yield). MS m/z=420.1 [M+H]⁺. Calc'd for C21H15F2N7O: 419.40.

EXAMPLE 84

N-((6-(3H-1,2,3-triazol-4-yl)-[1,2,4]triazolo[4,3-b]pyridazin-3-yl)methyl)-7-methoxy-1,5-naphthyridin-4-amine 1) Preparation of tert-butyl (6-(3H-1,2,3-triazol-4-yl)-[1,2,4]triazolo[4,3-b]pyridazin-3-yl)methylcarbamate

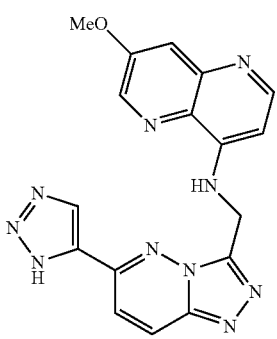 [SMILES: COc1cnc2c(NCc3nnc4ccc(-c5cnn[nH]5)nn34)ccnc2c1]

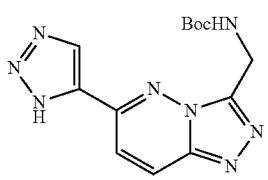 [SMILES: CC(C)(C)OC(=O)NCc1nnc2ccc(-c3cnn[nH]3)nn12]

tert-Butyl (6-ethynyl-[1,2,4]triazolo[4,3-b]pyridazin-3-yl)methylcarbamate (0.109 g, 0.399 mmol) and sodium azide (0.0285 g, 0.439 mmol) were dissolved DMF (2 mL) at RT. The reaction mixture was stirred overnight at RT then at 70° C. for 3 h. Water was added at RT and the aqueous layer was extracted with EtOAc and 1-butanol. The organic extracts were washed with brine, dried over MgSO₄, filtered and concentrated in vacuo. Used without further purification.

2) Preparation of N-((6-(3H-1,2,3-triazol-4-yl)-[1,2,4]-triazolo[4,3-b]pyridazin-3-yl)methyl)-7-methoxy-1,5-naphthyridin-4-amine

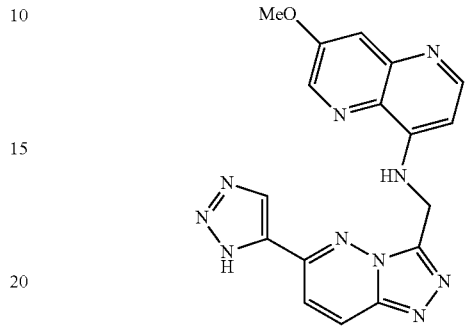

Prepared by a method similar to 7-methoxy-N-((6-(3-methylisothiazol-5-yl)-[1,2,4]triazolo[4,3-b]pyridazin-3-yl)methyl)-1,5-naphthyridin-4-amine MS m/z=375.1 [M+H]⁺. Calc'd for C17H14N10O: 374.37

EXAMPLE 85

4-((8-fluoro-6-(3-methylisothiazol-5-yl)-[1,2,4]triazolo[4,3-a]pyridin-3-yl)methoxy)-7-methoxyquinoline

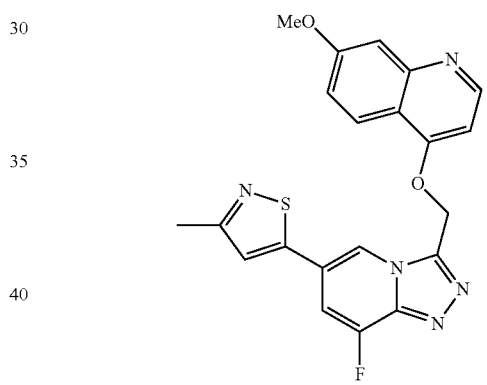

Dioxane (3.6 mL) was added to 4-((6-chloro-8-fluoro-[1,2,4]triazolo[4,3-a]pyridin-3-yl)methoxy)-7-methoxyquinoline (175 mg, 488 μmol), X-Phos (32.6 mg, 68.3 μmol), 3-methyl-5-(trimethylstannyl)isothiazole (153 mg, 585 μmol), palladium acetate (7.67 mg, 34.1 μmol). The flask was purged with argon and sealed. The reaction mixture was stirred at 80° C. for 2d. More X-Phos (32.6 mg, 68.3 μmol), palladium acetate (7.67 mg, 34.1 μmol) and 3-methyl-5-(trimethylstannyl)isothiazole (153 mg, 585 μmol) were added and stirring was continued at 80° C. overnight. The reaction mixture was cooled at RT, concentrated in vacuo and urified by MPLC (CH₂Cl₂/MeOH: 100/0 to 90/10). Further purification by MPLC (ISCO, EtOAc/MeOH:9/1, isocratic) afforded the title compound (105 mg, 51% yield). MS m/z=422.0 [M+H]⁺. Calc'd for C21H16FN5O2S: 421.46

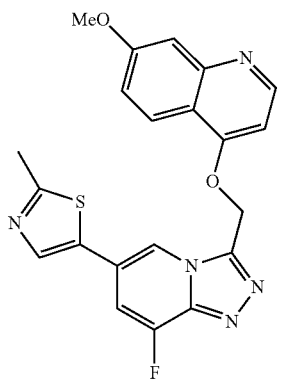 [SMILES: COc1ccc2c(OCc3nnc4c(F)cc(-c5cnc(C)s5)cn34)ccnc2c1]

EXAMPLE 86

4-((8-fluoro-6-(2-methylthiazol-5-yl)-[1,2,4]triazolo[4,3-a]pyridin-3-yl)methoxy)-7-methoxyquinoline 1) Preparation of 2-methyl-5-(trimethylstannyl)thiazole

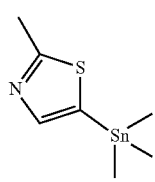

Butyllithium (1.6M in THF, 3.5 ml, 5.5 mmol) was added to a stirred solution of 2-methylthiazole (0.45 ml, 5.0 mmol) in THF (15 mL) at −78° C. The reaction mixture was stirred at −78° C. for 40 min. Chlorotrimethylstannane (1M in THF, 5.0 ml, 5.0 mmol) was added. Stirring was continued at −78° C. for 45 min. The reaction mixture was quenched with a satured aqueous solution of NaHCO$_3$. The aqueous layer was extracted with Et$_2$O. The organic extracts were dried over MgSO$_4$, filtered and concentrated in vacuo. Used in the next step without purification (obtained 1.29 g). MS m/z=264.1. Calc'd for C7H13NSSn: 261.94.

2) Preparation of 4-((8-fluoro-6-(2-methylthiazol-5-yl)-[1,2,4]triazolo[4,3-a]pyridin-3-yl)methoxy)-7-methoxyquinoline Prepared by a method similar to 4-((8-fluoro-6-(3-methyl-isothiazol-5-yl)-[1,2,4]triazolo[4,3-a]pyridin-3-yl)methoxy)-7-methoxyquinoline. MS m/z=422.1 [M+H]$^+$. Calc'd for C21H16FN5O2S: 421.46

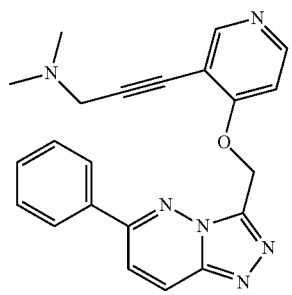 [SMILES: CN(C)CC#Cc1cnccc1OCc1nnc2ccc(-c3ccccc3)nn12]

EXAMPLE 87

N,N-dimethyl-3-(4-((6-phenyl-[1,2,4]triazolo[4,3-b]pyridazin-3-yl)methoxy)pyridin-3-yl)prop-2-yn-1-amine 1) Preparation of 3-((3-iodopyridin-4-yloxy)methyl)-6-phenyl-[1,2,4]triazolo[4,3-b]pyridazine

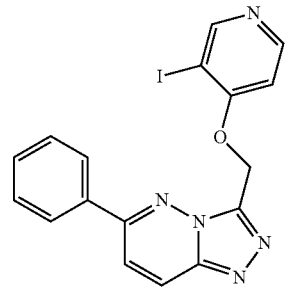 [SMILES: Ic1cnccc1OCc1nnc2ccc(-c3ccccc3)nn12]

Cesium carbonate (354 mg, 1087 μmol) was added to a mixture of (6-phenyl-[1,2,4]triazolo[4,3-b]pyridazin-3-yl)methanol (123 mg, 544 μmol) (named 77289-19-99) and (6-phenyl-[1,2,4]triazolo[4,3-b]pyridazin-3-yl)methanol (123 mg, 544 μmol) in DMSO (1.8 mL). The reaction mixture was stirred at 120° C. for 2 h under micro-waves irradiation. The reaction mixture was diluted with EtOAc. The organic layer was washed with water. The water layer extracted with EtOAc. The organic layer was dried over MgSO$_4$, filtered and concentrated in vacuo. Purification by MPLC afforded the title compound (161 mg, 69% yield).

2) Preparation of N,N-dimethyl-3-(4-((6-phenyl-[1,2,4]-triazolo[4,3-b]pyridazin-3-yl)methoxy)pyridin-3-yl)prop-2-yn-1-amine

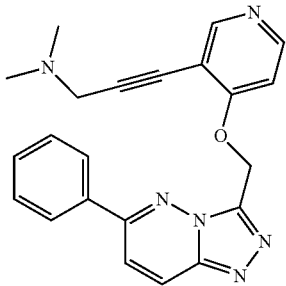 [SMILES: CN(C)CC#Cc1cnccc1OCc1nnc2ccc(-c3ccccc3)nn12]

Tetrakis(triphenylphosphine)palladium(0) (14.4 mg, 12.5 µmol) was added to a suspension of 3-((3-iodopyridin-4-yloxy)methyl)-6-phenyl-[1,2,4]triazolo[4,3-b]pyridazine (107 mg, 249 mmol) and 1-dimethylamino-2-propyne (80.4 µl, 748 µmol) in THF (0.6 mL) and triethylamine (591 µl, 4238 µmol) at RT. Copper(i) iodide, 99.999% (4.75 mg, 24.9 µmol) was added and the reaction mixture was stirred at 75° C. (oil bath) for ~75 min. The reaction mixture was cooled at RT, concentrated in vacuo. Purification by MPLC (ISCO, CH$_2$Cl$_2$/MeOH: 100/0 to 90/10) afforded the title compound. MS m/z=385.1 [M+H]$^+$. Calc'd for C22H20N6O: 384.44

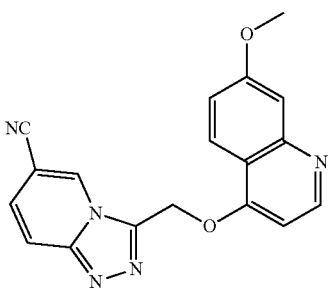 [SMILES: COc1ccc2c(OCc3nnc4ccc(C#N)cn34)ccnc2c1]

EXAMPLE 88

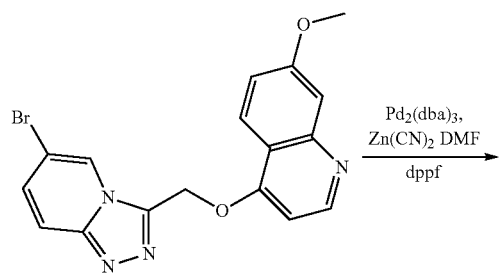

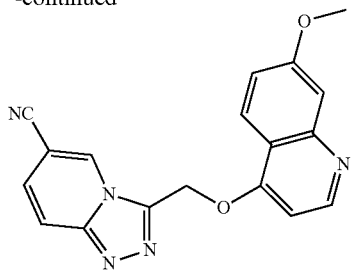

Preparation of 3-((7-methoxyquinolin-4-yloxy)methyl)-[1,2,4]triazolo[4,3-a]pyridine-6-carbonitrile 4-((6-Bromo-[1,2,4]triazolo[4,3-a]pyridin-3-yl)methoxy)-7-methoxyquinoline was prepared as previously described in general Method A.

4-((6-Bromo-[1,2,4]triazolo[4,3-a]pyridin-3-yl)methoxy)-7-methoxyquinoline (0.050 g, 0.13 mmol) was dissolved in DMF (1 mL) then added zinc cyanide (0.023 g, 0.19 mmol), 1,1'-bis(diphenylphosphino)ferrocene (0.0072 g, 0.013 mmol) and tris(dibenzylideneacetone)dipalladium(0) (0.0059 g, 0.0065 mmol). The reaction mixture was heated at 100° C. for 8 hours. Additional zinc cyanide (0.012 g, 0.095 mmol), 1,1'-bis(diphenylphosphino)ferrocene (0.004 g, 0.0065 mmol) and tris(dibenzylideneacetone)dipalladium(0) (0.003 g, 0.0032 mmol) were added and heating was continued at 100° C. for 6 hours. The reaction mixture was concentrated under vacuum. The sample was purified by preparative TLC eluting with 10% 7N ammonia in methanol/dichloromethane to afford 3-((7-methoxyquinolin-4-yloxy)methyl)-[1,2,4]triazolo[4,3-a]pyridine-6-carbonitrile (23 mg, 53% yield) as a white solid.

MS (ESI pos. ion) m/z: 332.1 (MH$^+$).

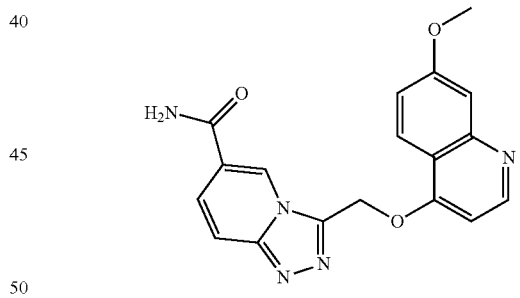

EXAMPLE 89

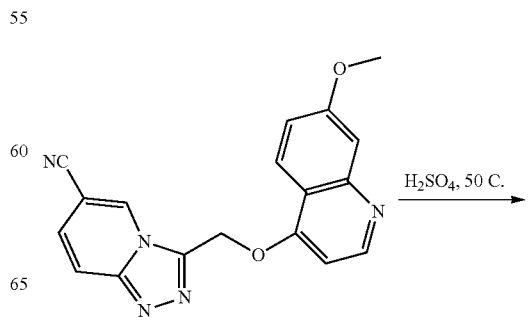

-continued

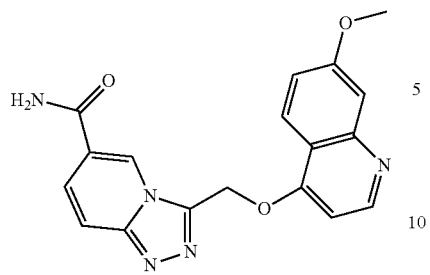

Preparation of 3-((7-methoxyquinolin-4-yloxy)methyl)-[1,2,4]-triazolo[4,3-a]pyridine-6-carboxamide 3-((7-Methoxyquinolin-4-yloxy)methyl)-[1,2,4]triazolo[4,3-a]pyridine-6-carbonitrile was prepared as previously described.

3-((7-Methoxyquinolin-4-yloxy)methyl)-[1,2,4]triazolo[4,3-a]pyridine-6-carbonitrile (0.050 g, 0.15 mmol) was dissolved in concentrated sulfuric acid (0.5 mL). The reaction mixture was heated at 50° C. for 30 minutes. The reaction mixture was slowly poured in to cold saturated aqueous sodium bicarbonate. A precipitate formed which was collected on a glass frit, washing with water. The solid was transferred with dichloromethane/methanol to a flask and dried under high vacuum to afford 3-((7-methoxyquinolin-4-yloxy)methyl)-[1,2,4]triazolo[4,3-a]pyridine-6-carboxamide (0.050 g, 95% yield) as a tan solid.

MS (ESI pos. ion) m/z: 350.2 (MH+).

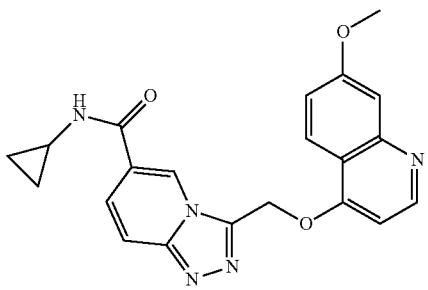 [SMILES: COc1ccc2c(OCc3nnc4ccc(C(=O)NC5CC5)cn34)ccnc2c1]

EXAMPLE 90

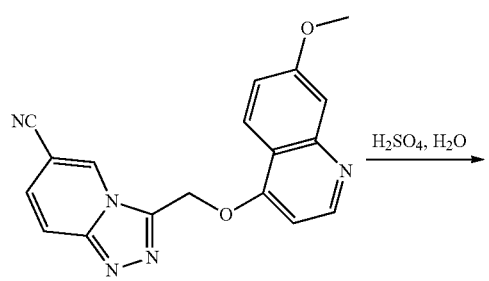

-continued

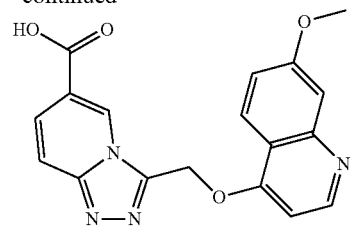

Preparation of 3-((7-methoxyquinolin-4-yloxy)methyl)-[1,2,4]-triazolo[4,3-a]pyridine-6-carboxylic acid 3-((7-Methoxyquinolin-4-yloxy)methyl)-[1,2,4]triazolo[4,3-a]pyridine-6-carbonitrile was prepared as previously described.

3-((7-Methoxyquinolin-4-yloxy)methyl)-[1,2,4]triazolo[4,3-a]pyridine-6-carbonitrile (0.050 g, 0.15 mmol) was dissolved in concentrated sulfuric acid (0.375 mL) and water (0.125 mL). The reaction mixture was heated at 100° C. for 3.5 hours then slowly poured in to ice. The mixture was adjusted to approx. pH 7 with saturated aqueous sodium carbonate. A precipitate formed which was collected on a glass frit, washing with water. The solid was dried under high vacuum to afford 3-((7-methoxyquinolin-4-yloxy)methyl)-[1,2,4]triazolo[4,3-a]pyridine-6-carboxylic acid (0.047 g, 89% yield) as a tan solid.

MS (ESI pos. ion) m/z: 351.1 (MH+).

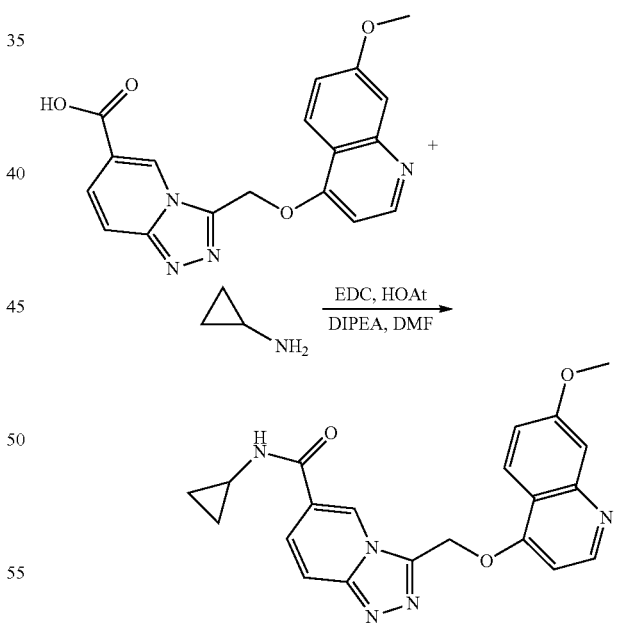

Preparation of N-cyclopropyl-3-((7-methoxyquinolin-4-yloxy)methyl)-[1,2,4,]-triazolo[4,3-a]pyridine-6-carboxamide 3-((7-Methoxyquinolin-4-yloxy)methyl)-[1,2,4]triazolo[4,3-a]pyridine-6-carboxylic acid (0.047 g, 0.13 mmol), cyclopropanamine (0.011 ml, 0.16 mmol), 1-hydroxy-7-azabenzotriazole (0.018 g, 0.13 mmol), and N-ethyl-N'-(3-dimethylaminopropyl)carbodiimide hydrochloride, (0.039 g, 0.20 mmol) were added to a reaction flask then suspended in DMF (1 mL). N-Ethyldiisopropylamine (0.070 ml, 0.40 mmol) was added to the reaction mixture. The clear reaction mixture was stirred at 20° C. overnight. The reaction mixture was concentrated under vacuum then triturated with water. The solid was collected on a glass frit, washing with water. The sample was purified by preparative TLC eluting with 8% 7N ammonia in methanol/dichloromethane to afford N-cyclopropyl-3-((7-methoxyquinolin-4-yloxy)methyl)-[1,2,4]triazolo[4,3-a]pyridine-6-carboxamide (0.023 g, 44% yield) as a tan solid.

MS (ESI pos. ion) m/z: 390.2 (MH⁺).

(3 mL) then added concentrated hydrochloric acid (0.500 ml, 6.0 mmol). The reaction mixture was stirred at room temperature overnight then concentrated under vacuum. The remaining solid was suspended in methanol (1 mL) then added triethylamine (0.40 ml, 2.9 mmol). The clear solution was stirred at room temperature for 2 hours then concentrated under vacuum. The sample was purified by flash chromatography eluting with 8% 7N ammonia in methanol/dichloromethane to afford 7-methoxy-4-((6-(1,2,3,6-tetrahydropyridin-4-yl)-[1,2,4]triazolo[4,3-a]pyridin-3-yl)methoxy)quinoline (0.038 g, 42% yield) as a tan solid.

MS (ESI pos. ion) m/z: 388.1 (MH⁺).

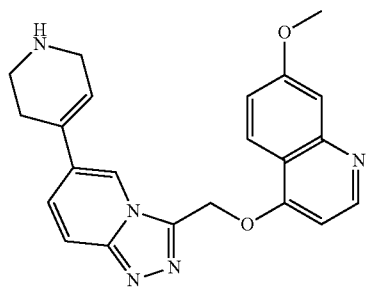 [SMILES: COc1ccc2c(OCc3nnc4ccc(C5=CCNCC5)cn34)ccnc2c1]

EXAMPLE 91

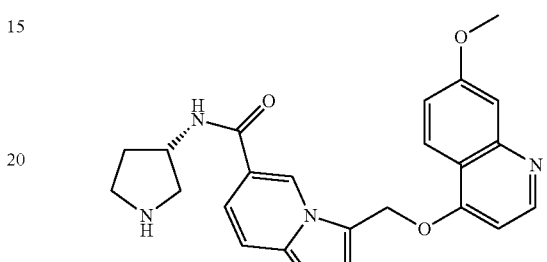

EXAMPLE 92

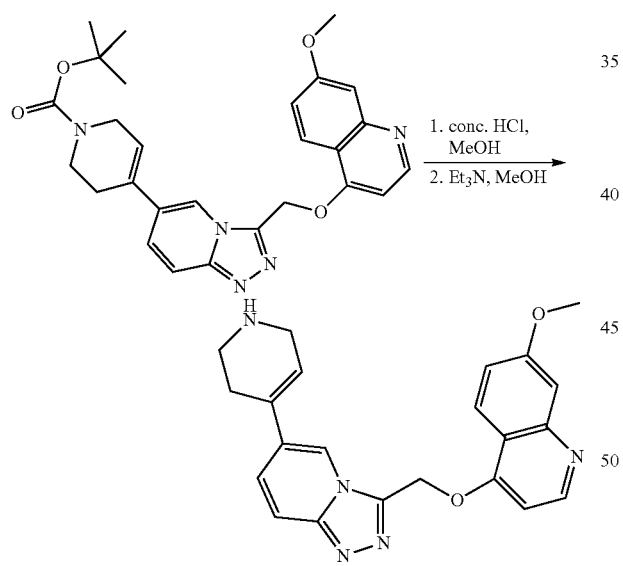

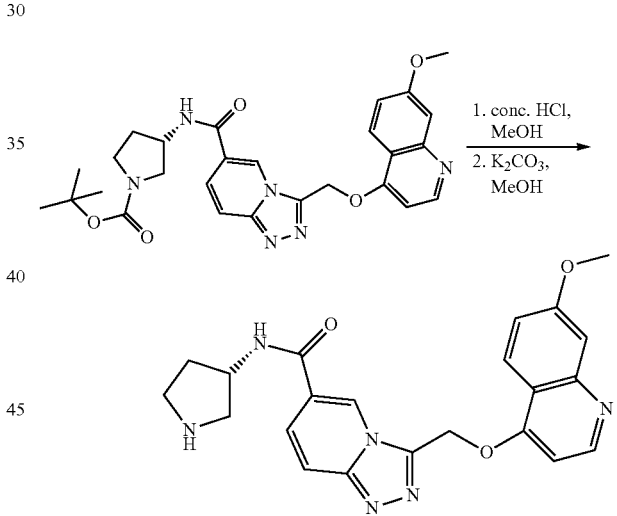

Preparation of 7-methoxy-4-((6-(1,2,3,6-tetrahydropyridin-4-yl)-[1,2,4,]-triazolo[4,3-a]pyridin-3-yl)methoxy)quinoline tert-Butyl 4-(3-((7-methoxyquinolin-4-yloxy)methyl)-[1,2,4]triazolo[4,3-b]pyridazin-6-yl)-5,6-dihydropyridine-1(2H)-carboxylate was prepared as described in general Method A.

tert-Butyl 4-(3-((7-methoxyquinolin-4-yloxy)methyl)-[1,2,4]triazolo[4,3-a]pyridin-6-yl)-5,6-dihydropyridine-1(2H)-carboxylate (0.113 g, 0.23 mmol) was dissolved in methanol Preparation of (S)-3-((7-methoxyquinolin-4-yloxy)methyl)-N-(pyrrolidin-3-yl)-[1,2,4]-triazolo[4,3-a]pyridine-6-carboxamide (S)-tert-Butyl 3-(3-((7-methoxyquinolin-4-yloxy)methyl)-[1,2,4]triazolo[4,3-a]pyridine-6-carboxamido)pyrrolidine-1-carboxylate was prepared as previously described for N-cyclopropyl-3-((7-methoxyquinolin-4-yloxy)methyl)-[1,2,4]triazolo[4,3-a]pyridine-6-carboxamide.

(S)-tert-Butyl 3-(3-((7-methoxyquinolin-4-yloxy)methyl)-[1,2,4]triazolo[4,3-a]pyridine-6-carboxamido)pyrrolidine-1-carboxylate (0.050 g, 0.096 mmol) was dissolved in methanol (1.5 mL) then added concentrated hydrochloric acid (0.400 ml, 4.8 mmol). The reaction mixture was stirred at room temperature for 5 hours then concentrated under vacuum. The remaining solid was dissolved in methanol (1 mL) then added potassium carbonate (0.062 g, 0.45 mmol). The reaction mixture was stirred at room temperature for 1 hour and concentrated under vacuum. The sample was purified by flash chromatography eluting with 10%-15% 7N ammonia in methanol/dichloromethane to afford (S)-3-((7-methoxyquinolin-4-yloxy)methyl)-N-(pyrrolidin-3-yl)-[1,2,4]triazolo[4,3-a]pyridine-6-carboxamide (0.039 g, 97% yield) as a pale yellow solid.

MS (ESI pos. ion) m/z: 419.2 (MH$^+$).

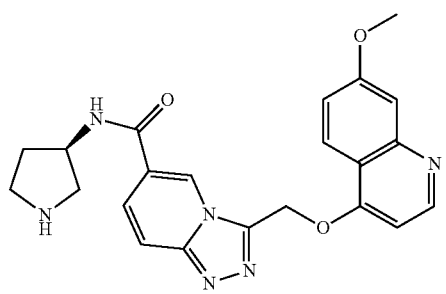 [SMILES: COc1ccc2c(OCc3nnc4ccc(C(=O)N[C@@H]5CCNC5)cn34)ccnc2c1]

EXAMPLE 93

(R)-3-((7-Methoxyquinolin-4-yloxy)methyl)-N-(pyrrolidin-3-yl)-[1,2,4,]triazolo[4,3-a]pyridine-6-carboxamide was prepared as previously described for (S)-3-((7-methoxyquinolin-4-yloxy)methyl)-N-(pyrrolidin-3-yl)-[1,2,4]triazolo[4,3-a]pyridine-6-carboxamide.

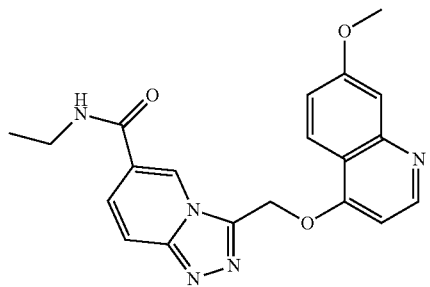 [SMILES: CCNC(=O)c1ccc2nnc(COc3ccnc4cc(OC)ccc34)n2c1]

EXAMPLE 94

N-Ethyl-3-((7-methoxyquinolin-4-yloxy)methyl)-[1,2,4]triazolo[4,3-a]pyridine-6-carboxamide was prepared as previously described for N-cyclopropyl-3-((7-methoxyquinolin-4-yloxy)methyl)-1,2,4triazolo[4,3-a]pyridine-6-carboxamide.

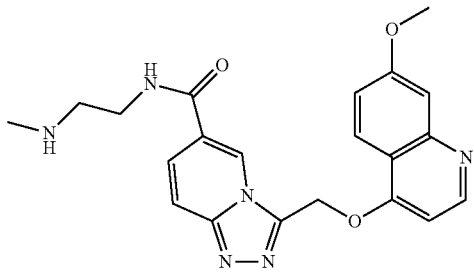 [SMILES: CNCCNC(=O)c1ccc2nnc(COc3ccnc4cc(OC)ccc34)n2c1]

EXAMPLE 95

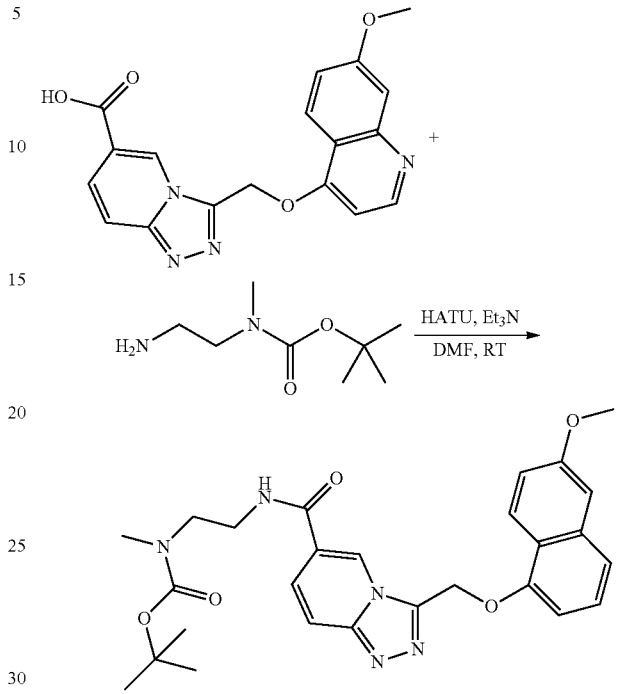

Preparation of tert-butyl 2-(3-((7-methoxyquinolin-4-yloxy)methyl)-[1,2,4,]-triazolo[4,3-a]pyridine-6-carboxamido)ethyl(methyl)carbamate 3-((7-Methoxyquinolin-4-yloxy)methyl)-[1,2,4]triazolo[4,3-a]pyridine-6-carboxylic acid was prepared as previously described.

3-((7-Methoxyquinolin-4-yloxy)methyl)-[1,2,4]triazolo[4,3-a]pyridine-6-carboxylic acid (0.072 g, 0.21 mmol) was dissolved in DMF (1.5 mL) then added N-(2-aminoethyl)-N-methyl carbamic acid tert-butyl ester (0.054 ml, 0.31 mmol), 2-(7-aza-1H-benzotriazole-1-yl)-1,1,3,3-tetramethyluronium hexafluorophosphate (0.12 g, 0.31 mmol) and triethylamine (0.043 ml, 0.31 mmol). The reaction mixture was stirred at room temperature overnight then concentrated under vacuum. The sample was purified by flash chromatography eluting with 6% 7N ammonia in methanol/dichloromethane to afford tert-butyl 2-(3-((7-methoxyquinolin-4-yloxy)methyl)-[1,2,4]triazolo[4,3-a]pyridine-6-carboxamido)ethyl(methyl)carbamate (0.097 g, 93% yield) as a pale yellow solid. MS (ESI pos. ion) m/z: 507.3 (MH$^+$).

Preparation of 3-((7-methoxyquinolin-4-yloxy)methyl)-N-(2-(methylamino)ethyl)-[1,2,4]triazolo[4,3-a]pyridine-6-carboxamide tert-Butyl 2-(3-((7-methoxyquinolin-4-yloxy)methyl)-[1,2,4]triazolo[4,3-a]pyridine-6-carboxamido)ethyl(methyl) carbamate was deprotected as previously described for 7-methoxy-4-((6-(1,2,3,6-tetrahydropyridin-4-yl)-[1,2,4]triazolo[4,3-a]pyridin-3-yl)methoxy)quinoline.

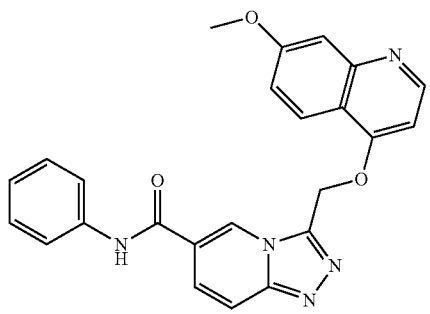 [SMILES: COc1ccc2c(OCc3nnc4ccc(C(=O)Nc5ccccc5)cn34)ccnc2c1]

EXAMPLE 96

3-((7-Methoxyquinolin-4-yloxy)methyl)-N-phenyl-[1,2,4]triazolo[4,3-a]pyridine-6-carboxamide was prepared as described for 3-((7-methoxyquinolin-4-yloxy)methyl)-N-(2-(methylamino)ethyl)-[1,2,4]triazolo[4,3-a]pyridine-6-carboxamide.

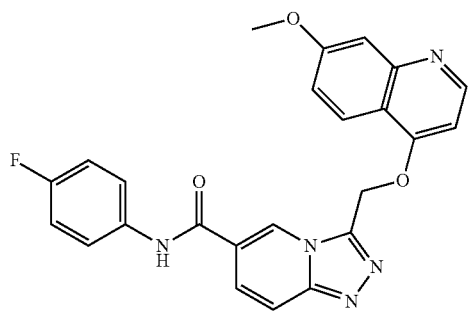 [SMILES: COc1ccc2c(OCc3nnc4ccc(C(=O)Nc5ccc(F)cc5)cn34)ccnc2c1]

EXAMPLE 97

N-(4-Fluorophenyl)-3-((7-methoxyquinolin-4-yloxy)methyl)-[1,2,4]triazolo[4,3-a]pyridine-6-carboxamide was prepared as described for 3-((7-methoxyquinolin-4-yloxy)methyl)-N-(2-(methylamino)ethyl)-[1,2,4]triazolo[4,3-a]pyridine-6-carboxamide.

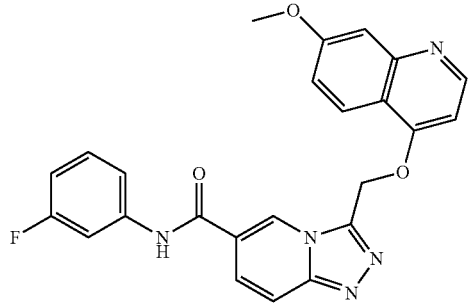 [SMILES: COc1ccc2c(OCc3nnc4ccc(C(=O)Nc5cccc(F)c5)cn34)ccnc2c1]

EXAMPLE 98

N-(3-Fluorophenyl)-3-((7-methoxyquinolin-4-yloxy)methyl)-[1,2,4]triazolo[4,3-a]pyridine-6-carboxamide was prepared as described for 3-((7-methoxyquinolin-4-yloxy)methyl)-N-(2-(methylamino)ethyl)-[1,2,4]triazolo[4,3-a]pyridine-6-carboxamide.

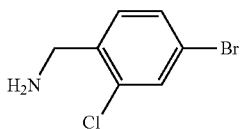

(4-bromo-2-chlorophenyl)methanamine

To a solution of 4-bromo-2-chlorobenzonitrile (2500 mg, 11549 μmol) in THF (20 mL) at 0° C. was added borane-methyl sulfide complex, 2.0 m sol in THF (28873 μl, 57747 μmol). Ice bath removed and reaction stirred overnight warming to 23° C. Reaction cooled to 0° C. and quenched with MeOH (15 mL). Reaction then partitioned between CHCl$_3$ (100 mL) and 1M NaOH (100 mL). Organic dried with brine and MgSO$_4$. Organic then concentrated to an oil under reduced pressure and purified on silica (80 g) eluting with 0>6% 2M NH$_3$ in MeOH/DCM and product isolated as a colorless oil. MS (ESI pos. ion) m/z: 220/222 (MH+). Calc'd exact mass for C$_7$H$_7$BrClN: 219/221

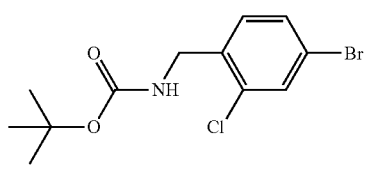 [SMILES: CC(C)(C)OC(=O)NCc1ccc(Br)cc1Cl]

tert-butyl 4-bromo-2-chlorobenzylcarbamate

To a stirring solution of (4-bromo-2-chlorophenyl)methanamine (2200 mg, 9978 μmol) in DCM (10 mL) was added BOC-Anhydride (9978 μl, 9978 μmol) [1M in THF] and stirred for 1 h at 23° C. after which ethylenediamine (1 mL) added. Solvents removed under reduce pressure and residue purified on 80 g silica eluting product with 0>50% Hex/EtOAc.

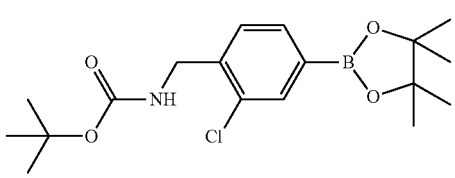 [SMILES: CC(C)(C)OC(=O)NCc1ccc(B2OC(C)(C)C(C)(C)O2)cc1Cl]

tert-butyl 2-chloro-4-(4,4,5,5-tetramethyl-1,3,2-dioxaborolan-2-yl)benzylcarbamate A suspension of tert-butyl 4-bromo-2-chlorobenzylcarbamate (1670 mg, 5209 μmol), bis(pinacolato)diboron (1455 mg, 5730 μmol), dichloro[1,1'bis(diphenylphoshino)ferrocene]palladium (ii)dichloromethane adduct (190.6 mg, 260.4 μmol), and potassium acetate (1022 mg, 10418 μmol) in dioxane (8 mL) was sparged with argon for 5 min then heated to 120° C. in an appropriately sealed vial with stirring. After 1 h, reaction partitioned between DCM (50 mL) and 5% NaHCO3 (25 mL). Organic dried over MgSO4, concentrated, then purified on 80 g silica eluting with 0>40% EtOAc/hexanes and product isolated as a viscous amber oil.

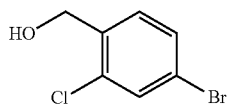

(4-bromo-2-chlorophenyl)methanol

To a stirring solution of 4-bromo-2-chlorobenzoic acid (11.1 g, 47 mmol) in THF (100 mL) at 0° C. under nitrogen was added borane-methyl sulfide complex (9.4 ml, 94 mmol) via syringe over 10 min. Gas evolution quite evident. Ice bath removed, and once gas evolution subsided reaction gently heated to reflux for 1 h. Reaction slowly quenched with MeOH (50 mL) and 2M HCl (20 mL). Aqueous extracted with 9:1 CHCl$_3$/IPA (150 mL). Organic dried with sat NH$_4$Cl, MgSO$_4$, then concentrated to a colorless oil under reduced pressure. Product crystallized after 1 week sitting neat.

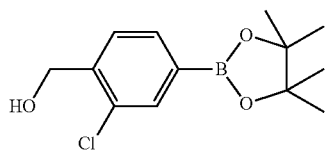 [SMILES: CC1(C)OB(c2ccc(CO)c(Cl)c2)OC1(C)C]

(2-chloro-4-(4,4,5,5-tetramethyl-1,3,2-dioxaborolan-2-yl)phenyl)

A suspension of (4-bromo-2-chlorophenyl)methanol (1000 mg, 4515 μmol), bis(pinacolato)diboron (1261 mg, 4967 μmol), dichloro[1,1'bis(diphenylphoshino)ferrocene]palladium(ii)dichloromethane adduct (165.2 mg, 225.8 μmol), and potassium acetate (886.2 mg, 9030 μmol) in dioxane (5 mL) was sparged with argon for 10 min then heated to 120° C. with stirring in an appropriately sealed vial. After 1 h, reaction then partioned between DCM (50 mL) and 5% NaHCO$_3$ (20 mL). Organic dried over MgSO$_4$, concentrated, then purified on 80 g silica eluting with 0>70% EtOAc/Hex. Product isolated as a light amber oil.

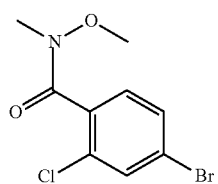

To a stirring solution of 4-bromo-2-chlorobenzoic acid (3.45 g, 15 mmol) and DIEA (7.7 ml, 44 mmol) in DMF (30 mL) was added HATU (6.1 g, 16 mmol) at 23° C. under nitrogen. Darkened suspension stirred for 1 h, then added n,o-dimethylhydroxylamine hydrochloride (2.1 g, 22 mmol). Solution stirred overnight at 23° C. Reaction then partitioned between 2.5% NaHCO$_3$ (250 mL) and diethyl ether (100 mL). Aqueous further extracted with ether (2×50 mL). Combined ethereal extracts dried over MgSO$_4$, then concentrated an amber oil under reduced pressure. 4-bromo-2-chloro-N-methoxy-N-methylbenzamide isolated as a light amber oil.

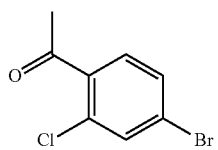

1-(4-bromo-2-chlorophenyl)ethanone

To a stirring solution of 4-bromo-2-chloro-N-methoxy-N-methylbenzamide (890 mg, 3195 μmol) in THF (10 mL) at −5° C. under nitrogen was slowly added methylmagnesium bromide 3.0 m in diethyl ether (1278 μl, 3834 μmol). After 30 min another 1.3 mL (3.8 mmol; 1.2 eq) of MeMgBr added at 23° C. After an additional hour, LCMS suggests 95% conversion. Reaction quenched with sat NH$_4$Cl (10 mL) and resulting white cake washed repeatedly with diethyl ether. Combined organics washed with water and sat NaCl then pushed through a plug of silica (10 g). 1-(4-bromo-2-chlorophenyl)ethanone isolated as a colorless oil.

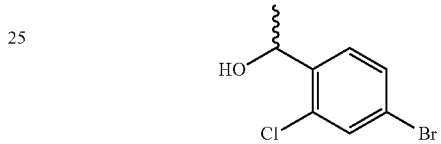

1-(4-bromo-2-chlorophenyl)ethanol

To a stirring solution of 1-(4-bromo-2-chlorophenyl)ethanone (700 mg, 2998 μmol) in THF (20 mL) was added sodium borohydride (340 mg, 8994 μmol) and methanol (5 mL). Reaction suspension stirred overnight at 30° C. Reaction then partioned between EtOAc (50 mL) and sat NH$_4$Cl (25 mL). Aqueous further extracted with EtOAc (2×25 mL). Combined organics dried over MgSO$_4$, concentrated, then purified on silica (40 g) eluting with 10>40% EtOAc/hexanes. Product isolated as a colorless oil.

1-(2-chloro-4-(4,4,5,5-tetramethyl-1,3,2-dioxaborolan-2-yl)phenyl)ethanol

A suspension of 1-(4-bromo-2-chlorophenyl)ethanol (600 mg, 2548 μmol), bis(pinacolato)diboron (712 mg, 2802 μmol), dichloro[1,1'bis(diphenylphoshino)ferrocene]palladium(ii)dichloromethane adduct (93.2 mg, 127 μmol), potassium acetate (319 μl, 5095 μmol) in dioxane (5 mL) was sparged with argon for 5 min then heated to 120° C. in an appropriately sealed vial. Reaction then partitioned between EtOAc (25 mL) and 5% NaHCO$_3$ (25 mL). Aqueous further washed with EtOAc (2×20 mL). Combined organics dried with sat NH$_4$Cl, MgSO$_4$, concentrated, then purified on silica (80 g) eluting with 10>35% EtOAc/Hex. Product isolated as a colorless oil.

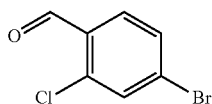

4-bromo-2-chlorobenzaldehyde

To a stirring solution of (4-bromo-2-chlorophenyl)methanol (4.5 g, 20 mmol) in DCM (50 mL) was added Dess-Martin periodinane (9.3 g) at 23° C. Reaction refluxed after addition. After 20 min, TLC (1:4 EtOAc/Hex) suggests full conversion of alcohol. Suspension then washed with 5% NaHCO$_3$ (100 mL plus 15 g dry NaHCO$_3$). Organic dried over MgSO$_4$, concentrated onto dry silica (15 g), then purified on silica (120 g) eluting with 0>10% EtOAc/hex. 4-bromo-2-chlorobenzaldehyde isolated as a white solid.

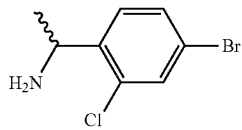

1-(4-bromo-2-chlorophenyl)ethanamine

A solution of 1-(4-bromo-2-chlorophenyl)ethanone (2.430 g, 10 mmol), ammonia, 2.0 m solution in methanol (26 ml, 52 mmol) and titanium (iv) isopropoxide (6 ml, 21 mmol) was stirred for 16 h in a sealed vessel. Reaction then added to a freshly made suspension of sodium borohydride powder, 98% (4 g, 104 mmol) in MeOH (20 mL). Exothermic reaction started at 9:45 am, then continued to stir with a 45° C. external heating bath for 45 min. Water (10 mL) then added to reaction and stirred for an additional 10 min. Resulting white solid removed via filtration through Celite, and filtrated reduced in volume under reduced pressure. This suspension then partioned between 9:1 CHCl$_3$/IPA (30 mL) and 1M NaOH (10 mL). Aqueous further extracted with 9:1 CHCl$_3$/IPA (2×10 mL). Combined organics dried over MgSO$_4$, concentrated, then purified on silica (80 g) eluting with 0>5% 2M NH$_3$ in MeOH/DCM. MS (ESI pos. ion) m/z: 234/236 (MH+). Calc'd exact mass for C$_8$H$_9$BrClN: 233/235. 1-(4-bromo-2-chlorophenyl)ethanamine isolated as a colorless oil.

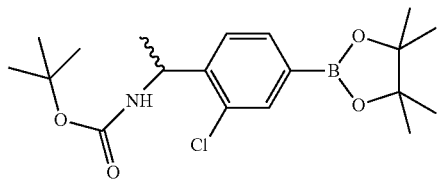 [SMILES: CC(NC(=O)OC(C)(C)C)c1ccc(B2OC(C)(C)C(C)(C)O2)cc1Cl]

tert-butyl 1-(2-chloro-4-(4,4,5,5-tetramethyl-1,3,2-dioxaborolan-2-yl)phenyl)ethylcarbamate To a stirring solution of 1-(4-bromo-2-chlorophenyl)ethanamine (950 mg, 4051 μmol) in DCM (5 mL) was added BOC-anhydride (4861 μl, 4861 μmol) [1M in THF]. Reaction stirred for 18 h at 23° C. Ethanolamine (0.25 mL) added and stirred for 5 min. Reaction then partitioned between diethyl ether (50 mL) and 5% NaHCO$_3$ (25 mL). Organic dried over MgSO$_4$, concentrated, then purified on silica (80 g) eluting with 0>20% EtOAc/hexanes. BOC-1.10 g. A suspension of the Bromo-BOC intermediate, bis(pinacolato)diboron (1132 mg, 4456 μmol), dichloro[1,1'bis(diphenylphoshino)ferrocene]palladium(ii)dichloromethane adduct (148 mg, 203 μmol), and potassium acetate (795 mg, 8102 μmol) in dioxane (8 mL) was sparged with argon for 5 min then heated to 120° C. in an appropriately sealed vessel for 2 h. Reaction then partitioned between 9:1 CHCl$_3$/IPA (50 mL) and sat. NH$_4$Cl (20 mL). Organic dried over MgSO$_4$, concentrated, and product purified on silica (80 g) eluting with 10>15% of EtOAc/Hex. tert-butyl 1-(2-chloro-4-(4,4,5,5-tetramethyl-1,3,2-dioxaborolan-2-yl)phenyl)ethylcarbamate isolated as a white foam.

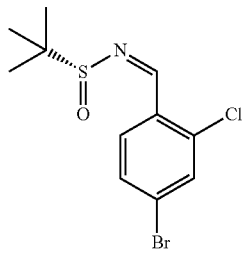 [SMILES: CC(C)(C)[S@@](=O)/N=C\c1ccc(Br)cc1Cl]

(R,Z)—N-(4-bromo-2-chlorobenzylidene)-2-methylpropane-2-sulfinamide

A suspension of 4-bromo-2-chlorobenzaldehyde (1150 mg, 5240 μmol), (r)-(+)-2-methyl-2-propanesulfinamide (1588 mg, 13100 μmol), copper(ii) sulfate (696.4 μl, 15720 μmol) in DCM (10 mL) was stirred at 37° C. for 78 h. Reaction filtered through Celite, and solid washed repeatedly with DCM. Filtrate concentrated then purified on silica (80 g) eluting product with 0>30% of EtOAc/Hex. MS (ESI pos. ion) m/z: 322/324 (MH+). Calc'd exact mass for C$_{11}$H$_{13}$BrClNOS: 321/323.

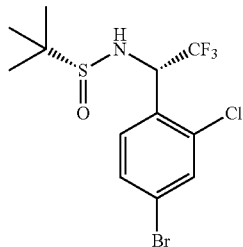 [SMILES: CC(C)(C)[S@@](=O)N[C@@H](c1ccc(Br)cc1Cl)C(F)(F)F]

(R)—N—((S)-1-(4-bromo-2-chlorophenyl)-2,2,2-trifluoroethyl)-2-methylpropane-2-sulfinamide To a stirring solution of (R,Z)—N-(4-bromo-2-chlorobenzylidene)-2-methylpropane-2-sulfinamide (1370 mg, 4246 μmol) and (trifluoromethyl)trimethylsilane (943 μl, 6369 μmol) in DMF (5 mL) was added 1,3-bis(1-adamantyl)imidazol-2-ylidene (143 mg, 425 μmol). Reaction stirred at 35° C. for 18 h then quenched with sat NH$_4$Cl (10 mL). Reaction partitioned between EtOAc (40 mL) and 5% NaHCO$_3$ (10 mL). Organic dried over MgSO4, concentrated to and oil from toluene, then purified on silica (80 g) eluting with 20>30% EtOAc/Hex. Product isolated as a white solid.

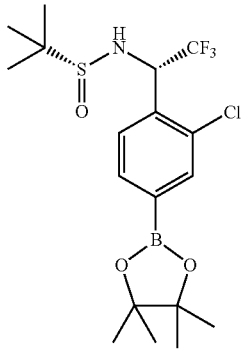 [SMILES: CC(C)(C)[S@@](=O)N[C@@H](c1ccc(B2OC(C)(C)C(C)(C)O2)cc1Cl)C(F)(F)F]

(R)—N—((S)-1-(2-chloro-4-(4,4,5,5-tetramethyl-1,3,2-dioxaborolan-2-yl)phenyl)-2,2,2-trifluoroethyl)-2-methylpropane-2-sulfinamide A suspension of (R)—N—((S)-1-(4-bromo-2-chlorophenyl)-2,2,2-trifluoroethyl)-2-methylpropane-2-sulfinamide (950 mg, 2419 μmol), bis(pinacolato)diboron (676 mg, 2661 μmol), dichloro[1,1'bis(diphenylphoshino)ferrocene]palladium(ii)dichloromethane adduct (88.5 mg, 121 μmol), and potassium acetate (475 mg, 4839 μmol) in dioxane (6 mL) was sparged with argon for 5 min. Reaction then appropriately sealed and heated to 120° C. with stirring for 1 h. Reaction then partitioned between EtOAc (25 mL) and 5% NaHCO$_3$ (10 mL). Organic dried over MgSO$_4$, concentrated, then purified on silica (120 g) eluting product with 10>20% of EtOAc/hexanes. Product isolated as a waxy white solid. MS (ESI pos. ion) m/z: 440 (MH+). Calc'd exact mass for $C_{18}H_{26}BClF_3NO_3S$: 439.

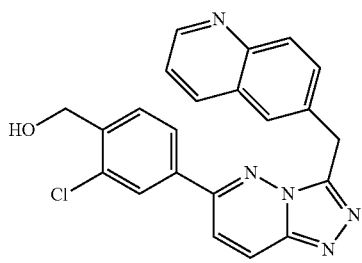 [SMILES: OCc1ccc(-c2ccc3nnc(Cc4ccc5ncccc5c4)n3n2)cc1Cl]

EXAMPLE 99

(2-chloro-4-(3-(quinolin-6-ylmethyl)-[1,2,4]-triazolo[4,3-b]pyridazin-6-yl)phenyl)methanol A suspension of 6-((6-chloro-[1,2,4]triazolo[4,3-b]pyridazin-3-yl)methyl)quinoline (170 mg, 575 μmol), (2-chloro-4-(4,4,5,5-tetramethyl-1,3,2-dioxaborolan-2-yl)phenyl)methanol (309 mg, 1150 μmol), dichloro[1,1'bis(diphenylphoshino)ferrocene]palladium(ii)dichloromethane adduct (126 mg, 172 μmol), cesium carbonate (749 mg, 2299 μmol) in Dioxane (0.3 mL) and water (0.3 mL) was sparged with argon for 5 min then heated to 100° C. with stirring. 1:30 am. After 90 min, LCMS suggests 95% conversion. Reaction then partitioned between 9:1 CHCl$_3$/IPA (25 mL) and 5% NaHCO$_3$ (15 mL). Aqueous further extracted with 9:1 CHCl$_3$/IPA (2×10 mL). Combined organics dried with MgSO$_4$, concentrated onto dry silica (10 g), and then purified on silica (12 g) eluting with 0>10% 2M NH$_3$ in MeOH/DCM. Resulting solid triturated with methanol (2 mL) and collected by filtration. MS (ESI pos. ion) m/z: 402 (MH+). Calc'd exact mass for $C_{22}H_{16}ClN_5O$: 401.

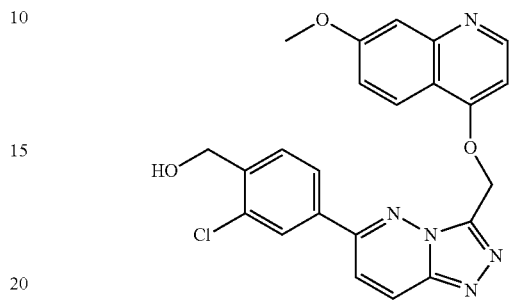

EXAMPLE 100

(2-chloro-4-(3-((7-methoxyquinolin-4-yloxy)methyl)-[1,2,4]triazolo[4,3-b]pyridazin-6-yl)phenyl)methanol A suspension of 4-((6-chloro-[1,2,4]triazolo[4,3-b]pyridazin-3-yl)methoxy)-7-methoxyquinoline (200 mg, 585 μmol), (3-chloro-4-(4,4,5,5-tetramethyl-1,3,2-dioxaborolan-2-yl)phenyl)methanol (173 mg, 644 μmol), dichloro[1,1'bis(diphenylphoshino)ferrocene]palladium(ii)dichloromethane adduct (21 mg, 29 μmol), and sodium carbonate (2M; 1170 μl, 2341 μmol) in DME (2 mL) was sparged with argon for 10 min then heated to 85° C. for 6 h. Reaction then partitioned between 9:1 CHCl$_3$/IPA (25 mL) and 5% NaHCO$_3$ (10 mL) and aqueous further extracted with 9:1 CHCl$_3$/IPA (2×10 mL). Combined organics dried with MgSO$_4$ then concentrated onto dry silica under reduced pressure. Product purified on 40 g silica eluting with 0>12% of 2M NH$_3$ in MeOH/DCM and isolated as an off white powder. MS (ESI pos. ion) m/z: 448 (MH+). Calc'd exact mass for $C_{23}H_{18}ClN_5O_3$: 447.

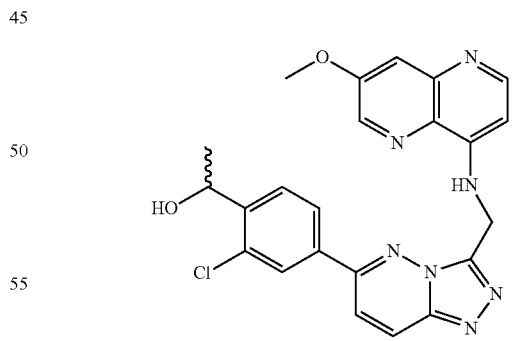

EXAMPLE 101

1-(2-chloro-4-(3-((7-methoxy-1,5-naphthyridin-4-ylamino)methyl)-[1,2,4]triazolo[4,3-b]pyridazin-6-yl)phenyl)ethanol A suspension of 1-(2-chloro-4-(4,4,5,5-tetramethyl-1,3,2-dioxaborolan-2-yl)phenyl)ethanol (228 mg, 807 μmol), N-((6-chloro-[1,2,4]triazolo[4,3-b]pyridazin-3-yl)methyl)-7-methoxy-1,5-naphthyridin-4-amine (197 mg, 576 µmol), dichloro[1,1'bis(diphenylphoshino)ferrocene]palladium(ii) dichloromethane adduct (127 mg, 173 µmol), cesium carbonate (751 mg, 2306 µmol) in dioxane (3 mL) and water (0.6 mL) was sparged with argon for 5 min then heated to 100° C. for 6 h. Reaction cooled then partitioned between 9:1 CHCl$_3$/IPA (20 mL) and 1M NaOH (15 mL). Aqueous further extracted with 9:1 CHCl$_3$/IPA (2×10 mL). The combined organics dried over MgSO$_4$. concentrated, then purified on 40 g silica eluting with an isocratic 7% 2M NH$_3$ in MeOH/DCM. Product further purified prep HPLC eluting with water/ACN (0.1% TFA). After collected fractions were reduced to a clear the residue was dissolved in 1:1 ACN/water and pH adjusted to 9 with 1M NaOH (3-4 drops). Resulting solid collected by filteration and solid washed with water (2 mL). MS (ESI pos. ion) m/z: 462 (MH+). Calc'd exact mass for C$_{23}$H$_{20}$ClN$_7$O$_2$: 461.

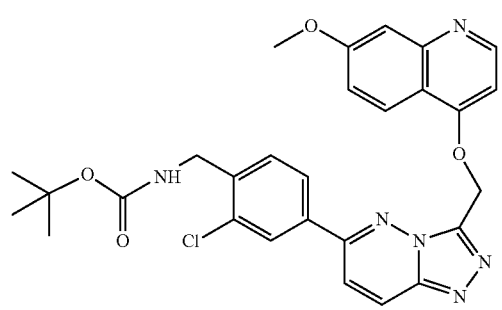 [SMILES: COc1ccc2c(OCc3nnc4ccc(-c5ccc(CNC(=O)OC(C)(C)C)c(Cl)c5)nn34)ccnc2c1]

EXAMPLE 102 tert-butyl (2-chloro-4-(3-((7-methoxyquinolin-4-yloxy)methyl)-[1,2,4]triazolo[4,3-b]pyridazin-6-yl)phenyl) methylcarbamate A suspension of 4-((6-chloro-[1,2,4]triazolo[4,3-b]pyridazin-3-yl)methoxy)-7-methoxyquinoline (200 mg, 585 µmol), tert-butyl 2-chloro-4-(4,4,5,5-tetramethyl-1,3,2-dioxaborolan-2-yl)benzylcarbamate (323 mg, 878 µmol), dichloro[1,1'bis(diphenylphoshino)ferrocene]palladium(ii) dichloromethane adduct (86 mg, 117 µmol), cesium carbonate (763 mg, 2341 µmol) in dioxane (3 mL) and water (0.3 mL) was sparged with argon for 10 min then heated to 100° C. for 18 h. Reaction then partitioned between 9:1 CHCl$_3$/IPA (50 mL) and 5% NaHCO$_3$ (25 mL). Aqueous further extracted with 9:1 CHCl$_3$/IPA (2×10 mL). Combined organics then dried over MgSO$_4$, concentrated, and purified on silica (40 g) eluting with 0>6% 2M NH$_3$ in MeOH/DCM. Product isolated as an off white solid. 84024-19-2 MS (ESI pos. ion) m/z: 547 (MH+). Calc'd exact mass for C$_{28}$H$_{27}$ClN$_6$O$_4$: 546.

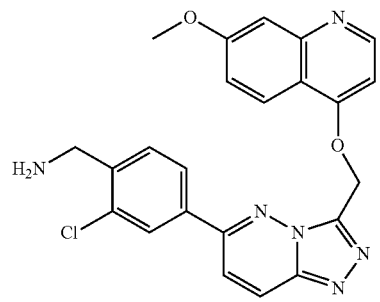 [SMILES: COc1ccc2c(OCc3nnc4ccc(-c5ccc(CN)c(Cl)c5)nn34)ccnc2c1]

EXAMPLE 103

2-chloro-4-(3-((7-methoxyquinolin-4-yloxy)methyl)-[1,2,4]triazolo[4,3-b]pyridazin-6-yl)phenyl)methanamine A solution of tert-butyl (2-chloro-4-(3-((7-methoxyquinolin-4-yloxy)methyl)-[1,2,4]triazolo[4,3-b]pyridazin-6-yl)phenyl)methylcarbamate (85 mg, 155 µmol) in DCM (2 mL) and TFA (2 mL) stirred for 30 min at 23° C. Solvents removed under reduced pressure, then residue partitioned between 9:1 DCM/IPA (10 mL) and 1M NaOH (5 mL). Aqueous further extracted with DCM (2×5 mL). Combined organics dried over MgSO$_4$, then reduced to an off white solid under reduced pressure. MS (ESI pos. ion) m/z: 447 (MH+). Calc'd exact mass for C$_{23}$H$_{19}$ClN$_6$O$_2$: 446.

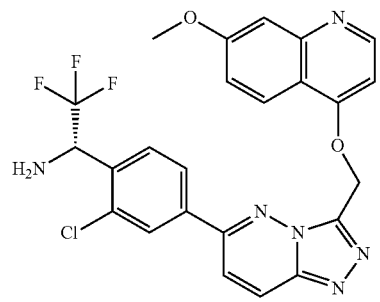 [SMILES: COc1ccc2c(OCc3nnc4ccc(-c5ccc([C@H](N)C(F)(F)F)c(Cl)c5)nn34)ccnc2c1]

EXAMPLE 104

(S)-1-(2-chloro-4-(3-((7-methoxyquinolin-4-yloxy)methyl)-[1,2,4]triazolo[4,3-b]pyridazin-6-yl)phenyl)-2,2,2-trifluoroethanamine A solution of (R)—N—((S)-1-(2-chloro-4-(3-((7-methoxyquinolin-4-yloxy)methyl)-[1,2,4]triazolo[4,3-b]pyridazin-6-yl)phenyl)-2,2,2-trifluoroethyl)-2-methylpropane-2-sulfinamide (135 mg, 218 µmol) in MeOH (2 mL) and 4M HCl (2 mL) was stirred for 30 min at 35° C. LCMS suggests full conversion. Solvents removed under reduced pressure with azeotroping from toluene. Residue dissolved in MeOH (10 mL) and Si-Carbonate (2 g; 1.4 mmol) added. Suspension stirred for 30 min, then filtrated collected by filtration. Solvents removed under reduced pressure and residue purified on silica (12 g) eluting product with 0>5% MeOH/DCM. MS (ESI pos. ion) m/z: 515 (MH+). Calc'd exact mass for C$_{24}$H$_{18}$ClF$_3$N$_6$O$_2$: 514.

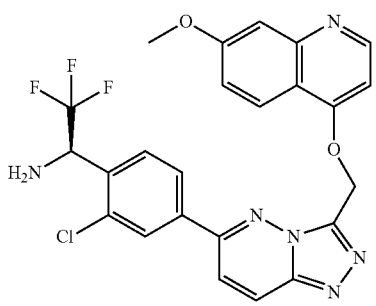 [SMILES: COc1ccc2c(OCc3nnc4ccc(-c5ccc([C@@H](N)C(F)(F)F)c(Cl)c5)nn34)ccnc2c1]

EXAMPLE 105

(R)-1-(2-chloro-4-(3-((7-methoxyquinolin-4-yloxy)methyl)-[1,2,4]triazolo[4,3-b]pyridazin-6-yl)phenyl)-2,2,2-trifluoroethanamine A solution of (S)—N-((R)-1-(2-chloro-4-(3-((7-methoxyquinolin-4-yloxy)methyl)-[1,2,4]triazolo[4,3-b]pyridazin-6-yl)phenyl)-2,2,2-trifluoroethyl)-2-methylpropane-2-sulfinamide (62 mg, 100 µmol) in MeOH (2 mL) and 5M HCl (2 mL) was stirred at 35° C. for 18 h. LCMS suggests full conversion. Solvents removed under reduced pressure and residue dissolved in MeOH (20 mL). Si-Carbonate (1.3 g; 0.9 mmol) added to solution and stirred for 2 h. Filtrated isolated by filtration and reduced to a film under reduced pressure. Product purified on silica (4 g) eluting with 7% 2M $NH_3$ in MeOH/DCM. MS (ESI pos. ion) m/z: 515 (MH+). Calc'd exact mass for $C_{24}H_{18}ClF_3N_6O_2$: 514.

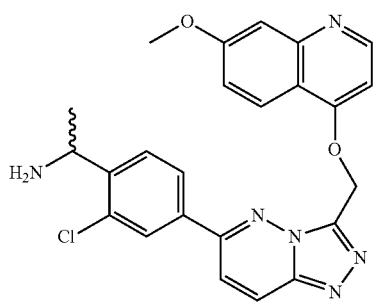

EXAMPLE 107

1-(2-chloro-4-(3-((7-methoxyquinolin-4-yloxy)methyl)-[1,2,4]-triazolo[4,3-b]pyridazin-6-yl)phenyl)ethanamine A solution of tert-butyl 1-(2-chloro-4-(3-((7-methoxyquinolin-4-yloxy)methyl)-[1,2,4]triazolo[4,3-b]pyridazin-6-yl)phenyl)ethylcarbamate (100 mg, 178 µmol) in DCM (2 mL) and TFA (2 mL) was stirred for 30 min at 23° C. Solvents removed under reduced pressure (not-toluene azeotroping is suggested!) and residue dissolved in $CHCl_3$/IPA (10 mL). Solution stirred as a suspension with Si-Carbonate (1.3 g; 1 mmol) for 30 min. Suspension filtered and filtrate reduced to an amber film (150 mg). Product purified on silica (12 g) eluting with 4-7% of 2M $NH_3$ in MeOH/DCM. MS (ESI pos. ion) m/z: 461 (MH+). Calc'd exact mass for $C_{24}H_{21}ClN_6O_2$: 460.

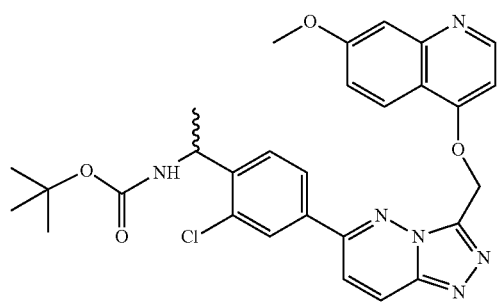 [SMILES: COc1ccc2c(OCc3nnc4ccc(-c5ccc(C(C)NC(=O)OC(C)(C)C)c(Cl)c5)nn34)ccnc2c1]

EXAMPLE 106 tert-butyl 1-(2-chloro-4-(3-((7-methoxyquinolin-4-yloxy)methyl)-[1,2,4]triazolo[4,3-b]pyridazin-6-yl)phenyl)ethylcarbamate. A suspension of 4-((6-chloro-[1,2,4]triazolo[4,3-b]pyridazin-3-yl)methoxy)-7-methoxyquinoline (180 mg, 527 µmol), tert-butyl 1-(2-chloro-4-(4,4,5,5-tetramethyl-1,3,2-dioxaborolan-2-yl)phenyl)ethylcarbamate (302 mg, 790 µmol), dichloro[1,1'bis(diphenylphoshino)ferrocene]palladium(ii)dichloromethane adduct (77.1 mg, 105 µmol), cesium carbonate (686 mg, 2107 µmol) in DMF (2 mL) and water (0.4 mL) was first sparged with argon for 5 min then heated to 100° C. with stirring. 2:20 pm After 10 min, LCMS suggests >95% conversion. Reaction then partitioned between 9:1 $CHCl_3$/IPA (20 mL) and 1M NaOH (5 mL). Organic then dried over MgSO4, concentrated, and purified on silica (40 g) eluting with isocratic 4% of 2M $NH_3$ in MeOH/DCM. MS (ESI pos. ion) m/z: 561 (MH+). Calc'd exact mass for $C_{29}H_{29}ClN_6O_4$: 560.

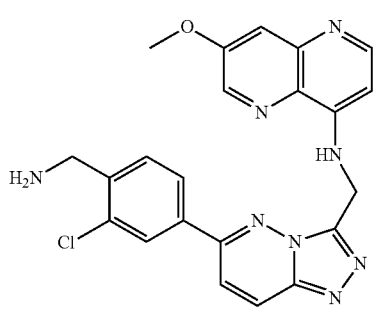 [SMILES: COc1cnc2c(NCc3nnc4ccc(-c5ccc(CN)c(Cl)c5)nn34)ccnc2c1]

EXAMPLE 108

N-((6-(4-(aminomethyl)-3-chlorophenyl)-[1,2,4]-triazolo[4,3-b]pyridazin-3-yl)methyl)-7-methoxy-1,5-naphthyridin-4-amine To a stirring solution of tert-butyl (2-chloro-4-(3-((7-methoxy-1,5-naphthyridin-4-ylamino)methyl)-[1,2,4]triazolo[4,3-b]pyridazin-6-yl)phenyl)methylcarbamate (70 mg, 128 µmol) in DCM (2 mL) was added TFA (2 mL). Reaction solution stirred for 30 min at 23° C. Solvents then removed under reduced pressure and residue purified on prep-HPLC using a water/ACN (0.1% TFA) gradient. Resulting solid was dissolved in 1:1 ACN/water (1 mL) and pH adjusted to 10 with 1M NaOH (approx 10 drops). Resulting solid collected by filtraton and washed with water (5 mL). MS (ESI pos. ion) m/z: 447 (MH+). Calc'd exact mass for $C_{22}H_{19}ClN_8O$: 446.

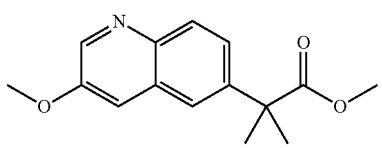

methyl 2-(3-methoxyquinolin-6-yl)-2-methylpropanoate

To a stirring solution of methyl 2-(3-methoxyquinolin-6-yl)acetate (450 mg, 1946 μmol) in THF (5 mL) at −70° C. under nitrogen was added lithium bis(trimethylsilyl)amide, 1.0 m solution in tetrahydrofuran (5838 μl, 5838 μmol). Dark red solution stirred for 10 min, then added iodomethane (364 μl, 5838 μmol) in THF (1 mL). Reaction removed from cooling bath, and monitored by LCMS after 45 min. LCMS suggests very clean conversion. Reaction quenched with sat NH$_4$Cl (5 mL) and NaHCO$_3$ (5 mL). Aqueous extracted with EtOAc (3×40 mL). Combined organics dried over MgSO4, concentrated, then purified on silica (40 g) eluting with 10>30% of EtOAc/Hex._MS (ESI pos. ion) m/z: 260 (MH+). Calc'd exact mass for $C_{15}H_{17}NO_3$: 259.

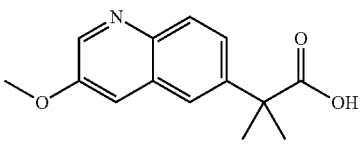 [SMILES: COc1cnc2ccc(C(C)(C)C(=O)O)cc2c1]

2-(3-methoxyquinolin-6-yl)-2-methylpropanoic acid

A solution of methyl 2-(3-methoxyquinolin-6-yl)-2-methylpropanoate (400 mg, 1543 μmol), LiOH (1928 μl, 7713 μmol) [4M], MeOH (2 mL), and THF (2 mL) was stirred at 50° C. overnight. LCMS suggests full conversion. Solution cooled, acidified to pH 1 with 5M HCl, and precipitate collected by filtration. White cake washed with water (2 mL) and EtOH (1 mL). Product air dried for 3 h and isolated as a white solid. MS (ESI pos. ion) m/z: 246 (MH+). Calc'd exact mass for $C_{14}H_{15}NO_3$: 245.

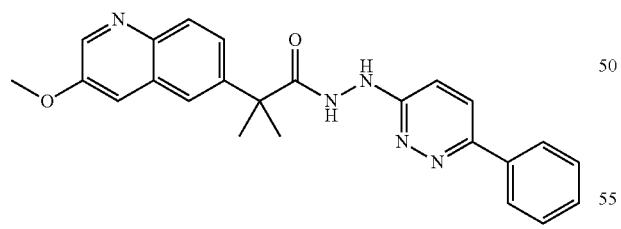

2-(3-methoxyquinolin-6-yl)-2-methyl-N'-(6-phenylpyridazin-3-yl)propanehydrazide

A suspension of 2-(3-methoxyquinolin-6-yl)-2-methylpropanoic acid (92 mg, 375 μmol), DIEA (66 μl, 375 μmol), and o-(7-azabenzotriazol-1-yl)-n,n,n',n-tetramethyl uronium hexafluorophosphate (143 mg, 375 μmol) in DMF was stirred for 2 h at 23° C. To the solution was added 1-(6-phenylpyridazin-3-yl)hydrazine (70 mg, 375 μmol) and stirred for 72 h at 23° C. Reaction partitioned between 9:1 CHCl$_3$/IPA (25 mL) and 1M NaOH (5 mL). Organic dried over MgSO$_4$ the concentrated to a solid from toluene under reduced pressure. Solid triturated with ACN (2 mL) and collected by filtration. 2-(3-methoxyquinolin-6-yl)-2-methyl-N'-(6-phenylpyridazin-3-yl)propanehydrazide isolated as a white solid. MS (ESI pos. ion) m/z: 414 (MH+). Calc'd exact mass for $C_{24}H_{23}N_5O_2$: 413.

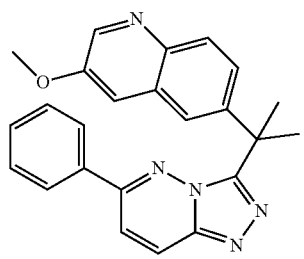 [SMILES: COc1cnc2ccc(C(C)(C)c3nnc4ccc(-c5ccccc5)nn34)cc2c1]

EXAMPLE 109

3-methoxy-6-(2-(6-phenyl-[1,2,4]triazolo[4,3-b]pyridazin-3-yl)propan-2-yl)quinoline A solution of 2-(3-methoxyquinolin-6-yl)-2-methyl-N'-(6-phenylpyridazin-3-yl)propanehydrazide (270 mg, 653 μmol) in TFA (2 mL) was heated to 150° C. in microwave (6 bar; 20 W) for 2 h. LCMS suggests very good conversion: 89425-17-1. Reaction concentrated under reduced pressure then partitioned between CHCl$_3$/IPA (50 mL) and 1M NaOH (50 mL). Aqueous further extracted with CHCl$_3$/IPA (15 mL) and combined organics dried over MgSO$_4$, concentrated, then dissolved in ACN (2 mL). Crystallized solid washed with ACN (1 mL) and dried under reduced pressure. MS (ESI pos. ion) m/z: 396 (MH+). Calc'd exact mass for $C_{24}H_{21}N_5O$: 395.

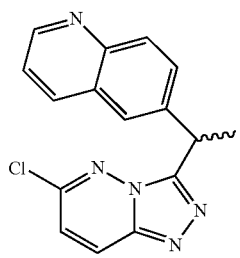 [SMILES: CC(c1ccc2ncccc2c1)c1nnc2ccc(Cl)nn12]

EXAMPLE 110

6-(1-(6-chloro-[1,2,4]triazolo[4,3-b]pyridazin-3-yl)ethyl)quinoline

A solution of N'-(6-chloropyridazin-3-yl)-2-(quinolin-6-yl)propanehydrazide (4300 mg, 13119 μmol) in TFA (40 mL) was heated to 120° C. with microwaves for 40 min. LCMS suggests very good converson. Solvents removed under reduced pressure and residue partitioned between 9:1 CHCl$_3$/IPA (75 mL) and 1M NaOH (100 mL).

Aqueous further extracted with 9:1 CHCl$_3$/IPA (2×25 mL). Combined organics dried over MgSO4, concentrated, and oily residue dissolved in ACN/MeOH (2 mL). Resulting solid after 2 h was isolated by filtration and washed with ACN (5 mL). 6-(1-(6-chloro-[1,2,4]triazolo[4,3-b]pyridazin-3-yl)ethyl)quinoline isolated as a white solid. MS (ESI pos. ion) m/z: 310 (MH+). Calc'd exact mass for $C_{16}H_{12}ClN_5$: 309.

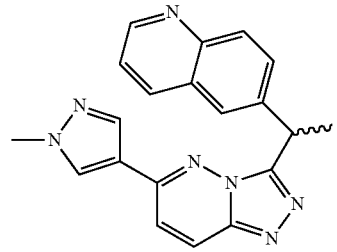 [SMILES: CC(c1ccc2ncccc2c1)c1nnc2ccc(-c3cnn(C)c3)nn12]

EXAMPLE 111

6-(1-(6-(1-methyl-1H-pyrazol-4-yl)-[1,2,4]triazolo[4,3-b]pyridazin-3-yl)ethyl)quinoline A suspension of 6-(1-(6-chloro-[1,2,4]triazolo[4,3-b]pyridazin-3-yl)ethyl)quinoline (106 mg, 342 µmol), 1-methyl-4-(4,4,5,5-tetramethyl-1,3,2-dioxaborolan-2-yl)-1H-pyrazole (142 mg, 684 µmol), dichloro[1,1'bis(diphenylphoshino)ferrocene]palladium(ii)dichloromethane adduct (25 mg, 34 µmol), and cesium carbonate (446 mg, 1369 µmol) in DMF (1 mL) and water (0.5 mL) was sparged for 5 min with argon then heated to 100° C. in an appropriately sealed vial for 30 min. Reaction then partitioned between 9:1 CHCl₃/IPA (20 mL) and 1M NaOH (5 mL). Aqueous further extracted with 9:1 CHCl₃/IPA (5 mL) and combined organics dried over MgSO4, concentrated to a solid from toluene, then purified on silica (12 g) eluting with 30>50% of 10% 2M NH₃ in MeOH/DCM. 6-(1-(6-(1-methyl-1H-pyrazol-4-yl)-[1,2,4]triazolo[4,3-b]pyridazin-3-yl)ethyl)quinoline isolated as off white crystals from ACN (1 mL). MS (ESI pos. ion) m/z: 356 (MH+). Calc'd exact mass for $C_{20}H_{17}N_7$: 355.

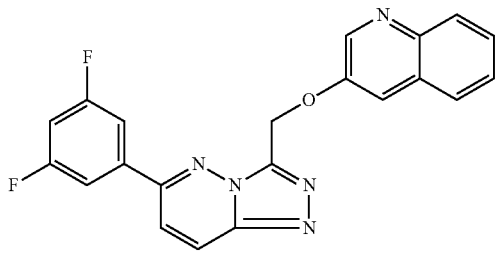 [SMILES: Fc1cc(F)cc(-c2ccc3nnc(COc4cnc5ccccc5c4)n3n2)c1]

EXAMPLE 112

3-(6-(3,5-difluorophenyl)-[1,2,4]triazolo[4,3-b]pyridazin-3-yl)methoxy)quinoline To a mixture of quinolin-3-ol (0.058 g, 0.40 mmol), (6-(3,5-difluorophenyl)-[1,2,4]triazolo[4,3-b]pyridazin-3-yl)methanol (0.104 g, 0.4 mmol), and triphenylphosphine (0.11 g, 0.44 mmol) in dry tetrahydrofuran (2 ml) and dry dichloromethane (2 ml) under argon, was added dropwise with stirring, diethyl azodicarboxylate (0.069 ml, 0.44 mmol). The resulting mixture was stirred at room temperature for 18 hours. The solvent was then stripped at reduced pressure, and the residue subjected to chromatography on Silica gel, eluent 5% methanol in dichloromethane to afford the title compound, which was recrystallised from hot toluene to give a colourless solid. M/e 390 (MH⁺)

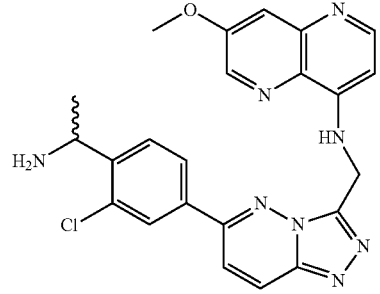 [SMILES: COc1cnc2c(NCc3nnc4ccc(-c5ccc(C(C)N)c(Cl)c5)nn34)ccnc2c1]

EXAMPLE 113

N-((6-(4-(1-aminoethyl)-3-chlorophenyl)-[1,2,4]triazolo[4,3-b]pyridazin-3-yl)methyl)-7-methoxy)-1,5-naphthyridin-4-amine A suspension of N-((6-chloro-[1,2,4]triazolo[4,3-b]pyridazin-3-yl)methyl)-7-methoxy-1,5-naphthyridin-4-amine (300 mg, 878 µmol), tert-butyl 1-(2-chloro-4-(4,4,5,5-tetramethyl-1,3,2-dioxaborolan-2-yl)phenyl)ethylcarbamate (419 mg, 1097 µmol), dichloro[1,1'bis(diphenylphoshino)ferrocene]palladium(ii)dichloromethane adduct (193 mg, 263 µmol), cesium carbonate (1144 mg, 3511 µmol) in dioxane (6 mL) and water (1 mL) was sparged with argon for 10 min then heated to 100° C. for 20 h with stirring. Reaction then partitioned between 9:1 CHCl₃/IPA (50 mL) and 1M NaOH (25 mL). Aqueous further extracted with 9:1 CHCl₃/IPA (20 mL). Combined organics then dried over MgSO4, concentrated, and purified on 40 g silica eluting with 7>8% of 2M NH₃ in MeOH/DCM. Product then further purified on prep HPLC eluting with water/ACN (0.1% TFA). BOC intermediate then stirred as a solution in DCM (1 mL) and TFA (3 mL) for 30 min. Solvents removed under reduced pressure and residue dissolved in MeOH (8 mL) and DCM (8 mL). Solution then stirred with Si-Carbonate from Silicycle (1 g/with a labeled loading of 0.77 mmol/g) for 1 h at 23° C. Suspension filtered and filtrate reduced to a film under reduced pressure. Product was lyophilized from 1:1 ACN/water (1.5 mL) to provide N-((6-(4-(1-aminoethyl)-3-chlorophenyl)-[1,2,4]triazolo[4,3-b]pyridazin-3-yl)methyl)-7-methoxy)-1,5-naphthyridin-4-amine as an off white fluffy solid. MS (ESI pos. ion) m/z: 461 (MH+). Calc'd exact mass for $C_{23}H_{21}ClN_8O$: 460.

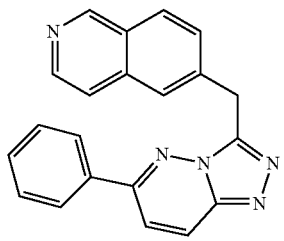 [SMILES: c1ccc(-c2ccc3nnc(Cc4ccc5cnccc5c4)n3n2)cc1]

EXAMPLE 114

6-((6-phenyl-[1,2,4]triazolo[4,3-b]pyridazin-3-yl)methyl)isoquinoline

Step 1. tert-Butyl 2-(isoquinolin-6-yl)acetate.

A dry, 25 mL, 1 neck round bottom flask was charged with a 0.5 M Et$_2$O solution of Zincate 2 (10.00 ml, 5.0 mmol, Reike Metals), and concentrated in vacuo. The vacuum was released with nitrogen, and the flask was charged with a stirbar, 5 mL dry THF, fitted with a reflux condenser and an Ar inlet. Upon dissolution of the solids, 6-bromoisoquinoline (0.516 g, 2.5 mmol) and tetrakis(triphenylphosphine)palladium (0.24 g, 0.21 mmol) was added. The solution was heated with an 80° C. oil bath for 5 h, and cooled. The solution was treated with 30 mL of 10% aqueous EDTA (pH adjusted to 6.1 with NaOH), and stirred for 1 h. A precipitate had formed that was removed by filtration of the biphasic solution through a sintered glass funnel and discarded. The filtrate was concentrated to ~35 mL, and extracted with DCM (4×30 mL). The combined extracts were washed with water (1×30 mL), and the water was back-extracted with DCM (1×10 mL). The DCM layers were dried over MgSO$_4$, and the resultant slurry filtered through a sintered glass funnel. The filtrate was concentrated in vacuo. The residue was dissolved in 10 mL DCM and treated with Si-carbonate (Silicycle, 5.5 g, 3.7 mmol). The slurry was swirled occasionally for 1 h, and filtered through a 0.22 uM PTFE membrane. The silica was washed with DCM (4×20 mL), and the combined filtrates were concentrated in vacuo. The residue was purified in three injections using a Waters Spherisorb S5 column (PN PSS830195, 20×250 mm, 60 Å pore, 5 μm particle size); flow=20 mL/min; A=DCE, B=EtOH; isocratic at 5% B. A band that eluted from 3.9 to 5.9 minutes was isolated. The solvent was removed in vacuo to afford ten-butyl 2-(isoquinolin-6-yl)acetate.

Step 2. 6-((6-phenyl-[1,2,4]triazolo[4,3-b]pyridazin-3-yl)methyl)isoquinoline hydrochloride.

A 10 mL, CEM microwave vessel was charged with 3 (0.1040 g, 0.427 mmol), 1-(5-phenylpyridin-2-yl)hydrazine (4, 0.119 g, 0.641 mmol), a stirbar and 1 mL concentrated HCl. The vessel was sealed, and fitted with an 18-gauge needle and an Argon inlet. The slurry was placed in a heating block at 115° C. for 15 minutes with stirring. A volatile substance evolved during this time. The vessel was briefly cooled, and the seal was replaced. The vessel was irradiated on a CEM Explorer using the following parameters: ramp time 20 s, hold time 10 min, hold temperature 150° C., powermax=on, 75 W max. The resultant turbid aqueous solution was filtered and concentrated in vacuo. The solids were suspended in 3 mL hot EtOH, and cooled. The precipitate was isolated by filtration and washed with EtOH (3×3 mL). The solids were taken up in 2 mL H$_2$O, and filtered through a 0.1 μm PVDF Ultra-free-CL centrifugal filter (Millipore Corp, PN UFC40W00, 2000 g for 5 minutes). The aqueous filtrate was lyophilized to afford 6-((6-phenyl-[1,2,4]triazolo[4,3-b]pyridazin-3-yl)methyl)isoquinoline hydrochloride. Anal. Calcd for C$_{21}$H$_{15}$N$_5$.HCl.1.7 H$_2$O: C, 62.36; H, 4.83; N, 17.31. Found: C, 62.39±0.08; H, 4.48±0.02; N, 17.28±0.03.

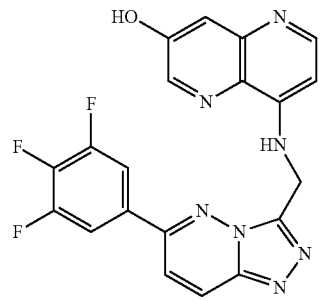 [SMILES: Oc1cnc2c(NCc3nnc4ccc(-c5cc(F)c(F)c(F)c5)nn34)ccnc2c1]

EXAMPLE 115

8-((6-(3,4,5-trifluorophenyl)-[1,2,4]triazolo[4,3-b]pyridazin-3-yl)methylamino)-1,5-naphthyridin-3-ol A sealed tube was charged with 7-methoxy-N-((6-(3,4,5-trifluorophenyl)-[1,2,4]triazolo[4,3-b]pyridazin-3-yl)methyl)-1,5-naphthyridin-4-amine hydrochloride (238 mg, 502 μmol) and HBr (5966 μl, 52740 μmol), sealed, then placed in a 120° C. oil bath for 48 h. Cooled to room temperature and brought to pH~14 with NaOH (6N). Isolated solid by filtration which was purified by RPHPLC to afford 8-((6-(3,4,5-trifluorophenyl)-[1,2,4]triazolo[4,3-b]pyridazin-3-yl)methylamino)-1,5-naphthyridin-3-ol as its formate salt. MS (ESI pos. ion) m/z: 424 (MH+). Calc'd exact mass for C$_{20}$H$_{12}$F$_3$N$_2$O: 423.

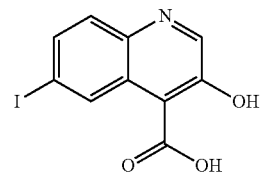 [SMILES: O=C(O)c1c(O)cnc2ccc(I)cc12]

3-hydroxy-6-iodoquinoline-4-carboxylic acid 5-iodoindoline-2,3-dione (50 g, 183 mmol) was dissolved in a hot solution containing potassium hydroxide (82 g, 1465 mmol) and water (250 mL). The reaction mixture was in homogeneous solution for 5 min then was precipitated out completely. Enough ethanol (30 ml) was added to redissolve the reaction mixture. After cooled to rt and mechanically stirred, 3-bromo-2-oxopropanoic acid hydrate (47 g, 256 mmol) was added portionwise—tremendous heat was generated (>80° C.). After the addition, the reaction mixture was cooled to rt and continued to stir for 3 days. The reaction mixture was treated with sat. solution of NaHSO$_3$ (sodium bisulfate, 12 g, 115.32 mmol) in order to prevent the development of color in the product. The resulting mixture was then acidified to pH=2 using concentrated HCl. After stirred for 1 h, the yellow ppt. that was formed in the solution mixture was collected by filtration. The solid was washed with water and suspended in water with SO$_2$ bubbling in the solution. After 30 minutes the solid again was separated by filtration. This wet solid was suspended in water, stirred, and dissolved by gradual addition of solid Na$_2$CO$_3$. The solution was treated with a saturated solution of NaHSO$_3$ and filtered. The filtrate was acidified to pH=2 using concentrated HCl. The solid that was formed in the solution mixture was collected by filtration. The solid was washed with water, then resuspended in water, and again filtered. The solid was suspended in EtOH, separated by filtration, and airdried to afford the desired product as a brown solid. MS m/z: 316.2 (M+H). Calc'd. for C$_{10}$H$_6$INO$_3$-315.06.

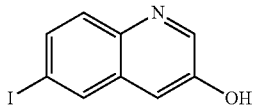 [SMILES: Oc1cnc2ccc(I)cc2c1]

6-iodoquinolin-3-ol.

3-hydroxy-6-iodoquinoline-4-carboxylic acid (22 g, 70 mmol) was suspended in 1-nitrobenzene (143 ml, 1397 mmol) followed by adding Hunig's base (25 mL)—the suspension was completely dissolved. The resulting mixture was heated to reflux (210° C.) under N$_2$. After 3 h, LC/MS showed no sign of starting material mass. The reaction mixture was cooled to rt; solvent was removed as much as possible in vacuo. The crude product was redissolved in DCM/MeOH and the solid was collected by filtration. The solid was rinsed with hexane and either and dried as brownish solid. The filtrate was removed excess solvent and purified using SiO$_2$ chromatography (Teledyne Isco RediSep®, P/N 68-2203-058, 330 g SiO$_2$, solvent system: hexanes:acetone=80%:20%, Flow=100 mL/min) to afford the desired product as brown solid. MS m/z: 272.3 (M+H). Calc'd. for C$_9$H$_6$INO—271.05.

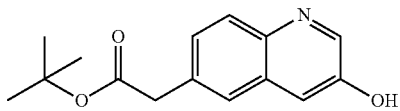 [SMILES: CC(C)(C)OC(=O)Cc1ccc2ncc(O)cc2c1]

tert-butyl 2-(3-hydroxyquinolin-6-yl)acetate

A stirred solution of 6-iodoquinolin-3-ol (1.76 g, 6 mmol) in THF (10 mL) was treated with 2-tert-butoxy-2-oxoethylzinc chloride (39 ml, 19 mmol) followed by tetrakis(triphenylphosphine)palladium(0) (0.8 g, 0.6 mmol). After the addition, it was heated to reflux (75° C.) under N$_2$. After 3 h, TLC 89368-3-1 showed no sign of starting material. Reaction was stop. The reaction was cooled to rt. Solvent was removed. The residue was stirred in EtOAc/10% EDTA (50 mL/50 mL) solution mixture. After 1 h, the organic layer was separated. The aqueous layer was extracted with more EtOAc (2×25 mL). The combined organic layers were washed with water, brine, dried over MgSO$_4$, and removed solvent. The crude product was purified using SiO$_2$ chromatography (Teledyne Isco RediSep®, P/N 68-2203-026, 12 g SiO$_2$, hex:acetone=80%:20%, Flow=30 mL/min) to afford the desired product as brownish liquid. MS m/z: 260.3 (M+H). Calc'd. for C$_{15}$H$_{17}$NO$_3$—259.2.

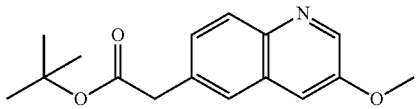 [SMILES: COc1cnc2ccc(CC(=O)OC(C)(C)C)cc2c1]

tert-butyl 2-(3-methoxyquinolin-6-yl)acetate

To a suspension of tert-butyl 2-(3-hydroxyquinolin-6-yl) acetate (0.1 g, 0.4 mmol) in benzene (5 mL) was added methanol (0.05 ml, 1 mmol) and tributylphosphine (0.1 ml, 0.6 mmol). The resulting mixture was cooled to 0° C. followed by adding 1.1'-(azodicarbonyl)dipiperidine (0.1 g, 0.6 mmol). After 10 min, ice bath was removed; the reaction mixture was warmed up to rt. The reaction mixture was continued to stir for 20 h. TLC showed about 80% conversion. More MeOH (1 ml), tibutylphosphine (0.05 mL), and ADDP (50 mg) were added and allowed to stir for 3 h. Hexane was added to the reaction mixture and dihydro-ADDP separated out and was filtered off. The filtrate was concentrated. The crude product was purified using SiO$_2$ chromatography (Teledyne Isco RediSep®, P/N 68-2203-027, 40 g SiO$_2$) to afford the desired product as colorless liquid. MS m/z: 274.3 (M+H). Calc'd. for C$_{16}$H$_{19}$NO$_3$—273.2.

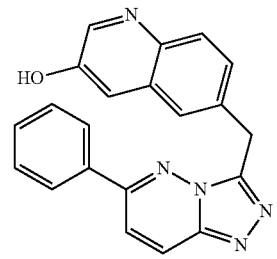 [SMILES: Oc1cnc2ccc(Cc3nnc4ccc(-c5ccccc5)nn34)cc2c1]

6-((6-phenyl-[1,2,4]triazolo[4,3-b]pyridazin-3-yl) methyl)quinolin-3-ol

To a 5 ml CEM microwave tube was added tert-butyl 2-(3-methoxyquinolin-6-yl)acetate (0.3 g, 1 mmol), 1-(6-phenylpyridazin-3-yl)hydrazine (0.3 g, 2 mmol), and HYDROCHLORIC ACID (0.3 ml, 11 mmol) as solvent. The vial was sealed and first heated at 100° C. for 20 min then placed into CEM microwave for 20 min. at 180° C., with 100 Watts of power via Powermax. The reaction mixture was adjusted the pH to 7 by adding 5 N NaOH. The ppt. was collected by filtration. The ppt. was washed with water and dried. The solid was purified using SiO$_2$ chromatography (Teledyne Isco RediSep®, P/N 68-2203-027, 40 g SiO$_2$, DCM:MeOH=95%:5%, Flow=40 mL/min) to afford the desired product as gray solid. MS m/z: 354.2 (M+H). Calc'd. for C$_{21}$H$_{15}$N$_5$O–353.37.

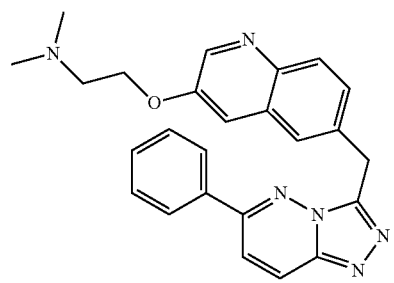 [SMILES: CN(C)CCOc1cnc2ccc(Cc3nnc4ccc(-c5ccccc5)nn34)cc2c1]

EXAMPLE 116

N,N-dimethyl-2-(6-(((6-phenyl-[1,2,4]triazolo[4,3-b]pyridazin-3-yl)methyl)quinolin-3-yloxy)ethanamine 6-((6-phenyl-[1,2,4]triazolo[4,3-b]pyridazin-3-yl)methyl)quinolin-3-ol (0.05 g, 0.1 mmol) was dissolved in DMF (8 mL). SODIUM HYDRIDE (0.01 g, 0.3 mmol) was added and allowed to stir for 1 h at rt. 2-chloro-N,N-dimethylethanamine hydrochloride (0.06 g, 0.4 mmol), which was free-based using 5 N NaOH then extracted with ether, was added. The resulting mixture was continued to stir for 20 h at rt. Solvent was removed in vacuo. The crude material was purified using $SiO_2$ chromatography (Teledyne Isco RediSep®, P/N 68-2203-026, 12 g $SiO_2$, solvent system: DCM:MeOH (2M $NH_3$)=95%:5%, Flow=30 mL/min) to afford the title compound MS m/z: 425.3 (M+H). Calc'd. for $C_{25}H_{24}N_6O$—424.49.

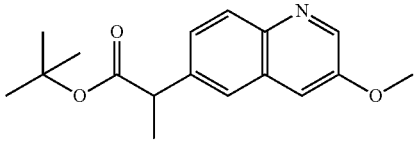 [SMILES: COc1cnc2ccc(C(C)C(=O)OC(C)(C)C)cc2c1]

tert-butyl 2-(3-methoxyquinolin-6-yl)propanoate

To a flame-dry 100 ml 3-neck round-bottomed flask was added lithium bis(trimethylsilyl)amide, 1.0 m solution in tetrahydrofuran (5 ml, 5 mmol) and THF (20 mL). The mixture was cooled to –78° C. followed by adding tert-butyl 2-(3-methoxyquinolin-6-yl)acetate (0.88 g, 3 mmol) in THF (10 mL) dropwise via addition funnel. After stirring at –78° C. for 30 min, iodomethane (0.4 ml, 6 mmol) was added. The reaction mixture was stirred for 30 min at –78° C. then allowed to warm to rt and stir for 1 h. The mixture was then quenched with sat. $NH_4Cl$ (3 mL). Solvent was removed. The residue was partitioned between EtOAc/water. The organic layer was washed with brine, dried over $MgSO_4$ and removed solvent. The crude material was purified using $SiO_2$ chromatography (Teledyne Isco RediSep®, P/N 68-2203-027, 40 g $SiO_2$, solvent system: hexane:acetone=90%:10%, Flow=30 mL/min) to afford a final product as yellowish liquid. MS m/z: 288.4 (M+H). Calc'd. for $C_{17}H_{21}NO_3$—287.3.

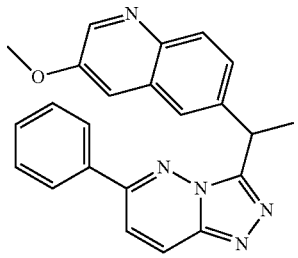 [SMILES: COc1cnc2ccc(C(C)c3nnc4ccc(-c5ccccc5)nn34)cc2c1]

EXAMPLE 117

3-methoxy-6-(1-(6-phenyl-[1,2,4]triazolo[4,3-b]pyridazin-3-yl)ethyl)quinoline

To a 5 ml CEM microwave tube was added tert-butyl 2-(3-methoxyquinolin-6-yl)propanoate (0.130 g, 0.45 mmol), 1-(6-phenylpyridazin-3-yl)hydrazine (0.17 g, 0.90 mmol), HYDROCHLORIC ACID (0.11 ml, 1.4 mmol), and water (0.2 mL) as solvent. The vial was sealed and first heated at 90° C. for 30 min then placed into CEM microwave for 15 min. at 140° C., with 100 Watts of power via Powermax. The reaction mixture was adjusted the pH to 7 by adding 5 N NaOH and the solid was collected by filtration. The brown ppt. was dissolved in DCM. The organic was washed with water, dried over $MgSO_4$, and removed solvent in vacuo. The crude product was purified using $SiO_2$ chromatography (Teledyne Isco RediSep®, P/N 68-2203-027, 40 g $SiO_2$, DCM:MeOH=97%:3%, Flow=40 mL/min) to afford the desired product as light yellowish solid. MS m/z: 382.3 (M+H). Calc'd. for $C_{23}H_{19}N_5O$—381.43.

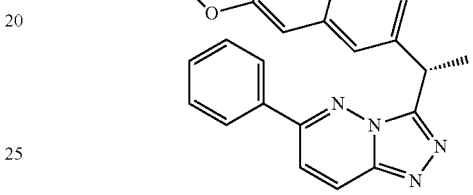

EXAMPLE 118

(S)-3-methoxy-6-(1-(6-phenyl-[1,2,4]-triazolo[4,3-b]pyridazin-3-yl)ethyl)quinoline Chiral separation. MS m/z: 382.3 (M+H). Calc'd. for $C_{23}H_{19}N_5O$—381.43.

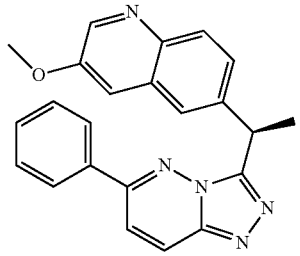 [SMILES: COc1cnc2ccc([C@@H](C)c3nnc4ccc(-c5ccccc5)nn34)cc2c1]

EXAMPLE 119

(R)-3-methoxy-6-(1-(6-phenyl-[1,2,4]triazolo[4,3-b]pyridazin-3-yl)ethyl)quinoline Chiral separation. MS m/z: 382.3 (M+H). Calc'd. for $C_{23}H_{19}N_5O$—381.43.

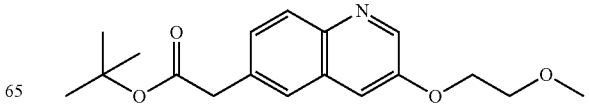

tert-butyl 2-(3-(2-methoxyethoxy)quinolin-6-yl)acetate

To a suspension of tert-butyl 2-(3-hydroxyquinolin-6-yl) acetate (0.1 g, 0.4 mmol) in benzene (5 mL) was added 2-methoxyethanol (0.09 ml, 1 mmol) and tri-n-butylphosphine (0.1 ml, 0.6 mmol). The resulting mixture was cooled to 0° C. followed by adding 1.1'-(azodicarbonyl)dipiperidine (0.1 g, 0.6 mmol). After 10 min, ice bath was removed; the reaction mixture was warmed up to rt. After 2 h, TLC showed there still existed 50% starting material. More methoxymethanol (2 eq, 0.06 mL) was added. The reaction mixture was continued to stir for 20 h. Hexane was added to the reaction mixture and dihydro-ADDP separated out was filtered off. The filtrate was concentrated. The crude product was purified using $SiO_2$ chromatography (Teledyne Isco RediSep®, P/N 68-2203-027, 40 g $SiO_2$, hexane:acetone=85%:15%, Flow=40 mL/min) to afford the desired product as colorless liquid. MS m/z: 318.4 (M+H). Calc'd. for $C_{18}H_{23}NO_4$—317.38.

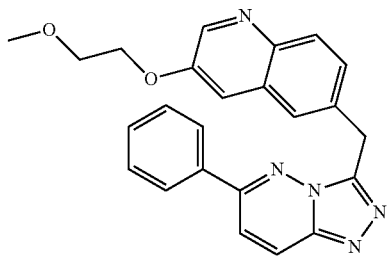 [SMILES: COCCOc1cnc2ccc(Cc3nnc4ccc(-c5ccccc5)nn34)cc2c1]

EXAMPLE 120

3-(2-methoxyethoxy)-6-((6-phenyl-[1,2,4]triazolo[4,3-b]pyridazin-3-yl)methyl)quinoline To a 5 ml CEM microwave tube was added tert-butyl 2-(3-(2-methoxyethoxy)quinolin-6-yl)acetate (0.080 g, 0.25 mmol), 1-(6-phenylpyridazin-3-yl)hydrazine (0.094 g, 0.50 mmol), HYDROCHLORIC ACID (0.063 ml, 0.76 mmol), and water (0.2 mL) as solvent. The vial was sealed and first heated at 90° C. for 30 min then placed into CEM microwave for 15 min. at 140° C., with 100 Watts of power via Powermax. The reaction mixture was adjusted the pH to 7 by adding 5 N NaOH and the precipitate was collected via filtration. The brown ppt. was dissolved in DCM. The organic was washed with water, dried over $MgSO_4$, and removed solvent in vacuo. The crude product was purified using $SiO_2$ chromatography (Teledyne Isco RediSep®, P/N 68-2203-026, 12 g $SiO_2$, DCM:EtOAc:MeOH=60%:37%:3%, Flow=30 mL/min) to afford the desired product as light yellowish solid. MS m/z: 412.3 (M+H). Calc'd. for $C_{24}H_{21}N_5O_2$–411.45.

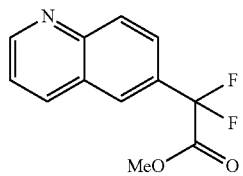 [SMILES: COC(=O)C(F)(F)c1ccc2ncccc2c1]

methyl 2,2-difluoro-2-(quinolin-6-yl)acetate

To a stirring solution of methyl 2-(quinolin-6-yl)acetate (450 mg, 2236 μmol) in THF (2 mL) at −70° C. under nitrogen was added lithium bis(trimethylsilyl)amide, 1.0 m solution in tetrahydrofuran (5144 μl, 5144 μmol) and stirred for 10 min. To this solution was added n-fluorobis(phenylsulfonyl)amine (1481 mg, 4696 μmol) in THF (5 mL) and slowly warmed to 0° C. over the course of 1 h. Reaction stirred for an additional 1 h at 23° C., and resulting solid (sulfonamide) removed by filtration. The filtrate was concentrated to a solid under reduced pressure. The resulting solid was then partitioned between EtOAc (20 mL) and sat $NH_4Cl$ (10 mL). The organic layer was dried over $MgSO_4$ then concentrated to a solid under reduced pressure and used without further purification.

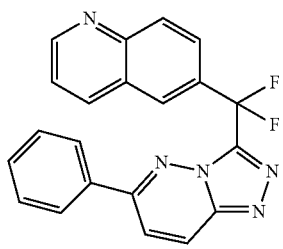 [SMILES: FC(F)(c1ccc2ncccc2c1)c1nnc2ccc(-c3ccccc3)nn12]

EXAMPLE 121

6-(difluoro(6-phenyl-[1,2,4]triazolo[4,3-b]pyridazin-3-yl)methyl)quinoline

A mixture of methyl 2,2-difluoro-2-(quinolin-6-yl)acetate (0.50 g, 2.1 mmol), 1-(6-phenylpyridazin-3-yl)hydrazine (0.39 g, 2.1 mmol) and p-toluenesulfonic acid monohydrate (0.20 g, 1.1 mmol) in 5 mL of dioxane was heated at 150° C. for 1 hour in a microwave tube in the microwave. The mixture was diluted with 70 mL of EtOAc and 40 mL of satd. $NaHCO_3$ solution. The organic phase was separated and washed with 40 mL of brine, dried over $Na_2SO_4$ and concentrated in vacuo. The residue was purified by a silica gel column chromatography (EtOAc to 15% MeOH/EtOAc) to give yellow solid as desired product 6-(difluoro(6-phenyl-[1,2,4]triazolo[4,3-b]pyridazin-3-yl)methyl)quinoline. MS (ESI pos. ion) m/z: 374.1 (M+H). Calc'd Exact Mass for $C_{21}H_{13}F_2N_5$: 373.1.

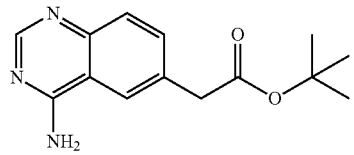 [SMILES: CC(C)(C)OC(=O)Cc1ccc2ncnc(N)c2c1]

tert-butyl 2-(4-aminoquinazolin-6-yl)acetate

To a solution of 6-bromoquinazolin-4-amine (0.400 g, 1.79 mmol), tris(dibenzylideneacetone)dipalladium (o) (0.163 g, 0.179 mmol) and Q-phos (0.20 g) in 10 mL of THF was added 2-tert-butoxy-2-oxoethylzinc chloride 0.5 m in diethyl ether (10.7 ml, 5.36 mmol). The reaction was heated at 50° C. for 16 hours and was quenched with 50 mL of satd. $NH_4Cl$. The mixture was diluted with 60 mL of EtOAc. The organic phase was separated, washed with brine, dried over $Na_2SO_4$ and concentrated in vacuo to give red solid. The residue was purified by a silica gel column chromatography (5% EtOAc/hex to EtOAC) to give red solid tert-butyl 2-(4-aminoquinazolin-6-yl)acetate which was used without further purification. MS (ESI pos. ion) m/z: 260.1 (M+H). Calc'd Exact Mass for $C_{14}H_{12}N_3O_2$: 259.1.

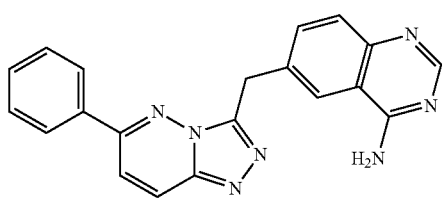 [SMILES: Nc1ncnc2ccc(Cc3nnc4ccc(-c5ccccc5)nn34)cc12]
EXAMPLE 122
6-((6-phenyl-[1,2,4]triazolo[4,3-b]pyridazin-3-yl)methyl)quinazolin-4-amine
Prepared according to example 121 from tert-butyl 2-(4-aminoquinazolin-6-yl)acetate. MS (ESI pos. ion) m/z: 354 (M+H). Calc'd Exact Mass for $C_{20}H_{15}N_7$: 353.
| EX. | Structure | MW | Mass Found | General Method |
|---|---|---|---|---|
| 123 | 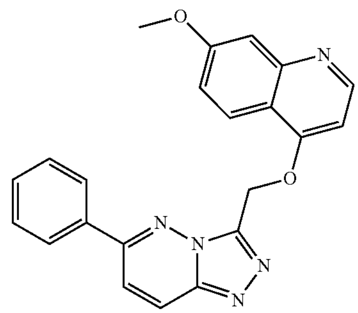 [SMILES: COc1ccc2c(OCc3nnc4ccc(-c5ccccc5)nn34)ccnc2c1] | 383 | 384 | A |
| 124 | 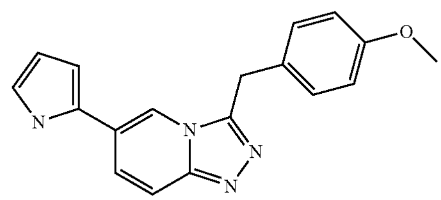 [SMILES: COc1ccc(Cc2nnc3ccc(-c4ccc[nH]4)cn23)cc1] | 304 | 305 | A |
| 125 | 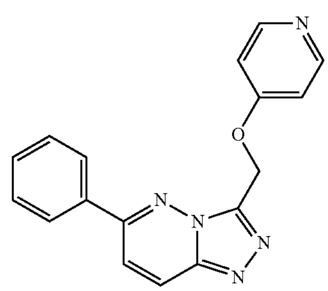 [SMILES: c1ccc(-c2ccc3nnc(COc4ccncc4)n3n2)cc1] | 303 | 304 | B |
| 126 | 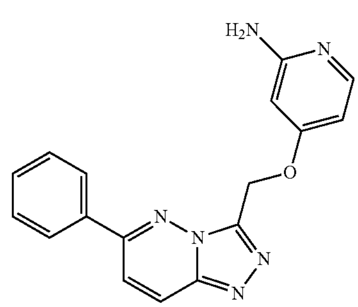 [SMILES: Nc1cc(OCc2nnc3ccc(-c4ccccc4)nn23)ccn1] | 318 | 319 | C |

-continued
| EX. | Structure | MW | Mass Found | General Method |
|---|---|---|---|---|
| 127 | 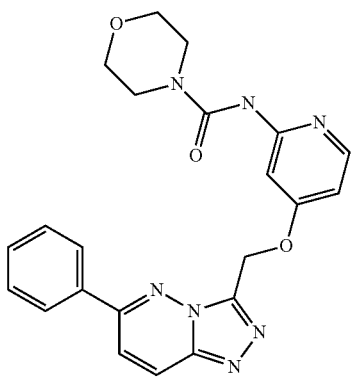 [SMILES: O=C(Nc1cc(OCc2nnc3ccc(-c4ccccc4)nn23)ccn1)N1CCOCC1] | 431 | 432 | C |
| 128 | 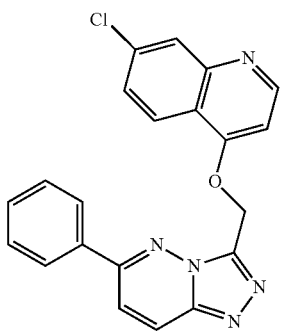 [SMILES: Clc1ccc2c(OCc3nnc4ccc(-c5ccccc5)nn34)ccnc2c1] | 388 | 388 | A |
| 129 | 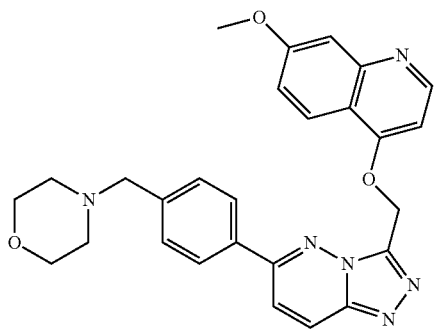 [SMILES: COc1ccc2c(OCc3nnc4ccc(-c5ccc(CN6CCOCC6)cc5)nn34)ccnc2c1] | 483 | 483 | A |
| 130 | 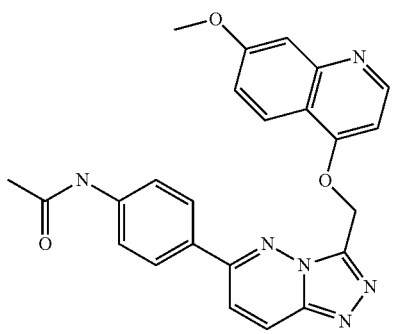 [SMILES: COc1ccc2c(OCc3nnc4ccc(-c5ccc(NC(C)=O)cc5)nn34)ccnc2c1] | 440 | 441 | A |

| EX. | Structure | MW | Mass Found | General Method |
|---|---|---|---|---|
| 131 | 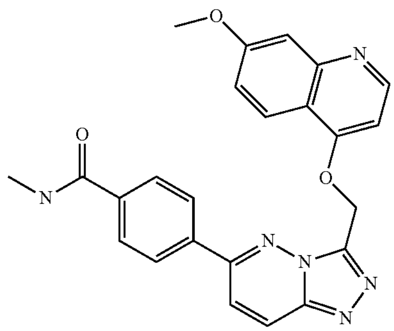 [SMILES: CNC(=O)c1ccc(-c2ccc3nnc(COc4ccnc5cc(OC)ccc45)n3n2)cc1] | 440 | 441 | A |
| 132 | 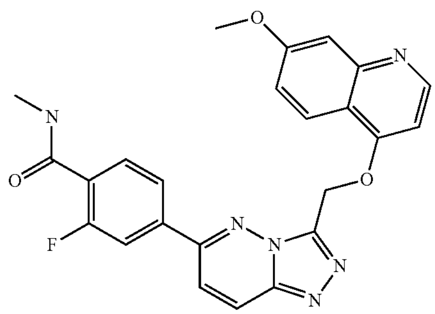 [SMILES: CNC(=O)c1ccc(-c2ccc3nnc(COc4ccnc5cc(OC)ccc45)n3n2)cc1F] | 458 | 459 | A |
| 133 | 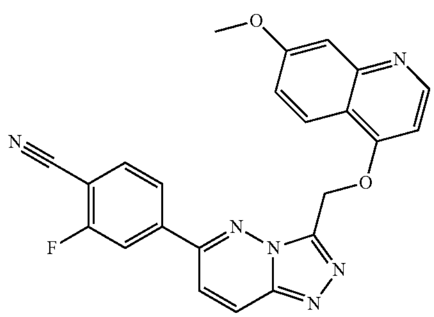 [SMILES: COc1ccc2c(OCc3nnc4ccc(-c5ccc(C#N)c(F)c5)nn34)ccnc2c1] | 426 | 427 | A |
| 134 | 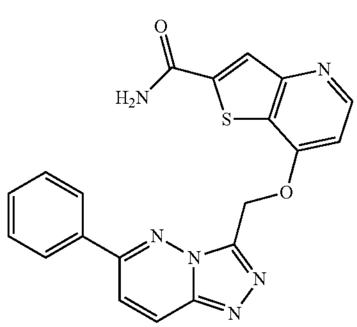 [SMILES: NC(=O)c1cc2nccc(OCc3nnc4ccc(-c5ccccc5)nn34)c2s1] | 402 | 403 | B |

-continued
| EX. | Structure | MW | Mass Found | General Method |
|---|---|---|---|---|
| 135 | 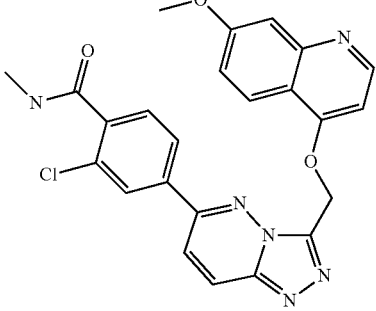 | 475 | 475 | A |
| 136 | 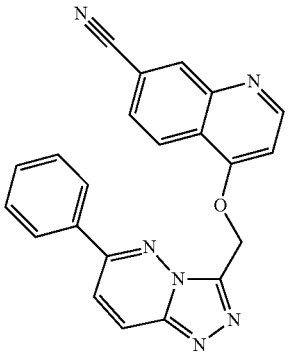 [SMILES: N#Cc1ccc2c(OCc3nnc4ccc(-c5ccccc5)nn34)ccnc2c1] | 378 | 379 | B |
| 137 | 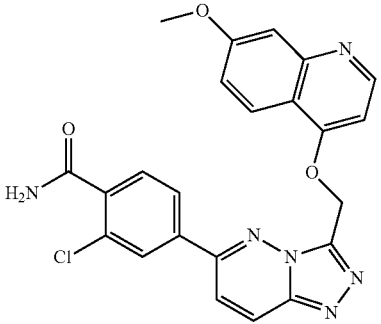 [SMILES: COc1ccc2c(OCc3nnc4ccc(-c5ccc(C(N)=O)c(Cl)c5)nn34)ccnc2c1] | 461 | 461 | A |
| 138 | 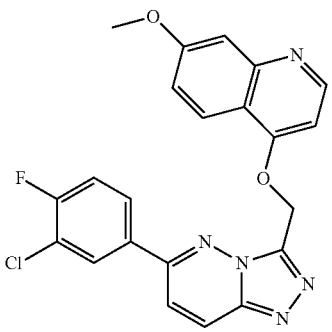 [SMILES: COc1ccc2c(OCc3nnc4ccc(-c5ccc(F)c(Cl)c5)nn34)ccnc2c1] | 436 | 436 | A |

| EX. | Structure | MW | Mass Found | General Method |
|---|---|---|---|---|
| 139 | 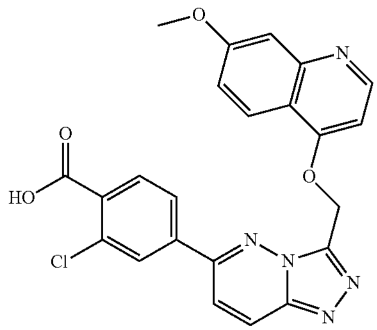 [SMILES: COc1ccc2c(OCc3nnc4ccc(-c5ccc(C(=O)O)c(Cl)c5)nn34)ccnc2c1] | 462 | 462 | A |
| 140 | 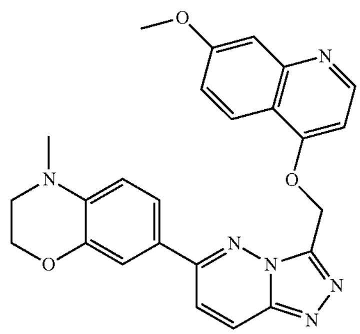 [SMILES: COc1ccc2c(OCc3nnc4ccc(-c5ccc6c(c5)OCCN6C)nn34)ccnc2c1] | 454 | 455 | A |
| 141 | 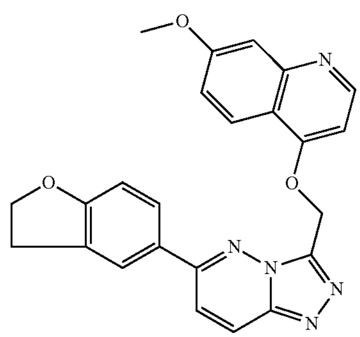 [SMILES: COc1ccc2c(OCc3nnc4ccc(-c5ccc6c(c5)CCO6)nn34)ccnc2c1] | 425 | 426 | A |
| 142 | 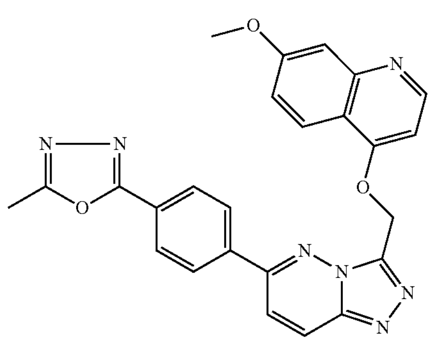 [SMILES: COc1ccc2c(OCc3nnc4ccc(-c5ccc(-c6nnc(C)o6)cc5)nn34)ccnc2c1] | 465 | 466 | A |

| EX. | Structure | MW | Mass Found | General Method |
|---|---|---|---|---|
| 143 | 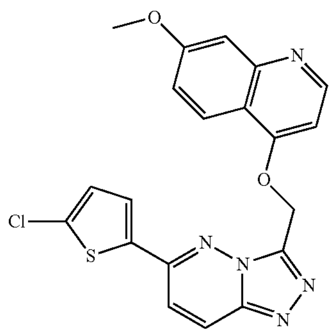 [SMILES: COc1ccc2c(OCc3nnc4ccc(-c5ccc(Cl)s5)nn34)ccnc2c1] | 424 | 424 | A |
| 144 | 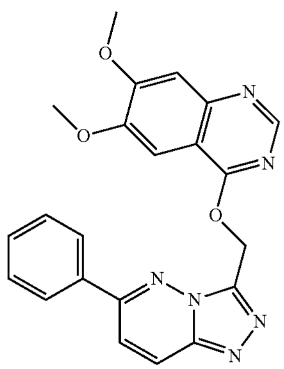 | 414 | 415 | B |
| 145 | 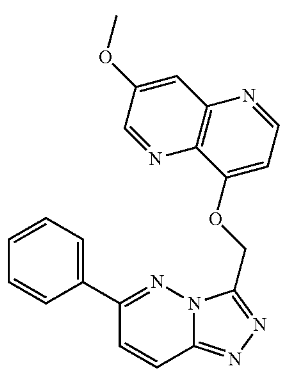 [SMILES: COc1cnc2c(OCc3nnc4ccc(-c5ccccc5)nn34)ccnc2c1] | 384 | 385 | B |
| 146 | 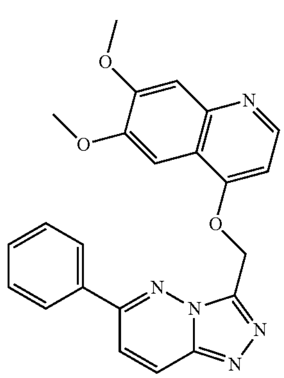 [SMILES: COc1cc2nccc(OCc3nnc4ccc(-c5ccccc5)nn34)c2cc1OC] | 413 | 414 | B |

-continued

| EX. | Structure | MW | Mass Found | General Method |
|---|---|---|---|---|
| 147 | 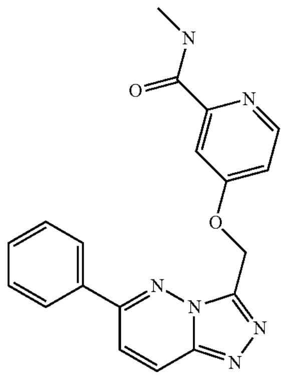 [SMILES: CNC(=O)c1cc(OCc2nnc3ccc(-c4ccccc4)nn23)ccn1] | 360 | 361 | B |
| 148 | 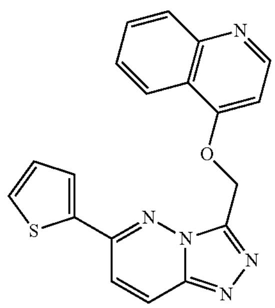 [SMILES: c1csc(-c2ccc3nnc(COc4ccnc5ccccc45)n3n2)c1] | 359 | 360 | B |
| 149 | 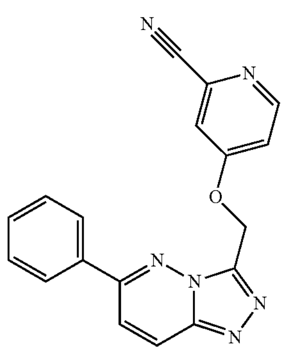 [SMILES: N#Cc1cc(OCc2nnc3ccc(-c4ccccc4)nn23)ccn1] | 328 | 329 | B |
| 150 | 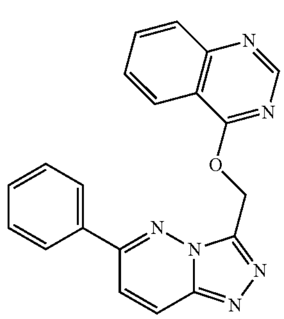 [SMILES: c1ccc(-c2ccc3nnc(COc4ncnc5ccccc45)n3n2)cc1] | 354 | 355 | B |

-continued
| EX. | Structure | MW | Mass Found | General Method |
|---|---|---|---|---|
| 151 | 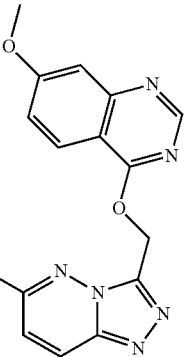 | 384 | 385 | B |
| 152 | 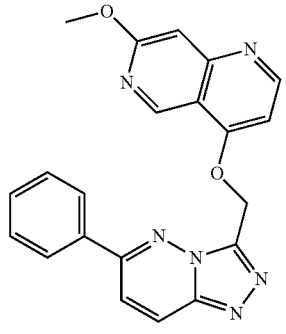 [SMILES: COc1cc2nccc(OCc3nnc4ccc(-c5ccccc5)nn34)c2cn1] | 384 | 385 | B |
| 153 | 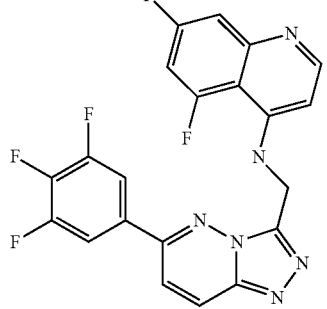 | 442 | 443 | D |
| 154 | 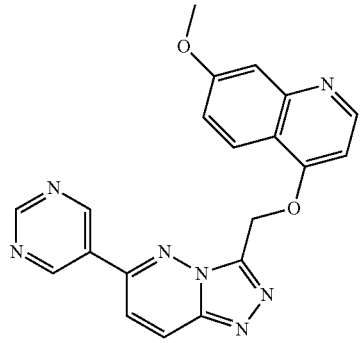 [SMILES: COc1ccc2c(OCc3nnc4ccc(-c5cncnc5)nn34)ccnc2c1] | 385 | 386 | A |

| EX. | Structure | MW | Mass Found | General Method |
|---|---|---|---|---|
| 155 | 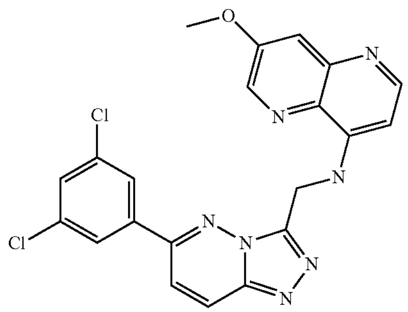 [SMILES: COc1cnc2c(NCc3nnc4ccc(-c5cc(Cl)cc(Cl)c5)nn34)ccnc2c1] | 452 | 453 | A |
| 156 | 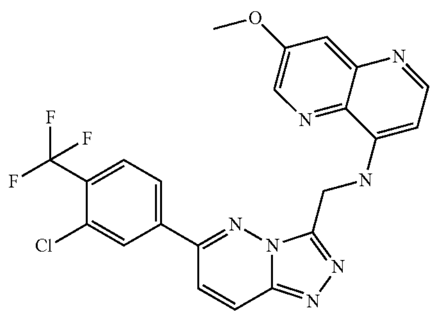 [SMILES: COc1cnc2c(NCc3nnc4ccc(-c5ccc(C(F)(F)F)c(Cl)c5)nn34)ccnc2c1] | 486 | 486 | A |
| 157 | 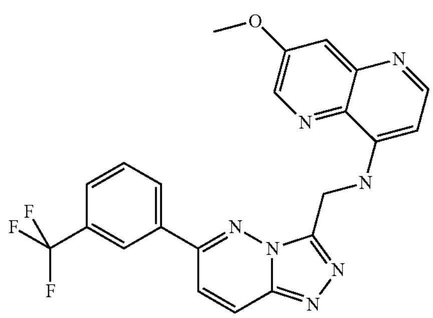 [SMILES: COc1cnc2c(NCc3nnc4ccc(-c5cccc(C(F)(F)F)c5)nn34)ccnc2c1] | 451 | 452 | A |
| 158 | 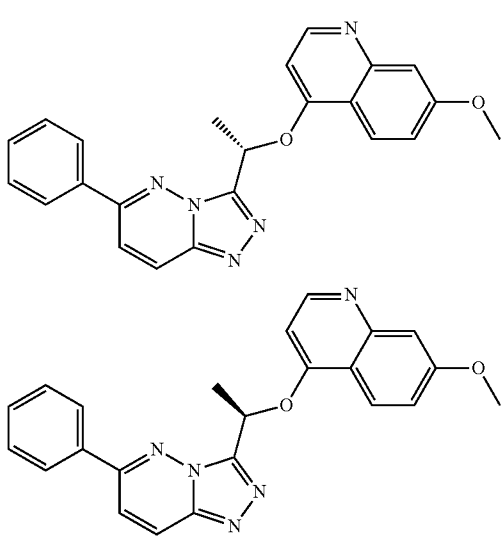 [SMILES: COc1ccc2c(O[C@@H](C)c3nnc4ccc(-c5ccccc5)nn34)ccnc2c1 ; COc1ccc2c(O[C@H](C)c3nnc4ccc(-c5ccccc5)nn34)ccnc2c1] | 398 | 398 | B |

-continued

| EX. | Structure | MW | Mass Found | General Method |
|---|---|---|---|---|
| 159 | 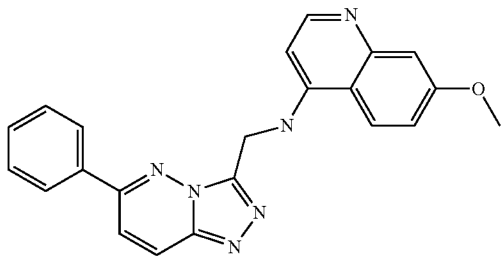 [SMILES: COc1ccc2c(NCc3nnc4ccc(-c5ccccc5)nn34)ccnc2c1] | 382 | 383 | D |
| 160 | 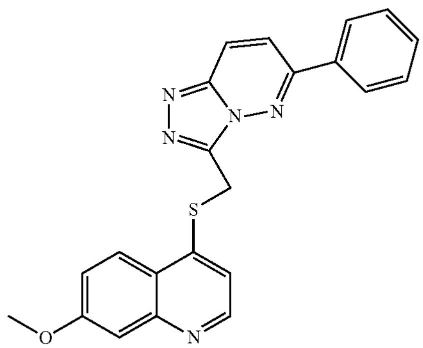 [SMILES: COc1ccc2c(SCc3nnc4ccc(-c5ccccc5)nn34)ccnc2c1] | 399 | 400 | B |
| 161 | 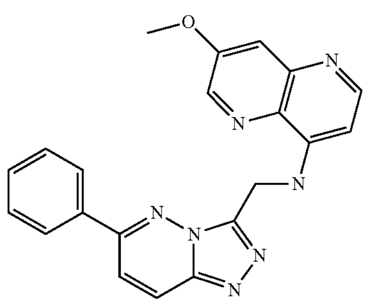 [SMILES: COc1cnc2c(NCc3nnc4ccc(-c5ccccc5)nn34)ccnc2c1] | 383 | 384 | D |
| 162 | | 412 | 412 | B |

-continued

| EX. | Structure | MW | Mass Found | General Method |
|---|---|---|---|---|
| 163 | 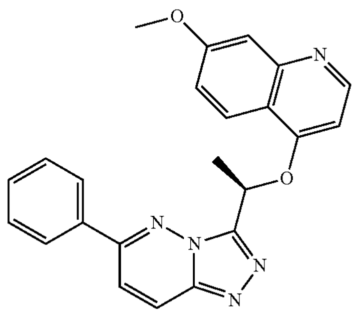 [SMILES: COc1ccc2c(O[C@H](C)c3nnc4ccc(-c5ccccc5)nn34)ccnc2c1] | 397 | 398 | B |
| 164 | 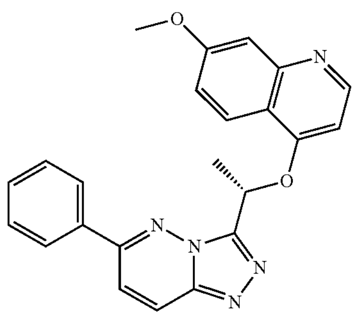 [SMILES: COc1ccc2c(O[C@@H](C)c3nnc4ccc(-c5ccccc5)nn34)ccnc2c1] | 397 | 398 | B |
| 165 | 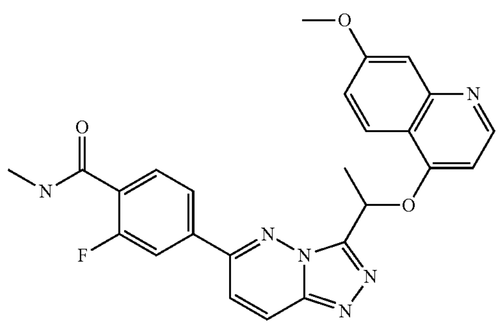 [SMILES: CNC(=O)c1ccc(-c2ccc3nnc(C(C)Oc4ccnc5cc(OC)ccc45)n3n2)cc1F] | 472 | 473 | B |
| 166 | 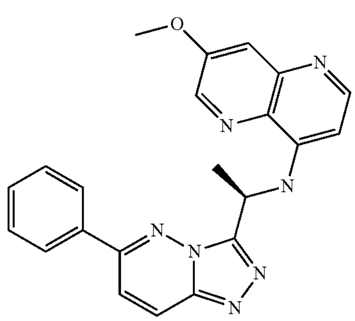 [SMILES: COc1cnc2c(N[C@H](C)c3nnc4ccc(-c5ccccc5)nn34)ccnc2c1] | 397 | 398 | D |
| 167 | 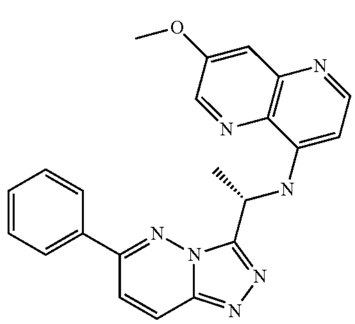 [SMILES: COc1cnc2c(N[C@@H](C)c3nnc4ccc(-c5ccccc5)nn34)ccnc2c1] | 397 | 398 | D |

-continued

| EX. | Structure | MW | Mass Found | General Method |
|---|---|---|---|---|
| 168 | | 398 | 399 | B |
| 169 | 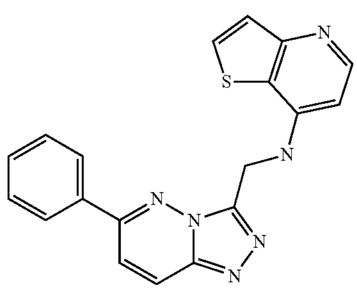 [SMILES: c1ccc(-c2ccc3nnc(CNc4ccnc5ccsc45)n3n2)cc1] | 358 | 359 | D |
| 170 | 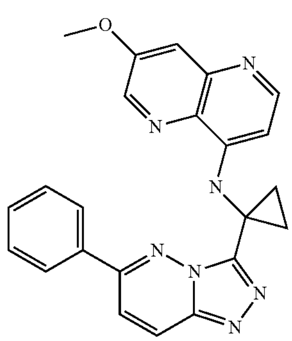 [SMILES: COc1cnc2c(NC3(c4nnc5ccc(-c6ccccc6)nn45)CC3)ccnc2c1] | 409 | 410 | D |
| 171 | 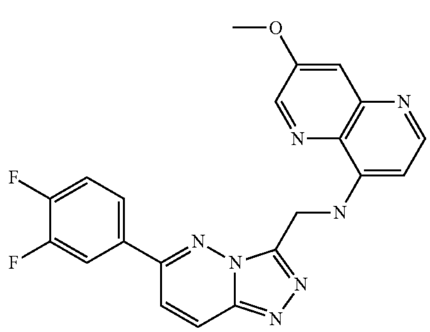 [SMILES: COc1cnc2c(NCc3nnc4ccc(-c5ccc(F)c(F)c5)nn34)ccnc2c1] | 419 | 420 | A |

-continued

| EX. | Structure | MW | Mass Found | General Method |
|---|---|---|---|---|
| 172 | 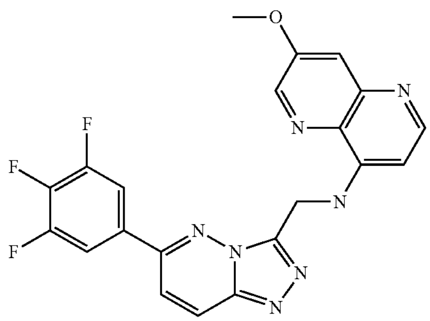 [SMILES: COc1cnc2c(NCc3nnc4ccc(-c5cc(F)c(F)c(F)c5)nn34)ccnc2c1] | 437 | 438 | A |
| 173 | 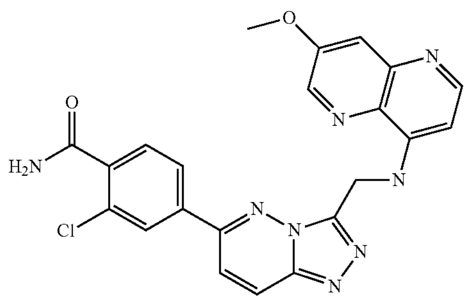 [SMILES: COc1cnc2c(NCc3nnc4ccc(-c5ccc(C(N)=O)c(Cl)c5)nn34)ccnc2c1] | 461 | 461 | A |
| 174 | 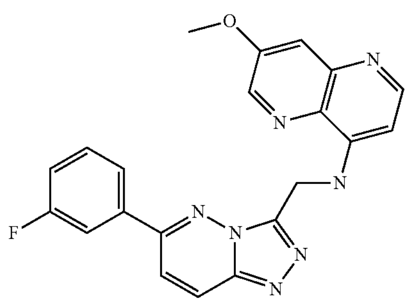 [SMILES: COc1cnc2c(NCc3nnc4ccc(-c5cccc(F)c5)nn34)ccnc2c1] | 401 | 402 | A |
| 175 | 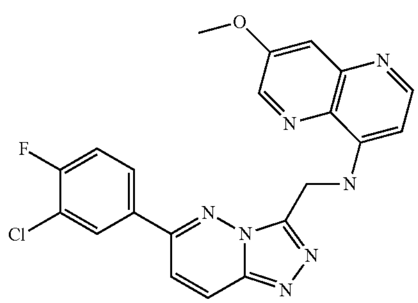 [SMILES: COc1cnc2c(NCc3nnc4ccc(-c5ccc(F)c(Cl)c5)nn34)ccnc2c1] | 436 | 436 | A |
| 176 | 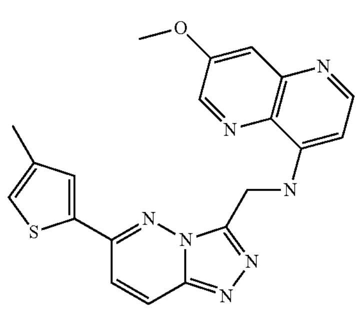 [SMILES: COc1cnc2c(NCc3nnc4ccc(-c5cc(C)cs5)nn34)ccnc2c1] | 403 | 404 | A |

-continued

| EX. | Structure | MW | Mass Found | General Method |
|---|---|---|---|---|
| 177 | 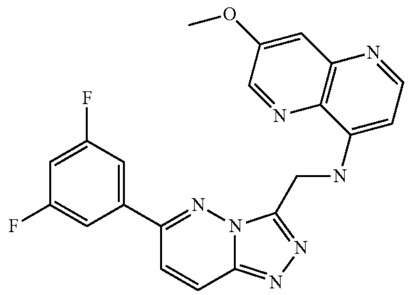 [SMILES: COc1cnc2c(NCc3nnc4ccc(-c5cc(F)cc(F)c5)nn34)ccnc2c1] | 419 | 420 | A |
| 178 | 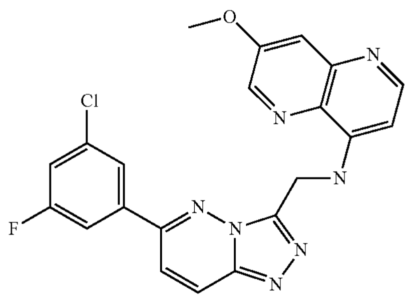 [SMILES: COc1cnc2c(NCc3nnc4ccc(-c5cc(F)cc(Cl)c5)nn34)ccnc2c1] | 436 | 436 | A |
| 179 | 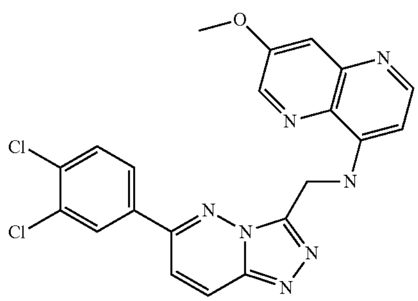 [SMILES: COc1cnc2c(NCc3nnc4ccc(-c5ccc(Cl)c(Cl)c5)nn34)ccnc2c1] | 452 | 452 | A |
| 180 | 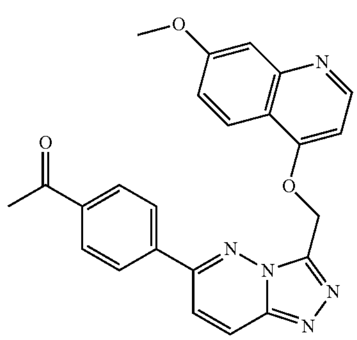 [SMILES: COc1ccc2c(OCc3nnc4ccc(-c5ccc(C(C)=O)cc5)nn34)ccnc2c1] | 425 | 425 | A |
| 181 | 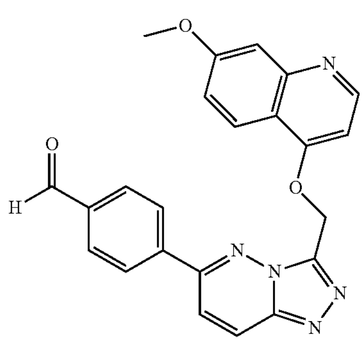 [SMILES: COc1ccc2c(OCc3nnc4ccc(-c5ccc(C=O)cc5)nn34)ccnc2c1] | 411 | 411 | A |

-continued

| EX. | Structure | MW | Mass Found | General Method |
|---|---|---|---|---|
| 182 | 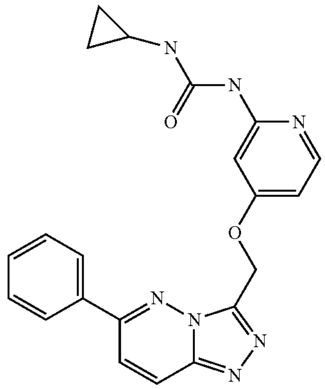 [SMILES: O=C(Nc1cc(OCc2nnc3ccc(-c4ccccc4)nn23)ccn1)NC1CC1] | 401 | 401 | C |
| 183 | 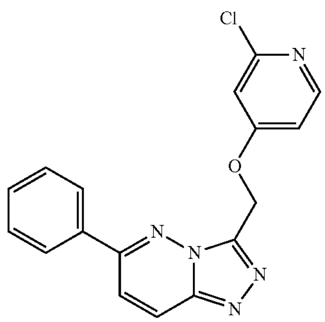 [SMILES: Clc1cc(OCc2nnc3ccc(-c4ccccc4)nn23)ccn1] | 338 | 337 | C |
| 184 | 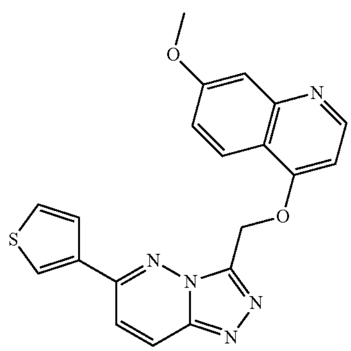 [SMILES: COc1ccc2c(OCc3nnc4ccc(-c5ccsc5)nn34)ccnc2c1] | 389 | 390 | A |
| 185 | 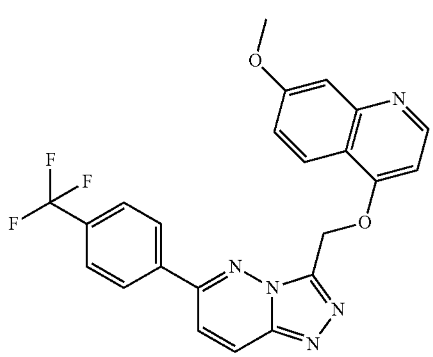 [SMILES: COc1ccc2c(OCc3nnc4ccc(-c5ccc(C(F)(F)F)cc5)nn34)ccnc2c1] | 451 | 452 | A |

-continued
| EX. | Structure | MW | Mass Found | General Method |
|---|---|---|---|---|
| 186 | 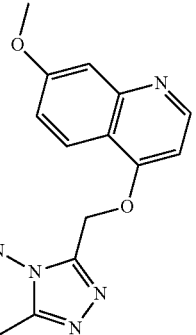 | 414 | 415 | A |
| 187 | 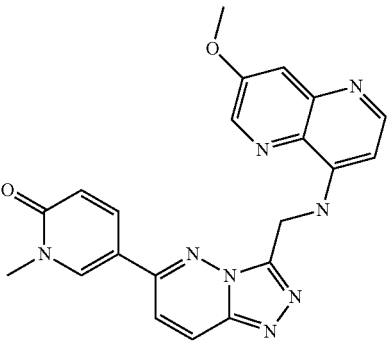 [SMILES: COc1cnc2c(NCc3nnc4ccc(-c5ccc(=O)n(C)c5)nn34)ccnc2c1] | 414 | 415 | D |
| 188 | 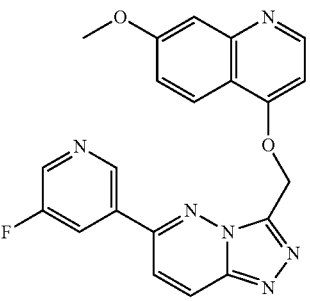 | 402 | 403 | A |
| 189 | 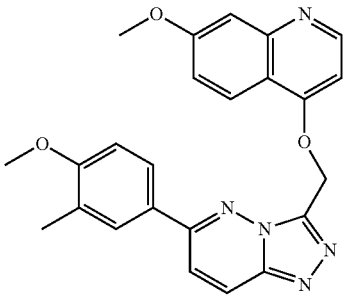 [SMILES: COc1ccc2c(OCc3nnc4ccc(-c5ccc(OC)c(C)c5)nn34)ccnc2c1] | 427 | 428 | A |

-continued
| EX. | Structure | MW | Mass Found | General Method |
|---|---|---|---|---|
| 190 | 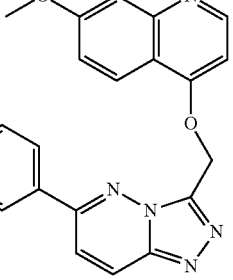 | 411 | 412 | A |
| 191 | 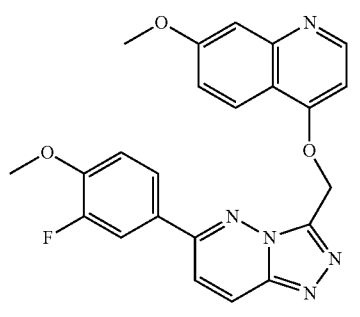 | 431 | 432 | A |
| 192 | 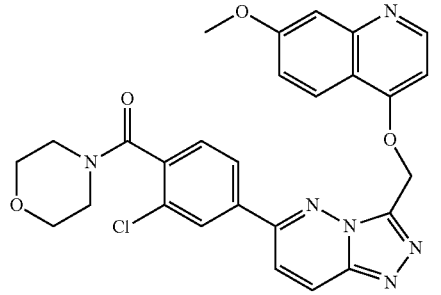 [SMILES: COc1ccc2c(OCc3nnc4ccc(-c5ccc(C(=O)N6CCOCC6)c(Cl)c5)nn34)ccnc2c1] | 531 | 531 | A |
| 193 | 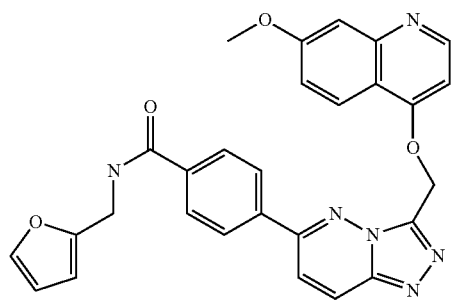 [SMILES: COc1ccc2c(OCc3nnc4ccc(-c5ccc(C(=O)NCc6ccco6)cc5)nn34)ccnc2c1] | 507 | 507 | A |
| 194 | 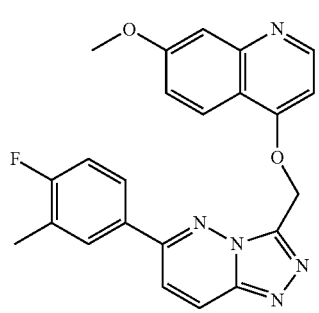 | 415 | 416 | A |

-continued

| EX. | Structure | MW | Mass Found | General Method |
|---|---|---|---|---|
| 195 | 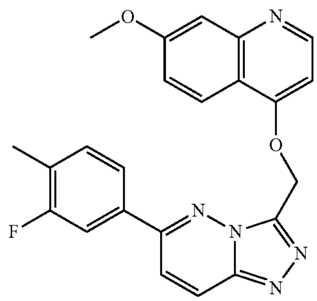 [SMILES: COc1ccc2c(OCc3nnc4ccc(-c5ccc(C)c(F)c5)nn34)ccnc2c1] | 415 | 416 | A |
| 196 | 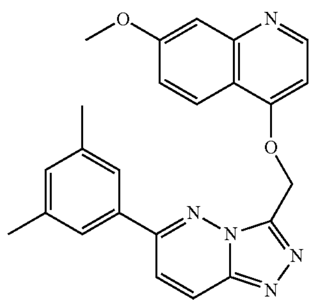 [SMILES: COc1ccc2c(OCc3nnc4ccc(-c5cc(C)cc(C)c5)nn34)ccnc2c1] | 411 | 412 | A |
| 197 | 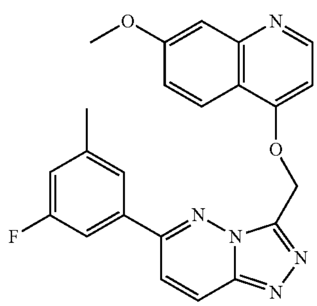 [SMILES: COc1ccc2c(OCc3nnc4ccc(-c5cc(C)cc(F)c5)nn34)ccnc2c1] | 415 | 416 | A |
| 198 | 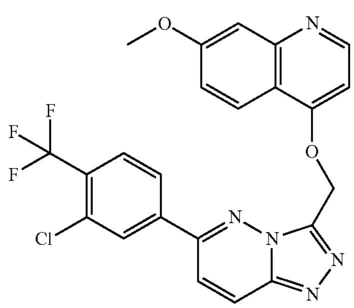 [SMILES: COc1ccc2c(OCc3nnc4ccc(-c5ccc(C(F)(F)F)c(Cl)c5)nn34)ccnc2c1] | 486 | 486 | A |
| 199 | 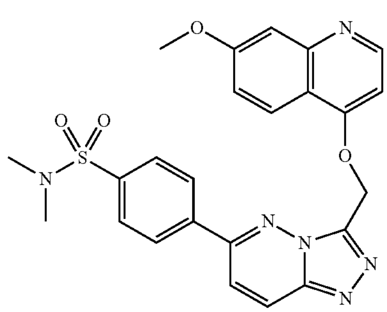 [SMILES: COc1ccc2c(OCc3nnc4ccc(-c5ccc(S(=O)(=O)N(C)C)cc5)nn34)ccnc2c1] | 491 | 491 | A |

| EX. | Structure | MW | Mass Found | General Method |
|-----|-----------|-----|------------|----------------|
| 200 | 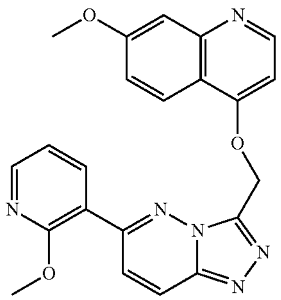 [SMILES: COc1ccc2c(OCc3nnc4ccc(-c5cccnc5OC)nn34)ccnc2c1] | 414 | 415 | A |
| 201 | 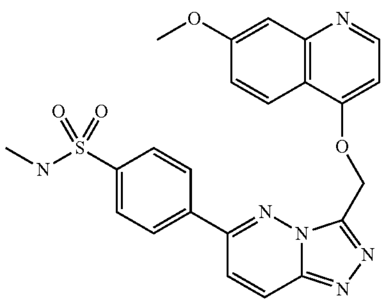 [SMILES: CNS(=O)(=O)c1ccc(-c2ccc3nnc(COc4ccnc5cc(OC)ccc45)n3n2)cc1] | 477 | 477 | A |
| 202 | 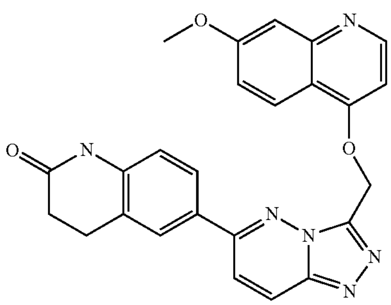 [SMILES: COc1ccc2c(OCc3nnc4ccc(-c5ccc6c(c5)CCC(=O)N6)nn34)ccnc2c1] | 452 | 453 | A |
| 203 | 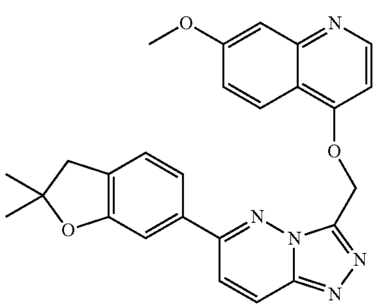 [SMILES: COc1ccc2c(OCc3nnc4ccc(-c5ccc6c(c5)OC(C)(C)C6)nn34)ccnc2c1] | 453 | 454 | A |
| 204 | 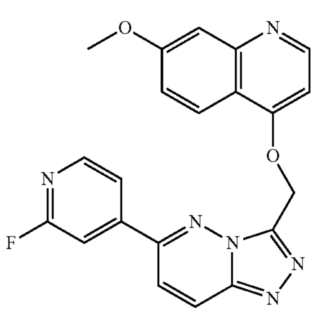 [SMILES: COc1ccc2c(OCc3nnc4ccc(-c5ccnc(F)c5)nn34)ccnc2c1] | 402 | 403 | A |

| EX. | Structure | MW | Mass Found | General Method |
|---|---|---|---|---|
| 205 | 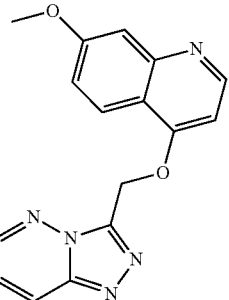 | 384 | 385 | A |
| 206 | 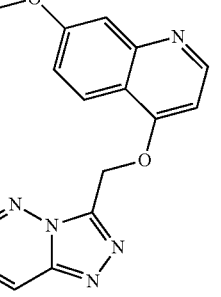 | 389 | 390 | A |
| 207 | 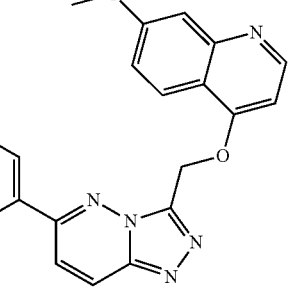 | 413 | 414 | A |
| 208 | 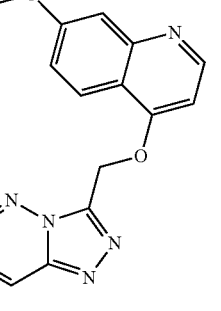 | 372 | 373 | A |
| 209 | 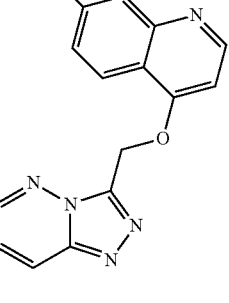 | 384 | 385 | A |

| EX. | Structure | MW | Mass Found | General Method |
|---|---|---|---|---|
| 210 | 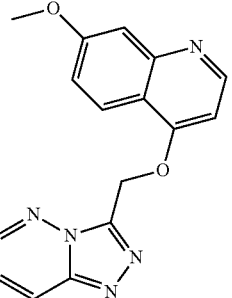 | 462 | 462 | A |
| 211 | 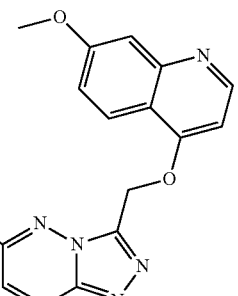 | 408 | 409 | A |
| 212 | 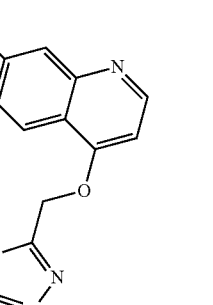 | 401 | 402 | A |
| 213 | 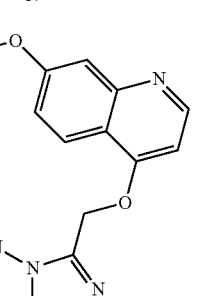 | 401 | 402 | A |
| 214 | 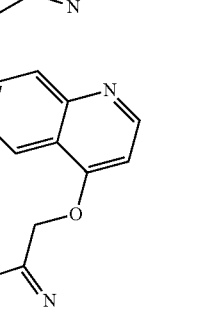 | 373 | 374 | A |

| EX. | Structure | MW | Mass Found | General Method |
|---|---|---|---|---|
| 215 | 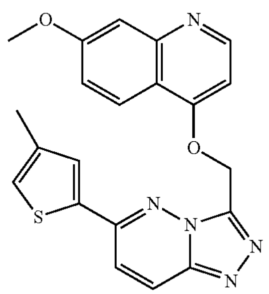 [SMILES: COc1ccc2c(OCc3nnc4ccc(-c5cc(C)cs5)nn34)ccnc2c1] | 403 | 404 | A |
| 216 | 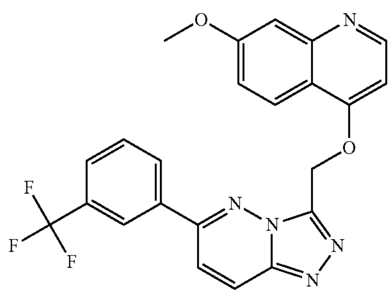 [SMILES: COc1ccc2c(OCc3nnc4ccc(-c5cccc(C(F)(F)F)c5)nn34)ccnc2c1] | 451 | 452 | A |
| 217 | 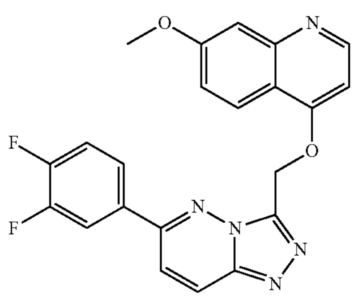 [SMILES: COc1ccc2c(OCc3nnc4ccc(-c5ccc(F)c(F)c5)nn34)ccnc2c1] | 419 | 420 | A |
| 218 | 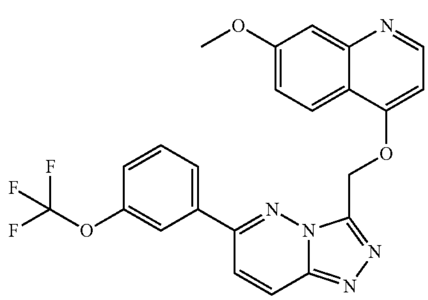 [SMILES: COc1ccc2c(OCc3nnc4ccc(-c5cccc(OC(F)(F)F)c5)nn34)ccnc2c1] | 467 | 468 | A |
| 219 | 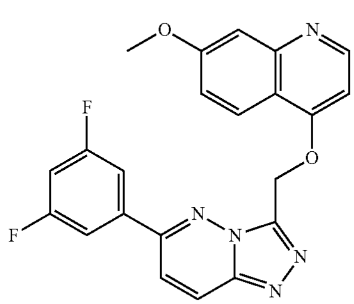 [SMILES: COc1ccc2c(OCc3nnc4ccc(-c5cc(F)cc(F)c5)nn34)ccnc2c1] | 419 | 420 | A |

-continued

| EX. | Structure | MW | Mass Found | General Method |
|---|---|---|---|---|
| 220 | 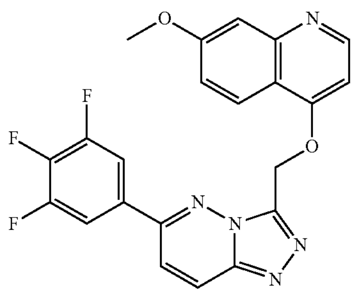 [SMILES: COc1ccc2c(OCc3nnc4ccc(-c5cc(F)c(F)c(F)c5)nn34)ccnc2c1] | 437 | 438 | A |
| 221 | 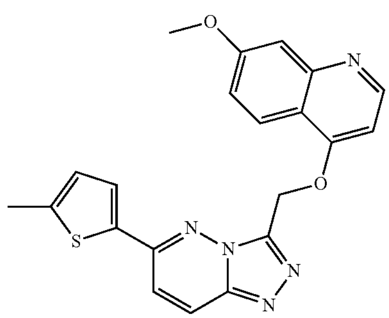 [SMILES: COc1ccc2c(OCc3nnc4ccc(-c5ccc(C)s5)nn34)ccnc2c1] | 403 | 404 | A |
| 222 | 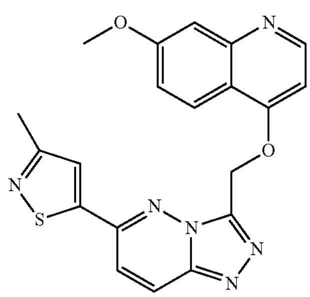 [SMILES: COc1ccc2c(OCc3nnc4ccc(-c5cc(C)ns5)nn34)ccnc2c1] | 404 | 405 | A |
| 223 | 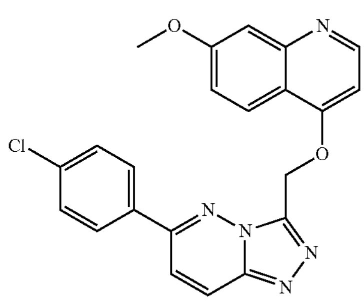 [SMILES: COc1ccc2c(OCc3nnc4ccc(-c5ccc(Cl)cc5)nn34)ccnc2c1] | 418 | 418 | A |
| 224 | 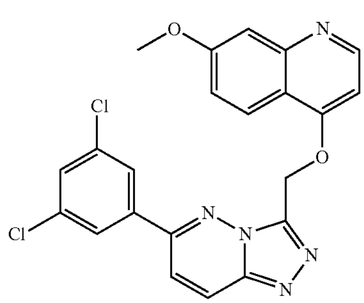 [SMILES: COc1ccc2c(OCc3nnc4ccc(-c5cc(Cl)cc(Cl)c5)nn34)ccnc2c1] | 452 | 452 | A |

-continued
| EX. | Structure | MW | Mass Found | General Method |
|---|---|---|---|---|
| 225 | 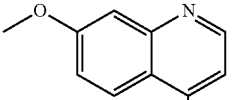 | 452 | 452 | A |
| 226 | 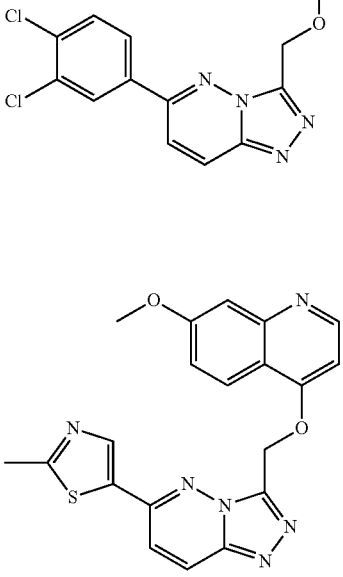 | 404 | 405 | A |
| 227 | 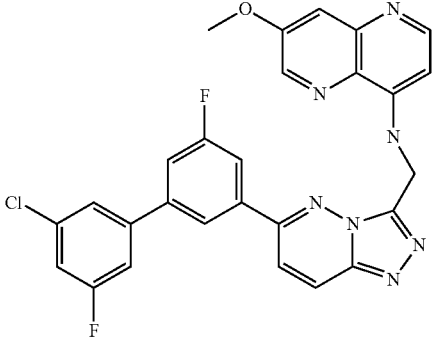 [SMILES: COc1cnc2c(NCc3nnc4ccc(-c5cc(F)cc(-c6cc(F)cc(Cl)c6)c5)nn34)ccnc2c1] | 530 | 530 | D |
| 228 | 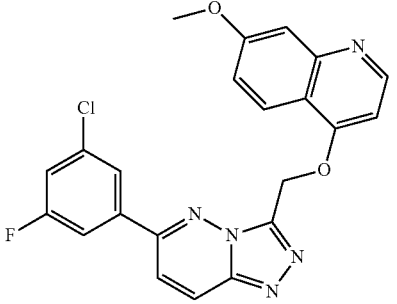 [SMILES: COc1ccc2c(OCc3nnc4ccc(-c5cc(F)cc(Cl)c5)nn34)ccnc2c1] | 436 | 436 | A |

-continued
| EX. | Structure | MW | Mass Found | General Method |
|---|---|---|---|---|
| 229 | 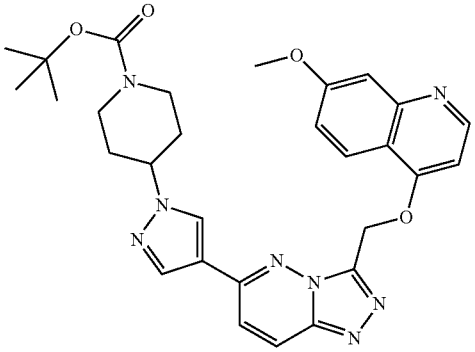 [SMILES: COc1ccc2c(OCc3nnc4ccc(-c5cnn(C6CCN(C(=O)OC(C)(C)C)CC6)c5)nn34)ccnc2c1] | 557 | 557 | A |
| 230 | 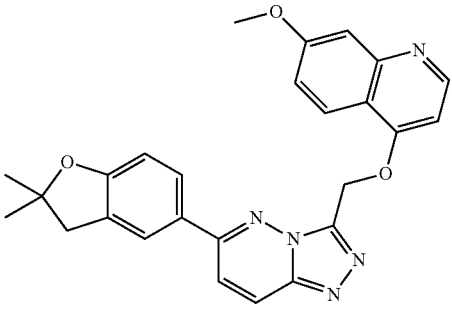 [SMILES: COc1ccc2c(OCc3nnc4ccc(-c5ccc6c(c5)CC(C)(C)O6)nn34)ccnc2c1] | 453 | 454 | A |
| 231 | 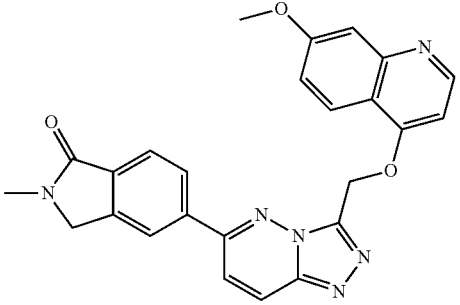 [SMILES: COc1ccc2c(OCc3nnc4ccc(-c5ccc6c(c5)CN(C)C6=O)nn34)ccnc2c1] | 452 | 453 | A |
| 232 | 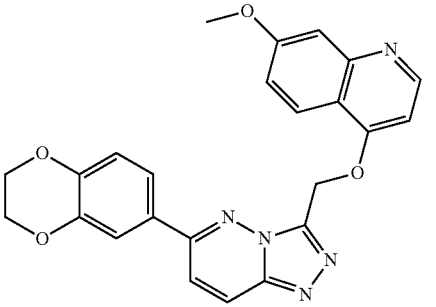 [SMILES: COc1ccc2c(OCc3nnc4ccc(-c5ccc6c(c5)OCCO6)nn34)ccnc2c1] | 441 | 442 | A |

-continued

| EX. | Structure | MW | Mass Found | General Method |
|---|---|---|---|---|
| 233 | 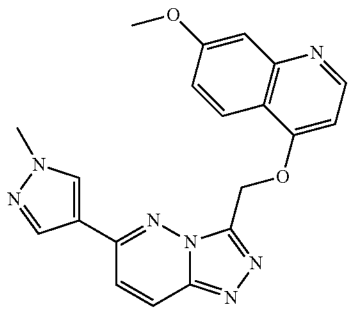 | 387 | 388 | A |
| 234 | 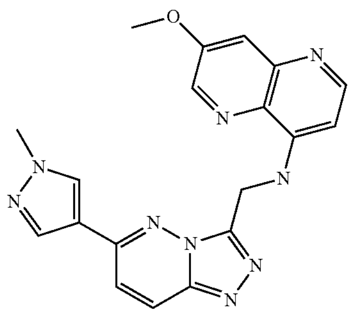 [SMILES: COc1cnc2c(NCc3nnc4ccc(-c5cnn(C)c5)nn34)ccnc2c1] | 387 | 388 | D |
| 235 | 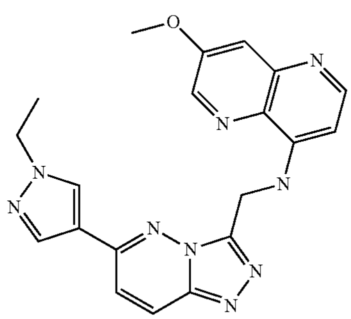 [SMILES: CCn1cc(-c2ccc3nnc(CNc4ccnc5cc(OC)cnc45)n3n2)cn1] | 401 | 402 | D |
| 236 | 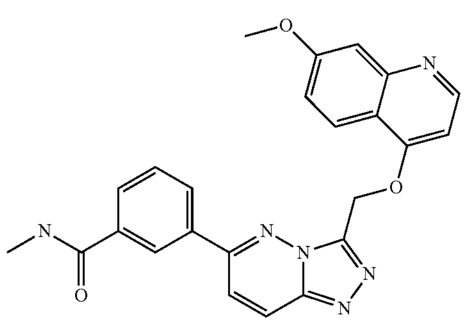 [SMILES: CNC(=O)c1cccc(-c2ccc3nnc(COc4ccnc5cc(OC)ccc45)n3n2)c1] | 440 | 441 | A |
| 237 | 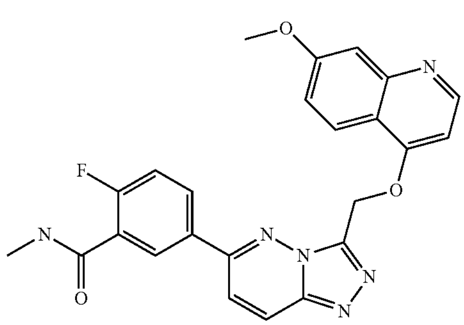 [SMILES: CNC(=O)c1cc(-c2ccc3nnc(COc4ccnc5cc(OC)ccc45)n3n2)ccc1F] | 458 | 459 | A |

| EX. | Structure | MW | Mass Found | General Method |
|---|---|---|---|---|
| 238 | 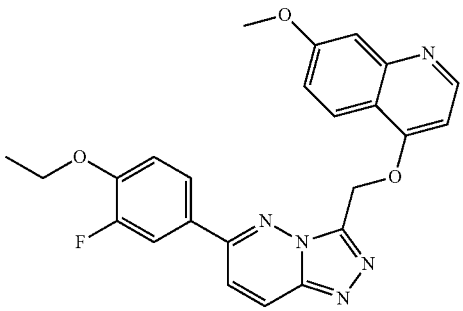 [SMILES: CCOc1ccc(-c2ccc3nnc(COc4ccnc5cc(OC)ccc45)n3n2)cc1F] | 445 | 446 | A |
| 239 | 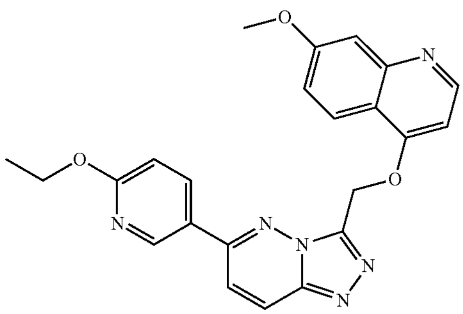 [SMILES: CCOc1ccc(-c2ccc3nnc(COc4ccnc5cc(OC)ccc45)n3n2)cn1] | 428 | 429 | A |
| 240 | 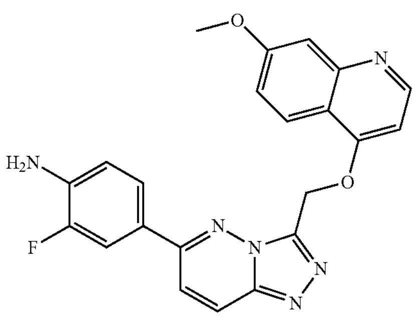 [SMILES: COc1ccc2c(OCc3nnc4ccc(-c5ccc(N)c(F)c5)nn34)ccnc2c1] | 416 | 417 | A |
| 241 | 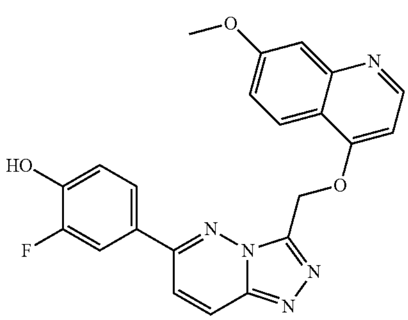 [SMILES: COc1ccc2c(OCc3nnc4ccc(-c5ccc(O)c(F)c5)nn34)ccnc2c1] | 417 | 418 | A |
| 242 | 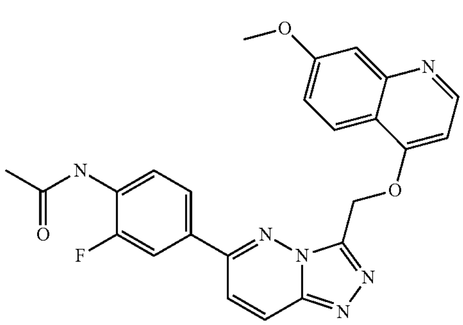 [SMILES: COc1ccc2c(OCc3nnc4ccc(-c5ccc(NC(C)=O)c(F)c5)nn34)ccnc2c1] | 458 | 459 | A |

-continued

| EX. | Structure | MW | Mass Found | General Method |
|---|---|---|---|---|
| 243 | 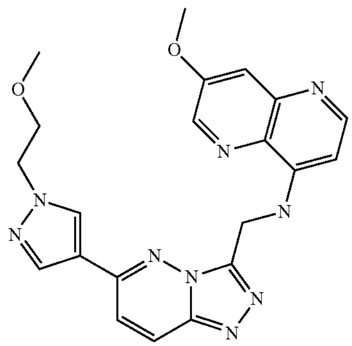 [SMILES: COCCn1cc(-c2ccc3nnc(CNc4ccnc5cc(OC)cnc45)n3n2)cn1] | 431 | 432 | D |
| 244 | 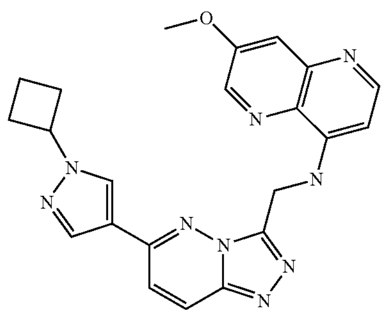 [SMILES: COc1cnc2c(NCc3nnc4ccc(-c5cnn(C6CCC6)c5)nn34)ccnc2c1] | 427 | 428 | D |
| 245 | 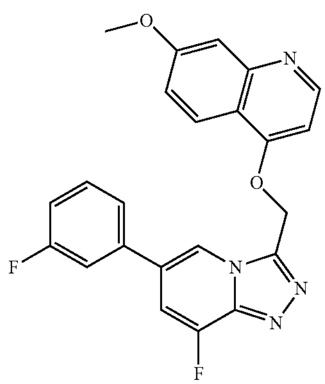 [SMILES: COc1ccc2c(OCc3nnc4c(F)cc(-c5cccc(F)c5)cn34)ccnc2c1] | 418 | 419 | A |
| 246 | 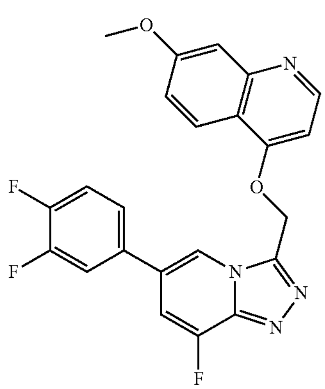 [SMILES: COc1ccc2c(OCc3nnc4c(F)cc(-c5ccc(F)c(F)c5)cn34)ccnc2c1] | 436 | 437 | A |

| EX. | Structure | MW | Mass Found | General Method |
|---|---|---|---|---|
| 247 | 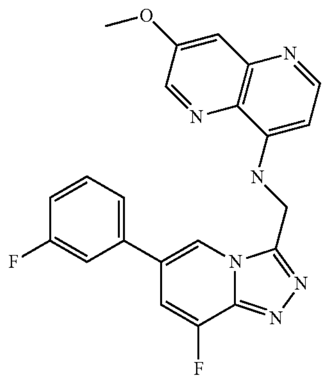 [SMILES: COc1cnc2c(NCc3nnc4c(F)cc(-c5cccc(F)c5)cn34)ccnc2c1] | 418 | 419 | D |
| 248 | 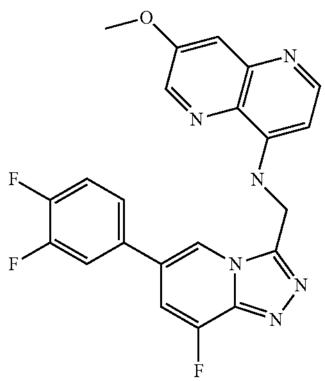 [SMILES: COc1cnc2c(NCc3nnc4c(F)cc(-c5ccc(F)c(F)c5)cn34)ccnc2c1] | 436 | 437 | D |
| 249 | 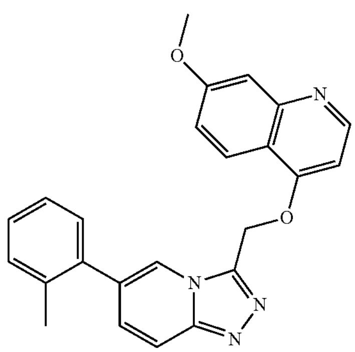 [SMILES: COc1ccc2c(OCc3nnc4ccc(-c5ccccc5C)cn34)ccnc2c1] | 396 | 397 | A |
| 250 | 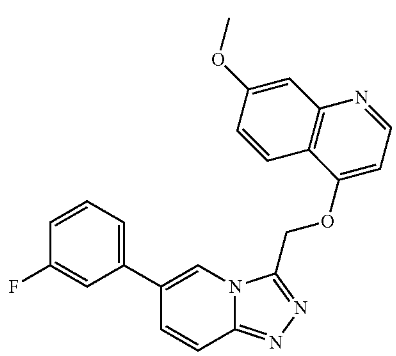 [SMILES: COc1ccc2c(OCc3nnc4ccc(-c5cccc(F)c5)cn34)ccnc2c1] | 400 | 401 | A |

-continued

| EX. | Structure | MW | Mass Found | General Method |
|---|---|---|---|---|
| 251 | 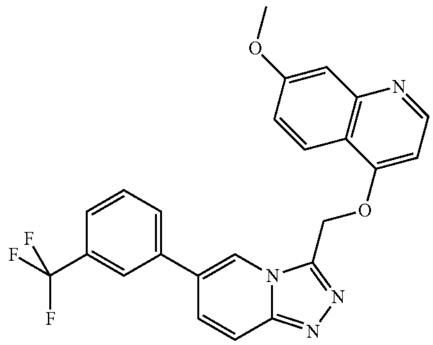 [SMILES: COc1ccc2c(OCc3nnc4ccc(-c5cccc(C(F)(F)F)c5)cn34)ccnc2c1] | 450 | 451 | A |
| 252 | 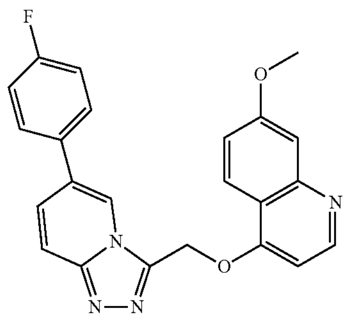 [SMILES: COc1ccc2c(OCc3nnc4ccc(-c5ccc(F)cc5)cn34)ccnc2c1] | 400 | 401 | A |
| 253 | 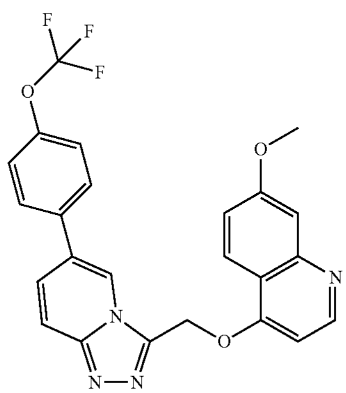 [SMILES: COc1ccc2c(OCc3nnc4ccc(-c5ccc(OC(F)(F)F)cc5)cn34)ccnc2c1] | 466 | 467 | A |
| 254 | 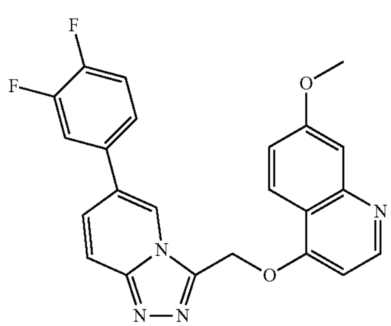 [SMILES: COc1ccc2c(OCc3nnc4ccc(-c5ccc(F)c(F)c5)cn34)ccnc2c1] | 418 | 419 | A |

-continued
| EX. | Structure | MW | Mass Found | General Method |
|---|---|---|---|---|
| 255 | 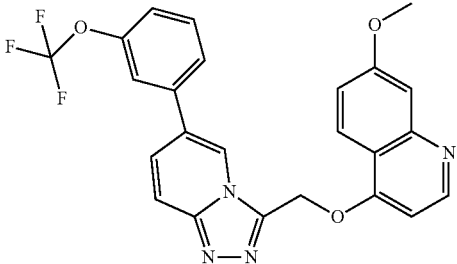 [SMILES: COc1ccc2c(OCc3nnc4ccc(-c5cccc(OC(F)(F)F)c5)cn34)ccnc2c1] | 466 | 467 | A |
| 256 | 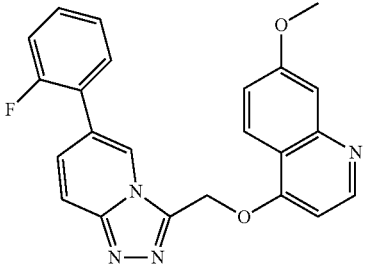 [SMILES: COc1ccc2c(OCc3nnc4ccc(-c5ccccc5F)cn34)ccnc2c1] | 400 | 401 | A |
| 257 | 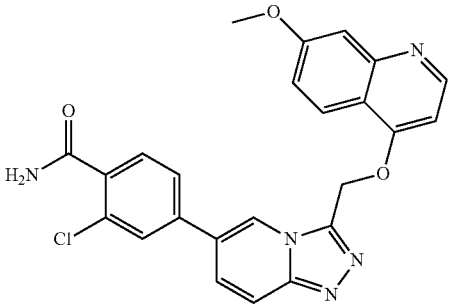 [SMILES: COc1ccc2c(OCc3nnc4ccc(-c5ccc(C(N)=O)c(Cl)c5)cn34)ccnc2c1] | 460 | 460 | A |
| 258 | 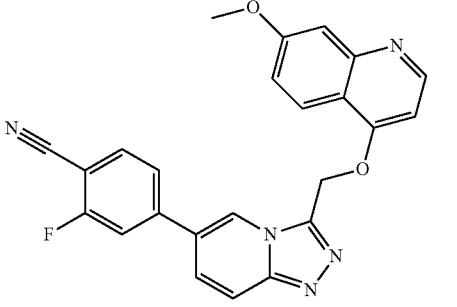 [SMILES: COc1ccc2c(OCc3nnc4ccc(-c5ccc(C#N)c(F)c5)cn34)ccnc2c1] | 425 | 426 | A |
| 259 | 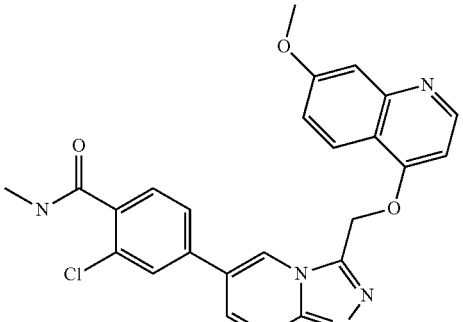 | 474 | 474 | A |

-continued
| EX. | Structure | MW | Mass Found | General Method |
|---|---|---|---|---|
| 260 | 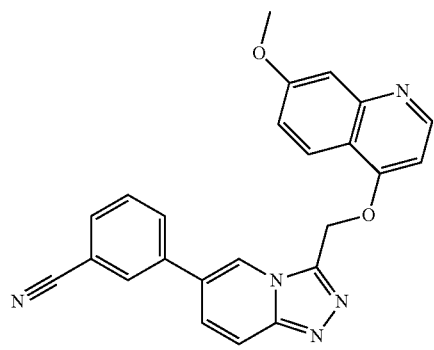 [SMILES: COc1ccc2c(OCc3nnc4ccc(-c5cccc(C#N)c5)cn34)ccnc2c1] | 407 | 408 | A |
| 261 | 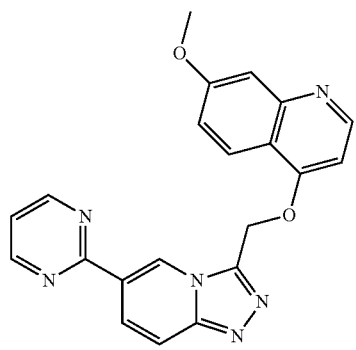 [SMILES: COc1ccc2c(OCc3nnc4ccc(-c5ncccn5)cn34)ccnc2c1] | 384 | 385 | A |
| 262 | 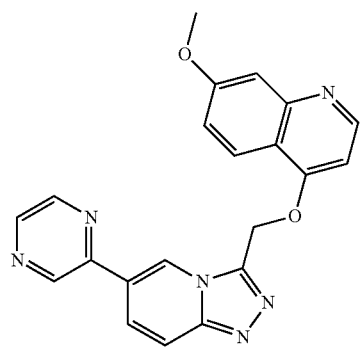 [SMILES: COc1ccc2c(OCc3nnc4ccc(-c5cnccn5)cn34)ccnc2c1] | 384 | 385 | A |
| 263 | 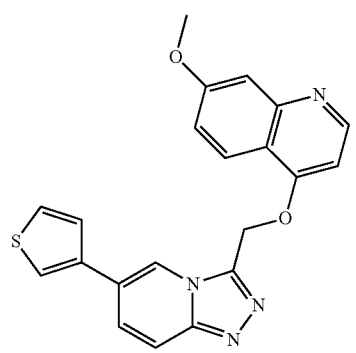 [SMILES: COc1ccc2c(OCc3nnc4ccc(-c5ccsc5)cn34)ccnc2c1] | 388 | 389 | A |

-continued

| EX. | Structure | MW | Mass Found | General Method |
|---|---|---|---|---|
| 264 | 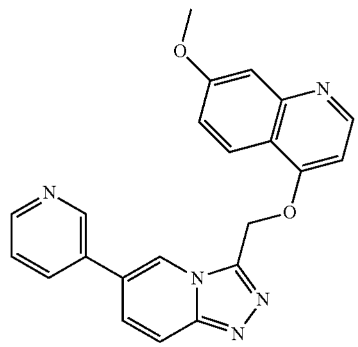 [SMILES: COc1ccc2c(OCc3nnc4ccc(-c5cccnc5)cn34)ccnc2c1] | 383 | 384 | A |
| 265 | 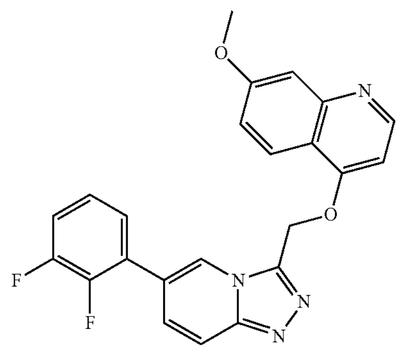 [SMILES: COc1ccc2c(OCc3nnc4ccc(-c5cccc(F)c5F)cn34)ccnc2c1] | 418 | 419 | A |
| 266 | 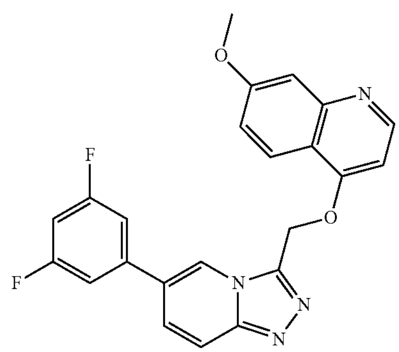 [SMILES: COc1ccc2c(OCc3nnc4ccc(-c5cc(F)cc(F)c5)cn34)ccnc2c1] | 418 | 419 | A |
| 267 | 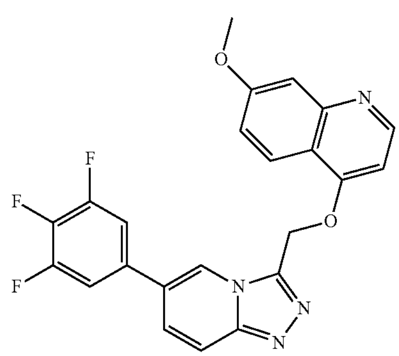 [SMILES: COc1ccc2c(OCc3nnc4ccc(-c5cc(F)c(F)c(F)c5)cn34)ccnc2c1] | 436 | 437 | A |

-continued

| EX. | Structure | MW | Mass Found | General Method |
|---|---|---|---|---|
| 268 | 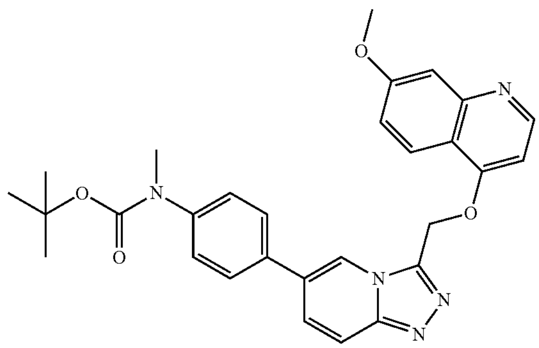 [SMILES: COc1ccc2c(OCc3nnc4ccc(-c5ccc(N(C)C(=O)OC(C)(C)C)cc5)cn34)ccnc2c1] | 512 | 512 | A |
| 269 | 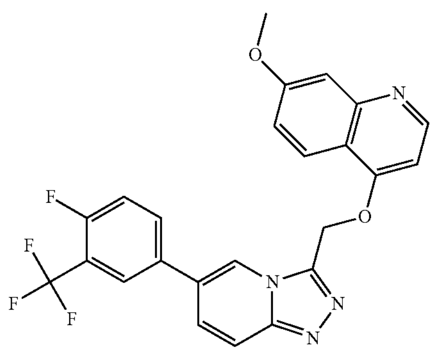 [SMILES: COc1ccc2c(OCc3nnc4ccc(-c5ccc(F)c(C(F)(F)F)c5)cn34)ccnc2c1] | 468 | 469 | A |
| 270 | 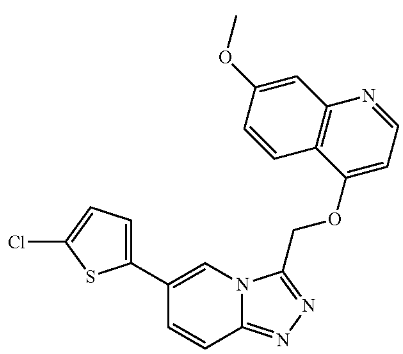 [SMILES: COc1ccc2c(OCc3nnc4ccc(-c5ccc(Cl)s5)cn34)ccnc2c1] | 423 | 423 | A |
| 271 | 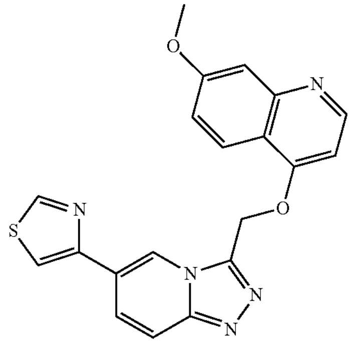 [SMILES: COc1ccc2c(OCc3nnc4ccc(-c5cscn5)cn34)ccnc2c1] | 389 | 390 | A |

-continued
| EX. | Structure | MW | Mass Found | General Method |
|---|---|---|---|---|
| 272 | 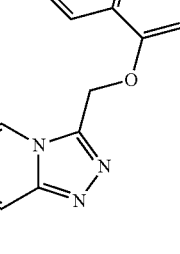 | 414 | 415 | A |
| 273 | 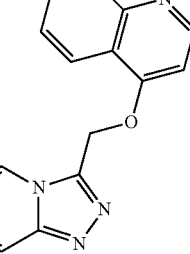 | 414 | 415 | A |
| 274 | 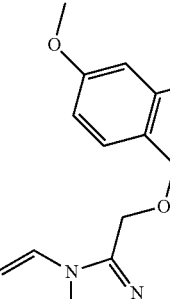 | 426 | 427 | A |
| 275 | 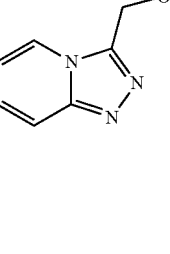 | 430 | 431 | A |

-continued
| EX. | Structure | MW | Mass Found | General Method |
|---|---|---|---|---|
| 276 | 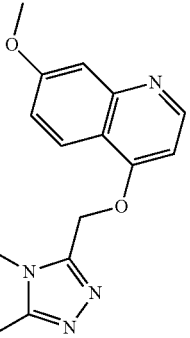 | 435 | 435 | A |
| 277 | 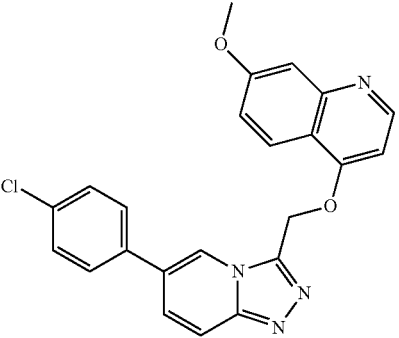 [SMILES: COc1ccc2c(OCc3nnc4ccc(-c5ccc(Cl)cc5)cn34)ccnc2c1] | 417 | 417 | A |
| 278 | 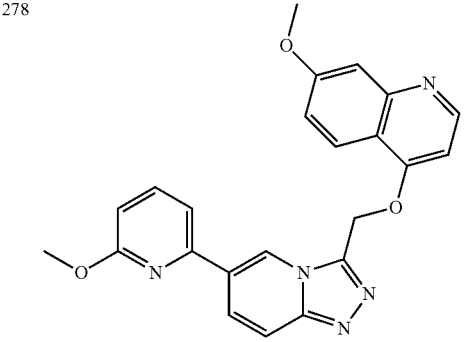 | 413 | 414 | A |
| 279 | 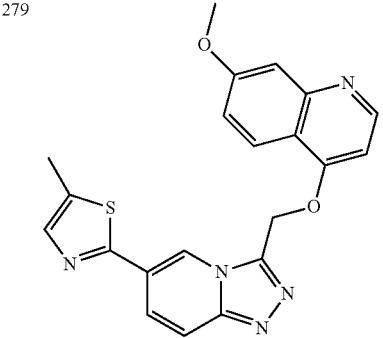 [SMILES: COc1ccc2c(OCc3nnc4ccc(-c5nc(C)cs5)cn34)ccnc2c1] | 403 | 404 | A |

-continued
| EX. | Structure | MW | Mass Found | General Method |
|---|---|---|---|---|
| 280 | 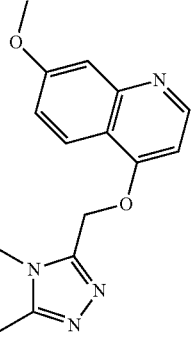 | 403 | 404 | A |
| 281 | 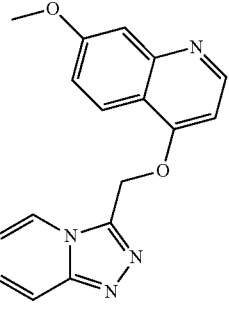 | 384 | 385 | A |
| 282 | 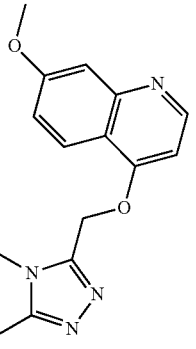 | 383 | 384 | A |
| 283 | 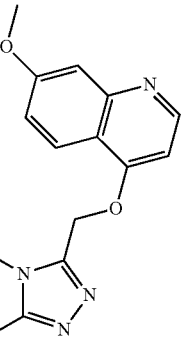 | 371 | 372 | A |

-continued
| EX. | Structure | MW | Mass Found | General Method |
|---|---|---|---|---|
| 284 | 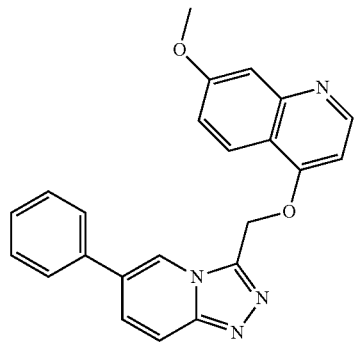 [SMILES: COc1ccc2c(OCc3nnc4ccc(-c5ccccn5)cn34)ccnc2c1] | 382 | 383 | A |
| 285 | 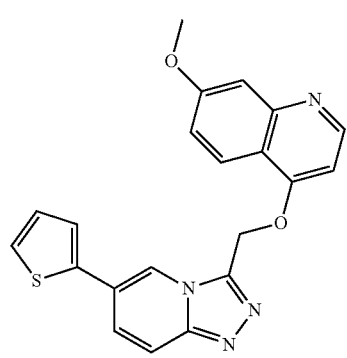 [SMILES: COc1ccc2c(OCc3nnc4ccc(-c5ccc[nH]5)cn34)ccnc2c1] | 388 | 389 | A |
| 286 | 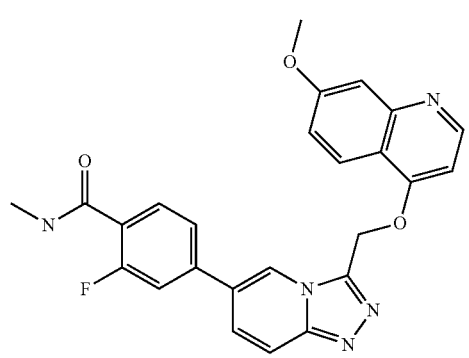 [SMILES: CNC(=O)c1ccc(-c2ccc3nnc(COc4ccnc5cc(OC)ccc45)n3c2)cc1F] | 457 | 458 | A |
| 287 | 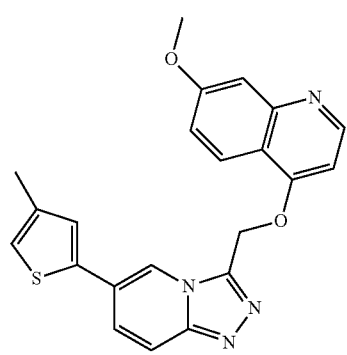 [SMILES: COc1ccc2c(OCc3nnc4ccc(-c5cc(C)cs5)cn34)ccnc2c1] | 402 | 403 | A |

-continued
| EX. | Structure | MW | Mass Found | General Method |
|---|---|---|---|---|
| 288 | 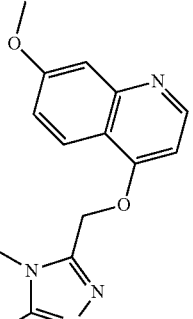 | 389 | 390 | A |
| 289 | 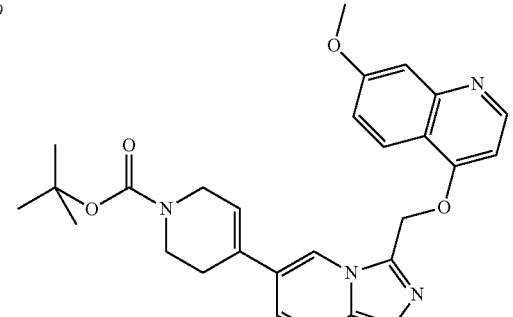 | 488 | 488 | A |
| 290 | 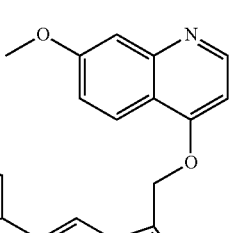 | 389 | 390 | A |
| 291 | 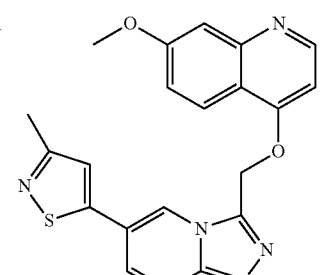 | 403 | 404 | A |
| 292 | 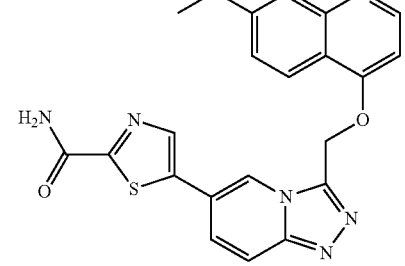 | 432 | 433 | A |

-continued
| EX. | Structure | MW | Mass Found | General Method |
|---|---|---|---|---|
| 293 | 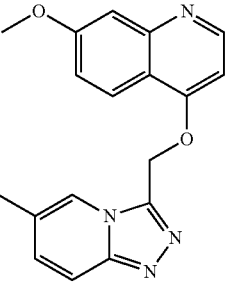 | 403 | 404 | A |
| 294 | 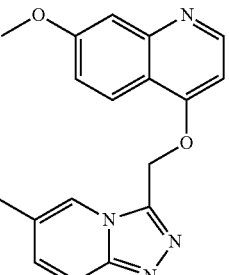 | 437 | 438 | A |
| 295 | 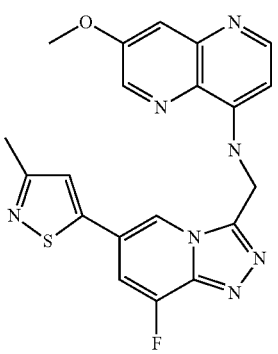 [SMILES: COc1cnc2c(NCc3nnc4c(F)cc(-c5cc(C)ns5)cn34)ccnc2c1] | 421 | 422 | D |
| 296 | 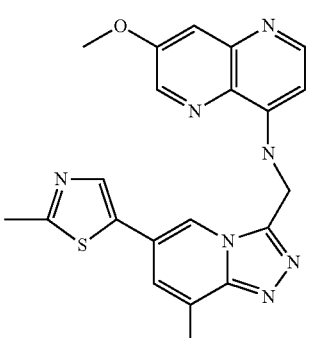 | 421 | 422 | D |
| 297 | 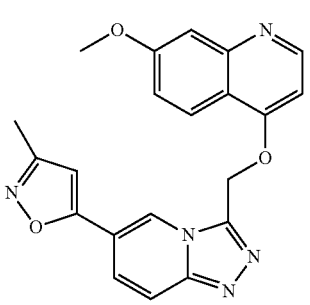 [SMILES: COc1ccc2c(OCc3nnc4ccc(-c5cc(C)no5)cn34)ccnc2c1] | 387 | 388 | A |

-continued

| EX. | Structure | MW | Mass Found | General Method |
|---|---|---|---|---|
| 298 | 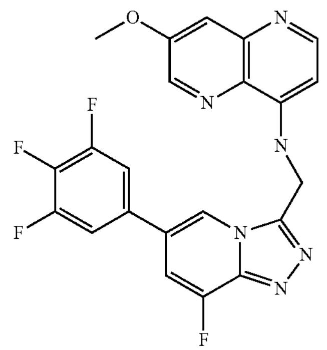 [SMILES: COc1cnc2c(NCc3nnc4c(F)cc(-c5cc(F)c(F)c(F)c5)cn34)ccnc2c1] | 454 | 455 | D |
| 299 | 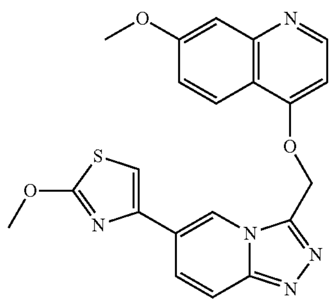 [SMILES: COc1ccc2c(OCc3nnc4ccc(-c5csc(OC)n5)cn34)ccnc2c1] | 419 | 420 | A |
| 300 | 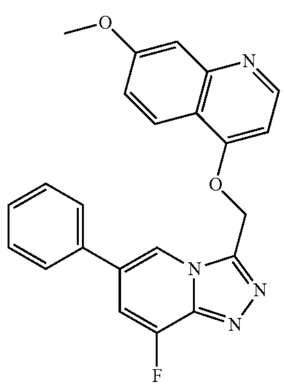 [SMILES: COc1ccc2c(OCc3nnc4c(F)cc(-c5ccccc5)cn34)ccnc2c1] | 400 | 401 | A |
| 301 | 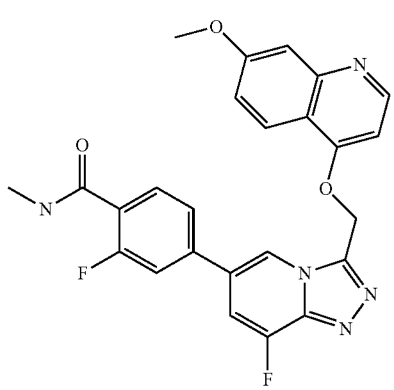 [SMILES: CNC(=O)c1ccc(-c2cc(F)c3nnc(COc4ccnc5cc(OC)ccc45)n3c2)cc1F] | 475 | 476 | A |

-continued
| EX. | Structure | MW | Mass Found | General Method |
|---|---|---|---|---|
| 302 | 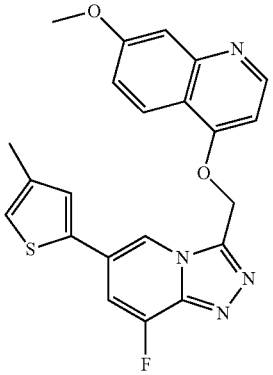 [SMILES: COc1ccc2c(OCc3nnc4c(F)cc(-c5cc(C)cs5)cn34)ccnc2c1] | 420 | 421 | A |
| 303 | 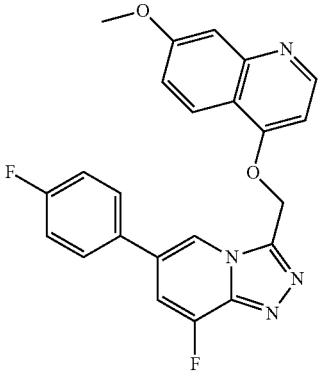 [SMILES: COc1ccc2c(OCc3nnc4c(F)cc(-c5ccc(F)cc5)cn34)ccnc2c1] | 418 | 419 | A |
| 304 | 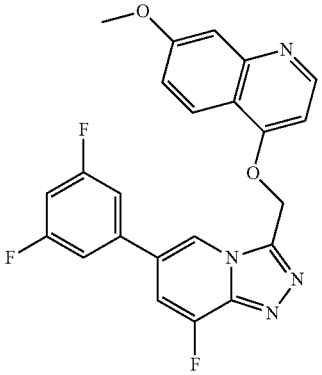 [SMILES: COc1ccc2c(OCc3nnc4c(F)cc(-c5cc(F)cc(F)c5)cn34)ccnc2c1] | 436 | 437 | A |
| 305 | 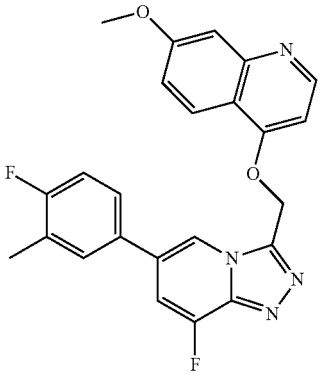 [SMILES: COc1ccc2c(OCc3nnc4c(F)cc(-c5ccc(F)c(C)c5)cn34)ccnc2c1] | 432 | 433 | A |

-continued

| EX. | Structure | MW | Mass Found | General Method |
|---|---|---|---|---|
| 306 | 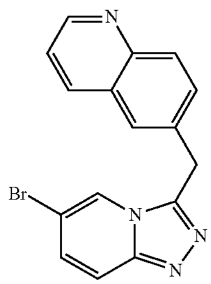 [SMILES: Brc1ccc2nnc(Cc3ccc4ncccc4c3)n2c1] | 339 | 339.1, 341.3 | B |
| 307 | 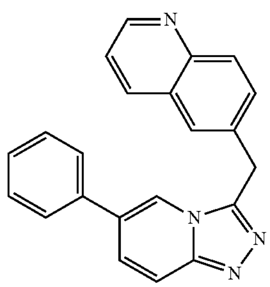 [SMILES: c1ccc(-c2ccc3nnc(Cc4ccc5ncccc5c4)n3c2)cc1] | 336 | 337 | A |
| 308 | 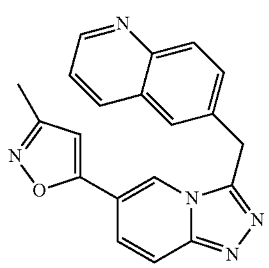 [SMILES: Cc1cc(-c2ccc3nnc(Cc4ccc5ncccc5c4)n3c2)on1] | 341 | 342 | A |
| 309 | 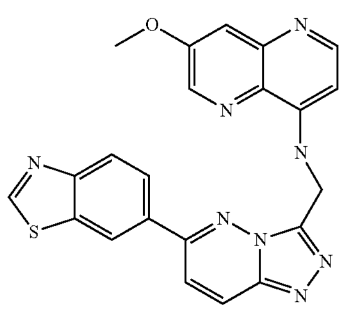 [SMILES: COc1cnc2c(NCc3nnc4ccc(-c5ccc6ncsc6c5)nn34)ccnc2c1] | 440 | 441 | D |
| 310 | 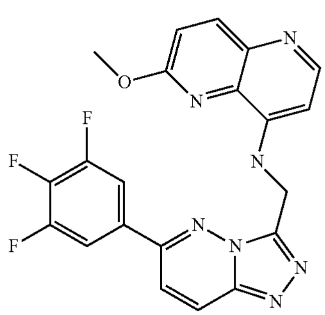 [SMILES: COc1ccc2nccc(NCc3nnc4ccc(-c5cc(F)c(F)c(F)c5)nn34)c2n1] | 437 | 438 | D |

-continued

| EX. | Structure | MW | Mass Found | General Method |
|---|---|---|---|---|
| 311 | 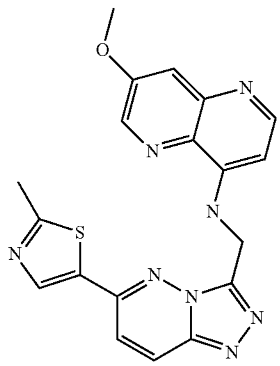 [SMILES: COc1cnc2c(NCc3nnc4ccc(-c5cnc(C)s5)nn34)ccnc2c1] | 404 | 405 | D |
| 312 | 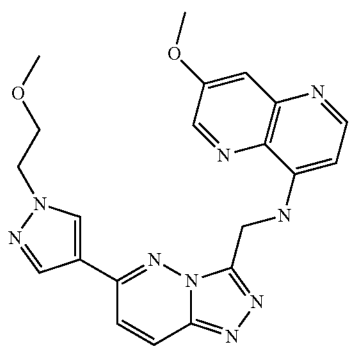 [SMILES: COCCn1cc(-c2ccc3nnc(CNc4ccnc5cc(OC)cnc45)n3n2)cn1] | 431 | 432 | D |
| 313 | 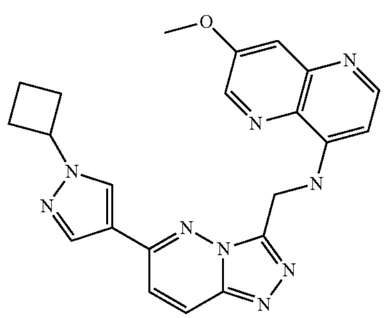 [SMILES: COc1cnc2c(NCc3nnc4ccc(-c5cnn(C6CCC6)c5)nn34)ccnc2c1] | 427 | 428 | D |
| 314 | 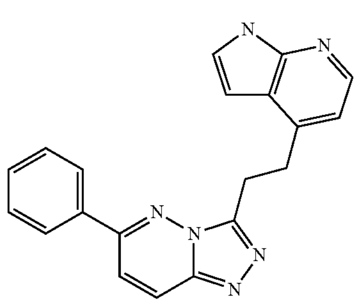 [SMILES: c1ccc(-c2ccc3nnc(CCc4ccnc5[nH]ccc45)n3n2)cc1] | 340 | 341 | E |

-continued
| EX. | Structure | MW | Mass Found | General Method |
|---|---|---|---|---|
| 315 | 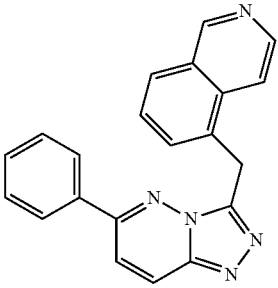 [SMILES: c1ccc(-c2ccc3nnc(Cc4cccc5cnccc45)n3n2)cc1] | 337 | 338 | E |
| 316 | 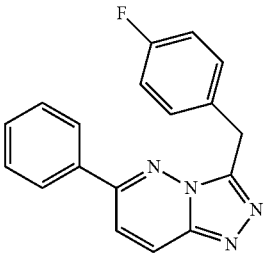 [SMILES: Fc1ccc(Cc2nnc3ccc(-c4ccccc4)nn23)cc1] | 304 | 305 | A |
| 317 | 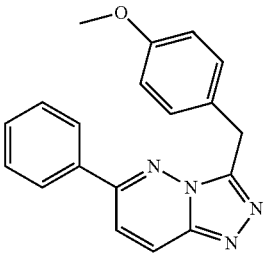 [SMILES: COc1ccc(Cc2nnc3ccc(-c4ccccc4)nn23)cc1] | 316 | 317 | A |
| 318 | 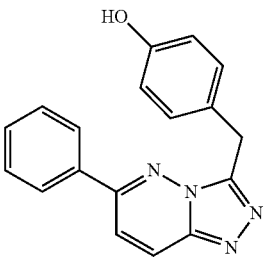 [SMILES: Oc1ccc(Cc2nnc3ccc(-c4ccccc4)nn23)cc1] | 302 | 303 | B |
| 319 | 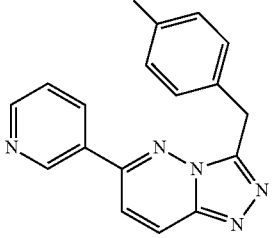 | 303 | 304 | A |

| EX. | Structure | MW | Mass Found | General Method |
|---|---|---|---|---|
| 320 | 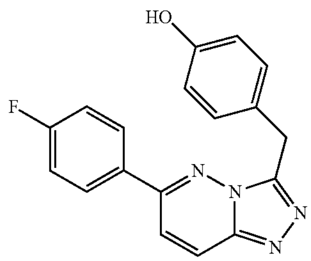 [SMILES: Oc1ccc(Cc2nnc3ccc(-c4ccc(F)cc4)nn23)cc1] | 320 | 321 | A |
| 321 | 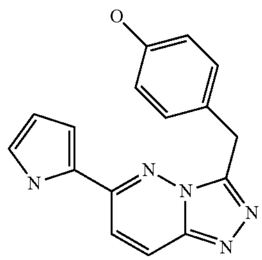 [SMILES: Oc1ccc(Cc2nnc3ccc(-c4ccc[nH]4)nn23)cc1] | 291 | 292 | A |
| 322 | 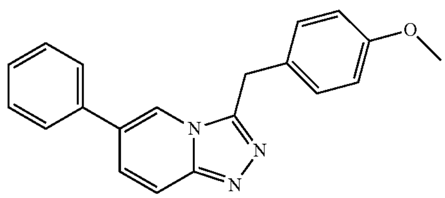 [SMILES: COc1ccc(Cc2nnc3ccc(-c4ccccc4)cn23)cc1] | 315 | 316 | A |
| 323 | 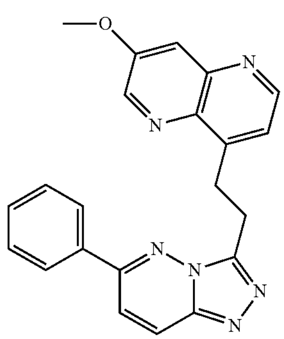 [SMILES: COc1cnc2c(CCc3nnc4ccc(-c5ccccc5)nn34)ccnc2c1] | 382 | 383 | E |
| 324 | 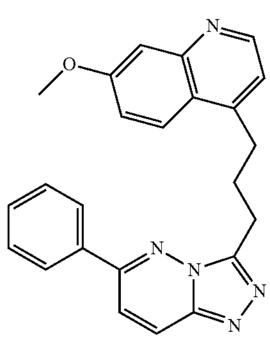 [SMILES: COc1ccc2c(CCCc3nnc4ccc(-c5ccccc5)nn34)ccnc2c1] | 395 | 396 | E |

-continued
| EX. | Structure | MW | Mass Found | General Method |
|---|---|---|---|---|
| 325 | 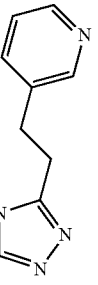 | 301 | 459 | E |
| 326 | 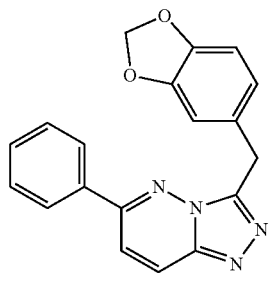 [SMILES: c1ccc(-c2ccc3nnc(Cc4ccc5c(c4)OCO5)n3n2)cc1] | 330 | 331 | A |
| 327 | 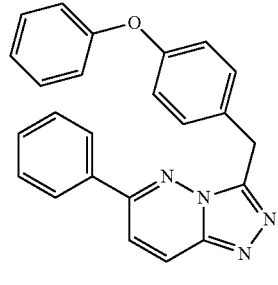 [SMILES: c1ccc(Oc2ccc(Cc3nnc4ccc(-c5ccccc5)nn34)cc2)cc1] | 378 | 379 | A |
| 328 | 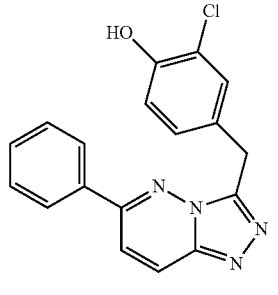 [SMILES: Oc1ccc(Cc2nnc3ccc(-c4ccccc4)nn23)cc1Cl] | 337 | 337 | A |
| 329 | 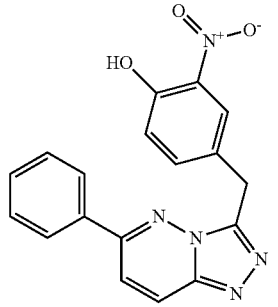 [SMILES: O=[N+]([O-])c1cc(Cc2nnc3ccc(-c4ccccc4)nn23)ccc1O] | 347 | 348 | A |

| EX. | Structure | MW | Mass Found | General Method |
|---|---|---|---|---|
| 330 | 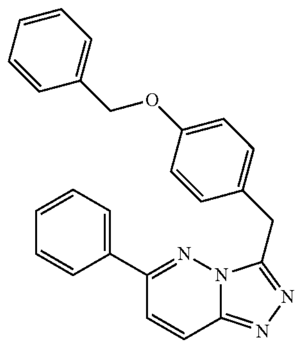 [SMILES: c1ccc(COc2ccc(Cc3nnc4ccc(-c5ccccc5)nn34)cc2)cc1] | 392 | 393 | A |
| 331 | 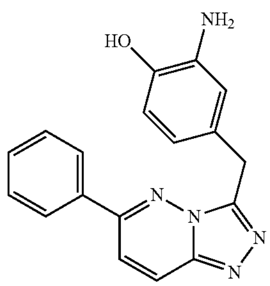 [SMILES: Nc1cc(Cc2nnc3ccc(-c4ccccc4)nn23)ccc1O] | 317 | 318 | A |
| 332 | 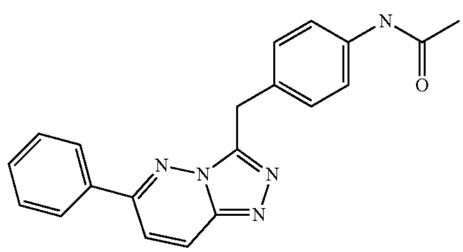 [SMILES: CC(=O)Nc1ccc(Cc2nnc3ccc(-c4ccccc4)nn23)cc1] | 343 | 344 | A |
| 333 | 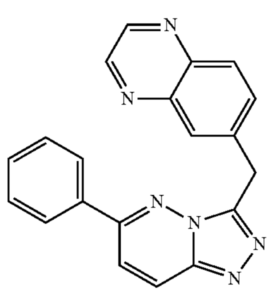 [SMILES: c1ccc(-c2ccc3nnc(Cc4ccc5nccnc5c4)n3n2)cc1] | 338 | 339 | A |
| 334 | 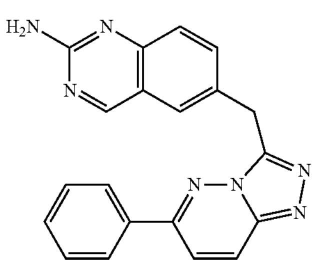 [SMILES: Nc1ncc2cc(Cc3nnc4ccc(-c5ccccc5)nn34)ccc2n1] | 353 | 354 | A |

| EX. | Structure | MW | Mass Found | General Method |
|---|---|---|---|---|
| 335 | 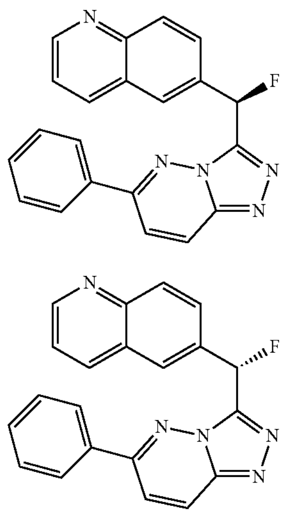 | 355 | 356 | A |
| 336 | 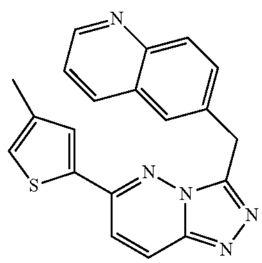 [SMILES: Cc1csc(-c2ccc3nnc(Cc4ccc5ncccc5c4)n3n2)c1] | 357 | 358 | A |
| 337 | 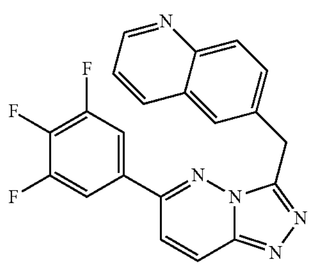 | 391 | 393 | A |
| 338 | 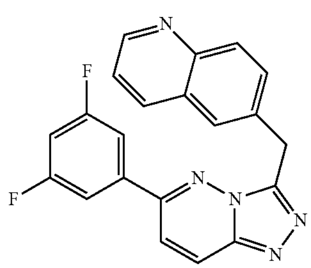 [SMILES: Fc1cc(F)cc(-c2ccc3nnc(Cc4ccc5ncccc5c4)n3n2)c1] | 373 | 374 | A |
| 339 | 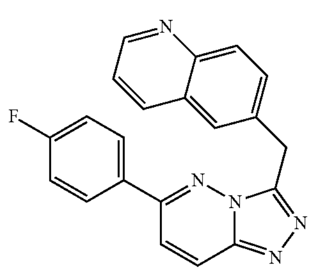 [SMILES: Fc1ccc(-c2ccc3nnc(Cc4ccc5ncccc5c4)n3n2)cc1] | 355 | 356 | A |

-continued

| EX. | Structure | MW | Mass Found | General Method |
|---|---|---|---|---|
| 340 | 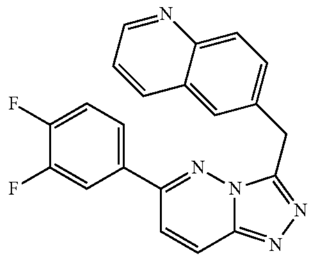 [SMILES: Fc1ccc(-c2ccc3nnc(Cc4ccc5ncccc5c4)n3n2)cc1F] | 373 | 375 | A |
| 341 | 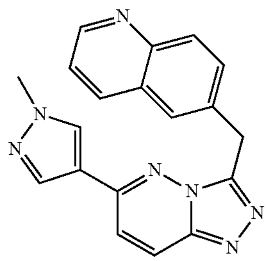 [SMILES: Cn1cc(-c2ccc3nnc(Cc4ccc5ncccc5c4)n3n2)cn1] | 341 | 343 | A |
| 342 | 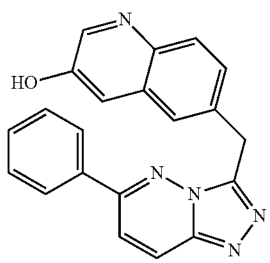 [SMILES: Oc1cnc2ccc(Cc3nnc4ccc(-c5ccccc5)nn34)cc2c1] | 353 | 354 | E |
| 343 | 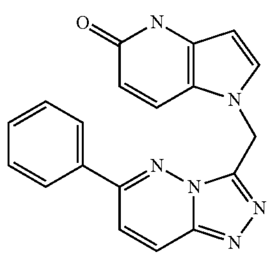 [SMILES: O=c1ccc2c(ccn2Cc2nnc3ccc(-c4ccccc4)nn23)[nH]1] | 342 | 343 | E |
| 344 | 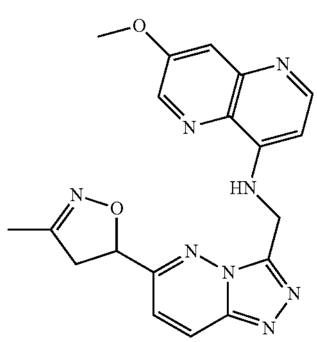 [SMILES: COc1cnc2c(NCc3nnc4ccc(C5CC(C)=NO5)nn34)ccnc2c1] | 390 | 391 | D |

| EX. | Structure | MW | Mass Found | General Method |
|---|---|---|---|---|
| 345 | 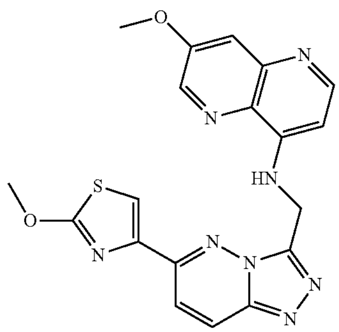 [SMILES: COc1cnc2c(NCc3nnc4ccc(-c5csc(OC)n5)nn34)ccnc2c1] | 420 | 421 | D |
| 346 | 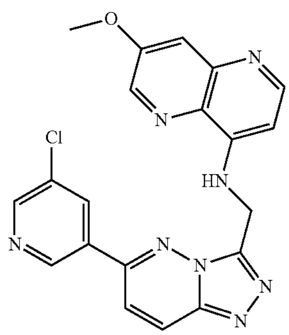 [SMILES: COc1cnc2c(NCc3nnc4ccc(-c5cncc(Cl)c5)nn34)ccnc2c1] | 418 | 419 | D |
| 347 | 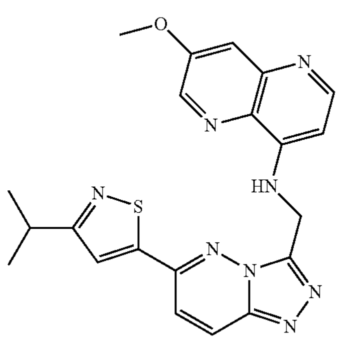 [SMILES: COc1cnc2c(NCc3nnc4ccc(-c5cc(C(C)C)ns5)nn34)ccnc2c1] | 432 | 433 | D |
| 348 | 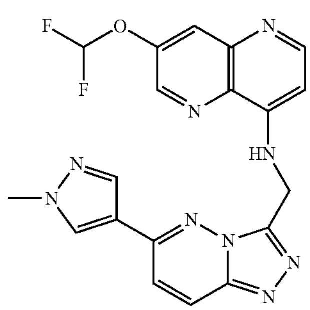 [SMILES: Cn1cc(-c2ccc3nnc(CNc4ccnc5cc(OC(F)F)cnc45)n3n2)cn1] | 423 | 424 | D |

-continued
| EX. | Structure | MW | Mass Found | General Method |
|---|---|---|---|---|
| 349 | 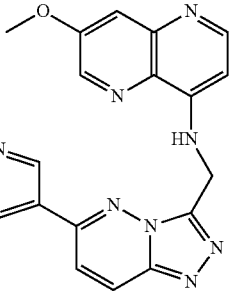 | 449 | 450 | D |
| 350 | 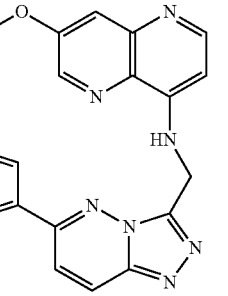 | 455 | 456 | D |
| 351 | 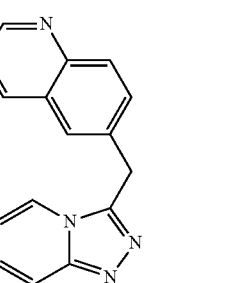 | 402 | 403 | A |
| 352 | 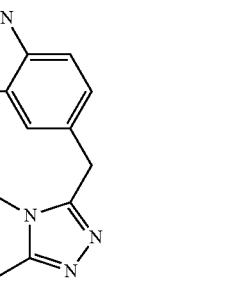 | 387 | 388 | A |
| 353 | 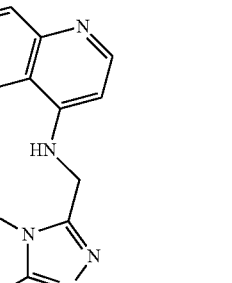 | 358 | 359 | D |

-continued

| EX. | Structure | MW | Mass Found | General Method |
|---|---|---|---|---|
| 354 | 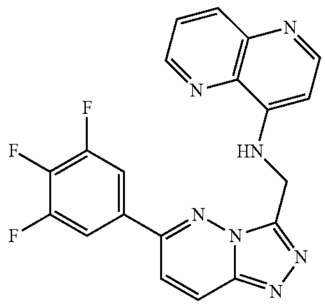 [SMILES: Fc1cc(-c2ccc3nnc(CNc4ccnc5cccnc45)n3n2)cc(F)c1F] | 407 | 408 | D |
| 355 | 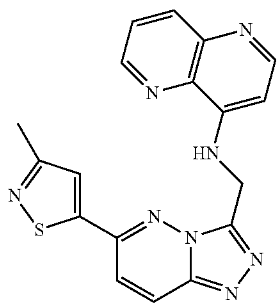 [SMILES: Cc1cc(-c2ccc3nnc(CNc4ccnc5cccnc45)n3n2)sn1] | 374 | 375 | D |
| 356 | 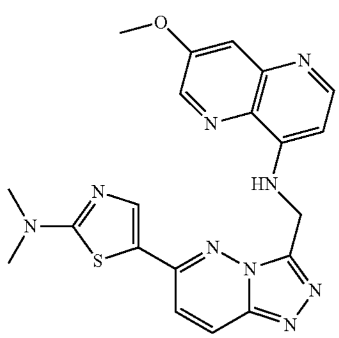 [SMILES: COc1cnc2c(NCc3nnc4ccc(-c5cnc(N(C)C)s5)nn34)ccnc2c1] | 433 | 434 | D |
| 357 | 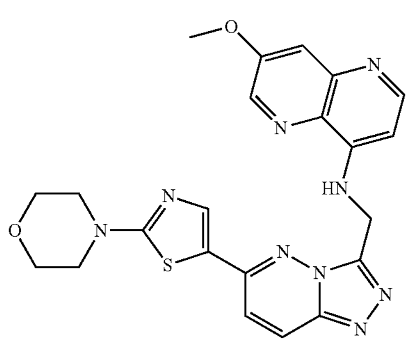 [SMILES: COc1cnc2c(NCc3nnc4ccc(-c5cnc(N6CCOCC6)s5)nn34)ccnc2c1] | 475 | 476 | D |

-continued
| EX. | Structure | MW | Mass Found | General Method |
|---|---|---|---|---|
| 358 | 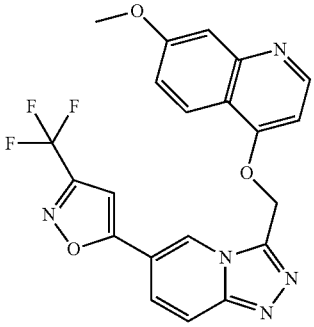 [SMILES: COc1ccc2c(OCc3nnc4ccc(-c5cc(C(F)(F)F)no5)cn34)ccnc2c1] | 441 | 442 | A |
| 359 | 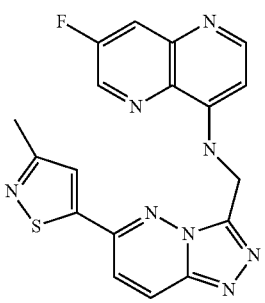 [SMILES: Cc1cc(-c2ccc3nnc(CNc4ccnc5cc(F)cnc45)n3n2)sn1] | 392 | 393 | D |
| 360 | 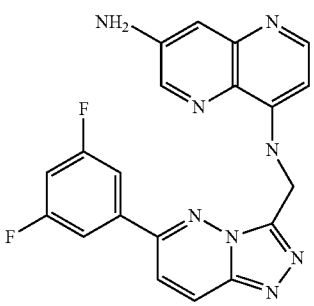 [SMILES: Nc1cnc2c(NCc3nnc4ccc(-c5cc(F)cc(F)c5)nn34)ccnc2c1] | 404 | 405 | D |
| 361 | 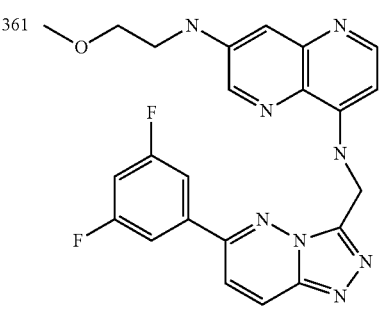 | 462 | 463 | D |
| 362 | 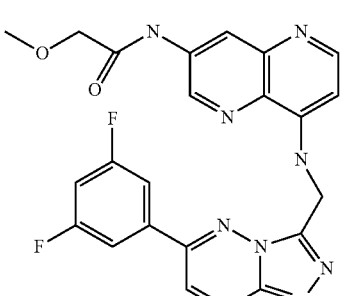 | 476 | 477 | D |

| EX. | Structure | MW | Mass Found | General Method |
|---|---|---|---|---|
| 363 | 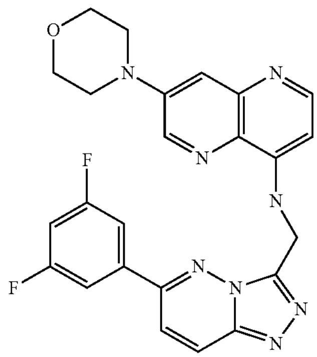 [SMILES: Fc1cc(F)cc(-c2ccc3nnc(CNc4ccnc5cc(N6CCOCC6)cnc45)n3n2)c1] | 474 | 475 | D |
| 364 | 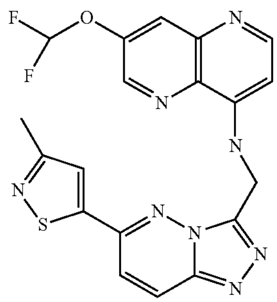 [SMILES: Cc1cc(-c2ccc3nnc(CNc4ccnc5cc(OC(F)F)cnc45)n3n2)sn1] | 440 | 441 | D |
| 365 | 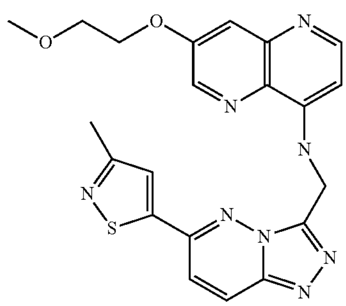 [SMILES: COCCOc1cnc2c(NCc3nnc4ccc(-c5cc(C)ns5)nn34)ccnc2c1] | 448 | 449 | D |
| 366 | 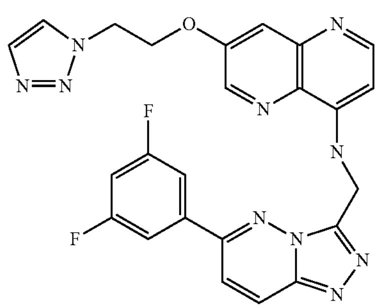 [SMILES: Fc1cc(F)cc(-c2ccc3nnc(CNc4ccnc5cc(OCCn6ccnn6)cnc45)n3n2)c1] | 500 | 501 | D |
| 367 | 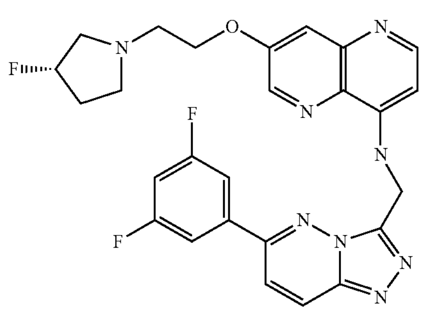 [SMILES: Fc1cc(F)cc(-c2ccc3nnc(CNc4ccnc5cc(OCCN6CC[C@H](F)C6)cnc45)n3n2)c1] | 520 | 521 | D |

| EX. | Structure | MW | Mass Found | General Method |
|---|---|---|---|---|
| 368 | 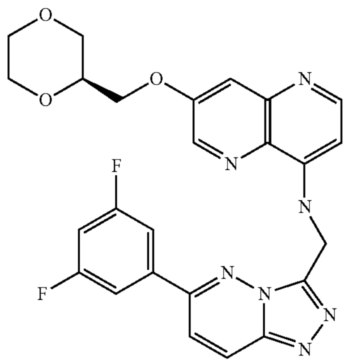 [SMILES: Fc1cc(F)cc(-c2ccc3nnc(CNc4ccnc5cc(OC[C@@H]6COCCO6)cnc45)n3n2)c1] | 505 | 506 | D |
| 369 | 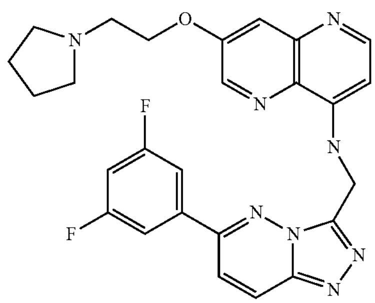 [SMILES: Fc1cc(F)cc(-c2ccc3nnc(CNc4ccnc5cc(OCCN6CCCC6)cnc45)n3n2)c1] | 502 | 503 | D |
| 370 | 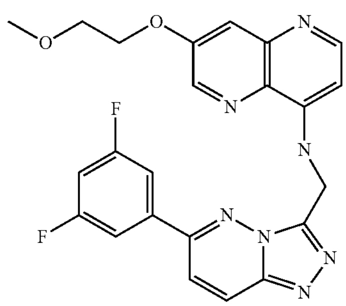 [SMILES: COCCOc1cnc2c(NCc3nnc4ccc(-c5cc(F)cc(F)c5)nn34)ccnc2c1] | 463 | 464 | D |
| 371 | 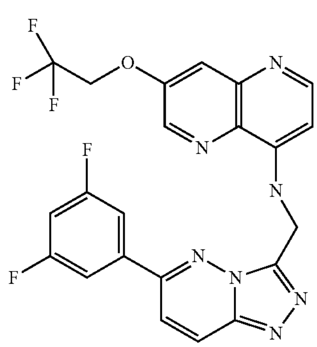 [SMILES: Fc1cc(F)cc(-c2ccc3nnc(CNc4ccnc5cc(OCC(F)(F)F)cnc45)n3n2)c1] | 487 | 488 | D |

-continued
| EX. | Structure | MW | Mass Found | General Method |
|---|---|---|---|---|
| 372 | 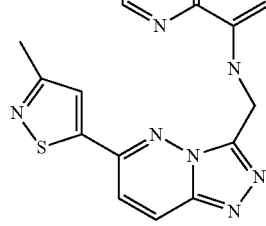 | 472 | 473 | D |
| 373 | 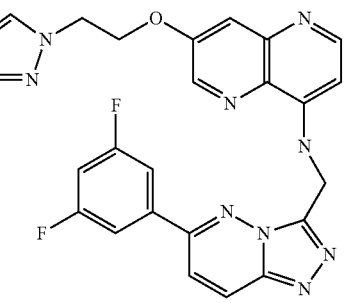 | 500 | 501 | D |
| 374 | 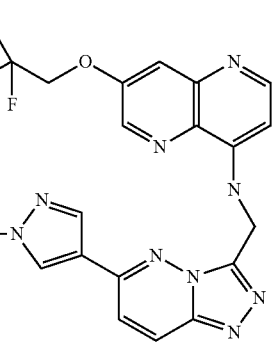 | 455 | 456 | D |
| 375 | 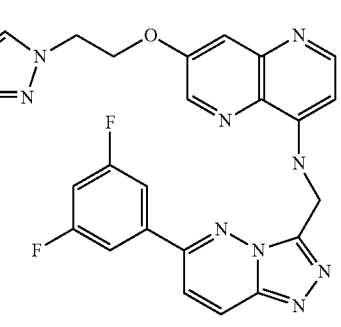 | 499 | 500 | D |
| 376 | 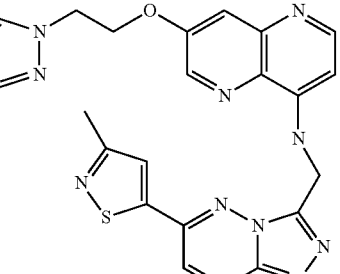 | 484 | 485 | D |

| EX. | Structure | MW | Mass Found | General Method |
|---|---|---|---|---|
| 377 | 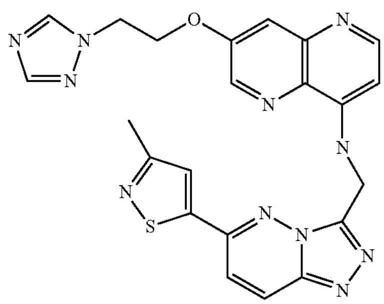 [SMILES: Cc1cc(-c2ccc3nnc(CNc4ccnc5cc(OCCn6cncn6)cnc45)n3n2)sn1] | 485 | 486 | D |
| 378 | 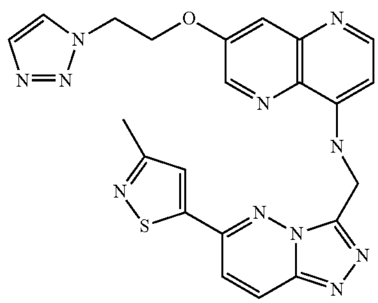 [SMILES: Cc1cc(-c2ccc3nnc(CNc4ccnc5cc(OCCn6ccnn6)cnc45)n3n2)sn1] | 485 | 485 | D |
| 379 | 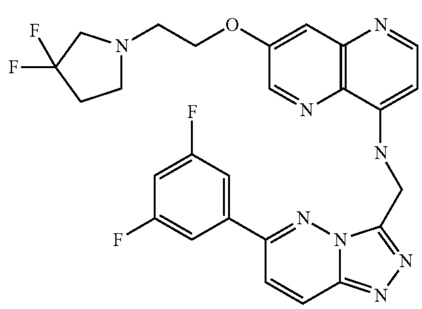 [SMILES: Fc1cc(F)cc(-c2ccc3nnc(CNc4ccnc5cc(OCCN6CCC(F)(F)C6)cnc45)n3n2)c1] | 538 | 539 | D |
| 380 | 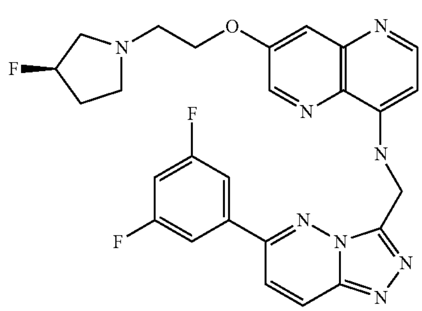 [SMILES: Fc1cc(F)cc(-c2ccc3nnc(CNc4ccnc5cc(OCCN6CC[C@@H](F)C6)cnc45)n3n2)c1] | 520 | 521 | D |
| 381 | 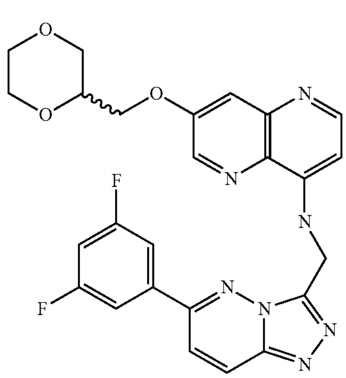 [SMILES: Fc1cc(F)cc(-c2ccc3nnc(CNc4ccnc5cc(OCC6COCCO6)cnc45)n3n2)c1] | 505 | 506 | D |

| EX. | Structure | MW | Mass Found | General Method |
|---|---|---|---|---|
| 382 | 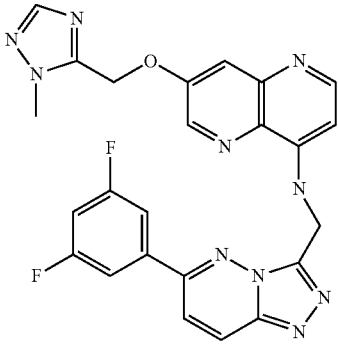 [SMILES: Cn1ncnc1COc1cnc2c(NCc3nnc4ccc(-c5cc(F)cc(F)c5)nn34)ccnc2c1] | 500 | 501 | D |
| 383 | 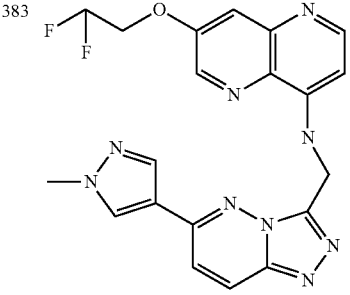 | 437 | 438 | D |
| 384 | 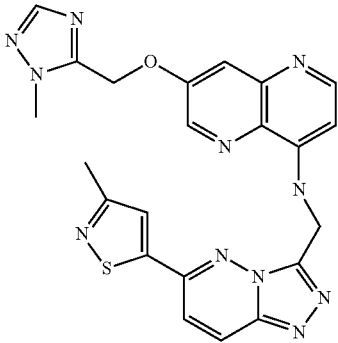 [SMILES: Cc1cc(-c2ccc3nnc(CNc4ccnc5cc(OCc6ncnn6C)cnc45)n3n2)sn1] | 485 | 486 | D |
| 385 | 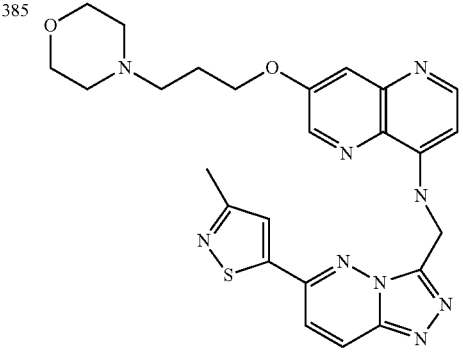 | 517 | 518 | D |

| EX. | Structure | MW | Mass Found | General Method |
|---|---|---|---|---|
| 386 | 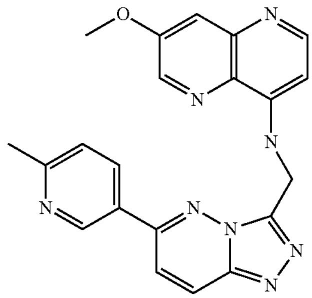 [SMILES: COc1cnc2c(NCc3nnc4ccc(-c5ccc(C)nc5)nn34)ccnc2c1] | 398 | 399 | D |
| 387 | 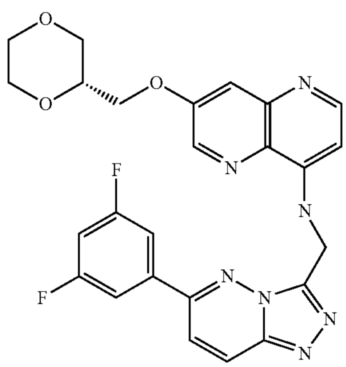 [SMILES: Fc1cc(F)cc(-c2ccc3nnc(CNc4ccnc5cc(OC[C@H]6COCCO6)cnc45)n3n2)c1] | 505 | 506 | D |
| 388 | 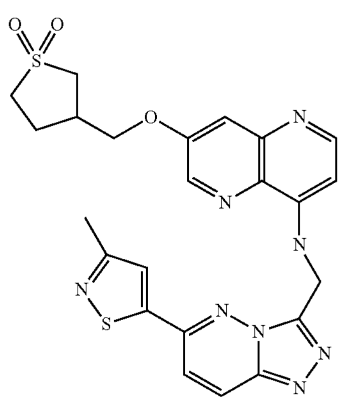 [SMILES: Cc1cc(-c2ccc3nnc(CNc4ccnc5cc(OCC6CCS(=O)(=O)C6)cnc45)n3n2)sn1] | 522 | 523 | D |
| 389 | 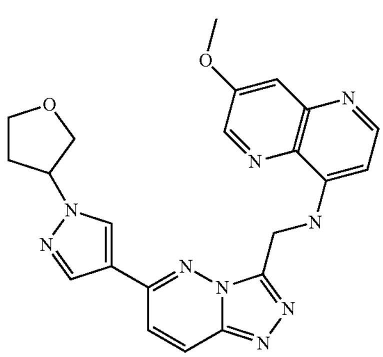 [SMILES: COc1cnc2c(NCc3nnc4ccc(-c5cnn(C6CCOC6)c5)nn34)ccnc2c1] | 443 | 444 | D |

-continued
| EX. | Structure | MW | Mass Found | General Method |
|---|---|---|---|---|
| 390 | 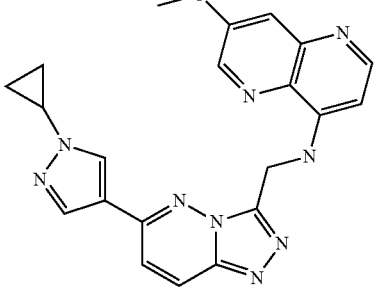 | 413 | 414 | D |
| 391 | 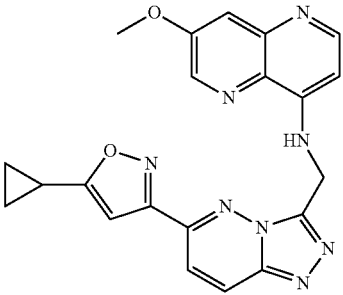 [SMILES: COc1cnc2c(NCc3nnc4ccc(-c5cc(C6CC6)on5)nn34)ccnc2c1] | 414 | 415 | D |
| 392 | 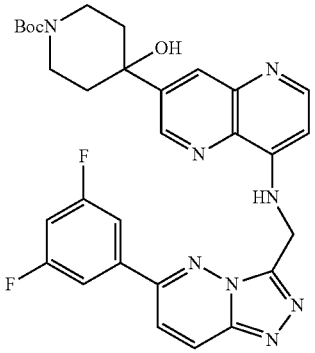 [SMILES: CC(C)(C)OC(=O)N1CCC(O)(c2cnc3c(NCc4nnc5ccc(-c6cc(F)cc(F)c6)nn45)ccnc3c2)CC1] | 488 | 489 | D |
| 393 | 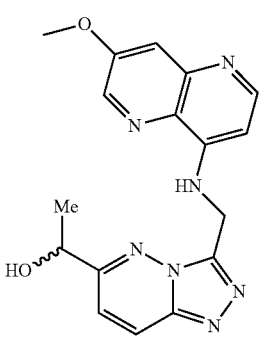 [SMILES: COc1cnc2c(NCc3nnc4ccc(C(C)O)nn34)ccnc2c1] | 351 | 352 | D |

| EX. | Structure | MW | Mass Found | General Method |
|---|---|---|---|---|
| 394 | 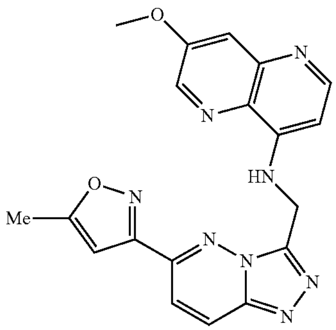 [SMILES: COc1cnc2c(NCc3nnc4ccc(-c5cc(C)on5)nn34)ccnc2c1] | 388 | 388 | D |
| 395 | 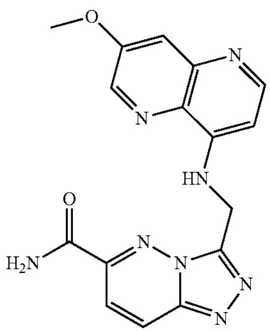 [SMILES: COc1cnc2c(NCc3nnc4ccc(C(N)=O)nn34)ccnc2c1] | 350 | 351 | D |
| 396 | 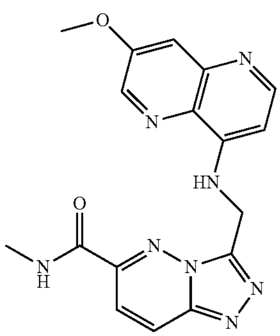 [SMILES: CNC(=O)c1ccc2nnc(CNc3ccnc4cc(OC)cnc34)n2n1] | 364 | 365 | D |
| 397 | 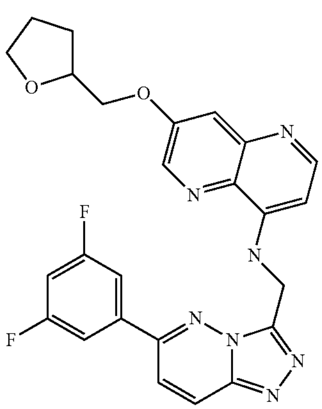 [SMILES: Fc1cc(F)cc(-c2ccc3nnc(CNc4ccnc5cc(OCC6CCCO6)cnc45)n3n2)c1] | 489 | 490 | D |

-continued
| EX. | Structure | MW | Mass Found | General Method |
|---|---|---|---|---|
| 398 | 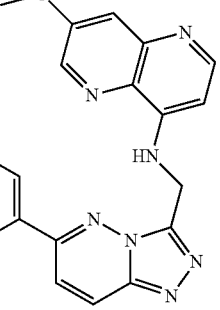 | 440 | 441 | D |
| 399 | 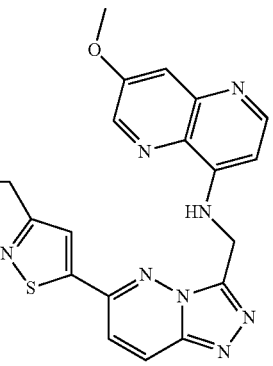 | 420 | 421 | D |
| 400 | 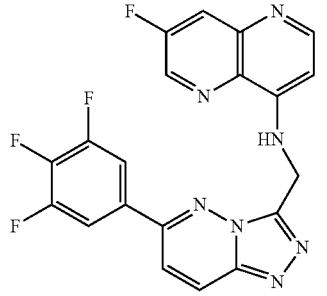 [SMILES: Fc1cnc2c(NCc3nnc4ccc(-c5cc(F)c(F)c(F)c5)nn34)ccnc2c1] | 425 | 426 | D |
| 401 | 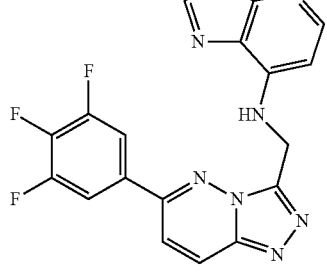 | 396 | 397 | D |

-continued

| EX. | Structure | MW | Mass Found | General Method |
|---|---|---|---|---|
| 402 | 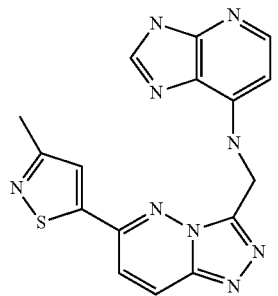 [SMILES: Cc1cc(-c2ccc3nnc(CNc4ccnc5[nH]cnc45)n3n2)sn1] | 363 | 364 | D |

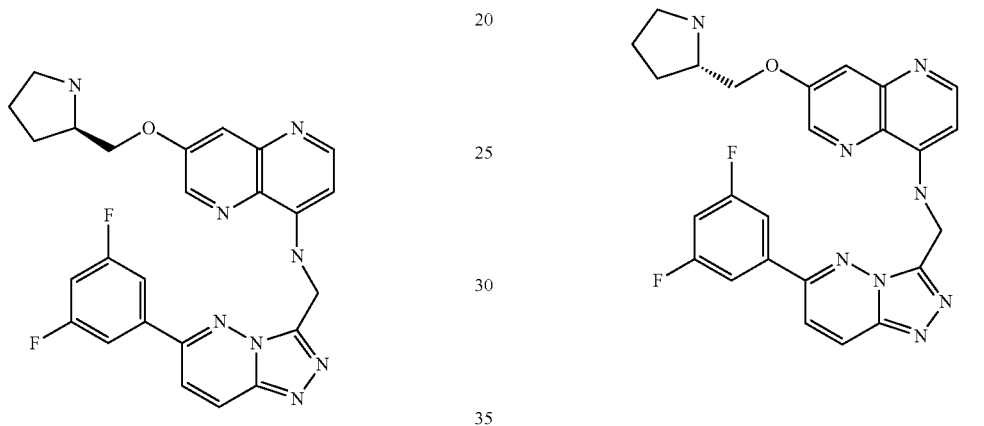

EXAMPLE 403

(R)—N-((6-(3,5-difluorophenyl)-[1,2,4]triazolo[4,3-b]pyridazin-3-yl)methyl)-7-(pyrrolidin-2-ylmethoxy)-1,5-naphthyridin-4-amine a) (R)-tert-butyl 2-((8-((6-((3,5-difluorophenyl)-[1,2,4]triazolo[4,3-b]pyridazin-3-yl)methylamino)-1,5-naphthyridin-3-yloxy)methyl)pyrrolidine-1-carboxylate was prepared according to method D.

b) (R)—N-(6-(3,5-difluorophenyl)-[1,2,4]triazolo[4,3-b]pyridazin-3-yl)methyl)-7-(pyrrolidin-2-ylmethoxy)-1,5-naphthyridin-4-amine. The title compound was prepared from (R)-tert-butyl 2-((8-((6-((3,5-difluorophenyl)-[1,2,4]triazolo[4,3-b]pyridazin-3-yl)methylamino)-1,5-naphthyridin-3-yloxy)methyl)pyrrolidine-1-carboxylate following the procedure used to make 7-methoxy-4-((6-(6-(piperazin-1-yl)pyridin-3-yl)-[1,2,4]triazolo[4,3-b]pyridazin-3-yl)methoxy)quinoline. m/z: 489 (M+H). Calc'd. for $C_{25}H_{22}F_2N_8O$—488.

EXAMPLE 404

(S)—N-((6-(3,5-difluorophenyl)-[1,2,4]triazolo[4,3-b]pyridazin-3-yl)methyl)-7-(pyrrolidin-2-ylmethoxy)-1,5-naphthyridin-4-amine The title compound was prepared in the same manner as (R)—N-((6-(3,5-difluorophenyl)-[1,2,4]triazolo[4,3-b]pyridazin-3-yl)methyl)-7-(pyrrolidin-2-ylmethoxy)-1,5-naphthyridin-4-amine m/z: 489 (M+H). Calc'd. for $C_{25}H_{22}F_2N_8O$—488.

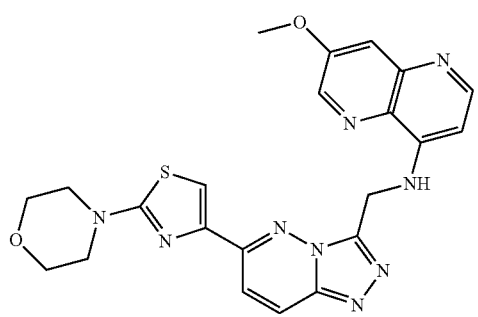 [SMILES: COc1cnc2c(NCc3nnc4ccc(-c5csc(N6CCOCC6)n5)nn34)ccnc2c1]

EXAMPLE 405

7-methoxy-N-((6-(2-morpholinothiazol-4-yl)-[1,2,4] triazolo[4,3-b]pyridazin-3-yl)methyl)-1,5-naphthyridin-4-amine 1) 4-(4-bromothiazol-2-yl)morpholine

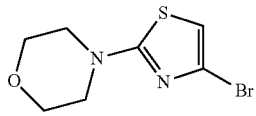

To a microwave vial was added N,N-diisopropylethylamine (0.86 ml, 4.9 mmol), 2,4-dibromothiazole (1.00 g, 4.1 mmol), and morpholine (0.43 ml, 4.9 mmol) in EtOH (4 mL). The mixture was heated under microwave irradiation at 140° C. for 35 minutes. The reaction mixture was concentrated in vacuo. The crude material was dissolved in minimal DCM/MeOH and purified via MPLC (eluting with 0-30% EtOAc in hexanes) to yield 4-(4-bromothiazol-2-yl)morpholine (0.700 g, 68% yield) as a white solid.

2) 4-(4-(trimethylstannyl)thiazol-2-yl)morpholine

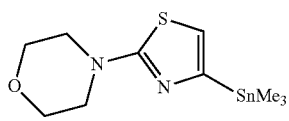

Prepared in a method similar to 3-methyl-5-trimethylstannyl)isothiazole.

3) Bis-tert-butyl(6-chloro-[1,2,4]-triazolo[4,3-b]pyridazin-3-yl)methylcarbamate

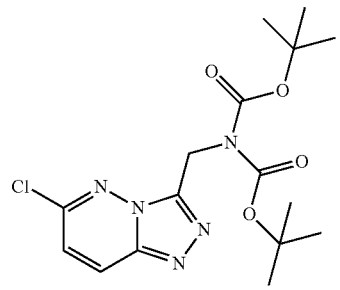 [SMILES: CC(C)(C)OC(=O)N(Cc1nnc2ccc(Cl)nn12)C(=O)OC(C)(C)C]

Di-tert-butyl dicarbonate (24.42 g, 111.9 mmol) was added to a stirred suspension of tert-butyl (6-chloro-[1,2,4]triazolo[4,3-b]pyridazin-3-yl)methylcarbamate (10.58 g, 37.3 mmol) in acetonitrile (200 mL) at 0° C. followed by 4-dimethylaminopyridine (4.556 g, 37.3 mmol). Stirring was continued at 0° C. for ~10 min then the cooling bath was removed and stirring was continued at room temperature overnight. The reaction mixture was concentrated in vacuo, diluted with EtOAc and washed with water. The organic layer was dried over MgSO₄, filtered and concentrated in vacuo. Purification via MPLC (EtOAc/MeOH: 100/0 to 90/10) afforded the title compound (14.3 g, 37.3 mmol, 100% yield).

4) (6-(2-morpholinothiazol-4-yl)-[1,2,4]-triazolo[4,3-b]pyridazin-3-yl)methyl di-tert-butyl carbamate

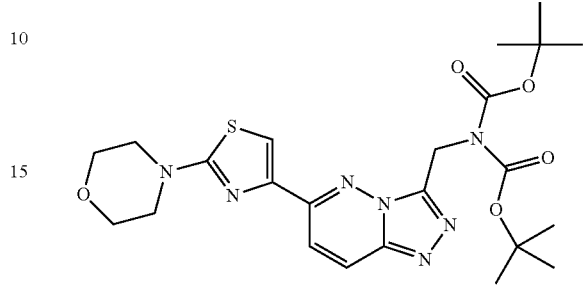

To a pressure vessel purged with argon was added palladium (II) acetate (0.0029 g, 0.013 mmol), Xantphos (0.015 g, 0.026 mmol) and bis-tert-butyl(6-chloro-[1,2,4]triazolo[4,3-b]pyridazin-3-yl)methylcarbamate (0.100 g, 0.26 mmol) in 1,4-dioxane (0.17 M, 1.5 mL). 4-(4-(trimethylstannyl)thiazol-2-yl)morpholine (0.13 g, 0.39 mmol) and degassed water (0.0094 ml, 0.52 mmol) were added, once more purging the flask with argon. The reaction mixture was stirred at 100° C. for 4 h until complete consumption of the starting material. The reaction mixture was concentrated in vacuo. The crude material was dissolved in minimal EtOAc and purified via MPLC (eluting with 100% EtOAc). (6-(2-morpholinothiazol-4-yl)-[1,2,4]triazolo[4,3-b]pyridazin-3-yl)methyl di-tert-butyl carbamate (0.086 g, 64% yield) was obtained as a solid. The material was carried forward without further purification.

5) 7-methoxy-N-((6-(2-morpholinothiazol-4-yl)-[1,2,4]triazolo[4,3-b]pyridazin-3-yl)methyl)-1,5-naphthyridin-4-amine

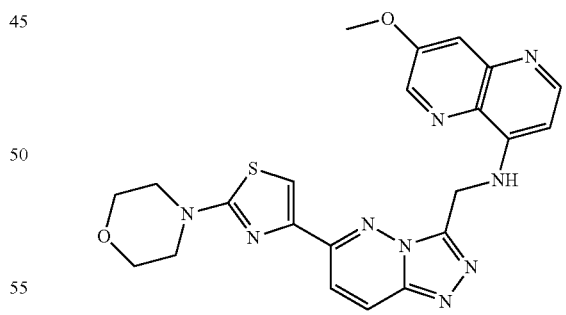

To a microwave vial was added (6-(2-morpholinothiazol-4-yl)-[1,2,4]triazolo[4,3-b]pyridazin-3-yl)methyl di-tert-butyl carbamate (0.086 g, 0.17 mmol) and 8-chloro-3-methoxy-1,5-naphthyridine (0.036 g, 0.18 mmol) in 2-butanol (1.0 mL). The vial was sealed and heated under microwave irradiation at 120° C. for 6 h. The reaction was concentrated in vacuo. The crude material was dissolved in 2M ammonia in methanol and purified via MPLC (eluting with 0-10% 1% NH₄OH/in DCM). 7-methoxy-N-((6-(2-morpholinothiazol-4-yl)-[1,2,4]triazolo[4,3-b]pyridazin-3-yl)methyl)-1,5- naphthyridin-4-amine (0.031 g, 39% yield) was obtained as a yellow solid. m/z: 476.0 (M+H). Calc'd. for $C_{22}H_{21}N_9O_2S$—475.53.

The following example compounds 406 and 407 were prepared using the method to make 7-methoxy-N-((6-(2-morpholinothiazol-4-yl)-[1,2,4]triazolo[4,3-b]pyridazin-3-yl)methyl)-1,5-naphthyridin-4-amine:

| Ex | Structure | MW | Mass Found |
|----|-----------|----|----|
| 406 | 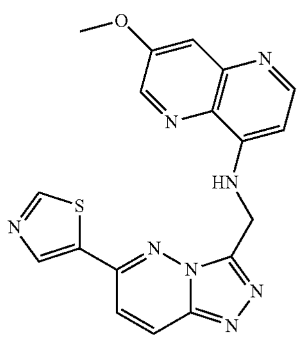 [SMILES: COc1cnc2c(NCc3nnc4ccc(-c5cncs5)nn34)ccnc2c1] | 390 | 391 |
| 407 | 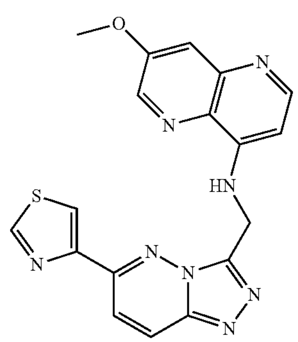 [SMILES: COc1cnc2c(NCc3nnc4ccc(-c5cscn5)nn34)ccnc2c1] | 390 | 391 |

The following example compounds 408-428 were prepared using steps 1 and 2 of Method A. Where applicable, enantiomer was obtained via SFC:

| Ex | Structure | MW | Mass Found |
|----|-----------|----|----|
| 408 | | 389 | 390 |
| 409 | 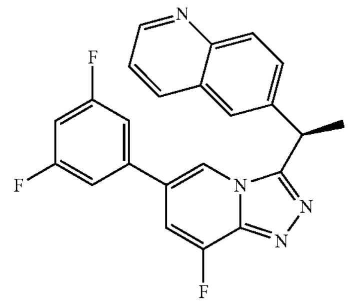 [SMILES: C[C@H](c1ccc2ncccc2c1)c1nnc2c(F)cc(-c3cc(F)cc(F)c3)cn12] | 404 | 405 |
| 410 | 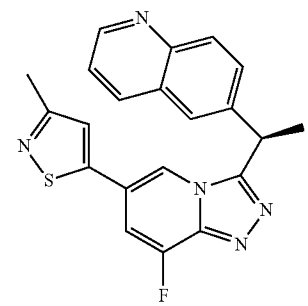 | 389 | 389 |
| 411 | 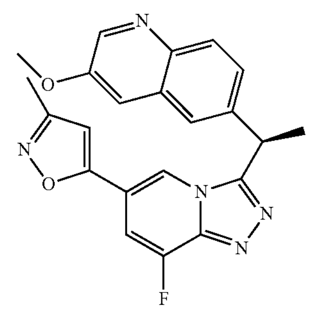 [SMILES: COc1cnc2ccc([C@@H](C)c3nnc4c(F)cc(-c5cc(C)no5)cn34)cc2c1] | 403 | 404 |
| 412 | 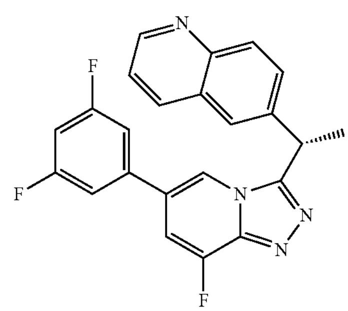 [SMILES: C[C@@H](c1ccc2ncccc2c1)c1nnc2c(F)cc(-c3cc(F)cc(F)c3)cn12] | 404 | 405 |
| 413 | 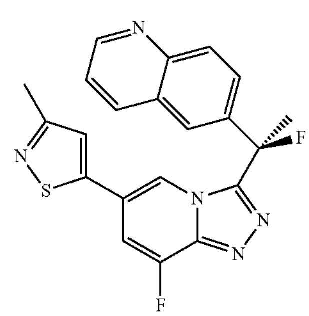 [SMILES: Cc1cc(-c2cc(F)c3nnc([C@](C)(F)c4ccc5ncccc5c4)n3c2)sn1] | 407 | 408 |

-continued

| Ex | Structure | MW | Mass Found |
|---|---|---|---|
| 414 | 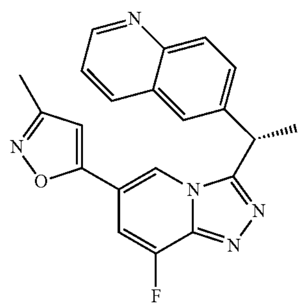 | 373 | 374 |
| 415 | 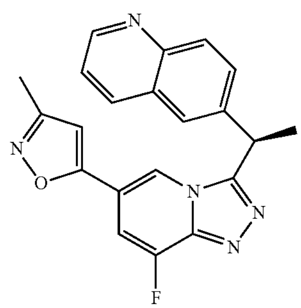 [SMILES: Cc1cc(-c2cc(F)c3nnc([C@H](C)c4ccc5ncccc5c4)n3c2)on1] | 373 | 374 |
| 416 | 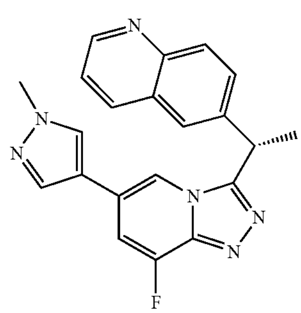 [SMILES: C[C@@H](c1ccc2ncccc2c1)c1nnc2c(F)cc(-c3cnn(C)c3)cn12] | 372 | 373 |
| 417 | 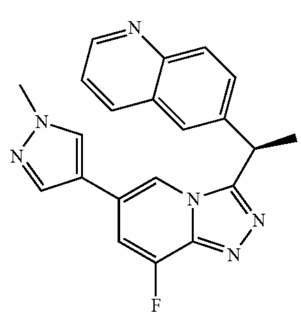 [SMILES: C[C@H](c1ccc2ncccc2c1)c1nnc2c(F)cc(-c3cnn(C)c3)cn12] | 372 | 373 |

-continued

| Ex | Structure | MW | Mass Found |
|---|---|---|---|
| 418 | 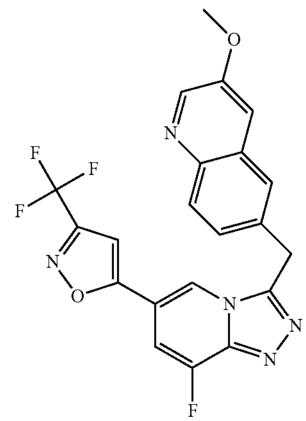 [SMILES: COc1cnc2ccc(Cc3nnc4c(F)cc(-c5cc(C(F)(F)F)no5)cn34)cc2c1] | 443 | 444 |
| 419 | 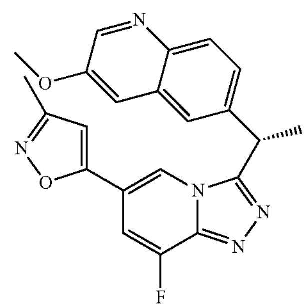 [SMILES: COc1cnc2ccc([C@H](C)c3nnc4c(F)cc(-c5cc(C)no5)cn34)cc2c1] | 403 | 404 |
| 420 | 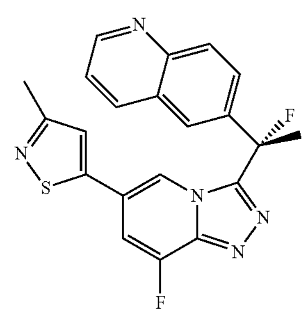 [SMILES: Cc1cc(-c2cc(F)c3nnc([C@@](C)(F)c4ccc5ncccc5c4)n3c2)sn1] | 407 | 408 |
| 421 | 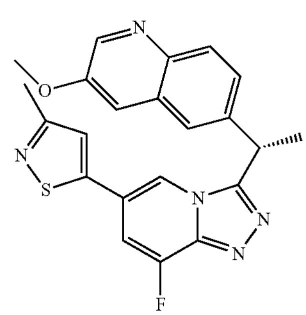 | 419 | 420 |

-continued

| Ex | Structure | MW | Mass Found |
|---|---|---|---|
| 422 | 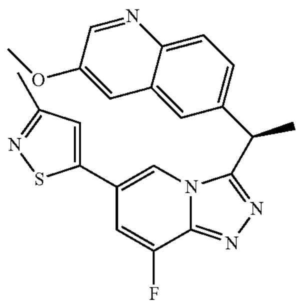 [SMILES: COc1cnc2ccc([C@@H](C)c3nnc4c(F)cc(-c5cc(C)ns5)cn34)cc2c1] | 419 | 420 |
| 423 | 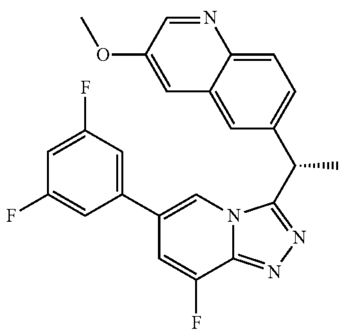 [SMILES: COc1cnc2ccc([C@H](C)c3nnc4c(F)cc(-c5cc(F)cc(F)c5)cn34)cc2c1] | 434 | 435 |
| 424 | 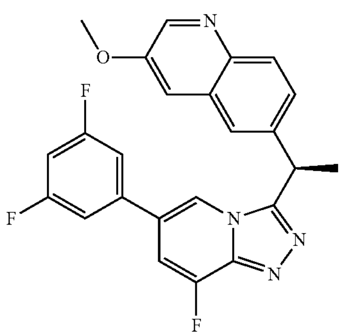 [SMILES: COc1cnc2ccc([C@@H](C)c3nnc4c(F)cc(-c5cc(F)cc(F)c5)cn34)cc2c1] | 434 | 435 |
| 425 | 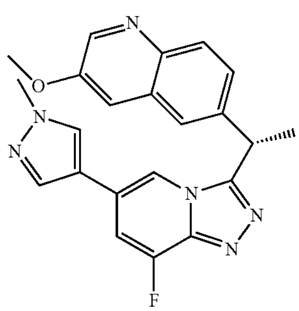 [SMILES: COc1cnc2ccc([C@H](C)c3nnc4c(F)cc(-c5cnn(C)c5)cn34)cc2c1] | 402 | 403 |
| 426 | 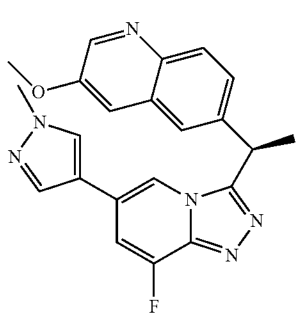 [SMILES: COc1cnc2ccc([C@@H](C)c3nnc4c(F)cc(-c5cnn(C)c5)cn34)cc2c1] | 402 | 403 |
| 427 | | 422 | 423 |
| 428 | | 422 | 423 |

1-(3-fluoro-5-(3-methylisothiazol-5-yl)pyridin-2-yl)hydrazine 5-chloro-2,3-difluoropyridine (0.069 ml, 0.67 mmol), X-Phos (0.045 g, 0.094 mmol) and palladium (II) acetate (0.011 g, 0.047 mmol) were combined in 1,4-dioxane (0.2 M, 3.4 mL). To the reaction vessel was added 3-methyl-5-(trimethylstannyl)isothiazole (0.53 g, 2.0 mmol) and, after purging with argon, the reaction was stirred at 100° C. for 2 h and then concentrated in vacuo. The crude material was dissolved in minimal DCM and purified via MPLC (eluting first with 100% EtOAc followed by 20% EtOAc in hexanes-isocratic) to yield 2,3-difluoro-5-(3-methylisothiazol-5-yl)pyridine (0.139 g, 98% yield) as a yellow solid. 2,3-difluoro-5-(3-methylisothiazol-5-yl)pyridine was converted to the title compound using a procedure similar to 1-(4-methyl-6-phenylpyridazin-3-yl)hydrazine.

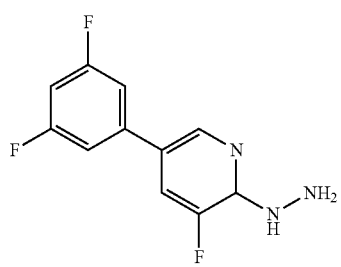 [SMILES: NNC1NC=C(c2cc(F)cc(F)c2)C=C1F]

1-(5-(3,5-difluorophenyl)-3-fluoropyridin-2-yl)hydrazine

A mixture of palladium (II) acetate (0.0375 g, 0.167 mmol), potassium phosphate (2.13 g, 10.0 mmol), 3,5-difluorophenylboronic acid (1.58 g, 10.0 mmol), X-Phos (0.159 g, 0.334 mmol) and 5-chloro-2,3-difluoropyridine (0.347 ml, 3.34 mmol) was diluted with 1,4-dioxane (0.1M, 33.4 mL) and water (0.3M, 11.0 mL) and was heated under nitrogen at 100° C. for 45 minutes. The reaction was concentrated in vacuo. The concentrated material was triturated with water, filtered and rinsed with MeCN. The crude solid was taken up in dichloromethane and filtered over a plug of Celite to eliminate residual palladium. The material was dissolved in minimal DCM, and purified via MPLC (eluting with 0-10% EtOAc in hexanes) to yield 5-(3,5-difluorophenyl)-2,3-difluoropyridine. The material was converted to the hydrazine in a method similar to that in the synthesis of (S)-6-(1-(8-fluoro-6-(3-methylisothiazol-5-yl)-[1,2,4]triazolo[4,3-α]pyridin-3-yl)ethyl)quinoline.

The following compounds were prepared using a similar method as 1-(5-(3,5-difluorophenyl)-3-fluoropyridin-2-yl) hydrazine:

1) 1-(3-fluoro-5-(1-methyl-1H-pyrazol-4-yl)pyridin-2-yl)hydrazin

The following compounds were prepared using a similar method (using either the trimethyl- or tributyl-stannnane) as 1-(3-fluoro-5-(3-methylisothiazol-5-yl)pyridin-2-yl)hydrazine:
1-(3-fluoro-5-(3-methylisoxazol-5-yl)pyridin-2-yl)hydrazine; and
1-(3-fluoro-5-(3-trifluoromethylisoxazol-5-yl)pyridin-2-yl) hydrazine.

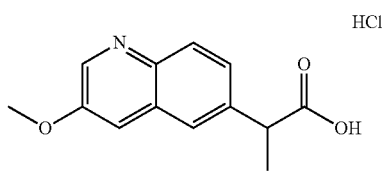 [SMILES: Cl ; COc1cnc2ccc(C(C)C(=O)O)cc2c1]

2-(3-methoxyquinolin-6-yl)propanoic acid hydrochloride

Tert-butyl 2-(3-methoxyquinolin-6-yl)propanoate (0.865 g, 3.01 mmol) was dissolved in EtOAc (0.2M, 15 mL), and HCl (g) (0.0915 ml, 3.01 mmol) was bubbled through the solution for approximately 5 minutes. The reaction vessel was sealed and the reaction was stirred at room temperature for 1.5 h until completion. The reaction mixture was concentrated in vacuo to yield 2-(3-methoxyquinolin-6-yl)propanoic acid hydrochloride (0.805 g, 99.9% yield) as an orange solid.

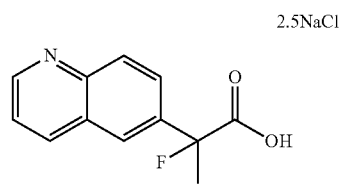 [SMILES: CC(F)(C(=O)O)c1ccc2ncccc2c1]

2-fluoro-2-(quinolin-6-yl)propanoic acid

To a solution of methyl 2-(quinolin-6-yl)propanoate (0.868 g, 4.03 mmol) in THF (1.1M, 3.7 mL) at −78° C. was added LiHMDS (1M in THF) (5.24 ml, 5.24 mmol). The reaction was stirred at −78° C. for ~15 minutes, then to it was added a solution of N-fluorobenzenesulfonimide (1.40 g, 4.44 mmol) in THF (1.0M, 4.5 mL). The reaction was allowed to warm to −10° C. over 2 h. The reaction was filtered through a plug of Celite, washed with EtOAc and the filtrate was then concentrated in vacuo. The concentrated material was rediluted with EtOAc and washed with saturated NH4Cl solution. The aqueous layer was then extracted with EtOAc, and the organic layers were dried over MgSO4, filtered and concentrated in vacuo. The crude material was dissolved in minimal DCM and purified via MPLC (eluting with isocratic 40% EtOAc:Hexanes to yield methyl 2-fluoro-2-(quinolin-6-yl) propanoate (0.709 g, 75.4% yield) as a yellow oil. To synthesize the corresponding acid, methyl 2-fluoro-2-(quinolin-6-yl)propanoate was saponified in a method similar to that of 2-(quinolin-6-yl)propanoic acid.

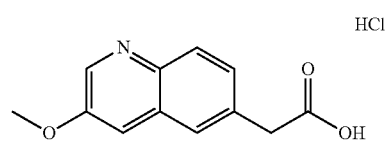 [SMILES: Cl ; COc1cnc2ccc(CC(=O)O)cc2c1]

2-(3-methoxyquinolin-6-yl)acetic acid hydrochloride tert-Butyl 2-(3-methoxyquinolin-6-yl)acetate was saponified in a method similar to 2-(3-methoxyquinolin-6-yl)propanoic acid hydrochloride.

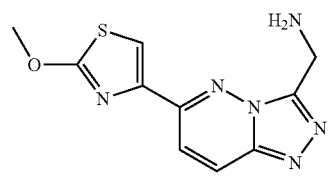 [SMILES: COc1nc(-c2ccc3nnc(CN)n3n2)cs1]

(6-(2-methoxythiazol-4-yl)-[1,2,4]-triazolo[4,3-b]pyridazin-3-yl)methanamine

The di-tert-butyl carbonate precursor ((6-(2-methoxy-4-yl)-[1,2,4]triazolo[4,3-b]pyridazin-3-yl)methyl di-tert-butyl carbamate) was synthesized in a method similar to (6-(2- morpholinothiazol-4-yl)-[1,2,4]triazolo[4,3-b]pyridazin-3-yl)methyl di-tert-butyl carbamate, using 2-methoxy-4-(tributylstannyl)thiazole as the organostannane, followed by TFA deprotection similar to the method described for (6-(3-methylisothiazol-5-yl)-[1,2,4]triazolo[4,3-b]pyridazin-3-yl)methanamine.

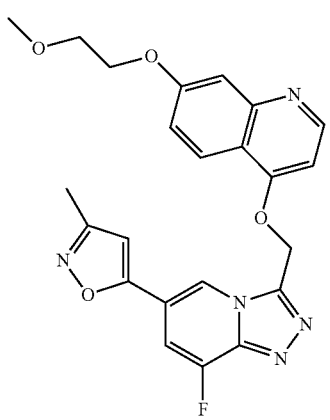 [SMILES: COCCOc1ccc2c(OCc3nnc4c(F)cc(-c5cc(C)no5)cn34)ccnc2c1]

EXAMPLE 429

4-((8-fluoro-6-(3-methylisoxazol-5-yl)-[1,2,4]triazolo[4,3-a]pyridin-3-yl)methoxy)-7-(2-methoxyethoxy)quinoline 1) 2-(7-hydroxyquinolin-4-yloxy)acetic acid hydrobromide

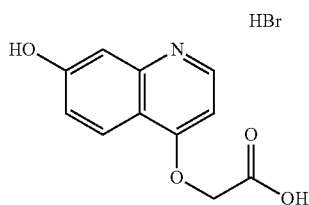 [SMILES: Br ; O=C(O)COc1ccnc2cc(O)ccc12]

To a pressure vial was added 2-(7-methoxyquinolin-4-yloxy)acetic acid (1.00 g, 4.29 mmol) in DCE (0.6 M, 7 mL). The vial was cooled in an ice bath and to the solution was added BBr$_3$ (1.62 ml, 17.2 mmol). The reaction was allowed to warm to room temperature and stirred overnight. While some starting material remained, the reaction was stopped and diluted with DCM (keep in hood due to fuming). The solids were filtered and dried over high vacuum to yield a light brown crude solid (~1.8 g). The material was used without further purification.

2) 4-((8-fluoro-6-(3-methylisoxazol-5-yl)-[1,2,4]triazolo[4,3-a]pyridin-3-yl)methoxy)quinolin-7-ol

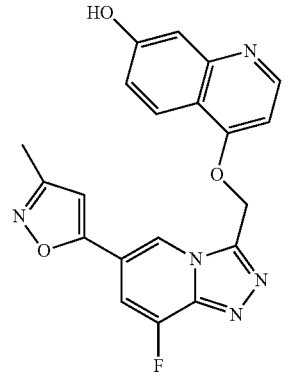 [SMILES: Cc1cc(-c2cc(F)c3nnc(COc4ccnc5cc(O)ccc45)n3c2)on1]

The material was prepared using general method A (with 2-(7-hydroxyquinolin-4-yloxy)acetic acid hydrobromide and 1-(3-fluoro-5-(3-methylisoxazol-5-yl)pyridin-2-yl)hydrazine 3) 4-((8-fluoro-6-(3-methylisoxazol-5-yl)-[1,2,4]triazolo[4,3-a]pyridin-3-yl)methoxy)-7-(2-methoxyethoxy)quinoline

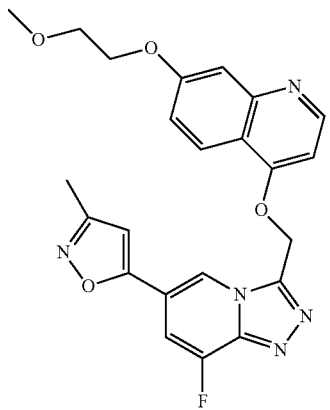 [SMILES: COCCOc1ccc2c(OCc3nnc4c(F)cc(-c5cc(C)no5)cn34)ccnc2c1]

4-((8-fluoro-6-(3-methylisoxazol-5-yl)-[1,2,4]triazolo[4,3-a]pyridin-3-yl)methoxy)quinolin-7-ol (0.110 g, 0.28 mmol), PPh$_3$ (polymer supported: 2.3 mmol/g) (1.2 g, 2.8 mmol) and 2-methoxyethanol (0.11 ml, 1.3 mmol) were combined in DCM (11 ml, 0.28 mmol). The mixture was cooled to 0° C., and DEAD (0.089 ml, 0.56 mmol) was added dropwise. The reaction was removed from the ice bath, and stirred at RT for 1 h. The material was diluted with DCM, and the PS-PPh$_3$ was filtered off and washed thoroughly with DCM. The filtrate was concentrated in vacuo. The crude material was dissolved in minimal DCM and purified via MPLC (eluting with 0-100% 90:10:1 DCM:MeOH:NH$_4$OH in DCM) to yield 4-((8-fluoro-6-(3-methylisoxazol-5-yl)-[1,2,4]triazolo[4,3-a]pyridin-3-yl)methoxy)-7-(2-methoxyethoxy)quinoline (0.070 g, 55% yield) as a white solid. MS (ESI pos. ion) m/z: 450.0 (M+H). Calc'd Exact Mass for $C_{23}H_{20}FN_5O_4$: 449.44

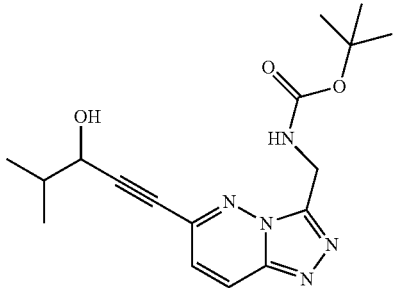 [SMILES: CC(C)C(O)C#Cc1ccc2nnc(CNC(=O)OC(C)(C)C)n2n1]

tert-Butyl (6-(3-hydroxy-4-methylpent-1-ynyl)-[1,2,4]-triazolo[4,3-b]pyridazin-3-yl)methylcarbamate In a 15-mL sealed tube flushed with nitrogen, tert-butyl (6-chloro-[1,2,4]triazolo[4,3-b]pyridazin-3-yl)methylcarbamate (2.00 g, 7.0 mmol), $PdCl_2$(dppf)-$CH_2Cl_2$ adduct (0.58 g, 0.70 mmol), and copper (I) iodide (0.34 g, 1.8 mmol) were diluted in MeCN (70 mL). To the reaction mixture was first added 4-methylpent-1-yn-3-ol (3.7 ml, 35 mmol), followed by triethylamine (25 ml, 176 mmol). The reaction was then heated at 50° C. for 7.5 h. The crude material was dissolved in minimal DCM and purified via MPLC (twice) (eluting with 0-10% MeOH/$NH_4OH$:DCM) to yield tert-butyl (6-(3-hydroxy-4-methylpent-1-ynyl)-[1,2,4]triazolo[4,3-b]pyridazin-3-yl)methylcarbamate (1.823 g, 75% yield) as a light brown solid.

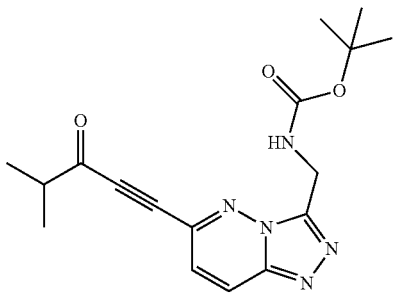 [SMILES: CC(C)C(=O)C#Cc1ccc2nnc(CNC(=O)OC(C)(C)C)n2n1]

tert-Butyl (6-(4-methyl-3-oxopent-1-ynyl)-1,2,41 triazolo[4,3-b]pyridazin-3-yl)methylcarbamate tert-Butyl (6-(3-hydroxy-4-methylpent-1-ynyl)-[1,2,4] triazolo[4,3-b]pyridazin-3-yl)methylcarbamate (1.82 g, 5.27 mmol) and manganese dioxide (activated) (9.16 g, 105 mmol) were dissolved in DCM (263 mL) and stirred at room temperature over two days. Additional manganese dioxide (activated) (4.58 g, 52.7 mmol) was added and stirring continued overnight. The reaction mixture was filtered over a plug of Celite and washed with DCM to yield tert-butyl (6-(4-methyl-3-oxopent-1-ynyl)-[1,2,4]triazolo[4,3-b]pyridazin-3-yl)methylcarbamate (0.917 g, 50.7% yield) after concentration in vacuo.

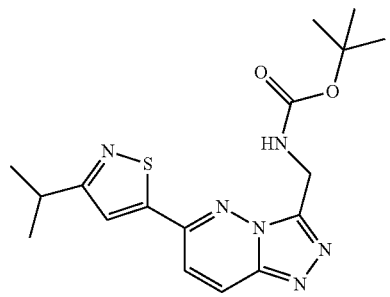 [SMILES: CC(C)c1cc(-c2ccc3nnc(CNC(=O)OC(C)(C)C)n3n2)sn1]

tert-Butyl (6-(3-isopropylisothiazol-5-O-[1,2,4]triazolo[4,3-b]pyridazin-3-yl)methylcarbamate An aqueous mixture of tert-butyl (6-(4-methyl-3-oxopent-1-ynyl)-[1,2,4]triazolo[4,3-b]pyridazin-3-yl)methylcarbamate (0.800 g, 2.33 mmol) and hydroxylamine-O-sulfonic acid (0.263 g, 2.33 mol) in water (8.0 mL) and 1,4-dioxane (8.0 mL) was stirred at 0° C. until complete consumption of the organic starting material was observed. The mixture was then carefully treated with solid sodium bicarbonate (0.196 g, 2.33 mmol), followed by treatment with 1.4 M aqueous sodium hydrosulfide (1.83 ml, 2.56 mmol). The reaction was stirred at room temperature overnight. The reaction mixture was diluted with water (20 mL) and extracted with DCM (40 mL), dried over sodium sulfate, filtered and concentrated in vacuo. The concentrated crude material was dissolved in minimal DCM and was purified via MPLC (eluting with 0-10% MeOH/$NH_4OH$ in DCM) to yield tert-butyl (6-(3-isopropylisothiazol-5-yl)-[1,2,4]triazolo[4,3-b]pyridazin-3-yl)methylcarbamate (0.196 g, 22.5% yield) with 82% purity. MS (ESI pos. ion) m/z: 433.0 (M+H). Calc'd Exact Mass for $C_{21}H_{20}N_8OS$: 432.51.

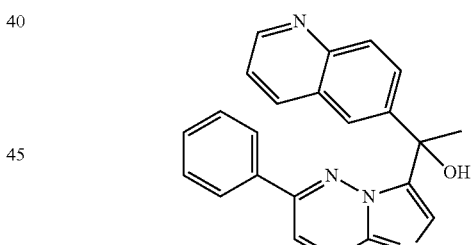

EXAMPLE 430

1-(6-Phenylimidazo[1,2-b]pyridazin-3-yl)-1-(quinolin-6-yl)ethanol a) N-methoxy-N-methylquinoline-6-carboxamide A 250 mL RB flask was charged with quinoline-6-carboxylic acid (5.00 g, 28.9 mmol), DCM (100 ml, 1554 mmol), oxalyl chloride (3.79 ml, 43.3 mmol), and a few drops of DMF and stirred at RT for 2 hours, then concentrated. The residue was taken up in DCM (100 ml, 1554 mmol), cooled to 0° C., then Hunig's Base (17.7 ml, 101 mmol) and N-methoxymethanamine hydrochloride (2.96 g, 30.3 mmol) were added slowly. The mixture was stirred at room temperature for 16 hours (91463-3-1). The mixture was diluted with DCM (200 mL), then washed with water (250 mL), sat. NaHCO₃ (250 mL), and brine (250 mL). The organic layer was dried with MgSO₄, filtered, and concentrated to give a brown oil, which was purified by MPLC eluting with 2-6% MeOH/DCM to give N-methoxy-N-methylquinoline-6-carboxamide (5.943 g, 95.2% yield) as a brown oil.

b) 1-(quinolin-6-yl)ethanone

A 250 mL RB flask was charged with N-methoxy-N-methylquinoline-6-carboxamide (5.943 g, 27.5 mmol) and THF (100 ml, 1220 mmol), then cooled to 0 C. Methylmagnesium bromide (18.3 ml, 55.0 mmol) was added dropwise and the mixture was allowed to warm to room temperature and stirred for 3 hours. The reaction was not quite complete, so additional MeMgBr (3 mL) was added and the mixture was stirred overnight. The mixture was then neutralized using 2N HCl and the aqueous layer was extracted with DCM (200 mL×2) and EtOAc (200 mL×2). The organic layer was dried with MgSO₄, filtered, and concentrated to give a yellow oil. The aqueous layer contained some product, so the layer was concentrated and then filtered thru a reverse phase C₁₈ column, first eluting with water than with MeOH. The MeOH layer was concentrated to give a yellow oil which was combined with the yellow oil from the organic layer. The combined portions were purified by MPLC eluting with a gradient of 2-6% MeOH/DCM. 1-(quinolin-6-yl)ethanone (4.074 g, 86.6% yield) was isolated as a yellow oil which solidified upon standing.

c) 2-bromo-1-(quinolin-6-yl)ethanone hydrobromide

A 250 mL RB flask was charged with 1-(quinolin-6-yl)ethanone (3.82 g, 22.3 mmol) and 30% HBr/AcOH (45.0 ml). Bromine (1.14 ml, 22.1 mmol) was added slowly. This was stirred at room temperature for 4 hours, at which point full conversion to product (with a small amount of dibrominated side product) was observed. The reaction mixture was filtered and the solid was washed with Et₂O to give 2-bromo-1-(quinolin-6-yl)ethanone hydrobromide (5.6359 g, 76.3% yield). The compound was used in the next step without further purification.

d) (E)-N'-(6-chloropyridazin-3-yl)-N,N-dimethylformamidine

A 500 mL RB flask was charged with 6-chloropyridazin-3-amine (10.0 g, 77.2 mmol) and dimethoxy-N,N-dimethylmethanamine (206 ml, 1544 mmol), equipped with a reflux condenser, then heated to 110° C. for 3 hours then left at room temperature for 16 hours. The precipitate was collected by filtration. The mother liqour was concentrated down to give an yellow solid, which was triturated with EtOAc and collected. The solids were combined to give (E)-N'-(6-chloropyridazin-3-yl)-N,N-dimethylformamidine (11.81 g, 82.9% yield) as a white solid e) (6-Chloroimidazo[1,2-b]pyridazin-3-yl)(quinolin-6-yl)methanone A 100 mL RB flask was charged with 2-bromo-1-(quinolin-6-yl)ethanone (0.7011 g, 2.80 mmol), (E)-N'-(6-chloropyridazin-3-yl)-N,N-dimethylformamidine (0.518 g, 2.80 mmol), and DMF (10.0 ml, 129 mmol), equipped with a reflux condenser, then heated at 105° C. for 3 hours. The reaction mixture was concentrated, then triturated with MeOH to yield (6-chloroimidazo[1,2-b]pyridazin-3-yl)(quinolin-6-yl)methanone (0.530 g, 1.72 mmol, 61%) as a brown solid.

f) (6-Phenylimidazo[1,2-b]pyridazin-3-yl)(quinolin-6-yl)methanone

A 48 mL sealed tube was charged with (6-chloroimidazo[1,2-b]pyridazin-3-yl)(quinolin-6-yl)methanone (0.530 g, 1.72 mmol), phenylboronic acid (0.314 g, 2.58 mmol), cesium carbonate (1.68 g, 5.15 mmol), PdCl₂(dppf)-CH₂Cl₂ adduct (0.0701 g, 0.0858 mmol), 1,4-dioxane (6.31 ml, 73.8 mmol), and water (1.11 ml, 61.8 mmol), flushed with argon, sealed, then placed in an 80° C. oil bath for 8 hours. The mixture was concentrated then triturated with water, followed by MeOH/DCM to give (6-phenylimidazo[1,2-b]pyridazin-3-yl)(quinolin-6-yl)methanone as a reddish brown solid.

g) 1-(6-Phenylimidazo[1,2-b]pyridazin-3-yl)-1-(quinolin-6-yl)ethanol

A 25 mL RB flask was charged with (6-phenylimidazo[1,2-b]pyridazin-3-yl)(quinolin-6-yl)methanone (0.200 g, 0.57 mmol) and THF (2.00 ml, 24 mmol), then cooled to 0° C. methylmagnesium bromide (0.76 ml, 2.2 mmol) was added dropwise and the mixture was stirred at room temperature for 5 hours. This was diluted with 2 N HCl (1 mL) and water (25 mL), then extracted with DCM (25 mL×2) and EtOAc (25 mL). The combined organics were washed with brine and dried with MgSO₄, filtered, and concentrated. The resulting oil was purified by MPLC using a 40 g RediSep column, eluting with 2-6% MeOH/DCM over 40 minutes. 1-(6-phenylimidazo[1,2-b]pyridazin-3-yl)-1-(quinolin-6-yl)ethanol (0.082 g, 39% yield) was isolated as a tan solid. MS (ESI pos. ion) m/z: 367 (MH+). Calc'd exact mass for $C_{23}H_{18}N_4O$: 366.

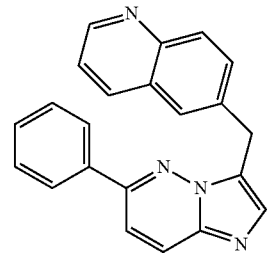 [SMILES: c1ccc(-c2ccc3ncc(Cc4ccc5ncccc5c4)n3n2)cc1]

EXAMPLE 431

6-((6-Phenylimidazo[1,2-b]pyridazin-3-yl)methyl)quinoline

A 10-20 mL microwave vial was charged with hydrazine hydrate (0.0312 ml, 0.642 mmol), (6-phenylimidazo[1,2-b]pyridazin-3-yl)(quinolin-6-yl)methanone (0.150 g, 0.428 mmol), KOH (0.0961 g, 1.71 mmol), and diethylene glycol (4.09 ml, 42.8 mmol), sealed, then placed in a Personal Chemistry microwave at 130° C. for 20 minutes after a 5 minute pre-stir. The mixture was diluted with water (75 mL), then extracted with DCM (2×75 mL). The combined organics were washed with brine (75 mL), then dried with MgSO₄, filtered, and concentrated to give a brown solid, then purified by prep HPLC to give the product as the formic acid salt. MS (ESI pos. ion) m/z: 337 (MH+). Calc'd exact mass for $C_{22}H_{16}N_4$: 336.

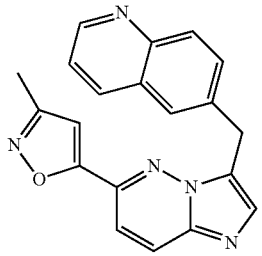 [SMILES: Cc1cc(-c2ccc3ncc(Cc4ccc5ncccc5c4)n3n2)on1]

EXAMPLE 432

6-((6-(3-Methylisoxazol-5-yl)imidazo[1,2-b]pyridazin-3-yl)methyl)quinoline

A 16 mm test tube was charged with hydrazine hydrate (0.0273 ml, 0.563 mmol), (6-(3-methylisoxazol-5-yl)imidazo[1,2-b]pyridazin-3-yl)(quinolin-6-yl)methanone (prepared using a similar procedure as (6-phenylimidazo[1,2-b]pyridazin-3-yl)(quinolin-6-yl)methanone) (0.100 g, 0.281 mmol), sodium tert-butoxide (0.0406 g, 0.422 mmol), and 1-butanol (0.670 ml, 7.32 mmol), sealed, then heated to 150° C. for 2 hours (96979-1-1). The mixture was diluted with water, neutralized with 2 N HCl, then extracted with DCM (3×30 mL). The combined organics were dried with $MgSO_4$, filtered, then concentrated. 6-((6-(3-methylisoxazol-5-yl)imidazo[1,2-b]pyridazin-3-yl)methyl)quinoline was purified by prep HPLC and isolated as the TFA salt. MS (ESI pos. ion) m/z: 341 (MH+). Calc'd exact mass for $C_{20}H_{15}N_5O$: 341.

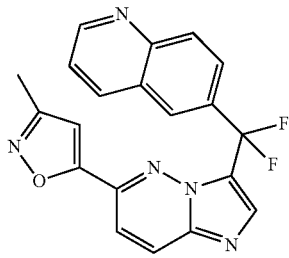 [SMILES: Cc1cc(-c2ccc3ncc(C(F)(F)c4ccc5ncccc5c4)n3n2)on1]

EXAMPLE 433

6-(difluoro(6-(3-methylisoxazol-5-yl)imidazo[1,2-b]pyridazin-3-yl)methyl)quinoline A 25 mm test tube was charged with 2,2-difluoro-1,3-dimethylimidazolidine (DFI) (0.24 g, 1.8 mmol), (6-(3-methylisoxazol-5-yl)imidazo[1,2-b]pyridazin-3-yl)(quinolin-6-yl)methanone (0.125 g, 0.35 mmol), and MeCN (2.00 ml, 38 mmol), sealed, then heated at 84° C. for 36 hours, adding additional 2,2-difluoro-1,3-dimethylimidazolidine (DFI) (0.24 g, 1.8 mmol) after 16 hours. The mixture was diluted with water (50 mL), then extracted with DCM (2×40 mL). The combined organics were washed with brine (40 mL), dried with $MgSO_4$, filtered, then concentrated to give a brown residue. This was purified by MPLC using a 40 g RediSep column, eluting with 20-50% (90:10:1 DCM:MeOH:$NH_4OH$ mixture) in EtOAc over 40 minutes. The purest fractions were collected—these still contained DFI, so the residue was triturated with EtOAc and decanted. 6-(difluoro(6-(3-methylisoxazol-5-yl)imidazo[1,2-b]pyridazin-3-yl)methyl)quinoline was isolated as a light yellow solid.

MS (ESI pos. ion) m/z: 378 (MH+). Calc'd exact mass for $C_{20}H_{13}F_2N_5O$: 377.

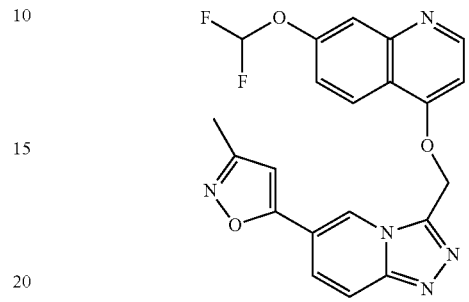

EXAMPLE 434

7-(difluoromethoxy)-4-((6-(3-methylisoxazol-5-yl)-[1,2,4]-triazolo[4,3-a]pyridin-3-yl)methoxy)quinoline

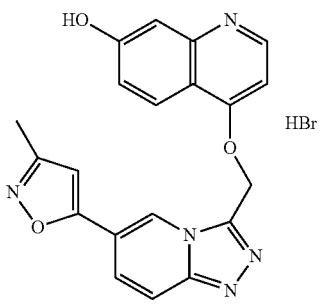 [SMILES: Cc1cc(-c2ccc3nnc(COc4ccnc5cc(O)ccc45)n3c2)on1 ; Br]

1) 4-((6-(3-methylisoxazol-5-yl)-[1,2,4]triazolo[4,3-a]pyridin-3-yl)methoxy)quinolin-7-ol hydrobromide A 150 mL tube was charged with 7-methoxy-4-((6-(3-methylisoxazol-5-yl)-[1,2,4]triazolo[4,3-a]pyridin-3-yl)methoxy)quinoline (1.44 g, 3.72 mmol) and HBr (30.3 ml, 558 mmol), sealed, then placed in a 120° C. for 5 hours. The reaction mixture was slowly neutralized with 6N NaOH until a precipitate crashed out of solution (pH ~5)—the solid was collected to give 4-((6-(3-methylisoxazol-5-yl)-[1,2,4]triazolo[4,3-a]pyridin-3-yl)methoxy)quinolin-7-ol hydrobromide.

2) 7-(difluoromethoxy)-4-((6-(3-methylisoxazol-5-yl)-[1,2,4]triazolo[4,3-a]pyridin-3-yl)methoxy)quinoline A 48 mL tube was charged with sodium 2-chloro-2,2-difluoroacetate (0.15 g, 1.0 mmol), 4-((6-(3-methylisoxazol-5-yl)-[1,2,4]triazolo[4,3-a]pyridin-3-yl)methoxy)quinolin-7-ol hydrobromide (0.200 g, 0.44 mmol), cesium carbonate (0.43 g, 1.3 mmol), and DMF (1.7 ml, 22 mmol), flushed with argon, sealed, then placed in a 100° C. oil bath for 5 hours.

The reaction mixture was concentrated, then diluted with DCM and chloroform. This was washed with water, sat. NaHCO₃, and brine, then dried with MgSO₄, filtered, and concentrated to give a brown oil. This was purified by HPLC to give 7-(difluoromethoxy)-4-((6-(3-methylisoxazol-5-yl)-[1,2,4]triazolo[4,3-a]pyridin-3-yl)methoxy)quinoline (0.025 g, 13% yield) as the formic acid salt. MS (ESI pos. ion) m/z: 424 (MH+). Calc'd exact mass for $C_{21}H_{15}F_2N_5O_3$: 423.

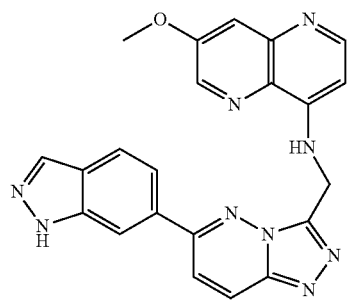 [SMILES: COc1cnc2c(NCc3nnc4ccc(-c5ccc6cn[nH]c6c5)nn34)ccnc2c1]

EXAMPLE 435

N-((6-(1H-indazol-6-yl)-[1,2,4]triazolo[4,3-b]pyridazin-3-yl)methyl)-7-methoxy-1,5-naphthyridin-4-amine a) 6-(3-((7-Methoxy-1,5-naphthyridin-4-ylamino)methyl)-[1,2,4]triazolo[4,3-b]pyridazin-6-yl)-1H-indazole-1-carboxylate. A tube was charged with N-((6-chloro-[1,2,4]triazolo[4,3-b]pyridazin-3-yl)methyl)-7-methoxy-1,5-naphthyridin-4-amine (0.250 g, 0.732 mmol), tert-butyl 6-(4,4,5,5-tetramethyl-1,3,2-dioxaborolan-2-yl)-1H-indazole-1-carboxylate (0.378 g, 1.10 mmol), PdCl2(dppf)-CH2Cl2Adduct (0.0597 g, 0.0732 mmol), potassium carbonate (0.303 g, 2.19 mmol), DMF (5.01 ml, 64.4 mmol), and water (1.16 ml, 64.4 mmol), flushed with argon, sealed, then placed in a 60° C. oil bath for 6 hours. The reaction mixture was concentrated, then triturated with water to give a black solid. The material was used directly in the next step.

b) N-((6-(1H-indazol-6-yl)-[1,2,4]triazolo[4,3-b]pyridazin-3-yl)methyl)-7-methoxy-1,5-naphthyridin-4-amine. The title compound was prepared in the same manner as 7-methoxy-4-((6-(6-(piperazin-1-yl)pyridin-3-yl)-[1,2,4]triazolo[4,3-b]pyridazin-3-yl)methoxy)quinoline MS (ESI pos. ion) m/z: 424 (MH+). Calc'd exact mass for $C_{22}H_{17}N_9O$: 423.

4-bromo-1-(2,2,2-trifluoroethyl)-1H-pyrazole

A 250 mL RB flask was charged with 4-bromo-1H-pyrazole (2.00 g, 13.6 mmol), 2,2,2-trifluoroethyl trifluoromethanesulfonate (2.35 ml, 17.0 mmol), cesium carbonate (8.87 g, 27.2 mmol), and 1,4-dioxane (40.0 ml, 468 mmol), capped, and stirred at room temperature for 20 hours. The reaction mixture was filtered and the solid washed with dioxane; the filtrate was then concentrated to give 4-bromo-1-(2,2,2-trifluoroethyl)-1H-pyrazole (2.402 g, 77.1% yield) as a crude oil.

4-(4,4,5,5-tetramethyl-1,3,2-dioxaborolan-2-yl)-1-(2,2,2-trifluoroethyl)-1H-pyrazole The title compound was prepared in the same manner as 1-ethyl-4-(4,4,5,5-tetramethyl-1,3,2-dioxaborolan-2-yl)-1H-pyrazole starting with 4-bromo-1-(2,2,2-trifluoroethyl)-1H-pyrazole.

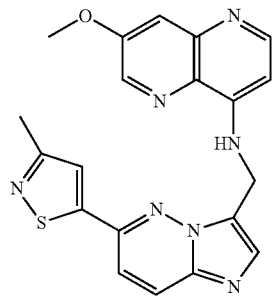 [SMILES: COc1cnc2c(NCc3cnc4ccc(-c5cc(C)ns5)nn34)ccnc2c1]

EXAMPLE 436

7-methoxy-N-((6-(3-methylisothiazol-5-yl)imidazo[1,2-b]pyridazin-3-yl)methyl)-1,5-naphthyridin-4-amine The title compound was prepared in the same manner as 7-Methoxy-N-((6-(3,4,5-trifluorophenyl)imidazo[1,2-b]pyridazin-3-yl)methyl)-1,5-naphthyridin-4-amine MS (ESI pos. ion) m/z: 404 (MH+). Calc'd exact mass for $C_{20}H_{17}N_7OS$: 403.

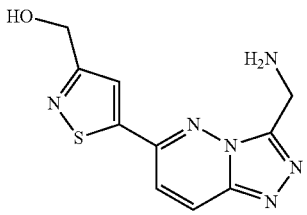 [SMILES: NCc1nnc2ccc(-c3cc(CO)ns3)nn12]

(5-(3-(aminomethyl)-[1,2,4]-triazolo[4,3-b]pyridazin-6-yl)isothiazol-3-yl)methanol

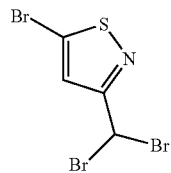

1) 5-bromo-3-(dibromomethyl) isothiazole. 5-Bromo-3-methylisothiazole (2.15 g, 12 mmol) was dissolved in dichloroethane (20 mL) then added N-bromosuccinimide (4.5 g, 25 mmol) and AIBN (0.50 g, 3.0 mmol). The reaction mixture was heated at 100° C. for 4 hours. Additional AIBN (0.50 g, 3.0 mmol) and bromine (0.062 ml, 1.2 mmol) were added to the mixture and continued heating at 100° C. for 4 hours. N-bromosuccinimide (4.5 g, 25 mmol) and AIBN (0.50 g, 3.0 mmol) were added then continued heating at 100° C. for 4 hours. Again, N-bromosuccinimide (4.5 g, 25 mmol) and AIBN (0.30 g, 1.8 mmol) were added and the mixture was heated at 100° C. for 4 hours. The reaction mixture was diluted with ethyl acetate and washed with water, saturated sodium bicarbonate and brine. The organic layer was dried over sodium sulfate and concentrated under vacuum. The sample was purified by flash chromatography eluting with 0-10% ethyl acetate/hexane to afford 5-bromo-3-(dibromomethyl)isothiazole (2.07 g, 51% yield) as a colorless liquid.

2) 5-bromoisothiazole-3-carbaldehyde. 5-Bromo-3-(dibromomethyl)isothiazole (1.00 g, 3.0 mmol) was dissolved in DME (10 mL) then added a solution of silver nitrate (0.56 g, 3.3 mmol) in water (1.6 mL). A white precipitate formed. The reaction mixture was heated at 100° C. for 1.5 hours. Additional silver nitrate (0.56 g, 3.3 mmol) in water (1.6 mL) was added and heating was continued at 100° C. for 2.5 hours. The reaction mixture was filtered through a pad of Celite washing with THF then ethyl acetate. The filtrate was concentrated under vacuum and the remaining oil was diluted with ethyl acetate. The organic layer was washed with water then dried over sodium sulfate and concentrated under vacuum to afford 5-bromoisothiazole-3-carbaldehyde (0.536 g, 94% yield) as a light yellow oil.

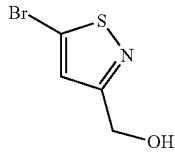

3)(5-bromoisothiazol-3-yl)methanol. 5-Bromoisothiazole-3-carbaldehyde (0.533 g, 2.8 mmol) was dissolved in ethanol (40 mL) then added sodium borohydride (0.11 g, 2.8 mmol). The reaction mixture was stirred at room temperature for 3 hours. Added more sodium borohydride (0.026 g, 0.69 mmol) and continued stirring at room temperature for 4.5 hours. Additional sodium borohydride (0.11 g, 2.8 mmol) was added once again and stirring was continued at room temperature overnight. The reaction was quenched with saturated aqueous ammonium chloride then concentrated under vacuum. The remaining aqueous layer was diluted with water then extracted with ethyl acetate (2×). The organic layer was dried over sodium sulfate and concentrated under vacuum to afford (5-bromoisothiazol-3-yl)methanol (0.430 g, 80% yield) as an orange oil.
MS (ESI pos. ion) m/z: 194.0 and 196.0 (MH$^+$).

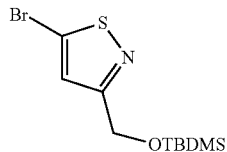 [SMILES: CC(C)(C)[Si](C)(C)OCc1cc(Br)sn1]

4) 5-bromo-3-((tert-butyldimethylsilyl oxy)methyl) isothiazole. (5-Bromoisothiazol-3-yl)methanol (0.380 g, 1.96 mmol) was dissolved in DMF (4 mL) then added tert-butyldimthylsilyl chloride (0.443 g, 2.94 mmol) and imidazole (0.400 g, 5.87 mmol). The reaction mixture was stirred at room temperature overnight. The reaction mixture was combined with previous reactions and concentrated under vacuum. The sample was purified by flash chromatography eluting with 0-15% ethyl acetate/hexane to afford 5-bromo-3-((tert-butyldimethylsilyloxy)methyl)isothiazole as a pale yellow liquid. MS (ESI pos. ion) m/z: 308.0 and 310.0 (MH$^+$).

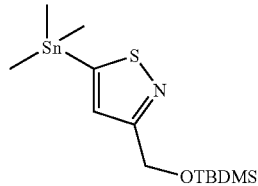 [SMILES: CC(C)(C)[Si](C)(C)OCc1c[c]([Sn]([CH3])([CH3])[CH3])sn1]

5) 3-((tert-butyldimethylsilyloxy)methyl)-5-(trimethylstannyl)isothiazole. 5-Bromo-3-((tert-butyldimethylsilyloxy)methyl)isothiazole (0.100 g, 0.324 mmol) was dissolved in THF (1 mL) then cooled to −78° C. and added 1.6 M n-BuLi in hexane (0.223 ml, 0.357 mmol) dropwise via syringe. The reaction mixture became yellow and stirring was continued at −78° C. for 45 minutes. 1M Trimethyltin chloride in THF (0.324 ml, 0.324 mmol) was added to the mixture dropwise via syringe. No color change was observed. Continued stirring at −78° C. for 1.5 hours. The reaction was quenched with saturated aqueous sodium bicarbonate at −78° C. then warmed to room temperature. The mixture was diluted with water then extracted with ether. The organic layer was dried over sodium sulfate and concentrated under vacuum to afford 3-((tert-butyldimethylsilyloxy)methyl)-5-(trimethylstannyl)isothiazole (0.121 g, 95.1% yield) as a light yellow liquid.

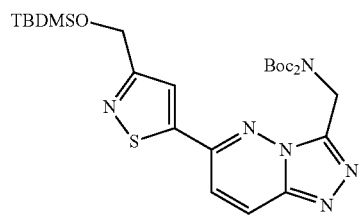

6) bis(1,1-dimethylethyl)(6-(3-((((1,1-dimethylethyl)(dimethyl)silyl)oxy)methyl)-5-isothiazolyl)[1,2,4]triazolo[4,3-b]pyridazin-3-yl)methylimidodicarbonate. Bis(1,1-dimethylethyl)(6-chloro[1,2,4]triazolo[4,3-b]pyridazin-3-yl)methylimidodicarbonate (0.200 g, 0.521 mmol) was suspended in dioxane (3 mL) then added 3-((tert-butyldimethylsilyloxy)methyl)-5-(trimethylstannyl)isothiazole (0.429 g, 1.09 mmol), xantphos (0.0301 g, 0.0521 mmol), palladium (II) acetate (0.00585 g, 0.0261 mmol), and water (0.0188 ml, 1.04 mmol). The reaction mixture was heated at 100° C. for 3 hours. The reaction mixture was concentrated under vacuum. The sample was purified by flash chromatography eluting with 0-100% ethyl acetate to afford bis(1,1-dimethylethyl)(6-(3-((((1,1-dimethylethyl)(dimethyl)silyl)oxy)methyl)-5-isothiazolyl)[1,2,4]triazolo[4,3-b]pyridazin-3-yl)methylimidodicarbonate (0.170 g, 56.6% yield) as a yellow oil. MS (ESI pos. ion) m/z: 577.2 (MH$^+$).

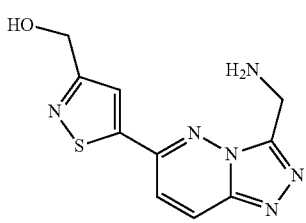 [SMILES: NCc1nnc2ccc(-c3cc(CO)ns3)nn12]

7) (5-(3-(aminomethyl)-[1,2,4]triazolo[4,3-b]pyridazin-6-yl)isothiazol-3-yl)methanol. Bis(1,1-dimethylethyl)(6-(3-(((((1,1-dimethylethyl)(dimethyl)silyl)oxy)methyl)-5-isothiazolyl)[1,2,4]triazolo[4,3-b]pyridazin-3-yl)methylimidodicarbonate (0.170 g, 0.29 mmol) was dissolved in ethyl acetate (5 mL) then hydrochloric acid gas was bubbled through the mixture for approx. 5 minutes. A precipitate formed and stirring was continued at room temperature for 1.5 hours. The reaction was concentrated under vacuum then mostly redissolved in methanol (3.5 mL) and added ammonium hydroxide (0.052 ml, 1.3 mmol). The mixture was stirred at room temperature for 2 hours then concentrated under vacuum. The sample was purified by flash chromatography eluting with 50-100% 90:10:1 dichloromethane/methanol/NH4OH followed by 100% 90:10:1 dichloromethane/methanol/NH4OH to afford (5-(3-(aminomethyl)-[1,2,4]triazolo[4,3-b]pyridazin-6-yl)isothiazol-3-yl)methanol (0.066 g, 85% yield) as a white solid. MS (ESI pos. ion) m/z: 263.0 (MH$^+$).

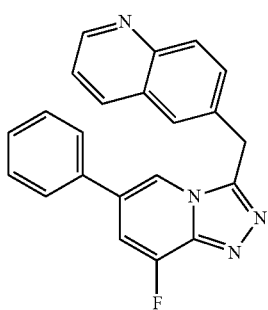 [SMILES: Fc1cc(-c2ccccc2)cn2c(Cc3ccc4ncccc4c3)nnc12]

EXAMPLE 437

6-((8-fluoro-6-phenyl-[1,2,4]-triazolo[4,3-a]pyridin-3-yl)methyl)quinoline 1) 6-((6-chloro-8-fluoro-[1,2,4]triazolo[4,3-a]pyridin-3-yl)methyl)quinoline. A mixture of 1-(5-chloro-3-fluoropyridin-2-yl)hydrazine (500 mg, 3095 μmol) and methyl 2-(quinolin-6-yl)acetate (600 mg, 2982 μmol) in HCl (conc., 600 μL, 7200 μmol) was heat at 100° C. for 20 min. The mixture was then heated in a microwave at 180° C. for 40 min. The mixture was quenched with NaOH (5 N, 1.5 mL) and the suspension was filtered and washed with H$_2$O. The resulting brown solid is mostly the desired product. The solid was then triturated with NaOH (5 N, 1 mL), filtered, and washed with H$_2$O. LCMS (ESI pos. ion): calc'd for C$_{16}$H$_{10}$ClFN$_4$: 312.0. found: 313.1 (M+1).

2) 6-((8-fluoro-6-phenyl-[1,2,4]triazolo[4,3-a]pyridin-3-yl)methyl)quinoline. A mixture of Pd(OAc)$_2$ (6.46 mg, 28.8 μmol), potassium phosphate (367 mg, 1727 μmol), phenylboronic acid (211 mg, 1727 μmol), dicyclohexyl(2-(2,4,6-triisopropylcyclohexa-1,3-dienyl)phenyl)phosphine (27.6 mg, 57.6 μmol), and 6-((6-chloro-8-fluoro-[1,2,4]triazolo[4,3-a]pyridin-3-yl)methyl)quinoline (180 mg, 576 μmol) in dioxane (6 mL)-H$_2$O (2 mL) was heated to 100° C. under nitrogen for 20 h. The mixture was cooled to rt and partitioned between H$_2$O and CH$_2$Cl$_2$. The organic layer was dried over MgSO$_4$ and concentrated. The residual was purified on silica using MeOH in DCM (0-5%) to give a pink solid. This solid was triturated with hexane-EtOAc-DCM (hot) to give a brown solid (105 mg). LCMS (ESI pos. ion): calc'd for C$_{22}$H$_{15}$FN$_4$: 354.1. found: 355.2 (M+1).

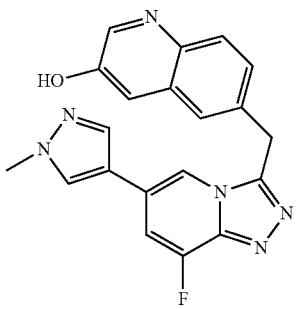 [SMILES: Cn1cc(-c2cc(F)c3nnc(Cc4ccc5ncc(O)cc5c4)n3c2)cn1]

EXAMPLE 438

6-((8-fluoro-6-(1-methyl-1H-pyrazol-4-yl)-[1,2,4]-triazolo[4,3-a]pyridin-3-yl)methyl)quinolin-3-ol A mixture of crude 6-((6-chloro-8-fluoro-[1,2,4]triazolo[4,3-a]pyridin-3-yl)methyl)-3-methoxyquinoline (200 mg, 584 μmol), 1-methyl-4-(4,4,5,5-tetramethyl-1,3,2-dioxaborolan-2-yl)-1H-pyrazole (600 mg, 2884 μmol), PdCl$_2$(dppf)-CH$_2$Cl$_2$ adduct (24 mg, 29 μmol), and Na$_2$CO$_3$ (500 mg, 4717 μmol) in DME (7 mL)-H$_2$O (5 mL) was heated at 100° C. under nitrogen. After overnight, the sludge was treated with DMSO (10 mL) and filtered. The DMSO solution was purified on HPLC (10-60%/10 min). The product fraction was concentrated to dryness with toluene. The solid was then triturated with MeOH-hexane (1:2) to give a brown powder (60 mg). LCMS (ESI pos. ion): calc'd for C$_{20}$H$_{15}$FN$_6$O: 374.1. found 375.1 (M+1).

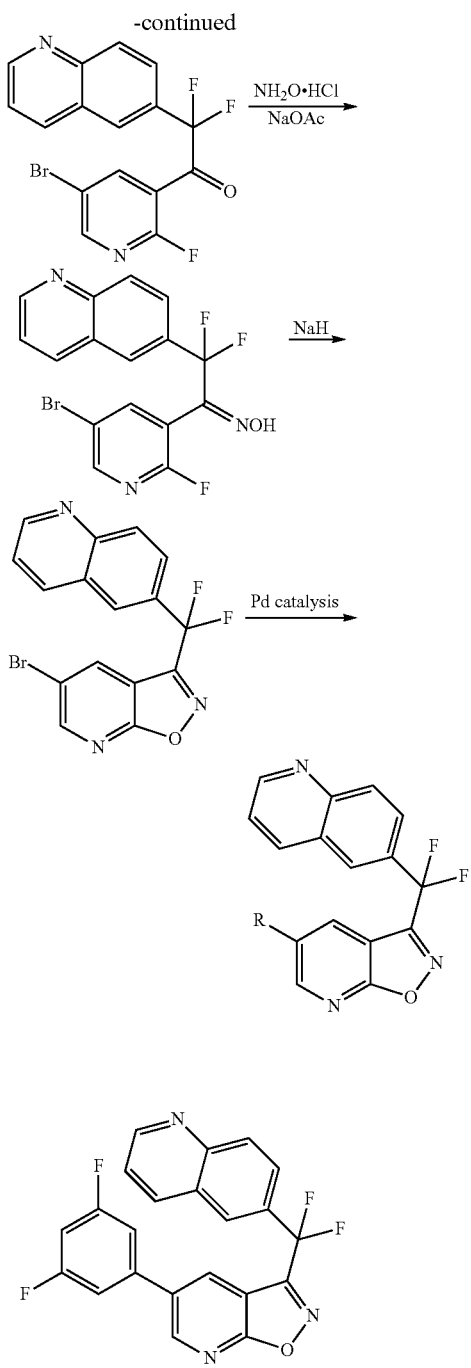

EXAMPLE 439

6-((5-(3,5-difluorophenyl)isoxazolo[5,4-b]pyridin-3-yl)difluoromethyl)quinoline 1) 2,2-difluoro-2-(quinolin-6-yl)acetic acid. To a solution of methyl 2,2-difluoro-2-(quinolin-6-yl)acetate (2.0 g, 8.4 mmol) in dioxane (4 mL) and water (12 mL) was added lithium hydroxide monohydrate (0.53 g, 12 mmol). After stirring at 50° C. for thirty minutes, the solution was brought to pH 4 with 2.0 N HCl. The solution was concentrated and dried on a lyophilizer overnight to yield the product as an orange solid. MS m/z=224.0 [M+1

2) 2,2-difluoro-2-(quinolin-6-yl)acetyl chloride hydrochloride. To a suspension of 2,2-difluoro-2-(quinolin-6-yl) acetic acid (1.9 g, 8.4 mmol) in dichloromethane (16 mL) was added oxalyl chloride (7.4 mL, 84 mmol). The mixture was stirred at 45° C. for one hour. The suspension was filtered and the resulting filtrate concentrated to yield the product as an orange oil (1.8 g, 73% step 1 and 2 combined).

3) 1-(5-bromo-2-fluoropyridin-3-yl)-2,2-difluoro-2-(quinolin-6-yl)ethanone. To a solution of 3,5-dibromo-2-fluoropyridine (3.1 g, 12 mmol) in anhydrous THF (12 mL) under argon was added isopropylmagnesium chloride (2.0 M in THF, 6.0 mL, 12 mmol). The solution was stirred at room temperature for ten minutes, then was added via cannula to a solution of 2,2-difluoro-2-(quinolin-6-yl)acetyl chloride hydrochloride (1.8 g, 6.1 mmol) in anhydrous THF (20 mL) at −78° C. The solution was allowed to rise to −40° C. over one hour; then was stirred at 0° C. for one hour. The reaction was quenched with water and extracted with ethyl acetate; organic extracts were dried over magnesium sulfate and concentrated. Purification by MPLC (eluted with a gradient of 20 to 80% ethyl acetate in hexanes) afforded the product as a tan solid (0.90 g, 38%).

4) 1-(5-bromo-2-fluoropyridin-3-yl)-2,2-difluoro-2-(quinolin-6-yl)ethanone oxime. To a pressure vessel was added hydroxylamine hydrochloride (1.6 g, 24 mmol), sodium acetate (2.9 g, 35 mmol) and 1-(5-bromo-2-fluoropyridin-3-yl)-2,2-difluoro-2-(quinolin-6-yl)ethanone (0.90 g, 2.4 mmol) in acetic acid (20 mL). The suspension was sealed and stirred at 100° C. for fifteen minutes, then was concentrated, triturated with water and filtered. Purification of the resulting solid by MPLC (eluted with a gradient of 0-10% methanol in dichloromethane) afforded the product as a beige solid (0.59 g, 63%). MS m/z=396.0 [M+1]$^+$ 5) 645-bromoisoxazolo[5,4-b]pyridin-3-yl)difluoromethyl)quinoline. To a solution of 1-(5-bromo-2-fluoropyridin-3-yl)-2,2-difluoro-2-(quinolin-6-yl)ethanone oxime (0.59 g, 1.5 mmol) in anhydrous THF (10 mL) was added sodium hydride (0.090 g, 2.3 mmol) at 0° C. After ten minutes, the solution was diluted with ethyl acetate and washed with water, organic extracts were dried over magnesium sulfate. Purification by MPLC (eluted with a gradient of 20-50% ethyl acetate in hexanes) afforded the product as a white solid (0.39 g, 70%). MS m/z=377.0 [M+1]$^+$ Calc'd for $C_{16}H_8BrF_2N_3O$: 376.2

6) 6-((5-(3,5-difluorophenyl)isoxazolo[5,4-b]pyridin-3-yl)difluoromethyl)quinoline. To a pressure vessel was added $PdCl_2$(dppf)-$CH_2Cl_2$ adduct (0.0076 g, 0.0093 mmol), cesium carbonate (0.13 g, 0.40 mmol), 6-((5-bromoisoxazolo[5,4-b]pyridin-3-yl)difluoromethyl)quinoline (0.050 g, 0.13 mmol) and 3,5-difluorophenylboronic acid (0.031 g, 0.020 mmol) in DMF (1.0 mL) water (0.25 mL). The vessel was purged with argon, sealed and stirred at 80° C. for two hours. The mixture was concentrated, triturated with water an filtered; purification of the resulting precipitate by MPLC (eluted with a gradient of 20 to 50% ethyl acetate in hexanes afforded the product as a white solid (27 mg, 53%).

General Method G

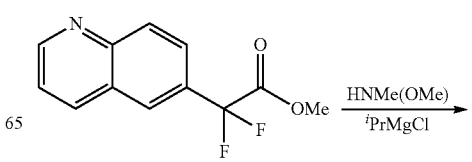

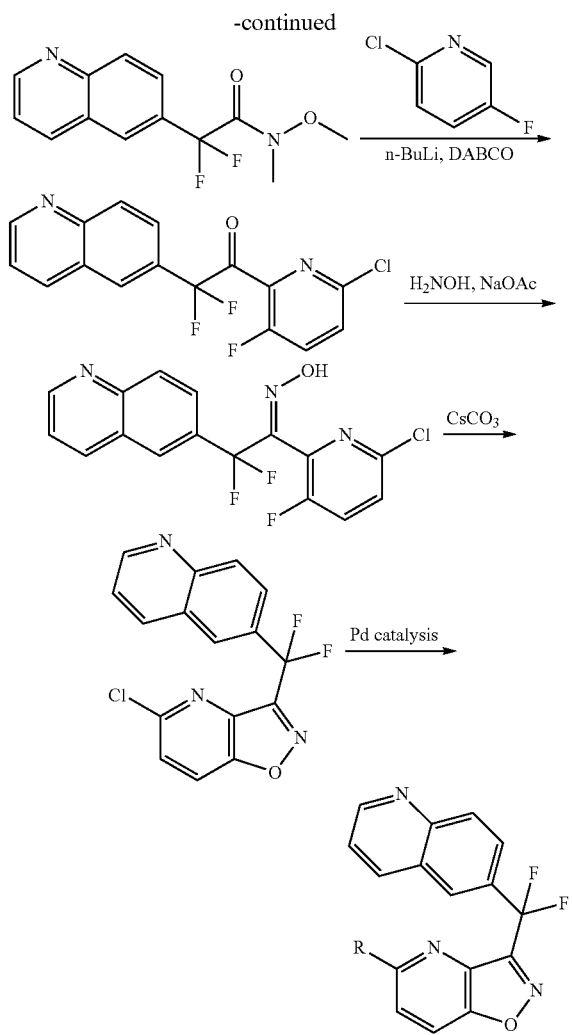

EXAMPLE 440

6-(difluoro(5-(1-methyl-1H-pyrazol-4-yl)isoxazolo[4,5-b]pyridin-3-yl)methyl)quinoline 1) 2,2-difluoro-N-methoxy-N-methyl-2-(quinolin-6-yl)acetamide. To a solution of N-methoxymethanamine hydrochloride (3.7 g, 38 mmol) and methyl 2,2-difluoro-2-(quinolin-6-yl)acetate (6.0 g, 25 mmol) in anhydrous THF (30 mL) was added isopropylmagnesium chloride (2.0 M, 38 mL, 76 mmol) at −20° C. After thirty minutes the reaction was quenched with saturated ammonium chloride and extracted with diethyl ether; organic extracts were dried over magnesium sulfate. Purification by MPLC (eluted with a gradient of 10 to 70% ethyl acetate in hexanes) afforded the product as an orange solid. MS m/z=267.2 [M+1]⁺.

2) 1-(6-chloro-3-fluoropyridin-2-yl)-2,2-difluoro-2-(quinolin-6-yl)ethanone. n-Butyllithium (2.5M in hexanes, 3.70 ml, 9.25 mmol) was added to a stirred solution of DABCO (1.04 g, 9.25 mmol) in Et₂O (46 mL) at −78° C. The reaction mixture was stirred 1 h at −20° C. and then cooled again at −78° C. 2-Chloro-5-fluoropyridine (0.939 ml, 9.25 mmol) in Et₂O (5 mL) was added. Stirring was continued at −78° C. for 1 h. 2,2-Difluoro-N-methoxy-N-methyl-2-(quinolin-6-yl)acetamide (2.24 g, 8.41 mmol) in Et₂O (20 mL) was added by cannula. The reaction mixture was stirred at −78° C. for 70 min. The cooling bath was replaced by an ice/water bath. After 10 min of stirring at 0° C., the reaction mixture was quenched with water. The water layer was extracted with EtOAc and DCM/MeOH(9/1). The organic layers were combined, dried over MgSO₄, filtered and concentrated in vacuo. Purification by MPLC (hexanes/EtOAc: 100/0 to 40/60) afforded the title compound (2.27 g, 80% yield).

3) 1-(6-chloro-3-fluoropyridin-2-yl)-2,2-difluoro-2-(quinolin-6-yl)ethanone oxime. To a pressure vessel was added 1-(6-chloro-3-fluoropyridin-2-yl)-2,2-difluoro-2-(quinolin-6-yl)ethanone (1.0 g, 3.0 mmol), sodium acetate (3.7 g, 45 mmol) and hydroxylamine hydrochloride (2.1 g, 30 mmol) in acetic acid (15 mL). The vessel was sealed and the suspension was stirred at 100° C. for twenty minutes. Following concentration and trituration with water, a white precipitate was collected via filtration. Purification of the solid by MPLC (eluted with 0-10% methanol in dichloromethane) afforded the product as a white solid (0.85 g, 82%)
MS m/z=352.0 [M+1]⁺.

4) 6-((5-chloroisoxazolo[4,5-b]pyridin-3-yl)difluoromethyl)quinoline. To a pressure vessel was added 1-(6-chloro-3-fluoropyridin-2-yl)-2,2-difluoro-2-(quinolin-6-yl)ethanone oxime (0.050 g, 0.14 mmol) and cesium carbonate (0.14 g, 0.43 mmol) in anhydrous DMF (1 mL). After stirring at 80° C. for 30 minutes, the solution was diluted with ethyl acetate and washed with water. Organic extracts were dried over magnesium sulfate and purified by MPLC (eluted with a gradient of 10 to 50% ethyl acetate in hexanes) to yield the product as a white solid (35 mg, 74%) MS m/z=332.2 [M+1]⁺. Calc'd for C16H8ClF2N3O: 331.7.

5) 6-(difluoro(5-(1-methyl-1H-pyrazol-4-yl)isoxazolo[4,5-b]pyridin-3-yl)methyl)quinoline. To a pressure vessel was added 6-((5-chloroisoxazolo[4,5-b]pyridin-3-yl)difluoromethyl)quinoline) (0.10 g, 0.30 mmol), PdCl₂(dppf)-CH₂Cl₂ adduct (0.012 g, 0.015 mmol), cesium carbonate (0.29 g, 0.90 mmol) and 1-methyl-4-(4,4,5,5-tetramethyl-1,3,2-dioxaborolan-2-yl)-1H-pyrazole (0.094 g, 0.45 mmol) in DMF (2 mL) and water (0.5 mL). The vessel was purged with argon, sealed and stirred at 80° C. for forty minutes. The mixture was diluted with ethyl acetate and washed with water, organic extracts were dried over magnesium sulfate. Purification by MPLC (eluted with a gradient of 0 to 10% methanol in dichloromethane) afforded the product as a light yellow solid (45 mg, 40%). MS m/z=378.2 [M+1]⁺ Calc'd for C₂₀H₁₃F₂N₅O: 377.3.

General Method H

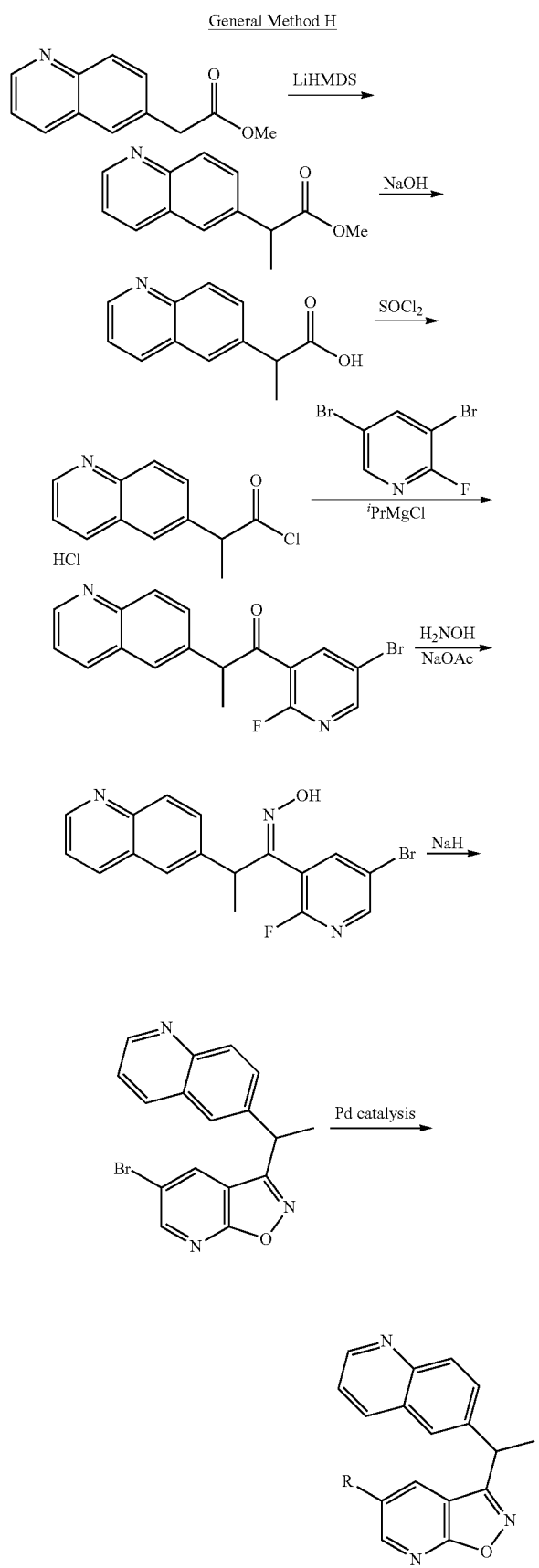

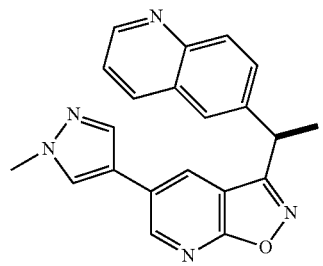 [SMILES: C[C@H](c1ccc2ncccc2c1)c1noc2ncc(-c3cnn(C)c3)cc12]

EXAMPLE 441

6-((R)-1-(5-(1-methyl-1H-pyrazol-4-yl)isoxazolo[5,4-b]pyridin-3-yl)ethyl)quinoline 1) Methyl 2-(quinolin-6-yl)propanoate. To a solution of methyl 2-(quinoline-6-yl)acetate (7.0 g, 35 mmol) in anhydrous THF (70 mL) was added lithium bis(trimethylsilyl)amide (1.0 M in THF, 35 mL, 35 mmol) and solution of methyl iodide (2.2 mL, 35 mmol) in anhydrous THF (1 mL) at −78° C. The dry ice in acetone bath was removed and the mixture was stirred for 35 minutes, then was quenched with saturated ammonium chloride (30 mL), diluted with ethyl acetate and washed with saturated sodium bicarbonate. Organic extracts were dried over magnesium sulfate and purified via MPLC (eluted with a gradient of 10 to 30% ethyl acetate in hexanes) to yield the product as a light yellow oil (6.5 g, 87%).

2) 2-(quinolin-6-yl)propanoic acid. To a solution of methyl 2-(quinolin-6-yl)propanoate (1.4 g, 6.5 mmol) in methanol (7 mL) and water (1.5 mL) was added sodium hydroxide (6 N, 2.7 mL, 16 mmol) and the solution was stirred at 50° C. for one hour. The solution was concentrated, brought to pH 4 with 2.0 N HCl and the product was isolated via filtration as a white solid (0.94 g, 72%).

3) 2-(quinolin-6-yl)propanoyl chloride hydrochloride. To a suspension of 2-(quinolin-6-yl)propanoic acid (0.73 g, 3.6 mmol) in anhydrous dichloromethane (15 mL) was added thionyl chloride (1.3 mL, 18 mmol) and the solution was stirred at room temperature for ten minutes. The solution was concentrated to yield the product as an orange solid.

4) 1-(5-bromo-2-fluoropyridin-3-yl)-2-(quinolin-6-yl)propan-1-one. To a solution of 3,5-dibromo-2-fluoropyridine (2.4 g, 9.3 mmol) in anhydrous THF (10 mL) was added isopropylmagnesium chloride (2.0 M in THF, 4.7 mL, 9.3 mmol) and stirred at room temperature for ten minutes. The solution was added via cannula to a solution of 2-(quinolin-6-yl)propanoyl chloride hydrochloride (0.79 g, 3.1 mmol) in anhydrous THF (10 mL) at −78° C. and the combined reaction mixture was allowed to rise to −40° C. over one hour. The mixture was stirred at −40° C. for an additional 90 minutes, then was quenched with saturated sodium bicarbonate and extracted with ethyl acetate. Organic extracts were dried over magnesium sulfate and purified via MPLC (eluted with a gradient of 10-80% ethyl acetate in hexanes) to yield the product as a yellow oil (0.60 g, 54%).

5) 1-(5-bromo-2-fluoropyridin-3-yl)-2-(quinolin-6-yl)propan-1-one oxime. To a pressure vial was added sodium acetate (2.0 g, 24 mmol), hydroxylamine hydrochloride (1.1 g, 16 mmol) and 1-(5-bromo-2-fluoropyridin-3-yl)-2-(quinolin-6-yl)propan-1-one (0.58 g, 1.6 mmol) in acetic acid (10 mL). The vial was sealed and stirred at 100° C. for one hour, then was concentrated, diluted with ethyl acetate and washed with water. Organic extracts were concentrated and purified by MPLC (eluted with 0-10% methanol in dichloromethane) to yield the product as a tan oil (0.50 g, 83%).

6) 6-(1-(5-bromoisoxazolo[5,4-b]pyridin-3-yl)ethyl)quinoline. To a solution of 1-(5-bromo-2-fluoropyridin-3-yl)-2-(quinolin-6-yl)propan-1-one oxime (0.58 g, 1.6 mmol) in THF (15 mL) was added sodium hydride (60% in mineral oil, 0.093, 2.3 mmol) at 0° C. The solution was stirred at 0° C. for ten minutes, then was diluted with ethyl acetate and washed with water. Organic extracts were concentrated and purified by MPLC (eluted with a gradient of 10 to 50% ethyl acetate in hexanes) to yield the product as a colorless oil (0.10 g, 19%). MS m/z=354.0 [M+1]$^+$. Calc'd for $C_{17}H_{12}BrN_3O$: 354.2

7) 6-((R)-1-(5-(1-methyl-1H-pyrazol-4-yl)isoxazolo[5,4-b]pyridin-3-yl)ethyl)quinoline. To a pressure vial was added 6-(1-(5-bromoisoxazolo[5,4-b]pyridin-3-yl)ethyl)quinoline (0.09 g, 0.25 mmol), PdCl$_2$(dppf)-CH$_2$Cl$_2$ adduct (0.010 g, 0.013 mmol), cesium carbonate (0.25 g, 0.76 mmol) and 1-methyl-4-(4,4,5,5-tetramethyl-1,3,2-dioxaborolan-2-yl)-1H-pyrazole (0.079 g, 0.38 mmol) in DMF (2.5 mL) and water (0.5 mL). The vessel was flushed with argon, sealed and stirred at 90° C. for one hour. The mixture was concentrated, triturated in water and a brown solid was collected via filtration. Purification by MPLC (eluted with a gradient of 10 to 50% ethyl acetate) afforded a racemic mixture of the product. The desired enantiomer (>99% ee) was obtained via SFC. MS m/z=356.2 [M+1]$^+$ Calc'd for $C_{21}H_{17}N_5O$: 355.4

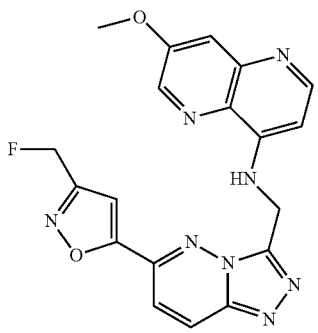 [SMILES: COc1cnc2c(NCc3nnc4ccc(-c5cc(CF)no5)nn34)ccnc2c1]

EXAMPLE 442

N-((6-(3-(fluoromethyl)isoxazol-5-yl)-[1,2,4]-triazolo[4,3-b]pyridazin-3-yl]methyl)-7-methoxy-1,5-naphthyridin-4amine To a suspension of (5-(3-((7-methoxy-1,5-naphthyridin-4-ylamino)methyl)-[1,2,4]triazolo[4,3-b]pyridazin-6-yl)isoxazol-3-yl)methanol (0.080 g, 0.20 mmol) in anhydrous dichloromethane (3 mL) was added deoxofluor (0.10 mL, 0.060 mmol) under argon at 0° C. The solution was brought to room temperature over one hour and stirred three additional hours. The reaction was quenched with saturated sodium bicarbonate and stirred for 15 minutes; a brown gum was collected by filtration. Purification via MPLC (eluted with a gradient of 0 to 10% methanol in dichloromethane) afforded the product as an off-white solid (9.0 mg, 11%). MS m/z=407.2 [M+1]$^+$. Calc'd for $C_{19}H_{15}FN_8O_2$: 406.4

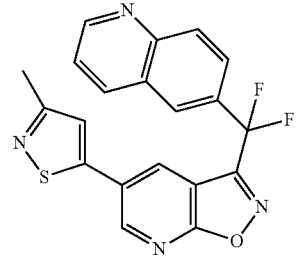 [SMILES: Cc1cc(-c2cnc3onc(C(F)(F)c4ccc5ncccc5c4)c3c2)sn1]

EXAMPLE 443

6-(difluoro(5-(3-methylisothiazol-5-yl)isoxazolo[5,4-b]pyridin-3-yl)methyl)quinoline To a pressure vial was added 2-(dicyclohexylphosphino)biphenyl (9.3 mg, 0.013 mmol), 6-((5-bromoisoxazolo[5,4-b]pyridin-3-yl)difluoromethyl)quinoline (0.10 g, 0.27 mmol), 3-methyl-5-(trimethylstannyl)isothiazole (0.14 g, 0.53 mmol) and Pd$_2$(dba)$_3$ (12 mg, 0.013 mmol) in anhydrous DMF (5 mL). The vessel was purged with argon, sealed and stirred at 80° C. for ninety minutes. The mixture was concentrated and purified by MPLC (eluted with a gradient of 10 to 50% ethyl acetate in hexanes) to yield the product as a light yellow solid. MS m/z=395.0 [M+1]$^+$ Calc'd for $C_{20}H_{12}F_2N_4OS$: 394.4.

The following example compounds 444-448 were prepared using a method similar to 6-(difluoro(5-(3-methylisothiazol-5-yl)isoxazolo[5,4-b]pyridin-3-yl)methyl)quinoline:

| Ex | Structure | MW | Mass Found |
|---|---|---|---|
| 444 | 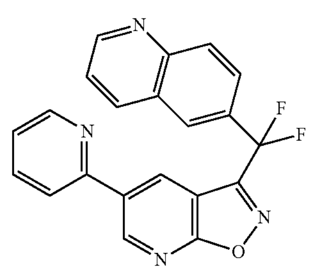 [SMILES: FC(F)(c1ccc2ncccc2c1)c1noc2ncc(-c3ccccn3)cc12] | 374 | 375 |
| 445 | 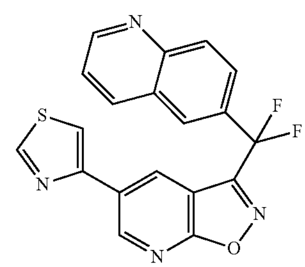 [SMILES: FC(F)(c1ccc2ncccc2c1)c1noc2ncc(-c3cscn3)cc12] | 380 | 381 |

-continued

| Ex | Structure | MW | Mass Found |
|---|---|---|---|
| 446 | 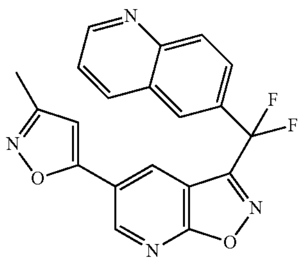 [SMILES: Cc1cc(-c2cnc3onc(C(F)(F)c4ccc5ncccc5c4)c3c2)on1] | 378 | 379 |
| 447 | 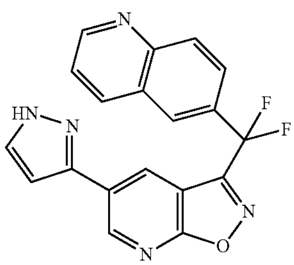 [SMILES: FC(F)(c1ccc2ncccc2c1)c1noc2ncc(-c3cc[nH]n3)cc12] | 363 | 364 |
| 448 | 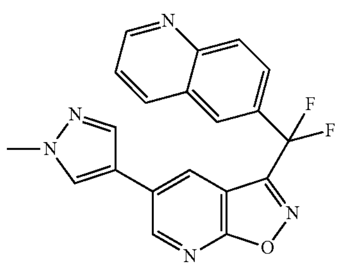 [SMILES: Cn1cc(-c2cnc3onc(C(F)(F)c4ccc5ncccc5c4)c3c2)cn1] | 377 | 378 |

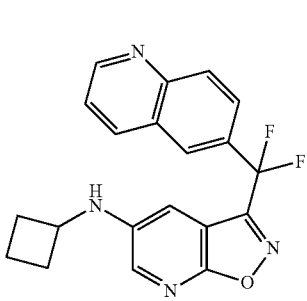 [SMILES: FC(F)(c1ccc2ncccc2c1)c1noc2ncc(NC3CCC3)cc12]

EXAMPLE 449

N-cyclobutyl-3-(difluoro(quinolin-6-yl)methyl)isoxazolo[5,4-b]pyridin-5-amine

To a pressure vial was added sodium tert-butoxide (38 mg, 0.40 mmol), xantphos (0.12 g, 0.20 mmol), Pd$_2$(dba)$_3$ (61 mg, 0.066 mmol), 645-bromoisoxazolo[5,4-b]pyridin-3-yl)difluoromethyl)quinoline (0.10 g, 0.27 mmol), and cyclobutanamine (0.025 mL, 0.29 mmol) in toluene (3 mL). The mixture was stirred at 80° C. for two hours then was diluted with dichloromethane and filtered through celite. Purification of the filtrate by MPLC (eluted with a gradient of 10 to 50% ethyl acetate in hexanes) afforded the product as a yellow oil (5.1 mg, 5%). MS m/z=367.0 [M+1]$^+$ Calc'd for C$_{20}$H$_{16}$F$_2$N$_4$O: 366.4

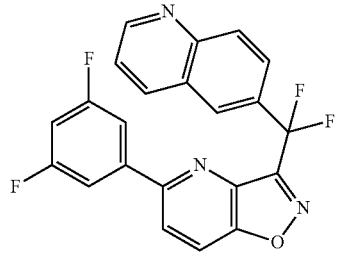 [SMILES: Fc1cc(F)cc(-c2ccc3onc(C(F)(F)c4ccc5ncccc5c4)c3n2)c1]

EXAMPLE 450

6-((5-(3,5-difluorophenyl)isoxazolo[5,4-b]pyridin-3-yl)difluoromethyl)quinoline

To a pressure vessel was added cesium carbonate (0.61 g, 1.9 mmol), PdCl$_2$(dppf)-CH$_2$Cl$_2$ adduct (26 mg, 0.031 mmol), 1-(6-chloro-3-fluoropyridin-2-yl)-2,2-difluoro-2-(quinolin-6-yl)ethanone oxime (0.26 g, 0.63 mmol) and 3,5-difluorophenylboronic acid (0.15 g, 0.94 mmol) in anhydrous DMF (5 mL) and water (1 mL). The mixture flushed with argon, sealed and stirred at 80° C. for one hour. The suspension was concentrated, triturated with water and filtered to afford a tan solid, purification by MPLC (eluted with a gradient of 20 to 50% ethyl acetate in hexanes) afforded the product as a white solid (23 mg, 9%). MS m/z=410.0 [M+1]$^+$ Calc'd for C$_{22}$H$_{11}$F$_4$N$_3$O: 409.3.

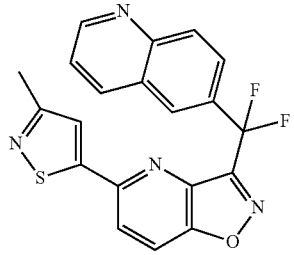 [SMILES: Cc1cc(-c2ccc3onc(C(F)(F)c4ccc5ncccc5c4)c3n2)sn1]

EXAMPLE 451

6-(difluoro(5-(3-methylisothiazol-5-yl)isoxazolo[4,5-b]pyridin-3-yl)methyl)quinoline To a solution of 5-bromo-3-methylisothiazole (0.19 g, 1.1 mmol) in anhydrous THF (3 mL) was added isopropylmagnesium lithium chloride (1.0 M in THF, 1.5 mL, 1.5 mmol) at −40° C. The mixture was stirred at −40° C. for twenty minutes followed by the addition of zinc chloride (0.5 M in THF, 3.1 mL, 1.6 mmol). The mixture was brought to room temperature and stirred for thirty minutes followed by the addition of Q-Phos (0.12 g, 0.17 mmol), Pd$_2$(dba)$_3$ (0.097 g, 0.110 mmol), 6-((5-chloroisoxazolo[4,5-b]pyridin-3-yl)difluoromethyl)quinoline (0.10 g, 0.30 mmol), and anhydrous dimethylacetamide (3.5 mL). The mixture was stirred at 50° C. for ninety minutes then was diluted with ethyl acetate and washed with water. Organic extracts were dried over magnesium sulfate and purified by MPLC (eluted with a gradient of 10 to 50% ethyl acetate in hexanes), then purified by HPLC (eluted with a gradient of 15 to 90% acetonitrile in water) to afford the product as a white solid (4.2 mg, 3%). MS m/z=395.2 [M+1]$^+$ Calc'd for C$_{23}$H$_{15}$F$_2$N$_3$O: 394.4.

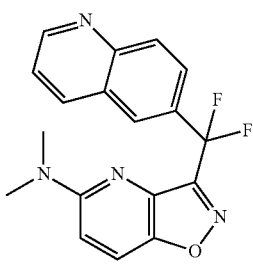 [SMILES: CN(C)c1ccc2onc(C(F)(F)c3ccc4ncccc4c3)c2n1]

EXAMPLE 452

3-(difluoro(quinolin-6-yl)methyl)-N,N-dimethyl-isoxazolo[4,5-b]pyridin-5-amine

To a microwave vial was added dimethylamine (2.0 M in THF, 0.75 mL, 1.5 mmol) and, 6-((5-chloroisoxazolo[4,5-b]pyridin-3-yl)difluoromethyl)quinoline (0.10 g, 0.30 mmol) in ethanol (3 mL). The mixture was stirred at 140° under microwave irradiation for two hours then was concentrated and purified by MPLC (eluted with a gradient of 10 to 50% ethyl acetate in hexanes) to yield the product as a light yellow solid (87 mg, 85%). MS m/z=341.2 [M+1]$^+$ Calc'd for $C_{18}H_{14}F_2N_4O$: 340.3.

| Ex | Structure | MW | Mass Found | Method |
|---|---|---|---|---|
| 453 | 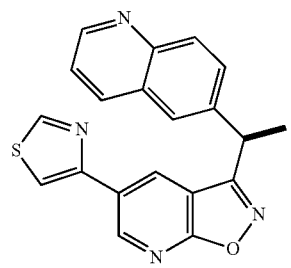 [SMILES: C[C@H](c1ccc2ncccc2c1)c1noc2ncc(-c3cscn3)cc12] | 387 | 388 | H |
| 454 | 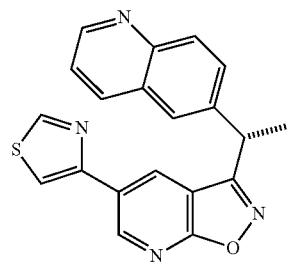 [SMILES: C[C@@H](c1ccc2ncccc2c1)c1noc2ncc(-c3cscn3)cc12] | 387 | 388 | H |

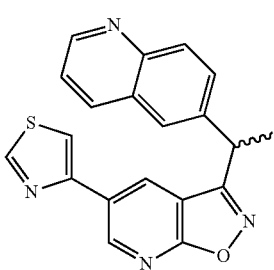

EXAMPLE 455

6-(1-(5-(thiazol-4-yl)isoxazolo[5,4-b]pyridin-3-yl)ethyl)quinoline

To a pressure vessel was added 2-(dicyclohexylphosphino)biphenyl (12 mg, 0.42 mmol), 6-(1-(5-bromoisoxazolo[5,4-b]pyridin-3-yl)ethyl)quinoline (0.10 g, 0.28 mmol), and 4-(tributylstannyl)thiazole (0.16 g, 0.42 mmol) in anhydrous DMF (3 mL). The vial was flushed with argon, sealed and stirred at 90° C. for two hours. The mixture was concentrated and purified by MPLC (eluted with a gradient of 0 to 10% methanol in dichloromethane) to afford the product as an off-white solid. MS m/z=359.0 [M+1]$^+$ Calc'd for $C_{20}H_{14}N_4OS$: 358.4.

EXAMPLE 456

6-((R)-1-(5-(thiazol-4-yl)isoxazolo[5,4-b]pyridin-3-yl)ethyl)quinoline

To a pressure vessel was added 2-(dicyclohexylphosphino)biphenyl (12 mg, 0.42 mmol), 6-(1-(5-bromoisoxazolo[5,4-b]pyridin-3-yl)ethyl)quinoline (0.10 g, 0.28 mmol), 4-(tributylstannyl)thiazole (0.16 g, 0.42 mmol) in anhydrous DMF (3 mL). The vial was flushed with argon, sealed and stirred at 90° C. for two hours. The mixture was concentrated and purified by MPLC (eluted with a gradient of 0 to 10% methanol in dichloromethane) to yield the racemic product as an off-white solid. The desired enantiomer (>99% ee) was obtained via SFC. MS m/z=359.0 [M+1]$^+$ Calc'd for $C_{20}H_{14}N_4OS$: 358.4

EXAMPLE 457

6-((S)-1-(5-(thiazol-4-yl)isoxazolo[5,4-b]pyridin-3-yl)ethyl)quinoline

Prepared by a method similar to 6-((R)-1-(5-(thiazol-4-yl)isoxazolo[5,4-b]pyridin-3-yl)ethyl)quinoline. MS m/z=359.0 [M+1]$^+$ Calc'd for $C_{20}H_{14}N_4OS$: 358.4.

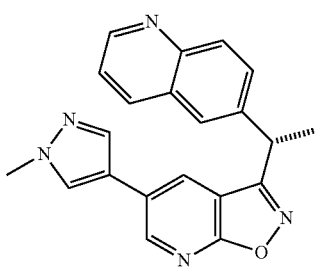 [SMILES: C[C@@H](c1ccc2ncccc2c1)c1noc2ncc(-c3cnn(C)c3)cc12]

EXAMPLE 458

6-((S)-1-(5-(1-methyl-1H-pyrazol-4-yl)isoxazolo[5,4-b]pyridin-3-yl)ethyl)quinoline Prepared by a method similar to 6-((R)-1-(5-(1-methyl-1H-pyrazol-4-yl)isoxazolo[5,4-b]pyridin-3-yl)ethyl)quinoline. MS m/z=356.2 [M+1]$^+$ Calc'd for $C_{21}H_{17}N_5O$: 355.4

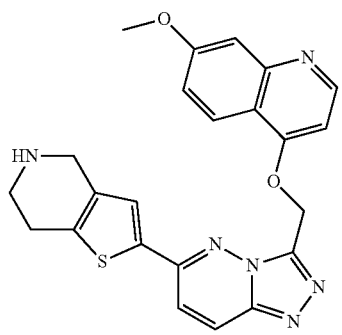 [SMILES: COc1ccc2c(OCc3nnc4ccc(-c5cc6c(s5)CCNC6)nn34)ccnc2c1]

EXAMPLE 459

7-methoxy-4-((6-(4,5,6,7-tetrahydrothieno[3,2-c]pyridin-2-yl)-[1,2,4]-triazolo[4,3-b]pyridazin-3-yl)methoxy)quinoline To a solution of tert-butyl 2-(3-((7-methoxyquinolin-4-yloxy)methyl)-[1,2,4]triazolo[4,3-b]pyridazin-6-yl)-6,7-dihydrothieno[3,2-c]pyridine-5(4H)-carboxylate (0.27 g, 0.50 mmol) (prepared according to general method A) was added trifluoroacetic acid (0.77 mL, 10 mmol). The mixture was stirred at room temperature for 90 minutes, then was concentrated, taken up in 2.0 M ammonia in methanol and purified by MPLC (eluted with a gradient of 0 to 10% methanol in dichloromethane) to yield the product as a pink solid. MS m/z=445.0 [M+1]$^+$Calc'd for $C_{23}H_{20}N_6O_2S$: 444.51.

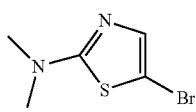

5-bromo-N,N-dimethylthiazol-2-amine

To a microwave vial was added N-ethyl-N-isopropylpropan-2-amine (0.72 mL, 4.1 mmol), 2,5-dibromothiazole (1.00 g, 4.1 mmol) and dimethylamine (40% in water, 0.52 mL, 4.1 mmol) in ethanol (10 mL). The vial was sealed and stirred at 140° C. under microwave irradiation for one hour, then was concentrated and purified by MPLC (eluted with a gradient of 0-50% ethyl acetate in hexanes) to yield the product as a white, crystalline solid (0.25 g, 29%).

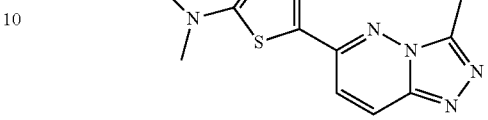

tert-butyl (6-(2-(dimethylamino)thiazol-5-yl)-[1,2,4]-triazolo[4,3-b]pyridazin-3-yl)methylcarbamate To a solution of 5-bromo-N,N-dimethylthiazol-2-amine (0.73 g, 3.53 mmol) in anhydrous THF (9 mL) was added isopropylmagnesium lithium chloride (1.0 M in THF, 4.8 mL, 4.8 mmol) at −40° C. The solution was stirred for twenty minutes followed by the dropwise addition of zinc chloride (0.5 M in THF, 10 mL, 5.2 mmol). The mixture was brought to room temperature and stirred for thirty minutes followed by the addition of dimethylacetamide (12 mL), $Pd_2(dba)_3$, (0.32 g, 0.35 mmol), Q-Phos (0.34 g, 0.56 mmol), and tert-butyl (6-chloro-[1,2,4]triazolo[4,3-b]pyridazin-3-yl)methylcarbamate (0.29 g, 1.0 mmol). The mixture was stirred at 50° for two hours then was quenched with saturated ammonium chloride and purified by MPLC chromatography (eluted with a gradient of 0 to 10% (1:10:90 $NH_4OH:MeOH:DCM$) in DCM) to yield the product as a light orange solid (0.27 g, 71%).

General Method I

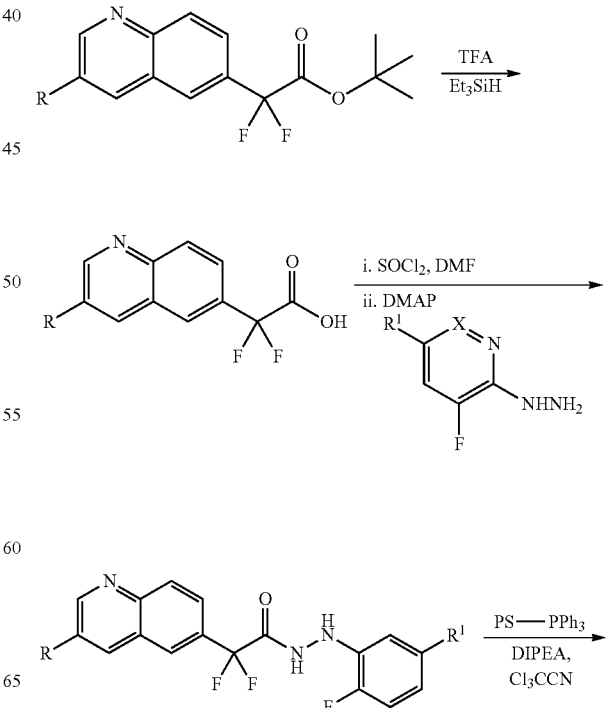

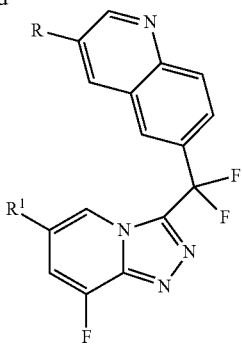

EXAMPLE 460

6-(difluoro(8-fluoro-6-(1-methyl-1H-pyrazol-4-yl)-[1,2,4]-triazolo[4,3-a]pyridin-3-yl)methyl)-3-methoxyquinoline

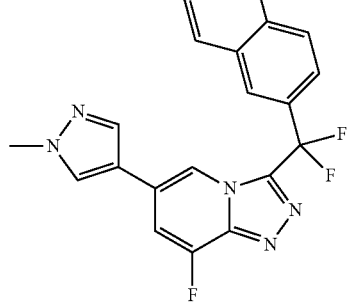

1) tert-butyl 2,2-difluoro-2-(3-methoxyquinolin-6-yl)acetate

The title compound was made from tert-butyl 2-(3-methoxyquinolin-6-yl)acetate in a similar fashion to the procedure reported for the synthesis of methyl 2,2-difluoro-2-(quinolin-6-yl)acetate.

2) 2,2-difluoro-2-(3-methoxyquinolin-6-yl)acetic acid

A 200 mL round bottom flask was charged with tert-butyl 2,2-difluoro-2-(3-methoxyquinolin-6-yl)acetate (5.06 g, 16 mmol) then CH$_2$Cl$_2$, then trifluoroacetic acid (16 ml, 213 mmol) followed by triethylsilane (6.5 ml, 41 mmol). The solution was maintained at rt for 24 h until LCMS showed disappearance of starting material. The solution was concentrated and was subjected to high vacuum for 40 h to give 4.1 g (99% yield) of 2,2-difluoro-2-(3-methoxyquinolin-6-yl)acetic acid as a brown solid. The material was of sufficient purity for use in subsequent steps.

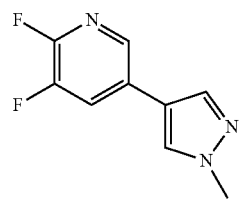

3) 2,3-difluoro-5-(1-methyl-1H-pyrazol-4-yl)pyridine

A sealable flask was charged with 5-chloro-2,3-difluoropyridine (1.541 g, 10.3 mmol), palladium(ii) acetate (0.116 g, 0.515 mmol), potassium phosphate tribasic (6.56 g, 30.9 mmol), 1-methyl-4-(4,4,5,5-tetramethyl-1,3,2-dioxaborolan-2-yl)-1H-pyrazole (2.57 g, 12.4 mmol), and X-Phos (0.491 g, 1.03 mmol). The flask was sealed with a septum cap, then dioxane (20 mL) and H2O (2 mL) were added. The resulting mixture was sparged with N$_2$ for 10 min, and then heated at 100° C. for 2 h. The solution was cooled to rt and then concentrated and purified by flash chromatography using eluent 99:1 Hexanes:EtOAc to 60:40 Hexanes:EtOAc gradient to afford 2,3-difluoro-5-(1-methyl-1H-pyrazol-4-yl)pyridine (1.78 g, 88.5% yield) as a colorless film. LRMS (ESI) m/z calcd for C$_9$H$_7$F$_2$N$_3$ (M+H) 197.1. found 197.4.

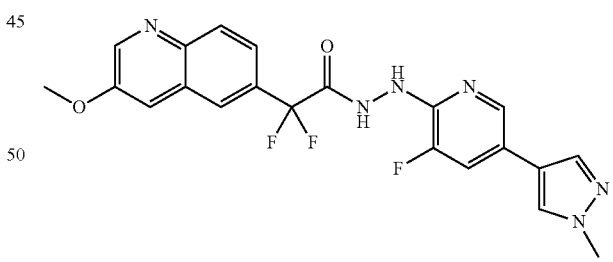

4) 2,2-difluoro-N'-(2-fluoro-5-(1-methyl-1H-pyrazol-4-yl)phenyl)-2-(3-methoxyquinolin-6-yl)acetohydrazide A round bottom flask was charged with 2,2-difluoro-2-(3-methoxyquinolin-6-yl)acetic acid (389 mg, 1536 μmol) and DMF (8 mL). The solution was cooled to 0 C, thionyl chloride (224 μl, 3073 mmol), was added and the resulting solution was maintained 1 h at 0° C. Then, triethylamine (641 μl, 4609 μmol) was added via syringe, followed by 1-(3-fluoro-5-(1-methyl-1H-pyrazol-4-yl)pyridin-2-yl)hydrazine (382 mg, 1844 µmol) and 4-(dimethylamino)pyridine (18.8 mg, 154 µmol); both added as solids. The heterogeneous solution was stirred at 0° C. for 1 h, then allowed to warm to rt and stir for 18 h. The mixture was quenched with saturated aqueous NaHCO$_3$ (50 mL) and the resulting mixture was extracted with CH$_2$Cl$_2$ (3×50 mL). The combined organic layers were concentrated (heating to 50° C.) and the residue purified by SiO$_2$ chromatography solvent system: CH$_2$Cl$_2$:MeOH 99%:1% gradient 90:10 CH$_2$Cl$_2$ to yield 2,2-difluoro-N'-(3-fluoro-5-(1-methyl-1H-pyrazol-4-yl)pyridin-2-yl)-2-(3-methoxyquinolin-6-yl)acetohydrazide (225 mg, 33.1% yield) as a brown amorphous solid.

5) 6-(difluoro(8-fluoro-6-(1-methyl-1H-pyrazol-4-yl)-[1,2,4]-triazolo[4,3-a]pyridin-3-yl) methyl)-3-methoxyquinoline A sealable microwave vial was charged with 2,2-difluoro-N'-(3-fluoro-5-(1-methyl-1H-pyrazol-4-yl)pyridin-2-yl)-2-(3-methoxyquinolin-6-yl)acetohydrazide (225 mg, 509 µmol) and polymer supported triphenylphosphine (2.3 mmol/g, 221 mg, 509 µmol). The flask was sealed and dichloroethane (4 mL) was added followed by diisopropylethylamine (89 µl, 509 µmol) and 2,2,2-trichloroacetonitrile (127 µl, 1271 µmol). The resulting mixture was irradiated in a microwave (Biotage Initiator) at 150° C. for 40 min. The reaction mixture was filtered and the filter cake was washed with CH$_2$Cl$_2$ (15 mL) and MeOH (10 mL). The filtrate was concentrated in vacuo and the resulting crude residue was purified by MPLC using 100% CH$_2$Cl$_2$ to 98:2 CH$_2$Cl$_2$: MeOH to afford 6-(difluoro(8-fluoro-6-(1-methyl-1H-pyrazol-4-yl)-[1,2,4]triazolo[4,3-a]pyridin-3-yl)methyl)-3-methoxyquinoline (94 mg, 44% yield) as a tan amorphous solid. LRMS (ESI) m/z calcd for C$_{21}$H$_{16}$F$_3$N$_6$O (M+H) 425.1. found 425.4.

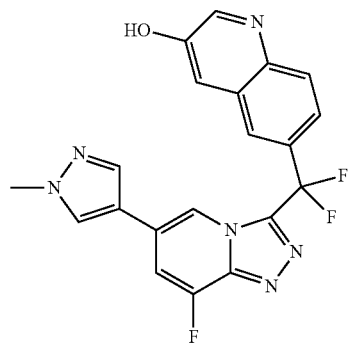 [SMILES: Cn1cc(-c2cc(F)c3nnc(C(F)(F)c4ccc5ncc(O)cc5c4)n3c2)cn1]

EXAMPLE 461

6-(difluoro(8-fluoro-6-(1-methyl-1H-pyrazol-4-yl)-[1,2,4]triazolo[4,3-a]pyridin-3-yl)methyl)quinolin-3-ol To a flask charged with 3-(benzyloxy)-6-(difluoro(8-fluoro-6-(1-methyl-1H-pyrazol-4-yl)-[1,2,4]triazolo[4,3-a]pyridin-3-yl)methyl)quinoline (10 mg, 20 µmol) was added trifluoroacetic acid (1.5 mL, 20 mmol). The resulting solution was heated at 65° C. for 18 h. The solution was concentrated for purification by MPLC using 98:2 CH$_2$Cl$_2$: MeOH to 90:10 CH$_2$Cl$_2$: MeOH gradient to afford 6-(difluoro(8-fluoro-6-(1-methyl-1H-pyrazol-4-yl)-[1,2,4]triazolo[4,3-a]pyridin-3-yl)methyl)quinolin-3-ol (3.6 mg, 44% yield) as a colorless solid. LRMS (ESI) m/z calcd for C$_{20}$H$_{14}$F$_3$N$_6$O (M+H) 411.1. found 411.3.

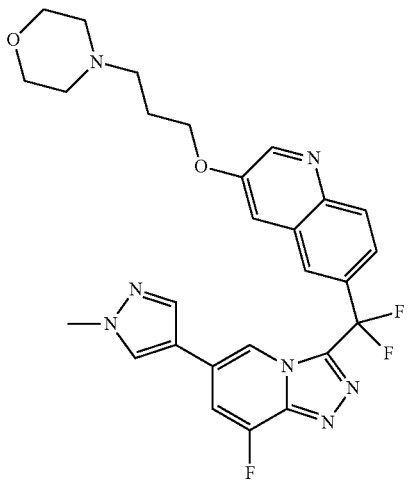 [SMILES: Cn1cc(-c2cc(F)c3nnc(C(F)(F)c4ccc5ncc(OCCCN6CCOCC6)cc5c4)n3c2)cn1]

EXAMPLE 462

6-(difluoro(8-fluoro-6-(1-methyl-1H-pyrazol-4-yl)-[1,2,4]-triazolo[4,3-a]pyridin-3-yl)methyl)-3-(3-morpholinopropoxy)quinoline To a flask charged with 6-(difluoro(8-fluoro-6-(1-methyl-1H-pyrazol-4-yl)-[1,2,4]triazolo[4,3-a]pyridin-3-yl)methyl)quinolin-3-ol (17.3 mg, 42 µmol), was added triphenylphosphine (55 mg, 211 µmol), THF (1 mL), and 4-(3-hydroxypropyl)-morpholine, 95% (31 µl, 211 µmol). The mixture was placed under N$_2$ and cooled to 0° C. Di-tert-butyl azodicarboxylate (49 mg, 211 µmol) was added as a solid in a single portion and the solution was allowed to warm to rt and was maintained for 48 h. The solution was concentrated for purification by MPLC (Teledine Isco combiFlash Companion). The crude residue was taken up in minimal CH$_2$Cl$_2$ and absorbed onto a 5 g loading cartridge and passed through a Redi-Sep® pre-packed silica gel column (40 g) using 99:1 CH$_2$Cl$_2$: MeOH to 90:10 CH$_2$Cl$_2$: MeOH gradient to afford 6-(difluoro(8-fluoro-6-(1-methyl-1H-pyrazol-4-yl)-[1,2,4]triazolo[4,3-a]pyridin-3-yl)methyl)-3-(3-morpholinopropoxy)quinoline (7.5 mg, 33% yield) as a colorless solid. LRMS (ESI) m/z calcd for C$_{27}$H$_{27}$F$_3$N$_7$O$_2$ (M+H) 538.2. found 538.2.

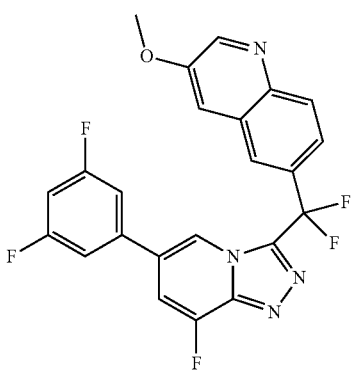 [SMILES: COc1cnc2ccc(C(F)(F)c3nnc4c(F)cc(-c5cc(F)cc(F)c5)cn34)cc2c1]

EXAMPLE 463

6-((6-(3,5-difluorophenyl)-8-fluoro-[1,2,4]triazolo[4,3-a]pyridin-3-yl)difluoromethyl)-3-methoxyquinoline

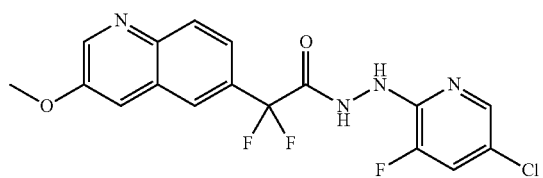 [SMILES: COc1cnc2ccc(C(F)(F)C(=O)NNc3ncc(Cl)cc3F)cc2c1]

a) N'-(5-chloro-3-fluoropyridin-2-yl)-2,2-difluoro-2-(3-methoxyquinolin-6-yl)acetohydrazide. This compound was assembled from 2,2-difluoro-2-(3-methoxyquinolin-6-yl) acetic acid and 1-(5-chloro-3-fluoropyridin-2-yl)hydrazine according to General Method I. LRMS (ESI) m/z calcd for $C_{17}H_{13}ClF_3N_4O_2S$ (M+H) 397.1. found 397.2.

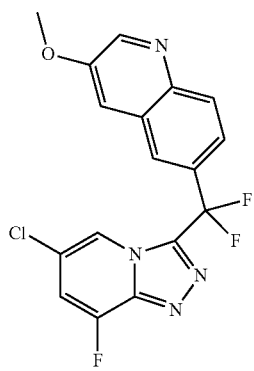 [SMILES: COc1cnc2ccc(C(F)(F)c3nnc4c(F)cc(Cl)cn34)cc2c1]

b) 6-((6-chloro-8-fluoro-[1,2,4]triazolo[4,3-a]pyridin-3-yl)difluoromethyl)-3-methoxyquinoline. This compound was made from N'-(5-chloro-3-fluoropyridin-2-yl)-2,2-difluoro-2-(3-methoxyquinolin-6-yl)acetohydrazide according to General Method I. LRMS (ESI) m/z calcd for $C_{12}H_{11}ClF_3N_4O$ (M+H) 379.1. found 379.2.

c) 6-((6-(3,5-difluorophenyl)-8-fluoro-[1,2,4]triazolo[4,3-a]pyridin-3-yl)difluoromethyl)-3-methoxyquinoline. A sealable microwave vial was charged with 6-((6-chloro-8-fluoro-[1,2,4]triazolo[4,3-a]pyridin-3-yl)difluoromethyl)-3-methoxyquinoline (342.05 mg, 903 µmol), palladium(II) acetate (30 mg, 135 µmol), potassium phosphate (575 mg, 2709 mmol), 3,5-difluorophenylboronic acid (285 mg, 1806 µmol), and X-Phos (129 mg, 271 µmol). The tube was sealed, and flushed with $N_2$. Dioxane (9 mL), then $H_2O$ (1 mL) were added and the mixture was sparged with $N_2$ for 10 min, then heated at 100° C. for 24 h. The mixture was cooled to rt and concentrated absorbed onto a 5 g loading cartridge for MPLC purification using a 98:2 $CH_2Cl_2$: MeOH to 90:10 $CH_2Cl_2$: MeOH gradient to give 6-((6-(3,5-difluorophenyl)-8-fluoro-[1,2,4]triazolo[4,3-a]pyridin-3-yl)difluoromethyl)-3-methoxyquinoline (72 mg, 17% yield). LRMS (ESI) m/z calcd for $C_{23}H_{14}F_5N_4O$ (M+H) 457.1. found 457.0.

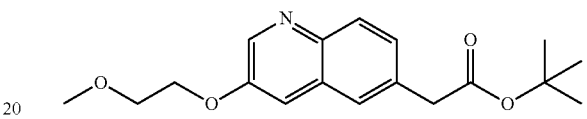

tert-butyl 2-(3-(2-methoxyethoxy)quinolin-6-yl)acetate

A flask was charged with tert-butyl 2-(3-hydroxyquinolin-6-yl)acetate (581.04 mg, 2.241 mmol) and triphenylphosphine (1.175 g, 4.482 mmol) then sealed with a septum and an placed under $N_2$. Benzene (10 mL) was added, followed by 2-methoxyethanol (0.8838 ml, 11.20 mmol). The heterogeneous solution was cooled to 0° C., and di-tert-butyl azodicarboxylate (1.032 g, 4.482 mmol) was added as a solid in a single portion. The solution was allowed to warm to rt and maintained 20 h. The solution was then partitioned between saturated aqueous. $NH_4Cl$, and the layers separated. The aqueous layer was extracted with EtOAc (2×50 mL), and the combined organic layers were washed with brine, dried (MgSO4), and concentrated in vacuo. The resulting residue was purified by MPLC (Teledine Isco combiFlash Companion), 80 g $SiO_2$, solvent system: 90:10 hexanes:EtOAc gradient to 50:50 hexanes:EtOAc to give tert-butyl 2-(3-(2-methoxyethoxy)quinolin-6-yl)acetate (585. 2 mg, 82% yield). LRMS (ESI) m/z calcd for $C_{18}H_{24}NO_4$ (M+H) 318.2. found 318.3.

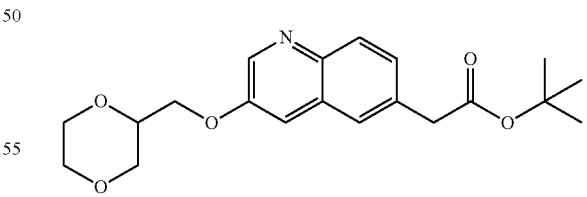

tert-butyl 2-(3-((1,4-dioxan-2-yl)methoxy)quinolin-6-yl)acetate (racemate)

The title compound was assembled from tert-butyl 2-(3-hydroxyquinolin-6-yl)acetate and (1,4-dioxan-2-yl)methanol according to the procedure described for tert-butyl 2-(3-(2-methoxyethoxy)quinolin-6-yl)acetate.

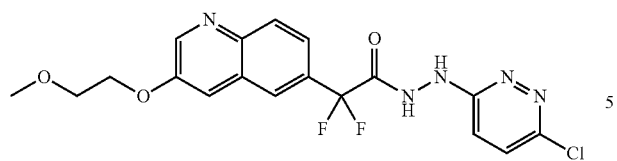

N'-(6-chloropyridazin-3-yl)-2,2-difluoro-2-(3-(2-methoxyethoxy)quinolin-6-yl)acetohydrazide The title compound was assembled from 1-(6-chloropyridazin-3-yl)hydrazine and tert-butyl 2-(3-(2-methoxyethoxy)quinolin-6-yl)acetate as described in General Method I. LRMS (ESI) m/z calcd for $C_{18}H_{12}ClF_2N_5O_3$ (M+H) 424.1. found 424.2.

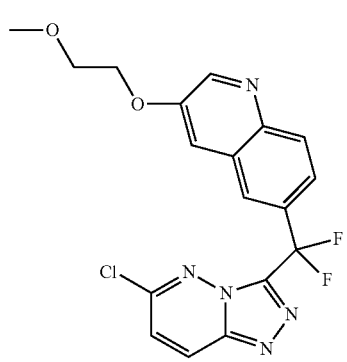 [SMILES: COCCOc1cnc2ccc(C(F)(F)c3nnc4ccc(Cl)nn34)cc2c1]

EXAMPLE 464

6-((6-chloro-[1,2,4]-triazolo[4,3-b]pyridazin-3-yl)difluoromethyl)-3-(2-methoxyethoxy)quinoline A sealable microwave vial was charged with N'-(6-chloropyridazin-3-yl)-2,2-difluoro-2-(3-(2-methoxyethoxy)quinolin-6-yl)acetohydrazide (46.98 mg, 111 μmol), 1,2-dimethoxyethane (1.5 mL), and 1 drop of conc. HCl. The vial was sealed and heated at 130° C. for 40 min. The solution was concentrated and purified by MPLC (Teledine Isco combi-Flash Companion). The residue was taken up in minimal $CH_2Cl_2$ and absorbed onto a 5 g loading cartridge and passed through a Redi-Sep® pre-packed silica gel column (12 g) using 98:2 $CH_2Cl_2$: MeOH to 90:10 $CH_2Cl_2$: MeOH to afford 6-((6-chloro-[1,2,4]triazolo[4,3-b]pyridazin-3-yl)difluoromethyl)-3-(2-methoxyethoxy)quinoline (25.3 mg, 56.2% yield) as a colorless solid. LRMS (ESI) m/z calcd for $C_{18}H_{15}ClF_2N_5O_2$ (M+H) 406.1. found 406.2.

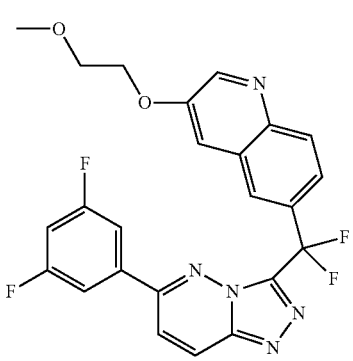 [SMILES: COCCOc1cnc2ccc(C(F)(F)c3nnc4ccc(-c5cc(F)cc(F)c5)nn34)cc2c1]

EXAMPLE 465

6-((6-(3,5-difluorophenyl)-[1,2,4]triazolo[4,3-b]pyridazin-3-yl)difluoromethyl)-3-(2-methoxyethoxy)quinoline The title compound was synthesized from 6-((6-chloro-[1,2,4]triazolo[4,3-b]pyridazin-3-yl)difluoromethyl)-3-(2-methoxyethoxy)quinoline and 3,5-difluorophenylboronic acid in a similar manner as that described for 6-((6-(3,5-difluorophenyl)-8-fluoro-[1,2,4]triazolo[4,3-a]pyridin-3-yl)difluoromethyl)-3-methoxyquinoline. LRMS (ESI) m/z calcd for $C_{24}H_{18}F_4N_5O_2$ (M+H) 484.1. found 484.2.

General Method J

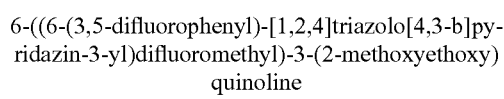

known compound

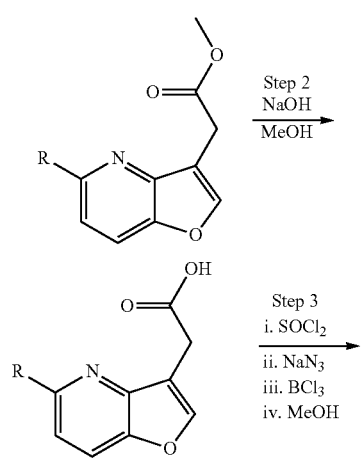

-continued

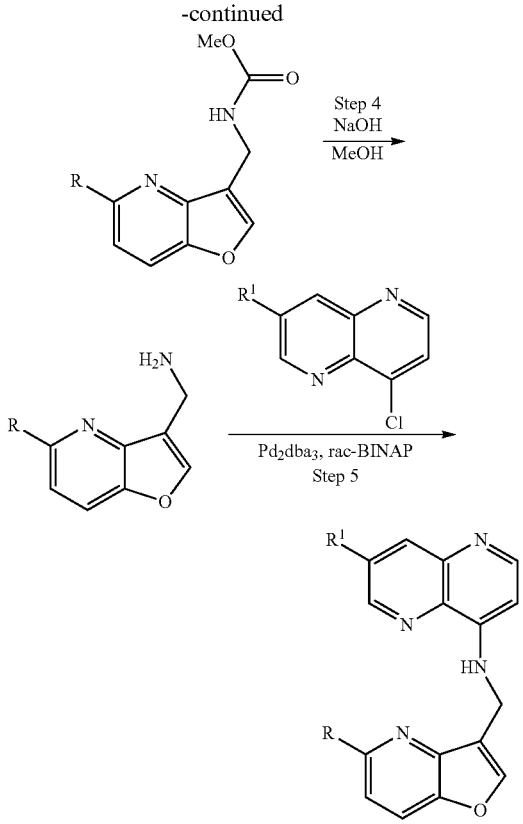

EXAMPLE 466

N-((5-(3,5-difluorophenyl)furo[3,2-b]pyridin-3-yl)methyl)-7-methoxy-1,5-naphthyridin-4-amine

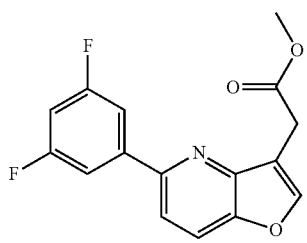 [SMILES: COC(=O)Cc1coc2ccc(-c3cc(F)cc(F)c3)nc12]

1) methyl 2-(5-(3,5-difluorophenyl)furo[3,2-b]pyridin-3-yl)acetate

A sealable microwave vial was charged with methyl 2-(5-chlorofuro[3,2-b]pyridin-3-yl)acetate (1.30 g, 5.74 mmol), palladium(II) acetate (0.129 g, 0.574 mmol), potassium phosphate (3.66 g, 17.2 mmol), 3,5-difluorophenylboronic acid (1.81 g, 11.5 mmol), and X-Phos (0.548 g, 1.15 mmol). The vial was sealed, flushed with $N_2$, then dioxane (20 mL) and $H_2O$ (2 mL) were added. The solution was sparged with $N_2$ for 10 min, then heated at 100° C. for 24 h. The mixture was then cooled to rt and concentrated for purification by MPLC (Teledine Isco combiFlash Companion). The crude residue was taken up in minimal $CH_2Cl_2$ and absorbed onto a 25 g loading cartridge and passed through a Redi-Sep® prepacked silica gel column (120 g) using 98:2 Hexanes:EtOAc to 70:30 Hexanes:EtOAc gradient to afford methyl 2-(5-(3,5-difluorophenyl)furo[3,2-b]pyridin-3-yl)acetate (1.46 g, 83.8% yield) as a colorless amorphous solid. LRMS (ESI) m/z calcd for $C_{16}H_{12}F_2NO_3$ (M+H) 304.1. found 304.2.

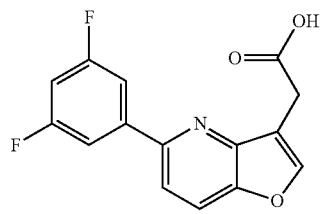 [SMILES: O=C(O)Cc1coc2ccc(-c3cc(F)cc(F)c3)nc12]

2) 2-(5-(3,5-difluorophenyl)furo[3,2-b]pyridin-3-yl)acetic acid

To a flask charged with methyl 2-(5-(3,5-difluorophenyl)furo[3,2-b]pyridin-3-yl)acetate (1.46 g, 5 mmol) was added MeOH (1.5 mL), $H_2O$ (0.5 mL), followed by NaOH (2 mL, 6 M, 12 mmol) to generate a yellow solution, which was capped and maintained at rt for 18 h. The solution was acidified with conc. HCl to pH=3 and poured into $CH_2Cl_2$. The layers were separated and the organic layer was extracted with $CH_2Cl_2$ (2×10 mL), followed by EtOAc (2×10 mL). The combined organic extracts were dried over $Na_2SO_4$ and concentrated in vacuo to produce a colorless solid, which was of sufficient purity for use in the next step.

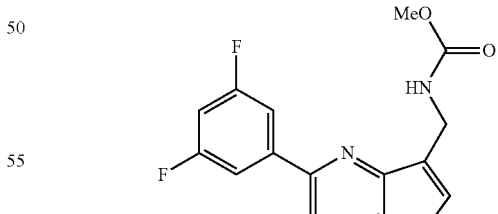

3) methyl (5-(3,5-difluorophenyl)furo[3,2-b]pyridin-3-yl)methylcarbamate

To a flask under $N_2$ charged with 2-(5-(3,5-difluorophenyl)furo[3,2-b]pyridin-3-yl)acetic acid (1.033 g, 3.57 mmol) was added anhydrous $CH_2Cl_2$ (40 mL). The heterogeneous solution was cooled to 0° C. and oxalyl chloride (1.6 mL, 17.8 mmol) was added, followed by a catalytic amount of DMF. The solution was warmed to rt and maintained for 1 h. The solution was concentrated, then taken up in anhydrous acetone and added to a stirring aqueous solution of sodium azide (1.62 g, 25.0 mmol, in 10 mL $H_2O$) at 0° C. to generate a homogeneous orange solution. After 15 min at 0° C., the mixture was diluted further with $CH_2Cl_2$ and stirred an additional 5 min to give a homogeneous solution. The solution was then partitioned between $H_2O$ and $CH_2Cl_2$, and the layers were separated. The aqueous layer was extracted with $CH_2Cl_2$ (2×10 mL) and the combined organic layers were dried ($Na_2SO_4$) and concentrated in vacuo. The residue was transferred to a dry flask, evacuated and flushed with $N_2$ (5×), and anhydrous $CH_2Cl_2$ (30 mL) was added. The solution was cooled to −78° C., and boron trichloride (5.4 mL, 5.4 mmol, 1.0 M in $CH_2Cl_2$) was added dropwise. The cold bath was removed and the solution was allowed to warm to rt, and maintained 48 h. Anhydrous methanol (5 mL) was added and the solution maintained at rt for 3 h at which time it was concentrated for purification by MPLC (Teledine Isco combiFlash Companion). The residue was taken up in minimal $CH_2Cl_2$ and absorbed onto a 25 g loading cartridge and passed through a Redi-Sep® pre-packed silica gel column (80 g) using 99:1 $CH_2Cl_2$: MeOH to 90:10:1 $CH_2Cl_2$: MeOH: $NH_4OH$ to afford methyl (5-(3,5-difluorophenyl)furo[3,2-b]pyridin-3-yl)methylcarbamate (680 mg, 60% yield) as a brown amorphous solid. LRMS (ESI) m/z calcd for $C_{16}H_{13}F_2N_2O_3$ $(M+H)$ 319.1. found 319.2.

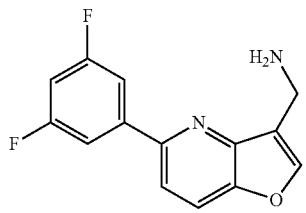 [SMILES: NCc1coc2ccc(-c3cc(F)cc(F)c3)nc12]

4) (5-(3,5-difluorophenyl)furo[3,2-b]pyridin-3-yl) methanamine

To a flask charged with methyl (5-(3,5-difluorophenyl)furo[3,2-b]pyridin-3-yl)methylcarbamate (680 mg, 2137 μmol) was added MeOH (20 mL), then aqueous NaOH (18 mL, 6 N, 106 mmol). The solution was heated at reflux for 60 h. The solution was concentrated to remove MeOH, then partitioned between $CH_2Cl_2$ (30 mL) and $NaHCO_3$ (10 mL). The layers were separated and the aqueous layer was extracted with $CH_2Cl_2$ (1×10 mL), then EtOAc (4×25 mL). The combined organic layers were concentrated to give a total of (5-(3,5-difluorophenyl)furo[3,2-b]pyridin-3-yl)methanamine (306.6 mg, 55% yield) as a brown foam. LRMS (ESI) m/z calcd for $C_{14}H_{11}F_2N_2O$ (M+H) 261.1. found 261.2.

5) N-((5-(3,5-difluorophenyl)furo[3,2-b]pyridin-3-yl)methyl)-7-methoxy-1,5-naphthyridin-4-amine A sealable microwave vial was charged with (5-(3,5-difluorophenyl)furo[3,2-b]pyridin-3-yl)methanamine (177.6 mg, 682 μmol), 8-chloro-3-methoxy-1,5-naphthyridine (146 mg, 751 μmol), and potassium phosphate (435 mg, 2047 μmol). A septum was attached and the vial was flushed with $N_2$, then toluene (5 mL) and H2O (1 mL) were added and the was solution sparged with $N_2$ for 5 min. The septum was then quickly removed and tris(dibenzylideneacetone)dipalladium (0) (15.6 mg, 17.1 μmol) and rac-2,2'-bis(diphenylphosphino)-1,1'-binaphthyl (42.5 mg, 68.2 μmol) were added together as solids. The vial was then sealed and the resulting purple solution was sparged again for 5 min. The mixture was then heated at 100° C. for 20 h. The mixture was concentrated in vacuo for purification by MPLC (Teledine Isco combiFlash Companion). The crude residue was taken up in minimal $CH_2Cl_2$ and absorbed onto a 25 g loading cartridge and passed through a Redi-Sep® pre-packed silica gel column (80 g) using 98:2 $CH_2Cl_2$: MeOH to 90:10 $CH_2Cl_2$: MeOH gradient to afford a tan amorphous solid. This solid was additionally triturated with $CH_2Cl_2$ (2×0.5 mL) to give N-((5-(3,5-difluorophenyl)furo[3,2-b]pyridin-3-yl)methyl)-7-methoxy-1,5-naphthyridin-4-amine (103 mg, 36.1% yield). LRMS (ESI) m/z calcd for $C_{23}H_{17}F_2N_4O_2$ (M+H) 419.1. found 419.2.

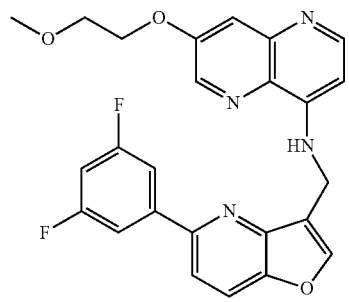 [SMILES: COCCOc1cnc2c(NCc3coc4ccc(-c5cc(F)cc(F)c5)nc34)ccnc2c1]

EXAMPLE 467

N-((5-(3,5-difluorophenyl)furo[3,2-b]pyridin-3-yl) methyl)-7-(2-methoxyethoxy)-1,5-naphthyridin-4-amine The title compound was assembled from (5-(3,5-difluorophenyl)furo[3,2-b]pyridin-3-yl)methanamine and 8-chloro-3-(2-methoxyethoxy)-1,5-naphthyridine in the manner described for 7-methoxy-N-((5-(3-methylisoxazol-5-yl)furo[3,2-b]pyridin-3-yl)methyl)-1,5-naphthyridin-4-amine LRMS (ESI) m/z calcd for $C_{25}H_{21}F_2N_4O_3$ (M+H) 463.2. found 463.2.

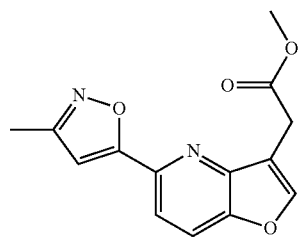 [SMILES: COC(=O)Cc1coc2ccc(-c3cc(C)no3)nc12]

Methyl 2-(5-(3-methylisoxazol-5-yl)furo[3,2-b]pyridin-3-yl)acetate

A sealable flask was charged with methyl 2-(5-chlorofuro[3,2-b]pyridin-3-yl)acetate, palladium (II) acetate (49.8 mg, 222 μmol), X-Phos (211 mg, 443 μmol), and 3-methyl-5-(tributylstannyl)isoxazole (1319 mg, 3546 μmol). The flask was sealed and dioxane (20 mL) was added. The mixture was sparged with $N_2$ for 10 min, then heated at 100° C. for 48 h.

The mixture was cooled to rt and concentrated for purification by MPLC (Teledine Isco combiFlash Companion). The crude residue was taken up in minimal CH$_2$Cl$_2$ and absorbed onto a 25 g loading cartridge and passed through a Redi-Sep® pre-packed silica gel column (40 g) using 98:2 CH$_2$Cl$_2$: MeOH to 90:10 CH$_2$Cl$_2$: MeOH to afford methyl 2-(5-(3-methylisoxazol-5-yl)furo[3,2-b]pyridin-3-yl)acetate (581 mg, 96.3% yield). LRMS (ESI) m/z calcd for C$_{14}$H$_{13}$N$_2$O$_4$ (M+H) 273.1. found 273.3.

| Ex | Structure | MW (M + H) | Mass Found | Method |
|---|---|---|---|---|
| 468 | | 426 | 426 | I |
| 469 | | 442 | 442 | I |
| 470 | | 396 | 396 | I |
| 471 | 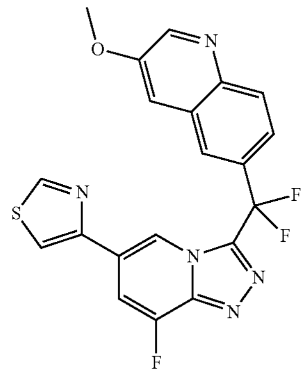 [SMILES: COc1cnc2ccc(C(F)(F)c3nnc4c(F)cc(-c5cscn5)cn34)cc2c1] | 428 | 428 | I |
| 472 | 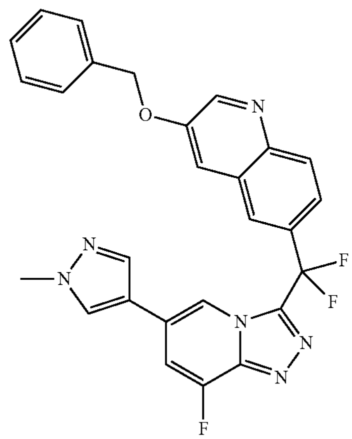 [SMILES: Cn1cc(-c2cc(F)c3nnc(C(F)(F)c4ccc5ncc(OCc6ccccc6)cc5c4)n3c2)cn1] | 501 | 501 | I |
| 473 | 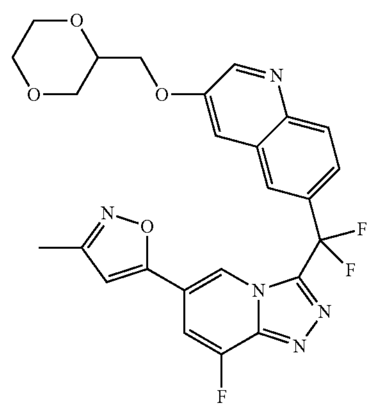 [SMILES: Cc1cc(-c2cc(F)c3nnc(C(F)(F)c4ccc5ncc(OCC6COCCO6)cc5c4)n3c2)on1] | 512 | 512 | I |
| 474 | 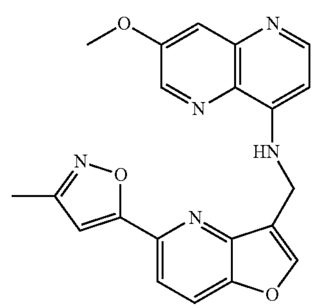 [SMILES: COc1cnc2c(NCc3coc4ccc(-c5cc(C)no5)nc34)ccnc2c1] | 388 | 388 | J |

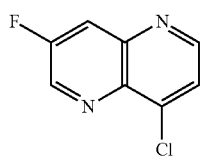

8-chloro-3-fluoro-1,5-naphthyridine 1) 5-((5-fluoropyridin-3-ylamino)methylene)-2,2-dimethyl-1,3-dioxane-4,6-dione A 150 mL sealed tube was charged with 2,2-dimethyl-1,3-dioxane-4,6-dione (6.0 g, 41.6 mmol) and trimethyl orthoformate (41.6 mL, 41.6 mmol). This was heated to 100° C., and stirred at this temperature for 2 hours. Reaction then cooled to 30° C. and 5-fluoropyridin-3-amine (4.7 g, 41.6 mmol) added portion-wise. Reaction vessel resealed and mixture stirred at 100° C. for 3 hours. LC/MS shows completion. Reaction mixture was cooled to room temperature, diluted with hexane, filtered, and air dried to yield 5-((5-fluoropyridin-3-ylamino)methylene)-2,2-dimethyl-1,3-dioxane-4,6-dione (9.1 g, 82% yield) as a bright yellow solid. MS [M+H]=267.2. Calc'd for $C_{12}H_{11}FN_2O_4$=266.2.

2) 7-fluoro-1,5-naphthyridin-4(1H)-one

A 500 mL round bottom flask equipped with a reflux condenser was charged with 5-((5-fluoropyridin-3-ylamino)methylene)-2,2-dimethyl-1,3-dioxane-4,6-dione (8.0 g, 30.0 mmol) and diphenyl ether (83.5 mL). This was heated to 250° C. in heating mantle and allowed to stay at this temperature for five minutes. Cooled to room temperature, diluted with hot hexanes, and filtered to afford 7-fluoro-1,5-naphthyridin-4(1H)-one (2.2 g, 45% yield) as a crude brown solid. The title compound was used without further purification. MS [M+H]=165.2, Calc'd for $C_8H_5FN_2O$=164.14.

3) 8-chloro-3-fluoro-1,5-naphthyridine

A pressure resistant vial was charged with 7-fluoro-1,5-naphthyridin-4(1H)-one (600 mg, 3.66 mmol) and POCl$_3$ (6.8 mL, 73.1 mmol). Vessel sealed and stirred at 110° C. for 16 hrs. Reaction mixture was cooled to room temperature and poured onto ice while stirring vigorously. While keeping reaction mixture at 0° C., it was basified to pH~8 with 6N NaOH. Product extracted with dichloromethane. Organic layer collected, dried over sodium sulfate and concentrated to afford desired material. This was passed through a silica plug in 1-5% (90:10:1 DCM/MeOH/NH$_4$OH)/DCM to afford 8-chloro-3-fluoro-1,5-naphthyridine (430 mg, 64% yield) as a tan solid. MS [M+H]=182.9. Calc'd for $C_8H_4ClFN_2$=182.58

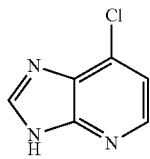

7-chloro-3H-imidazo[4,5-b]pyridine 1) 4-azabenzimidazole N-oxide

Hydrogen peroxide (30 wt % solution in water, 38.0 ml, 372 mmol) was added to a suspension of 3H-imidazo[4,5-b]pyridine (4.93 g, 41.4 mmol) in AcOH (40 mL) at room temperature. The resulting reaction mixture was stirred at 80° C. for 3 h, cooled to RT and concentrated in vacuo to a volume ~50 mL. Concentration to dryness was done using a stream of N$_2$. The resulting residue was suspended in water (~10 mL). Filtration afforded the title compound (4.61 g, 82.4% yield).

2) 7-chloro-3H-imidazol-[4,5-b]pyridine

A 50 mL round bottom flask set up with a reflux condenser under nitrogen atmosphere was charged 4-azabenzimidazole N-oxide (1.2 g, 8.88 mmol) and 11 mL of DMF. This was heated to 50° C. and methanesulfonyl chloride (1.86 ml, 23.98 mmol) was added dropwise via syringe. The resulting mixture was heated to 80° C. and stirred at this temperature for 16 hours. This was cooled to room temperature and quenched with water (approximately 10 mL) and reaction mixture brought to pH 7 by adding 6N NaOH aqueous solution. The reaction was extracted four times with dichloromethane (50 mL). Some product was present in aqueous layer; this was concentrated and residue set aside. The combined organic layers were dried with sodium sulfate, filtered, and concentrated. The material was purified via column chromatography (RediSep 40 g column, gradient elution 0-10% MeOH:DCM) to afford 7-chloro-3H-imidazo[4,5-b]pyridine (450 mg, 33.0% yield). MS [M+H]=154.2. Calc'd $C_6H_4ClN_3$=153.56.

8-chloro-1,5-naphthyridin-3-ol

A pressure-resistant vial was charged with 8-chloro-3-methoxy-1,5-naphthyridine (2.5 g, 12.8 mmol), boron tribromide (13.4 mL, 141.3 mmol) and dichloroethane (0.6M, 21.4 mL). Vessel sealed and mixture stirred at 60° C. for 16 hrs. Next day the reaction mixture was chilled in ice bath and diluted with dichloromethane (200 mL). This was allowed to sit under nitrogen system until all fuming ceased. The resulting yellow solid material was then filtered and dried under high vacuum. This was suspended in 40% (90:10:1 DCM/MeOH/NH4OH)/DCM and purified in this system by ISCO silica gel chromatography (80 g) afford 8-chloro-1,5-naphthyridin-3-ol (1.3 g, 56% yield). MS [M+H]=181.2. Calc'd for $C_8H_5ClN_2O$=180.59.

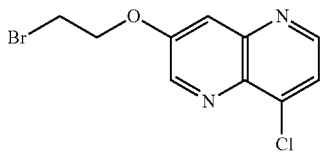 [SMILES: Clc1ccnc2cc(OCCBr)cnc12]

3-(2-bromoethoxy)-8-chloro-1,5-naphthyridine

A resealable pressure bottle was charged with 8-chloro-1,5-naphthyridin-3-ol (400 mg, 2.2 mmol), 2-dibromoethane (3.2 mL, 37.7 mmol), and DMF (0.15M, 14.8 mL). Vessel sealed and placed in a pre-heated at 65° C. oil bath. Reaction allowed to stir at this temperature for 4 hrs. Reaction cooled to room temperature and passed through a pad of celite. Filtrate concentrated and purified by ISCO silica gel chromatography (20-40% EtOAc/Hexanes) to afford 3-(2-bromoethoxy)-8-chloro-1,5-naphthyridine (460 mg, 72% yield). MS [M+H]= 289.0 Calc'd for $C_{10}H_8BrClN_2O$=287.54

The following compound was prepared using the procedure for 3-(2-bromoethoxy)-8-chloro-1,5-naphthyridine:
8-chloro-3-((tetrahydrofuran-2-yl)methoxy)-1,5-naphthyridine;
8-chloro-3-((tetrahydrothiophen-1,1-dioxide-3-yl)methoxy)-1,5-naphthyridine (starting with the alkyl chloride).

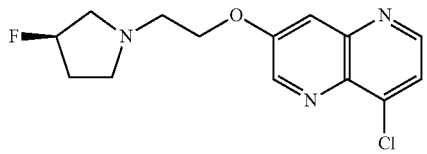 [SMILES: F[C@@H]1CCN(CCOc2cnc3c(Cl)ccnc3c2)C1]

(R)-8-chloro-3-(2-(3-fluoropyrrolidin-1-yl)ethoxy)-1,5-naphthyridine

A 25 mL round bottom flask at rt was charged with (R)-3-fluoropyrrolidine hydrochloride (124 mg, 0.99 mmol). To this was added potassium carbonate (365 mg, 2.64 mmol), 3-(2-bromoethoxy)-8-chloro-1,5-naphthyridine (190 mg, 0.66 mmol), sodium iodide (149 mg, 0.99 mmol) and DMF (2 mL). Reaction mixture placed in oil bath preheated to 60° C. and allowed to stir for 16 hrs. Reaction mixture passed through celite cake, rinsed with 10% MeOH/DCM and filtrate concentrated to afford yellow oil. This was purified by ISCO silica gel chromatography (20-40% EtOAC/Hexanes) to afford (R)-8-chloro-3-(2-(3-fluoropyrrolidin-1-yl)ethoxy)-1,5-naphthyridine (105 mg, 54% yield). MS [M+H]=296.2. Calc'd for $C_{14}H_{15}ClFN_3O$=295.7.

The following compounds were prepared in a similar fashion as 8-chloro-3-(2-(3-fluoropyrrolidin-1-yl)ethoxy)-1,5-naphthyridine:
8-chloro-3-(2-(3-fluoropyrrolidin-1-yl)ethoxy)-1,5-naphthyridine;
8-chloro-3-(2-(3,3-difluoropyrrolidin-1-yl)ethoxy)-1,5-naphthyridine;
1-(2-(8-chloro-1,5-naphthyridin-3-yloxy)ethyl)pyrrolidin-3-ol;
3-(2-(1H-1,2,4-triazol-1-yl)ethoxy)-8-chloro-1,5-naphthyridine (using NaH as the base);
3-(2-(1H-pyrazol-1-yl)ethoxy)-8-chloro-1,5-naphthyridine;
3-(2-(1H-1,2,3-triazol-1-yl)ethoxy)-8-chloro-1,5-naphthyridine.

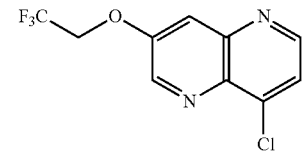 [SMILES: FC(F)(F)COc1cnc2c(Cl)ccnc2c1]

8-chloro-3-(2,2,2-trifluoroethoxy)-1,5-naphthyridine

A resealable pressure bottle was charged with 8-chloro-1,5-naphthyridin-3-ol (80 mg, 0.44 mmol), cesium carbonate (433 mg, 1.3 mmol), 2,2,2-trifluoroethyl trifluoromethanesulfonate (360 mg, 1.55 mmol), and DMF (0.9 ml). Vessel sealed and placed in a pre-heated at 50° C. oil bath. Reaction allowed to stir at this temperature for 45 minutes. LC/MS shows complete conversion. Quench with water, dilute with aqueous sodium bicarbonate solution and dichloromethane. Layers separated, organic layer collected and dried over sodium sulfate. This was concentrated to afford yellow oil; which was purified by ISCO silica gel chromatography (20-40% EtOAc/Hexanes) to afford 8-chloro-3-(2,2,2-trifluoroethoxy)-1,5-naphthyridine (65 mg, 56% yield). MS [M+H]= 263.0@1.89 minutes. Calc'd for $C_{10}H_6ClF_3N_2O$=262.6.

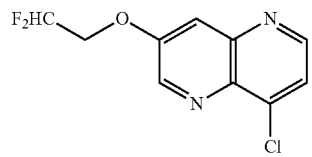 [SMILES: FC(F)COc1cnc2c(Cl)ccnc2c1]

8-chloro-3-(2,2-difluoroethoxy)-1,5-naphthyridine

The title compound was prepared using the method described for 8-chloro-3-(2,2,2-trifluoroethoxy)-1,5-naphthyridine.

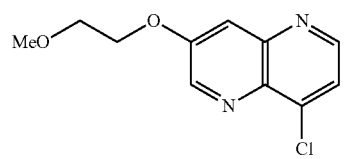 [SMILES: COCCOc1cnc2c(Cl)ccnc2c1]

8-chloro-3-(2-methoxyethoxy)-1,5-naphthyridine

A round bottom flask under nitrogen environment was charged with 8-chloro-1,5-naphthyridin-3-ol (1.05 g, 5.8 mmol), 22.8 g of PS-Triphenylphosphine (loading: 2.2 mmol/g), 2-methoxyethanol (2.2 mL, 27.9 mmol), and THF (29.1 ml, 5814 mmol)/DCM (58.1 mL). Mixture cooled to 0° C. and to this was added DEAD (1.84 mL) dropwise via syringe. Reaction mixture allowed to stir at room temperature for 16 hours. Diluted with 50 mL of 10% MeOH/dichloromethane and resin bound reagent filtered. Filtrate concentrated under reduced pressure and purified by ISCO silica gel chromatography (10-30% EtOAc/Hexanes) to afford 8-chloro-3-(2-methoxyethoxy)-1,5-naphthyridine (770 mg, 55% yield) as white solid. MS [M+H]=238.9. Calc'd for $C_{11}H_{11}ClN_2O_2$=238.67.

The following compounds were prepared in a similar fashion as 8-chloro-3-(2-methoxyethoxy)-1,5-naphthyridine:
8-chloro-3-(2-(pyrrolidin-1-yl)ethoxy)-1,5-naphthyridine;
8-chloro-3-(3-morpholinopropoxy)-1,5-naphthyridine;
3-((1,4-dioxan-2-yl)methoxy)-8-chloro-1,5-naphthyridine;
8-chloro-3-(pyrrolidin-2-ylmethoxy)-1,5-naphthyridine.

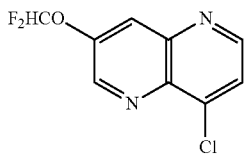 [SMILES: FC(F)Oc1cnc2c(Cl)ccnc2c1]

8-chloro-3-(difluoromethoxy)-1,5-naphthyridine

A round bottom flask under nitrogen atmosphere was charged with sodium 2-chloro-2,2-difluoroacetate (0.49 g, 3.2 mmol), 8-chloro-1,5-naphthyridin-3-ol (0.25 g, 1.4 mmol), cesium carbonate (1.4 g, 4.2 mmol), and DMF (2.8 mL, 0.5M). This was then placed in a 100° C. preheated oil bath and stirred at this temperature for 3 hours. Reaction mixture diluted with 10% Methanol/Dichloromethane and filtered over celite. Filtrate concentrated and purified by ISCO silica gel chromatography (40 g) in 1% MeOH/DCM to afford pure 8-chloro-3-(difluoromethoxy)-1,5-naphthyridine (0.18 g, 56% yield) as white solid. MS [M+H]=231.2. Calc'd for $C_9H_5ClF_2N_2O$=230.60.

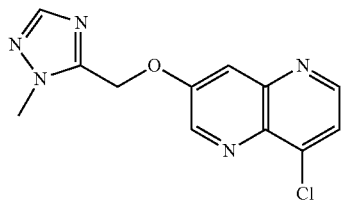 [SMILES: Cn1ncnc1COc1cnc2c(Cl)ccnc2c1]

8-chloro-3-((2-methyl-2H-1,2,4-triazol-3-yl)methoxy)-1,5-naphthyridine 1) 2-methyl-2H-1,2,4-triazole-3-carbaldehyde A dry round bottom flask under nitrogen atmosphere was charged with 1-methyl-1H-1,2,4-triazole (1.0 g, 12.04 mmol) and THF (6.0 ml, 2M). This was cooled to 0° C. followed by addition of 2M solution of isopropylmagnesium chloride in THF (6.6 mL, 13.24 mmol) via syringe. Ice bath removed and reaction allowed to stir at room temperature for 1.5 hours. Reaction mixture cooled back to 0° C. and N,N-dimethylformamide (1.39 ml, 18.05 mmol) added dropwise via syringe. Reaction mixture allowed to warm up to room temperature over 1 hour and stirred at this temperature for 16 hours. Next day reaction mixture was quenched with 2N HCl and mixture diluted with dichloromethane. Layers separated, and aqueous layer neutralized with aq. sodium bicarbonate solution and extracted with dichloromethane. All organic layers combined, dried over sodium sulfate and concentrated at room temperature (most THF remains) to afford clear material. This was purified by ISCO silica gel chromatography (10-40% EtOAc/Hex) to afford 2-methyl-2H-1,2,4-triazole-3-carbaldehyde (1.0 g, 75% yield). Yield was estimated based on H'NMR. Product was isolated as a solution in EtOAc (did not remove all EtOAc due to volatility of aldehyde, b.p.~60° C.). MS [M+H]=112.2; MS [M+H+$H_2O$]=130.2@0.23 minutes. Calc'd for $C_4H_5N_3O$=111.10.

2) (2-methyl-2H-1,2,4-triazol-3-yl)methanol 2-methyl-2H-1,2,4-triazole-3-carbaldehyde (0.50 g, 4.50 mmol) in MeOH (10 mL) was treated with sodium borohydride (0.17 g, 4.50 mmol) at room temperature and allowed to stir for 2 hours. Reaction mixture was quenched with aqueous sodium bicarbonate solution, diluted with 10% MeOH/DCM, and organic layer collected. Aqueous layer was saturated with sodium sulfate and extracted with 50 mL of dichloromethane (3 times). Organic portions combined, dried over sodium sulfate and concentrated to ¼ volume at room temp. This was then diluted with ether, causing a precipitate to form. This was concentrated yielding 2-methyl-2H-1,2,4-triazol-3-yl)methanol as a foamy white solid (0.44 g, 86.4% yield). This was used 'as is' for next step.
MS [M+H]=114.2. Calc'd for $C_4H_2N_3O$=113.1.

3) 8-chloro-3-((2-methyl-2H-1,2,4-triazol-3-yl)methoxy)-1,5-naphthyridine

The title compound was prepared in a similar fashion as 8-chloro-3-(2-methoxyethoxy)-1,5-naphthyridine.

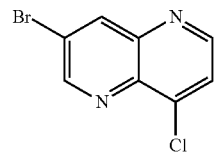 [SMILES: Clc1ccnc2cc(Br)cnc12]

3-bromo-8-chloro-1,5-naphthyridine 1) 5-((5-bromopyridin-3-ylamino)methylene)-2,2-dimethyl-1,3-dioxane-4,6-dione A 350 mL sealed tube was charged with 2,2-dimethyl-1,3-dioxane-4,6-dione (21.6 g, 150.0 mmol) and triethyl orthoformate (150 mL, 150.0 mmol). This was heated to 100° C., and stirred at this temperature for 2 hours. Reaction then cooled to 30° C. and 55-bromopyridin-3-amine (25.95 g, 150.0 mmol) added portion-wise. Reaction vessel resealed and mixture stirred at 100° C. for 3 hours. LC/MS shows completion. Reaction mixture was cooled to room temperature, diluted with hexane, filtered, and air dried to yield 5-((5-bromopyridin-3-ylamino)methylene)-2,2-dimethyl-1,3-dioxane-4,6-dione (41.5 g, 85% yield) as a yellow solid. MS [M+H]=327.0. Calc'd for $C_{12}H_{11}BrN_2O_4$=327.1.

2) 7-bromo-1,5-naphthyridin-4(1H)-one

A 500 mL round bottom flask equipped with a reflux condenser was charged with 5-((5-bromopyridin-3-ylamino)methylene)-2,2-dimethyl-1,3-dioxane-4,6-dione (10.5 g, 32.1 mmol) and diphenyl ether (84.5 mL, 32.1 mmol). This was heated to 250° C. in heating mantle and allowed to stay at this temperature for 1 hour. Reaction mixture was cooled to room temperature and diluted with 300 mL of Hexanes. This was heated to 60° C. and triturated in this system for 3 hrs to afford 7-bromo-1,5-naphthyridin-4(1H)-one (6.05 g, 84% yield) as a crude brown solid. This was used without further purification. MS[M+H]=227.0. Calc'd for $C_8H_5BrN_2O$=225.0.

3) 3-bromo-8-chloro-1,5-naphthyridine 7-bromo-1,5-naphthyridin-4(1H)-one (23.8 g, 105.8 mmol), acetonitriel (192 mL, 105.8 mmol), and DMF (2.05 mL, 26.5 mmol) were placed in a 3-necked round bottom flask set up with a reflux condenser. Argon bubbled through. Reaction mixture brought to reflux (~95° C.). Oxalyl chloride (28.7 ml, 328.1 mmol) was added dropwise via addition funnel over 40 minutes and reaction allowed to stir at this temperature for 16 hrs. Reaction mixture cooled to 0° C. and basified to pH ~8 with aqueous sodium bicarbonate solution. Product extracted with DCM (500 mL) three times. Organic layers combined, dried over sodium sulfate and concentrated to afford brown solid. This was purified by ISCO silica gel chromatography to afford 3-bromo-8-chloro-1,5-naphthyridine (3.6 g, 14% yield) as fluffy tan solid.

MS[M+H]=245.0@. Calc'd for $C_8H_4BrClN_2$=243.5.

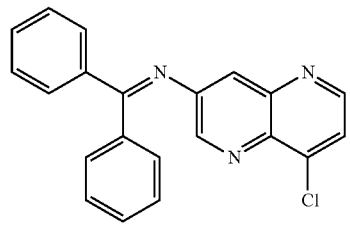 [SMILES: Clc1ccnc2cc(N=C(c3ccccc3)c3ccccc3)cnc12]

8-chloro-N-(diphenylmethylene)-1,5-naphthyridin-3-amine

A 25 ml round bottom flask set up under nitrogen was charged with $Pd_2(dba)_3$ (301 mg, 0.33 mmol), BINAP (614 mg, 0.99 mmol) and sodium tert-butoxide (237 mg, 2.46 mmol). System was purged with Argon and 3-bromo-8-chloro-1,5-naphthyridine (400 mg, 1.64 mmol), diphenylmethanimine (0.28 mL, 1.64 mmol), and toluene (1M, 1.64 mL) were added. This was placed in a preheated oil bath at 80° C. and stirred at this temperature for 16 hours. Reaction cooled to room temperature, diluted with dichloromethane, and passed over a celite cake. Filtrate collected was concentrated to afford brown oil. This was purified by ISCO silica gel chromatography (40 g, 1% MeOH/DCM over 50 mins) to afford clean 8-chloro-N-(diphenylmethylene)-1,5-naphthyridin-3-amine (280 mg, 50% yield). MS[M+H]=344.0. Calc'd for $C_{21}H_{14}ClN_3$=343.8.

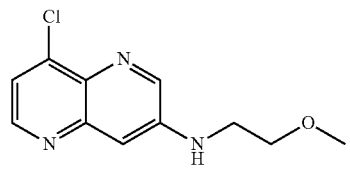 [SMILES: COCCNc1cnc2c(Cl)ccnc2c1]

8-chloro-N-(2-methoxyethyl)-1,5-naphthyridin-3-amine

1) 8-chloro-1,5-naphthyridin-3-amine

A round bottom flask under nitrogen was charged with 8-chloro-N-(diphenylmethylene)-1,5-naphthyridin-3-amine (315 mg, 0.92 mmol), 2M aqueous HCl (1.42 mL, 2.84 mmol), and tetrahydrofuran (0.25M, 3.67 mL). This was stirred at RT for 30 minutes. Reaction basified with aq. sodium bicarbonate solution and product extracted with dichloromethane. This was dried over sodium sulfate and concentrated to afford orange solid; which was purified via ISCO silica gel chromatography, 40 g column, 30% (90/10/1 DCM:MeOH:NH4OH)/DCM over 40 minutes to afford 7-amino-1,5-naphthyridin-4-ol (140 mg, 95% yield) as yellow solid. MS[M+H]=180.2. Calc'd for $C_8H_6ClN_3$=179.6.

2) 8-chloro-N-(2-methoxyethyl)-1,5-naphthyridin-3-amine

A round bottom flask under nitrogen atmosphere was charged with 8-chloro-1,5-naphthyridin-3-amine (160 mg, 0.89 mmol), DMF (2.2 mL, 0.89 mmol). This was cooled to 0° C. and SODIUM HYDRIDE (60% dispersion in oil) (107 mg, 4.45 mmol) added portionwise. This was quickly followed by addition of 1-bromo-2-methoxyethane (0.12 mL, 1.25 mmol) dropwise via syringe. Ice bath removed and reaction mixture heated to 85° C. and stirred at this temperature for 16 hours. Reaction diluted with 5 mL of 5% MeOH/Dichloromethane, loaded onto silica gel column and eluted with 2% MeOH/DCM to afford 8-chloro-N-(2-methoxyethyl)-1,5-naphthyridin-3-amine (70 mg, 33% yield) as a light yellow solid.

MS[M+H]=238.2. Calc'd for $C_{11}H_{12}ClN_3O$=237.7.

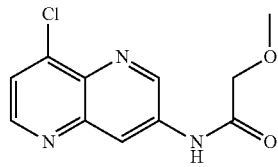 [SMILES: COCC(=O)Nc1cnc2c(Cl)ccnc2c1]

N-(8-chloro-1,5-naphthyridin-3-yl)-2-methoxyacetamide

A round bottom flask under nitrogen was charged with 8-chloro-1,5-naphthyridin-3-amine (41 mg, 0.23 mmol), triethylamine (64 μl, 0.46 mmol), and dichloromethane (1 mL). To this was added 2-methoxyacetyl chloride (42 μl, 0.46 mmol) dropwise via syringe and reaction allowed to stir overnight at room temperature. Next day reaction mixture was diluted with dichloromethane and washed with aqueous sodium bicarbonate solution. Layers separated and organic layer dried over sodium sulfate to afford yellow oil. This was purified by ISCO silica gel chromatography (2-5% MeOH/DCM) to afford N-(8-chloro-1,5-naphthyridin-3-yl)-2-methoxyacetamide (43 mg, 75% yield) as light yellow solid. MS[M+H]=251.9. Calc'd for $C_{11}H_{10}ClN_3O_2$=251.7.

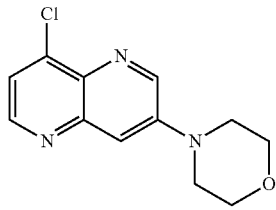 [SMILES: Clc1ccnc2cc(N3CCOCC3)cnc12]

8-chloro-3-morpholino-1,5-naphthyridine

A round bottom flask under nitrogen atmosphere was charged with $Pd_2(dba)_3$ (578 mg, 0.63 mmol), Xantphos (1.1 g, 1.89 mmol), and sodium tert-butoxide (364 mg, 3.79 mmol). This was purged with Argon followed by addition of 3-bromo-8-chloro-1,5-naphthyridine (615 mg, 2.53 mmol), morpholine (0.22 mL, 2.53 mmol), and toluene (1M, 2.53 mL). This was then placed in a preheated oil bath at 80° C. After 2.5 hours, reaction was stopped, cooled to room temp and diluted with Dichloromethane. This was passed over a celite cake and filtrate concentrated to afford brown oil; which was purified by ISCO silica gel chromatography (40 g, 1% MeOH/DCM over 50 mins) to afford 8-chloro-3-morpholino-1,5-naphthyridine (200 mg, 32% yield). MS[M+H]= 250.2. Calc'd for $C_{12}H_{12}ClN_3O$=249.7.

4-bromo-1-phenyl-1H-pyrazole

A sealable tube was charged with 4-bromopyrazole (4.000 g, 27.2 mmol), 1-iodobenzene (3.64 ml, 32.7 mmol), (+/−)-trans-1,2-diaminocyclohexane (0.654 ml, 5.44 mmol), Copper iodide (I) (0.518 g, 2.72 mmol), potassium carbonate (8.28 g, 59.9 mmol) and 13 mL dioxane added. The mixture was blanketed with N2, the vessel sealed and heated to 100 C for 16 h. The mixture was allowed to cool to rt, diluted with EtOAc, washed with water, and an emullsion formed. The organic layer separated and the aqueous emulsion mixture was filter through a pad of celite and rinsed with EtOAc, and sat. $NaHCO_3$. The combined organig layers were dried over $Na_2SO_4$, filtered and evaporate. The mixture was purified via flash chromatography using a 0% to 100% $CH_2Cl_2$ in hexanes gradient. The title compound was collected as a yellow solid (3.18 g)

1-phenyl-4-(4,4,5,5-tetramethyl-1,3,2-dioxaborolan-2-O-1H-pyrazole

The title compound was prepared in the same manner as 1-ethyl-4-(4,4,5,5-tetramethyl-1,3,2-dioxaborolan-2-yl)-1H-pyrazole starting with 4-bromo-1-phenyl-1H-pyrazole.

4-bromo-1-(tetrahydrofuran-3-yl)-1H-pyrazole

The title compound was prepared in the same manner as 4-bromo-1-(cyclobutyl)-1H-pyrazole, but using tetrahydrofuran-3-yl methanesulfonate (prepared according to procedures known in the art).

1-(tetrahydrofuran-3-O-4-(4,4,5,5-tetramethyl-1,3,2-dioxaborolan-2-O-1H-pyrazole The title compound was prepared in the same manner as 1-ethyl-4-(4,4,5,5-tetramethyl-1,3,2-dioxaborolan-2-yl)-1H-pyrazole starting with 4-bromo-1-(tetrahydrofuran-3-yl)-1H-pyrazole.

4-(4,4,5,5-tetramethyl-1,3,2-dioxaborolan-2-yl)-1-cyclopropyl-1H-pyrazole a) 1-cyclopropyl-1H-pyrazole. In a 1000 mL 3-neck flask, to a mixture of potassium hydroxide (104 g, 1857 mmol) in water (200 mL) was added cyclopropylamine (131 ml, 1857 mmol) and the mixture stirred at 50 C. A solution of hydroxylamine-O-sulfonic acid (HOS) (30.00 g, 265 mmol) in 100 mL water was added dropwise resulting in the formation of a white precipitate after the first few drops. The stirring stopped during the first half of the addition and some cyclopropylamine condensed on top of the HOS soln. Additional amine (10 mL) was added to the reaction and addition of HOS solution continuted. Mixture bubbles during the addition. The flask was remove from heat and cool in ice bath to 25 C. HCl (conc) was added slowly, 150-200 mL, to achieve PH 3. The mixture was filtered to remove the white solid and the filtrate heated with 1,1,3,3-tetramethoxypropane (43.7 ml, 265 mmol). The mixture took 1.5 h to reach 90 C, maintained the temperature at 90 for 1 h, then allowed the mixture to cool to 40 C with stirring for an additional 17 h. The mixture was allowed to cool to ~35 C and extracted with $Et_2O$ (400 mL then 2×100 mL), the combined organic layers were with water, 6N NaOH, 2N NaOH, then sat NaHCO3, and the organic layer dried over $Na_2SO_4$, filtered and evaporate gently. Upon evaporation, when volume is reduced from ~600 mL to ~100 mL, the white solid that has precipitated was filtered. The title compound was obtained as a golden liquid (~2 g).

b) 4-bromo-1-cyclopropyl-1H-pyrazole. To a golden solution of 1-cyclopropyl-1H-pyrazole (2.360 g, 22 mmol) in 100 mL chloroform, was added bromine (1.2 ml, 24 mmol) as a soln in 100 mL $CHCl_3$ dropwise over 1.5 h. the mixture was heated in oil bath to 60 C for 2 h. The mixture was allowed to cool to RT, washed with sat $NaHCO_3$, dried over $Na_2SO_4$, filtered and evaporated to afford the title compound as a tan liquid (3.64 g).

c) 4-(4,4,5,5-tetramethyl-1,3,2-dioxaborolan-2-yl)-1-cyclopropyl-1H-pyrazole.

The title compound was prepared in the same manner as 1-ethyl-4-(4,4,5,5-tetramethyl-1,3,2-dioxaborolan-2-yl)-1H-pyrazole starting with 4-bromo-1-cyclopropyl-1H-pyrazole.

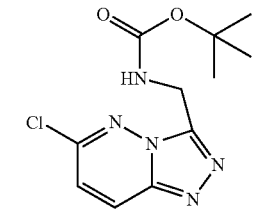 [SMILES: CC(C)(C)OC(=O)NCc1nnc2ccc(Cl)nn12]

tert-butyl (6-chloro-[1,2,4]triazolo[4,3-b]pyridazin-3-yl)methylcarbamate

A 2-L round bottom flask flask equipped with a magnetic stirbar was charged with di(1H-imidazol-1-yl)methanone (121 g, 749 mmol) and acetonitrile (500 mL). The stirred slurry was cooled by immersing the flask in an ice bath. A solution of N-Boc glycine (125 g, 714 mmol) in acetonitrile (500 mL) was added via a 500-mL addition funnel over the course of 30-45 min. The mixture was aged for 1 h while a 5-L, 3-neck, round bottom flask equipped with a mechanical overhead stirrer and a thermocouple w/adapter was charged with 1-(6-chloropyridazin-3-yl)hydrazine (108 g, 749 mmol) and acetonitrile (900 mL) and cooled to <5 deg C. in an ice bath. The cold solution of the acylimidazole was then transferred via a polyethylene cannula into the thick suspension of the hydrazine over a period of 30-45 min). The ice bath was removed, and the mixture was allowed to warm. After 2.5 h of stirring, 4-methylbenzenesulfonic acid hydrate (143 g, 749 mmol) was added. The flask was then equipped with a heating mantle and a reflux condenser and was heated to reflux (82 deg C.) for 13 h, then cooled back to about 60 deg C. At this point, the warm solution was vacuum filtered through paper. The brown filtrate was then concentrated by rotary evaporation. The resulting thick yellow-brown slurry was stirred in an ice bath and diluted with ACN (about 100 mL). After stirring for 1 h, the solids were isolated by vacuum filtration, washed with ice-cold 1:1 ACN/H$_2$O (2×150 mL) and air-dried on the filter until a freely flowing solid was obtained (159 g, 78.5% yield).

General Method K

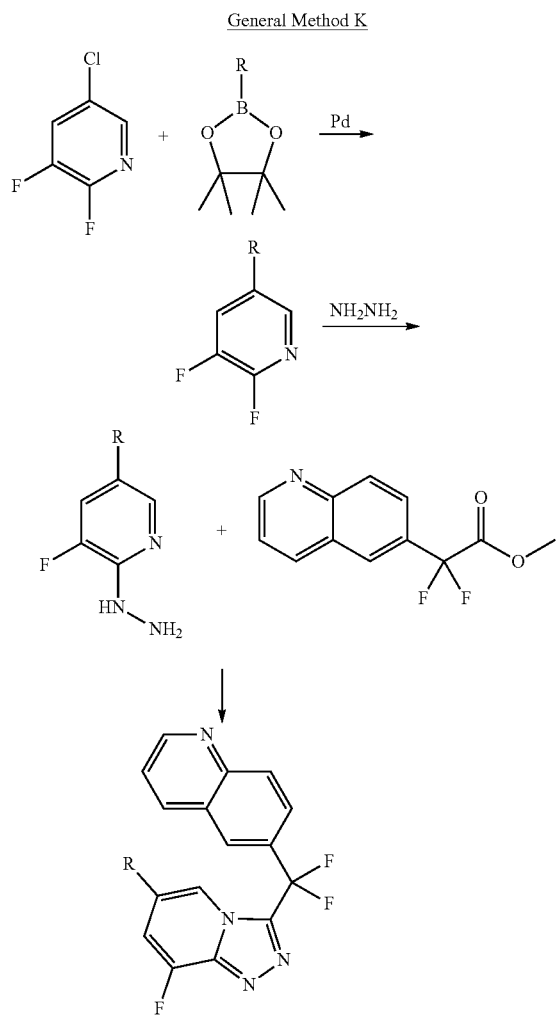

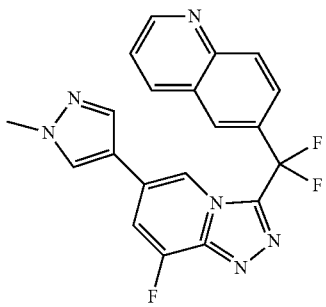

EXAMPLE 475

6-(Difluoro(8-fluoro-6-(1-methyl-1H-pyrazol-4-yl)-[1,2,4]-triazolo[4,3-a]pyridin-3-yl)methyl)quinoline To a stirring suspension of 1-(3-fluoro-5-(1-methyl-1H-pyrazol-4-yl)pyridin-2-yl)hydrazine (190 mg, 917 µmol), methyl 2,2-difluoro-2-(quinolin-6-yl)acetate (218 mg, 917 µmol), triphenylphosphine polymer supported (241 mg, 917 µmol), DIEA (200 µl, 1146 µmol) in DCM (4 mL) was added 2,2,2-trichloroacetonitrile (92 µl, 917 µmol). The reaction vessel was then appropriately sealed and heated to 150° C. with microwaves for 15 min. The reaction was then concentrated onto dry silica under reduced pressure and product purified on silica (40 g) eluting with 1-4% of 2 M NH$_3$ in MeOH/DCM. The product was then further purified by RP-HPLC eluting with water/ACN (0.1% TFA). Collected fractions concentrated under reduced pressure, dissolved in MeOH/DCM (5 mL) and stirred with Si-Carbonated (300 mg; 0.2 mmol) for 30 min at 23° C. Solids were then removed by filtration, and washed with MeOH (3×1 mL). The filtrate was then concentrated under reduced pressure, and product isolated as an off white solid. MS (ESI pos. ion) m/z: 395 (MH+). Calc'd exact mass for C$_{20}$H$_{13}$F$_3$N$_6$: 394.

General Method L

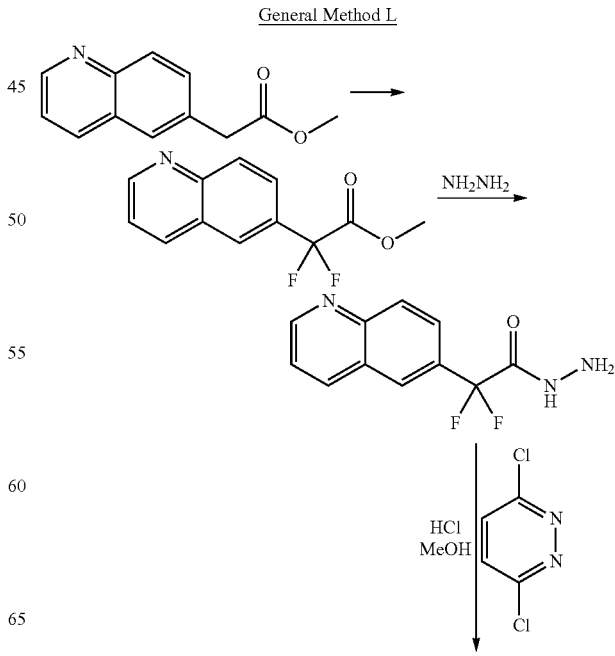

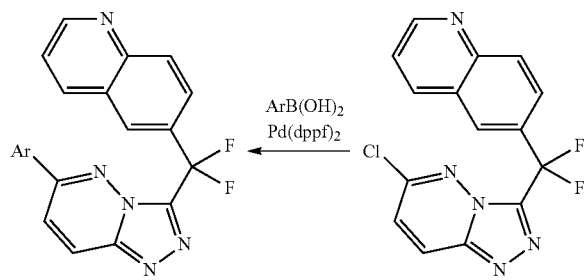

2,2-Difluoro-2-(quinolin-6-yl)acetohydrazide

A solution methyl 2,2-difluoro-2-(quinolin-6-yl)acetate (400 mg, 1686 mmol) and anhydrous hydrazine (2153 μl, 67453 mmol) in MeOH (4 mL) was stirred for 1 h at 23° C. The solvents were then removed under reduced pressure to provide product as a white solid. MS (ESI pos. ion) m/z: 238 (MH+). Calc'd exact mass for $C_{11}H_9F_2N_3O$: 237.

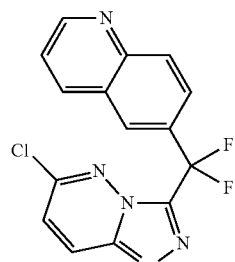

EXAMPLE 476

6-((6-chloro-[1,2,4]triazolo[4,3-b]pyridazin-3-yl)difluoromethyl)quinoline

A suspension of 2,2-difluoro-2-(quinolin-6-yl)acetohydrazide (2000 mg, 8432 μmol) and 3,6-dichloropyridazine (3768 mg, 25295 μmol) in 1.25 M HCl in MeOH (20 mL) was heated to 90° C. with microwaves for 50 min. The solvents were then removed under reduced pressure and residue partitioned between 9:1 CHCl$_3$/IPA (60 mL) and 1 M NaOH (20 mL). The organic phase then dried over MgSO$_4$, concentrated, then purified on silica (120 g) eluting with 1>2.5% of 2 M NH$_3$ in MeOH/DCM to provide product isolated as a dark tan solid. MS (ESI pos. ion) m/z: 332 (MH+). Calc'd exact mass for $C_{15}H_8ClF_2N_5$: 331.

| Ex | Structure | MW | Mass Found | Method |
|---|---|---|---|---|
| 477 | 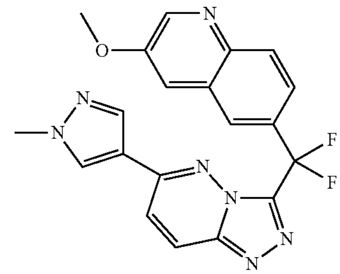 [SMILES: COc1cnc2ccc(C(F)(F)c3nnc4ccc(-c5cnn(C)c5)nn34)cc2c1] | 407 | 408 | L |
| 478 | 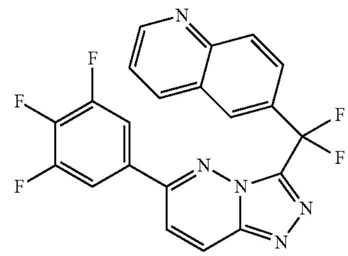 [SMILES: Fc1cc(-c2ccc3nnc(C(F)(F)c4ccc5ncccc5c4)n3n2)cc(F)c1F] | 427 | 428 | L |
| 479 | 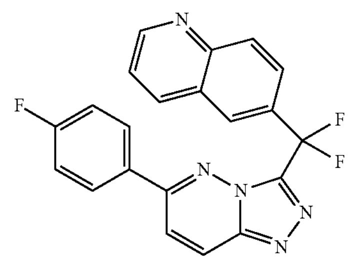 [SMILES: Fc1ccc(-c2ccc3nnc(C(F)(F)c4ccc5ncccc5c4)n3n2)cc1] | 391 | 392 | L |
| 480 | 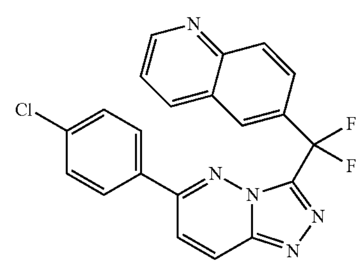 [SMILES: FC(F)(c1ccc2ncccc2c1)c1nnc2ccc(-c3ccc(Cl)cc3)nn12] | 407 | 408 | L |
| 481 | 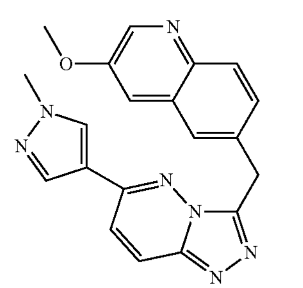 [SMILES: COc1cnc2ccc(Cc3nnc4ccc(-c5cnn(C)c5)nn34)cc2c1] | 371 | 372 | M |

-continued

| Ex | Structure | MW | Mass Found | Method |
|---|---|---|---|---|
| 482 | 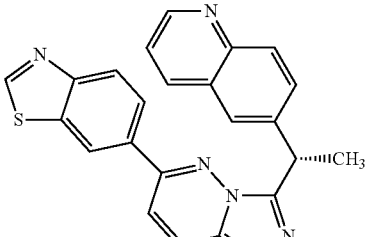 | 408 | 409 | M |
| 483 | 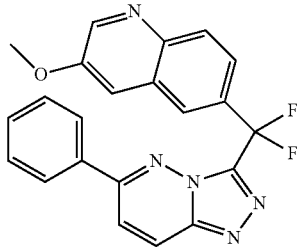 [SMILES: COc1cnc2ccc(C(F)(F)c3nnc4ccc(-c5ccccc5)nn34)cc2c1] | 403 | 404 | M |

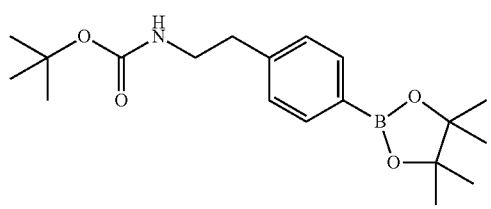 [SMILES: CC(C)(C)OC(=O)NCCc1ccc(B2OC(C)(C)C(C)(C)O2)cc1]

tert-Butyl 4-(4,4,5,5-tetramethyl-1,3,2-dioxaborolan-2-yl)phenethylcarbamate

A suspension of tert-butyl 4-bromophenethylcarbamate (2700 mg, 8994 µmol), bis(pinacolato)diboron (2284 mg, 8994 µmol), bis(pinacolato)diboron (2284 mg, 8994 µmol), potassium acetate (1765 mg, 17989 µmol) in dioxane (12 mL) was sparged with argon for 5 min then heated to 120° C. in an appropriately sealed vessel for 1 h. The reaction was then partitioned between ether (50 mL) and 5% NaHCO$_3$ (25 mL). The organic phase was then dried over MgSO$_4$, concentrated, then purified on silica (120 g) eluting with 10>30% EtOAc/Hexanes. The product tert-butyl 4-(4,4,5,5-tetramethyl-1,3,2-dioxaborolan-2-yl)phenethylcarbamate (2200 mg, 70% yield) was isolated as a white solid. MS (ESI pos. ion) m/z: 292 (MH+1-56). Calc'd exact mass for $C_{19}H_{30}BNO_4$: 347.

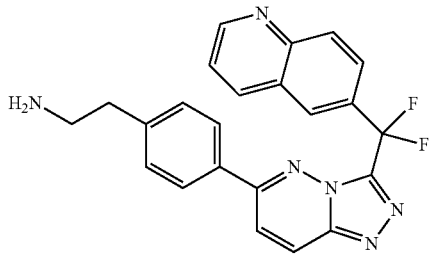 [SMILES: NCCc1ccc(-c2ccc3nnc(C(F)(F)c4ccc5ncccc5c4)n3n2)cc1]

EXAMPLE 484

2-(4-(3-(Difluoro(quinolin-6-yl)methyl)-[1,2,4]triazolo[4,3-b]pyridazin-6-yl)phenyl)ethanamine a) tert-Butyl 2-(4-(3-(difluoro(quinolin-6-yl)methyl)-[1,2,4]-triazolo[4,3-b]pyridazin-6-yl)phenyl)ethylcarbamate. A suspension of 6-((6-chloro-[1,2,4]triazolo[4,3-b]pyridazin-3-yl)difluoromethyl)quinoline (350 mg, 1055 µmol), tert-butyl 4-(4,4,5,5-tetramethyl-1,3,2-dioxaborolan-2-yl)phenethylcarbamate (733 mg, 2110 µmol), 1,1'-bis(diphenylphosphino)ferrocene-palladium(ii)dichloride dichloromethane complex (77 mg, 106 µmol), Na2CO3 (447 mg, 4221 µmol) in DME (4 mL) and water (2 mL) was sparged with argon for 5 min then heated to 85° C. in an appropriately sealed vessel for 4 h. The reaction was then partitioned between DCM (30 mL) and 1 M NaOH (10 mL). The organic phase was then dried over MgSO$_4$, concentrated, then purified on silica (40 g) eluting with 1>4% of 2 M NH$_3$ in MeOH/DCM. The product was isolated as an off white solid.

b) 2-(4-(3-(Difluoro(quinolin-6-yl)methyl)-[1,2,4]-triazolo[4,3-b]pyridazin-6-yl)phenyl)ethanamine A solution of tert-butyl 2-(4-(3-(difluoro(quinolin-6-yl)methyl)-[1,2,4]triazolo[4,3-b]pyridazin-6-yl)phenyl)ethylcarbamate (70 mg, 136 µmol) in DCM (1 mL) and TFA (1 mL) was stirred for 30 min at 23° C. The solvents were then removed under reduced pressure and crude product purified by RP-HPLC eluting with water/ACN (0.1% TFA). The desired collected fractions were then concentrated under reduced pressure and the resulting residue dissolved in MeOH/DCM (5 mL). Solution was then stirred as a suspension with Si-Carbonated (300 mg; 0.2 mmol) for 30 min at 23° C. The solids were then removed by filtration, washed with MeOH (3×1 mL), and filtrate concentrated under reduced pressure. The product was isolated as a white fluffy solid. MS (ESI pos. ion) m/z: 417 (MH+). Calc'd exact mass for $C_{23}H_{18}F_2N_6$: 416.

General Method M

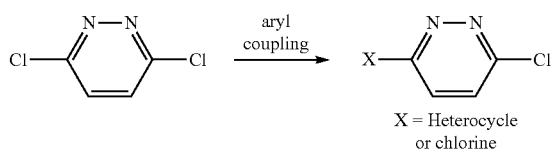

X = Heterocycle or chlorine

347

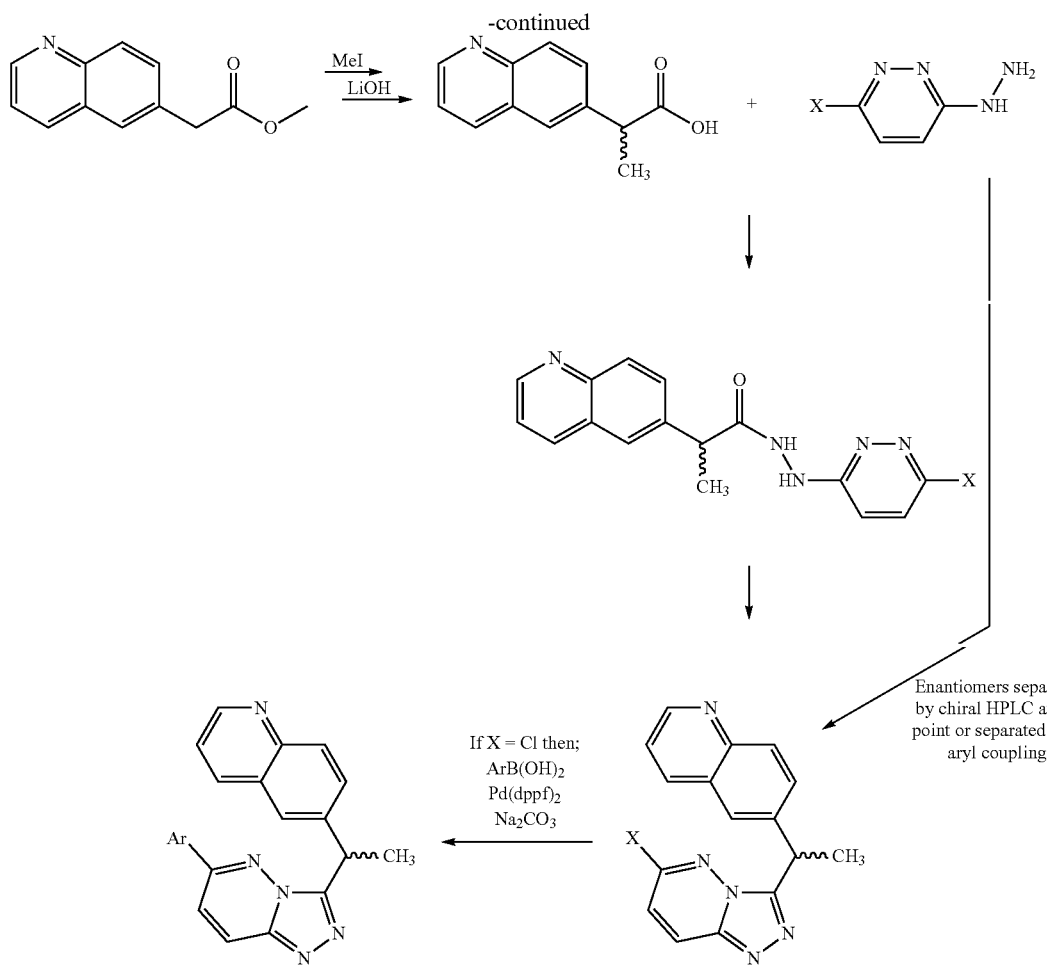

N'-(6-chloropyridazin-3-O-2-(quinolin-6-yl)propane-hydrazide

To a stirring solution of 2-(quinolin-6-yl)propanoic acid (3260 mg, 16201 μmol) and DIEA (2830 μl, 16201 μmol) in DMF (25 mL) was added o-(7-azabenzotriazol-1-yl)-n,n,n',n-tetramethyl uronium hexafluorophosphate (6160 mg, 16201 μmol) whole at 23° C. under nitrogen. The solution was stirred for 60 min, cooled to 0° C., then added 1-(6-chloropyridazin-3-yl)hydrazine (2342 mg, 16201 μmol). After 20 h stirring at 23° C., the reaction was then partitioned between 9:1 CHCl$_3$/IPA (100 mL) and 5% NaHCO$_3$ (50 mL). The organic phase was then dried over MgSO$_4$, concentrated to an oil, then purified on silica (120 g) eluting with 0>10% of 2 M NH$_3$ in MeOH/DCM. The product was isolated as an off white solid. MS (ESI pos. ion) m/z: 328 (MH+). Calc'd exact mass for C$_{16}$H$_{14}$ClN$_5$O: 327.

348

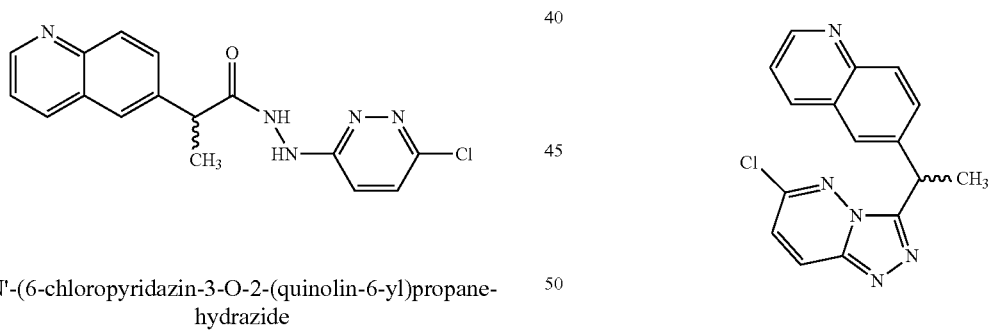

6-(1-(6-chloro-[1,2,4]triazolo[4,3-b]pyridazin-3-yl)ethyl)quinoline

A solution of N'-(6-chloropyridazin-3-yl)-2-(quinolin-6-yl)propanehydrazide (2700 mg, 8238 μmol) in TFA (20 mL) was heated to 120° C. with microwaves (2 bar; 10 watts) for 40 min. The solution was concentrated under reduced pressure then partitioned between 9:1 CHCl3/IPA (75 mL) and 1 M NaOH (100 mL). The aqueous layer was further extracted with 9:1 CHCl$_3$/IPA (2×20 mL). The combined organics were dried over MgSO$_4$ then concentrated to an amber oil under reduced pressure. The product was isolated as off white crystalline solid from ACN. MS (ESI pos. ion) m/z: 310 (MH+). Calc'd exact mass for C$_{16}$H$_{12}$ClN$_5$: 309. Enantiomer resolved with: Chiralpak AD-H (3×25 cm) column using 45% ethanol (0.1% DEA)/CO2

The following compounds were prepared using same method as tert-Butyl 2-(4-(3-(difluoro(quinolin-6-yl)methyl)-[1,2,4]triazolo[4,3-b]pyridazin-6-yl)phenyl)ethylcarbamate and resolved from racemic mixtures:

| Ex | Structure | MW | Mass Found | Peak # |
|---|---|---|---|---|
| 485 | 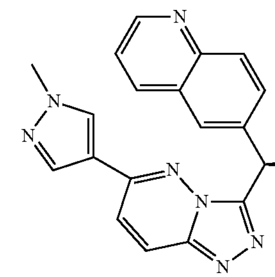 | 355 | 356 | 1 |
| 486 | 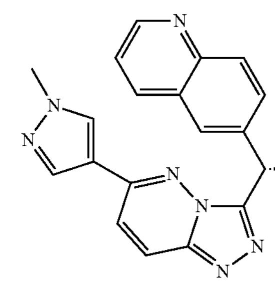 | 355 | 356 | 2 |
| 487 | 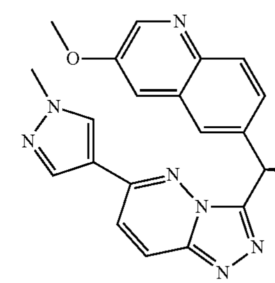 | 385 | 386 | 1 |
| 488 | 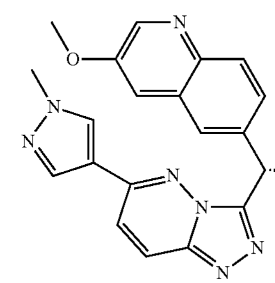 | 385 | 386 | 2 |
| 489 | 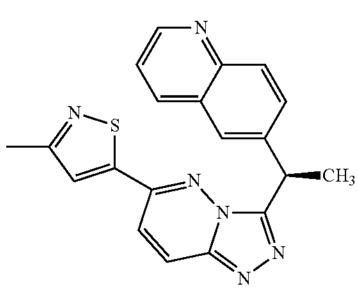 [SMILES: Cc1cc(-c2ccc3nnc([C@H](C)c4ccc5ncccc5c4)n3n2)sn1] | 372 | 373 | 1 |

-continued

| Ex | Structure | MW | Mass Found | Peak # |
|---|---|---|---|---|
| 490 | 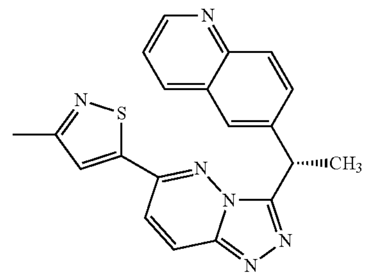 [SMILES: Cc1cc(-c2ccc3nnc([C@@H](C)c4ccc5ncccc5c4)n3n2)sn1] | 372 | 373 | 2 |

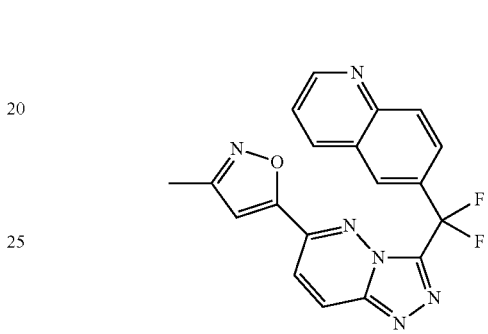

EXAMPLE 491

6-(difluoro(6-(3-methylisoxazol-5-yl)-[1,2,4]triazolo[4,3-b]pyridazin-3-yl)methyl)quinoline A suspension of 1-(6-(3-methylisoxazol-5-yl)pyridazin-3-yl)hydrazine hydrochloride (200 mg, 879 μmol) and methyl 2,2-difluoro-2-(quinolin-6-yl)acetate (208 mg, 879 μmol) in 5 M HCl (1 mL) was appropriately sealed and heated to 150° C. with microwaves for 4 h. The reaction was then quenched by a dropwise into cold 5 M NaOH (2 mL) and aqueous extracted with $CHCl_3$/IPA (25 mL). The organic phase was then dried over $MgSO_4$, concentrated, and purified with silica (40 g) eluting with 1>5% 2 M $NH_3$ in MeOH/DCM. The product was then further purified on RP-HPLC eluting with water/ACN (0.1% TFA). Combined fractions concentrated, dissolved in DCM (5 mL) and MeOH (5 mL), then stirred with Si-Carbonate (0.5 g; 35 mmol) for 1 h. Si-Carbonate removed by filtration and filtrated concentrated with <0.5 mL remaining with product isolated by trituration. MS (ESI pos. ion) m/z: 379 (MH+). Calc'd exact mass for $C_{19}H_{12}F_2N_6O$: 378.

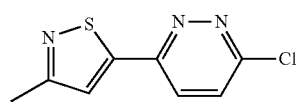

3-chloro-6-(3-methylisothiazol-5-yl)pyridazine

To a solution of 5-bromo-3-methylisothiazole (2.42 g, 14 mmol) in 20 mL of THF at −45° C. was added isopropylmagnesium chloride (19 ml, 19 mmol) in THF (1 M). After 20 minutes, zinc(II) chloride (41 ml, 20 mmol) in THF (0.5 M)

was added and the solution was warmed up to rt. 3,6-dichloropyridazine (2.4 g, 16 mmol), 3,6-dichloropyridazine (2.4 g, 16 mmol) and Q-Phos (2.5 g) were added and the reaction was heated to 50° C. for 16 hours. The reaction was then cooled to 23° C. and quenched with 60 mL of satd. NH$_4$Cl aq. solution. The mixture was mixed with celite and 100 mL of EtOAc. The insoluble material was removed by filtration. The filtrate was diluted with 40 mL of EtOAc and 30 mL of water. The organic phase was separated and washed with 60 mL of brine, dried over Na$_2$SO$_4$ and concentrated in vacuo. The residue was purified by a silica gel column chromatography (10% to 80% hex/EtOAc) to afford red solid as desired product. MS (ESI pos. ion) m/z: 212 (MH+). Calc'd exact mass for C$_8$H$_6$ClN$_3$S: 211.

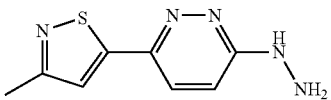

1-(6-(3-methylisothiazol-5-yl)pyridazin-3-yl)hydrazine

A mixture of 3-chloro-6-(3-methylisothiazol-5-yl)pyridazine (0.85 g, 4.0 mmol) and anhydrous hydrazine (3.8 ml, 120 mmol) in 30 mL of sec-BuOH was heated at 130° C. for 3 hours. The mixture was cooled to 23° C. and diluted with 5 mL of water. The solid was collected by filtration and was washed by 2 mL of water to produce a yellow solid. MS (ESI pos. ion) m/z: 208 (MH+). Calc'd exact mass for C$_8$H$_6$ClN$_3$S: 207.

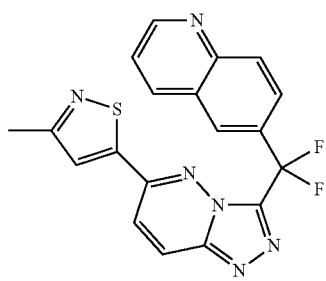 [SMILES: Cc1cc(-c2ccc3nnc(C(F)(F)c4ccc5ncccc5c4)n3n2)sn1]

EXAMPLE 492

6-(difluoro(6-(3-methylisothiazol-5-yl)-[1,2,4]triazolo[4,3-b]pyridazin-3-yl)methyl)quinoline A mixture of methyl 2,2-difluoro-2-(quinolin-6-yl)acetate (0.50 g, 2.1 mmol), 1-(6-(3-methylisothiazol-5-yl)pyridazin-3-yl)hydrazine (0.25 g, 1.2 mmol) and p-toluenesulfonic acid monohydrate (0.40 g, 2.1 mmol) in 5 mL of dioxane was heated at 150° C. for 1 hour in a microwave. The mixture was then diluted with 70 mL of EtOAc and 40 mL of satd. NaHCO$_3$ solution. The organic phase was separated and washed with 40 mL of brine, dried over Na$_2$SO$_4$ and concentrated in vacuo. The residue was purified by a silica gel column chromatography (EtOAc to 10% MeOH/EtOAc) to give yellow glass. The product was further purified by a prep-HPLC to give yellow glass. MS (ESI pos. ion) m/z: 395 (MH+). Calc'd exact mass for C$_{19}$H$_{12}$F$_2$N$_6$S: 394.

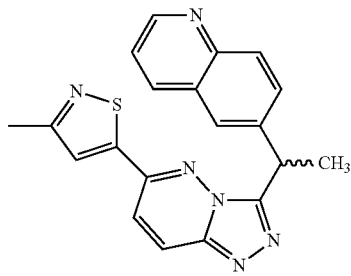 [SMILES: Cc1cc(-c2ccc3nnc(C(C)c4ccc5ncccc5c4)n3n2)sn1]

EXAMPLE 493

6-(1-(6-(3-methylisothiazol-5-yl)-[1,2,4]-triazolo[4,3-b]pyridazin-3-yl)ethyl)quinoline To a solution of 5-bromo-3-methylisothiazole (1.00 g, 5.6 mmol) in 10 mL of THF at −45° C. (CH$_3$CN/dry ice) was added isopropylmagnesium chloride LiCl complex (7.9 ml, 7.9 mmol) (LiCl complex, 1 M in THF). The mixture was stirred at −45° C. for 20 minutes and to this was added zinc chloride, 0.5 M in THF (17 ml, 8.4 mmol) slowly via a syringe. The mixture was then warmed up to rt and continued to stir for additional 30 minutes. 6-(1-(6-chloro-[1,2,4]triazolo[4,3-b]pyridazin-3-yl)ethyl)quinoline (0.5787 g, 1.9 mmol), tris(dibenzylideneacetone)dipalladium (0) (0.51 g, 0.56 mmol) and Q-Phos (0.65 g) in 15 mL of N,N-dimethyl acetamide was added to the reaction mixture. The reaction was warmed up to 50° C. for 6 hours and was quenched with 50 mL of satd. NH$_4$Cl aq. solution. The mixture was extracted with 150 mL of EtOAc and the organic phase was washed with 60 mL of brine. The aqueous phases were further extracted with 100 mL EtOAc. The combined organics were dried over Na$_2$SO$_4$ and concentrated in vacuo. The residue was purified by a silica gel column chromatography (EtOAc to 15% MeOH in EtOAc) to give afford a red solid. MS (ESI pos. ion) m/z: 373 (MH+). Calc'd exact mass for C$_{20}$H$_{16}$N$_6$S: 372.

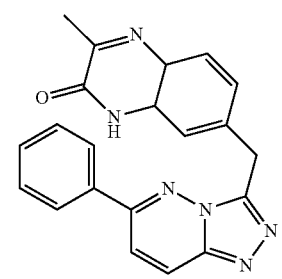 [SMILES: CC1=NC2C=CC(Cc3nnc4ccc(-c5ccccc5)nn34)=CC2NC1=O]

EXAMPLE 494

3-methyl-6-((6-phenyl-[1,2,4]triazolo[4,3-b]py-ridazin-3-yl)methyl)quinoxalin-2(1H)-one (See Example 495)

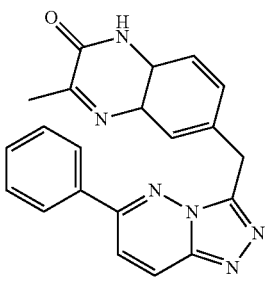 [SMILES: CC1=NC2C=C(Cc3nnc4ccc(-c5ccccc5)nn34)C=CC2NC1=O]

EXAMPLE 495

3-methyl-7-((6-phenyl-[1,2,4]-triazolo[4,3-b]py-ridazin-3-yl)methyl)quinoxalin-2(1H)-one A mixture of tert-butyl 2-(2-methyl-3-oxo-3,4-dihydro-quinoxalin-6-yl)acetate (0.10 g, 0.36 mmol), tert-butyl 2-(3-methyl-2-oxo-1,2-dihydroquinoxalin-6-yl)acetate (0.10 g, 0.36 mmol), 1-(6-phenylpyridazin-3-yl)hydrazine (0.081 g, 0.44 mmol) and p-toluenesulfonic acid monohydrate (0.069 g, 0.36 mmol) in 3 mL of dioxane was heated with microwave at 150° C. for 1 hour. The mixture was diluted with 70 mL of EtOAc and 40 mL of satd. NaHCO$_3$ solution. The organic phase was separated and was washed with 40 mL of brine, dried over Na$_2$SO$_4$ and concentrated in vacuo. The residue was purified by prep-HPLC to resolve the regiostereomers as example compounds 494 and 495. For each regiosteroemer MS (ESI pos. ion) m/z: 369 (MH+). Calc'd exact mass for C$_{21}$H$_{16}$N$_6$O: 368.

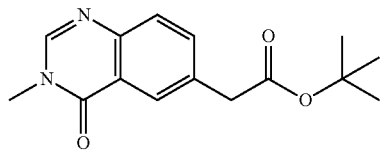 [SMILES: Cn1cnc2ccc(CC(=O)OC(C)(C)C)cc2c1=O]

tert-butyl 2-(3-methyl-4-oxo-3,4-dihydroquinazolin-6-yl)acetate

To a solution of 6-bromo-3-methylquinazolin-4(3H)-one (0.485 g, 2.0 mmol), tris(dibenzylideneacetone)dipalladium (0) (0.19 g, 0.20 mmol) and Q-phos (0.20 g) in 40 mL of THF was added 2-tert-butoxy-2-oxoethylzinc chloride 0.5 M in diethyl ether (8.1 ml, 4.1 mmol). The reaction was heated at 50° C. for 16 hours and was quenched with 40 mL of satd. NH$_4$Cl. The mixture was diluted with 60 mL of EtOAc. The organic phase was separated, washed with brine, dried over Na$_2$SO$_4$ and concentrated in vacuo to give red solid. The residue was purified by a silica gel column chromatography (5% EtOAc/Hex to EtOAC) to provide a red solid. MS (ESI pos. ion) m/z: 275 (MH+). Calc'd exact mass for C$_{15}$H$_{18}$N$_2$O$_3$:

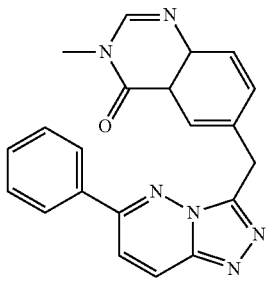 [SMILES: CN1C=NC2C=CC(Cc3nnc4ccc(-c5ccccc5)nn34)=CC2C1=O]

EXAMPLE 496

3-Methyl-6-((6-phenyl-[1,2,4]-triazolo[4,3-b]py-ridazin-3-yl)methyl)quinazolin-4(3H)-one The title compound was prepared using the method for 3-methyl-6-((6-phenyl-[1,2,4]triazolo[4,3-b]pyridazin-3-yl)methyl)quinoxalin-2(1H)-one. MS (ESI pos. ion) m/z: 369 (MH+). Calc'd exact mass for C$_{21}$H$_{16}$N$_6$O: 368.

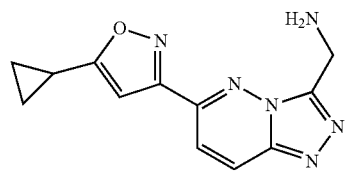 [SMILES: NCc1nnc2ccc(-c3cc(C4CC4)on3)nn12]

(6-(5-cyclopropylisoxazol-3-yl)-[1,2,4]-triazolo[4,3-b]pyridazin-3-yl)methanamine

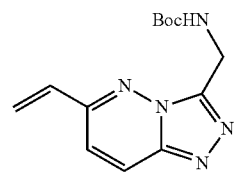 [SMILES: C=Cc1ccc2nnc(CNC(=O)OC(C)(C)C)n2n1]

1) tert-butyl (6-vinyl-[1,2,4]triazolo[4,3-b]pyridazin-3-yl)methylcarbamate

To an argon purged flask were added 4,4,5,5-tetramethyl-2-vinyl-1,3,2-dioxaborolane (7.65 ml, 45.1 mmol), tert-butyl (6-chloro-[1,2,4]triazolo[4,3-b]pyridazin-3-yl)methylcarbamate (3.20 g, 11.3 mmol), cesium carbonate (11.0 g, 33.8 mmol), and PdCl$_2$(dppf)-CH$_2$Cl$_2$ (0.461 g, 0.564 mmol). The mixture was dissolved in 38 mL of dioxane and 4 mL of water (0.25M 10:1) and was heated to 80° C. for 12 h. The mixture was cooled to room temperature, concentrated, and purified directly via MPLC (DCM/MeOH+1% NH$_4$OH) to afford the title compound (3.0 g, 95% yield).

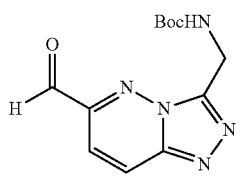 [SMILES: CC(C)(C)OC(=O)NCc1nnc2ccc(C=O)nn12]

2) tert-butyl (6-formyl-[1,2,4]-triazolo[4,3-b]pyridazin-3-yl)methylcarbamate

Tert-butyl (6-vinyl-[1,2,4]triazolo[4,3-b]pyridazin-3-yl)methylcarbamate (485 mg, 1.76 mmol) was dissolved in 5 mL of THF and 5 mL of water then osmium tetroxide (0.687 mL (4% water solution), 0.0176 mmol) was added and stirred for 5 min. Sodium periodate was added (141, 3.53 mmol) and the reaction was stirred for 2 h. The reaction was then extracted with dichloromethane (3×10 mL), dried over $Na_2SO_4$ and concentrated. Purification via MPLC (DCM/MeOH+1% $NH_4OH$) afforded title compound as a tan solid (350 mg, 72% yield).

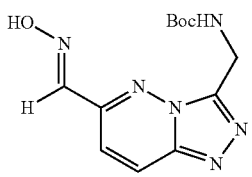 [SMILES: CC(C)(C)OC(=O)NCc1nnc2ccc(/C=N/O)nn12]

3) (E)-tert-butyl (6-((hydroxyimino)methyl)-[1,2,4]-triazolo[4,3-b]pyridazin-3-yl)methylcarbamate Tert-butyl (6-formyl-[1,2,4]triazolo[4,3-b]pyridazin-3-yl)methylcarbamate (400 mg, 1.44 mmol) and hydroxylamine hydrochloride (200 mg, 2.86 mmol) were combined in a flask with 25 mL of THF and 25 mL of 1 N NaOH solution. Stirred at rt for 1 h. Then added dichloromethane (50 mL) and extracted the aqueous layer 3 times with DCM (50 mL), dried over $Na_2SO_4$ and concentrated. Purified the oxime via MPLC (DCM/MeOH+1% $NH_4OH$) to give title compound (200 mg, 47% yield) as a tan solid.

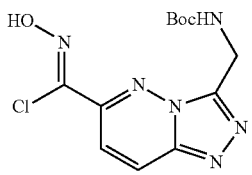

4) (Z)-tert-butyl (6-(chloro(hydroxyimino)methyl)-[1,2,4]triazolo[4,3-b]pyridazin-3-yl)methylcarbamate Dissolved (E)-tert-butyl (6-((hydroxyimino)methyl)-[1,2,4]triazolo[4,3-b]pyridazin-3-yl)methylcarbamate (200 mg, 0.684 mmol) in 25 mL of DMF and added 1-chloropyrrolidine-2,5-dione (95.9 mg, 0.718 mmol). Let stir at rt for 2 h. Poured reaction mixture onto water (20 mL) and extracted with ether (3×20 mL). Washed organics with water (2×20 mL), brine (1×20 ml), dried over sodium sulfate, filtered and concentrated. Title compound used without further purification (220 mg, 97% yield).

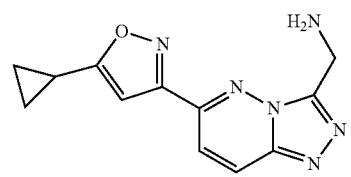 [SMILES: NCc1nnc2ccc(-c3cc(C4CC4)on3)nn12]

5) (6-(5-cyclopropylisoxazol-3-yl)-[1,2,4]-triazolo[4,3-b]pyridazin-3-yl)methanamine Dissolved (Z)-tert-butyl (6-(chloro(hydroxyimino)methyl)-[1,2,4]triazolo[4,3-b]pyridazin-3-yl)methylcarbamate (110 mg, 337 μmol), ethynylcyclopropane (28 μl, 337 μmol), and potassium hydrogencarbonate (67.4 mg, 673 μmol) in 0.3 mL of EtOAc and heated to 60° C. for 12 h to afford the protected intermediate. The solvent was removed by rotary evaporation and the residue was redissolved in dicholoromethane (5 mL) and TFA (2 mL) and stirred for 30 min at room temperature. The solvent was then removed and the residue was redissolved in MeOH. Solid $K_2CO_3$ was added and the mixture was stirred for 1 h to free base the title compound. Purified the amine via MPLC (DCM/MeOH+1% $NH_4OH$) to afford the title compound (20 mg, 23% yield).

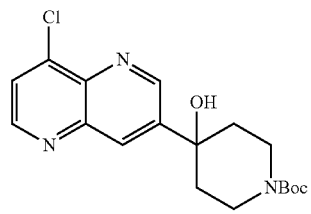 [SMILES: CC(C)(C)OC(=O)N1CCC(O)(c2cnc3c(Cl)ccnc3c2)CC1]

tert-butyl 4-(8-chloro-1,5-naphthyridin-3-O-4-hydroxypiperidine-1-carboxylate

Dissolved 3-bromo-8-chloro-1,5-naphthyridine (210 mg, 862 μmol) in 8 mL of THF and cooled to −78° C. Then added butyllithium (517 μl, 1294 μmol) and stirred for 15 min. Added tert-butyl 4-oxopiperidine-1-carboxylate (258 mg, 1294 μmol) and let warm to room temperature over 1 h. The reaction was quenched with saturated $NH_4Cl$ and extracted with dichloromethane (3×20 mL), dried over $NaSO_4$ and concentrated. Intermediate was purified via MPLC (DCM/MeOH/NHOH) to yield tert-butyl 4-(8-chloro-1,5-naphthyridin-3-yl)-4-hydroxypiperidine-1-carboxylate (120 mg, 38% yield.

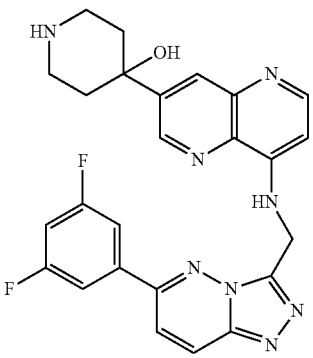 [SMILES: OC1(c2cnc3c(NCc4nnc5ccc(-c6cc(F)cc(F)c6)nn45)ccnc3c2)CCNCC1]

EXAMPLE 497

4-(8-(((6-(3,5-difluorophenyl)-[1,2,4]triazolo[4,3-b]pyridazin-3-yl)methylamino)-1,5-naphthyridin-3-yl)piperidin-4-ol Deprotection of tert-butyl 4-(8-(((6-(3,5-difluorophenyl)-[1,2,4]triazolo[4,3-b]pyridazin-3-yl)methylamino)-1,5-naphthyridin-3-yl)-4-hydroxypiperidine-1-carboxylate using the method described for (6-(3-methylisothiazol-5-yl)-[1,2,4]triazolo[4,3-b]pyridazin-3-yl)methanamine M/Z=489.2 [M+H], calc 488.19 for $C_{25}H_{22}F_2N_8O$.

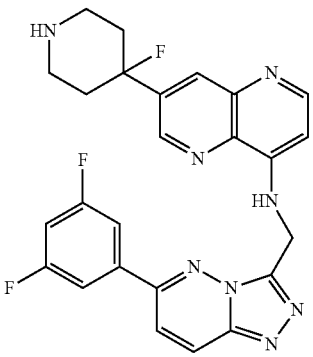 [SMILES: Fc1cc(F)cc(-c2ccc3nnc(CNc4ccnc5cc(C6(F)CCNCC6)cnc45)n3n2)c1]

EXAMPLE 498

N-((6-(3,5-difluorophenyl)-[1,2,4]triazolo[4,3-b]pyridazin-3-yl)methyl)-7-(4-fluoropiperidin-4-yl)-1,5-naphthyridin-4-amine A solution of tert-butyl 4-(8-(((6-(3,5-difluorophenyl)-[1,2,4]triazolo[4,3-b]pyridazin-3-yl)methylamino)-1,5-naphthyridin-3-yl)-4-hydroxypiperidine-1-carboxylate (30 mg, 51 μmol) in 0.5 mL of DCM was cooled to −78 C. Then added DAST (13 μl, 102 μmol) and let stir to room temperature over 30 min. TFA was then added to the reaction mixture and stirred for 30 min. The solvent was then removed by rotary evaporation and the residue was redissolved in MeOH and free based through a cation exchange column. Purification via MPLC (DCM/MeOH+1% NH$_4$OH) yielded the title compound (15 mg, 60% yield). M/Z=491.2 [M+H], calc 490.18 for $C_{25}H_{21}F_3N_8$.

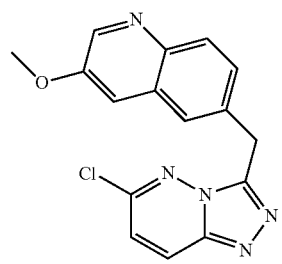 [SMILES: COc1cnc2ccc(Cc3nnc4ccc(Cl)nn34)cc2c1]

EXAMPLE 499

6-((6-chloro-[1,2,4]-triazolo[4,3-b]pyridazin-3-yl)methyl)-3-methoxyquinoline

To a 5 ml CEM microwave tube was added tert-butyl 2-(3-methoxyquinolin-6-yl)acetate (0.05 g, 0.2 mmol), 1-(6-chloropyridazin-3-yl)hydrazine (0.04 g, 0.3 mmol), water (0.5 mL) and hydrochloric acid (0.05 ml, 0.5 mmol). The vial was sealed and first heated at 90° C. for 30 min then placed into CEM microwave for 10 min. at 100° C., with 100 Watts of power via Powermax. The reaction mixture was adjusted the pH to 7 by adding 5 N NaOH—brown ppt. was generated. The brown ppt. was dissolved in DCM. The organic was washed with water, dried over MgSO$_4$, and removed solvent in vacuo. The crude product was purified using SiO$_2$ chromatography (Teledyne Isco RediSep®, P/N 68-2203-026, 12 g SiO$_2$, DCM:EtOAc:MeOH=75%:20%:5%, Flow=30 mL/min). A peak at 25 min was collected. The solvent was removed in vacuo to afford the desired product as light yellowish solid. Wt: 20.0 mg. MS (ESI pos. ion) m/z: 326.53. Calc'd exact mass for $C_{16}H_{12}ClN_5O$: 325.75.

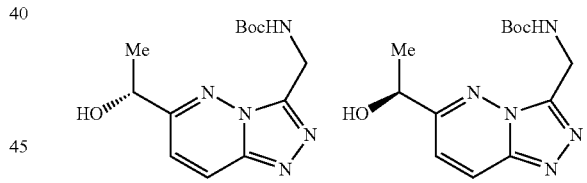

(R/S)-tert-butyl (6-(1-hydroxyethyl)[1,2,4]triazolo[4,3-b]pyridazin-3-yl)methylcarbamate In a 10 mL round bottom flask under N$_2$ was dissolved tert-butyl (6-formyl-[1,2,4]triazolo[4,3-b]pyridazin-3-yl)methylcarbamate (200 mg, 721 μmol) in 3 mL of THF then cooled at −78° C. and treated with methylmagnesium bromide (721 μl, 2164 μmol). After 30 minutes, the reaction mixture was warmed to 0° C. over 1 h. After 1 h the reaction mixture based on LC-MS was neutralized with NH$_4$Cl (sat.). The aqueous phase was extracted 3× with DCM then the organic layer was dried over Na$_2$SO$_4$, filtered and concentrated under reduced pressure. The crude tert-butyl (6-(1-hydroxyethyl)-[1,2,4]triazolo[4,3-b]pyridazin-3-yl)methylcarbamate (202 mg, 95.5% yield) was used without further purification in the next step. MS m/z=294.4 [M+1]$^+$. Calc'd for $C_{13}H_{19}N_5O_3$: 293.3.

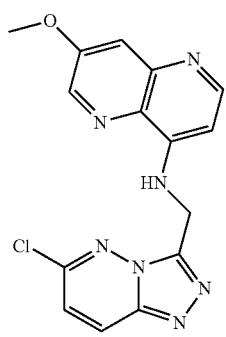 [SMILES: COc1cnc2c(NCc3nnc4ccc(Cl)nn34)ccnc2c1]

EXAMPLE 500

N-((6-chloro-[1,2,4]-triazolo[4,3-b]pyridazin-3-yl)methyl)-7-methoxyquinolin-4-amine

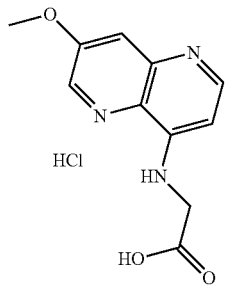 [SMILES: COc1cnc2c(NCC(=O)O)ccnc2c1 ; Cl]

a) 2-(7-methoxy-1,5-naphthyridin-4-ylamino)acetic acid hydrochloride. In a 100 mL round bottom flask were dissolved 8-chloro-3-methoxy-1,5-naphthyridine (5.00 g, 25.7 mmol) and glycine tert-butyl ester hydrochloride (17.2 g, 103 mmol) in 50 mL of 2-BuOH then stirred and heated at 100° C. After 5 h the solvent based on LC-MS was removed by reduced pressure and then the solid was dissolved in 200 mL of HCl 1N and stirred at 60° C. overnight. After 10 h the reaction mixture based on LC-MS was cooled down to rt then 0° C. and the desired acid precipitate. Filtered the solid (3.97 g) then evaporated the aqueous solution and triturated in 75 mL of H$_2$O at 0° C. then filter again and washed with 25 mL of H$_2$O at 0° C. (1.58 g) to afforded total 2-(7-methoxy-1,5-naphthyridin-4-ylamino)acetic acid hydrochloride (5.55 g, 80.1% yield) as a tan solid. MS m/z=234.1 [M+1]$^+$. Calc'd for C$_{11}$H$_{11}$N$_3$O$_3$: 233.1.

b) N-((6-chloro-[1,2,4]-triazolo[4,3-b]pyridazin-3-yl)methyl)-7-methoxy-1,5-naphthyridin-4-amine. In a 250 mL round bottom flask under N$_2$ were dissolved HATU (1762 mg, 4635 µmol), 1-(6-chloropyridazin-3-yl)hydrazine (536 mg, 3708 µmol), 2-(7-methoxy-1,5-naphthyridin-4-ylamino)acetic acid hydrochloride (1.00 g, 3708 µmol) in 25 mL of MeCN then stirred and cooled down at −40° C. then treated with TRIETHYLAMINE (2584 µl, 18540 µmol) and warmed to rt. After 30 min the reaction mixture based on LC-MS was evaporated under reduced pressure and dry under high vacuum. The crude solid was dissolved in 100 mL of i-PrOH then treated with Ts-OH (2821 mg, 14832 µmol) and heated at 80° C. After 3 h the reaction mixture based on LC-MS was diluted with DCM then neutralized with NaOH (1N). The aqueous phase was extracted 3× with DCM with 10% MeOH then the organic layer was dried over Na$_2$SO$_4$, filtered and concentrated under reduced pressure. The crude mixture was triturated with hot i-PrOH then cooled down and filtered (662 mg) and the mother liquor was evaporated under reduced pressure and purified by MPLC (ISCO) (210 mg) with DCM:MeOH 100:0 to 90:10 to afforded in combined yields N-((6-chloro-[1,2,4]triazolo[4,3-b]pyridazin-3-yl)methyl)-7-methoxy-1,5-naphthyridin-4-amine (872 mg, 69% yield) as a off-white solid. MS m/z=342.1 [M+1]$^+$. Calc'd for C$_{15}$H$_{12}$ClN$_2$O: 341.7.

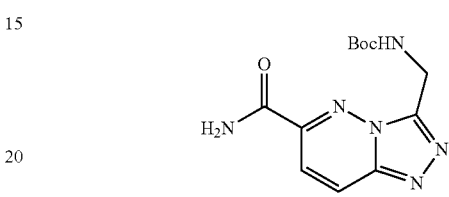

tert-Butyl (6-carbamoyl-[1,2,4]-triazolo[4,3-b]pyridazin-3-yl)methylcarbamate a) 3-((tert-butoxycarbonyl)methyl)-[1,2,4]-triazolo[4,3-b]pyridazine-6-carboxylic acid. In a 25 mL round bottom flask were dissolved 2-methyl-2-butene (21639 µl, 43278 µmol), potassium dihydrogen phosphate (2356 mg, 17311 µmol) and tert-butyl (6-formyl-[1,2,4]triazolo[4,3-b]pyridazin-3-yl)methylcarbamate (600 mg, 2164 µmol) in 5 mL of t-BuOH and 5 mL of water then was added at 0° C. sodium chlorite (783 mg, 8656 µmol) and the reaction mixture was warmed to rt. After 10 h the reaction mixture based on LC-MS was concentrated under reduced pressure and the crude acid was extract from the solid salts mixture with MeOH, filtered and the solvent was concentrated under reduced pressure. The crude 3-((tert-butoxycarbonyl)methyl)-[1,2,4]triazolo[4,3-b]pyridazine-6-carboxylic acid (635 mg, 100% yield) was used without further purification in the next step. MS m/z=294.2 [M+1]$^+$. Calc'd for C$_{12}$H$_{15}$N$_5$O$_4$: 293.1 b) tert-butyl (6-carbamoyl-[1,2,4]triazolo[4,3-b]pyridazin-3-yl)methylcarbamate. In a 10 mL round bottom flask under N$_2$ were dissolved 3-((tert-butoxycarbonyl)methyl)-[1,2,4]triazolo[4,3-b]pyridazine-6-carboxylic acid (250 mg, 852 µmol), HATU (389 mg, 1023 µmol), triethylamine (356 µl, 2557 µmol) in 1.5 mL of DMF then was treated with a (92 µl, 4262 µmol) and stirred at rt. After 2 h the reaction mixture based on LC-MS was concentrated under reduced pressure and then purified by MPLC (ISCO) with DCM:MeOH+ NH$_4$OH (1%) 100:0 to 90:10 to afforded tert-butyl (6-carbamoyl-[1,2,4]triazolo[4,3-b]pyridazin-3-yl)methylcarbamate (129 mg, 52% yield). MS m/z=293.2 [M+1]$^+$. Calc'd for C$_{12}$H$_{16}$N$_6$O$_3$: 292.3.

3-(aminomethyl)-N-methyl-[1,2,4]triazolo[4,3-b]pyridazine-6-carboxamide

The title compound was made using the same conditions as tert-butyl (6-carbamoyl-[1,2,4]triazolo[4,3-b]pyridazin-3-yl)methylcarbamate.

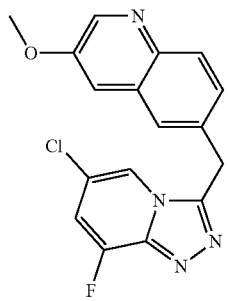 [SMILES: COc1cnc2ccc(Cc3nnc4c(F)cc(Cl)cn34)cc2c1]

EXAMPLE 501

6-((6-chloro-8-fluoro-[1,2,4]triazolo[4,3-a]pyridin-3-yl)methyl)-3-methoxyquinoline a) 1-(5-chloro-3-fluoropyridin-2-yl)hydrazine. A mixture of 5-chloro-2,3-difluoropyridine (10.0 g, 66.9 mmol) and hydrazine (10.0 ml, 319 mmol) in PrOH (50 mL) was heated to 65-70° C. for 6 hours. The mixture was cooled to 23° C., filtered, and washed with $Na_2CO_3$ (satd), and $H_2O$. Product isolated as a white solid. MS (ESI pos. ion) m/z: 162 (MH+). Calc'd exact mass for $C_5H_5ClFN_3$: 161.

b) 6-((6-chloro-8-fluoro-[1,2,4]-triazolo[4,3-a]pyridin-3-yl)methyl)-3-methoxyquinolin. To a mixture of 2-(3-methoxyquinolin-6-yl)acetic acid (0.22 g, 1.0 mmol), 1-(5-chloro-3-fluoropyridin-2-yl)hydrazine (0.11 g, 0.68 mmol) and triphenylphosphine (0.97 g, 2.0 mmol) (on solid support) in DCM (5 mL) was added DIEA (0.24 ml, 1.4 mmol) followed by 2,2,2-trichloroacetonitrile (0.14 ml, 1.4 mmol) via a syringe. The mixture was then heated to 150° C. for 15 minutes in an appropriately sealed vial. The mixture was filtered and the filtrate was diluted with 50 mL of EtOAc. The solution was washed with 30 mL of satd. $NaHCO_3$ followed by 30 mL of brine, dried over $Na_2SO_4$ and concentrated in vacuo. The crude product was purified by a silica gel column chromatography (EtOAc to 10% MeOH/EtOAc) to give light yellow solid as desired product. MS (ESI pos. ion) m/z: 343 (MH+). Calc'd exact mass for $C_{12}H_{12}ClFN_4O$: 342.

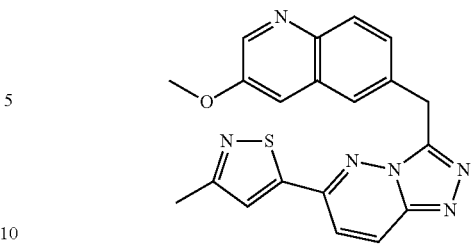

EXAMPLE 502

3-Methoxy-6-((6-(3-methylisothiazol-5-yl)-[1,2,4]triazolo[4,3-b]pyridazin-3-yl)methyl)quinoline A flask charged with 5-bromo-3-methylisothiazole (0.049 g, 0.28 mmol) and 0.3 mL dry THF was cooled to 0° C., and isopropylmagnesium chloride (0.30 ml, 0.30 mmol) added dropwise over 5 minutes and the mixture stirred an additional 5 minutes before allowing to warm to rt. The mixture was stirred at rt 10 minutes and the mixture cannulated to a solution of zinc(II) chloride (0.30 ml, 0.30 mmol) [1M] and the slurry stirred 10 minutes. The zincate was treated with 6-((6-iodo-[1,2,4]triazolo[4,3-b]pyridazin-3-yl)methyl)-3-methoxyquinoline (0.0890 g, 0.21 mmol), 1 mL dry THF, and a preformed solution of 4,5-bis(diphenylphosphino)-9,9-dimethyl-9H-xanthene (0.012 g, 0.021 mmol) and $Pd(OAc)_2$ (0.0024 g, 0.011 mmol) dissolved in 1 mL dry THF. The flask was fitted with a reflux condenser and heated with a 90° C. oil bath for 24 h. The zincate portion of this procedure was repeated, added to the reaction mixture, and the mixture heated at 90° C. for 1 h. The mixture was allowed to cool to rt and loaded onto 10 g of $SiO_2$ wet-packed with THF, and eluted with 200 mL THF. The eluents were concentrated in vacuo, and taken up in 5 mL EtOH. To the solution was added Si-sulfonic acid (1.5 g, 1.1 mmol) and the mixture stirred at room temperature for 24 h, and the solid collected. The solid was washed with EtOH (discarded), and then 2M $NH_3$ in EtOH (5×5 mL). The ammoniacal eluents were concentrated and the residue purified by HPLC to afford 3-methoxy-6-((6-(3-methylisothiazol-5-yl)-[1,2,4]triazolo[4,3-b]pyridazin-3-yl)methyl)quinoline (0.0013 g, 1.6% yield).

| Example | 1H NMR Data |
|---|---|
| 4 | (400 MHz, DMSO-$d_6$) ppm 8.54 (d, J = 9.73 Hz, 1H), 8.51 (d, J = 2.78 Hz, 1H), 8.42 (d, J = 5.31 Hz, 1H), 8.09 (s, 1H), 7.94 (d, J = 9.73 Hz, 2H), 7.58 (d, J = 2.78 Hz, 1H), 6.83 (d, J = 5.31 Hz, 1 H), 5.15 (d, J = 6.19 Hz, 1H), 3.94 (s, 1H), 3.94 (s, 3H), 2.52 (s, 3 H) |
| 14 | (400 MHz, DMSO-$d_6$) ppm 6.26 (s, 2H), 7.57-7.64 (m, 3H), 7.73 (d, J = 5.56 Hz, 1H), 8.01 (d, J = 9.73 Hz, 1H), 8.07-8.13 (m, 2H), 8.35 (d, J = 5.56 Hz, 1H), 8.47 (d, J = 9.73 Hz, 1H), 8.64 (s, 1 H), 8.95 (s, 1H) |
| 34 | (400 MHz, DMSO-$d_6$) ppm 2.39 (s, 3H) 3.95 (s, 3H) 5.16 (d, J = 5.94 Hz, 2H) 6.82 (d, J = 5.43 Hz, 1H) 7.38 (d, J = 7.58 (d, J = 2.78 Hz, 1H) 7.88 (d, J = 9.73 Hz, 1H) 7.95 (t, J = 5.87 Hz, 1H) 8.41 (d, J = 5.31 Hz, 1H) 8.52 (d, J = 2.78 Hz, 1H) 8.55 (d, J = 9.73 Hz, 1H) |
| 38 | (400 MHz, DMSO-$d_6$) ppm 3.88 (s, 3H) 6.00 (s, 2H) 6.52 (d, J = 7.58 Hz, 1H) 7.13 (dd, J = 2.46 Hz, 2H) 7.27 (d, J = 5.31 Hz, 1 H) 7.34 (d, J = 2.40 Hz, 1H) 7.64 (t, J = 7.64 Hz, 1H) 7.80-8.11 (m, 3H) 8.75 (d, J = 5.31 Hz, 1H) 9.24 (s, 1H) 11.42 (s, 1H) |
| 39 | (400 MHz, DMSO-$d_6$) ppm 4.71 (s, 2H), 7.49 (d, J = 9.54 Hz, 1 H), 7.51 (dd, J = 8.35, 3.51 Hz, 1H), 7.75 (dd, J = 8.53, 1.51 Hz, 1 H), 7.87 (s, 1H), 7.98 (d, J = 8.53 Hz, 1H), 8.31 (d, J = 8.53 Hz, 1 H), 8.46 (d, J = 10.04 Hz, 1H), 8.87 (d, J = 5.52 Hz, 1H) |

-continued

| Example | 1H NMR Data |
|---|---|
| 40 | (400 MHz, DMSO-$d_6$) ppm 3.89 (s, 3H), 4.79 (s, 2H), 7.56-7.61 (m, 3H), 7.64 (dd, J = 8.61, 1.96 Hz, 1H), 7.72 (d, J = 2.74 Hz, 1H), 7.83 (d, J = 1.37 Hz, 1H), 7.91 (d, J = 8.61 Hz, 1H), 7.96 (d, J = 9.78 Hz, 1H), 8.07-8.12 (m, 2H), 8.45 (d, J = 9.78 Hz, 1H), 8.58 (d, J = 2.93 Hz, 1H) |
| 41 | (400 MHz, MeOH) ppm 8.73 (s, 1H), 8.22 (d, J = 9.0 Hz, 1H), 7.87 (d, J = 4.3 Hz, 2H), 7.71-7.75 (m, 1H), 7.66 (d, J = 9.0 Hz, 3H), 7.45-7.53 (m, 3H), 7.36-7.42 (m, 1H), 7.01-7.03 (m, 1H), 6.91 (d, J = 2.2 Hz, 1H), 4.29 (s, 2H), 3.90 (s, 3H). |
| 42 | (400 MHz, DMSO-$d_6$) ppm 13.01 (s, 1H), 8.44 (d, J = 9.73 Hz, 1H), 8.18-8.30 (m, 2H), 8.14 (s, 1H), 7.94-8.06 (m, 3H), 7.49-7.59 (m, 3H), 5.36 (s, 2H). |
| 45 | (400 MHz, MeOH) ppm 9.27 (s, 1H), 8.70 (d, J = 5.30 Hz, 1H), 8.41 (d, J = 9.85 Hz, 1H), 8.06-8.10 (m, 2H), 7.90-7.99 (m, 2H), 7.62-7.67 (m, 2H), 7.30-7.33 (m, 2H), 7.10-7.14 (m, 1H), 6.08 (s, 2H), 3.92 (s, 3H). |
| 51 | (400 MHz, DMSO-$d_6$) ppm 13.98 (s, 1H), 9.82 (s, 1H), 8.73 (d, J = 1.26 Hz, 1H), 8.59 (s, 1H), 8.51 (d, J = 9.85 Hz, 1H), 8.16 (d, J = 12.00 Hz, 1H), 8.07 (d, J = 9.73 Hz, 2H), 7.62-7.73 (m, 2H), 7.22 (d, J = 6.06 Hz, 1H), 5.43 (d, J = 5.68 Hz, 2H), 4.01 (s, 3H), 3.86 (t, J = 6.95 Hz, 2H), 2.50-2.47 (m, 2H), 2.11-2.21 (m, 2H). |
| 53 | (400 MHz, DMSO-$d_6$) ppm 8.59 (s, 1H), 8.51 (d, J = 2.8 Hz, 1H), 8.41 (d, J = 5.5 Hz, 1H), 8.34 (d, J = 9.7 Hz, 1H), 8.21-8.22 (m, 1H), 7.95-7.98 (m, 1H), 7.73 (d, J = 9.7 Hz, 1H), 7.57 (d, J = 2.8 Hz, 1H), 6.83 (d, J = 5.2 Hz, 1H), 5.13 (d, J = 6.3 Hz, 2H), 4.55-4.63 (m, 1H), 3.93 (s, 3H), 1.49 (s, 3H), 1.47 (s, 3H). |
| 56 | (400 MHz, DMSO-$d_6$) ppm 3.87 (s, 3H), 5.84 (s, 2H), 7.07-7.12 (m, 1H), 7.27-7.33 (m, 2H), 7.46-7.53 (m, 3H), 7.88-7.96 (m, 2H), 8.01-8.06 (m, 2H), 8.12 (s, 1H), 8.30 (d, J = 9.47 Hz, 1H), 8.72 (d, J = 5.18 Hz, 1H). |
| 58 | (400 MHz, DMSO-$d_6$) ppm 3.88 (s, 3H) 5.86 (s, 2H) 7.09 (dd, J = 9.09, 2.27 Hz, 1H) 7.29 (d, J = 5.43 Hz, 1H) 7.30-7.34 (m, 1H) 7.55-7.63 (m, 1H) 7.90-7.98 (m, 3H) 8.07-8.15 (m, 2H) 8.33 (d, J = 9.60 Hz, 1H) 8.72 (d, J = 5.31 Hz, 1H) |
| 60 | (400 MHz, DMSO-$d_6$) ppm 3.32 (s, 3H) 6.09 (d, J = 0.88 Hz, 2H) 7.07 (dd, J = 9.28, 2.46 Hz, 1H) 7.37 (d, J = 2.53 Hz, 1H) 7.47-7.54 (m, 2H) 7.55-7.60 (m, 1H) 7.86-7.92 (m, 3H) 8.04 (d, J = 9.85 Hz, 1H) 8.52 (d, J = 9.85 Hz, 1H) 8.89 (d, J = 3.79 Hz, 1H). |
| 61 | (400 MHz, DMSO-$d_6$) ppm 3.92 (s, 3H) 5.07 (d, J = 6.19 Hz, 2H) 6.82 (d, J = 5.43 Hz, 1H) 7.54 (d, J = 2.78 Hz, 1H) 7.88-7.91 (m, 2H) 8.00 (t, J = 6.20 Hz, 1H) 8.19-8.28 (m, 3H) 8.38 (d, J = 5.43 Hz, 1H) 8.47 (d, J = 2.91 Hz, 1H). |
| 65 | (400 MHz, DMSO-$d_6$) ppm 8.53 (s, 1H), 8.40 (d, J = 5.05 Hz, 1H), 8.13-8.19 (m, 2H), 8.00 (t, J = 6.00 Hz, 1H), 7.86 (s, 1H), 7.56-7.61 (m, 4H), 6.83 (d, J = 5.31 Hz, 1H), 5.19 (d, J = 6.06 Hz, 2H), 3.93 (s, 3H), 2.67 (s, 3H). |
| 66 | (400 MHz, DMSO-$d_6$) ppm 9.30 (s, 1H), 8.58 (s, 1H), 7.83 (d, J = 9.47 Hz, 1H), 7.67-7.73 (m, 3H), 7.51 (t, J = 7.58 Hz, 2H), 7.43 (t, J = 7.26 Hz, 1H), 7.14 (d, J = 8.34 Hz, 2H), 6.69 (d, J = 8.34 Hz, 2H), 4.51 (s, 2H). |
| 69 | (400 MHz, DMSO-$d_6$) ppm 11.44 (s, 1H), 9.31 (s, 1H), 8.53 (s, 1H), 7.65-7.76 (m, 2H), 7.13 (d, J = 8.08 Hz, 2H), 6.96 (s, 1H), 6.69 (d, J = 8.34 Hz, 2H), 6.62 (s, 1H), 6.16 (s, 1H), 4.38 (s, 2H) |
| 70 | (300 MHz, DMSO-$d_6$) ppm 4.76 (s, 2H) 7.54-7.68 (m, 4H) 7.85 (dd, J = 8.33, 2.05 Hz, 1H) 7.95 (d, J = 9.79 Hz, 1H) 8.05 (s, 1H) 8.09-8.17 (m, 2H) 8.19 (d, J = 1.90 Hz, 1H) 8.44 (d, J = 9.79 Hz, 1H). |
| 77 | (400 MHz, DMSO-$d_6$) ppm 1.96 (d, J = 7.2 Hz, 3H), 5.15 (d, J = 7.2 Hz, 1H), 7.50 (dd, J = 8.4, 4.1 Hz, 1H), 7.52-7.57 (m, 3H), 7.83 (dd, J = 8.7, 1.9 Hz, 1H), 7.92 (d, J = 9.8 Hz, 1H), 7.97-8.03 (m, 4H), 8.35 (d, J = 7.4 Hz, 1H), 8.42 (d, J = 9.8 Hz, 1H), 8.84 (dd, J = 4.1, 1.6 Hz, 1H). |
| 89 | (400 MHz, DMSO-$d_6$) ppm 9.23 (s, 1H), 8.74 (d, J = 5.05 Hz, 1H), 8.19 (s, 1H), 7.86-7.97 (m, 3H), 7.70 (s, 1H), 7.34 (s, 1H), 7.24 (d, J = 5.05 Hz, 1H), 7.14 (dd, J = 9.16, 1.83 Hz, 1H), 5.98 (s, 2H), 3.89 (s, 3H). |
| 94 | (400 MHz, DMSO-$d_6$) ppm 9.16 (t, J = 1.26 Hz, 1H), 8.68-8.75 (m, 2H), 7.91-7.97 (m, 2H), 7.85-7.88 (m, 1H), 7.34 (d, J = 2.53 Hz, 1H), 7.25 (d, J = 5.43 Hz, 1H), 7.14 (dd, J = 9.16, 2.59 Hz, 1H), 6.00 (s, 2H), 3.89 (s, 3H), 3.26-3.32 (m, 2H), 1.11 (t, J = 7.20 Hz, 3H). |
| 117 | (300 MHz, CHLOROFORM-d) δ ppm 2.09 (d, J = 7.31 Hz, 3H) 3.92 (s, 3H) 5.08 (q, J = 7.21 Hz, 1H) 7.33 (d, J = 2.78 Hz, 1H) 7.48-7.55 (m, 4H) 7.72 (dd, J = 8.62, 2.05 Hz, 1H) 7.77 (s, 1H) |

| Example | 1H NMR Data |
|---|---|
| | 7.84 (dd, J = 7.45, 2.19 Hz, 2H) 8.01 (d, J = 8.62 Hz, 1H) 8.14 (d, J = 9.79 Hz, 1H) 8.62 (d, J = 2.92 Hz, 1H). |
| 118 | (300 MHz, CHLOROFORM-d) δ ppm 2.09 (d, J = 7.31 Hz, 3H) 3.92 (s, 3H) 5.08 (q, J = 7.31 Hz, 1H) 7.33 (d, J = 2.78 Hz, 1H) 7.47-7.56 (m, 4H) 7.72 (dd, J = 8.55, 1.97 Hz, 1H) 7.77 (s, 1H) 7.84 (dd, J = 7.45, 2.19 Hz, 2H) 8.01 (d, J = 8.62 Hz, 1H) 8.14 (d, J = 9.65 Hz, 1H) 8.62 (d, J = 2.92 Hz, 1H). |
| 119 | (300 MHz, CHLOROFORM-d) δ ppm 2.09 (d, J = 7.31 Hz, 3H) 3.92 (s, 3H) 5.08 (q, J = 7.21 Hz, 1H) 7.33 (d, J = 2.78 Hz, 1H) 7.47-7.55 (m, 4H) 7.72 (dd, J = 8.62, 2.05 Hz, 1H) 7.77 (s, 1H) 7.82-7.88 (m, 2H) 8.01 (d, J = 8.62 Hz, 1H) 8.14 (d, J = 9.65 Hz, 1H) 8.62 (d, J = 2.92 Hz, 1H). |
| 120 | (300 MHz, CHLOROFORM-d) δ ppm 3.48 (s, 3H) 3.79-3.87 (m, 2H) 4.18-4.27 (m, 2H) 4.82 (s, 2H) 7.33 (d, J = 2.78 Hz, 1H) 7.50-7.59 (m, 4H) 7.71 (d, J = 8.48 Hz, 1H) 7.78 (s, 1H) 7.90-7.96 (m, 2H) 8.00 (d, J = 8.48 Hz, 1H) 8.15 (d, J = 9.65 Hz, 1H) 8.68 (d, J = 2.92 Hz, 1H). |
| 123 | (400 MHz, DMSO-$d_6$) ppm 3.88 (s, 3H), 6.02 (s, 2H), 7.12 (dd, J = 9.16, 2.46 Hz, 1H), 7.30-7.36 (m, 2H), 7.50-7.61 (m, 3H), 7.97 (d, J = 9.22 Hz, 1H), 8.03-8.10 (m, 3H), 8.55 (d, J = 9.73 Hz, 1H), 8.73 (d, J = 5.30 Hz, 1H) |
| 125 | (400 MHz, DMSO-$d_6$) ppm 5.83 (s, 2H), 7.21 (d, J = 5.94 Hz, 2H), 7.55-7.63 (m, 3H), 8.06 (d, J = 9.73 Hz, 1H), 8.08-8.14 (m, 2H), 8.45 (d, J = 5.81 Hz, 2H), 8.53 (d, J = 9.60 Hz, 1H) |
| 126 | (400 MHz, DMSO-$d_6$) ppm 5.66 (s, 2H), 5.89 (s, 2H), 6.18 (s, 1H), 6.31 (d, J = 3.92 Hz, 1H), 7.60 (s, 3H), 7.76 (d, J = 5.68 Hz, 1H), 8.05 (d, J = 9.73 Hz, 1H), 8.08-8.16 (m, 2H), 8.53 (d, J = 9.73 Hz, 1H) |
| 131 | (400 MHz, DMSO-$d_6$) ppm 2.81 (s, 3H), 3.88 (s, 3H), 6.03 (s, 2H), 7.11 (d, J = 8.72 Hz, 1H), 7.28-7.38 (m, 2H), 7.92-8.02 (m, 3H), 8.10 (d, J = 9.60 Hz, 1H), 8.15 (d, J = 7.58 Hz, 2H), 8.52-8.64 (m, 2H), 8.73 (d, J = 4.42 Hz, 1H) |
| 132 | (400 MHz, DMSO-$d_6$) ppm 2.79 (d, J = 4.42 Hz, 3H), 3.89 (s, 3H), 6.05 (s, 2H), 7.12 (dd, J = 9.16, 2.46 Hz, 1H), 7.31-7.35 (m, 2H), 7.76 (t, J = 7.64 Hz, 1H), 7.95-8.05 (m, 3H), 8.12 (d, J = 9.85 Hz, 1H), 8.39 (d, J = 4.80 Hz, 1H), 8.60 (d, J = 9.85 Hz, 1H), 8.73 (d, J = 5.18 Hz, 1H) |
| 135 | (400 MHz, DMSO-$d_6$) ppm 2.77 (d, J = 4.55 Hz, 3H), 3.88 (s, 3H), 6.05 (s, 2H), 7.12 (dd, J = 9.16, 2.34 Hz, 1H), 7.32 (d, J = 5.31 Hz, 1H), 7.34 (s, 1H), 7.58 (d, J = 7.96 Hz, 1H), 7.98 (d, J = 9.09 Hz, 1H), 8.08 (d, J = 8.08 Hz, 1H), 8.12 (d, J = 9.85 Hz, 1H), 8.18 (s, 1H), 8.42-8.50 (m, 1H), 8.58 (d, J = 9.85 Hz, 1H), 8.73 (d, J = 5.31 Hz, 1H) |
| 155 | (400 MHz, DMSO-$d_6$) ppm 3.94 (s, 3H) 5.25 (d, J = 6.19 Hz, 2H) 6.89 (d, J = 5.68 Hz, 1H) 7.57 (d, J = 2.65 Hz, 1H) 7.88 (t, J = 1.83 Hz, 1H) 8.07 (d, J = 9.73 Hz, 1H) 8.27 (d, J = 1.77 Hz, 3H) 8.43 (d, J = 5.56 Hz, 1H) 8.50 (d, J = 9.85 Hz, 1H) 8.55 (d, J = 2.78 Hz, 1H) |
| 155 | (400 MHz, DMSO-$d_6$) ppm 3.94 (s, 3H) 5.25 (d, J = 6.19 Hz, 2H) 6.89 (d, J = 5.68 Hz, 1H) 7.57 (d, J = 2.65 Hz, 1H) 7.88 (t, J = 1.83 Hz, 1H) 8.07 (d, J = 9.73 Hz, 1H) 8.27 (d, J = 1.77 Hz, 3H) 8.43 (d, J = 5.56 Hz, 1H) 8.50 (d, J = 9.85 Hz, 1H) 8.55 (d, J = 2.78 Hz, 1H) |
| 157 | (400 MHz, DMSO-$d_6$) ppm 3.93 (s, 3H) 5.23 (d, J = 6.19 Hz, 2H) 6.85 (d, J = 5.18 Hz, 1H) 7.57 (d, J = 2.65 Hz, 1H) 7.85 (t, J = 7.83 Hz, 1H) 7.93-8.04 (m, 2H) 8.10 (d, J = 9.85 Hz, 1H) 8.40 (d, J = 5.43 Hz, 1H) 8.45-8.54 (m, 4H) |
| 157 | (400 MHz, DMSO-$d_6$) ppm 3.93 (s, 3H) 5.23 (d, J = 6.19 Hz, 2H) 6.85 (d, J = 5.18 Hz, 1H) 7.57 (d, J = 2.65 Hz, 1H) 7.85 (t, J = 7.83 Hz, 1H) 7.93-8.04 (m, 2H) 8.10 (d, J = 9.85 Hz, 1H) 8.40 (d, J = 5.43 Hz, 1H) 8.45-8.54 (m, 4H) |
| 158 | (400 MHz, DMSO-$d_6$) ppm 8.63 (d, J = 5.31 Hz, 1H), 8.49 (d, J = 9.73 Hz, 1H), 8.02 (t, J = 9.54 Hz, 2H), 7.93 (d, J = 7.20 Hz, 2H), 7.56 (t, J = 7.20 Hz, 1H), 7.50 (t, J = 7.39 Hz, 2H), 7.31 (d, J = 2.40 Hz, 1H), 7.16 (d, J = 5.43 Hz, 1H), 7.12 (dd, J = 9.22, 2.53 Hz, 1H), 6.61 (q, J = 6.44 Hz, 1H), 3.87 (s, 3H), 2.07 (d, J = 6.57 Hz, 3H) |
| 159 | (400 MHz, DMSO-$d_6$) ppm 8.46 (d, J = 9.73 Hz, 1H), 8.32 (d, J = 5.31 Hz, 1H), 8.19 (s, 1H), 8.12-8.18 (m, 2H), 7.99 (d, J = 9.85 Hz, 1H), 7.85 (t, J = 5.49 Hz, 1H), 7.53-7.63 (m, 3H), 7.17 (d, J = 2.53 Hz, 1H), 7.07 (dd, J = 9.16, 2.59 Hz, 1H), 6.66 (d, J = 5.43 Hz, 1H), 5.13 (d, J = 5.56 Hz, 2H), 3.85 (s, 3H) |
| 160 | (400 MHz, DMSO-$d_6$) ppm 8.69 (d, J = 4.67 Hz, 1H), 8.46 (d, J = 9.85 Hz, 1H), 8.08-8.16 (m, 2H), 8.00 (d, J = 9.73 Hz, 1H), 7.95 (d, J = 9.22 Hz, 1H), 7.77 (d, J = 4.80 Hz, 1H), 7.56-7.65 (m, 3H), 7.36 (d, J = 2.40 Hz, 1H), 7.23 (dd, J = 9.22, 2.40 Hz, 1H), 5.12 (s, 2H), 3.89 (s, 3H) |

-continued

| Example | 1H NMR Data |
|---|---|
| 161 | (400 MHz, DMSO-d$_6$) ppm 8.52 (d, J = 2.78 Hz, 1H), 8.45 (d, J = 9.85 Hz, 1H), 8.41 (d, J = 5.30 Hz, 1H), 8.14-8.21 (m, 2H), 7.94-8.04 (m, 2H), 7.54-7.63 (m, 4H), 6.85 (d, J = 5.31 Hz, 1 H), 5.20 (d, J = 6.06 Hz, 2H), 3.93 (s, 3H) |
| 171 | (400 MHz, DMSO-d$_6$) ppm 8.52 (d, J = 2.78 Hz, 1H), 8.48 (d, J = 9.73 Hz, 1H), 8.40 (d, J = 5.31 Hz, 1H), 8.34-8.40 (m, 1H), 8.05-8.15 (m, 2H), 8.02 (d, J = 9.85 Hz, 1H), 7.63-7.77 (m, 1 H), 7.57 (d, J = 2.78 Hz, 1H), 6.85 (d, J = 5.56 Hz, 1H), 5.21 (d, J = 6.19 Hz, 2H), 3.93 (s, 3H) |
| 172 | (400 MHz, DMSO-d$_6$) ppm 8.51 (d, J = 6.19 Hz, 1H), 8.50 (s, 1 H), 8.40 (d, J = 5.31 Hz, 1H), 8.23-8.33 (m, 2H), 8.12 (t, J = 5.68 Hz, 1H), 8.03 (d, J = 9.85 Hz, 1H), 7.56 (d, J = 2.53 Hz, 1H), 6.86 (d, J = 5.43 Hz, 1H), 5.21 (d, J = 6.06 Hz, 2H), 3.93 (s, 3H) |
| 176 | (400 MHz, DMSO-d$_6$) ppm 8.51 (d, J = 2.91 Hz, 1H), 8.36-8.43 (m, 2H), 7.85-7.95 (m, 3H), 7.57 (d, J = 2.78 Hz, 1H), 7.47 (s, 1H), 6.83 (d, J = 5.31 Hz, 1H), 5.11 (d, J = 5.94 Hz, 2H), 3.94 (s, 3H), 2.29 (s, 3H) |
| 182 | (300 MHz, DMSO-d$_6$) ppm 2.56 (s, 4H), 2.59-2.68 (m, 1H), 4.09 (s, 2H), 6.87 (dd, J = 5.92, 2.27 Hz, 1H), 7.21 (s, 1H), 7.63 (s, 1H), 7.65 (d, J = 1.75 Hz, 1H), 8.08-8.16 (m, 2H), 8.17 (d, J = 1.75 Hz, 2H), 8.58 (d, J = 9.79 Hz, 1H), 9.10 (s, 1H) |
| 184 | (400 MHz, DMSO-d$_6$) ppm 8.73 (d, J = 5.18 Hz, 1H), 8.48-8.55 (m, 2H), 8.03 (d, J = 9.85 Hz, 1H), 7.96 (d, J = 9.09 Hz, 1H), 7.70-7.75 (m, 2H), 7.30-7.35 (m, 2H), 7.12 (dd, J = 9.22, 2.40 Hz, 1H), 5.98 (s, 2H), 3.88 (s, 3H). |
| 194 | (400 MHz, MeOH) ppm 8.69 (d, J = 4.93 Hz, 1H), 8.35 (d, J = 9.85 Hz, 1H), 8.08 (d, J = 9.22 Hz, 1H), 8.00 (d, J = 9.85 Hz, 1 H), 7.85-7.93 (m, 2H), 7.29-7.33 (m, 2H), 7.10-7.20 (m, 2 H), 6.05 (s, 2H), 3.93 (s, 3H), 2.28 (s, 3H). |
| 198 | (400 MHz, MeOH) ppm 8.68 (d, J = 5.43 Hz, 1H), 8.42 (d, J = 9.73 Hz, 2H), 8.26 (d, J = 6.82 Hz, 1H), 8.06 (dd, J = 9.47, 2.78 Hz, 2H), 7.78 (d, J = 8.72 Hz, 1H), 7.28-7.31 (m, 2H), 7.08-7.12 (m, 1H), 6.07 (s, 2H), 3.92 (s, 3H). |
| 215 | (400 MHz, DMSO-d$_6$) ppm 2.33 (s, 3H) 3.96 (s, 3H) 6.00 (s, 2 H) 7.19 (dd, J = 9.16, 2.46 Hz, 1H) 7.38 (d, J = 5.31 Hz, 1H) 7.40 (d, J = 2.27 Hz, 1H) 7.48 (s, 1H) 7.99 (s, 1H) 8.01-8.10 (m, 2H) 8.54 (d, J = 9.73 Hz, 1H) 8.80 (d, J = 5.31 Hz, 1H) |
| 219 | (400 MHz, DMSO-d$_6$) ppm 3.89 (s, 3H) 6.06 (s, 2H) 7.12 (d, J = 9.09 Hz, 1H) 7.29-7.38 (m, 2H) 7.51 (t, J = 9.03 Hz, 1H) 7.86 (d, J = 6.44 Hz, 2H) 7.98 (d, J = 9.09 Hz, 1H) 8.12 (d, J = 9.98 Hz, 1 H) 8.62 (d, J = 9.35 Hz, 1H) 8.74 (d, J = 4.80 Hz, 1H) |
| 220 | (400 MHz, DMSO-d$_6$) ppm 3.90 (s, 3H) 6.06 (s, 2H) 7.13 (d, J = 8.59 Hz, 1H) 7.32 (d, J = 5.05 Hz, 1H) 7.35 (s, 1H) 7.99 (d, J = 9.35 Hz, 1H) 8.05-8.15 (m, 3H) 8.62 (d, J = 9.73 Hz, 1H) 8.74 (d, J = 5.05 Hz, 1H) |
| 222 | (400 MHz, DMSO-d$_6$) ppm 2.50 (s, 3H) 3.89 (s, 3H) 5.98 (s, 2 H) 7.12 (d, J = 8.84 Hz, 1H) 7.32 (d, J = 14.91 Hz, 2H) 7.93-8.06 (m, 2H) 8.09 (s, 1H) 8.63 (d, J = 8.97 Hz, 1H) 8.74 (s, 1H) |
| 224 | (400 MHz, DMF) ppm 4.31 (s, 3H) 6.49 (s, 2H) 7.55 (dd, J = 8.84, 2.02 Hz, 1H) 7.74 (d, J = 5.18 Hz, 1H) 7.76 (s, 1H) 8.27 (s, 1H) 8.41 (d, J = 9.22 Hz, 1H) 8.54 (d, J = 1.14 Hz, 2H) 8.58 (s, 1H) 9.02 (d, J = 9.60 Hz, 1H) 9.16 (d, J = 5.31 Hz, 1H) |
| 233 | (400 MHz, DMSO-d$_6$) ppm 3.89 (s, 3H) 3.90 (s, 3H) 5.93 (s, 2H) 7.13 (dd, J = 9.16, 2.59 Hz, 1H) 7.30 (d, J = 5.31 Hz, 1H) 7.34 (d, J = 2.40 Hz, 1H) 7.79 (d, J = 9.73 Hz, 1H) 7.96 (d, J = 9.22 Hz, 1 H) 8.09 (s, 1H) 8.44 (d, J = 9.73 Hz, 1H) 8.46 (s, 1H) 8.73 (d, J = 5.30 Hz, 1H). |
| 234 | (400 MHz, DMSO-d$_6$) ppm 3.93 (s, 3H) 3.94 (s, 3H) 5.12 (d, J = 6.19 Hz, 2H) 6.82 (d, J = 5.43 Hz, 1H) 7.57 (d, J = 2.78 Hz, 1H) 7.70 (d, J = 9.73 Hz, 1H) 7.96 (t, J = 6.19 Hz, 1H) 8.21 (s, 1H) 8.34 (d, J = 9.73 Hz, 1H) 8.41 (d, J = 5.43 Hz, 1H) 8.51 (d, J = 2.78 Hz, 1H) 8.52 (s, 1H). |
| 238 | (400 MHz, DMSO-d$_6$) ppm 1.37 (t, J = 6.95 Hz, 3H), 3.89 (s, 3 H), 4.19 (q, J = 6.95 Hz, 2H), 6.01 (s, 2H), 7.12 (dd, J = 8.91, 2.46 Hz, 1H), 7.28-7.36 (m, 3H), 7.92 (d, J = 7.71 Hz, 1H), 7.97 (d, J = 9.09 Hz, 2H), 8.06 (d, J = 9.85 Hz, 1H), 8.51 (d, J = 9.85 Hz, 1 H), 8.73 (d, J = 5.18 Hz, 1H) |
| 245 | (400 MHz, DMSO-d$_6$) ppm 3.88 (s, 3H), 6.03 (s, 2H), 7.12 (dd, J = 9.16, 2.46 Hz, 1H), 7.25 (d, J = 5.31 Hz, 1H), 7.27-7.31 (m, 1H), 7.34 (d, J = 2.53 Hz, 1H), 7.50-7.59 (m, 1H), 7.63-7.74 (m, 2H), 7.90-8.00 (m, 2H), 8.74 (d, J = 5.31 Hz, 1H), 9.02 (s, 1H) |
| 245 | (400 MHz, DMSO-d$_6$) ppm 3.88 (s, 3H), 6.04 (s, 2H), 7.13 (d, J = 10.86 Hz, 1H), 7.24 (d, J = 5.31 Hz, 1H), 7.34 (s, 1H), 7.45 (d, J = 6.44 Hz, 1H), 7.50 (t, J = 6.63 Hz, 2H), 7.78 (d, J = 7.45 Hz, 2 H), 7.89 (d, J = 12.25 Hz, 1H), 7.97 (d, J = 9.22 Hz, 1H), 8.74 (d, J = 6.19 Hz, 1H), 8.94 (s, 1H) |

-continued

| Example | 1H NMR Data |
|---|---|
| 247 | (400 MHz, DMSO-$d_6$) ppm 3.91 (s, 3H), 5.16 (d, J = 5.94 Hz, 1 H), 6.91 (d, J = 5.31 Hz, 1H), 7.32 (t, J = 8.34 Hz, 1H), 7.55 (d, J = 2.53 Hz, 1H), 7.57-7.63 (m, 1H), 7.64-7.74 (m, 2H), 7.83 (d, J = 12.51 Hz, 1H), 8.34-8.45 (m, 2H), 8.50 (d, J = 2.53 Hz, 1 H), 9.11 (s, 2H) |
| 252 | (400 MHz, DMSO-$d_6$) ppm 3.88 (s, 3H) 6.02 (s, 2H) 7.12 (dd, J = 9.16 Hz, 1H) 7.25 (d, J = 5.31 Hz, 1H) 7.30-7.42 (m, 3H) 7.73-7.89 (m, 3H) 7.89-8.01 (m, 2H) 8.73 (d, J = 5.31 Hz, 1H) 9.01 (s, 1H) |
| 252 | (400 MHz, DMSO-$d_6$) ppm 3.88 (s, 3H) 6.02 (s, 2H) 7.12 (dd, J = 9.16 Hz, 1H) 7.25 (d, J = 5.31 Hz, 1H) 7.30-7.42 (m, 3H) 7.73-7.89 (m, 3H) 7.89-8.01 (m, 2H) 8.73 (d, J = 5.31 Hz, 1H) 9.01 (s, 1H) |
| 254 | (400 MHz, DMSO-$d_6$) ppm 3.88 (s, 3H) 6.00 (s, 2H) 7.12 (dd, J = 9.09 Hz, 1H) 7.26 (d, J = 5.43 Hz, 1H) 7.33 (d, J = 2.40 Hz, 1H) 7.51-7.71 (m, 2H) 7.81-8.02 (m, 4H) 8.74 (d, J = 5.30 Hz, 1H) 9.08 (s, 1H) |
| 259 | (400 MHz, DMSO-$d_6$) ppm 2.76 (d, J = 4.29 Hz, 3H) 3.88 (s, 3 H) 6.03 (s, 2H) 7.13 (d, J = 8.84 Hz, 1H) 7.26 (d, J = 5.05 Hz, 1H) 7.33 (s, 1H) 7.54 (d, J = 7.58 Hz, 1H) 7.79 (d, J = 7.83 Hz, 1H) 7.85-8.04 (m, 4H) 8.39 (d, J = 3.66 Hz, 1H) 8.74 (d, J = 5.31 Hz, 1H) 9.12 (s, 1H) |
| 263 | (400 MHz, DMSO-$d_6$) ppm 3.88 (s, 3H) 6.00 (s, 2H) 7.12 (dd, J = 9.09 Hz, 1H) 7.26 (d, J = 5.18 Hz, 1H) 7.33 (d, J = 2.27 Hz, 1H) 7.65-7.69 (m, 1H) 7.69-7.74 (m, 1H) 7.92-7.97 (m, 3H) 8.08 (d, J = 2.27 Hz, 1H) 8.74 (d, J = 5.18 Hz, 1H) 9.07 (s, 1H) |
| 266 | (400 MHz, DMSO-$d_6$) ppm 3.88 (s, 3H) 6.01 (s, 2H) 7.11 (dd, J = 9.22 Hz, 1H) 7.26 (d, J = 5.30 Hz, 1H) 7.29-7.37 (m, 2H) 7.60 (d, J = 6.95 Hz, 2H) 7.89-8.01 (m, 3H) 8.75 (d, J = 5.31 Hz, 1H) 9.16 (s, 1H) |
| 267 | (400 MHz, DMSO-$d_6$) ppm 3.88 (s, 3H) 5.99 (s, 2H) 7.11 (dd, J = 2.40 Hz, 1H) 7.26 (d, J = 5.31 Hz, 1H) 7.34 (d, J = 2.27 Hz, 1H) 7.79-7.93 (m, 3H) 7.93-8.04 (m, 2H) 8.75 (d, J = 5.31 Hz, 1H) 9.14 (s, 1H) |
| 270 | (400 MHz, DMSO-$d_6$) ppm 3.89 (s, 3H) 6.01 (s, 2H) 7.14 (dd, J = 9.16 Hz, 1H) 7.22-7.26 (m, 2H) 7.35 (d, J = 2.53 Hz, 1H) 7.55 (d, J = 3.92 Hz, 1H) 7.78 (dd, J = 9.60 Hz, 1H) 7.93-8.00 (m, 2H) 8.74 (d, J = 5.31 Hz, 1H) 8.97 (t, 1H) |
| 279 | (400 MHz, DMSO-$d_6$) ppm 2.50 (s, 3H) 3.89 (s, 3H) 6.06 (s, 2 H) 7.13 (d, J = 7.58 Hz, 1H) 7.25 (d, J = 2.40 Hz, 1H) 7.35 (s, 1H) 7.66 (s, 1H) 7.91-8.01 (m, 3H) 8.74 (d, J = 5.68 Hz, 1H) 9.18 (s, 1H) |
| 283 | (400 MHz, DMSO-$d_6$) ppm 3.88 (s, 3H) 5.92 (s, 2H) 6.15 (s, 1 H) 6.69 (s, 1H) 6.94 (s, 1H) 7.12 (dd, J = 8.91, 1.96 Hz, 1H) 7.29 (d, J = 5.18 Hz, 1H) 7.34 (d, J = 1.77 Hz, 1H) 7.81-7.90 (m, 2H) 7.98 (d, J = 9.22 Hz, 1H) 8.76 (d, J = 5.18 Hz, 1H) 8.88 (s, 1H) 11.49 (s, 1H). |
| 284 | (400 MHz, DMSO-$d_6$) ppm 3.88 (s, 3H) 6.03 (s, 2H) 7.13 (dd, J = 9.16, 2.34 Hz, 1H) 7.25 (d, J = 5.30 Hz, 1H) 7.33 (d, J = 2.15 Hz, 1H) 7.43 (t, J = 7.14 Hz, 1H) 7.50 (t, J = 7.45 Hz, 2H) 7.75 (d, J = 7.45 Hz, 2H) 7.85 (d, J = 8.72 Hz, 1H) 7.96 (d, J = 9.22 Hz, 2H) 8.74 (d, J = 5.31 Hz, 1H) 9.00 (s, 1H). |
| 285 | (400 MHz, DMSO-$d_6$) ppm 3.89 (s, 3H) 6.03 (s, 2H) 7.11-7.21 (m, 2H) 7.24 (d, J = 5.30 Hz, 1H) 7.34 (d, J = 2.27 Hz, 1H) 7.62-7.67 (m, 2H) 7.81 (dd, J = 9.60, 1.14 Hz, 1H) 7.96 (dd, J = 16.55, 9.35 Hz, 2H) 8.73 (d, J = 5.18 Hz, 1H) 8.96 (s, 1H). |
| 287 | (400 MHz, DMSO-$d_6$) ppm 2.23 (s, 3H) 3.89 (s, 3H) 6.02 (s, 2H) 7.14 (dd, J = 9.16, 2.46 Hz, 1H) 7.20-7.26 (m, 2H) 7.34 (d, J = 2.53 Hz, 1H) 7.47 (s, 1H) 7.76 (dd, J = 9.66, 1.45 Hz, 1H) 7.94 (dd, J = 18.88, 9.41 Hz, 2H) 8.74 (d, J = 5.18 Hz, 1H) 8.92 (s, 1H). |
| 290 | (400 MHz, DMSO-$d_6$) ppm 3.89 (s, 3H) 6.02 (s, 2H) 7.15 (dd, J = 9.28, 2.34 Hz, 1H) 7.25 (d, J = 5.31 Hz, 1H) 7.35 (d, J = 2.27 Hz, 1H) 7.87 (d, J = 10.36 Hz, 1H) 7.98 (d, J = 8.84 Hz, 2H) 8.45 (s, 1H) 8.74 (d, J = 5.43 Hz, 1H) 9.06 (s, 1H) 9.17 (s, 1H) |
| 291 | (400 MHz, DMSO-$d_6$) ppm 2.46 (s, 3H) 3.89 (s, 3H) 6.01 (s, 2 H) 7.14 (dd, J = 9.22, 2.53 Hz, 1H) 7.25 (d, J = 5.31 Hz, 1H) 7.35 (d, J = 2.40 Hz, 1H) 7.73 (s, 1H) 7.77 (dd, J = 9.60, 1.52 Hz, 1H) 7.97 (d, J = 9.22 Hz, 1H) 8.00 (d, J = 9.60 Hz, 1H) 8.75 (d, J = 5.31 Hz, 1H) 9.19 (s, 1H) |
| 295 | (400 MHz, DMSO-$d_6$) ppm 3.93 (s, 3H) 5.14 (d, J = 5.94 Hz, 2 H) 6.91 (d, J = 5.18 Hz, 1H) 7.57 (d, J = 2.02 Hz, 1H) 7.73 (s, 1H) 7.76 (d, J = 11.37 Hz, 1H) 8.35 (t, J = 6.00 Hz, 1H) 8.43 (d, J = 4.80 Hz, 1H) 8.53 (d, J = 2.53 Hz, 1H) 9.17 (s, 1H) |
| 297 | (400 MHz, DMSO-$d_6$) ppm 2.30 (s, 3H) 3.89 (s, 3H) 6.03 (s, 2 H) 7.07 (s, 1H) 7.13 (dd, J = 9.09, 2.53 Hz, 1H) 7.25 (d, J = 5.43 Hz, 1H) 7.35 (d, J = 2.40 Hz, 1H) 7.88 (dd, J = 9.73, 1.39 Hz, 1H) 7.96 (d, J = 9.22 Hz, 1H) 8.04 (d, J = 9.60 Hz, 1H) 8.75 (d, J = 5.31 Hz, 1H) 9.29 (s, 1H) |

| Example | 1H NMR Data |
|---|---|
| 298 | (400 MHz, DMSO-d$_6$) ppm 3.93 (s, 3H) 5.16 (d, J = 5.94 Hz, 2 H) 6.91 (d, J = 5.43 Hz, 1H) 7.56 (d, J = 2.27 Hz, 1H) 7.83-7.94 (m, 3H) 8.34 (t, J = 5.75 Hz, 1H) 8.43 (d, J = 5.18 Hz, 1H) 8.52 (d, J = 2.27 Hz, 1H) 9.14 (s, 1H) |
| 302 | (400 MHz, DMSO-d$_6$) ppm 2.22 (s, 3H), 3.88 (s, 3H), 6.03 (s, 2H), 7.04-7.42 (m, 4H), 7.50 (s, 1H), 7.79 (d, J = 9.47 Hz, 1H), 7.97 (d, J = 6.06 Hz, 1H), 8.76 (d, J = 18.95, 2H) |
| 306 | (400 MHz, CHLOROFORM-d) ppm 4.72 (s, 1H) 7.27 (dd, J = 9.59, 1.56 Hz, 1H) 7.41 (dd, J = 8.31, 4.21 Hz, 1H) 7.62-7.66 (m, 2H) 7.69 (dd, J = 9.68, 0.88 Hz, 1H) 7.87-7.91 (m, 1H) 8.05-8.12 (m, 2H) 8.92 (dd, J = 4.21, 1.66 Hz, 1H) |
| 307 | (400 MHz, DMSO-d$_6$) ppm 5.03 (s, 2H) 7.49 (t, J = 7.34 Hz, 1 H) 7.57 (t, J = 7.43 Hz, 3H) 7.84 (d, J = 7.43 Hz, 2H) 7.93-8.02 (m, 1H) 8.08 (d, J = 9.59 Hz, 1H) 8.12-8.20 (m, 2H) 8.27 (s, 1 H) 8.35 (d, J = 7.82 Hz, 1H) 9.00 (d, J = 6.46 Hz, 1H) 9.11 (d, J = 5.09 Hz, 1H) 9.22 (d, J = 3.91 Hz, 1H). |
| 308 | (400 MHz, DMSO-d$_6$) ppm 2.32 (s, 3H) 5.00 (s, 2H) 7.92 (d, J = 9.54 Hz, 1H) 8.01 (t, J = 15.56, 6.53 Hz, 2H) 8.16 (d, J = 8.53 Hz, 1H) 8.25 (s, 1H) 8.37 (d, J = 9.03 Hz, 1H) 9.04 (d, J = 8.03 Hz, 1H) 9.21 (s, 1H) 9.23 (d, J = 4.52 Hz, 1H) |
| 315 | (400 MHz, DMSO-d$_6$) ppm 5.06 (s, 2H), 7.52-7.62 (m, 3H), 7.62-7.71 (m, 1H), 7.83 (d, J = 7.07 Hz, 1H) 7.93 (d, J = 9.73 Hz, 1H), 8.01-8.11 (m, 3H), 8.21 (d, J = 6.06 Hz, 1H), 8.41 (d, J = 9.85 Hz, 1H), 8.55 (d, J = 5.94 Hz, 1H), 9.32 (s, 1H) |
| 323 | (400 MHz, CDCl$_3$) ppm 3.84 (t, J = 7.33 Hz, 2H), 3.93-4.00 (m, 5H), 7.33 (d, J = 4.42 Hz, 1H), 7.48-7.56 (m, 4H), 7.59 (s, 1 H), 7.85 (dd, J = 7.45, 1.77 Hz, 2H), 8.11 (d, J = 9.73 Hz, 1H), 8.69 (d, J = 4.42 Hz, 1H), 8.72 (d, J = 2.90 Hz, 1H) |
| 328 | (300 MHz, DMSO-d$_6$) ppm 4.48 (s, 2H) 6.90 (d, J = 8.33 Hz, 1 H) 7.14 (dd, J = 8.11, 1.39 Hz, 1H) 7.42 (d, J = 1.46 Hz, 1H) 7.53-7.71 (m, 3H) 7.94 (d, J = 9.79 Hz, 1H) 8.05-8.22 (m, 2H) 8.42 (d, J = 9.79 Hz, 1H), 10.2 (br, 1H). |
| 332 | (300 MHz, DMSO-d$_6$) ppm 2.01 (s, 3H) 3.34 (s, 1H) 4.53 (s, 2 H) 7.32 (d, J = 7.60 Hz, 2H) 7.51 (d, J = 7.45 Hz, 2H) 7.59 (s, 3H) 7.94 (d, J = 9.50 Hz, 1H) 8.11 (s, 2H) 8.42 (d, J = 9.65 Hz, 1H) 9.89 (s, 1H). |
| 336 | (300 MHz, MeOH) δ ppm 2.31 (s, 3H) 4.79 (s, 2H) 7.29 (s, 1H) 7.51 (dd, J = 8.33, 4.38 Hz, 1H) 7.70 (s, 1H) 7.82 (d, J = 9.79 Hz, 1 H) 7.85-7.90 (m, 1H) 7.95-8.01 (m, 1H) 8.03 (s, 1H) 8.14 (d, J = 9.79 Hz, 1H) 8.34 (d, J = 8.62 Hz, 1H) 8.79 (dd, J = 4.31, 1.68 Hz, 1H). |
| 337 | (300 MHz, CHLOROFORM-d) δ ppm 4.85 (s, 2H) 7.35-7.48 (m, 2H) 7.57 (dd, J = 8.18, 6.43 Hz, 2H) 7.82 (d, J = 8.62 Hz, 1H) 7.91 (s, 1H) 8.08 (d, J = 8.62 Hz, 1H) 8.13 (d, J = 8.33 Hz, 1H) 8.21 (d, J = 9.79 Hz, 1H) 8.90 (d, J = 4.24 Hz, 1H). |
| 338 | (300 MHz, CHLOROFORM-d) δ ppm 4.85 (s, 2H) 6.97-7.06 (m, 1H) 7.35-7.43 (m, 1H) 7.43-7.51 (m, 3H) 7.84 (d, J = 8.62 Hz, 1H) 7.93 (t, J = 4.90 Hz, 1H) 8.08 (d, J = 8.48 Hz, 1H) 8.13 (d, J = 8.77 Hz, 1H) 8.20 (d, J = 9.65 Hz, 1H) 8.89 (dd, J = 4.17, 1.68 Hz, 1H). |
| 339 | (300 MHz, CHLOROFORM-d) δ ppm 4.84 (s, 2H) 7.17-7.26 (m, 2H) 7.39 (dd, J = 8.18, 4.24 Hz, 1H) 7.51 (d, J = 9.79 Hz, 1H) 7.85 (dd, J = 8.70, 1.97 Hz, 1H) 7.88-7.96 (m, 3H) 8.01-8.13 (m, 2H) 8.16 (d, J = 9.79 Hz, 1H) 8.89 (dd, J = 4.24, 1.61 Hz, 1H). |
| 340 | (300 MHz, CHLOROFORM-d) δ ppm 4.84 (s, 2H) 7.34 (d, J = 9.65 Hz, 1H) 7.40 (dd, J = 8.18, 4.24 Hz, 1H) 7.48 (d, J = 9.65 Hz, 1H) 7.61-7.69 (m, 1H) 7.74-7.80 (m, 1H) 7.83 (dd, J = 8.62, 2.05 Hz, 1H) 7.90 (s, 1H) 8.08 (d, J = 8.62 Hz, 1H) 8.12 (d, J = 9.06 Hz, 1H) 8.18 (d, J = 9.79 Hz, 1H) 8.89 (dd, J = 4.17, 1.68 Hz, 1H). |
| 341 | (300 MHz, CHLOROFORM-d) δ ppm 4.01 (s, 3H) 4.79 (s, 2H) 7.25 (s, 1H) 7.38 (dd, J = 8.33, 4.24 Hz, 1H) 7.81-7.89 (m, 2H) 7.91 (s, 1H) 8.00 (s, 1H) 8.03-8.10 (m, 2H) 8.11 (s, 1H) 8.88 (dd, J = 4.24, 1.61 Hz, 1H). |
| 342 | (300 MHz, DMSO-d$_6$) δ ppm 4.74 (s, 2H) 7.45 (d, J = 2.63 Hz, 1 H) 7.53 (dd, J = 8.62, 1.90 Hz, 1H) 7.56-7.61 (m, 3H) 7.79 (s, 1 H) 7.84 (d, J = 8.62 Hz, 1H) 7.94 (d, J = 9.79 Hz, 1H) 8.10 (dd, J = 6.65, 3.00 Hz, 2H) 8.42 (d, J = 9.79 Hz, 1H) 8.51 (d, J = 2.78 Hz, 1H) 10.29 (s, 1H). |
| 343 | (400 MHz, DMSO-d$_6$) ppm 5.98 (d, J = 2.74 Hz, 1H), 5.99 (s, 2 H), 6.05 (d, J = 9.39 Hz, 1H), 7.40 (d, J = 2.74 Hz, 1H), 7.58-7.64 (m, 3H), 7.93 (d, J = 9.59 Hz, 1H), 8.00 (d, J = 9.78 Hz, 1H), 8.10-8.16 (m, 2H), 8.46 (d, J = 9.78 Hz, 1H), 11.44 (br. s., 1H) |

| Cmpd # | 1H NMR data |
| --- | --- |
| 348 | 1H NMR (400 MHz, DMSO-d$_6$) ppm 8.70 (d, J = 2.74 Hz, 1H), 8.53 (s, 1H), 8.50 (d, J = 5.28 Hz, 1H), 8.35 (d, J = 9.68 Hz, 1H), 8.21 (d, J = 0.78 Hz, 1H), 8.17 (s, 1H), 7.94 (d, J = 2.64 Hz, 1H), 7.69-7.73 (m, 1H), 6.94 (d, J = 5.38 Hz, 1H), 5.15 (d, J = 6.16 Hz, 2H), 3.94 (s, 3H) |
| 351 | 1H NMR (400 MHz, CHLOROFORM-d) d ppm 8.66 (d, J = 1.56 Hz, 1H), 8.08 (d, J = 8.51 Hz, 1H), 7.83-7.93 (m, 2H), 7.61 (s, 1H), 7.53 (d, J = 8.61 Hz, 1H), 7.42 (d, J = 9.78 Hz, 1H), 7.33 (s, 1H), 6.80-6.95 (m, 3H), 4.78 (s, 2H), 3.93 (s, 3H). |
| 352 | 1H NMR (400 MHz, CHLOROFORM-d) d ppm 8.67 (d, J = 2.84 Hz, 1H), 8.15 (d, J = 8.51 Hz, 1H), 7.94-7.99 (m, 1H), 7.86 (dd, J = 9.59 Hz, 1H), 7.62 (s, 1H), 7.56 (dd, J = 8.61 Hz, 1H), 7.34-7.43 (m, 2H), 7.07 (s, 1H), 4.77 (s, 2H), 3.95 (s, 3H), 2.51 (s, 3H). |
| 355 | 1H NMR (400 MHz, DMSO-d$_6$) ppm 2.52 (s, 3H) 5.19 (d, J = 6.26 Hz, 2H) 6.95 (d, J = 5.38 Hz, 1H) 7.71 (dd, J = 8.51, 4.11 Hz, 1H) 7.94 (d, J = 9.78 Hz, 1H) 8.04 (t, J = 6.21 Hz, 1H) 8.09 (s, 1H) 8.21 (dd, J = 8.51, 1.56 Hz, 1H) 8.50 (d, J = 5.28 Hz, 1 H) 8.54 (d, J = 9.78 Hz, 1H) 8.79 (dd, J = 4.11, 1.56 Hz, 1H). |
| 359 | 1H NMR (400 MHz, DMSO-d$_6$) ppm 2.51 (s, 3H) 5.19 (d, J = 6.06 Hz, 2H) 6.96 (d, J = 5.48 Hz, 1H) 7.94 (d, J = 9.68 Hz, 1H) 8.05 (dd, J = 10.03, 2.49 Hz, 1H) 8.09 (s, 1H) 8.22 (s, 1H) 8.48-8.59 (m, 2H) 8.85 (d, J = 2.64 Hz, 1H) |
| 364 | 1H NMR (400 MHz, DMSO-d$_6$) ppm 2.51 (s, 3H) 5.17 (d, J = 6.16 Hz, 2H) 6.94 (d, J = 5.38 Hz, 1H) 7.53 (t, J = 73.21 Hz, 1H) 7.89-7.99 (m, 2H) 8.09 (s, 1H) 8.12 (t, J = 6.26 Hz, 1H) 8.51 (d, J = 5.28 Hz, 1H) 8.54 (d, J = 9.68 Hz, 1H) 8.70 (d, J = 2.74 Hz, 1H). |
| 365 | 1H NMR (400 MHz, DMSO-d$_6$) ppm 2.52 (s, 3H) 3.33 (s, 3H) 3.71-3.76 (m, 2 H) 4.27-4.31 (m, 2H) 5.14 (d, J = 6.16 Hz, 2H) 6.82 (d, J = 5.38 Hz, 1H) 7.59 (d, J = 2.74 Hz, 1H) 7.94 (d, J = 9.78 Hz, 2H) 8.09 (s, 1H) 8.41 (d, J = 5.28 Hz, 1H) 8.49-8.57 (m, 2H) |
| 370 | 1H NMR (400 MHz, MeOH) ppm 3.44 (s, 3H) 3.82-3.87 (m, 2H) 4.29-4.34 (m, 2H) 5.40 (s, 2H) 7.02 (d, J = 5.97 Hz, 1H) 7.19-7.27 (m, 1H) 7.51 (d, J = 2.64 Hz, 1H) 7.75-7.86 (m, 2H) 7.95 (d, J = 9.88 Hz, 1H) 8.33 (d, J = 9.88 Hz, 1H) 8.39 (d, J = 6.26 Hz, 1H) 8.59 (s, 1H) |
| 371 | 1H NMR (400 MHz, DMSO-d$_6$) ppm 5.02 (q, J = 8.80 Hz, 2H) 5.22 (d, J = 6.26 Hz, 2H) 6.91 (d, J = 5.48 Hz, 1H) 7.53 (t, J = 9.15 Hz, 1H) 7.79 (d, J = 2.64 Hz, 1H) 7.99-8.10 (m, 3H) 8.21 (t, J = 5.97 Hz, 1H) 8.44 (d, J = 5.28 Hz, 1H) 8.51 (d, J = 9.78 Hz, 1 H) 8.61 (d, J = 2.64 Hz, 1H) |
| 372 | 1H NMR (400 MHz, DMSO-d$_6$) ppm 2.52 (s, 3H) 5.02 (q, J = 8.90 Hz, 2H) 5.15 (d, J = 6.16 Hz, 2H) 6.87 (d, J = 5.38 Hz, 1H) 7.80 (d, J = 2.84 Hz, 1H) 7.94 (d, J = 9.78 Hz, 1H) 8.01 (t, J = 6.11 Hz, 1H) 8.09 (s, 1H) 8.45 (d, J = 5.28 Hz, 1H) 8.54 (d, J = 9.78 Hz, 1H) 8.62 (d, J = 2.84 Hz, 1H). |
| 383 | 1H NMR (400 MHz, DMSO-d$_6$) ppm 3.94 (s, 3H) 4.50-4.62 (m, 2H) 5.14 (d, J = 6.16 Hz, 2H) 6.30-6.64 (m, 1H) 6.87 (d, J = 5.48 Hz, 1H) 7.66-7.74 (m, 1H) 8.06 (t, J = 6.11 Hz, 1H) 8.21 (d, J = 0.68 Hz, 1H) 8.34 (d, J = 9.68 Hz, 1H) 8.44 (d, J = 5.38 Hz, 1H) 8.52 (s, 1H) 8.59 (d, J = 2.84 Hz, 1H). |
| 390 | (400 MHz, DMSO-d6) ppm 8.64 (s, 1H), 8.51 (d, J = 2.8 Hz, 1H), 8.40 (d, J = 5.2 Hz, 1H), 8.35 (d, J = 9.6 Hz, 1 Hz), 8.19 (s, 1H), 7.99 (t, J = 6.0 Hz, 1H), 7.72 (d, J = 10 Hz, 1H), 7.57 (d J = 2.8 Hz, 1H), 6.83 (d, J = 5.2 Hz, 1H), 5.12 (d, J = 6.0 Hz, 2H), 3.93 (s, 3H), 3.80-3.86 (m, 1H), 1.10-1015 (m, 2H), 1.00-1.08 (m, 2H). |
| 399 | 1H NMR (400 MHz, DMSO-d$_6$) d ppm 8.49-8.55 (m, 2H), 8.41 (d, J = 5.38 Hz, 1 H), 8.24 (s, 1H), 8.03 (d, J = 9.68 Hz, 1H), 7.94 (t, J = 6.16 Hz, 1H), 7.58 (d, J = 2.84 Hz, 1H), 6.83 (d, J = 5.38 Hz, 1H), 5.67 (t, J = 5.77 Hz, 1H), 5.15 (d, J = 6.16 Hz, 2 H), 4.63 (d, J = 5.67 Hz, 2H), 3.93 (s, 3H). |
| 400 | 1H NMR (400 MHz, DMSO-d$_6$) ppm 5.26 (d, J = 6.36 Hz, 2H) 7.02 (d, J = 5.38 Hz, 1H) 7.96-8.10 (m, 2H) 8.22-8.32 (m, 2H) 8.48-8.57 (m, 3H) 8.85 (d, J = 2.84 Hz, 1H) |
| 405 | 1H NMR (400 MHz, DMSO-d$_6$) ppm 3.43-3.53 (m, 4H) 3.70-3.80 (m, 4H) 3.94 (s, 3H) 5.16 (d, J = 6.16 Hz, 2H) 6.85 (d, J = 5.28 Hz, 1H) 7.57 (d, J = 2.74 Hz, 1 H) 7.87 (s, 1H) 7.90 (d, J = 9.68 Hz, 1H) 8.01-8.08 (m, 1H) 8.35-8.45 (m, 2H) 8.52 (d, J = 2.64 Hz, 1H) |
| 406 | 1H NMR (400 MHz, DMSO-d$_6$) ppm 3.94 (s, 3H) 5.19 (d, J = 6.26 Hz, 2H) 6.85 (d, J = 5.38 Hz, 1H) 7.57 (d, J = 2.93 Hz, 1H) 7.97-8.02 (m, 1H) 8.05 (d, J = 9.78 Hz, 1H) 8.42 (d, J = 5.28 Hz, 1H) 8.45 (d, J = 9.68 Hz, 1H) 8.52 (d, J = 2.84 Hz, 1H) 8.71 (d, J = 1.96 Hz, 1H) 9.36 (d, J = 1.96 Hz, 1H) |
| 408 | 1H NMR (400 MHz, DMSO-d$_6$) ppm 1.90 (d, J = 7.04 Hz, 3H) 2.44 (s, 3H) 5.24 (q, J = 7.01 Hz, 1H) 7.51 (dd, J = 8.27, 4.16 Hz, 1H) 7.64-7.73 (m, 2H) 7.81 (dd, J = 8.75, 2.01 Hz, 1H) 7.94 (d, J = 1.96 Hz, 1H) 8.00 (d, J = 8.61 Hz, 1H) 8.32 (d, J = 8.41 Hz, 1H) 8.64 (d, J = 1.17 Hz, 1H) 8.86 (dd, J = 4.16, 1.71 Hz, 1H) |
| 409 | 1H NMR (400 MHz, DMSO-d$_6$) ppm 1.92 (d, J = 7.14 Hz, 3H) 5.26 (q, 1H) 7.31 (t, J = 9.29 Hz, 1H) 7.49 (dd, J = 8.36, 4.16 Hz, 2H) 7.55 (d, J = 8.61 Hz, 1H) 7.77-7.86 (m, J = 8.22 Hz, 2H) 7.95 (s, 1H) 7.99 (d, J = 8.71 Hz, 1H) 8.31 (d, J = 7.24 Hz, 1 H) 8.68 (s, 1H) 8.85 (dd, J = 4.11, 1.66 Hz, 1H) |
| 411 | 1H NMR (400 MHz, DMSO-d$_6$) ppm 1.89 (d, J = 7.04 Hz, 3H) 2.27 (s, 3H) 3.88 (s, 3H) 5.22 (q, J = 6.98 Hz, 1H) 6.99 (s, 1H) 7.63 (dd, J = 8.71, 2.05 Hz, 1H) 7.67-7.70 (m, 1H) 7.72 (d, J = 1.86 Hz, 1H) 7.76 (d, J = 11.54, 1.17 Hz, 1H) 7.93 (d, J = 8.61 Hz, 1H) 8.58 (d, J = 2.93 Hz, 1H) 8.64 (d, J = 1.08 Hz, 1H) |
| 413 | 1H NMR (400 MHz, DMSO-d$_6$) ppm 2.40 (s, 3H) 2.44 (d, J = 23.28 Hz, 3H) 7.56-7.61 (m, 2H) 7.75 (dd, J = 8.90, 2.15 Hz, 1H) 7.80 (dd, J = 11.49, 1.22 Hz, 1H) 8.02 (d, J = 0.88 Hz, 1H) 8.09 (d, J = 8.90 Hz, 1H) 8.12 (d, J = 2.05 Hz, 1H) 8.43-8.47 (m, 1H) 8.95 (dd, J = 4.21, 1.76 Hz, 1H) |

| Cmpd # | 1H NMR data |
|---|---|
| 418 | 1H NMR (400 MHz, DMSO-$d_6$) ppm 3.89 (s, 3H) 4.88 (s, 2H) 7.61 (dd, J = 8.56, 2.01 Hz, 1H) 7.68 (d, J = 2.74 Hz, 1H) 7.70-7.75 (m, 1H) 7.83 (s, 1H) 7.89 (dd, J = 11.44, 1.08 Hz, 1H) 7.93 (d, J = 8.61 Hz, 1H) 8.59 (d, J = 2.84 Hz, 1H) 9.17 (d, J = 1.08 Hz, 1H) |
| 430 | 1H NMR (400 MHz, DMSO-$d_6$) ppm 8.84 (dd, J = 4.25, 1.71 Hz, 1H), 8.42-8.46 (m, 1H), 8.26 (d, J = 2.05 Hz, 1H), 8.15 (d, J = 9.49 Hz, 1H), 7.94 (s, 1H), 7.90 (d, J = 8.80 Hz, 1H), 7.67-7.76 (m, 4H), 7.52 (dd, J = 8.26, 4.25 Hz, 1H), 7.38-7.44 (m, 1H), 7.32-7.37 (m, 2H), 6.17 (s, 1H), 2.17 (s, 3H) |
| 431 | 1H NMR (400 MHz, DMSO-$d_6$) ppm 8.85 (dd, J = 4.21, 1.76 Hz, 1H), 8.31-8.35 (m, 1H), 8.21 (d, J = 9.59 Hz, 1H), 8.04-8.08 (m, 2H), 7.95-7.99 (m, 2H), 7.75-7.83 (m, 3H), 7.49-7.58 (m, 4H), 4.62 (s, 2H) |
| 433 | 1H NMR (400 MHz, DMSO-$d_6$) ppm 9.01 (dd, J = 4.21, 1.66 Hz, 1H), 8.54-8.59 (m, 1H), 8.47 (s, 1H), 8.44 (d, J = 9.59 Hz, 1H), 8.16 (d, J = 8.80 Hz, 1H), 8.13 (s, 1H), 8.00 (dd, J = 8.90, 2.05 Hz, 1H), 7.88 (d, J = 9.59 Hz, 1H), 7.64 (dd, J = 8.31, 4.21 Hz, 1H), 7.11 (s, 1H), 2.33 (s, 3H) |
| 436 | 1H NMR (400 MHz, DMSO-$d_6$) ppm 8.46 (d, J = 2.74 Hz, 1H), 8.38 (d, J = 5.38 Hz, 1H), 8.29 (d, J = 9.39 Hz, 1H), 8.00 (s, 1H), 7.76-7.82 (m, 3H), 7.54 (d, J = 2.84 Hz, 1H), 6.79 (d, J = 5.38 Hz, 1H), 4.98 (d, J = 6.36 Hz, 2H), 3.91 (s, 3H) |
| 437 | $^1$H NMR (400 MHz, CHLOROFORM-d) ppm 4.80 (s, 2H) 7.19 (dd, J = 10.76, 1.17 Hz, 1H) 7.31-7.35 (m, 2H) 7.38-7.43 (m, 4H) 7.65-7.71 (m, 3H) 8.07 (dd, J = 8.31, 0.88 Hz, 1H) 8.11 (d, J = 8.41 Hz, 1H) 8.91 (d, J = 4.21, 1.66 Hz, 1H). |
| 438 | $^1$H NMR (400 MHz, DMSO-$d_6$) ppm 3.88 (s, 3H) 4.76 (s, 2H) 7.52-7.59 (m, 1 H) 7.61 (s, 1H) 7.65 (d, J = 12.32 Hz, 1H) 7.80 (s, 1H) 7.91 (d, J = 8.80 Hz, 1H) 8.01 (s, 1H) 8.27 (s, 1H) 8.57-8.66 (m, 2H) 10.59 (br. s., 1H) |
| 439 | 1H NMR (400 MHz, DMF) ppm 7.69 (tt, J = 9.32, 2.27 Hz, 3H) 7.99 (dd, J = 8.31, 4.21 Hz, 1H) 8.01-8.09 (m, 2H) 8.43 (dd, J = 8.90, 2.15 Hz, 1H) 8.54 (d, J = 8.8 Hz 1H) 8.83-8.95 (m, 2H) 9.19 (d, J = 2.25 Hz, 1H) 9.37 (dd, J = 4.25, 1.71 Hz, 1H) 9.53 (d, J = 2.25 Hz, 1H). MS m/z = 410.0 [M + 1]$^+$ Calc'd for $C_{22}H_{11}F_4N_3O$: 409.3. |
| 442 | 1H NMR (400 MHz, DMSO-$d_6$) ppm 4.00 (s, 3H) 5.24 (d, J = 5.97 Hz, 2H) 5.76 (d, J = 46.46 Hz, 2H) 7.64 (d, J = 2.74 Hz, 1H) 7.77 (s, 1H) 8.01 (d, J = 9.68 Hz, 1H) 8.10 (t, J = 6.26 Hz, 1H) 8.48 (d, J = 5.28 Hz, 1H) 8.59 (d, J = 2.74 Hz, 1H) 8.64 (d, J = 9.68 Hz, 1H). |
| 443 | 1H NMR (400 MHz, DMSO-$d_6$) ppm 2.40-2.40 (m, 1H) 7.58 (dd, J = 8.31, 4.21 Hz, 1H) 7.81 (s, 1H) 8.00 (dd, J = 8.90, 2.25 Hz, 1H) 8.12 (d, J = 8.90 Hz, 1H) 8.44 (d, J = 1.27 Hz, 1H) 8.47 (dd, J = 8.46, 1.03 Hz, 1H) 8.70 (d, J = 2.25 Hz, 1H) 8.95 (dd, J = 4.26, 1.71 Hz, 1H) 9.07 (d, J = 2.15 Hz, 1H). |
| 444 | 1H NMR (400 MHz, DMSO-$d_6$) ppm 7.44-7.53 (m, 1H) 7.68 (dd, J = 8.31, 4.21 Hz, 1H) 8.00 (td, J = 7.78, 1.76 Hz, 1H) 8.11 (dd, J = 8.90, 2.05 Hz, 1H) 8.25 (dd, J = 15.60, 8.36 Hz, 2H) 8.55 (s, 1H) 8.58 (dd, J = 8.41, 0.78 Hz, 1H) 8.75 (dq, J = 4.77, 0.82 Hz, 1H) 9.01-9.11 (m, 2H) 9.53 (d, J = 2.15 Hz, 1H). |
| 450 | 1H NMR (400 MHz, DMSO-$d_6$) ppm 7.35-7.45 (m, 1H) 7.67 (dd, J = 8.31, 4.21 Hz, 1H) 7.73-7.85 (m, 2H) 8.11 (dd, J = 8.9, 2.0 Hz, 1H) 8.21 (d, J = 8.90 Hz, 1H) 8.48 (d, J = 9.10 Hz, 1H) 8.57 (s, 1H) 8.60 (m, 2H) 9.04 (dd, J = 4.11, 1.56 Hz, 1H). |
| 460 | 1H NMR (400 MHz, DMSO-$d_6$) ppm 3.89 (s, 3H); 3.89 (s, 3H); 4.01-4.02 (m, 1 H); 7.86 (dd, J = 8.8, 2.2 Hz, 1H); 7.91 (dd, J = 12.0, 1.0 Hz, 1H); 7.95 (d, J = 2.7 Hz, 1 H); 8.11 (d, J = 0.7 Hz, 1H); 8.15 (d, J = 8.7 Hz, 1H); 8.32 (d, J = 1.5 Hz, 1H); 8.56 (d, J = 0.7 Hz, 1H); 8.78 (d, J = 2.9 Hz, 1H) |
| 462 | 1H NMR (400 MHz, DMSO-$d_6$) ppm 1.93-2.07 (m, 2H) 2.30-2.42 (m, 4H) 2.43-2.49 (m, 2H) 3.50-3.65 (m, 4H) 3.89 (s, 3H) 4.20 (t, J = 6.41 Hz, 2H) 7.86 (dd, J = 8.75, 1.91 Hz, 1H) 7.96 (s, 1H) 7.98 (d, J = 2.64 Hz, 1H) 8.13 (s, 1H) 8.15 (d, J = 8.90 Hz, 1H) 8.32 (s, 1H) 8.46 (s, 1H) 8.57 (s, 1H) 8.78 (d, J = 2.84 Hz, 1H) |
| 468 | 1H NMR (400 MHz, CHLOROFORM-d) ppm 2.41 (s, 3H); 3.97 (s, 3H); 6.54 (s, 1H); 7.39 (dd, J = 9.8, 1.2 Hz, 1H); 7.47 (d, J = 2.8 Hz, 1H); 7.83 (dd, J = 8.8, 2.1 Hz, 1H); 8.17 (d, J = 1.1 Hz, 1H); 8.21 (d, J = 8.7 Hz, 1H) 8.75-8.84 (m, 2H) |
| 469 | 1H NMR (400 MHz, DMSO-$d_6$) ppm 3.95 (s, 3H); 7.83-7.92 (m, 2H); 7.93-8.03 (m, 2H); 8.18 (d, J = 5.6 Hz, 1H); 8.34 (s, 1H); 8.69 (s, 1H); 8.80 (d, J = 2.93 Hz, 1H) |
| 470 | 1H NMR (400 MHz, DMSO-$d_6$) ppm 2.34 (s, 3H); 7.26 (s, 1H); 7.69 (dd, J = 8.3, 4.2 Hz, 1H); 8.05 (dd, J = 8.8, 2.2 Hz, 1H); 8.09 (dd, J = 11.3, 1.1 Hz, 1H); 8.25 (d, J = 8.9 Hz, 1H); 8.50 (d, J = 1.7 Hz, 1H); 8.60 (s, 1H); 8.80 (d, J = 1.0 Hz, 1H); 9.08 (dd, J = 4.3, 1.7 Hz, 1H) |
| 471 | 1H NMR (400 MHz, DMSO-$d_6$) ppm 3.70 (s, 3H); 7.57-7.67 (m, 1H); 7.72 (s, 1 H); 7.87-8.16 (m, 3H); 8.29 (s, 1H); 8.55 (s, 1H); 8.70 (s, 1H) |
| 473 | 1H NMR (400 MHz, DMSO-$d_6$) ppm 2.32 (s, 3H); 3.47 (s, 1H); 3.55 (dd, J = 11.4, 2.01 Hz, 1H); 3.67 (s, 2H); 3.80 (s, 1H); 3.89 (s, 1H); 3.98 (s, 1H); 4.16 (d, J = 5.0 Hz, 2H); 7.22 (s, 1H); 7.87 (dd, J = 8.9, 2.0 Hz, 1H); 7.98 (d, J = 2.8 Hz, 1H); 8.05 (dd, J = 11.3, 0.6 Hz, 1H); 8.16 (d, J = 8.8 Hz, 1H); 8.31 (s, 1H); 8.74 (s, 1H); 8.81 (d, J = 2.9 Hz, 1H) |
| 474 | 1H NMR (400 MHz, DMSO-$d_6$) ppm 2.35 (s, 3H); 3.94 (s, 3H); 4.79 (d, J = 5.97 Hz, 2H); 6.76 (d, J = 5.4 Hz, 1H); 7.01 (s, 1H); 7.57 (d, J = 2.7 Hz, 1H); 7.89-7.94 (m, 1H); 7.93 (d, J = 8.6 Hz, 1H); 8.21 (d, J = 8.6 Hz, 1H); 8.34 (s, 1H); 8.40 (d, J = 5.4 Hz, 1H); 8.51 (d, J = 2.7 Hz, 1H) |
| 475 | $^1$H NMR (400 MHz, DMSO-$d_6$) ppm 3.89 (s, 3H) 7.68 (dd, J = 8.28, 4.27 Hz, 1H) 7.93 (d, J = 12.05 Hz, 1H) 8.04 (d, J = 8.53 Hz, 1H) 8.13 (s, 1H) 8.23 (d, J = 8.53 Hz, 1 H) 8.43-8.52 (m, 2H) 8.55-8.63 (m, 2H) 9.07 (d, J = 4.02 Hz, 1H). |
| 476 | $^1$H NMR (400 MHz, DMSO-$d_6$) d ppm 7.56-7.74 (m, 2H) 7.99 (d, J = 9.03 Hz, 1H) 8.21 (d, J = 8.53 Hz, 1H) 8.40 (s, 1H) 8.57 (d, J = 8.03 Hz, 1H) 8.63 (d, J = 10.04 Hz, 1 H) 9.05 (d, J = 4.02 Hz, 1H) |

-continued

| Cmpd # | 1H NMR data |
|---|---|
| 477 | $^1$H NMR (400 MHz, DMSO-$d_6$) d ppm 3.92 (s, 3H) 3.94 (s, 3H) 7.80-7.87 (m, 2 H) 8.01-8.07 (m, 1H) 8.11 (d, J = 9.04 Hz, 1H) 8.37 (s, 1H) 8.46-8.51 (m, 2H) 8.75 (d, J = 3.01 Hz, 1H) |
| 478 | $^1$H NMR (400 MHz, DMSO-$d_6$) d ppm 7.67 (dd, J = 8.03, 4.02 Hz, 1H) 7.80-7.89 (m, 2H) 8.17 (dd, J = 13.05, 9.54 Hz, 2H) 8.54 (s, 1H) 8.60 (d, J = 8.53 Hz, 1H) 8.69 (d, J = 10.04 Hz, 1H) 9.04 (d, J = 3.51 Hz, 1H) |
| 484 | $^1$H NMR (400 MHz, DMSO-$d_6$) d ppm 2.94 (t, J = 7.78 Hz, 2H) 3.03-3.14 (m, 2H) 7.44 (d, J = 8.03 Hz, 2H) 7.68 (dd, J = 8.28, 4.27 Hz, 1H) 7.85 (br. s., 2H) 7.95 (d, J = 8.03 Hz, 2H) 8.05 (d, J = 8.53 Hz, 1H) 8.12 (d, J = 9.54 Hz, 1H) 8.21 (d, J = 8.53 Hz, 1H) 8.49 (s, 1H) 8.57-8.66 (m, 2H) 9.05 (d, J = 4.02 Hz, 1H). |
| 490 | $^1$H NMR (300 MHz, CHLOROFORM-d) d ppm 2.10 (d, J = 7.16 Hz, 3H) 2.55 (s, 3H) 5.04 (q, J = 6.87 Hz, 1H) 7.27-7.52 (m, 3H) 7.82 (d, J = 8.62 Hz, 1H) 7.93 (s, 1H) 8.05 (d, J = 8.62 Hz, 1H) 8.15 (d, J = 9.21 Hz, 2H) 8.85 (d, J = 2.63 Hz, 1H). |
| 496 | $^1$H NMR (300 MHz, CHLOROFORM-d) ppm 3.58 (s, 3H) 4.78 (s, 2H) 7.48-7.63 (m, 4H) 7.66 (d, J = 8.48 Hz, 1H) 7.87 (d, J = 7.16 Hz, 1H) 7.91-8.06 (m, 3H) 8.14 (d, J = 9.65 Hz, 1H) 8.47 (s, 1H). |
| 499 | $^1$H NMR (300 MHz, CHLOROFORM-d) δ ppm 3.94 (s, 3H) 4.73 (s, 2H) 7.10 (d, J = 9.65 Hz, 1H) 7.33 (d, J = 2.78 Hz, 1H) 7.63 (d, J = 10.67 Hz, 1H) 7.76 (s, 1H) 8.00 (d, J = 8.48 Hz, 1H) 8.07 (d, J = 9.65 Hz, 1H) 8.64 (d, J = 2.92 Hz, 1H). |
| 501 | $^1$H NMR (300 MHz, MeOH) d ppm 4.05 (s, 11H) 4.82 (s, 7H) 7.40 (dd, J = 10.08, 1.46 Hz, 4H) 7.81 (dd, J = 8.77, 1.90 Hz, 4H) 7.96 (d, J = 0.88 Hz, 4H) 8.05 (d, J = 8.77 Hz, 4H) 8.21 (d, J = 2.78 Hz, 4H) 8.50 (d, J = 0.73 Hz, 3H) 8.85 (d, J = 2.92 Hz, 4H). |
| 502 | $^1$H NMR (400 MHz, CHLOROFORM-d) δ ppm 2.59 (s, 3H) 3.93 (s, 3H) 4.77 (s, 2H) 7.34 (d, J = 2.74 Hz, 1H) 7.38 (d, J = 9.68 Hz, 1H) 7.46 (s, 1H) 7.66 (dd, J = 8.61, 2.05 Hz, 1H) 7.84 (d, J = 1.96 Hz, 1H) 7.98 (d, J = 8.61 Hz, 1H) 8.16 (d, J = 9.59 Hz, 1H) 8.61 (d, J = 2.93 Hz, 1H). |

Although the pharmacological properties of the compounds of the current invention vary with structural change, in general, activity possessed by these compounds may be demonstrated in vivo. The pharmacological properties of the compounds of this invention may be confirmed by a number of pharmacological in vitro assays. The exemplified pharmacological assays, which follow, have been carried out with the compounds according to the invention. The exemplified compounds of the present invention demonstrated a $K_i$ between 20 μM and 0.1 nM. Illustrative activity values are provided in the following table.

| Ex. | cMet $K_i$ (μM) |
|---|---|
| 1 | 0.0070 |
| 3 | 0.4004 |
| 4 | 0.0032 |
| 12 | 20 |
| 13 | 6.6667 |
| 14 | 6.6667 |
| 17 | 0.0093 |
| 18 | 0.0066 |
| 19 | 1.9075 |
| 20 | 0.5562 |
| 21 | 0.8054 |
| 23 | 0.1329 |
| 24 | 0.0174 |
| 33 | 0.0732 |
| 34 | 0.0159 |
| 38 | 0.0370 |
| 39 | 0.0505 |
| 40 | 0.0075 |
| 41 | 4.2537 |
| 45 | 0.0121 |
| 50 | 0.0238 |
| 52 | 0.0050 |
| 53 | 0.0067 |
| 55 | 0.0009 |
| 58 | 2.0618 |
| 59 | 0.0845 |
| 61 | 0.3994 |
| 62 | 0.0017 |
| 66 | 1.2312 |
| 67 | 0.7584 |
| 68 | 0.5563 |
| 69 | 0.3749 |
| 70 | 0.0229 |
| 73 | 0.0128 |
| 75 | 0.0022 |
| 79 | 0.0834 |
| 82 | 0.2617 |
| 84 | 0.0261 |
| 85 | 0.0020 |
| 86 | 0.0024 |
| 87 | 20 |
| 88 | 0.1516 |
| 89 | 0.0079 |
| 91 | 0.0192 |
| 112 | 1.5765 |
| 118 | 0.0026 |
| 121 | 0.0054 |
| 122 | 0.0272 |
| 134 | 0.1161 |
| 140 | 0.0052 |
| 141 | 0.0029 |
| 144 | 0.1688 |
| 148 | 0.0092 |
| 152 | 0.4837 |
| 154 | 0.0502 |
| 164 | 0.1410 |
| 167 | 0.0733 |
| 170 | 0.0508 |
| 172 | 0.0027 |
| 176 | 0.0012 |
| 186 | 0.0062 |
| 187 | 0.0049 |
| 199 | 0.0345 |
| 202 | 0.0024 |
| 203 | 0.0075 |
| 208 | 0.0237 |
| 209 | 0.0089 |
| 214 | 0.0176 |
| 222 | 0.0016 |
| 226 | 0.0047 |
| 229 | 0.0402 |
| 231 | 0.0067 |

-continued

| Ex. | cMet $K_i$ (µM) |
|---|---|
| 232 | 0.0026 |
| 279 | 0.0197 |
| 281 | 0.0631 |
| 282 | 0.0095 |
| 283 | 0.0048 |
| 289 | 0.0526 |
| 294 | 0.0028 |
| 295 | 0.0269 |
| 296 | 0.0089 |
| 297 | 0.0032 |
| 302 | 0.0003 |
| 306 | 0.0490 |
| 309 | 0.0020 |
| 311 | 0.0070 |
| 314 | 3.2855 |
| 315 | 0.2199 |
| 317 | 0.8465 |
| 319 | 0.8532 |
| 321 | 0.2408 |
| 324 | 1.6093 |
| 325 | 20 |
| 326 | 0.3936 |
| 333 | 0.1071 |
| 334 | 0.4160 |
| 336 | 0.0007 |
| 341 | 0.0091 |
| 343 | 0.7203 |
| 373 | 0.0001 |
| 430 | 0.3480 |
| 437 | 0.0364 |
| 439 | 0.2531 |
| 440 | 0.1716 |
| 441 | 0.0286 |
| 447 | 0.0121 |
| 450 | 0.1823 |
| 466 | 0.6351 |

Biological Testing

The efficacy of the compounds of the invention as inhibitors of HGF related activity is demonstrated as follows.

c-Met Receptor Assay

Cloning, Expression and Purification of c-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCTAAATCCA-GAGCTGGTCCAGGCA-3' (SEQ ID NO. 1) and reverse primer 5'-ACAACAGAATTCAATACGGAGCGACA-CATTTTACGTT-3' (SEQ ID NO. 2). The PCR product is cloned into a modified pFastBac1 expression vector (harboring the gene for S. japonicum glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione Sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of Human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche #10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

| | Final concentration |
|---|---|
| a) 100 mM ATP (Sigma #A7699) | 25 mM |
| b) 1.0M $MgCl_2$ (Sigma #M-0250) | 100 mM |
| c) 200 mM Sodium Orthovanadate (Sigma #S-6508) | 15 mM |
| d) 1.0M Tris-HCl, pH 7.00 (in house) | 50 mM |
| e) $H_2O$ | |
| f) GST-cMET | 0.2-0.5 mg/mL |

After incubation, the solution is concentrated in a Vivaspin 20 ml Concentrator to a volume less than 2.00 ml. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

|  |  |  | Per 1 L |
|---|---|---|---|
| 60 mM HEPES $p$H 7.4 | 1M stock | 16.7 X | 60 mL |
| 50 mM NaCl | 5M stock | 100 X | 10 mL |
| 20 mM MgCl$_2$ | 1M stock | 50 X | 20 mL |
| 5 mM MnCl$_2$ | 1M stock | 200 X | 5 mL |

When the assay is carried out, freshly add:

| 2 mM DTT | 1M stock | 500 X |
|---|---|---|
| 0.05% BSA | 5% stock | 100 X |
| 0.1 mM Na$_3$OV$_4$ | 0.1M stock | 1000 X |

The HTRF buffer contains:
50 mM Tris-HCl (pH 7.5), 100 mM NaCl, 0.1% BSA, 0.05% Tween 20.5 mM EDTA
Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
  0.1 nM final Eu-PT66
  11 nM final SA-APC
Methods:
1. Dilute GST-cMet (P) enzyme in kinase buffer as follows:
  Prepare 8 nM GST-cMet (P) working solution (7.32 µM to 8 nM, 915×, 10 µL to 9.15 mL). In a 96 well clear plate [Costar #3365] add 100 µL in eleven columns, in one column add 100 µL kinase reaction buffer alone.
2. Assay plate preparation:
  Use Biomek FX to transfer 10 µL 8 nM GST-cMet (P) enzyme, 48.4 µL kinase reaction buffer, 1.6 µL compound (in DMSO) (Start concentration at 10 mM, 1 mM and 0.1 mM, sequential dilution 1:3 to reach 10 test points) in a 96 well costar clear plate [Costar #3365], mix several times. Then incubate the plate at RT for 30 min.
3. Prepare Gastrin and ATP working solution in kinase reaction buffer as follows:
  Prepare 4 µM Gastrin and 16 µM ATP working solution

|  |  | Per 10 mL |
|---|---|---|
| Gastrin 4 µM stock | (500 µM to 4 µM, 125 X) | 80 µL |
| ATP 16 µM stock | (1000 µM to 16 µM, 62.5 X) | 160 µL |

Use Biomek FX to add 20 µl ATP and Gastrin working solution to the assay plate to start reaction, incubate the plate at RT for 1 h.
4. Transfer 5 µL reaction product at the end of 1 h into 80 µL HTRF buffer in black plate [Costar #3356], read on Discover after 30 min incubation.
Assay Condition Summary:

| K$_M$ ATP * | 6 µM |
|---|---|
| [ATP] | 4 µM |
| K$_M$ Gastrin/p(EY) | 3.8 µM |
| [gastrin] | 1 µM |
| [enzyme] | 1 nM |

K$_M$ ATP, K$_M$ gastrin for various enzymes were determined by HTRF/$^{33}$P labeling and HTRF methods.

Examples 1-28, 30, 33-34, 36-37, and 39-48 exhibited activity with IC$_{50}$ values less than 0.5 µM.

c-Met Cell-Based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. 2×10$^4$ cells in medium were plated per well in a 96 well plate and incubated at 37° C. overnight. The cells were serum-starved by replacing the growth media with basic medium (DMEM low glucose+0.1 BSA, 120 µL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 µL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 µL, Roche Protease inhibitor (Complete, #1-697-498) 2 tablets, Phosphatase Inhibitor II (Sigma, #P-5726) 200 µL, and a sodium vanadate solution (containing 900 µL PBS, 100 µL 300 mM NaVO$_3$, 6 µL H$_2$O$_2$ (30% stock) and stirred at RT for 15 min) (90 µL). The cells were washed once with ice cold 1×PBS (GIBCO, #14190-136), then lysis buffer (60 µL) was added and the cells were incubated on ice for 20 min.

The IGEN assay was performed as follows: Dynabeads M-280 streptavidin beads were pre-incubated with biotinylated anti-human HGFR (240 µL anti-human-HGFR(R&D system, BAF527 or BAF328)@100 µg/mL+360 µL Beads (IGEN #10029+5.4 µL buffer–PBS/1% BSA/0.1% Tween20) by rotating for 30 min at RT. Antibody beads (25 µL) were transferred to a 96 well plate. Cell lysate solution (25 µL) was transferred added and the plate was shaken at RT for 1 h. Anti-phosphotyrosine 4G10 (Upstate 05-321) (19.7 µL antibody+6 mL 1×PBS) (12.5 µL) was added to each well, then incubated for 1 h at RT. Anti-mouse IgG ORI-Tag (ORIGEN #110087) (24 µL Antibody+6 mL buffer) (12.5 µL) was added to each well, then incubated at RT for 30 min. 1×PBS (175 µL) was added to each well and the electrochemiluminescence was read by an IGEN M8. Raw data was analyzed using a 4-parameter fit equation in XLFit. IC$_{50}$ values are then determined using Grafit software. Examples 2, 4, 6-8, 11, 13, 15-21, 23-26, 36-37, 39, 41, and 43-44 exhibited activity in PC3 cells with IC$_{50}$ values less than 1.0 µM. Examples 2, 4, 6-8, 11-13, 15-21, 23-26, 36-37, 41, and 43-44 exhibited activity in CT26 cells with IC$_{50}$ values less than 1.0 µM.

rhu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Tumor Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Formulations

Also embraced within this invention is a class of pharmaceutical compositions comprising the active compounds of the current invention in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:
1. A compound selected from
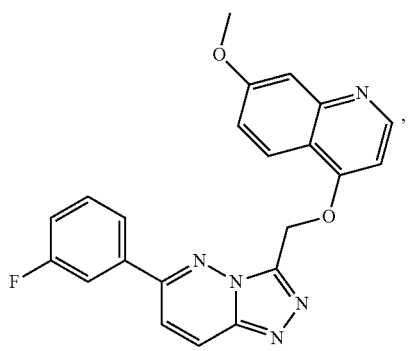
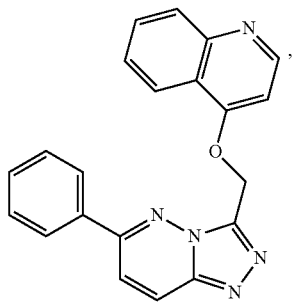
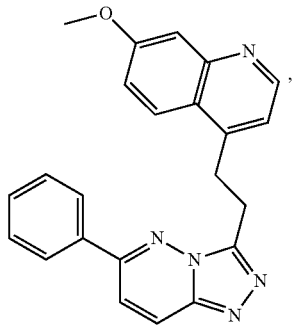
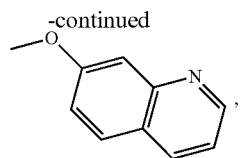
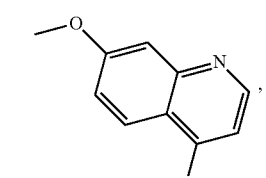
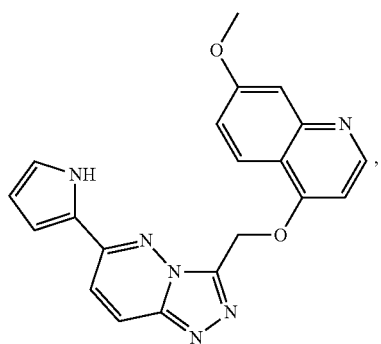

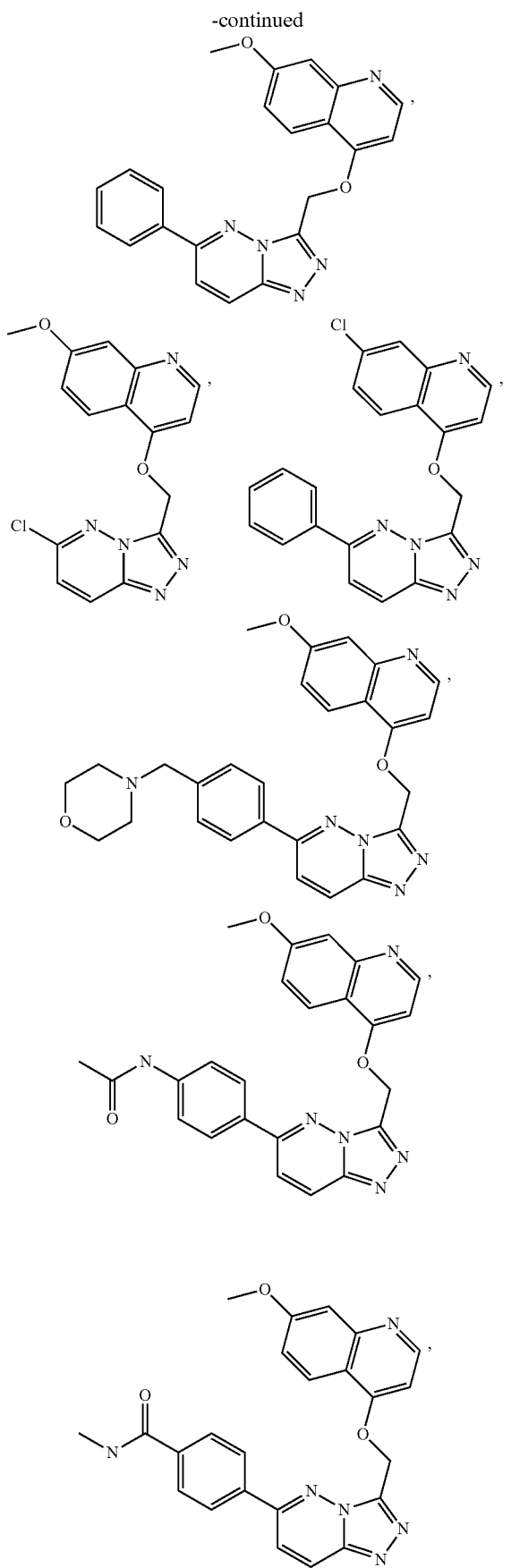
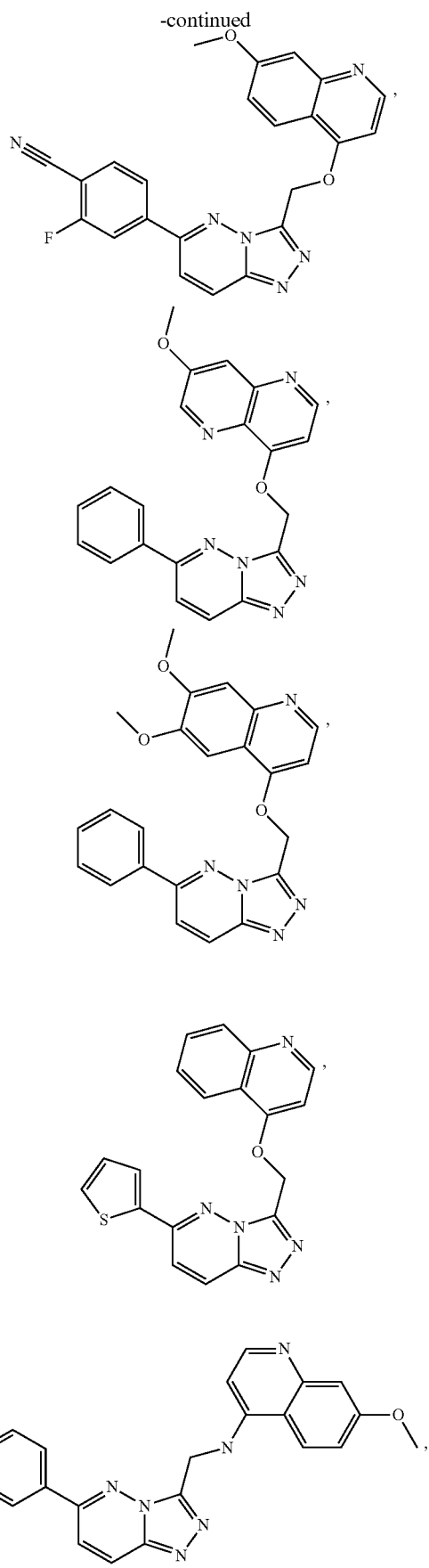

391
-continued
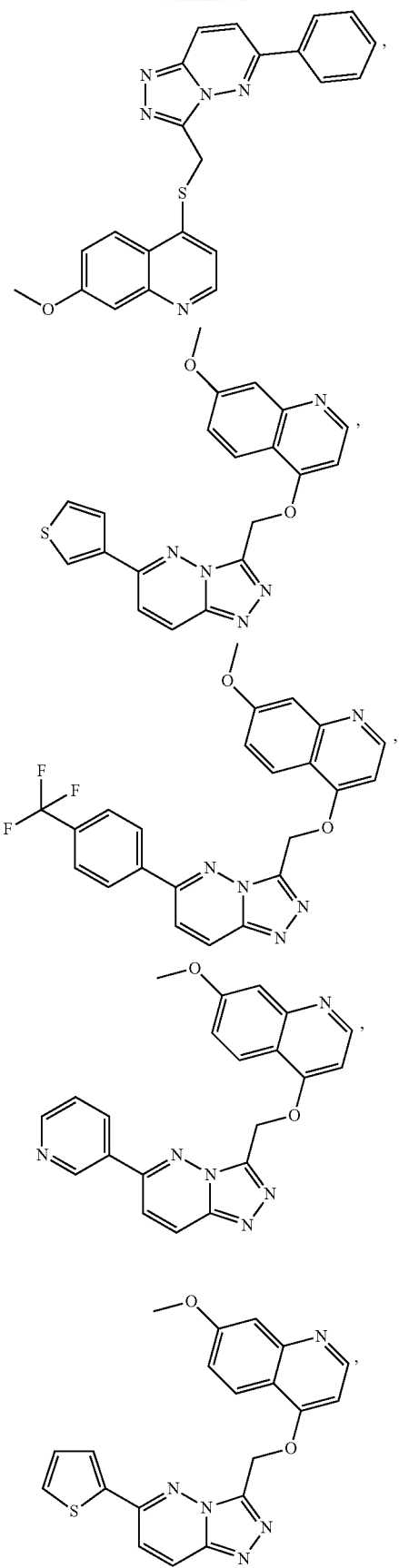
392
-continued
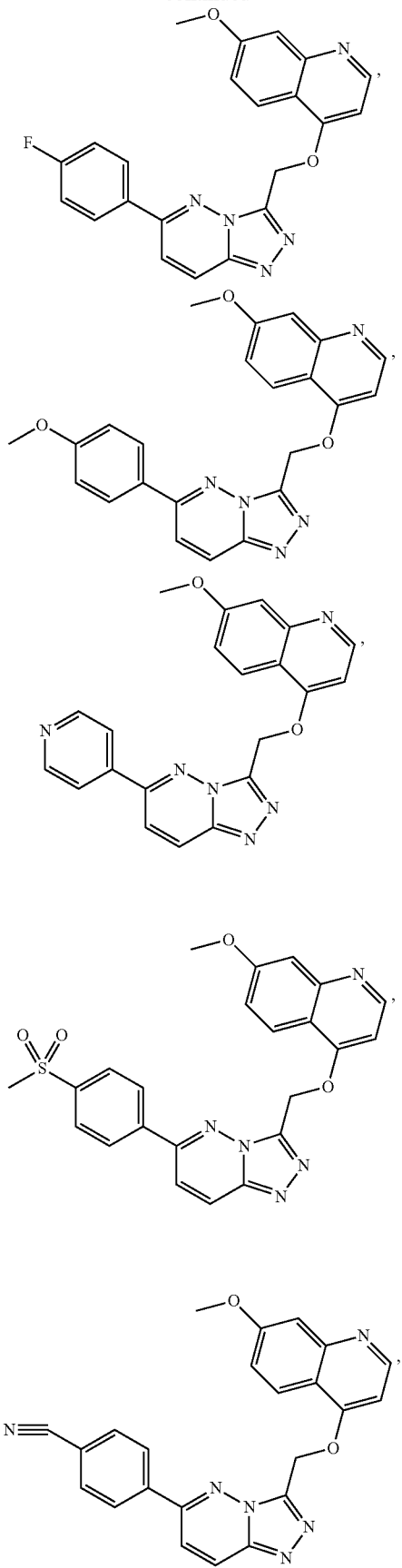

393
-continued
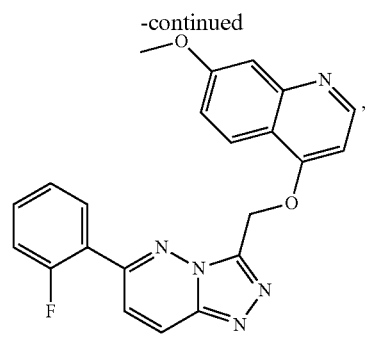
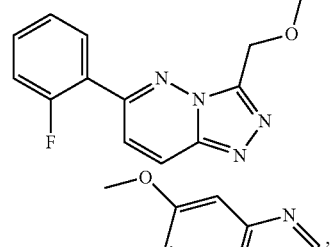
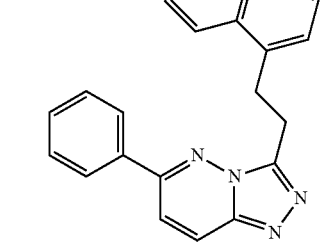
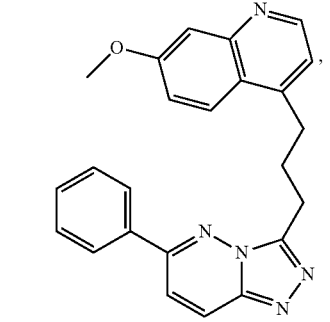
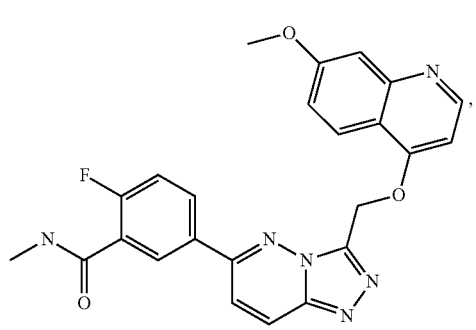
394
-continued
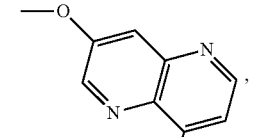
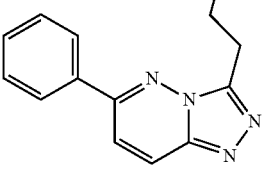
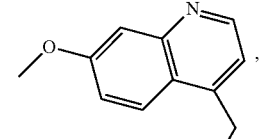
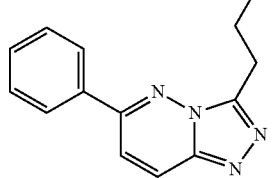
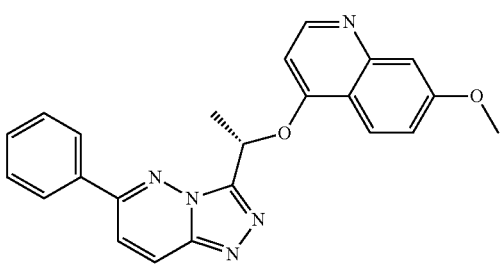
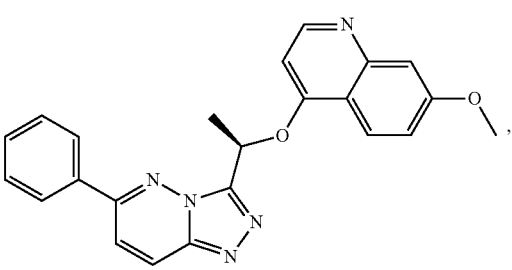

395
-continued
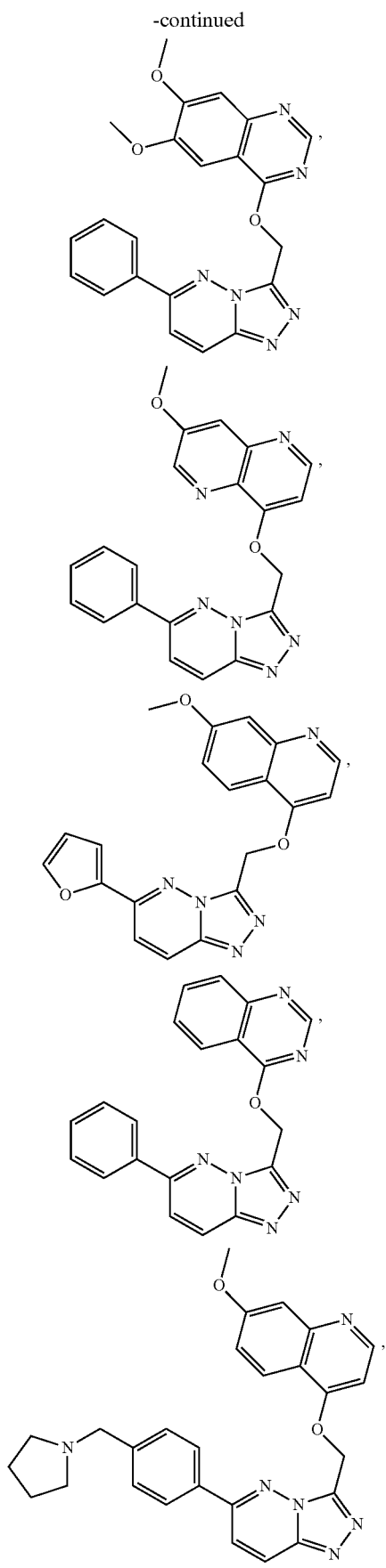
396
-continued
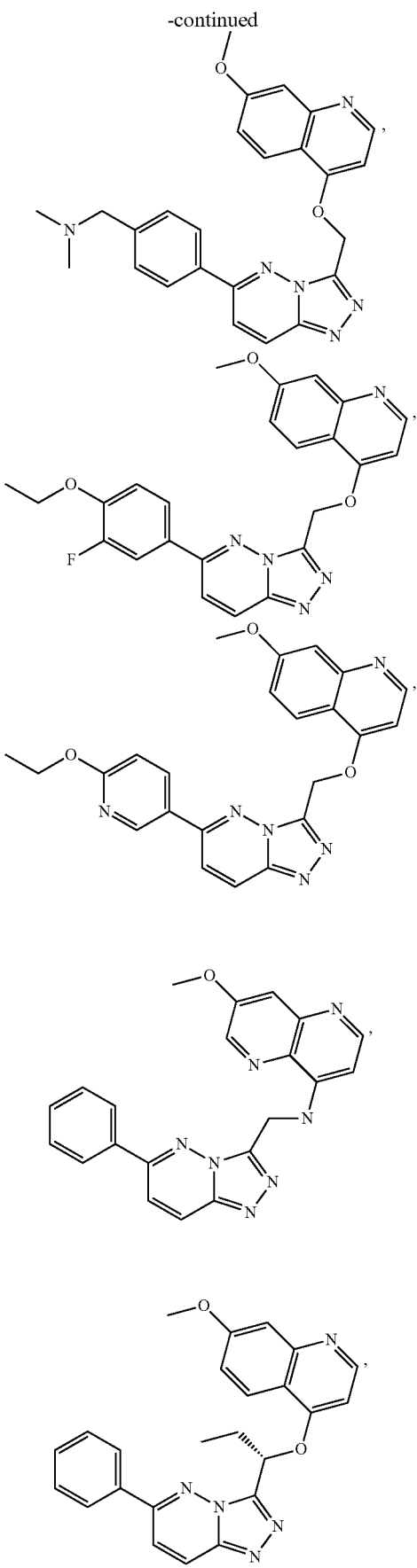

397
-continued
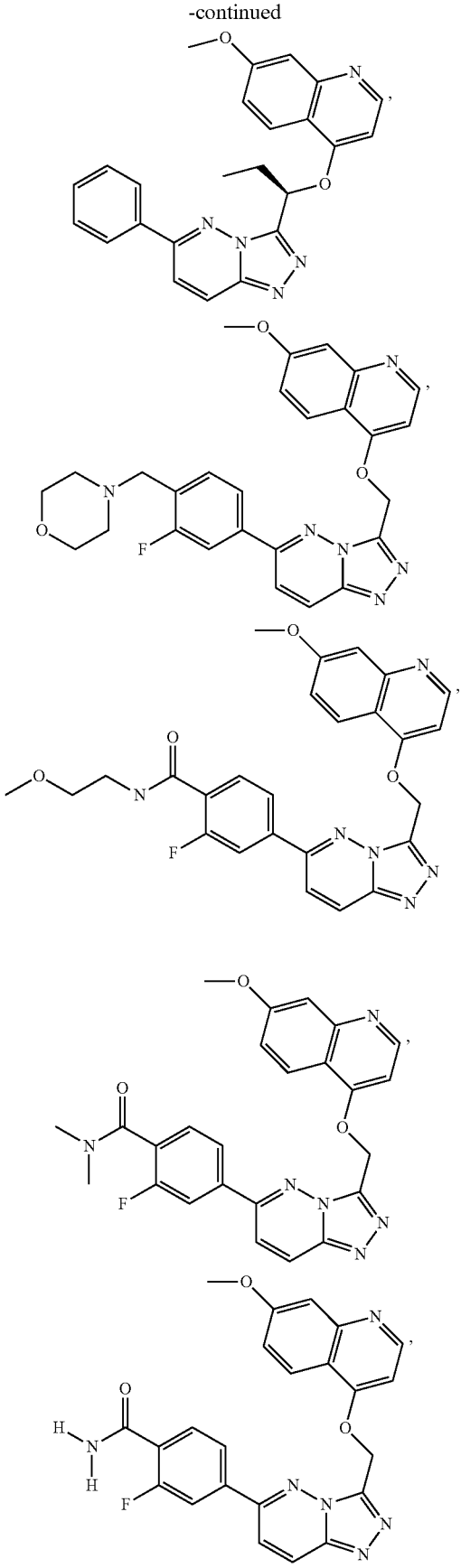
398
-continued
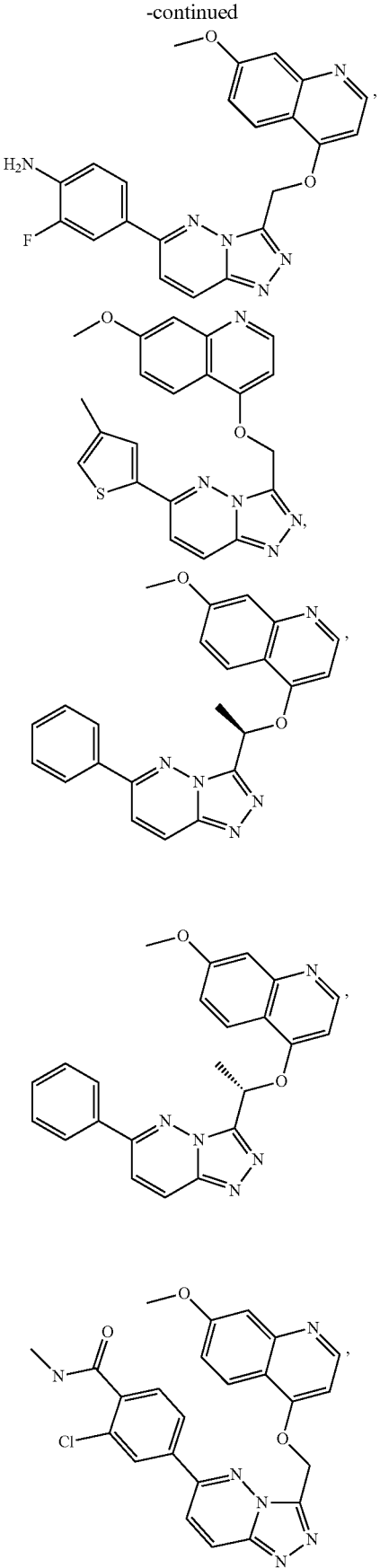

399
-continued
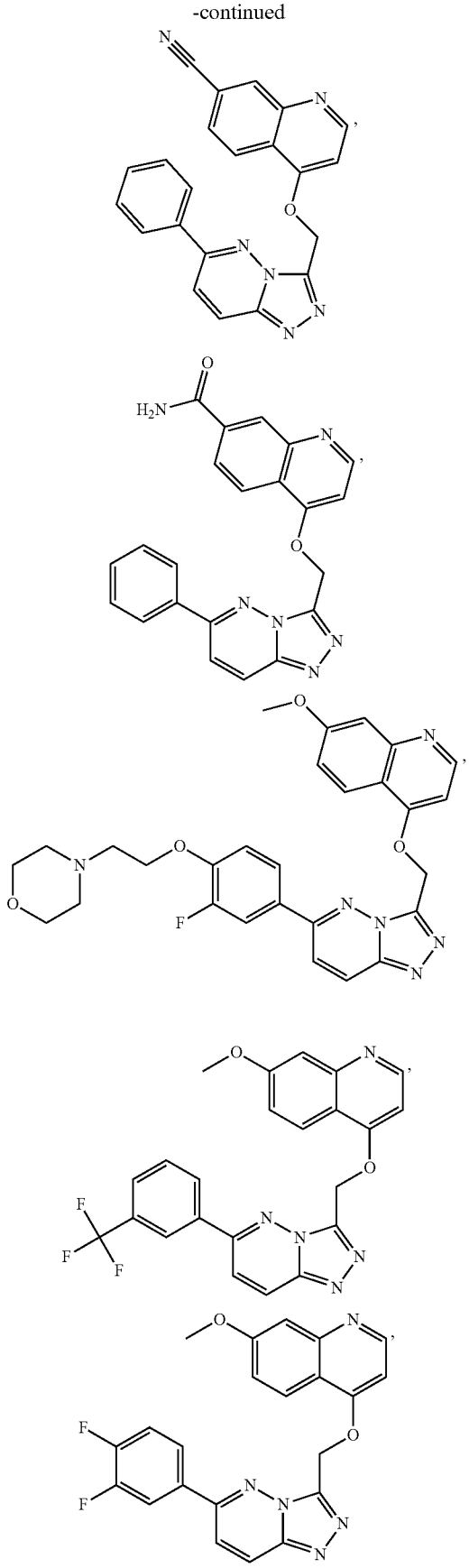
400
-continued
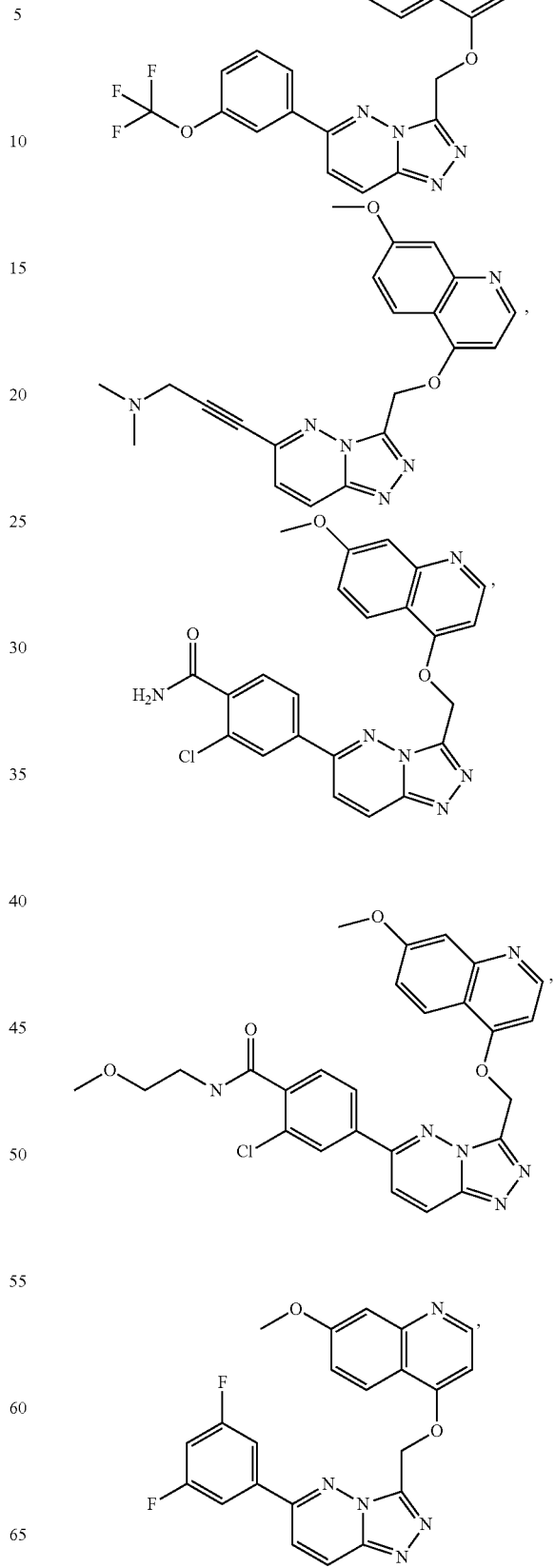

401
-continued
402
-continued
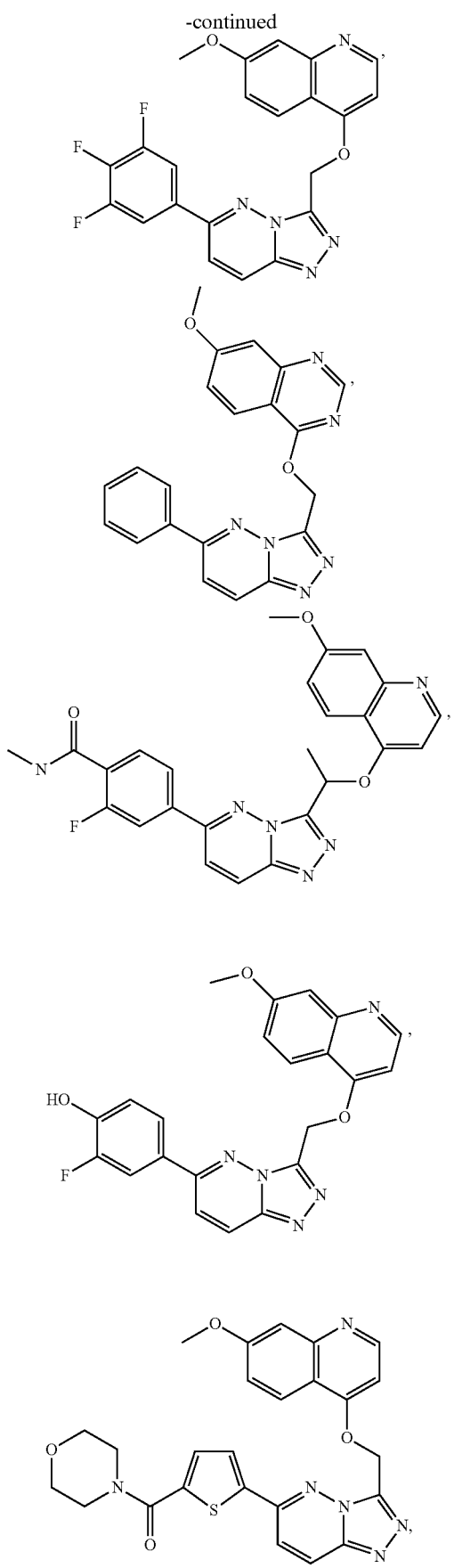
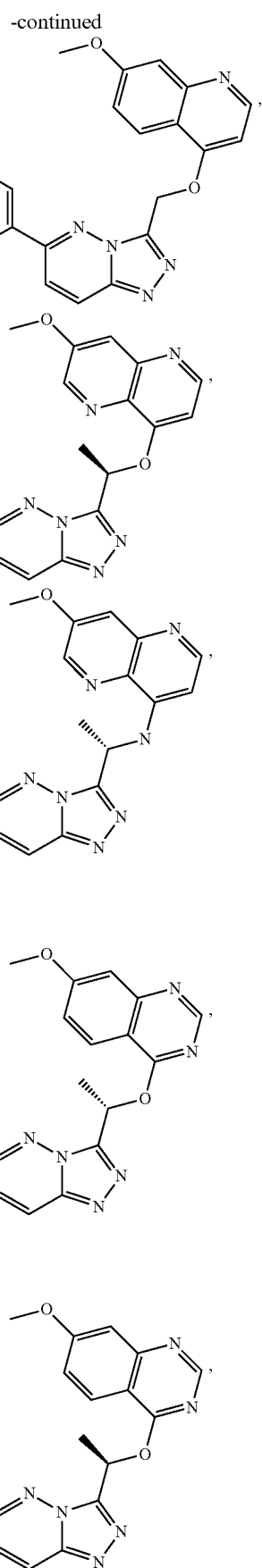

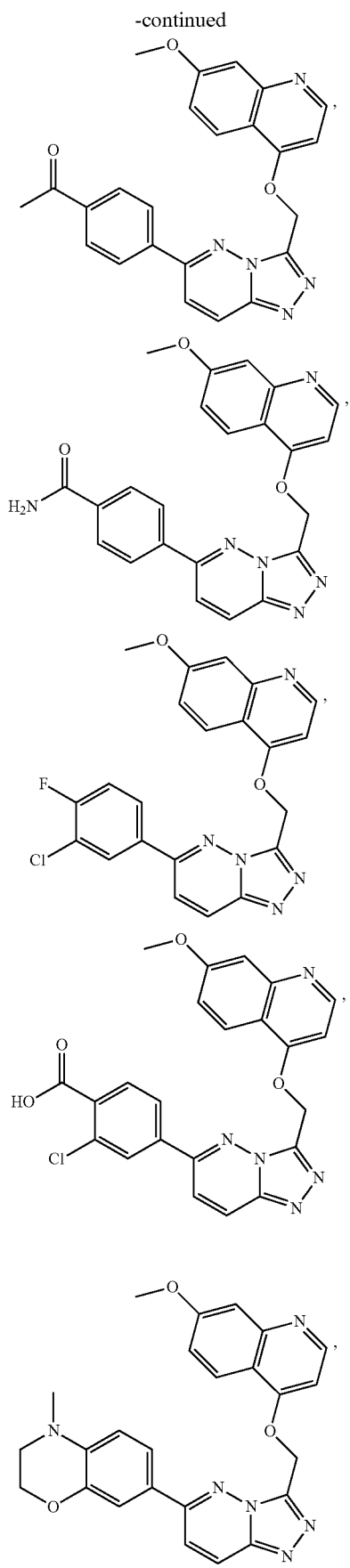
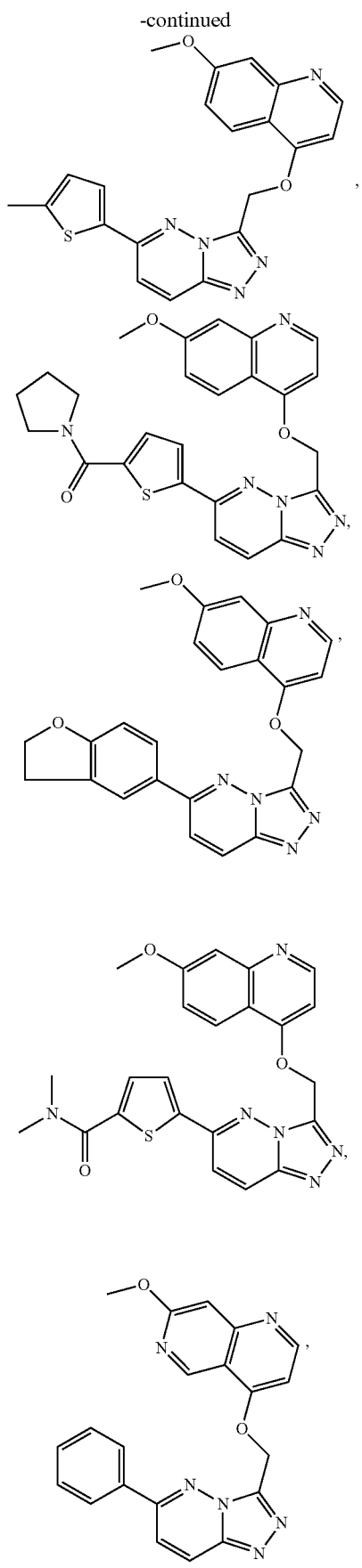

405
-continued
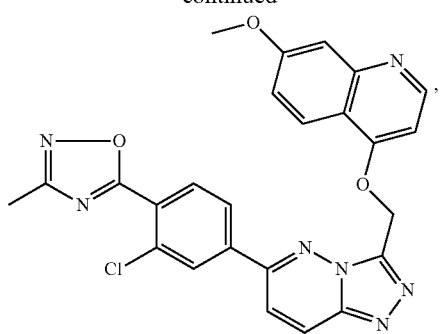
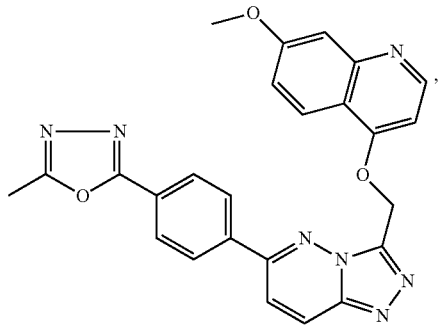
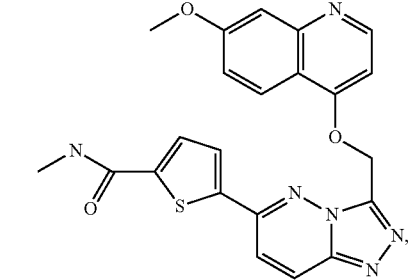
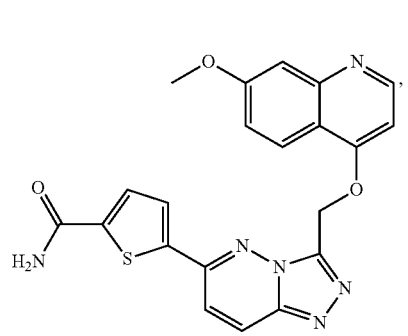
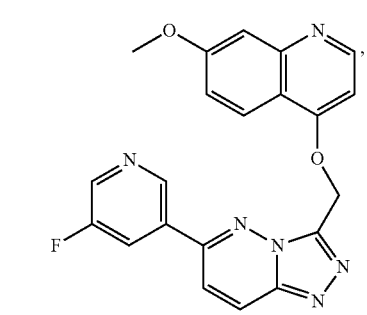
406
-continued
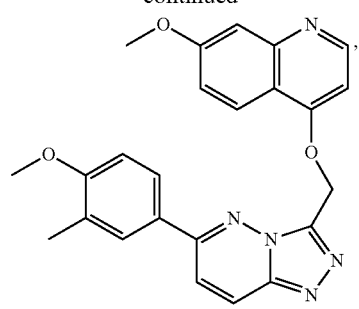
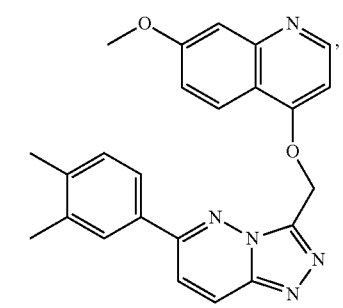
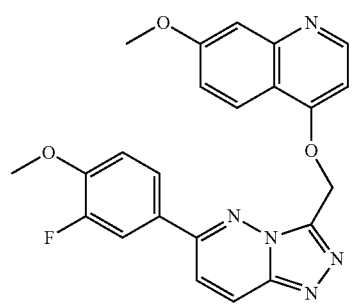
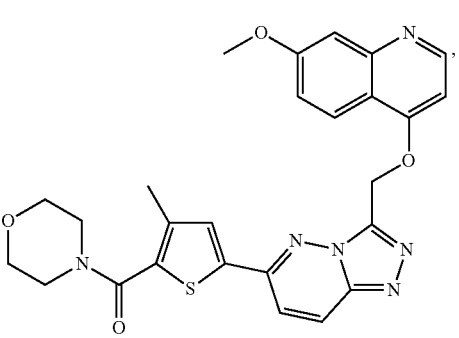
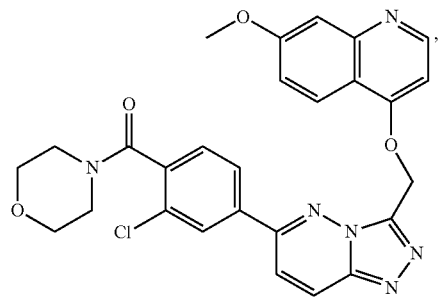

407
-continued
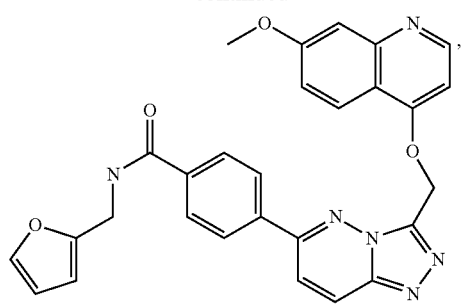
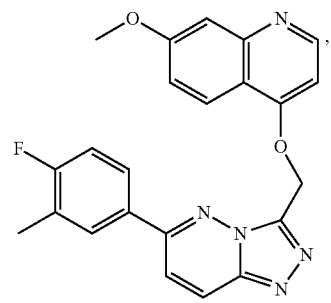
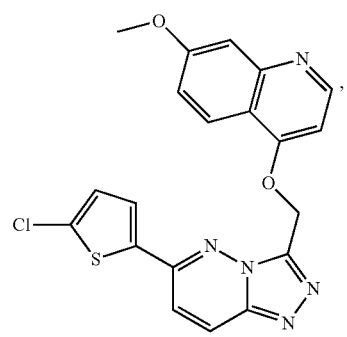
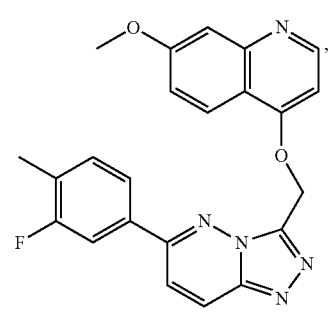
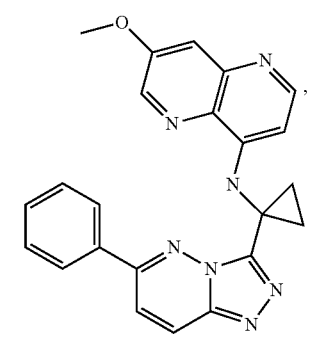
408
-continued
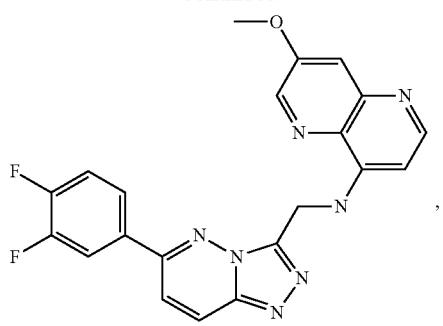
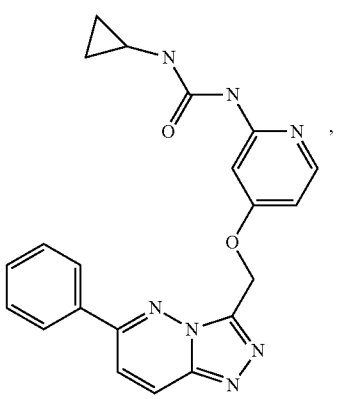
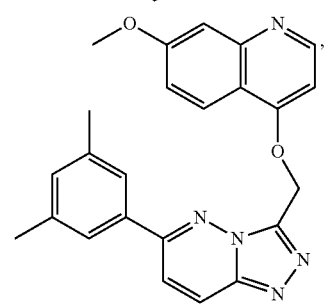
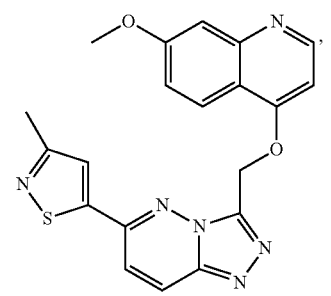
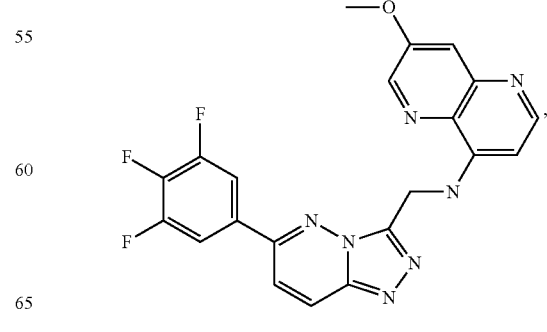

409
-continued
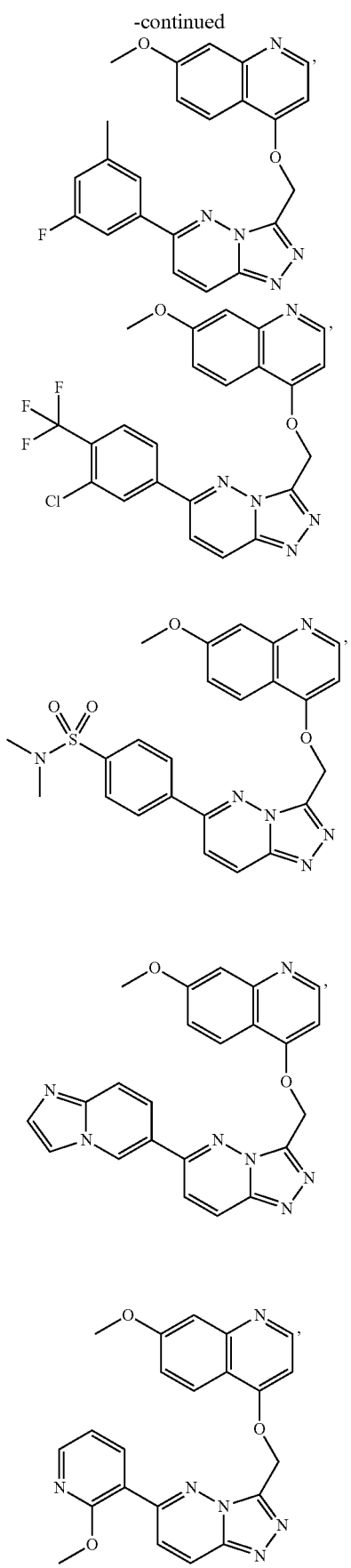
410
-continued
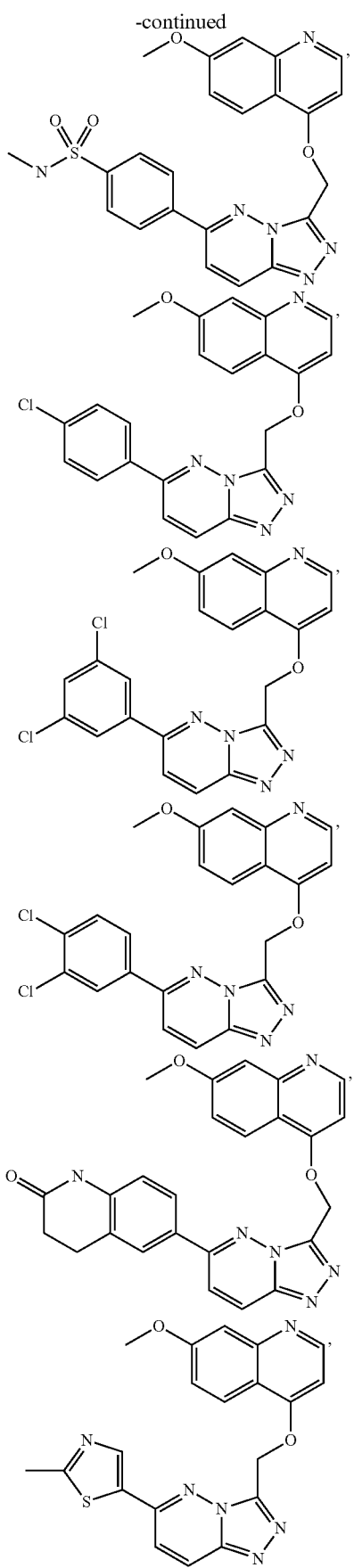

411
-continued
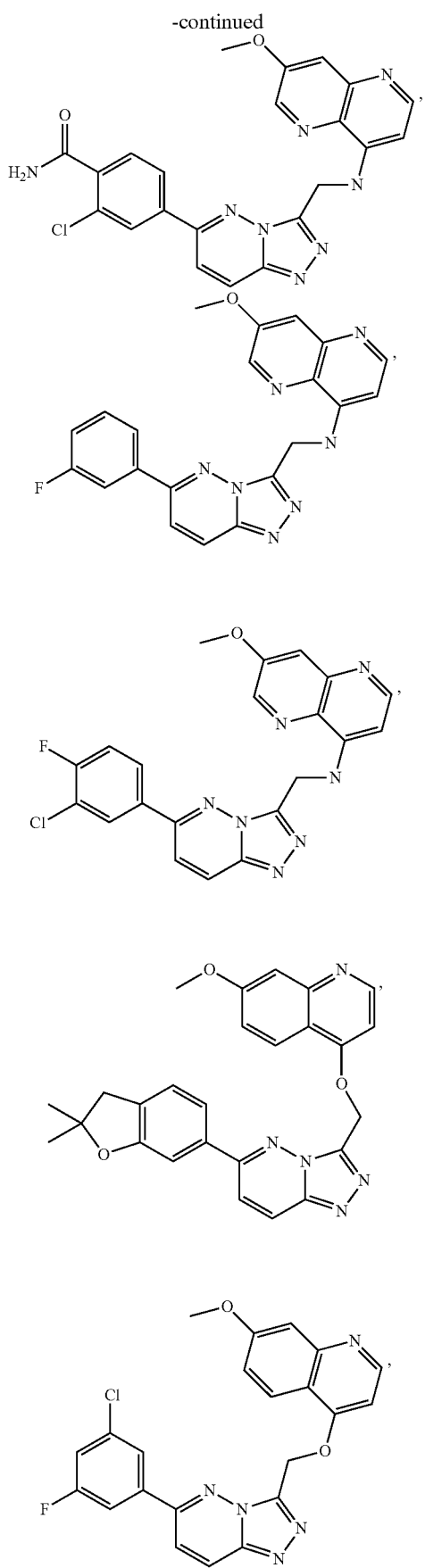
412
-continued
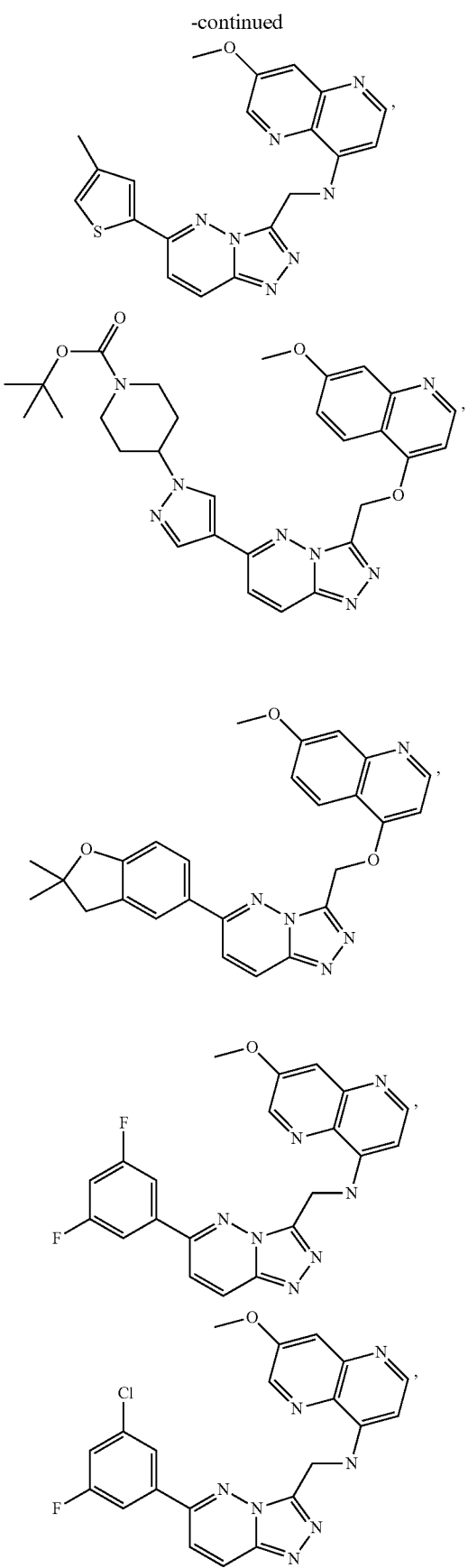

413
-continued
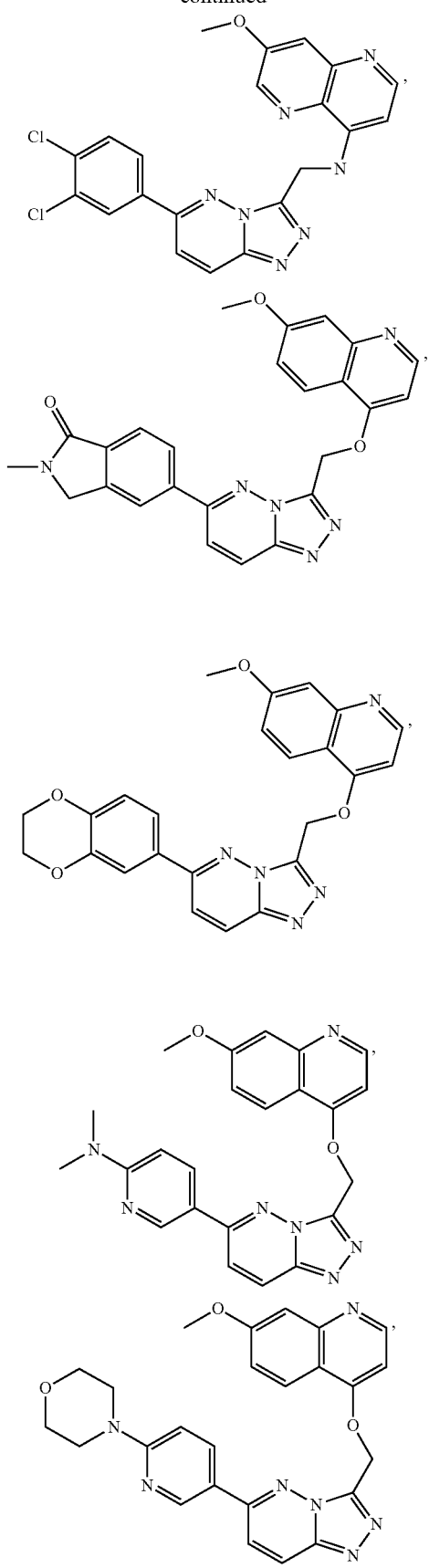
414
-continued
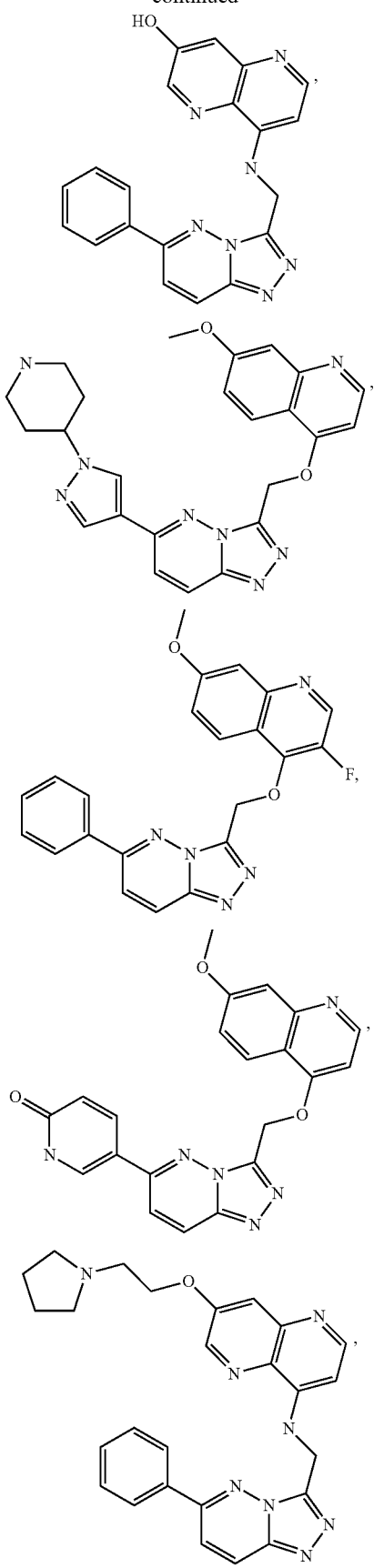

-continued
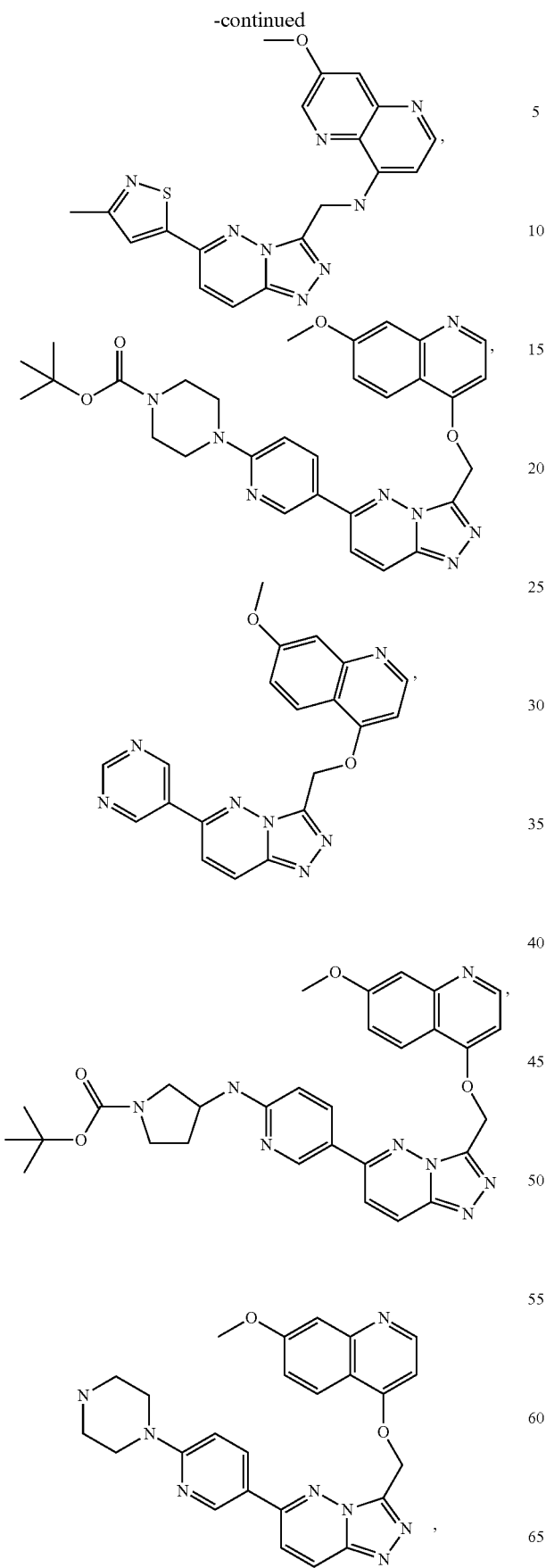
-continued
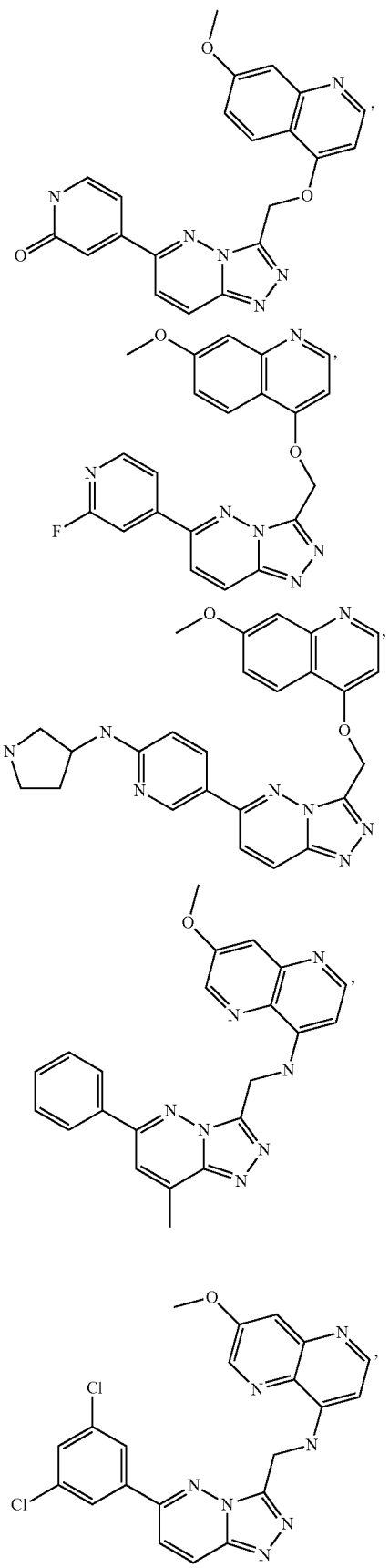

417
-continued
418
-continued
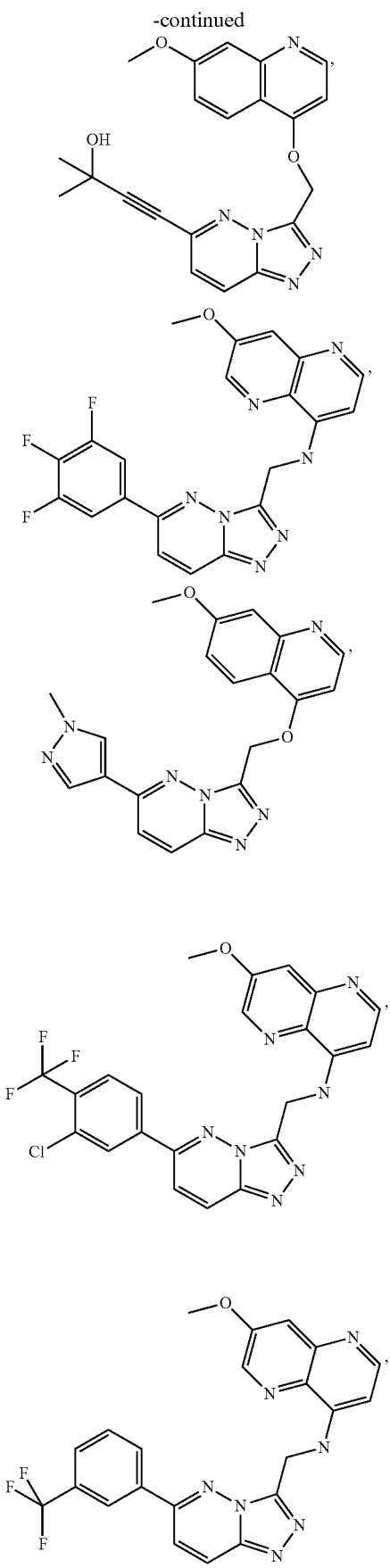
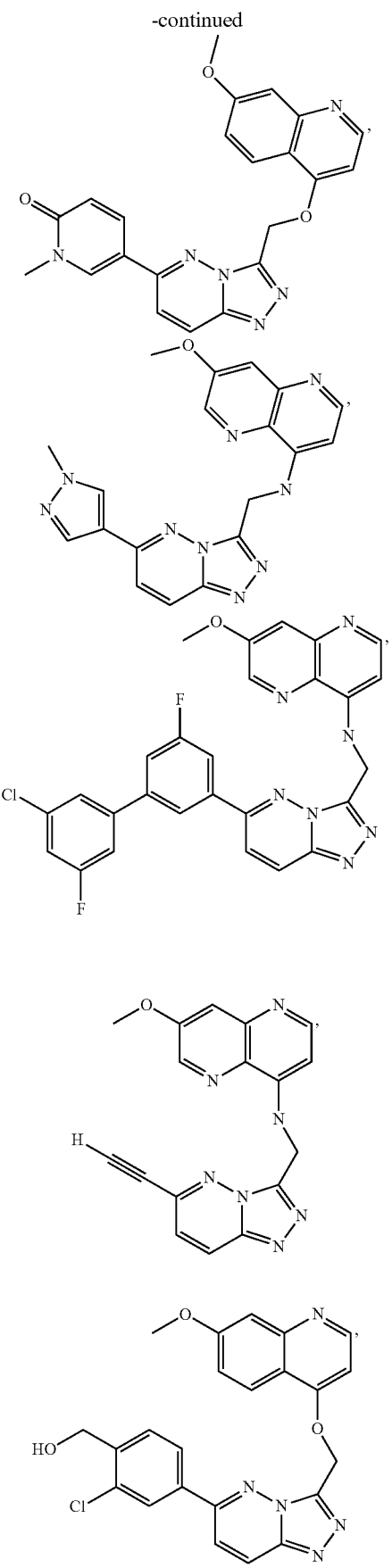

419
-continued
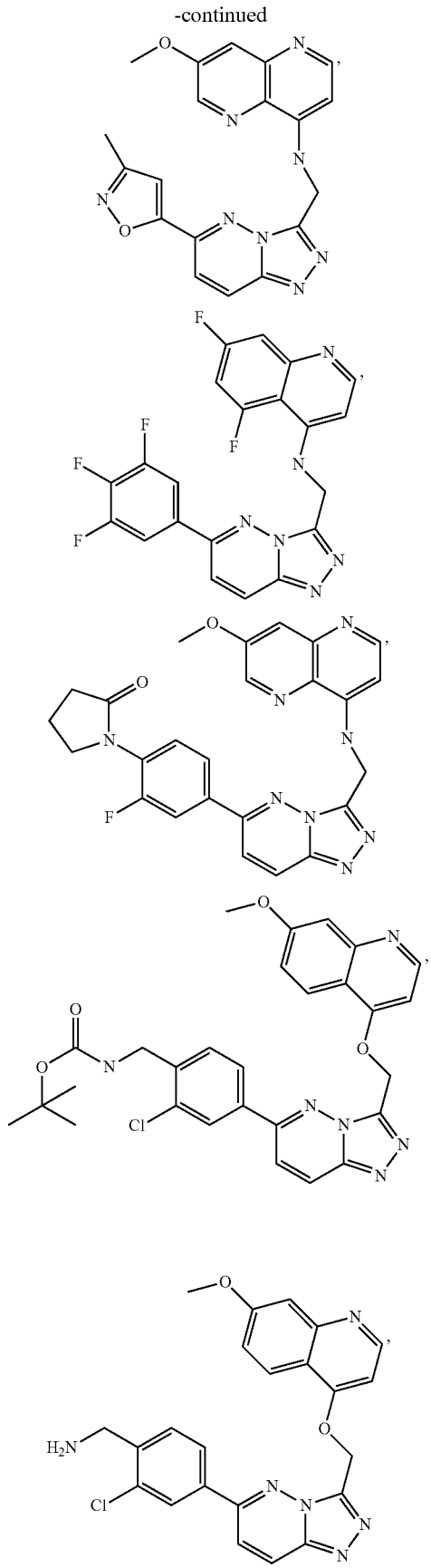
420
-continued
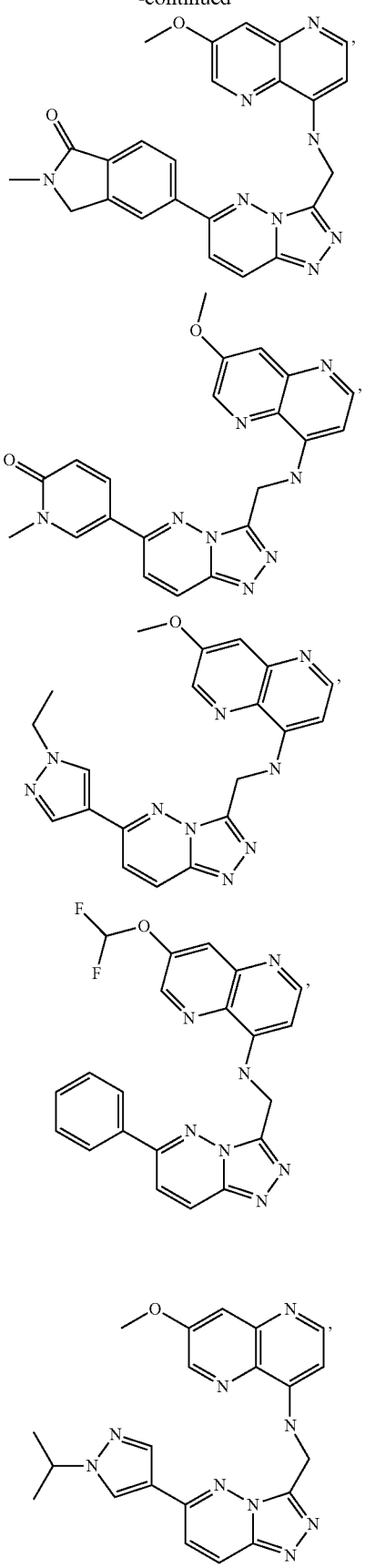

421
-continued
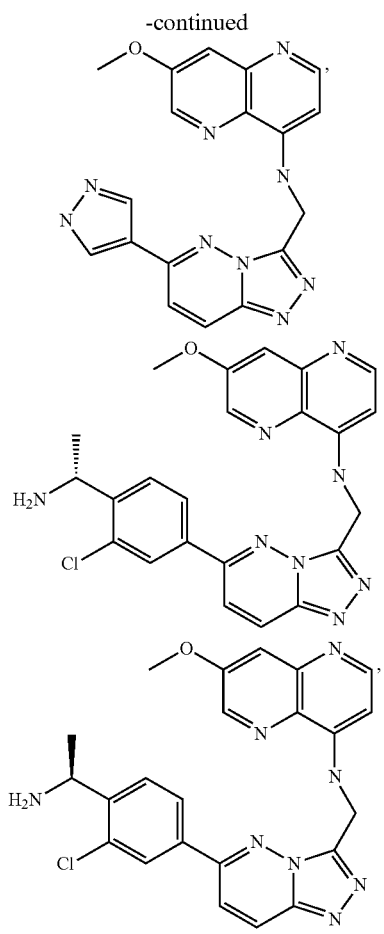
422
-continued
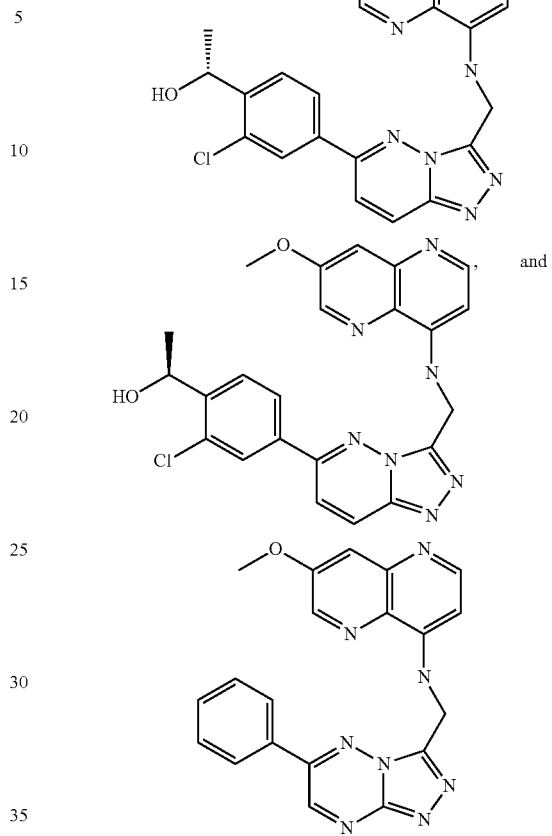
or a pharmaceutically acceptable salt thereof.
2. A compound or a pharmaceutically acceptable salt thereof, selected from
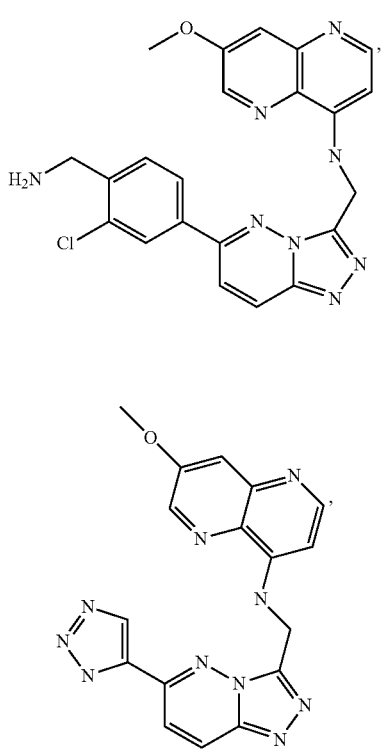
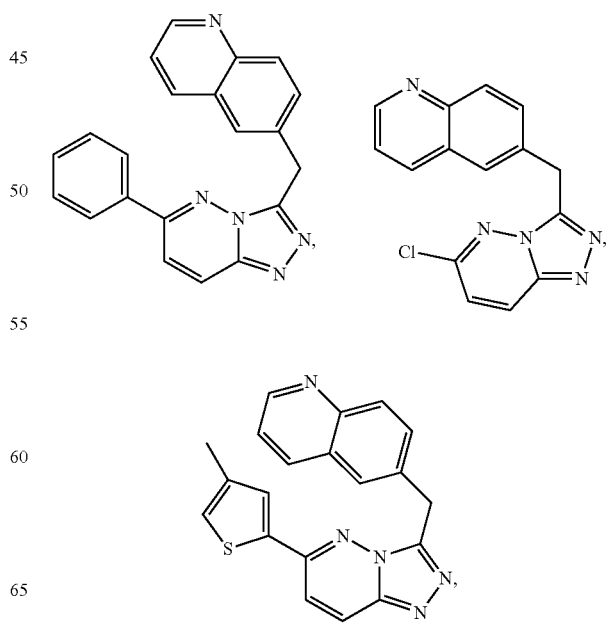

423
-continued
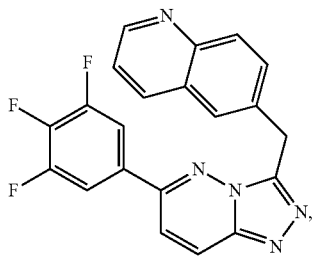
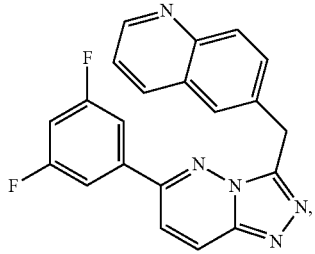
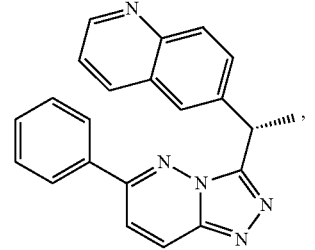
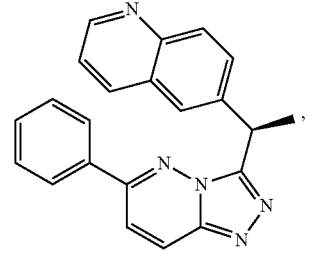
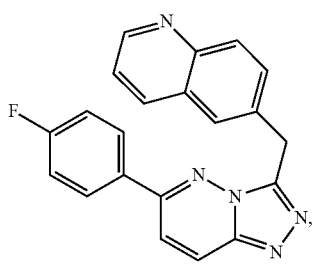
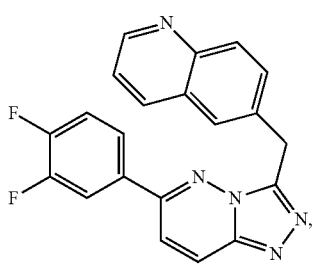
424
-continued
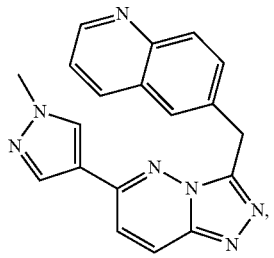
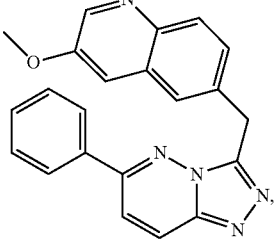
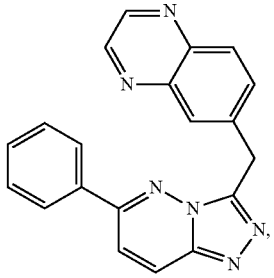
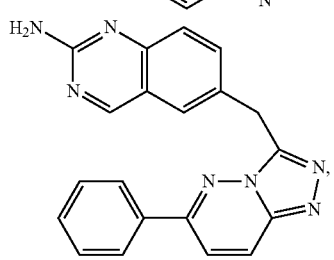
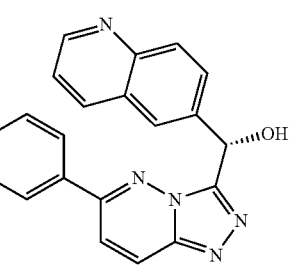
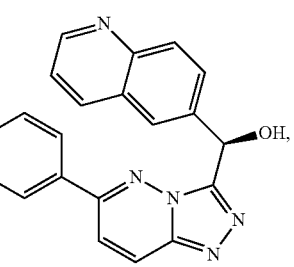

-continued
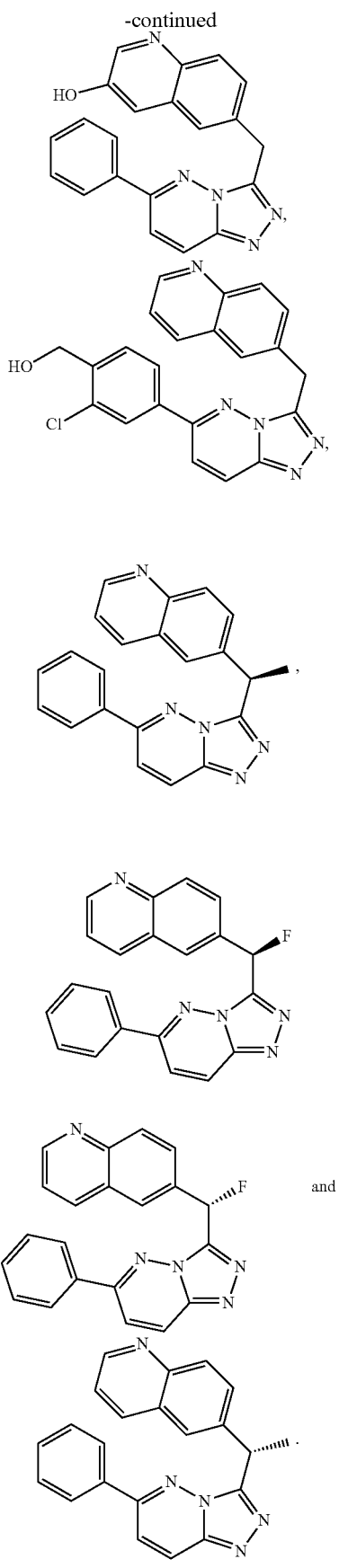
3. A compound or a pharmaceutically acceptable salt thereof, selected from
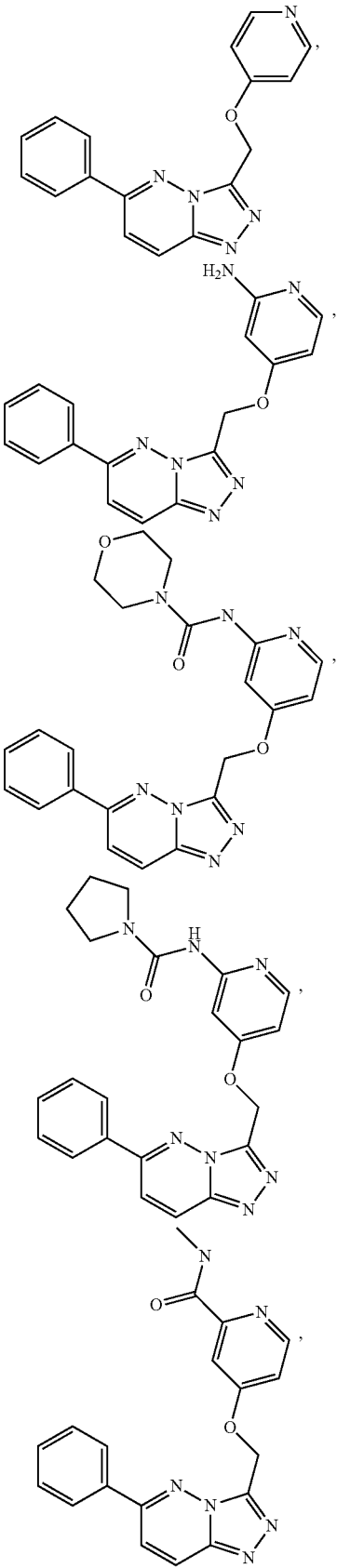

427
-continued
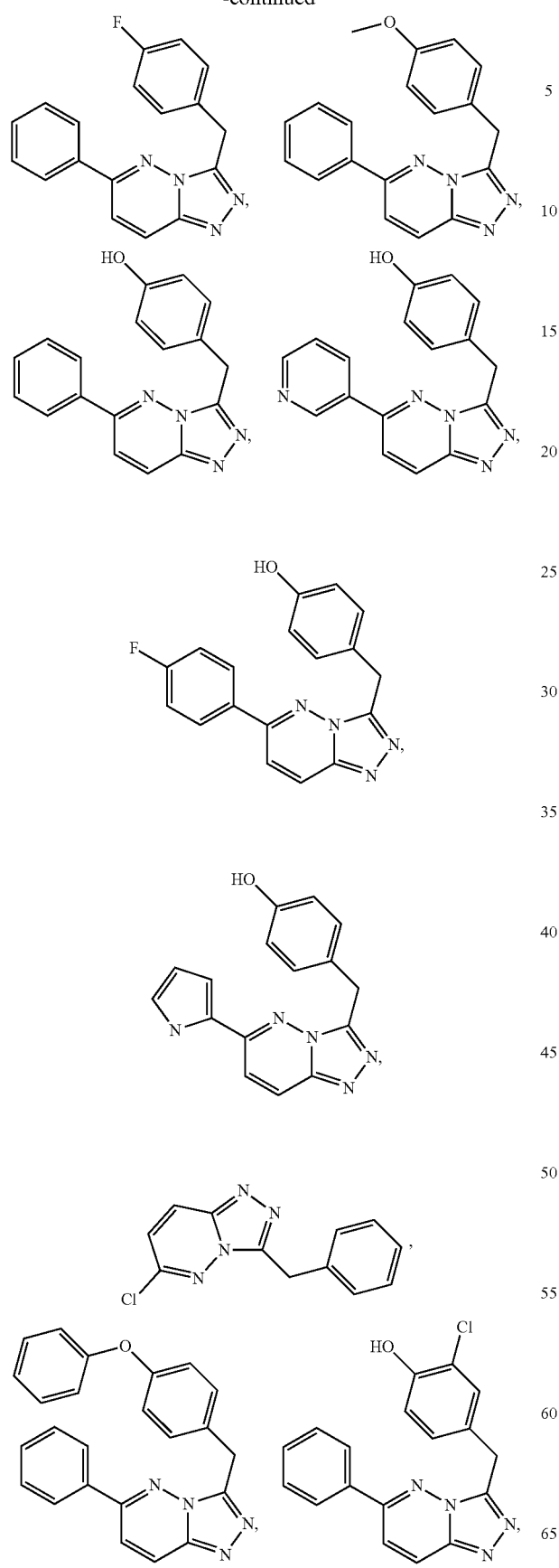
428
-continued
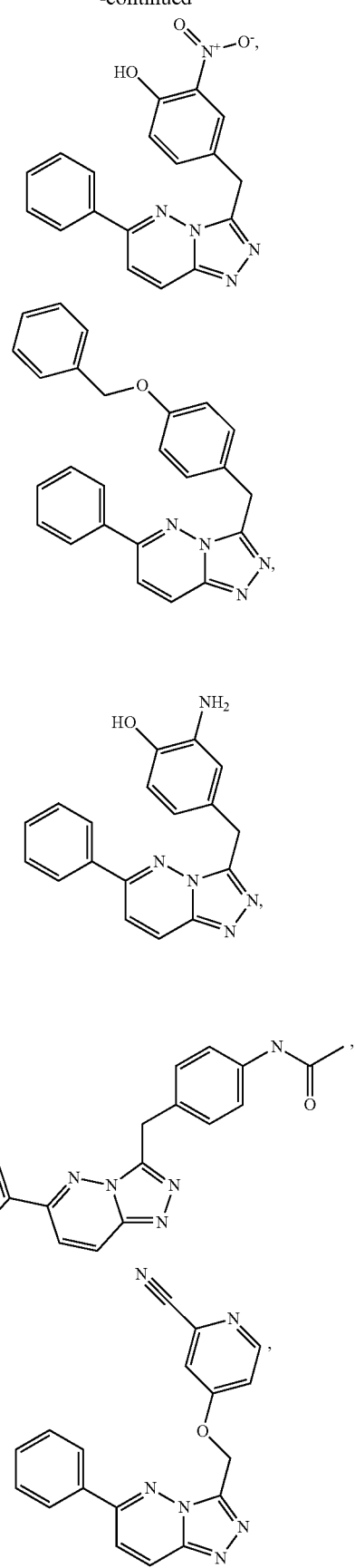

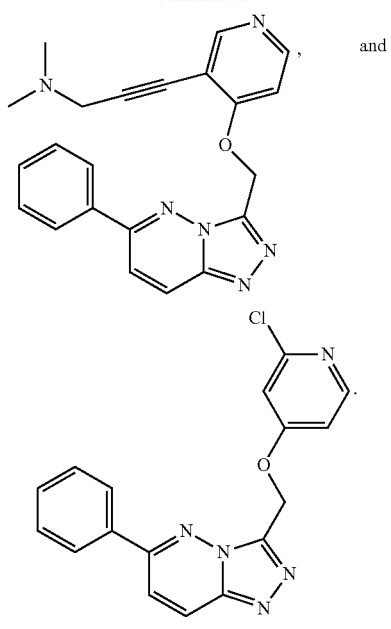
4. A compound or a pharmaceutically acceptable salt thereof, selected from
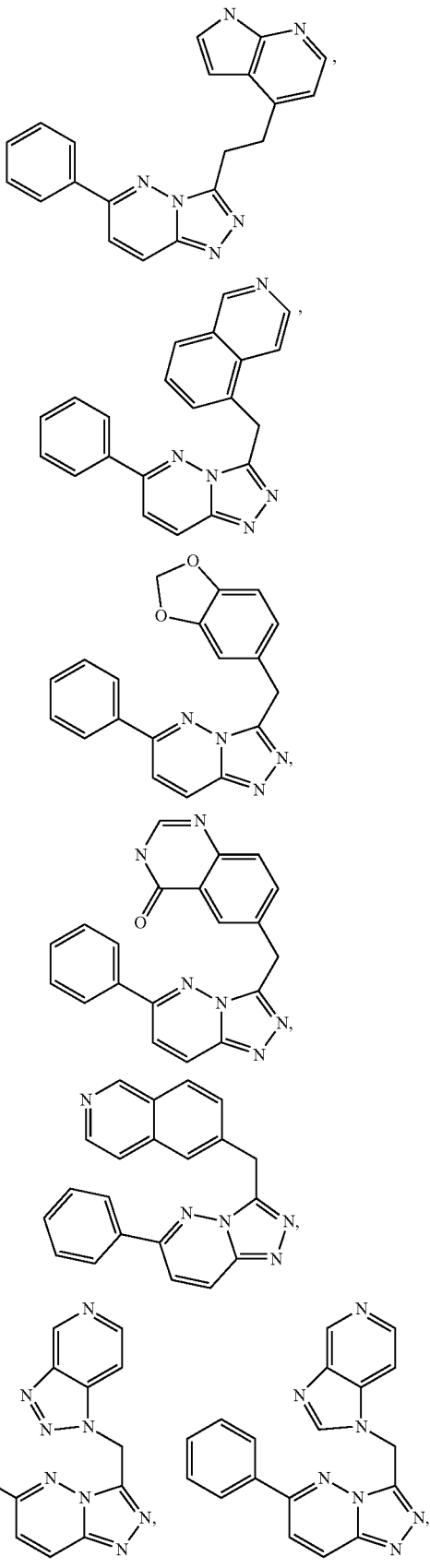

431
-continued
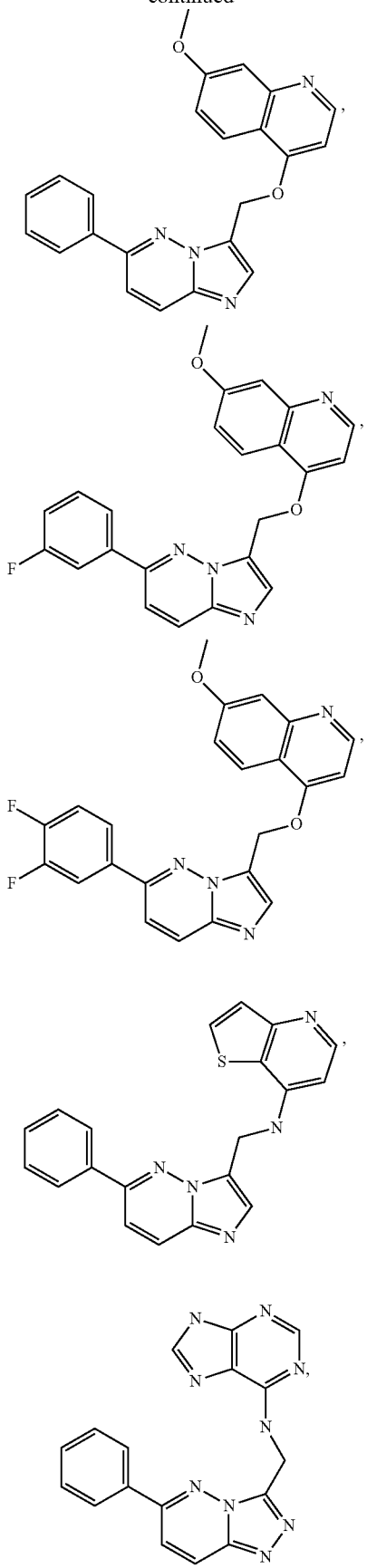
432
-continued
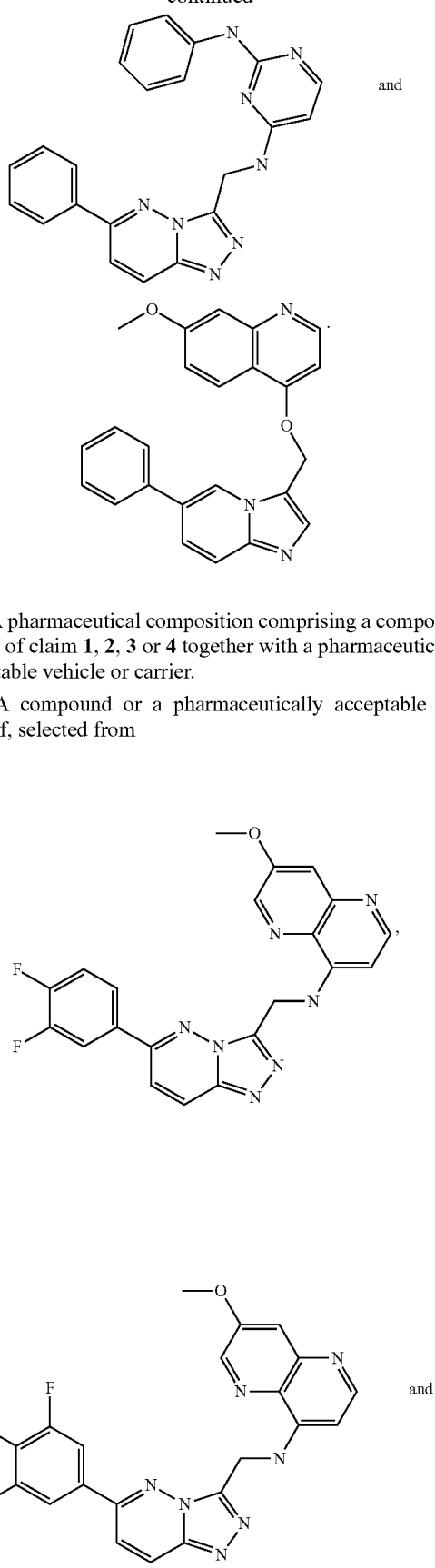
5. A pharmaceutical composition comprising a compound of any of claim 1, 2, 3 or 4 together with a pharmaceutically acceptable vehicle or carrier.
6. A compound or a pharmaceutically acceptable salt thereof, selected from -continued
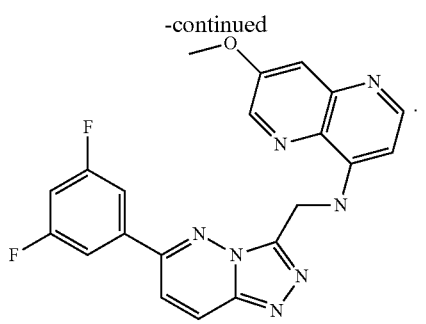
7. A pharmaceutical composition comprising a compound of claim 6 together with a pharmaceutically acceptable vehicle or carrier.
8. A method of treating gastric cancer or glioblastoma in a subject, said method comprising administering an effective amount of a compound as in any of the preceding claims.
* * * * *

SEQUENCE LISTING
<160> NUMBER OF SEQ ID NOS: 2
<210> SEQ ID NO 1
<211> LENGTH: 39
<212> TYPE: DNA
<213> ORGANISM: Homo sapiens
<400> SEQUENCE: 1
attgacggat ccatgctaaa tccagagctg gtccaggca          39
<210> SEQ ID NO 2
<211> LENGTH: 37
<212> TYPE: DNA
<213> ORGANISM: Homo sapiens
<400> SEQUENCE: 2
acaacagaat tcaatacgga gcgacacatt ttacgtt            37